(12) United States Patent
O'Toole et al.

(10) Patent No.: US 11,061,029 B2
(45) Date of Patent: Jul. 13, 2021

(54) METHODS OF DETERMINING COLORECTAL CANCER STATUS IN AN INDIVIDUAL

(71) Applicant: University College Cork—National University of Ireland, Cork, Cork (IE)

(72) Inventors: Paul O'Toole, Cork (IE); Burkhardt Flemer, Cork (IE); Fergus Shanahan, Cork (IE); Ian Jeffery, Cork (IE); Katryna Cisek, Cork (IE)

(73) Assignee: UNIVERSITY COLLEGE CORK - NATIONAL UNIVERSITY OF IRELAND, CORK, Cork (IE)

( * ) Notice: Subject to any disclaimer, the term of this patent is extended or adjusted under 35 U.S.C. 154(b) by 0 days.

(21) Appl. No.: 16/434,427

(22) Filed: Jun. 7, 2019

(65) Prior Publication Data

US 2020/0041510 A1    Feb. 6, 2020

Related U.S. Application Data

(63) Continuation of application No. PCT/EP2017/083176, filed on Dec. 15, 2017.

(30) Foreign Application Priority Data

Dec. 15, 2016   (EP) .................................... 16204532

(51) Int. Cl.
| | | |
|---|---|---|
| *C12Q 1/68* | (2018.01) | |
| *G01N 33/569* | (2006.01) | |
| *G16H 50/50* | (2018.01) | |
| *G16H 50/30* | (2018.01) | |
| *G16H 50/20* | (2018.01) | |

(52) U.S. Cl.
CPC ....... *G01N 33/56911* (2013.01); *G16H 50/20* (2018.01); *G16H 50/30* (2018.01); *G16H 50/50* (2018.01); *G01N 2570/00* (2013.01)

(58) Field of Classification Search
None
See application file for complete search history.

(56) References Cited

U.S. PATENT DOCUMENTS

2014/0107092 A1   4/2014 Meyerson et al.

FOREIGN PATENT DOCUMENTS

WO       2015018307 A1   3/2016

OTHER PUBLICATIONS

Abed et al (Cell Host Microbe. 2016. 20(2): 215-222).*
Yasuhiko et al (Gastroenterology. 150. No. 4. Suppl. 1. Apr. 2016; p. S430).*
Weng et al (J. Periodontology. Sep. 2014. 85(9): 1155-1157).*
Arora, N., Mishra, A. & Chugh, S. Microbial role in periodontitis: Have we reached the top? Some unsung bacteria other than red complex. J. Indian Soc. Periodontol. 18, 9-13 (2014).
Arthur, J. C. et al. Intestinal Inflammation Targets Cancer-Inducing Activity of the Microbiota. Science 338, 120-123 (2012).
Arumugam, M. et al. Enterotypes of the human gut microbiome. Nature 473, 174-180 (2011).
Bassis, C. M. et al. Analysis of the Upper Respiratory Tract Microbiotas as the Source of the Lung and Gastric Microbiotas in Healthy Individuals. mBio 6, e00037-15 (2015).
Baxter, N. T., Ruffin, M. T., Rogers, M. A. M. & Schloss, P. D. Microbiota-based model improves the sensitivity of fecal immunochemical test for detecting colonic lesions. Genome Med. 8, 1-10 (2016).
Benjamini Y, Hochberg Y. Controlling the false discovery rate: A practical and powerful approach to multiple testing.
Calle, M. et al. AUC-RF: A new strategy for genomic profiling with random forest, Human Heredity, 72(2): 121-132.
Caporaso JG, Kuczynski J, Stombaugh J et al. QIIMEe allows analysis of high-throughput community sequencing data. Nat Methods 2010;7:335-6. doi:10.1038/nmeth.f.303.
Castellarin, M. et al. Fusobacterium nucleatum infection is prevalent in human colorectal carcinoma. Genome Res. 22, 299-306 (2012).
Chen, X. et al. Oral Microbiota and Risk for Esophageal Squamous Cell Carcinoma in a High-Risk Area of China. PLOS ONE 10, e0143603 (2015).
Claesson MJ, Jeffery IB, Conde S et al. Gut microbiota composition correlates with diet and health in the elderly. Nature 2012;488:178-84. doi:10.1038/nature11319.
Dray S, Dufour A-B. The ade4 package: Implementing the duality diagram for ecologists. Journal of Statistical Software 2007;22:1-20. doi:10.18637/jss.v022.04.
Edgar RC. Search and clustering orders of magnitude faster than blast. Bioinformatics 2010;26:2460-1. doi:10.1093/bioinformatics/btq461.
Farrell, J. J. et al. Variations of oral microbiota are associated with pancreatic diseases including pancreatic cancer. Gut 61, 582-588 (2012).
Flanagan, L. et al. Fusobacterium nucleatum associates with stages of colorectal neoplasia development, colorectal cancer and disease outcome. Eur. J. Clin. Microbiol. Infect. Dis. 33, 1381-1390 (2014).
Flemer, B. et al. Tumour-associated and non-tumour-associated microbiota in colorectal cancer. Gut gutjnl-2015-309595 (2016). doi:10.1136/gutjnl-2015-309595.
Flemer B, Lynch DB, Brown JM et al. Tumour-associated and non-tumour-associated microbiota in colorectal cancer. Gut 2017;66:633-43. doi:10.1136/gutjnl-2015-309595.
Friedman EJ Jonathan and Alm. Inferring correlation networks from genomic survey data. PLOS Computational Biology 2012;8:1-11. doi:10.1371/journal.pcbi.1002687.

(Continued)

*Primary Examiner* — Jennifer E Graser
(74) *Attorney, Agent, or Firm* — Nixon Peabody LLP; David S. Resnick; Nicole D. Kling

(57) ABSTRACT

A method of determining colorectal cancer status in an individual, which comprises abundance profiling of the individual's microbiome.

10 Claims, 24 Drawing Sheets
Specification includes a Sequence Listing.

(56) References Cited

OTHER PUBLICATIONS

Gevers D, Kugathasan S, Denson LA et al. The treatment-naive microbiome in new-onset crohn's disease. Cell Host Microbe 2014;15:382-92. doi:10.1016/j.chom.2014.02.005.
Helicobacter pylori, gastric MALT lymphoma, and adenocarcinoma of the stomach. Go MF, Smoot DT. Semin Gastrointest Dis. Jul. 2000;11(3):134-41.
Heller, D. et al. Microbial Diversity in the Early In Vivo-Formed Dental Biofilm. Appl. Environ. Microbiol. 82, 1881-1888 (2016).
Hundt, S., Haug, U. & Brenner, H. Comparative Evaluation of Immunochemical Fecal Occult Blood Tests for Colorectal Adenoma Detection. Ann. Intern. Med. 150, 162-169 (2009).
Ito, M. et al. Association of Fusobacterium nucleatum with clinical and molecular features in colorectal serrated pathway. Int. J. Cancer 137, 1258-1268 (2015).
Jover-Díaz, F., Cuadrado, J. M., Laveda, R., Andreu, L. & Merino, J. Porphyromonas asaccharolytica liver abscess. Anaerobe 9, 87-89 (2003).
Kato, I. et al. Oral microbiome and history of smoking and colorectal cancer. J. Epidemiol. Res. 2, (2016).
Kostic, A. D. et al. Fusobacterium nucleatum Potentiates Intestinal Tumorigenesis and Modulates the Tumor-Immune Microenvironment. Cell Host Microbe 14, 207-215 (2013).
Kostic, A. D. et al. Genomic analysis identifies association of Fusobacterium with colorectal carcinoma. Genome Res. 22, 292-298 (2012).
Liang, J. Q. et al. Fecal Bacteria Act as Novel Biomarkers for Non-Invasive Diagnosis of Colorectal Cancer. Clin. Cancer Res. clincanres.1599.2016 (2016). doi:10.1158/1078-0432.CCR-16-1599.
Love MI, Huber W and Anders S (2014). "Moderated estimation of fold change and dispersion for RNA-seq data with DESeq2." Genome Biology, 15, pp. 550. doi: 10.1186/s13059-014-0550-8.
Magoc T, Salzberg SL. FLASH: Fast length adjustment of short reads to improve genome assemblies. Bioinformatics 2011;27:2957-63. doi:10.1093/bioinformatics/btr507.
Mandal S, Van Treuren W, White RA et al. Analysis of composition of microbiomes: A novel method for studying microbial composition. Microb Ecol Health Dis 2015;26:27663. doi:10.3402/mehd.v26.27663.
Martin M. Cutadapt removes adapter sequences from high-throughput sequencing reads. 2011 2011;17. doi:10.14806/ej.17.1.200 pp. 10-12.
Nakatsu, G. et al. Gut mucosal microbiome across stages of colorectal carcinogenesis. Nat. Commun. 6, 8727 (2015).
Oksanen J, Blanchet FG, Friendly M et al. Vegan: Community ecology package. 2017. https://CRAN.R-project.org/package=vegan.
Palmer Jr, R. J. Composition and development of oral bacterial communities. Periodontol. 2000 64, 20-39 (2014).
Polk, D. B. & Peek, R. M. Helicobacter pylori: gastric cancer and beyond. Nat. Rev. Cancer 10, 403-414 (2010).
Pushalkar, S. et al. Comparison of oral microbiota in tumor and non-tumor tissues of patients with oral squamous cell carcinoma. BMC Microbiol. 12, 144 (2012).
R Core Team. R: A language and environment for statistical computing. Vienna, Austria: R Foundation for Statistical Computing 2016. https://www.R-project.org/.
Robin X, Turck N, Hainard a et al. PROC: An open-source package for r and s+ to analyze and compare roc curves. BMC Bioinformatics 2011;12:77.
Rubinstein, M. R. et al. Fusobacterium nucleatum Promotes Colorectal Carcinogenesis by Modulating E-Cadherin/β-Catenin Signaling via its FadA Adhesin. Cell Host Microbe 14, 195-206 (2013).
Schloss PD, Westcott SL, Ryabin T et al. Introducing mothur: Open-source, platform-independent, community-supported software for describing and comparing microbial communities. Appl Environ Microbiol 2009;75:7537-41. doi:10.1128/AEM.01541-09.
Schmidt, B. L. et al. Changes in Abundance of Oral Microbiota Associated with Oral Cancer. PLOS ONE 9, e98741 (2014).
Segata, N. et al. Composition of the adult digestive tract bacterial microbiome based on seven mouth surfaces, tonsils, throat and stool samples. Genome Biol. 13, R42 (2012).
Shah MS, DeSantis TZ, Weinmaier T, et al, Leveraging sequence-based faecal microbial community survey data to identify a composite biomarker for colorectal cancer. Gut 2017 doi:10.1136/gutjnl-2016-313189.
Socransky, S. s., Haffajee, A. d., Cugini, M. A., Smith, C. & Kent, R. L. Microbial complexes in subgingival plaque. J. Clin. Periodontol. 25, 134-144 (1998).
Torres, P. J. et al. Characterization of the salivary microbiome in patients with pancreatic cancer. PeerJ 3, e1373 (2015).
Urrea V, Calle M. AUCRF: Variable selection with random forest and the area under the curve. 2012. https://CRAN.R-project.org/package=AUCRF.
Warren, R. L. et al. Co-occurrence of anaerobic bacteria in colorectal carcinomas. Microbiome 1, 16 (2013).
Wickham H. Ggplot2: Elegant graphics for data analysis. Springer-Verlag New York 2009. http://ggplot2.org.
Wu, S. et al. A human colonic commensal promotes colon tumorigenesis via activation of T helper type 17 T cell responses. Nat Med 15, (2009).
Youden, W.J. (1950). "Index for rating diagnostic tests". Cancer. 3: 32-35. doi:10.1002/1097-0142(1950)3:1&32::aid-cncr28200301063.0.co;2-3.
Zeller, G. et al. Potential of fecal microbiota for early-stage detection of colorectal cancer. Mol Syst Biol 10, (2014).
Zhang C, Derrien M, Levenez F, et al,. Ecological robustness of the gut microbiota in response to ingestion of transient food-borne microbes. ISME J 2016;10:2235-45.doi:10.1038/ismej.2016.13.
Flynn et al., "Metabolic and community synergy of oral bacteria in colorectal cancer." Msphere 1(3): e00102-16 pp. 1-6 (2016).

* cited by examiner

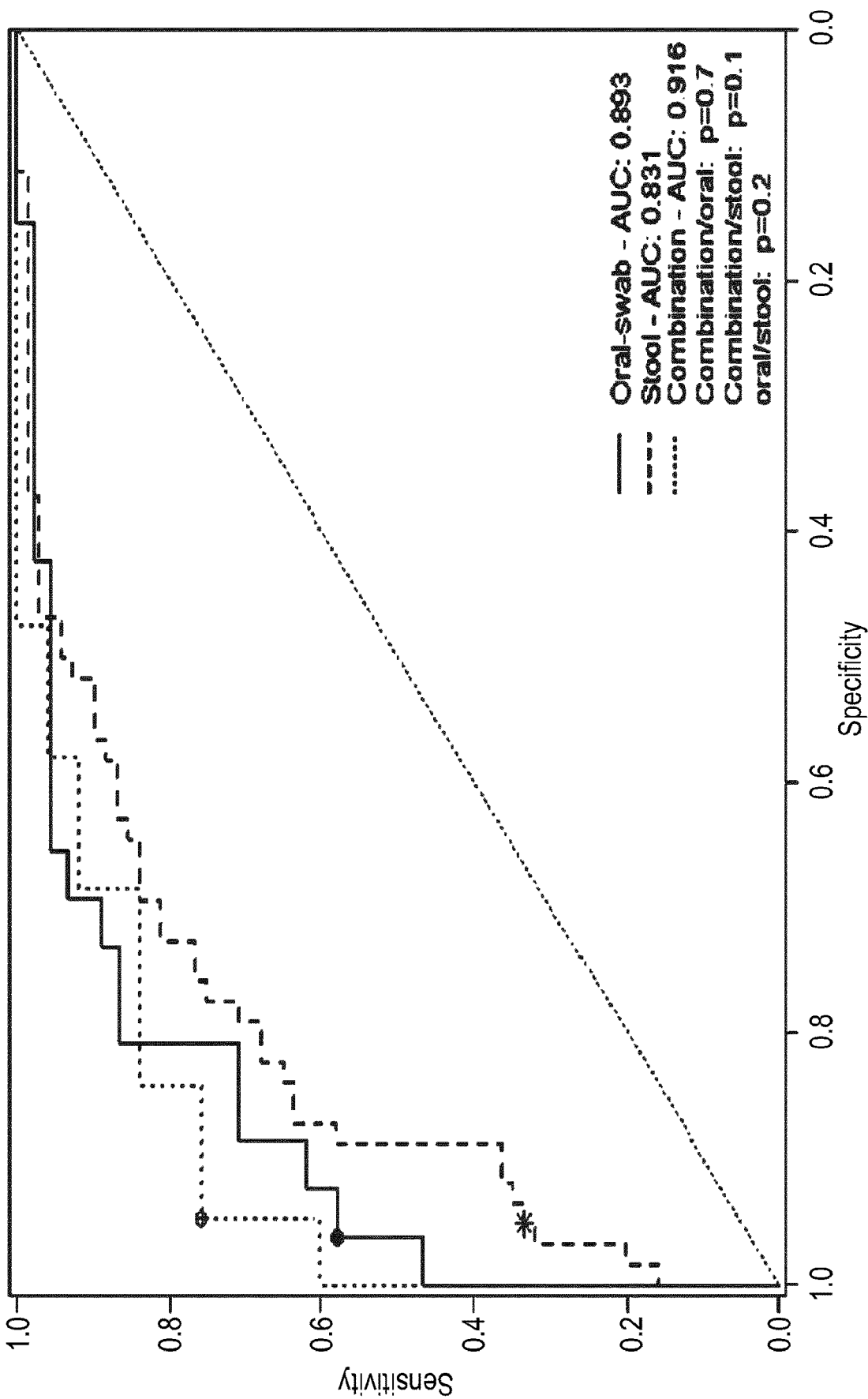

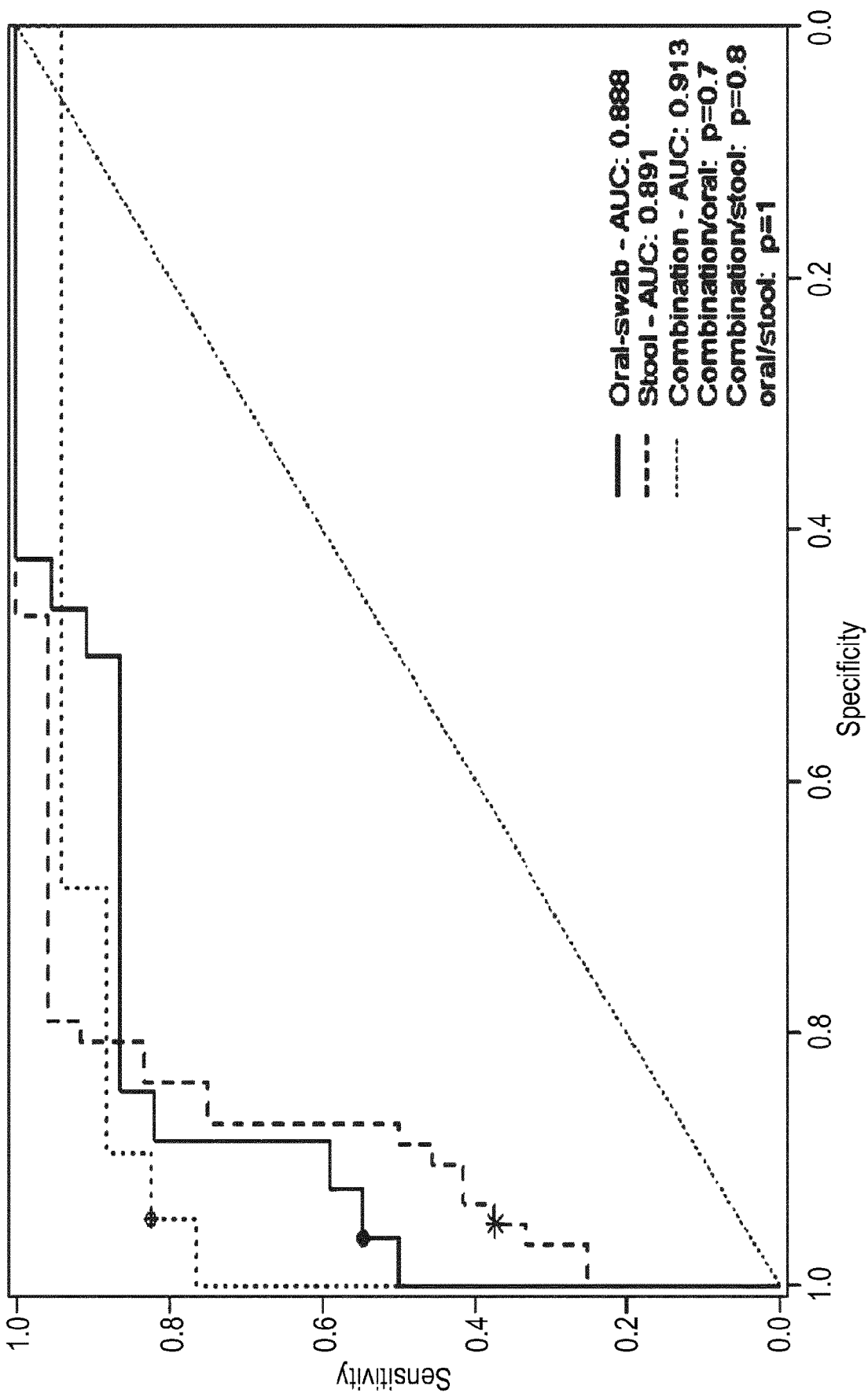

Oral Swab Microbiota
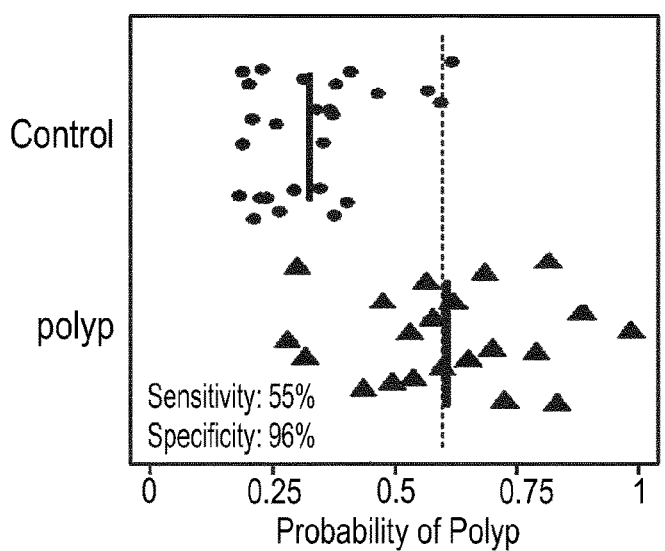
Stool Microbiota
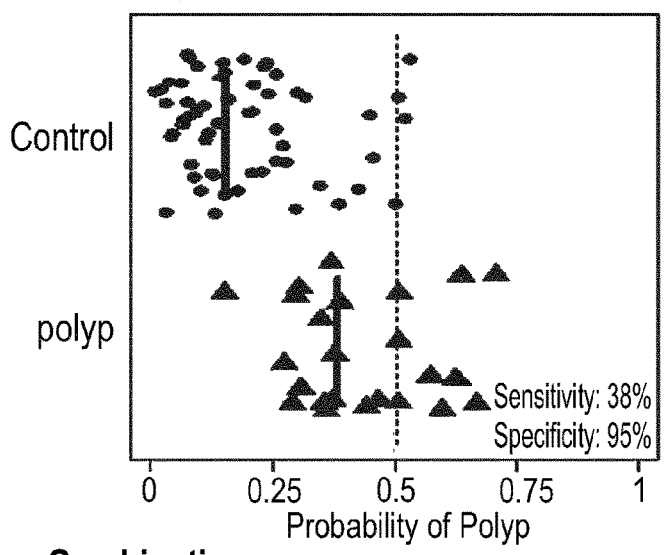
Combination
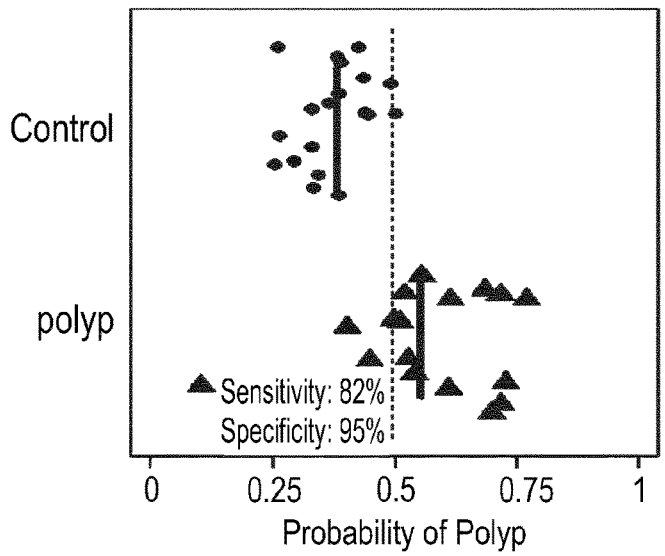
FIGURE 1C (contd)

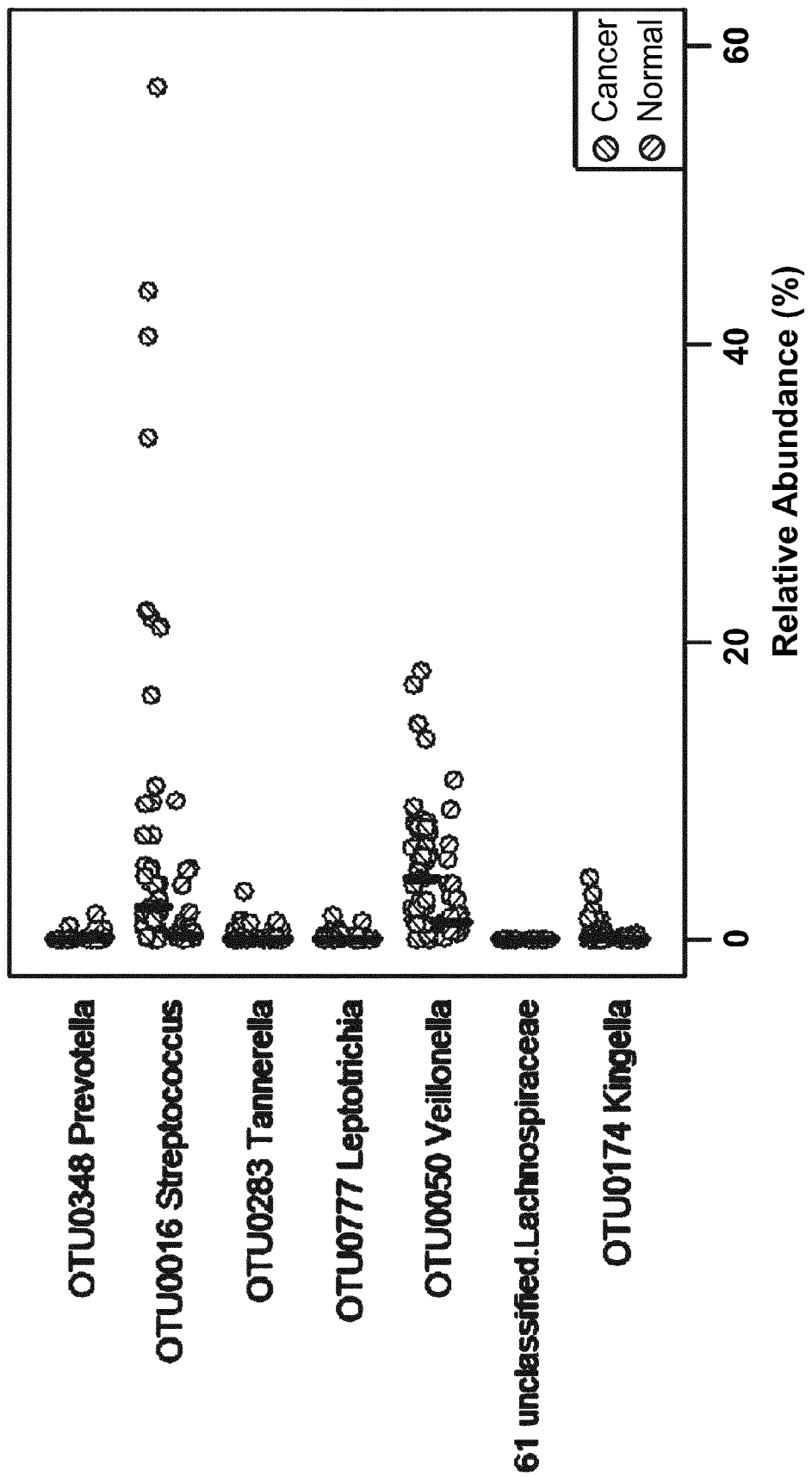

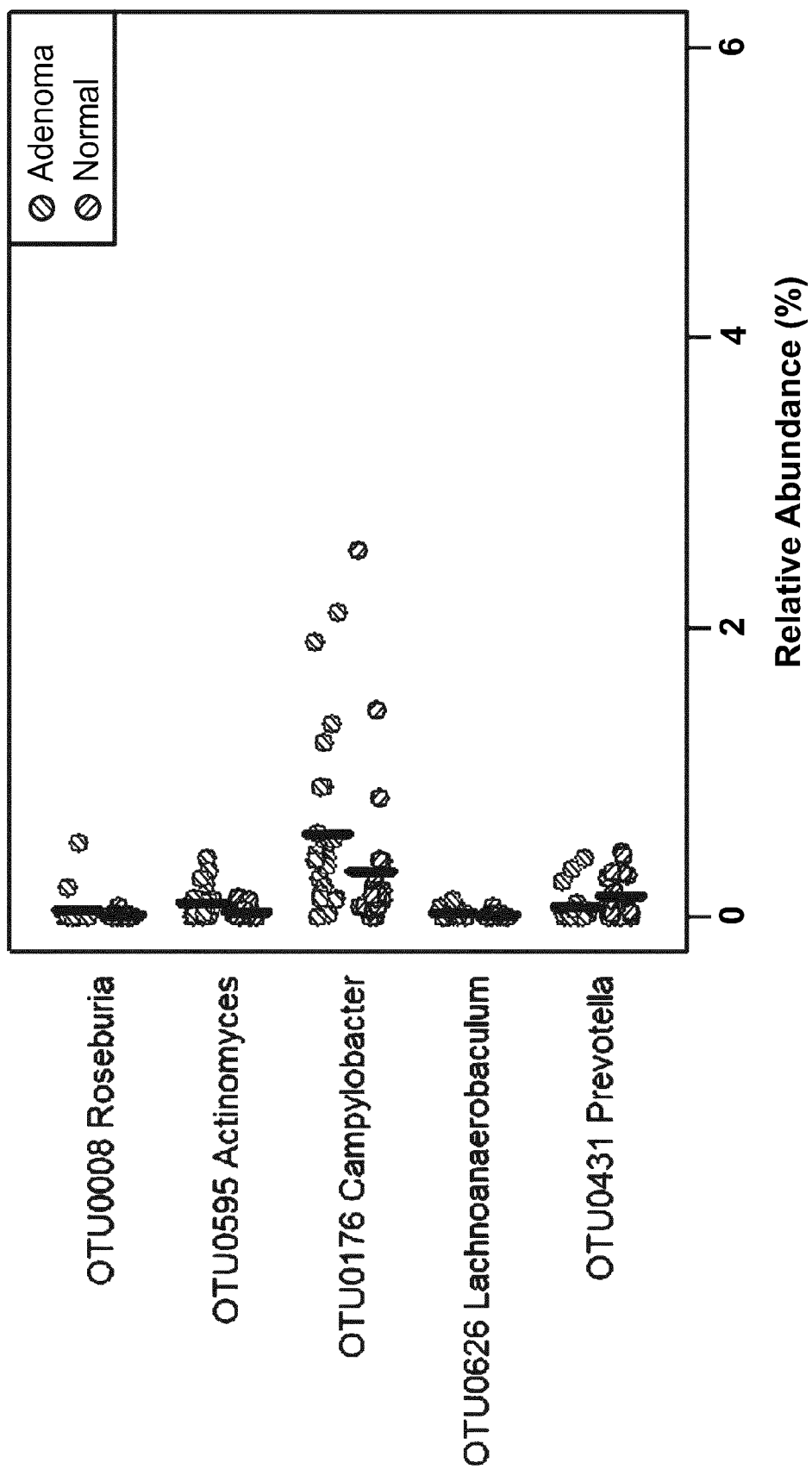

FIGURE 8

| ID | FDR_CRC vs Healthy Control | FDR Polyp vs Healthy Control | taxonomy.Genus | mean | mean CRC | mean polyp | mean Healthy Control | CRC vs Healthy Control | polyp vs Healthy Control | shared |
|---|---|---|---|---|---|---|---|---|---|---|
| OTU50037 | <.05 | ns | OTU50037 Haemophilus | 1.702235447 | 0.872756405 | 1.553966393 | 3.319843728 | 0.262890809 | 0.468084199 | nsh |
| OTU50103 | <.05 | <.05 | OTU50103 Parvimonas | 0.093031962 | 0.068091868 | 0.125007696 | 0.111064514 | 0.613083923 | 1.125541285 | sh |
| OTU50120 | <.05 | ns | OTU50120 Prevotella | 0.284241489 | 0.302822271 | 0.298858909 | 0.238517448 | 1.269602177 | 1.25298552 | nsh |
| OTU50189 | <.05 | ns | OTU50189 Prevotella | 0.16652789 | 0.04767736 | 0.318235336 | 0.253024591 | 0.188429749 | 1.257724932 | nsh |
| OTU50215 | <.05 | ns | OTU50215 Alloprevotella | 0.186134166 | 0.127621976 | 0.203536431 | 0.276838208 | 0.460998417 | 0.735217991 | nsh |
| OTU50465 | <.05 | ns | OTU50465 Lachnoanaerobaculum | 0.108663478 | 0.068213403 | 0.214782352 | 0.092406557 | 0.738187907 | 2.324319378 | nsh |
| OTU51421 | <.05 | ns | OTU51421 Neisseria | 0.242124829 | 0.092047268 | 0.349647329 | 0.421945539 | 0.218149642 | 0.828655113 | nsh |
| OTU52032 | <.05 | <.05 | OTU52032 Streptococcus | 0.037869942 | 0.038276673 | 0.021976721 | 0.050488132 | 0.758132093 | 0.435284886 | nsh |
| OTU50034 | <.1 | <.1 | OTU50034 Neisseria | 4.549435158 | 3.900559004 | 4.859619443 | 5.456857437 | 0.714799507 | 0.890552758 | nsh |
| OTU50236 | <.1 | <.05 | OTU50236 Leptotrichia | 0.409148565 | 0.422366845 | 0.382835253 | 0.407458845 | 1.036587744 | 0.939567904 | nsh |
| OTU51549 | ns | 0.05 | OTU51549 Prevotella | 0.009088186 | 0.008290417 | 0.006488252 | 0.012708115 | 0.652371886 | 0.51055975 | nsh |

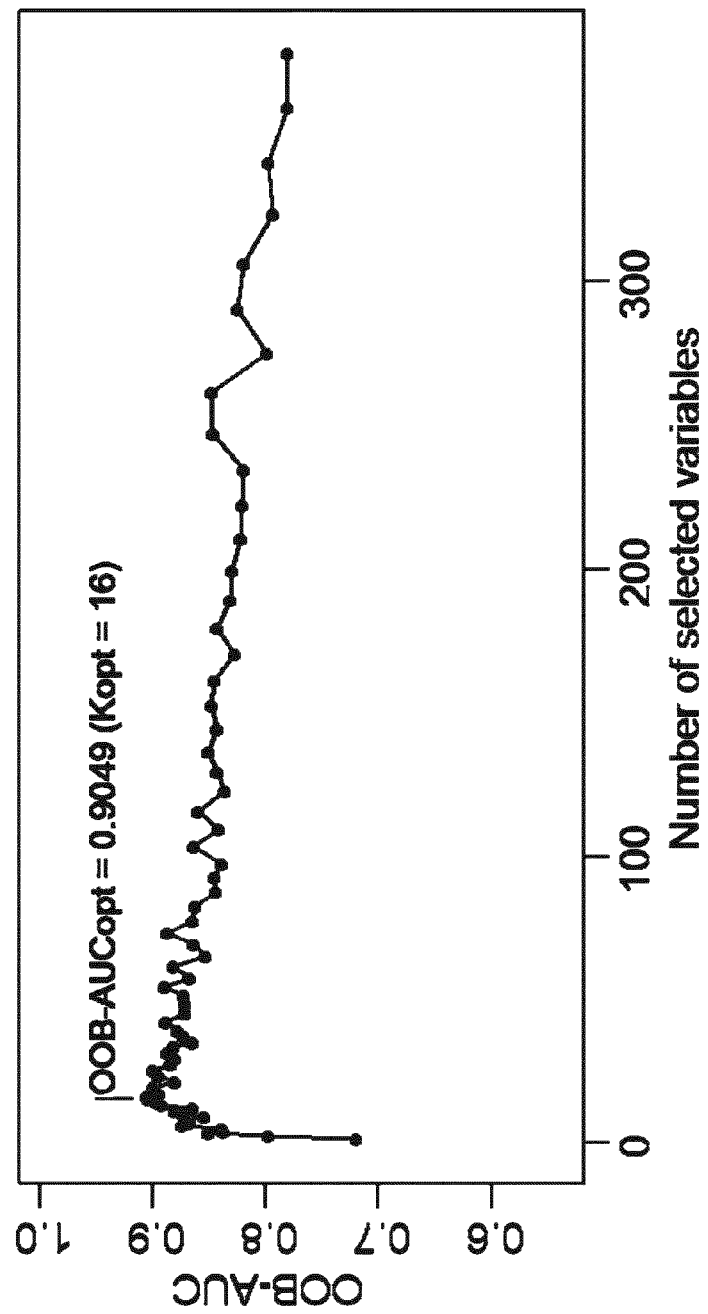

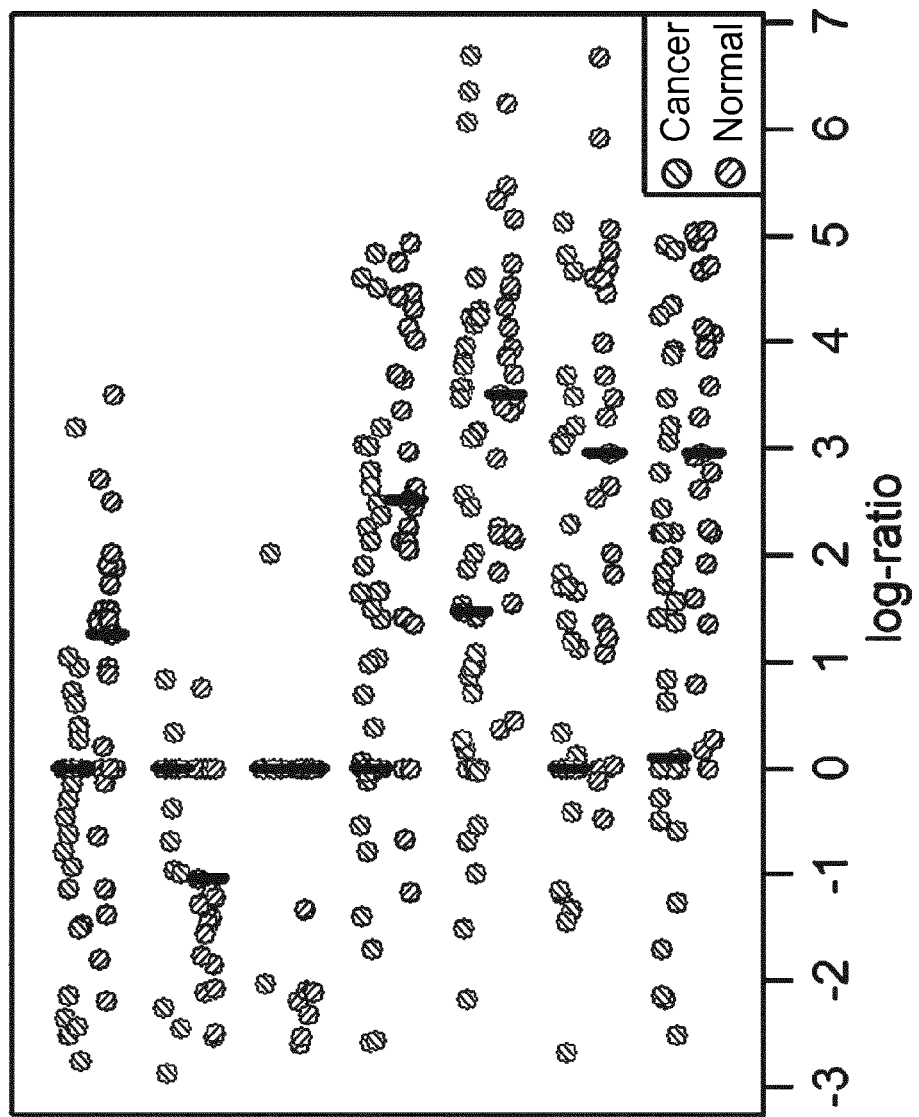

FIGURE 12

Supplementary Table 3: Results of the LASSO-RF results

| Statistics | Oralswab cancer | Oralswab adenoma | Oralstool cancer | Oralstool adenoma | Stool cancer | Stool adenoma |
|---|---|---|---|---|---|---|
| Dataset | | | | | | |
| Samples | 70 | 46 | 44 | 35 | 131 | 85 |
| Features/OTUs (preprocessed) | 385 | 385 | 1505 | 1505 | 1015 | 1015 |
| Random Forest Model | | | | | | |
| # selected features | 43 | 24 | 36 | 3 | 106 | 18 |
| pROC library 10XCV AUC | 0,96 | 0,91 | 0,98 | 0,93 | 0,94 | 0,86 |
| default threshold | 0,50 | 0,50 | 0,50 | 0,50 | 0,50 | 0,50 |
| default threshold 10XCV Sensitivity | 0,98 | 0,74 | 0,99 | 0,86 | 0,92 | 0,24 |
| default threshold 10X CV Specificity | 0,70 | 0,90 | 0,79 | 0,89 | 0,79 | 0,94 |
| Youden's threshold | 0,55 | 0,46 | 0,57 | 0,43 | 0,53 | 0,28 |
| Youden's threshold 10XCV Sensitivity | 0,95 | 0,84 | 0,96 | 0,89 | 0,86 | 0,85 |
| Youden's threshold 10X CV Specificity | 0,81 | 0,86 | 0,90 | 0,88 | 0,90 | 0,80 |

FIGURE 13

Clinical data of the studied individuals

| Sample type | Samples (n) | Age (mean±SD) | BMI (mean±SD) | Males | Tumour size (mean±SD) | Rectal bleeding (%) | Alcohol (1st quantile, third quantile) (units/week) | Currently smoking (%) |
|---|---|---|---|---|---|---|---|---|
| Tissue controls | 59 | 53.2±13.5 | 27.4±6.1 | 44.1 | NA | 57.7 | 1 (1, 10) | 4 |
| Off CRC | 74 | 66±11.3 | 28.7±5.7 | 66.7 | 3.2±1.8 | 65.6 | 2 (1, 10) | 10.4 |
| Off Polyps | 31 | 61.6±14.8 | 28.8±5 | 71 | NA | 38.7 | 1 (1, 10) | 13.3 |
| On CRC | 65 | 67±11.6 | 28.8±5.8 | 60.9 | 3.6±2 | 64.4 | 2 (0.8, 10) | 5 |
| On Polyps | 2 | 76.5±0.7 | 27.4±0.9 | 100 | NA | 50 | 7.5 (4.2, 10.8) | 0 |
| Stool controls | 62 | 63.9±11.1 | 28.2±5.4 | 50.9 | NA | 55.6 | 1 (0.2, 6.2) | 0 |
| Stool CRC | 69 | 65.3±10.8 | 28.4±6.1 | 66.7 | 3.1±1.7 | 65.5 | 2 (1, 11.2) | 11.3 |
| Stool polyp | 23 | 60.4±13.4 | 29.3±5.4 | 78.3 | NA | 39.1 | 4 (1, 13.5) | 17.4 |
| Swab controls | 25 | 51.5±12.4 | 27.1±5.5 | 37.5 | NA | 57.9 | 1 (1, 6) | 0 |
| Swab CRC | 45 | 65.7±10.9 | 27.1±5 | 56.1 | 3.3±1.9 | 66.7 | 2 (1, 9) | 0 |
| Swab polyp | 21 | 59.2±15.1 | 28.5±5.2 | 71.4 | NA | 38.1 | 1 (1, 10) | 10 |

BMI, body mass index; CRC, colorectal cancer.

METHODS OF DETERMINING COLORECTAL CANCER STATUS IN AN INDIVIDUAL

CROSS-REFERENCE

The application is a continuation of International Application No. PCT/EP2017/083176, filed Dec. 15, 2017, which claims the benefit of EP Application No. 16204532.2, filed Dec. 15, 2016, all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Dec. 13, 2017, is named 49455_720_601_SL.txt and is 222,305 bytes in size.

FIELD OF THE INVENTION

The present invention relates to methods of determining colorectal cancer status in an individual. Also contemplated are methods of treating colorectal cancer.

BACKGROUND TO THE INVENTION

Microbes have been implicated in the pathogenesis of several human cancers, most strikingly in the case of *Helicobacter pylori* and gastric carcinoma and some gastric lymphomas.[1,33] *H. pylori* is now recognized as a gastric carcinogen and a pre-clinical risk factor. In the case of colon cancer, current diagnostic approaches are focussed almost exclusively on detection of early disease but biomarkers of risk are required. We and others have reported changes in the faecal or colonic mucosal microbiota in patients with colorectal cancer[2-7] and several animal models have implicated the microbiota in the pathogenesis of colorectal cancer[8-11]. Our recent finding[2] of a microbiota configuration associated with benign colonic polyps that is intermediate to that of controls and those with cancer suggests that the microbiota might provide a potential biomarker predictive of the risk of later development of cancer and against which an intervention could theoretically be applicable years before the development of the disease. Microbes that are normally associated with the oral cavity have been located in the faecal and mucosal microbiota in patients with colorectal cancer[2-5,7,12]. Previously, several groups reported the applicability of faecal microbiota profiling as a tool for detection of CRCs[3,4,13], particularly in conjunction with the faecal occult blood test. Moreover, distinct bacterial profiles in the oral cavity have been associated with oral cancers[14,15] but also esophageal cancers[16] and pancreatic cancers[17,18]. A single study identified significant differences of bacteria in oral rinse samples from individuals with CRC compared to healthy controls[19].

SUMMARY OF THE INVENTION

The invention is based on the finding that the oral microbiome in an individual with colorectal cancer (CRC) or a colon polyp is different to the oral microbiome in a healthy control patient, and that the oral microbiome may therefore be employed as a diagnostic variable of CRC or colon polyps. The invention therefore provides the use of the oral microbiome to diagnose CRC or colorectal polyps. Also provided is the use of the oral microbiome as a diagnostic variable of CRC or colon polyps. Similarly, there is provided the oral microbiome for use in diagnosing CRC or colorectal polyps. Also provided is the oral microbiome as a diagnostic variable of CRC or colorectal polyps.

In particular, the applicant has identified a number of bacterial genera or Operational Taxonomic Unit (OTU)s present in the oral microbiome that exhibit modulated abundance in individuals with CRC compared with healthy control. These OTUs are provided in the Tables below. Detecting modulated abundance of these OTUs may therefore be employed to discriminate CRC patients from healthy controls, or identify individuals at risk of CRC due to the presence of colorectal polyps. The OTUs may be employed individually to determine risk of cancer, or combinations of panels of OTUs may be provided to increase the discriminatory power of the diagnostic method, and provide non-invasive methods of diagnosis of CRC or colorectal polyps. Positive diagnosis of colorectal polyp is indicative of a risk of the individual subsequently developing CRC.

The invention therefore provides the use of the finding of a modulated abundance in an individual of one or a number of bacterial genera or OTUs in the oral microbiome compared with the abundance of the one or a number of bacterial genera in the oral microbiome of a healthy control for identifying an individual with an increased risk of having CRC or colorectal polyps. In some embodiments, the method is for identifying patients having CRC or colorectal polyps.

Oral OTUs that exhibit modulated abundance in individuals with CRC or colorectal polyps are provided in Table 1 below. For example, the modulated abundance of a panel of oral OTUs (i.e. Table 2) may be employed to specifically detect CRC with a sensitivity of 58% (95% CI [35.56%, 84.44%]) and a specificity of 96% (AUC: 0.893; 95% CI [0.8181, 0.9682]). In another example, the modulated abundance of a panel of oral OTUs (i.e. Table 3) may be employed to specifically detect colorectal polyps with a sensitivity of 55% (95% CI [31.82%, 90.91%]) and a specificity of 96% (AUC: 0.888; 95% CI [0.7944,0.9819]).

Additional Oral OTUs that exhibit modulated abundance in individuals with CRC or colon polyps are provided in Table 11 below. For example, the modulated abundance of a panel of oral OTUs (i.e. Table 12) may be employed to specifically detect CRC with a sensitivity of 53% (95% CI [31.11% to 93.33%]) and a specificity of 96% (95% CI [0.83 to 0.9]). In another example, the modulated abundance of a panel of oral OTUs (i.e. Table 13) may be employed to specifically detect colon polyps with a sensitivity of 67% (95% CI [23.81% to 90.48%]) and a specificity of 96%.

Accordingly, there is provided a method of detecting CRC in an individual with a sensitivity of greater than 40% (e.g. greater than 45%, 50% or 52%, e.g. 53% or 58%) and a specificity of greater than 90% (e.g. greater than 93% or 95%, e.g. 96%). In some embodiments, the method detects the relative abundance of the panel of oral OTUs in Table 2 or Table 12. There is also provided a method of detecting colon polyps in an individual with a sensitivity of greater than 40% (e.g. greater than 45%, 50%, 52%, 54%, e.g. 55% or 67%) and a specificity of greater than 90% (e.g. greater than 93% or 95%, e.g. 96%). In some embodiments, the method detects the relative abundance of the panel of oral OTUs in Table 3 or Table 13. Such methods comprise use of the oral microbiome as described herein.

The Applicant has also discovered that combining oral microbiome abundance profiling with faecal microbiome abundance profiling increases the discriminatory power of the diagnostic method of the invention, and in particular increases the sensitivity of the assay. A panel of oral and faecal OTUs that are modulated in CRC or colorectal polyps are provided in the Tables below, especially Table 7, and panels of OTUs for predicting CRC and colorectal polyps are provided in Tables 8 and 9, respectively. For example, the modulated abundance of a panel of oral and faecal OTUs (i.e. Table 8) may be employed to specifically detect CRC with a sensitivity of 76% (95% CI [44%, 92%]) and a specificity of 96% (AUC: 0.893; 95% CI [0.8181, 0.9682]). In another example, the modulated abundance of a panel of oral and faecal OTUs (i.e. Table 9) may be employed to specifically detect colorectal polyps with a sensitivity of 82% (95% CI [31.82%, 90.91%]) and a specificity of 96% (AUC: 0.888; 95% CI [0.7944,0.9819]).

An additional panel of oral and faecal OTUs that are modulated in CRC or colon polyps are provided in Table 17, and sub-panels of OTUs for predicting CRC and colon are provided in Tables 18 and 19, respectively. For example, the modulated abundance of a panel of oral and faecal OTUs (i.e. Table 18) may be employed to specifically detect CRC with a sensitivity of 76% (95% CI [59.9% to 92%]) and a specificity of 94%. In another example, the modulated abundance of a panel of oral and faecal OTUs (i.e. Table 19) may be employed to specifically detect colon polyps with a sensitivity of 88% (95% CI [68.7% to 100%]).

Accordingly, there is also provided a method of increasing the sensitivity of detecting CRC or a colon polyp in an individual compared to the sensitivity obtained using abundance profiling of only the faecal microbiome, wherein the method comprises combining oral microbiome abundance profiling with faecal microbiome abundance profiling. There is also provided a method of detecting CRC in an individual with a sensitivity of greater than 60% (e.g. greater than 65%, 70% or 75%, e.g. 76%) and a specificity of greater than 90% (e.g. greater than 92% or 93%, e.g. 96%). There is also provided a method of detecting colon polyps in an individual with a sensitivity of greater than 60% (e.g. greater than 65%, 70%, 75%, 80%, 81%, e.g. 82% or 88%) and a specificity of greater than 90% (e.g. greater than 92% or 93%, e.g. 96%). Such methods comprise use of the oral microbiome in combination with the faecal microbiome, as described herein.

Particularly promising is the high sensitivity for the detection of adenomas such as colorectal polyps using the methods described herein because of the prognostic and therapeutic importance of early discovery of colonic disease. By comparison, Baxter et al [3] reported sensitivities below 20% for the detection of adenomas using either faecal immune test (FIT) or faecal microbiota composition alone and a sensitivity of below 40% when using a combination (specificity>90%).

According to a further aspect of the present invention, there is provided a method of determining colorectal cancer status in an individual comprising the steps of assaying a biological sample from an oral cavity of the individual for an abundance of a plurality of CRC-associated oral bacteria, wherein modulated abundance of the plurality of CRC-associated oral bacteria is indicative of positive colorectal cancer status. In preferred embodiments, the abundance of the bacterium or OTU in the sample as a proportion of the total microbiota in the sample is measured to determine the relative abundance of the bacterium or OTU. Then, in such preferred embodiments, the relative abundance of the bacterium or OTU in the sample is compared with the relative abundance in the same sample from a reference healthy individual (also referred to herein as the "reference relative abundance"). A difference in relative abundance of the bacterium or OTU in the sample, e.g. a decrease or an increase, compared to the reference relative abundance is a modulated relative abundance. As explained herein, detection of modulated abundance can also be performed in an absolute manner by comparing sample abundance values with absolute reference values. Therefore, the invention provides a method of determining colorectal cancer status in an individual comprising the step of assaying a biological sample from an oral cavity of the individual for a relative abundance of a plurality of CRC-associated oral bacteria, wherein a modulated relative abundance of the plurality of CRC-associated oral bacteria is indicative of positive colorectal cancer status. Similarly, the invention provides a method of determining whether an individual has an increased risk of having colorectal cancer or a colorectal polyp comprising the step of assaying a biological sample from an oral cavity of the individual for a relative abundance of a plurality of CRC-associated oral bacteria, wherein modulated relative abundance of the plurality of CRC-associated oral bacteria is indicative of an increased risk.

Also provided is a method of diagnosing CRC or colon polyps comprising determining whether an individual has a difference in its oral microbiome compared to the oral microbiome in a healthy patient, wherein the finding of a difference compared with a healthy control suggests an increased risk of the individual having colorectal cancer (CRC) or a colon polyp, respectively. The difference is preferably a difference in relative abundance of one or more bacterial genera or OTUs that exhibit modulated relative abundance in individuals with CRC or colon polyps compared with a healthy control. In some embodiments, the finding of a decrease in relative abundance of one or more bacterial genera or OTUs that exhibit decreased relative abundance in individuals with CRC or colon polyps compared with a healthy control suggests an increased risk of the individual having colorectal cancer (CRC) or a colon polyp, respectively. In some embodiments, the finding of an increase in relative abundance of one or more bacterial genera or OTUs that exhibit increased relative abundance in individuals with CRC or colon polyps compared with a healthy control suggests an increased risk of the individual having colorectal cancer (CRC) or a colon polyp, respectively. In some embodiments, the finding of a decrease in relative abundance of one or more bacterial genera or OTUs that exhibit decreased relative abundance in individuals with CRC or colon polyps compared with a healthy control together with the finding of an increase in relative abundance of one or more bacterial genera or OTUs that exhibit increased relative abundance in individuals with CRC or colon polyps compared with a healthy control suggests an increased risk of the individual having colorectal cancer (CRC) or a colon polyp, respectively.

As mentioned above, the OTUs may be employed individually to determine risk of cancer, or combinations of panels of OTUs may be provided to increase the discriminatory power of the diagnostic method. According, there is also provided a method of determining colorectal cancer status in an individual comprising the steps of assaying a biological sample from an oral cavity of the individual for a relative abundance of an individual CRC-associated oral bacterium or for a relative abundance of a plurality of CRC-associated oral bacteria, wherein modulated relative abundance of the individual CRC-associated oral bacterium or of the plurality of CRC-associated oral bacteria is indicative of positive CRC status. Similarly, there is provided a method of determining colorectal cancer status in an individual comprising the steps of assaying a biological sample from an oral cavity of the individual for a relative abundance of an individual CRC-associated oral bacterium or for a relative abundance of a plurality of CRC-associated oral bacteria, wherein a difference in the relative abundance of the individual CRC-associated oral bacterium or of the plurality of CRC-associated oral bacteria compared with a reference relative abundance is indicative of positive CRC status.

In some embodiments, the finding of a modulated relative abundance of an individual CRC-associated oral bacterium is indicative of positive colorectal cancer status. In some embodiments, modulated abundance of at least 2, e.g. at least 3 or at least 5, CRC-associated oral bactricia correlates with positive CRC status. In some embodiments, modulated abundance of at least 10, 15, 20, 25, 30, 35 or 40 CRC-associated oral bacteria correlates with positive CRC status.

In some embodiments, the CRC-associated oral bacteria are selected from at least one of (e.g. 1 or at least 2, 3, 4, 5 or all 6 of) *Streptococcus, Porphyromonas, Haemophilus, Prevotella, Actinobacteria* and Firmicutes. In some embodiments, the CRC-associated oral bacteria are selected from at least one of (e.g. 1 or at least 2, 3 or all 4 of) *Streptococcus, Porphyromonas, Haemophilus* and *Prevotella*. In some embodiments, the CRC-associated oral bacteria are selected from one or both of *Streptococcus* and *Prevotella*. In some embodiments, an increase in relative abundance of *Streptococcus* indicates a positive CRC status. In some embodiments, a decrease in relative abundance of at least one of (e.g. 1 or at least 2 or all 3 of) *Porphyromonas, Haemophilus* and *Prevotella* indicates a positive CRC status. In some embodiments, an increase in relative abundance of *Streptococcus* and a decrease in relative abundance of at least one of (e.g. 1 or at least 2 or all 3 of) *Porphyromonas, Haemophilus* and *Prevotella* indicates a positive CRC status. In some embodiments, the CRC-associated oral bacteria are members of the phyla *Actinobacteria* and/or Firmicutes. In some embodiments, an increase in the relative abundance of *Actinobacteria* and/or Firmicutes in the oral microbiota indicates a positive CRC status. In some embodiments, the finding of a modulated relative abundance of one or more of these bacteria is indicative of an increased risk of the individual having CRC (as opposed to CR polyps).

In additional embodiments, the CRC-associated oral bacterial are selected from at least one of (e.g. 1 or at least 2, 3, 4, 5, 6, or all 7 of) *Streptococcus, Haemophilus, Prevotella, Parvimonas, Alloprevotella, Lachnoanaerobaculum, Leptotricia*, and *Neisseria*. In some embodiments, a decrease in relative abundance of at least one of (e.g. 1 or at least 2, 3, 4, 5, or all 6 of) *Haemophilus, Prevotella, Parvimonas, Alloprevotella, Lachnoanaerobaculum, Leptotricia*, and *Neisseria* indicates a positive CRC status. In some embodiments, an increase in relative abundance of *Streptococcus* and a decrease in relative abundance of at least one of (e.g. 1 or at least 2, 3, 4, 5, or all 6 of) *Haemophilus, Prevotella, Parvimonas, Alloprevotella, Lachnoanaerobaculum, Neisseria* and *Leptotricia* indicates a positive CRC status. In some embodiments, the finding of a modulated relative abundance of one or more of these bacteria is indicative of an increased risk of the individual having CRC (as opposed to CR polyps).

In additional embodiments, the CRC-associated oral bacteria are selected from at least one of (e.g. 1 or at least 2, 3, 4, 5, 6, 7, 8, 9, 10, or all 11 of) *Streptococcus, Porphyromonas, Haemophilus, Prevotella, Actinobacteria*, Firmicutes, *Haemophilus, Parvimonas, Alloprevotella, Lachnoanaerobaculum*, and *Neisseria*. In some embodiments, a decrease in relative abundance of at least one of (e.g. 1 or at least 2, 3, 4, 5, 6, or all 7 of) *Porphyromonas, Haemophilus, Prevotella, Parvimonas, Alloprevotella, Lachnoanaerobaculum*, and *Neisseria* indicates a positive CRC status. In some embodiments, an increase in relative abundance of *Streptococcus* and a decrease in relative abundance of at least one of (e.g. 1 or at least 2, 3, 4, 5, 6, or all 7 of) *Porphyromonas, Haemophilus, Prevotella, Parvimonas, Alloprevotella, Lachnoanaerobaculum*, and *Neisseria* indicates a positive CRC status. In some embodiments, the finding of a modulated relative abundance of one or more of these bacteria is indicative of an increased risk of the individual having CRC (as opposed to CR polyps).

In one embodiment, the CRC-associated oral bacteria are selected from the group provided in the Tables below, and in particular Tables 1, 2, 3, 7, 8, 9, 11, 12, 13, 17, 18, and 19. In some embodiments, the bacteria in the Tables share 97% or greater residue identity in the sequences of their 16S rRNA gene amplicons, either the full length genes or variable regions therein, to their corresponding OTU sequence described in Appendix 1 and preferably wherein the bacteria are from the corresponding genera described in Appendix 1. The skilled person will, however, understand that other CRC-associated oral bacterial genera or OTUs that exhibit modulated relative abundance in individuals with CRC or colon polyps compared with a healthy control may also be used in the invention.

In some embodiments, the CRC-associated oral bacteria are not *Fusobacterium*. In some embodiments, the CRC-associated oral bacteria are not *Porphyromonas*. In some embodiments, the CRC-associated oral bacteria are not *Campylobacter*. In some embodiments, the CRC-associated oral bacteria are not *Leptotrichia*. However, in other embodiments, use of these CRC-associated oral bacteria is envisaged.

In one embodiment, the method is a method of detecting risk of the individual having CRC, in which case the CRC associated oral bacteria are selected from the OTUs of Table 2 or Table 12. In one embodiment, the method is a method of detecting risk of the individual having a colorectal polyp (and therefore prognosis of CRC risk), in which case the CRC associated oral bacteria are selected from the OTUs of Table 3 or Table 13. However, as mentioned above, the skilled person will understand that other CRC-associated oral bacterial genera or OTUs that exhibit modulated relative abundance in individuals with CRC or colon polyps, respectively, compared with a healthy control may also be used in the invention. Accordingly, in some embodiments, the method is a method of determining whether an individual has an increased risk of having CRC, and wherein the CRC-associated oral bacteria comprise CRC-associated oral bacterial genera or OTUs that exhibit modulated relative abundance in individuals with CRC compared with a healthy control. Some of all of these may be selected from Table 2 or Table 12, but additionally or alternatively other suitable CRC-associated oral bacteria may be used. Similarly, in some embodiments, the method is a method of determining whether an individual has an increased risk of having a colorectal polyp (and therefore prognosis of CRC risk), and the CRC-associated oral bacteria comprise CRC-associated oral bacterial genera or OTUs that exhibit modulated relative abundance in individuals with a colorectal polyp compared with a healthy control. Some of all of these may be selected from Table 3 or Table 13, but additionally or alternatively other suitable CRC-associated oral bacteria may be used.

TABLE 1

Oral colorectal cancer/polyp-associated bacteria (OTUs)

| OTU0348 | OTU0174 | OTU0092 | OTU0657 | OTU0406 | OTU0337 | OTU0544 |
|---|---|---|---|---|---|---|
| OTU0016 | OTU0217 | OTU0012 | OTU0141 | OTU0008 | OTU0008 | OTU1963 |
| OTU0283 | OTU1963 | OTU0087 | OTU0324 | OTU1423 | OTU0595 | OTU0016 |
| OTU0777 | OTU0458 | OTU0850 | OTU0412 | OTU0157 | OTU0176 | OTU0299 |
| OTU0050 | OTU0176 | OTU0041 | OTU1250 | OTU0317 | OTU0626 | OTU0350 |
| OTU0161 | OTU2703 | OTU0095 | OTU0663 | OTU0097 | OTU0431 | |

In one embodiment, modulated abundance of at least five CRC-associated oral bacteria correlates with positive CRC status.

In one embodiment, modulated abundance of at least 10, 15, 20, 25, 30, 35 or 40 CRC-associated oral bacteria correlates with positive CRC status.

In one embodiment, modulated abundance of substantially all of the CRC-associated oral bacteria of Table 1 correlate with positive CRC status. In some embodiments, modulated abundance of all of the CRC-associated oral bacteria of Table 1 correlate with positive CRC status.

In some embodiments, modulated abundance of at least 2, 3, 5, 10, 12, 15, 18, 20, 22 or all CRC-associated oral bacteria selected from *Prevotella, Streptococcus, Tannerella, Leptotrichia, Veillonella*, Lachnospiraceae, *Kingella, Alloprevotella, Lachnoanaerobaculum, Campylobacter, Haemophilus, Anaerostipes, Parvimonas, Neisseria, Candidatus_Saccharibacteria, Aggregatibacter, Selenomonas, Schwartzia, Roseburia, Peptostreptococcus, Cardiobacterium, Actinomyces* and *Abiotrophia* correlates with positive CRC status.

In some embodiments, modulated abundance of at least one (e.g. 1, 2 or 3) CRC-associated oral OTU selected from OTU0348 (preferably *Prevotella*), OTU0016 (preferably *Streptococcus*) and OTU0283 (preferably *Tannerella*) correlates with positive CRC status. In some embodiments, the oral OTU that exhibits modulated relative abundance is OTU0348 (preferably *Prevotella*). In some embodiments, the oral OTU that exhibits modulated relative abundance is OTU0016 (preferably *Streptococcus*). In some embodiments, the oral OTU that exhibits modulated relative abundance is OTU0283 (preferably *Tannerella*).

In some embodiments, the method is for determining whether an individual has an increased risk of having colorectal cancer (CRC). In some embodiments, the method is for determining whether an individual has colorectal cancer (CRC). In some embodiments, the method is for determining growth of a tumour in an individual, advancement of the stage of the cancer, recurrence of the cancer, metastasis of the cancer, or non-response to treatment.

In one embodiment, the CRC-associated oral bacteria that correlate with risk of colorectal cancer (as opposed to CR polyps) is the subset of bacteria (defined by the OTU numbers) provided in Table 2.

In one embodiment, modulated abundance of at least five CRC-associated oral bacteria of Table 2 correlates with risk of colorectal cancer (colorectal lesions).

In one embodiment, modulated abundance of at least 10, 15, 20, 25 or 30 CRC-associated oral bacteria of Table 2 correlates with risk of colorectal cancer (i.e. colorectal lesions).

In one embodiment, modulated abundance of substantially all of the CRC-associated oral bacteria of Table 2 correlate with risk of colorectal cancer (i.e. colorectal lesions). In some embodiments, modulated abundance of all of the CRC-associated oral bacteria of Table 2 correlate with risk of colorectal cancer (i.e. colorectal lesions).

In some embodiments, modulated abundance of at least 2, 3, 5, 10, 12, 15, 18, 20, or all CRC-associated oral bacteria selected from *Prevotella, Streptococcus, Tannerella, Leptotrichia, Veillonella*, Lachnospiraceae, *Kingella, Alloprevotella, Lachnoanaerobaculum, Campylobacter, Haemophilus, Anaerostipes, Parvimonas, Neisseria, Candidatus_Saccharibacteria, Aggregatibacter, Selenomonas, Schwartzia, Roseburia, Peptostreptococcus* and *Cardiobacterium* correlates with risk of colorectal cancer (i.e. colorectal lesions), In some embodiments, modulated abundance of at least one of (e.g. 1, or at least 2, 3, 4, 5, 6 or all 7 of) OTU0348 (preferably *Prevotella*), OTU0016 (preferably *Streptococcus*), OTU0283 (preferably *Tannerella*), OTU0777 (preferably *Leptotrichia*), OTU0050 (preferably *Veillonella*), OTU0161 (preferably Lachnospiraceae) and OTU0174 (preferably *Kingella*) correlates with risk of colorectal cancer (i.e. colorectal lesions). In some embodiments, modulated abundance of OTU0016 (preferably *Streptococcus*), OTU0050 (preferably *Veillonella*) and OTU0174 (preferably *Kingella*) correlates with risk of colorectal cancer (i.e. colorectal lesions). In some embodiments, modulated abundance of OTU0348 (preferably *Prevotella*), OTU0016 (preferably *Streptococcus*) and OTU0283 (preferably *Tannerella*) correlates with risk of colorectal cancer (i.e. colorectal lesions). In some embodiments, modulated abundance of OTU0016 (preferably *Streptococcus*), OTU0283 (preferably *Tannerella*), OTU0050 (preferably *Veillonella*) and OTU0174 (preferably *Kingella*) correlates with risk of colorectal cancer (i.e. colorectal lesions). In some embodiments, modulated abundance of OTU0348 (preferably *Pre-*

TABLE 2

Oral CRC-associated bacterial operational taxonomic units (OTUs) to identify individuals with colorectal lesions (CRCs). OTUs

| OTU0348 | OTU0161 | OTU0176 | OTU0850 | OTU0324 | OTU0008 | OTU0337 |
|---|---|---|---|---|---|---|
| OTU0016 | OTU0174 | OTU2703 | OTU0041 | OTU0412 | OTU1423 | |
| OTU0283 | OTU0217 | OTU0092 | OTU0095 | OTU1250 | OTU0157 | |
| OTU0777 | OTU1963 | OTU0012 | OTU0657 | OTU0663 | OTU0317 | |
| OTU0050 | OTU0458 | OTU0087 | OTU0141 | OTU0406 | OTU0097 | | votella), OTU0016 (preferably *Streptococcus*), OTU0283 (preferably *Tannerella*), OTU0050 (preferably *Veillonella*) and OTU0174 (preferably *Kingella*) correlates with risk of colorectal cancer (i.e. colorectal lesions). In some embodiments, the modulation of at least one of OTU0016 (preferably *Streptococcus*), OTU0283 (preferably *Tannerella*), OTU0050 (preferably *Veillonella*) and/or OTU0174 (preferably *Kingella*) is an increase in relative abundance compared to a healthy control. In some embodiments, the modulation of OTU0348 (preferably *Prevotella*) is a decrease in relative abundance compared to a healthy control.

In some embodiments, modulated abundance of at least one of (e.g. 1, or at least 2, 3, 4, 5, 6 or all 7 of) *Prevotella, Streptococcus, Tannerella, Leptotrichia, Veillonella,* Lachnospiraceae and *Kingella* correlates with risk of colorectal cancer (i.e. colorectal lesions). In some embodiments, modulated abundance of *Streptococcus, Veillonella* and *Kingella* correlates with risk of colorectal cancer (i.e. colorectal lesions). In some embodiments, modulated abundance of *Prevotella, Streptococcus* and *Tannerella* correlates with risk of colorectal cancer (i.e. colorectal lesions). In some embodiments, modulated abundance of *Streptococcus, Tannerella, Veillonella* and *Kingella* correlates with risk of colorectal cancer (i.e. colorectal lesions). In some embodiments, the modulation of *Streptococcus, Tannarella, Veillonella* and/or *Kingella* is an increase in relative abundance compared to a healthy control. In some embodiments, the modulation of *Prevotella* is a decrease in relative abundance compared to a healthy control.

In some embodiments, the method is for determining whether an individual has an increased risk of having a colorectal polyp. In some embodiments, the method is for determining whether an individual has a colorectal polyp. Having a colorectal polyp can indicate an increased risk of the individual developing CRC.

In one embodiment, the CRC-associated oral bacteria that correlate with risk of colorectal polyps (and therefore prognosis of risk of development of CRC) is the subset of bacteria provided in Table 3. In one embodiment, the method of the invention comprises determining modulated abundance of 2, 3, 4, 5, 6, 7, 8 or 9 of the bacteria of Table 3. In one embodiment, the method of the invention comprises determining modulated abundance of substantially all of the bacteria of Table 3. In one embodiment, the method of the invention comprises determining modulated abundance of all of the bacteria of Table 3.

TABLE 3

Oral colorectal polyp associated bacteria (OTUs)

| OTU0008 | OTU0176 | OTU0431 | OTU1963 | OTU0299 |
| OTU0595 | OTU0626 | OTU0544 | OTU0016 | OTU0350 |

In some embodiments, modulated abundance of at least 1, 2, 3, 4, 5, 6 or all CRC-associated oral bacteria selected from *Roseburia, Actinomyces, Campylobacter, Lachnoanaerobaculum, Prevotella, Abiotrophia* and *Streptococcus* correlates with risk of colorectal polyps.

In some embodiments, modulated abundance of at least one of (e.g. 1, or at least 2, 3, 4 or all 5 of) OTU0008 (preferably *Roseburia*), OTU0595 (preferably *Actinomyces*), OTU0176 (preferably *Campylobacter*), OTU0626 (preferably *Lachnoanaerobaculum*) and OTU0431 (preferably *Prevotella*) correlates with risk of colorectal polyps. In some embodiments, modulated abundance of OTU0008 (preferably *Roseburia*) and/or OTU0595 (preferably *Actinomyces*) correlates with risk of colorectal polyps. In some embodiments, modulated abundance of at least 1 of (e.g. 1 or at least 2, 3, 4 or all 5 of) OTU0008 (preferably *Roseburia*), OTU0595 (preferably *Actinomyces*), OTU0176 (preferably *Campylobacter*), OTU0626 (preferably *Lachnoanaerobaculum*) and OTU0431 (preferably *Prevotella*) correlates with risk of adenoma. In some embodiments, modulated abundance of OTU0008 (preferably *Roseburia*) and/or OTU0595 (preferably *Actinomyces*) correlates with risk of adenoma.

In some embodiments, modulated abundance of at least one of (e.g. 1, or at least 2, 3, 4 or all 5 of) CRC-associated oral bacteria selected from *Roseburia, Actinomyces, Campylobacter, Lachnoanaerobaculum* and *Prevotella* correlates with risk of colorectal polyps. In some embodiments, modulated abundance of CRC-associated oral bacteria *Roseburia* and *Actinomyces* correlates with risk of colorectal polyps.

In one embodiment, the method comprises a further step of assaying a faecal sample from the individual for abundance of a plurality of CRC-associated faecal bacteria, wherein modulated abundance of the plurality of CRC-associated faecal bacteria and the plurality of CRC-associated oral bacteria is indicative of positive CRC status. The positive CRC status may be diagnostic, for example indicate increased risk of the individual having colorectal cancer (i.e. a colorectal lesion), or prognostic, for example indicating risk of the individual having a colorectal polyp and therefore risk of development of colorectal cancer.

Accordingly, the invention also provides the use of the oral microbiome in combination with the faecal microbiome to diagnose CRC or colon polyps. Similarly, there is provided the oral microbiome in combination with the faecal microbiome for use in diagnosing CRC or colon polyps. Similarly, the invention provides the use of oral microbiome abundance profiling in combination with faecal microbiome abundance profiling to diagnose CRC or colon polyps. Also provided is a method of diagnosing CRC or colon polyps comprising determining whether an individual has a difference in its oral microbiome compared to the oral microbiome in a healthy patient and a difference in its faecal microbiome compared to the faecal microbiome in a healthy patient, wherein the finding of a difference in both of the oral and faecal microbiomes suggests an increased risk of the individual having colorectal cancer (CRC) or a colon polyp. The difference is preferably a difference in relative abundance of one or more bacterial genera or OTUs that exhibit modulated relative abundance in the oral and faecal microbiomes, respectively, in individuals with CRC or colon polyps compared with a healthy control. In some embodiments, the finding of a decrease in relative abundance of one or more bacterial genera or OTUs that exhibit decreased relative abundance in individuals with CRC or colon polyps compared with a healthy control suggests an increased risk of the individual having colorectal cancer (CRC) or a colon polyp, respectively. In some embodiments, the finding of an increase in relative abundance of one or more bacterial genera or OTUs that exhibit increased relative abundance in individuals with CRC or colon polyps compared with a healthy control suggests an increased risk of the individual having colorectal cancer (CRC) or a colon polyp, respectively. In some embodiments, the finding of a decrease in relative abundance of one or more bacterial genera or OTUs that exhibit decreased relative abundance in individuals with CRC or colon polyps compared with a healthy control together with the finding of an increase in relative abundance of one or more bacterial genera or OTUs that exhibit increased relative abundance in individuals with CRC or colon polyps compared with a healthy control suggests an increased risk of the individual having colorectal cancer (CRC) or a colon polyp, respectively.

A list of CRC-associated faecal bacteria (as provided by bacterial OTUs) is provided in Table 4. Thus, in some embodiments, the CRC-associated faecal bacteria are selected from Table 4. The skilled person will, however, understand that other CRC-associated faecal bacterial genera or OTUs that exhibit modulated relative abundance in individuals with CRC or colon polyps compared with a healthy control may also be used in the invention.

TABLE 4

Faecal colorectal cancer/polyp associated bacteria (OTUs)

| | | | | | | | |
|---|---|---|---|---|---|---|---|
| OTU0599 | OTU0001 | OTU0073 | OTU0978 | OTU0707 | OTU2176 | OTU1239 | OTU0016 |
| OTU0097 | OTU0109 | OTU0013 | OTU0031 | OTU1640 | OTU2203 | OTU0045 | OTU0588 |
| OTU3092 | OTU0012 | OTU1571 | OTU3831 | OTU1584 | OTU0018 | OTU0161 | |
| OTU1584 | OTU0112 | OTU0142 | OTU0063 | OTU0472 | OTU0427 | OTU0019 | |
| OTU1339 | OTU0476 | OTU0206 | OTU0876 | OTU0976 | OTU0089 | OTU0015 | |
| OTU1582 | OTU0045 | OTU0261 | OTU1292 | OTU0512 | OTU0943 | OTU2036 | |
| OTU0731 | OTU1376 | OTU0397 | OTU0395 | OTU0599 | OTU0026 | OTU0112 | |
| OTU0364 | OTU1550 | OTU0158 | OTU0511 | OTU0038 | OTU0251 | OTU0120 | |
| OTU0008 | OTU1999 | OTU0989 | OTU2397 | OTU0059 | OTU0171 | OTU0149 | |
| OTU0148 | OTU0892 | OTU0065 | OTU0726 | OTU0865 | OTU1280 | OTU1011 | |
| OTU0366 | OTU2229 | OTU0436 | OTU1128 | OTU0049 | OTU1080 | OTU0075 | |
| OTU1197 | OTU2137 | OTU0040 | OTU0371 | OTU2137 | OTU0773 | OTU0134 | |
| OTU1175 | OTU2689 | OTU0543 | OTU0006 | OTU0022 | OTU0114 | OTU0194 | |

In one embodiment, modulated abundance of at least five CRC-associated faecal bacteria correlates with positive CRC status.

In one embodiment, modulated abundance of at least 10, 15, 20, 25, 30, 35, 40, 45, 50, 55, 60, 65, 70, 75 or 80 CRC-associated faecal bacteria correlates with positive CRC status.

In one embodiment, modulated abundance of substantially all of the CRC-associated faecal bacteria of Table 4 correlate with positive CRC status. In some embodiments, modulated abundance of all of the CRC-associated faecal bacteria of Table 4 correlate with positive CRC status.

In some embodiments, modulated abundance of at least 2 (e.g. at least 3, 5, 10, 15, 20, 25, 30, 32, 33) or all of CRC-associated faecal bacteria selected from *Lachnospiraceae, Peptostreptococcus, Parabacteroides, Roseburia, Blautia, Clostridium*_XIVa, Clostridiales, *Flavonifractor,* Escherichia/Shigella, *Porphyromonas, Anaerostipes, Faecalibacterium, Coprococcus*, Clostridiales, Firmicutes, *Dialister, Clostridium* IV, *Gemmiger, Collinsella, Bacteroides, Clostridium*_sensu_stricto, *Fusobacterium, Ruminococcus*, Porphyromonadaceae, *Alistipes, Sutterella, Dorea, Barnesiella, Pseudoflavonifractor, Parasutterella, Haemophilus, Bifidobacterium, Phascolarctobacterium* and *Streptococcus* correlates with positive CRC status.

In one embodiment, the CRC-associated faecal bacteria that correlate with risk of the presence of colorectal cancer in the individual (i.e. a colorectal lesion) is the subset of bacteria provided in Table 5.

TABLE 5

Faecal colorectal cancer associated bacteria (OTUs)

| | | | | | | |
|---|---|---|---|---|---|---|
| OTU0599 | OTU0008 | OTU0112 | OTU2137 | OTU0397 | OTU0031 | OTU0726 |
| OTU0097 | OTU0148 | OTU0476 | OTU2689 | OTU0158 | OTU3831 | OTU1128 |
| OTU3092 | OTU0366 | OTU0045 | OTU0073 | OTU0989 | OTU0063 | OTU0371 |
| OTU1584 | OTU1197 | OTU1376 | OTU0013 | OTU0065 | OTU0876 | OTU0006 |
| OTU1339 | OTU1175 | OTU1550 | OTU1571 | OTU0436 | OTU1292 | OTU0707 |
| OTU1582 | OTU0001 | OTU1999 | OTU0142 | OTU0040 | OTU0395 | OTU1640 |
| OTU0731 | OTU0109 | OTU0892 | OTU0206 | OTU0543 | OTU0511 | |
| OTU0364 | OTU0012 | OTU2229 | OTU0261 | OTU0978 | OTU2397 | |

In one embodiment, modulated abundance of at least five CRC-associated faecal bacteria of Table 5 correlates with risk of the presence of colorectal cancer in the individual.

In one embodiment, modulated abundance of at least 10, 15, 20, 25, 30, 35, 40, 45 or 50 CRC-associated faecal bacteria of Table 5 correlates with risk of the presence of colorectal cancer in the individual.

In one embodiment, modulated abundance of substantially all of the CRC-associated faecal bacteria of Table 5 correlates with risk of the presence of colorectal cancer in the individual. In one embodiment, modulated abundance of all of the CRC-associated faecal bacteria of Table 5 correlates with risk of the presence of colorectal cancer in the individual.

In some embodiments, modulated abundance of at least 2 of (e.g. at least 3, 5, 10, 15, 20, 21, 22 of) or all CRC-associated faecal bacteria selected from *Lachnospiraceae*, *Peptostreptococcus*, *Parabacteroides*, *Roseburia*, *Blautia*, *Clostridium*_XIVa, Clostridiales, *Flavonifractor*, *Escherichia/Shigella*, *Porphyromonas*, *Anaerostipes*, *Faecalibacterium*, *Coprococcus*, Clostridiales, Firmicutes, *Dialister*, *Clostridium* IV, *Gemmiger*, *Collinsella*, *Bacteroides*, *Clostridium*_sensu_stricto, *Fusobacterium*, *Ruminococcus* and Porphyromonadaceae correlates with risk of the presence of colorectal cancer in the individual.

In one embodiment, the CRC-associated faecal bacteria that correlate with risk of colorectal polyps (and therefore prognosis of risk of development of CRC) is the subset of bacteria provided in Table 6.

In one embodiment, modulated abundance of at least 10, 15, 20, 25, 30, 35, 40, 45 or 50 CRC-associated faecal bacteria of Table 6 correlates with risk of colorectal polyps (and therefore prognosis of risk of development of CRC).

In one embodiment, modulated abundance of substantially all of the CRC-associated faecal bacteria of Table 6 correlates with risk of colorectal polyps (and therefore prognosis of risk of development of CRC). In some embodiments, modulated abundance of all of the CRC-associated faecal bacteria of Table 6 correlates with risk of colorectal polyps (and therefore prognosis of risk of development of CRC).

In some embodiments, modulated abundance of at least 2 (e.g. at least 3, 5, 10, 15, 16, 17 of) or all of the CRC-associated faecal bacteria selected from *Parabacteroides*, *Clostridium*_XIVa, *Lachnospiraceae*, *Alistipes*, *Sutterella*, *Blautia*, *Parabacteroides*, *Bacteroides*, *Gemmiger*, *Dorea*, *Barnesiella*, *Pseudoflavonifractor*, *Parasutterella*, *Clostridium*_sensu_stricto, *Haemophilus*, *Bifidobacterium*, *Phascolarctobacterium* and *Streptococcus* correlates with risk of colorectal polyps (and therefore prognosis of risk of development of CRC)I.

In a preferred embodiment of the invention, positive CRC status of the individual is determined by detecting modulated abundance of at least five faecal (stool) bacteria and at least five oral bacteria of Table 7. Detection of modulated abundance of at least five oral bacteria and at least five faecal

TABLE 6

| Faecal colorectal polyp associated bacteria (OTUs) | | | | | | |
|---|---|---|---|---|---|---|
| OTU1584 | OTU0059 | OTU2203 | OTU0251 | OTU1239 | OTU0112 | OTU0194 |
| OTU0472 | OTU0865 | OTU0018 | OTU0171 | OTU0045 | OTU0120 | OTU0016 |
| OTU0976 | OTU0049 | OTU0427 | OTU1280 | OTU0161 | OTU0149 | OTU0588 |
| OTU0512 | OTU2137 | OTU0089 | OTU1080 | OTU0019 | OTU1011 | |
| OTU0599 | OTU0022 | OTU0943 | OTU0773 | OTU0015 | OTU0075 | |
| OTU0038 | OTU2176 | OTU0026 | OTU0114 | OTU2036 | OTU0134 | |

In one embodiment, modulated abundance of at least five CRC-associated faecal bacteria of Table 6 correlates with risk of colorectal polyps (and therefore prognosis of risk of development of CRC) in the individual.

bacteria of Table 7 indicate positive CRC status, for example increased risk of the presence of a colorectal cancer (i.e. a colorectal lesion) in the individual, or increased risk of the presence of a colorectal polyp in the individual (i.e. prognosis of risk of developing colorectal cancer).

TABLE 7

| Oral plus faecal colorectal cancer/polyp associated bacteria (OTUs) | | | | | |
|---|---|---|---|---|---|
| OTU1487_stool | OTU0299_oral | OTU0040_stool | OTU0626_oral | OTU0093_stool | OTU0361_stool |
| OTU0348_oral | OTU0277_oral | OTU1254_stool | OTU0050_oral | OTU0050_oral | OTU1699_oral |
| OTU0075_stool | OTU0831_stool | OTU0206_stool | OTU0086_stool | OTU0350_oral | OTU0085_stool |
| OTU0030_oral | OTU0083_oral | OTU2137_stool | OTU0003_oral | OTU0187_stool | OTU0002_stool |
| OTU0016_oral | OTU3273_stool | OTU1292_stool | OTU0675_stool | OTU0544_oral | OTU0951_stool |
| OTU0963_stool | OTU0020_stool | OTU2689_stool | OTU1494_stool | OTU0012_stool | OTU0054_stool |
| OTU0158_stool | OTU0397_stool | OTU0142_stool | OTU0351_stool | OTU0114_stool | OTU0473_oral |
| OTU0135_stool | OTU0424_stool | OTU0105_stool | OTU0114_stool | OTU0963_stool | OTU0571_oral |
| OTU3755_stool | OTU0155_stool | OTU0042_stool | OTU1645_stool | OTU0081_oral | OTU0008_oral |
| OTU1963_oral | OTU1584_stool | OTU0369_stool | OTU0167_stool | OTU2176_stool | OTU0041_oral |
| OTU0092_oral | OTU0031_oral | OTU0389_oral | OTU0142_oral | OTU0595_oral | OTU0029_stool |
| OTU0395_stool | OTU0067_stool | OTU2738_stool | OTU0618_stool | OTU0161_stool | OTU0358_stool |
| OTU0015_oral | OTU0080_oral | OTU2762_stool | OTU0244_oral | OTU0176_oral | OTU0003_oral |
| OTU0007_oral | OTU1682_stool | OTU0174_oral | OTU0228_stool | OTU0130_oral | OTU1963_oral |
| OTU0427_stool | OTU0016_stool | OTU0306_stool | OTU0362_stool | OTU0115_stool | OTU0061_oral |
| OTU0031_stool | OTU0050_stool | OTU2771_stool | OTU1395_stool | OTU0173_stool | OTU0903_oral |
| OTU0664_stool | OTU3092_stool | OTU0210_stool | OTU3180_stool | OTU0433_oral | OTU0666_oral |
| OTU0380_stool | OTU0175_oral | OTU0176_oral | OTU0016_oral | OTU0472_stool | OTU0290_oral |
| OTU0097_oral | OTU2703_oral | OTU0359_stool | OTU0072_oral | OTU1610_stool | OTU0303_oral |
| OTU0850_oral | OTU0112_stool | OTU0337_oral | OTU2137_stool | OTU0233_oral | |

In one embodiment, modulated abundance of at least five CRC-associated faecal bacteria and at least five CRC-associated oral bacteria of Table 7 correlates with positive CRC status.

In one embodiment, modulated abundance of at least 10, 20, 30, 40 CRC-associated faecal bacteria and at least 10, 20, 30 or 40 CRC-associated oral bacteria of Table 7 correlates with positive CRC status.

In one embodiment, modulated abundance of at least 10, 20, 30, 40, 50, 60, 70, 80, 90, 100 or 115 CRC-associated bacteria of Table 7 correlates with positive CRC status.

exhibits modulated relative abundance is OTU1487. In some embodiments, the faecal OTU that exhibits modulated relative abundance is OTU0075. In some embodiments, the faecal OTU that exhibits modulated relative abundance is OTU0030.

In a preferred embodiment of the invention, detection of modulated abundance of at least five faecal (stool) bacteria and at least five oral bacteria of Table 8 indicates increased risk of the individual having colorectal cancer (i.e. a colorectal lesion).

TABLE 8

| Oral plus faecal colorectal cancer associated bacteria (OTUs) | | | | | |
|---|---|---|---|---|---|
| OTU1487_stool | OTU0007_oral | OTU0397_stool | OTU0112_stool | OTU2762_stool | OTU1494_stool |
| OTU0348_oral | OTU0427_stool | OTU0424_stool | OTU0040_stool | OTU0174_oral | OTU0351_stool |
| OTU0075_stool | OTU0031_stool | OTU0155_stool | OTU1254_stool | OTU0306_stool | OTU0114_stool |
| OTU0030_stool | OTU0664_stool | OTU1584_stool | OTU0206_stool | OTU2771_stool | OTU1645_stool |
| OTU0016_oral | OTU0380_stool | OTU0031_oral | OTU2137_stool | OTU0210_stool | OTU0167_stool |
| OTU0963_stool | OTU0097_stool | OTU0067_stool | OTU1292_stool | OTU0176_oral | OTU0142_oral |
| OTU0158_stool | OTU0850_oral | OTU0080_oral | OTU2689_stool | OTU0359_stool | OTU0618_stool |
| OTU0135_stool | OTU0299_oral | OTU1682_stool | OTU0142_stool | OTU0337_oral | OTU0244_oral |
| OTU3755_stool | OTU0277_oral | OTU0016_stool | OTU0105_stool | OTU0626_oral | OTU0228_stool |
| OTU1963_stool | OTU0831_stool | OTU0050_stool | OTU0042_stool | OTU0050_oral | OTU0362_stool |
| OTU0092_oral | OTU0083_oral | OTU3092_stool | OTU0369_stool | OTU0086_stool | OTU1395_stool |
| OTU0395_stool | OTU3273_stool | OTU0175_oral | OTU0389_oral | OTU0003_oral | OTU3180_stool |
| OTU0015_oral | OTU0020_stool | OTU2703_oral | OTU2738_stool | OTU0675_stool | |

In one embodiment, modulated abundance of substantially all of the CRC-associated bacteria of Table 7 correlates with positive CRC status. In one embodiment, modulated abundance of all of the CRC-associated bacteria of Table 7 correlates with positive CRC status.

In some embodiments, modulated abundance of at least five (e.g. at least 5, 10, 15, 20, 22, 23 or all) CRC-associated faecal bacteria selected from *Clostridium*_XIVa, *Coprococcus*, *Hespellia*, *Dorea*, *Clostridium*_sensu_stricto, Lachnospiraceae, *Bacteroides*, *Gemmiger*, *Veillonella*, *Lactobacillus*, *Parabacteroides*, *Streptococcus*, *Blautia*, *Clostridium* IV, *Dialister*, *Clostridium* XI, *Prevotella*, *Parasutterella*, *Paraprevotella*, *Anaerostipes*, *Blautia*, *Butyricimonas*, *Bilophila* and *Bifidobacterium* and at least five (e.g. at least 5, 10, 15, 20, 25, 27, 29 or all) CRC-associated oral bacteria selected from *Prevotella*, *Streptococcus*, *Haemophilus*, *Peptostreptococcus*, *Eikenella*, *Gemella*, *Clostridium*_sensu_stricto, *Aggregatibacter*, *Tannerella*, *Kingella*, *Campylobacter*, *Cardiobacterium*, *Lachnoanaerobaculum*, *Veillonella*, *Faecalibacterium*, *Dialister*, *Capnocytophaga*, *Actinomyces*, *Abiotrophia*, *Neisseria*, *Actinomyces*, *Solobacterium*, *Selenomonas*, *Capnocytophaga*, *Treponema*, *Roseburia*, *Faecalibacterium*, *Bifidobacterium*, *Leptotrichia* and Flavobacteriaceae correlates with positive CRC status.

In some embodiments, modulated abundance of at least one (e.g. 1, 2 or 3) CRC-associated oral OTU selected from OTU0348 (preferably *Prevotella*), OTU0016 (preferably *Streptococcus*) and OTU0283 (preferably *Tannerella*) in combination with at least one (e.g. 1, 2 or 3) CRC-associated faecal OTU selected from OTU1487 (preferably *Clostridium*_XIVa), OTU0075 (preferably *Clostridium*_XIVa) and OTU0030 (preferably *Coprococcus*) correlates with positive CRC status. In some embodiments, the oral OTU that exhibits modulated relative abundance is OTU0348. In some embodiments, the oral OTU that exhibits modulated relative abundance is OTU0016. In some embodiments, the oral OTU that exhibits modulated relative abundance is OTU0283. In some embodiments, the faecal OTU that In one embodiment, modulated abundance of at least five CRC-associated faecal bacteria and at least five CRC-associated oral bacteria of Table 8 correlates with risk of colorectal cancer.

In one embodiment, modulated abundance of at least 10, 20 or 30 CRC-associated faecal bacteria and at least 10, 20 or 30 CRC-associated oral bacteria of Table 8 correlates with risk of colorectal cancer.

In one embodiment, modulated abundance of at least 10, 20, 30, 40, 50, 60 or 70 CRC-associated bacteria of Table 8 correlates with risk of colorectal cancer.

In one embodiment, modulated abundance of substantially all of the CRC-associated bacteria of Table 8 correlates with risk of colorectal cancer. In some embodiments, modulated abundance of all of the CRC-associated bacteria of Table 8 correlates with risk of colorectal cancer. In some embodiments, modulated abundance of 53 CRC-associated stool bacteria and 24 CRC-associated oral bacteria of Table 8 correlates with risk of colorectal cancer.

In some embodiments, modulated abundance of at least 5, 10, 15, 16, 17 or all CRC-associated faecal bacteria selected from *Clostridium*_XIVa, *Coprococcus*, *Hespellia*, *Dorea*, *Clostridium*_sensu_stricto, Lachnospiraceae, *Bacteroides*, *Gemmiger*, *Veillonella*, *Lactobacillus*, *Parabacteroides*, *Streptococcus*, *Blautia*, *Clostridium*_IV, *Dialister*, *Clostridium*_XI, *Prevotella* and *Parasutterella*, and at least 5, 10, 15, 16 or all CRC-associated oral bacteria selected from *Prevotella*, *Streptococcus*, *Haemophilus*, *Peptostreptococcus*, *Eikenella*, *Gemella*, *Clostridium*_sensu_stricto, *Aggregatibacter*, *Tannerella*, *Kingella*, *Campylobacter*, *Cardiobacterium*, *Lachnoanaerobaculum*, *Veillonella*, *Faecalibacterium*, *Dialister* and *Capnocytophaga*, correlates with risk of colorectal cancer.

In a preferred embodiment of the invention, detection of modulated abundance of at least five faecal (stool) bacteria and at least five oral bacteria of Table 9 indicates increased risk of the individual having a colorectal polyp (and therefore a prognosis of risk of developing colorectal cancer).

TABLE 9

Oral plus faecal colorectal polyp associated bacteria (OTUs)

| OTU0016_oral | OTU0544_oral | OTU0161_stool | OTU1610_stool | OTU0054_stool | OTU0003_oral |
|---|---|---|---|---|---|
| OTU0072_oral | OTU0012_stool | OTU0176_oral | OTU0233_oral | OTU0473_oral | OTU1963_oral |
| OTU2137_stool | OTU0114_stool | OTU0130_oral | OTU0361_stool | OTU0571_oral | OTU0061_oral |
| OTU0093_stool | OTU0963_stool | OTU0115_stool | OTU1699_oral | OTU0008_oral | OTU0903_oral |
| OTU0050_oral | OTU0081_oral | OTU0173_stool | OTU0085_stool | OTU0041_oral | OTU0666_oral |
| OTU0350_oral | OTU2176_stool | OTU0433_oral | OTU0002_stool | OTU0029_stool | OTU0290_oral |
| OTU0187_stool | OTU0595_oral | OTU0472_stool | OTU0951_stool | OTU0358_stool | OTU0303_oral |

In one embodiment, modulated abundance of at least five CRC-associated faecal bacteria and at least five CRC-associated oral bacteria of Table 9 correlates with increased risk of the individual having a colorectal polyp (and therefore a prognosis of risk of developing colorectal cancer).

In one embodiment, modulated abundance of at least 10, 20 or 30 CRC-associated faecal bacteria and at least 10, 20 or 30 CRC-associated oral bacteria of Table 9 correlates with increased risk of the individual having a colorectal polyp (and therefore a prognosis of risk of developing colorectal cancer).

In one embodiment, modulated abundance of at least 10, 20, 30, 40, 50, 60 or 70 CRC-associated bacteria of Table 9 correlates with increased risk of the individual having a colorectal polyp (and therefore a prognosis of risk of developing colorectal cancer).

In one embodiment, modulated abundance of substantially all of the CRC-associated bacteria of Table 9 correlates with increased risk of the individual having a colorectal polyp (and therefore a prognosis of risk of developing colorectal cancer). In some embodiments, modulated abundance of all of the CRC-associated bacteria of Table 9 correlates with increased risk of the individual having a colorectal polyp (and therefore a prognosis of risk of developing colorectal cancer). In some embodiments, modulated abundance of at least 5, 10, 12, 15 or 18 CRC-associated faecal bacteria and at least 5, 10, 12, 15, 18 or 20 CRC-associated oral bacteria of Table 9 correlates with increased risk of the individual having a colorectal polyp (and therefore a prognosis of risk of developing colorectal cancer). In some embodiments, modulated abundance of 19 CRC-associated stool bacteria and 23 CRC-associated oral bacteria of Table 9 correlates with increased risk of the individual having a colorectal polyp (and therefore a prognosis of risk of developing colorectal cancer).

In some embodiments, modulated abundance of at least 5 (e.g. at least 8, 10 or all) CRC-associated faecal bacteria selected from *Clostridium* IV, *Paraprevotella*, *Anaerostipes*, *Parasutterella*, *Bacteroides*, Lachnospiraceae, *Clostridium*_XIVa, *Blautia*, *Butyricimonas*, *Bilophila* and *Bifidobacterium*, and at least 5 (e.g. at least 10, 12, 15, 17, 18, or all) CRC-associated oral bacteria selected from *Streptococcus*, *Veillonella*, *Actinomyces*, *Abiotrophia*, *Neisseria*, *Actinomyces*, *Campylobacter*, *Solobacterium*, *Selenomonas*, *Capnocytophaga*, *Lachnoanaerobaculum*, *Tannerella*, *Treponema*, *Roseburia*, *Faecalibacterium*, *Bifidobacterium*, *Prevotella*, *Leptotrichia* and Flavobacteriaceae correlates with increased risk of the individual having a colorectal polyp (and therefore a prognosis of risk of developing colorectal cancer).

In one embodiment, the CRC-associated oral bacteria that correlate with risk of colorectal cancer (as opposed to CR polyps) is the subset of bacteria (defined by the OTU numbers) provided in Table 11.

TABLE 11

Oral colorectal cancer/polyp-associated bacteria (OTUs)

| OTU50189 | OTU50037 | OTU50076 | OTU50299 | OTU50383 | OTU50270 |
|---|---|---|---|---|---|
| OTU51549 | OTU50041 | OTU58875 | OTU50458 | OTU52345 | |
| OTU50020 | OTU51260 | OTU50221 | OTU50442 | OTU50759 | |
| OTU50068 | OTU50097 | OTU51588 | OTU52070 | OTU50358 | |
| OTU50043 | OTU50010 | OTU55262 | OTU50171 | OTU50188 | |

In some embodiments, modulated abundance of at least 1, 2, 3, 4, 5, 6, 7, 8, 9, 10, 11, 12, 13, 14, 15, 16, 17, 18, 19, 20, 21, 22, 23, 24, 25, or all CRC-associated oral bacteria selected from *Prevotella*, *Anaerostipes*, *Porphyromonas*, *Neisseria*, *Haemophilus*, *Fusobacterium*, *Peptostreptococcus*, *Streptococcus*, *Alloprevotella*, *Megasphaera*, *Leptotrichia*, *Cardiobacterium*, *Selenomonus*, *Abiotrophia*, Flavobacteriacae, *Tannerella*, *Capnocytophaga* correlates with risk of colorectal cancer (i.e. colorectal lesions) or colorectal polyps.

In one embodiment, the CRC-associated oral bacteria that correlate with risk of colorectal cancer (as opposed to CR polyps) is the subset of bacteria (defined by the OTU numbers) provided in Table 12.

TABLE 12

Oral CRC-associated bacteria (OTUs)

| OTU50189 | OTU50068 | OTU50041 | OTU50010 | OTU50221 | OTU50299 |
|---|---|---|---|---|---|
| OTU51549 | OTU50043 | OTU51260 | OTU50076 | OTU51588 | |
| OTU50020 | OTU50037 | OTU50097 | OTU58875 | OTU55262 | |

In one embodiment, modulated abundance of at least five CRC-associated oral bacteria of Table 12 correlates with risk of colorectal cancer (colorectal lesions).

substantially all of the bacteria of Table 13. In one embodiment, the method of the invention comprises determining modulated abundance of all of the bacteria of Table 13.

TABLE 13

| Oral colorectal polyp associated bacteria (OTUs) | | | | | |
|---|---|---|---|---|---|
| OTU50458 | OTU50442 | OTU50171 | OTU52345 | OTU50759 | OTU50188 |
| OTU50043 | OTU52070 | OTU50383 | OTU51549 | OTU50358 | OTU50270 |

In one embodiment, modulated abundance of at least 1, 2, 3, 4, 5, 6, 7, 8, 9, 10, 11, 12, 13, 14, 15, or all CRC-associated oral bacteria of Table 12 correlates with risk of colorectal cancer (i.e. colorectal lesions).

In one embodiment, modulated abundance of substantially all of the CRC-associated oral bacteria of Table 12 correlate with risk of colorectal cancer (i.e. colorectal lesions). In some embodiments, modulated abundance of all of the CRC-associated oral bacteria of Table 12 correlate with risk of colorectal cancer (i.e. colorectal lesions).

In some embodiments, modulated abundance of at least 1, 2, 3, 4, 5, 6, 7, 8, 9, 10, 11, 12 or all CRC-associated oral bacteria selected from *Prevotella, Anaerostipes, Porphyromonas, Neisseria, Haemophilus, Fusobacterium, Peptostreptococcus, Streptococcus, Alloprevotella, Megasphaera, Neisseria, Leptotrichia*, and *Cardiobacterium* correlates with risk of colorectal cancer (i.e. colorectal lesions).

In some embodiments, modulated abundance of at least one of (e.g. 1, or at least 2, 3, 4, 5, 6, or all 7 of) OTU50189 (preferably *Prevotella*), OTU51549 (preferably *Prevotella*), OTU50020 (preferably *Anaerostipes*), OTU50068 (preferably *Porphyromonas*), OTU50043 (preferably *Neisseria*), OTU50037 (preferably *Haemophilus*), and OTU50041 (preferably *Fusobacterium*) correlates with risk of colorectal cancer (i.e. colorectal lesions). In some embodiments, modulated abundance of one or more of OTU51260 (preferably *Prevotella*), OTU50097 (preferably *Peptostreptococcus*), OTU50010 (preferably *Streptococcus*), OTU50076 (preferably *Alloprevotella*), OTU58875 (preferably *Fusobacterium*), OUT50221 (preferably *Megasphaera*), OTU51588 (preferably *Neisseria*), OTU55262 (preferably *Leptotichia*), OTU50299 (preferably *Cardiobacterium*) correlates with risk of colorectal cancer (i.e. colorectal lesions).

In one embodiment, the CRC-associated oral bacteria that correlate with risk of colorectal polyps (and therefore prognosis of risk of development of CRC) is the subset of bacteria provided in Table 13. In one embodiment, the method of the invention comprises determining modulated abundance of 2, 3, 4, 5, 6, 7, 8, 9, 10, 11, or all 12 of the bacteria of Table 13. In one embodiment, the method of the invention comprises determining modulated abundance of In some embodiments, modulated abundance of at least 1, 2, 3, 4, 5, 6, 7, 8, 9, 10, 11 or all CRC-associated bacteria selected from *Selenomonas, Neisseria, Abiotrophia, Haemophilus*, Flavobacteriaceae, *Tannerella, Prevotella, Capnocytophaga*, and *Porphyromonas* correlates with risk of colorectal polyps.

In some embodiments, modulated abundance of at least one of (e.g. 1, or at least 2, 3, 4, 5, 6, 7, 8, 9, 10, 11, or all 12 of) OTU50458 (preferably *Selenomonas*), OTU50043 (preferably *Neisseria*), OTU50442 (preferably *Abiotrophia*), OTU52070 (preferably *Haemophilus*), OTU50171 (preferably Flavobacteriaceae), OTU50383 (preferably *Tannerella*), OTU52345 (preferably *Neisseria*) OTU51549 (preferably *Prevotella*), OTU50759 (preferably *Prevotella*), OTU50358 (preferably *Capnocytophaga*), OTU50188 (preferably *Capnocytophaga*), OTU50270 (preferably *Porphyromonas*) correlates with the risk of colorectal polyps.

A list of CRC-associated faecal bacteria (as provided by bacterial OTUs) is provided in Table 14. Thus, in some embodiments, the CRC-associated faecal bacteria are selected from Table 14. The skilled person will, however, understand that other CRC-associated faecal bacterial genera or OTUs that exhibit modulated relative abundance in individuals with CRC or colon polyps compared with a healthy control may also be used in the invention.

TABLE 14

| Faecal colorectal cancer/polyp associated bacteria (OTUs) | | | | | |
|---|---|---|---|---|---|
| OTU50023 | OTU50046 | OTU50220 | OTU50062 | OTU53349 | OTU50086 |
| OTU51026 | OTU50833 | OTU50211 | OTU50177 | OTU51288 | OTU50038 |
| OTU50097 | OTU50223 | OTU50066 | OTU50143 | OTU56073 | OTU56780 |
| OTU50466 | OTU50735 | OTU50108 | OTU53773 | OTU50367 | |
| OTU50016 | OTU50092 | OTU58020 | OTU54992 | OTU50048 | |
| OTU50214 | OTU54957 | OTU51130 | OTU50413 | OTU53156 | |
| OTU56301 | OTU50100 | OTU50523 | OTU50150 | OTU53631 | |
| OTU50743 | OTU51546 | OTU59581 | OTU50101 | OTU50479 | |
| OTU59239 | OTU54023 | OTU50365 | OTU54003 | OTU51970 | |
| OTU50087 | OTU50080 | OTU50529 | OTU50233 | OTU50213 | |

In one embodiment, modulated abundance of at least five CRC-associated faecal bacteria correlates with positive CRC status.

In one embodiment, modulated abundance of at least 10, 15, 20, 25, 30, 35, 40, 45, or 50 CRC-associated faecal bacteria correlates with positive CRC status.

In one embodiment, modulated abundance of substantially all of the CRC-associated faecal bacteria of Table 14 correlate with positive CRC status. In some embodiments, modulated abundance of all of the CRC-associated faecal bacteria of Table 14 correlate with positive CRC status.

In some embodiments, modulated abundance of at least 2 (e.g. at least 3, 5, 10, 15, 20, 23, 24) or all of CRC-associated faecal bacteria selected from *Roseburia, Lachnospiraceae, Peptostreptococcus*, Ruminococcaeceae, *Alistipes, Blautia, Bacteroides, Clostridium*_XIVa, *Clostridium*_sensu_stricto, Clostridiales, *Coprococcus*, Firmicutes, *Akkermansia*, Clostridium_XIVb, *Howardella, Bilophila, Dialister, Acetanaerobacterium, Flavonifractor, Parabacteroides, Acidaminococcus, Lachnospira, Clostridium* IV, *Sutterella*, and *Faecalibacterium* correlates with positive CRC status.

In one embodiment, the CRC-associated faecal bacteria that correlate with risk of the presence of colorectal cancer in the individual (i.e. a colorectal lesion) is the subset of bacteria provided in Table 15.

TABLE 15

| Faecal colorectal cancer associated bacteria (OTUs) | | | | | |
|---|---|---|---|---|---|
| OTU50023 | OTU50743 | OTU50092 | OTU50211 | OTU50365 | OTU50413 |
| OTU51026 | OTU59239 | OTU54957 | OTU50066 | OTU50529 | |
| OTU50097 | OTU50087 | OTU50100 | OTU50108 | OTU50062 | |
| OTU50466 | OTU50046 | OTU51546 | OTU58020 | OTU50177 | |
| OTU50016 | OTU50833 | OTU54023 | OTU51130 | OTU50143 | |
| OTU50214 | OTU50223 | OTU50080 | OTU50523 | OTU53773 | |
| OTU56301 | OTU50735 | OTU50220 | OTU59581 | OTU54992 | |

In one embodiment, modulated abundance of at least five CRC-associated faecal bacteria of Table 15 correlates with risk of the presence of colorectal cancer in the individual.

In one embodiment, modulated abundance of at least 10, 15, 20, 25, 30, or 35 CRC-associated faecal bacteria of Table 15 correlates with risk of the presence of colorectal cancer in the individual.

In one embodiment, modulated abundance of substantially all of the CRC-associated faecal bacteria of Table 15 correlates with risk of the presence of colorectal cancer in the individual. In one embodiment, modulated abundance of all of the CRC-associated faecal bacteria of Table 15 correlates with risk of the presence of colorectal cancer in the individual.

In some embodiments, modulated abundance of at least 2 of (e.g. at least 3, 5, 10, 15, 17, 18) or all CRC-associated faecal bacteria selected from *Roseburia*, Lachnospiraceae, *Peptostreptococcus*, Ruminococcaeceae, *Alistipes, Blautia, Bacteroides, Clostridium*_XIVa, *Clostridium*_sensu_stricto, Clostridiales, *Coprococcus*, Firmicutes, *Akkermansia*, Clostridium_XIVb, *Howardella, Bilophila, Dialister, Acetanaerobacterium*, and *Flavonifractor* correlates with risk of the presence of colorectal cancer in the individual.

In one embodiment, the CRC-associated faecal bacteria that correlate with risk of colorectal polyps (and therefore prognosis of risk of development of CRC) is the subset of bacteria provided in Table 16.

TABLE 16

| Faecal colorectal polyp associated bacteria (OTUs) | | | | | |
|---|---|---|---|---|---|
| OTU50150 | OTU50233 | OTU56073 | OTU53156 | OTU51970 | OTU50038 |
| OTU50101 | OTU53349 | OTU50367 | OTU53631 | OTU50213 | OTU56780 |
| OTU54003 | OTU51288 | OTU50048 | OTU50479 | OTU50086 | |

In one embodiment, modulated abundance of at least five CRC-associated faecal bacteria of Table 6 correlates with risk of colorectal polyps (and therefore prognosis of risk of development of CRC) in the individual.

In one embodiment, modulated abundance of at least 10 or 15 CRC-associated faecal bacteria of Table 16 correlates with risk of colorectal polyps (and therefore prognosis of risk of development of CRC).

In one embodiment, modulated abundance of substantially all of the CRC-associated faecal bacteria of Table 16 correlates with risk of colorectal polyps (and therefore prognosis of risk of development of CRC). In some embodiments, modulated abundance of all of the CRC-associated faecal bacteria of Table 16 correlates with risk of colorectal polyps (and therefore prognosis of risk of development of CRC).

In some embodiments, modulated abundance of at least 2 (e.g. at least 3, 5, 10, 15, 16, 17 of) or all of the CRC-associated faecal bacteria selected from *Parabacteroides, Clostridium_XIVa*, Lachnospiraceae, *Acidaminococcus, Lachnospira, Clostridium* IV, *Coprococcus, Blautia, Bacteroides*, Ruminococcaceae, *Sutterella*, and *Faecalibacterium* correlates with risk of colorectal polyps (and therefore prognosis of risk of development of CRC).

In another embodiment, positive CRC status of the individual is determined by detecting modulated abundance of at least five faecal (stool) bacteria and at least five oral bacteria of Table 17. Detection of modulated abundance of at least five oral bacteria and at least five faecal bacteria of Table 17 indicate positive CRC status, for example increased risk of the presence of a colorectal cancer (i.e. a colorectal lesion) in the individual, or increased risk of the presence of a colorectal polyp in the individual (i.e. prognosis of risk of developing colorectal cancer).

Clostridiales, *Bacteroides, Clostrium sensu stricto, Parabacteroides, Collinsella*, Prevotellaceae, Ruminococcoaceae, *Paraprevotella, Flavonifractor, Anaerostipes, Barnesiella, Eubacterium, Faecalibacterium* correlates with positive CRC status.

In some embodiments, modulated abundance of at least one (e.g. 1, 2, 3, 4, 5, 10, 20, 30, 40 or all) CRC-associated oral OTU selected from OTU50189 (preferably *Prevotella*), OTU50017 (preferably *Gemella*), OTU51549 (preferably *Prevotella*), OTU50037 (preferably *Haemophilus*), OTU51588 (preferably *Nesseria*), OTU50041 (preferably *Fusobacterium*), OTU50944 (preferably *Rothia*), OTU52070 (preferably *Haemophilus*), OTU50001 (preferably *Streptococcus*), OTU57157 (preferably *Veillonella*), OTU59656 (preferably *Streptococcus*), OTU50221 (preferably *Megasphaera*), OTU50442 (preferably *Abiotrophia*), OTU50299 (preferably *Cardiobacterium*), OTU50208 (preferably *Tannerella*), OTU50020 (preferably *Anaerosti-*

TABLE 17

Oral plus faecal colorectal cancer/polyp associated bacteria (OTUs)

| | | | | |
|---|---|---|---|---|
| OTU50189_oral | OTU50221_oral | OTU50444_oral | OTU56581_stoo | OTU53773_stoo |
| OTU50017_oral | OTU50442_oral | OTU57750_stoo | OTU50018_stoo | OTU50128_oral |
| OTU50053_stoo | OTU50299_oral | OTU52704_stoo | OTU56772_oral | OTU50020_stoo |
| OTU51549_oral | OTU50064_stoo | OTU54670_stoo | OTU50547_oral | OTU51014_stoo |
| OTU50037_oral | OTU50095_stoo | OTU50177_oral | OTU52529_oral | OTU55821_stoo |
| OTU510131_sto | OTU50168_stoo | OTU50046_stoo | OTU50032_oral | OTU54910_stoo |
| OTU51588_oral | OTU50080_stoo | OTU50043_oral | OTU50213_stoo | OTU52070_oral |
| OTU50041_oral | OTU50172_stoo | OTU55394_stoo | OTU51549_oral | OTU50065_oral |
| OTU50944_oral | OTU50208_oral | OTU50150_stoo | OTU50124_oral | OTU51411_stoo |
| OTU50062_stoo | OTU50500_stoo | OTU51727_stoo | OTU56301_stoo | OTU51401_stoo |
| OTU52070_oral | OTU50479_stoo | OTU51260_oral | OTU57750_stoo | OTU50016_oral |
| OTU50122_stoo | OTU50012_stoo | OTU57512_stoo | OTU50255_stoo | OTU50458_oral |
| OTU52086_stoo | OTU50020_stoo | OTU50091_stoo | OTU50091_stoo | OTU50726_stoo |
| OTU50092_stoo | OTU53501_stoo | OTU50492_oral | OTU50101_stoo | OTU51343_stoo |
| OTU50001_oral | OTU50630_stoo | OTU50412_oral | OTU50138_oral | OTU52086_stoo |
| OTU50501_stoo | OTU51340_stoo | OTU50880_stoo | OTU50442_oral | |
| OTU57157_oral | OTU53463_stoo | OTU50593_oral | OTU53421_stoo | |
| OTU50112_stoo | OTU50097_oral | OTU56933_stoo | OTU50059_oral | |
| OTU59656_oral | OTU50552_oral | OTU51883_stoo | OTU52183_oral | |

In one embodiment, modulated abundance of at least five CRC-associated faecal bacteria and at least five CRC-associated oral bacteria of Table 17 correlates with positive CRC status.

In one embodiment, modulated abundance of at least 10, 20, 30, 40, 50, 60, 70, 80, or 90 CRC-associated bacteria of Table 17 correlates with positive CRC status.

In one embodiment, modulated abundance of substantially all of the CRC-associated bacteria of Table 17 correlates with positive CRC status. In one embodiment, modulated abundance of all of the CRC-associated bacteria of Table 17 correlates with positive CRC status.

In some embodiments, modulated abundance of at least five (e.g. at least 5, 10, 15, 20, 25, or all) CRC-associated oral bacteria selected from *Prevotella, Gemella, Haemophilus, Neisseria, Fusobacterium, Rothia, Streptococcus, Veillonella, Megasphaera, Abiotrophia, Cardiobacterium, Tannerella, Anaerostipes, Peptostreptococcus, Lachnoanaerobaculum, Mogibacterium, Dialister, Treponema, Alloprevotella, Corynoebacterium, Olsenella, Actinomycetales, Campylobacter, Atopobium, Selenomonas*, and *Roseburia* and at least five (e.g. at least 5, 10, 15, 20, 25, 29, or all) CRC-associated faecal bacteria selected from *Clostridium_XIVa, Parabacteroides, Bacteroides*, Erysipelotrichaceae, *Anaerotruncus, Clostridium* IV, *Clostridium* XVIII, *Oscillibacter, Veillonella, Clostridium_XIVb*, Lachnospiraceae, *Gemmiger, Blautia, Ruminococcus, Alistipes*,

*pes*), OTU50097 (preferably *Peptostreptococcus*), OTU50552 (preferably *Lachnoanaerobaculum*), OTU50444 (preferably *Mogibacterium*), OTU50177 (preferably *Dialisten*), OTU50043 (preferably *Neisseria*), OTU01260 (preferably *Prevotella*), OTU50492 (preferably *Treponema*), OTU50412 (preferably *Prevotella*), OTU50593 (preferably *Alloprevotella*), OTU56772 (preferably *Corynebacterium*), OTU50547 (preferably *Olsenella*), OTU52529 (preferably *Actinomycetales*), OTU50032 (preferably *Bacteroides*), OTU51549 (preferably *Prevotella*), OTU50124 (preferably *Campylobacter*), OTU50076 (preferably *Alloprevotella*), OTU50138 (preferably *Atopobium*), OTU50442 (preferably *Prevotella*), OTU52070 (preferably *Haemophilus*), OTU50065 (preferably *Streptococcus*), OTU50016 (preferably *Roseburia*), and OTU50458 (preferably *Selenomonas*) in combination with at least one (e.g. e.g. 1, 2, 3, 4, 5, 10, 20, 30, 40, or all) CRC-associated faecal OUT selected from OTU50053 (preferably *Clostridium_XIVa*), OTU510131 (preferably *Parabacteroides*), OTU50062 (preferably *Bacteroides*), OTU50122 (preferably Erysipelotrichaceae), OTU52086 (preferably *Clostridium_XIVa*), OTU50092 (preferably *Clostridium_XIVa*), OTU50501 (preferably *Anaerotruncus*), OTU50112 (preferably *Clostridium_IV*), OTU50064 (preferably *Clostridium* XVIII), OTU50095 (preferably *Oscillibacter*), OTU50168 (preferably *Veillonella*), OTU50080 (preferably *Clostridium_XIVb*), OTU50172 (preferably Lachnospiraceae), OTU50500 (preferably *Gemmiger*), OTU50479 (preferably *Blautia*), OTU50012 (preferably *Ruminococcus*), OTU53501 (preferably *Lachnospiraceae*), OTU50630 (preferably *Alistipes*), OTU51340 (preferably Clostridiales), OTU53463 (preferably *Clostridium*_XIVa), OTU57750 (preferably *Bacteroides*), OTU52704 (preferably *Gemmiger*), OTU54670 (preferably *Ruminococcus*), OTU50046 (preferably *Clostridium* sensu stricto), OTU55394 (preferably *Bacteroides*), OTU50150 (preferably *Parabacteroides*), OTU51727 (preferably *Ruminococcus*), OTU57512 (preferably Lachnospiraceae), OTU50091 (preferably *Collinsella*), OTU50880 (preferably Clostridiales), OTU56933 (preferably *Oscillibacter*), OTU51883 (preferably Prevotellaceae), OTU56581 (preferably Lachnospiraceae), OTU50018 (preferably *Bacteroides*), OTU50213 (preferably Ruminococcaceae), OTU56301 (preferably *Blautia*), OTU57750 (preferably *Bacteroides*), OTU50255 (preferably *Paraprevotella*), OTU50101 (preferably *Clostridium*_XIVa), OTU53421 (preferably *Bacteroides*), OTU53773 (preferably *Flavonifractor*), OTU50020 (preferably *Anaerostipes*), OTU51014 (preferably Lachnospiraceae), OTU55821 (preferably *Bamesiella*), OTU54910 (preferably *Clostridium*_XIVa), OTU51411 (preferably *Eubacterium*), OTU51401 (preferably *Clostridium*_IV), OTU50726 (preferably *Flavonifractor*), OTU51343 (preferably *Faecalibacterium*), and OTU52086 (preferably *Clostridium*_XIVa) correlates with positive CRC status.

In a preferred embodiment of the invention, detection of modulated abundance of at least five faecal (stool) bacteria and at least five oral bacteria of Table 18 indicates increased risk of the individual having colorectal cancer (i.e. a colorectal lesion).

In one embodiment, modulated abundance of at least five CRC-associated faecal bacteria and at least five CRC-associated oral bacteria of Table 18 correlates with risk of colorectal cancer.

In one embodiment, modulated abundance of at least 10, 20 or 30 CRC-associated faecal bacteria and at least 10, 20 or 29 CRC-associated oral bacteria of Table 15 correlates with risk of colorectal cancer.

In one embodiment, modulated abundance of at least 10, 20, 30, 40, 50, or 60 CRC-associated bacteria of Table 18 correlates with risk of colorectal cancer.

In one embodiment, modulated abundance of substantially all of the CRC-associated bacteria of Table 18 correlates with risk of colorectal cancer. In some embodiments, modulated abundance of all of the CRC-associated bacteria of Table 18 correlates with risk of colorectal cancer. In some embodiments, modulated abundance of 34 CRC-associated stool bacteria and 29 CRC-associated oral bacteria of Table 18 correlates with risk of colorectal cancer.

In some embodiments, modulated abundance of at least 5, 10, 15, 20, 22, or all CRC-associated oral bacteria selected from *Prevotella, Gemella, Haemophilus, Neisseria, Fusobacterium, Rothia, Streptococcus, Veillonella, Megasphaera, Abiotrophia, Cardiobacterium, Tannerella, Anaerostipes, Peptostreptococcus, Lachnoanaerobaculum, Mogibacterium, Dialister, Treponema, Alloprevotella, Corynebacterium, Olsenella, Actinomycetales*, and *Bacteroides* correlates with risk of colorectal cancer. In some embodiments, modulated abundance of at least 5, 10, 15, 17, or all CRC-associated faecal bacteria selected from *Clostridium*_XIVa, *Parabacteroides, Bacteroides*, Erysipelotrichaceae, *Anaerotruncus, Clostridium* IV, *Clostridium* XVIII, *Oscillibacter, Veillonella, Clostridium*_XIVb, Lachnospiraceae, *Gemmiger, Blautia, Ruminococcus, Alistipes*, Clostridiales, *Coffinsella*, and Prevotellaceae correlates with risk of colorectal cancer.

TABLE 18

| Oral plus faecal colorectal cancer associated bacteria (OTUs) | | | | |
|---|---|---|---|---|
| OTU50189_oral | OTU50001_oral | OTU50500_stoo | OTU50177_oral | OTU51883_stool |
| OTU50017_oral | OTU50501_stool | OTU50479_stoo | OTU50046_stoo | OTU56581_stool |
| OTU50053_stool | OTU57157_oral | OTU50012_stoo | OTU50043_oral | OTU50018_stool |
| OTU51549_oral | OTU50112_stool | OTU50020_oral | OTU55394_stoo | OTU56772_oral |
| OTU50037_oral | OTU59656_oral | OTU53501_stoo | OTU50150_stoo | OTU50547_oral |
| OTU510131_stool | OTU50221_oral | OTU50630_stoo | OTU51727_stoo | OTU52529_oral |
| OTU51588_oral | OTU50442_oral | OTU51340_stoo | OTU51260_oral | OTU50032_oral |
| OTU50041_oral | OTU50299_oral | OTU53463_stoo | OTU57512_stoo | |
| OTU50944_oral | OTU50064_stool | OTU50097_oral | OTU50091_stoo | |
| OTU50062_stool | OTU50095_stool | OTU50552_oral | OTU50492_oral | |
| OTU52070_oral | OTU50168_stool | OTU50444_oral | OTU50412_oral | |
| OTU50122_stool | OTU50080_stool | OTU57750_stoo | OTU50880_stoo | |
| OTU52086_stool | OTU50172_stool | OTU52704_stoo | OTU50593_oral | |
| OTU50092_stool | OTU50208_oral | OTU54670_stoo | OTU56933_stoo | |

In a preferred embodiment of the invention, detection of modulated abundance of at least five faecal (stool) bacteria (OTU) and at least five oral bacteria (OTU) of Table 19 indicates increased risk of the individual having a colorectal polyp (and therefore a prognosis of risk of developing colorectal cancer).

TABLE 19

| Oral plus faecal colorectal polyp associated bacteria (OTUs) | | | | |
|---|---|---|---|---|
| OTU50213_stoo | OTU50076_ora | OTU52183_ora | OTU54910_stoo | OTU50458_oral |
| OTU51549_oral | OTU50101_sto | OTU53773_sto | OTU52070_oral | OTU50726_stool |
| OTU50124_oral | OTU50138_sto | OTU50128_ora | OTU50065_oral | OTU51343_stool |
| OTU56301_stoo | OTU50442_ora | OTU50020_sto | OTU51411_stoo | OTU52086_stool |
| OTU57750_stoo | OTU53421_sto | OTU51014_sto | OTU51401_stoo | |
| OTU50255_stoo | OTU50059_ora | OTU55821_sto | OTU50016_oral | |

In one embodiment, modulated abundance of at least five CRC-associated faecal bacteria and at least five CRC-associated oral bacteria of Table 16 correlates with increased risk of the individual having a colorectal polyp (and therefore a prognosis of risk of developing colorectal cancer).

In one embodiment, modulated abundance of at least 5, 10, 14, 15, or all CRC-associated faecal bacteria and at least 5, 10, 11, or all CRC-associated oral bacteria of Table 19 correlates with increased risk of the individual having a colorectal polyp (and therefore a prognosis of risk of developing colorectal cancer).

In one embodiment, modulated abundance of at least 5,10, 20, 26, 27, or all CRC-associated bacteria of Table 19 correlates with increased risk of the individual having a colorectal polyp (and therefore a prognosis of risk of developing colorectal cancer).

In one embodiment, modulated abundance of substantially all of the CRC-associated bacteria of Table 19 correlates with increased risk of the individual having a colorectal polyp (and therefore a prognosis of risk of developing colorectal cancer). In some embodiments, modulated abundance of all of the CRC-associated bacteria of Table 19 correlates with increased risk of the individual having a colorectal polyp (and therefore a prognosis of risk of developing colorectal cancer). In some embodiments, modulated abundance of at least 5, 10, 15, or 16 CRC-associated faecal bacteria and at least 5, 10, 11, or 12 CRC-associated oral bacteria of Table 19 correlates with increased risk of the individual having a colorectal polyp (and therefore a prognosis of risk of developing colorectal cancer). In some embodiments, modulated abundance of 16 CRC-associated stool bacteria and 12 CRC-associated oral bacteria of Table 19 correlates with increased risk of the individual having a colorectal polyp (and therefore a prognosis of risk of developing colorectal cancer).

In some embodiments, modulated abundance of at least 5 (e.g. at least 5, 6, 7, 8, 9 or all) CRC-associated oral bacteria selected from *Prevotella, Campylobacter, Alloprevotella, Atopobium, Abiotrophia, Selenomonas, Haemophilus, Streptococcus*, and *Roseburia* correlates with increased risk of the individual having a colorectal polyp (and therefore a prognosis of risk of developing colorectal cancer). In some embodiments, modulated abundance of at least 5 (e.g. at least 5, 10, 11, or all) CRC-associated faecal bacteria selected from Ruminococcaceae, *Blautia, Bacteroides, Paraprevotella, Clostridium*_XIVa, *Flavonifractor, Anaerostipes*, Lachnospiraceae, *Bamesiellai, Eubacterium, Clostridium* IV, and *Faecalibacterium* correlates with increased risk of the individual having a polyp (and therefore a prognosis of risk of developing colorectal cancer).

In a further aspect, the invention provides a method of determining colorectal cancer status in an individual comprising the steps of assaying a biological sample from an oral cavity of the individual for an abundance of at least five CRC-associated oral bacteria, comparing the abundance of the at least three CRC-associated oral bacteria with a reference abundance for the CRC-associated oral bacteria to detect modulated abundance of CRC-associated oral bacteria, assaying a faecal sample from the individual for an abundance of at least three CRC-associated oral bacteria, and comparing the abundance of the at least five CRC-associated faecal bacteria with a reference abundance for the CRC-associated faecal bacteria to detect modulated abundance of the at least three CRC-associated faecal bacteria. In some embodiments, detection of modulated abundance of the at least three CRC-associated oral bacteria and the at least three CRC-associated faecal bacteria is indicative of the individual exhibiting a positive CRC status.

The steps of the methods described herein for determining an increased risk of an individual having a colorectal polyp may, in some embodiments, be used to determine whether an individual has an increased risk of having an adenoma.

In one embodiment, the individual is symptomatic for CRC or colorectal polyps. In one embodiment, the individual is asymptomatic for CRC or colorectal polyps. In one embodiment, the individual has a family history of CRC. In one embodiment, the individual has no family history of CRC.

In one embodiment, determination of positive CRC status is indicative that the individual should undergo a colonoscopy.

In one embodiment, the method of the invention is a method of detecting the response of a patient with CRC (or colorectal polyp) to a CRC therapy. Thus, the abundance profile of the oral microbiome, faecal microbiome, or a combination of both, may be employed to detect or predict the response of the individual to therapy.

In one embodiment, the method of the invention is a method of detecting or predicting recurrence of a CRC (or colorectal polyp) in an individual.

In one embodiment, the method of the invention is a method of detecting metastasis of a CRC (or colorectal polyp) in an individual.

In one embodiment, the method of the invention is a method of detecting the stage (i.e. staging) of a CRC in an individual.

In one embodiment, the invention relates to a method of treatment of CRC in an individual having or at risk of developing CRC, the method comprising a step of administering a therapeutically effective amount of a CRC therapy to the individual, wherein the individual is identified as being at risk of having or developing CRC using a method of the invention.

In one embodiment, the treatment is prophylactic in nature, where the individual is identified as being at risk of developing CRC (i.e. the patient is identified as being at risk of being positive for colorectal polyps), or is identified as being at risk of recurrence of CRC, or is identified at being of risk of CRC metastasis.

In one embodiment, the CRC therapy is selected from surgical resection, drug therapy (i.e. chemotherapy, immunotherapy) and radiotherapy.

In one aspect, a method of determining CRC status comprises assaying an oral sample from an individual and determining an abundance profile of the oral microbiome (individual oral microbiome abundance profile), comparing the individual oral microbiome abundance profile with a reference oral microbiome abundance profile, and correlating the difference between the individual oral microbiome abundance profile and the reference oral microbiome abundance profile with CRC status, wherein the oral microbiome comprises the CRC-associated oral bacteria of Table 1, or the subsets of Tables 2 or 3.

In one aspect, a method of determining CRC status comprises assaying an oral sample from an individual and determining an abundance profile of the oral microbiome (individual oral microbiome abundance profile), comparing the individual oral microbiome abundance profile with a reference oral microbiome abundance profile, and correlating the difference between the individual oral microbiome abundance profile and the reference oral microbiome abundance profile with CRC status, wherein the oral microbiome comprises the CRC-associated oral bacteria of Table 11, or the subsets of Tables 12 or 13.

In one aspect, a method of determining CRC status comprises assaying an oral sample and a faecal sample from an individual and determining an abundance profile of the oral and faecal microbiome (individual oral and faecal microbiome abundance profile), comparing the individual oral and faecal microbiome abundance profile with a reference oral and faecal microbiome abundance profile, and correlating the differences between the individual oral and faecal microbiome abundance profile and the reference oral and faecal microbiome abundance profile with CRC status, wherein the oral and faecal microbiome comprises the CRC-associated oral and faecal bacteria of Table 7, or the subsets of Tables 8 or 9.

In one aspect, a method of determining CRC status comprises assaying an oral sample and a faecal sample from an individual and determining an abundance profile of the oral and faecal microbiome (individual oral and faecal microbiome abundance profile), comparing the individual oral and faecal microbiome abundance profile with a reference oral and faecal microbiome abundance profile, and correlating the differences between the individual oral and faecal microbiome abundance profile and the reference oral and faecal microbiome abundance profile with CRC status, wherein the oral and faecal microbiome comprises the CRC-associated oral and faecal bacteria of Table 17, or the subsets of Tables 18 or 19.

In one embodiment of the methods of the invention described herein, the method involves determining an abundance of all bacteria (or substantially all bacteria) present in the oral and/or faecal microbiome. In one embodiment, the method involves determining an abundance of all bacterial OTUs (or substantially all OTUs) described herein in the oral and/or faecal microbiome.

For example, in some embodiments, the method involves determining an abundance of all bacteria/bacterial OTUs (or substantially all bacteria/bacterial OTUs) present in the oral and/or faecal microbiome, wherein modulated abundance of an individual CRC-associated oral bacterium or of a plurality of CRC-associated oral bacteria (optionally in combination with modulated abundance of an individual or plurality of CRC-associated faecal bacteria) is indicative of positive colorectal cancer status. For example, in some embodiments, the method involves determining an abundance of all bacteria/bacterial OTUs (or substantially all bacteria/bacterial OTUs) present in the oral and/or faecal microbiome, wherein modulated abundance of at least two, e.g. at least five CRC-associated oral bacterium (optionally in combination with modulated abundance of at least two, e.g. at least five CRC-associated faecal bacteria) is indicative of positive colorectal cancer status.

In one embodiment, the step of determining abundance of bacteria in the oral or faecal microbiome comprises a nucleic acid based quantification methodology, for example 16s rRNA gene amplicon sequencing. Methods for qualitative and quantitative determination of bacteria in a sample using 16s rRNA gene amplicon sequencing are described in the literature and will be known to a person skilled in the art. In one embodiment, bacteria in the oral or faecal microbiome are classified into OTUs.

In one embodiment, determining modulated abundance of an oral or faecal bacteria comprises comparing the detected abundance of the bacteria in the sample with a reference abundance that correlates with a healthy control. This comparison step may be carried out using a computer.

In one embodiment, the step of correlating abundance of OTUs in the oral and/or faecal sample with CRC status employs a mathematical model. In one embodiment, the mathematical model is a Random Forest Classification Model.

In one embodiment of the invention, the method of determining CRC status in an individual employs an additional CRC screening test, optionally selected from a high sensitivity fecal occult blood test (FOBT), a stool DNA test (FIT-DNA), Sigmoidoscopy, Standard (or optical) colonoscopy, Virtual colonoscopy, Double-contrast barium enema, detecting the level of methylation in the gene wif-1, abundance or expression of KEGG module markers, and abundance or expression of CAZy family markers.

Also described herein are systems for use in any of the methods described herein. In some embodiments, the systems may comprise a storage device, a comparison module, and a display module.

Also described herein are methods comprising obtaining a biological sample from an oral cavity of an individual. In some aspects, the method may further comprise determining in the biological sample an abundance of at least one CRC-associated oral bacterium. The determining an abundance of at least one CRC-associated oral bacterium may comprise amplifying a 16S rRNA polynucleotide sequence from the at least one CRC-associated oral bacterium to form an amplified 16S rRNA polynucleotide sequence. In some aspects, the amplified 16S rRNA sequence has at least 97% homology to a polynucleotide sequence selected from SEQ ID NOs 1 to SEQ ID NO 326. In some aspects, the method may further comprise measuring a modulated abundance of the at least one CRC-associated oral bacterium compared to a control biological sample taken from an oral cavity of a health individual. In some aspects, a modulated abundance of the at least one CRC-associated oral bacterium may be indicative of a positive colorectal cancer status. In some aspects, the method may further comprise determining the colorectal cancer status of the individual.

Other aspects and preferred embodiments of the invention are defined and described in the other claims set out below.

BRIEF DESCRIPTION OF THE FIGURES

FIGS. 1A-1C: Oral and stool microbiota as predictors of CRC. Receiver Operating Characteristic (ROC) curves for the prediction of CRC (FIG. 1A) and polyps (FIG. 1B) using microbiota profiles from oral swabs, stool, or a combination of both. (FIG. 1C) Strip-charts of the results of the classification model. Dashed lines indicate the respective threshold in each model.

FIGS. 2A-2C Details of the random forest classifier for distinguishing individuals with CRC from healthy persons using oral-swab microbiota. The optimal number of OTUs used in the model was 24 (FIG. 2A). Contribution of all OTUs to the model (FIG. 2B). Strip-chart of the relative abundance of the seven OTUs contributing most to the model (FIG. 2C).

FIGS. 3A-3C Details of the random forest classifier for distinguishing individuals with polyps from healthy persons using oral-swab microbiota. The optimal number of OTUs used in the model was seven (FIG. 3A). Contribution of all OTUs to the model (FIG. 3B). Strip-chart of the relative abundance of the five OTUs contributing most to the model (FIG. 3C).

FIG. 8: Analysis of composition of microbiomes (ANCOM) in oral microbiota.

(FIG. 9A and FIG. 9B) Receiver operating characteristic curves (ROC) and area under the curve (AUC) values for the prediction of CRC (FIG. 9A) and polyps (FIG. 9B) using microbiota profiles from oral swabs, stool or a combination of both. AUC values were highest for the combination test. Significance determined after DeLong (Materials and Methods). Sample numbers: swabs: n=25 (healthy controls), n=45 (CRCs), n=21 (polyps); stool: n=62 (healthy controls), n=69 (CRCs), n=23 (polyps); and combination: n=19 (healthy controls), n=25 (CRCs), n=16 (polyps). CRC, colorectal cancer; FPR, false-positive rate; TPR, true-positive rate.

FIGS. 10A-10C: Details of the Baxter pipeline random forest classifier for distinguishing individuals with CRC from healthy persons using oral-swab microbiota (FIG. 10A). 16 oral microbiota OTUs that distinguish individuals with CRC from healthy controls. Contribution of all 16 OTUs to the model (FIG. 10B). Strip-chart of the relative abundance of the seven OTUs contributing most to the model (FIG. 10C).

FIG. 12: Confirmation of predictive value of oral microbiota for CRC screening using LASSO-RF results.

FIG. 13: Summary of samples analysed in experiment 2.

DETAILED DESCRIPTION OF THE INVENTION

Figure 1C:
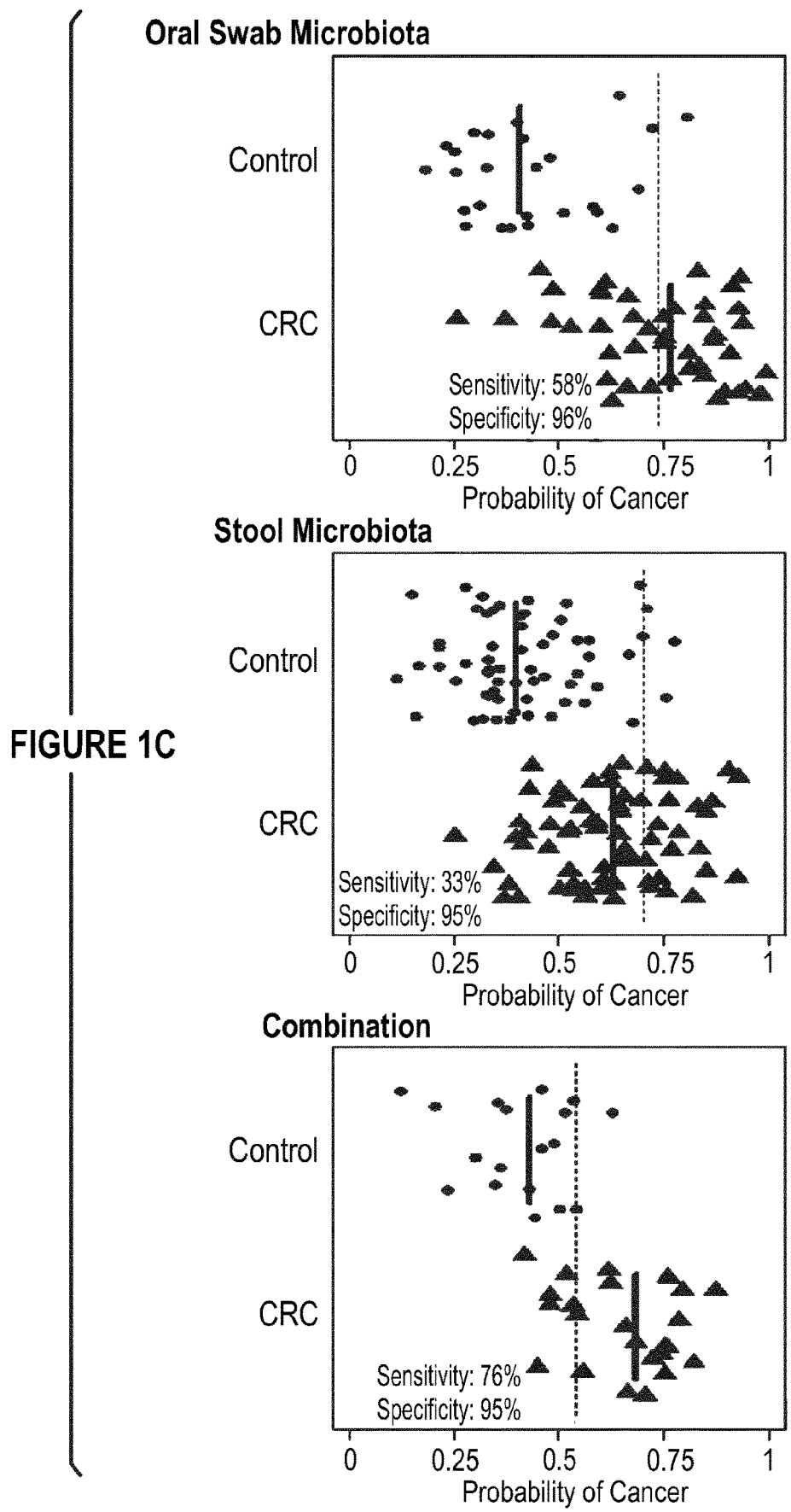

All publications, patents, patent applications and other references mentioned herein are hereby incorporated by reference in their entireties for all purposes as if each individual publication, patent or patent application were specifically and individually indicated to be incorporated by reference and the content thereof recited in full. Supporting information for Flemer B, Lynch D B, Brown J M et al. Tumour-associated and non-tumour-associated microbiota in colorectal cancer. Gut 2017; 66:633-43. doi:10.1136/gutjnl-2015-309595, which can be found at: http://gut.bmj.com/content/early/2017/10/07/gutjnl-2017-314814#DC1, is also hereby incorporated by reference in its entirety.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa.

The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated.

Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "colorectal cancer status" should be understood to mean risk of the individual having or developing colorectal cancer. Thus, the methods of the invention can be employed to identify an increased risk of the patient having CRC compared with the risk of the general population. At least two OTUs are employed, and the diagnostic or prognostic power of the method is generally proportional to the number of OTUs that are employed. In one embodiment, the individual is asymptomatic. In another embodiment, the individual exhibits one or more symptoms of CRC, in which case the methods of the invention can be employed to identify an increased risk of the symptomatic patient having or developing CRC compared with other individuals having the same symptoms. The methods of the invention can be employed to detect risk of the patient having CRC, or detect risk of the patient developing CRC (i.e. patients having colorectal polyps at risk of developing CRC). "Colorectal polyps" should be understood to mean polyps found in the colon or in the rectum. The term "colorectal cancer status" should also be understood to mean determining response of CRC or polyps to treatment, determining the stage of the cancer, monitoring for recurrence of the cancer, monitoring for metastasis of the cancer, or screening an individual to determine whether they should undergo a colonoscopy.

As used herein, the term "biological sample from the oral cavity" refers to a sample obtained from the oral cavity, for example a swab obtained from the cheek, gums, palate, teeth, lips, tongue, or a sample of saliva or a mouth rinse. In a preferred embodiment, the sample is a swab obtained from the individual's cheek.

As used herein, the term "relative abundance" as applied to a bacterium or OTU in a sample should be understood to mean the abundance of the bacterium or OTU in the sample as a proportion of the total microbiota in the sample.

As used herein, the term "modulated relative abundance" as applied to a bacterium or OTU in a sample from an individual should be understood to mean a difference in relative abundance of the bacterium or OTU in the sample compared with the relative abundance in the same sample from a reference healthy individual (hereafter "reference relative abundance"). In one embodiment, the bacterium or OTU exhibits increased relative abundance compared to the reference relative abundance. In one embodiment, the bacterium or OTU exhibits decreased relative abundance compared to the reference relative abundance. Detection of modulated abundance can also be performed in an absolute manner by comparing sample abundance values with absolute reference values. In one embodiment, the reference abundance values are obtained from age and/or sex matched individuals. In one embodiment, the reference abundance values are obtained from individuals from the same population as the sample (i.e. Celtic origin, North African origin, Middle Eastern origin). Method of isolating bacteria from oral and faecal sample are described below, as are methods for detecting abundance of bacteria. Any suitable method may be employed for isolating specific species or genera of bacteria, which methods will be apparent to a person skilled in the art. Any suitable method of detecting bacterial abundance may be employed, including agar plate quantification assays, fluorimetric sample quantification, qPCR, 16S rRNA gene amplicon sequencing, and dye-based metabolite depletion or metabolite production assays.

As used herein, the term "CRC-associated oral bacteria" refers to a bacterium or OTU that exhibits relative modulated abundance in the oral cavity of an individual with CRC or colorectal polyps compared with a reference relative abundance for the bacterium or OTU in the oral cavity of a healthy individual. In one embodiment, the CRC-associated oral bacteria are selected from the OTUs provided in Table 1 (or the subsets of OTUs provided in Tables 2 or 3). In one embodiment, the CRC-associated oral bacteria are selected from the oral OTUs provided in Table 7. (or the subsets of oral OTUs provided in Tables 8 or 9). In one embodiment, the CRC-associated oral bacteria are selected from the OTUs provided in Table 11 (or the subsets of OTUs provided in Tables 12 or 13). In one embodiment, the CRC-associated oral bacteria are selected from the oral OTUs provided in Table 17. (or the subsets of oral OTUs provided in Tables 18 or 19). However, the skilled person will understand that other bacteria or OTU that exhibit modulated relative abundance in the oral cavity of an individual with CRC or colorectal polyps compared with a reference relative abundance for the bacterium or OTU in the oral cavity of a healthy individual may alternatively or additionally be used.

As used herein, the term "CRC-associated faecal bacteria" refers to a bacterium or OTU that exhibits modulated abundance in a faecal sample of an individual with CRC or colorectal polyps compared with a reference relative abundance for the bacterium or OTU in a faecal sample of a healthy individual. In one embodiment, the CRC-associated faecal bacteria or OTUs are selected from the group provided in Table 4. (or the subsets of OTUs provided in Tables 5 or 6). In one embodiment, the CRC-associated faecal bacteria are selected from the faecal OTUs provided in Table 7 (or the subsets of faecal OTUs provided in Tables 8 or 9). In one embodiment, the CRC-associated faecal bacteria or OTUs are selected from the group provided in Table 14. (or the subsets of OTUs provided in Tables 15 or 16). In one embodiment, the CRC-associated faecal bacteria are selected from the faecal OTUs provided in Table 17 (or the subsets of faecal OTUs provided in Tables 18 or 19). However, the skilled person will understand that other bacteria or OTU that exhibit modulated relative abundance in a faecal sample of an individual with CRC or colorectal polyps compared with a reference relative abundance for the bacterium or OTU in a faecal sample of a healthy individual may alternatively or additionally be used.

As used herein, the term "positive CRC status" should be understood to mean increased risk of the individual having CRC, increased risk of the individual having a colorectal polyp (and therefore increased risk of the individual developing CRC, growth of the tumour, advancement of the stage of the cancer, recurrence of the cancer, metastasis of the cancer, or non-response to treatment.

As used herein, the term "symptomatic for CRC" as applied to an individual should be understood to mean that the individual exhibits at least one clinically recognised symptom of CRC. Examples of symptoms include blood in the faeces, persistent change in normal bowel habits (i.e. diarrhoea or constipation with no apparent cause, frequent or constant cramps, and/or stools that are narrower than usual).

As used herein, the term "CRC therapy" refers to a therapeutic intervention which prevents or delays the onset or progression of a colorectal cancer or reduces (or eradicates) its incidence within a treated population. In certain embodiments described herein, are methods described herein further comprising providing CRC therapy to an individual. The CRC therapy can be prophylactic or therapeutic. The CRC therapy can include drug therapy, surgical resection, or radiation therapy, or any combination thereof. The drug therapy may be chemotherapy or immunotherapy or any other (bio)pharmaceutical intervention. The drug may be chemical or a biopharmaceutical. Examples of drugs employs in the treatment or prevention of CRC include Avastin, Bevacizumab, Camptosar, Capacitibine, Cyramza, Oxamiplatin, Erbitux, %-fluorouracil, Irinotecan, Leucovorin calcium, Lonsurf, Panitumumab, Ramucirumab, Regorafenib, Stivarga, Wellcovorin and Xeloda.

As used herein, the term "OTU" should be understood to mean a sequence based bacterial division whereby bacteria are grouped in divisions that share 97% or greater residue identity in the sequences of their 16S rRNA gene amplicons, either the full length genes or variable regions therein. Thus the numerically assigned OTU groupings listed in the Tables in this document correspond to groups/divisions of bacteria that may be identified by an exemplar OTU sequence that all members of the division display 97% or greater sequence identity to. The corresponding OTU sequences, presented in Appendix 1 below, allow unambiguous identification of the range of organisms belonging to the respective OTU divisions. In some embodiments, an OTU comprises bacteria which share 97% or greater residue identity in the sequences of their 16S rRNA gene amplicons, either the full length genes or variable regions therein, to the corresponding OTU sequence described in Appendix 1. In some embodiments, an OTU comprises bacteria which share 97% or greater residue identity in the sequences of their 16S rRNA gene amplicons, either the full length genes or variable regions therein, to the corresponding OTU sequence described in Appendix 1 and wherein the bacteria are from the corresponding genus described in Appendix 1. For example, in some embodiments, OTU0348 comprises bacteria which share 97% or greater residue identity in the sequences of their 16S rRNA gene amplicons, either the full length genes or variable regions therein, to SEQ ID NO:88, wherein the bacteria are from the genus *Prevotella*. Table 21 provides a list of oral CRC-associated OTUs, the ratio of the relative abundance of the OTUs in CRC patients versus healthy individuals, the ratio of the relative abundance of the OTUs in patients with colorectal polyps versus healthy individuals, and the genera of the OTUs.

As used herein, the term "substantially all" as applied to the OTUs in any given Table (or Tables) refers to at least 50%, 60%, 70%, 80%, 90% or 95% of the OTUs in the Table (or Tables).

As used herein, the term "nucleic acid based quantification" as applied to a bacterium or bacterial OTU refers to a method of determining bacterial abundance based on amplification of bacterial nucleic acid. Exemplary methods are described in EP2955232 (Page 11) including PCR, rtPCR, qPCR, high throughput sequencing, metatranscriptomic sequencing, and 16S rRNA analysis. In the methods described herein, 16s rRNA analysis is employed using primers (SEQUENCE ID NO'S 189 and 190) specific for the V3/V4 variable region of the 16S rRNA gene.

As used herein, the term "correlating" as used herein to determine or calculate CRC status based on modulated abundance of bacterial OTUs should be understood to mean any of manual methods of correlation or algorithmic methods. The methodology described herein employs a mathematical modelling technique known as Random Forest Classification, but other modelling techniques may be employed. Thus, in one embodiment, the methods of the invention employ the Random Forest Classification method. Thus, in one embodiment, the methods of the invention may employ a computer program to correlate modulated abundance of multiple OTUs with CRC status.

Also described herein are methods comprising obtaining a biological sample from an oral cavity of an individual. In some aspects, the method may further comprise determining in the biological sample an abundance of at least one CRC-associated oral bacterium. The determining an abundance of at least one CRC-associated oral bacterium may comprise amplifying a 16S rRNA polynucleotide sequence from the at least one CRC-associated oral bacterium to form an amplified 16S rRNA polynucleotide sequence. In some aspects, the amplified 16S rRNA sequence has at least 97% homology to a polynucleotide sequence selected from SEQ ID NOs 1 to SEQ ID NO 326. In some aspects, the method may further comprise measuring a modulated abundance of the at least one CRC-associated oral bacterium compared to a control biological sample taken from an oral cavity of a health individual. In some aspects, a modulated abundance of the at least one CRC-associated oral bacterium may be indicative of a positive colorectal cancer status. In some aspects, the method may further comprise determining the colorectal cancer status of the individual. In some embodiments, the method may further comprise obtaining a faecal sample from the individual. In some embodiments, the method may further comprise measuring a modulated abundance at least one CRC-associated faecal bacteria in said faecal sample as compared to a faecal sample obtained from a normal individual.

In some embodiments, the methods disclosed herein may further comprise administering a pharmaceutical agent to the individual. In some embodiments, the pharmaceutical agent may comprise at least one of Avastin, Bevacizumab, Camptosar, Capacitibine, Cyramza, Oxamiplatin, Erbitux, %-fluorouracil, Irinotecan, Leucovorin calcium, Lonsurf, Panitumumab, Ramucirumab, Regorafenib, Stivarga, Wellcovorin and Xeloda.

Also provided are kits that find use in practicing the subject methods, as mentioned above. A kit can include one or more of the compositions described herein. A kit can comprise an oral swab. The oral swab may be configured to take a biological sample from an oral cavity of an individual. The individual may be suspected of having colorectal cancer. The individual may be suspected of being at increased risk of having colorectal cancer. A kit can comprise a sealable container configured to receive the biological sample. A kit can comprise polynucleotide primers. The polynucleotide primers may be configured for amplifying a 16S rRNA polynucleotide sequence from at least one CRC-associated oral bacterium to form an amplified 16S rRNA polynucleotide sequence, wherein the amplified 16S rRNA sequence has at least 97% homology to a polynucleotide sequence selected from SEQ ID NOs 1 to SEQ ID NO 326. A kit may comprise a detecting reagent for detecting the amplified 16S rRNA sequence. A kit may comprise instructions for use.

Figure 5:
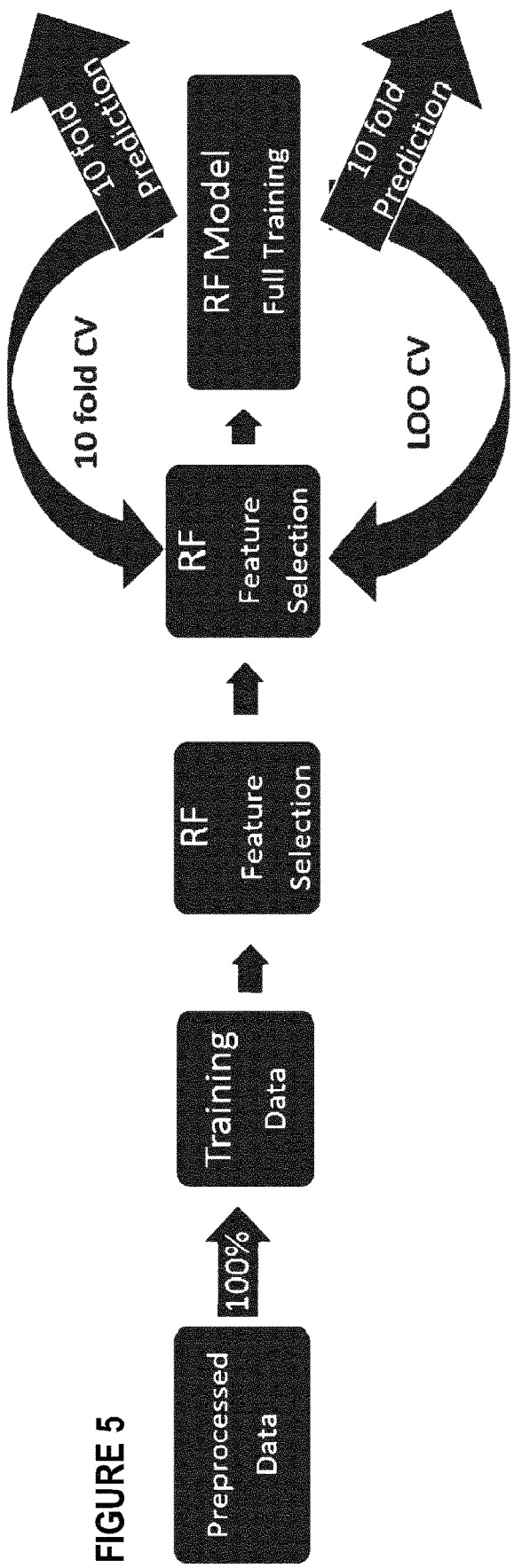
FIG. 5: The Baxter pipeline schematic showing the two feature section steps where the initial is before CV occurs.

In some embodiments, the Random Forest (RF) classifier uses log-ratio transformed values of OTUs present in at least 5% of individuals as input to the function AUCRF of the AUCRF package [50]. Significance of difference between ROC curves may be assessed using the function roc.test of the pROC package [51]. In some embodiments the Baxter pipeline is used [3]. A schematic is depicted in FIG. 5. Preferably, in the Baxter pipeline, the full dataset is pre-processed (i.e. filtered to exclude features which are present in less than 5% of individuals) and subsequently 100% of data is used as a training dataset for the rest of the pipeline. First, feature selection is preferably performed outside of CV using the RF algorithm as implemented by the AUCRF R statistical package [54]. Second, the training data is preferably used in 10 fold CV and/or a Leave-one-out (LOO) CV. There is no independent test set for validation of the final RF models.

In some embodiments, the Random Forest (RF) classifier is the LASSO pipeline method which comprises a two-step procedure—the Least Absolute Shrinkage and Selection Operator (LASSO) feature selection, followed by RF modelling. This is an in-house pipeline and is described further herein. It involves pre-processing the full dataset (i.e. so that it is preferably filtered to exclude features which were present in less than 5% of individuals). Ten-fold cross-validation (CV) is then preferably applied to the data. Within each iteration of the 10-fold CV, feature selection is performed using the LASSO algorithm on 90% of the dataset, which is used as a training set to generate a predictive model within each iteration. LASSO improves accuracy and interpretability of models by efficiently selecting the relevant features, a process which is tuned by the parameter lambda. The model may be generated within the 10-fold CV training data by filtering the dataset to include only the features selected by the LASSO algorithm, and RF is then used for subsequent modelling of this subset. Both LASSO feature selection and RF modelling can be performed within the 10-fold CV, which generates an internally validated list of features and an internal 10-fold prediction in order to generate an estimate of the predictive value of the overall model. A schematic for this protocol is presented in FIG. 6. In some embodiments, the threshold is Youden optimized[55] to improve the sensitivity and specificity.

Embodiments of the invention also provide for systems (and computer readable media for causing computer systems) to perform a method for determining CRC status in an individual. Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

Figure 4:
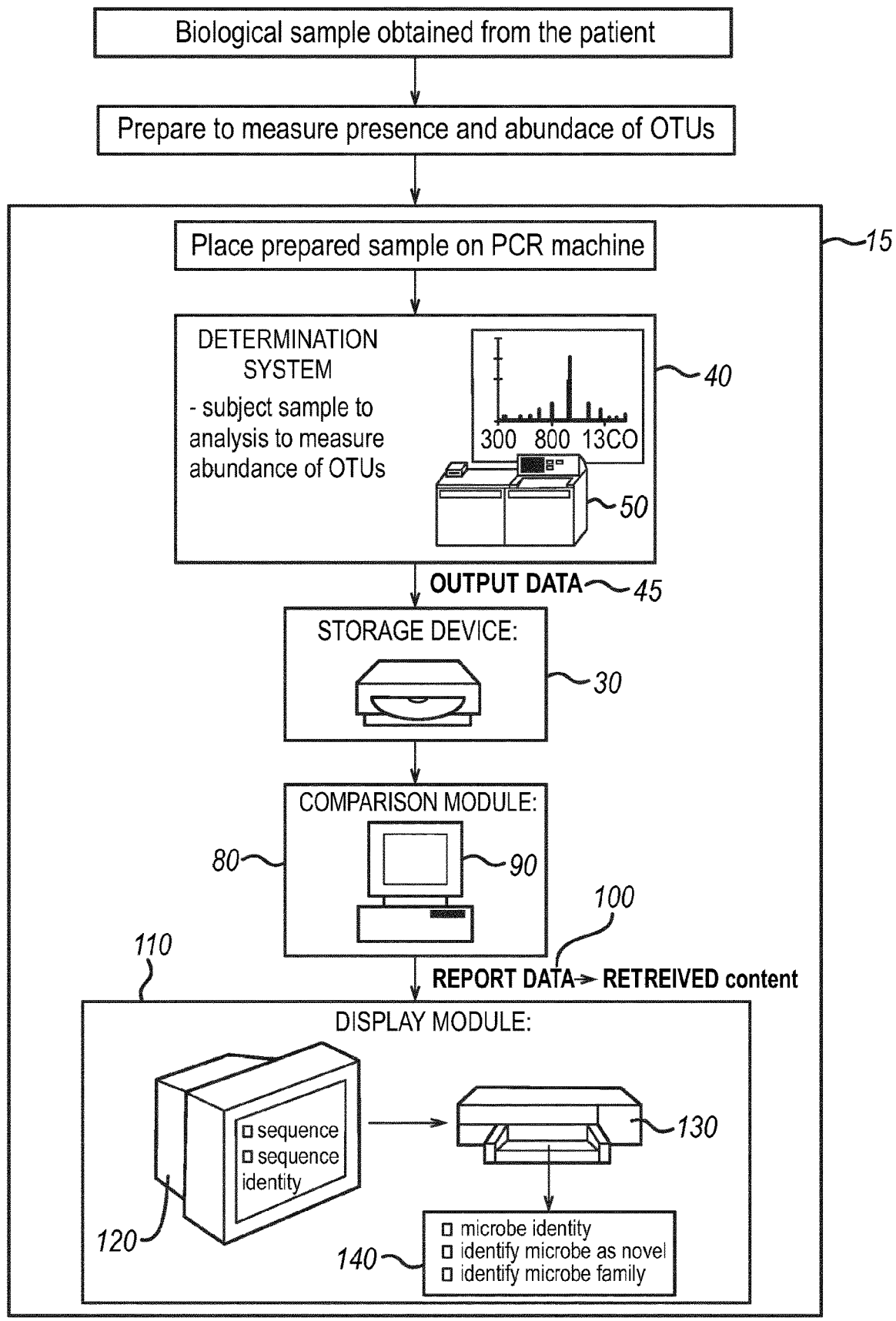
FIG. 4: An illustration of a system according to the invention for performing a method of determining colorectal cancer status in an individual.

Referring generally to FIG. 4, the computer readable storage media #30 can be any available tangible media that can be accessed by a computer. Computer readable storage media includes volatile and non-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable storage media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium described herein, may be distributed across one or more of such components.

The computer-readable storage media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system #40, optionally, a storage device #30, a comparison module #80, and a display module #110. The functional modules can be executed on one, or multiple, computers, or by using one, or multiple, computer networks. The determination system has computer executable instructions to provide e.g., sequence information in computer readable form.

The determination system #40, can comprise any system for detecting at least one of the OTUs described herein. Such systems will typically determine the relative abundance of OTUs in the biological sample. Standard procedures such as 16s rRNA gene analysis can be used.

Additionally one can determine other factors such as age, sex, weight, tobacco use and family history. These factors can be used in conjunction with the OTUs in assessing risk of CRC or colorectal polyps.

The information determined in the determination system can be read by the storage device #30. As used herein the "storage device" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to:

magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon metabolite abundance information. Such information may be provided in digital form that can be transmitted and read electronically, e.g., via the Internet, on diskette, via USB (universal serial bus) or via any other suitable mode of communication. As used herein, "stored" refers to a process for encoding information on the storage device. Those skilled in the art can readily adopt any of the presently known methods for recording information on known media to generate manufactures comprising information relating to these metabolites and other pregnancy factors.

In one embodiment the reference data stored in the storage device to be read by the comparison module is compared, e.g., relative abundance of a particular OTU in sample with a normal healthy or confirmed CRC control.

The "comparison module" #80 can use a variety of available software programs and formats for the comparison operative to compare OTU abundance information data determined in the determination system to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to the CRC-associated OTUs.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module #110.

The content based on the comparison result, may be from a healthy individual. Alternatively, the content based on the comparison result may be from an individual with CRC or a colorectal polyp.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module.

Thus, the user will typically point and click to user interface elements such as buttons, pull down menus, scroll bars and the like conventionally employed in graphical user interfaces. The methods described herein therefore provide for systems (and computer readable media for causing computer systems) to perform methods for determining CRC status in an individual.

Systems and computer readable media described herein are merely illustrative embodiments of the invention for performing methods of diagnosis or prognosis in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

The invention also provides a computer program which when executed on a computer causes the computer to perform a process for determining CRC status in an individual, the process comprising: inputting relative abundance data for a plurality of CRC associated oral or faecal OTUs; comparing the abundance of the OTUs with a reference abundance for the OTUs; and a correlation step to determine CRC status based on the comparison step.

Panels and combinations of oral and faecal OTUs are described above. Preferably, the step of determining the CRC status of the individual comprises determining the likelihood of CRC or colorectal polyps using a multivariate analysis which typically comprises using the relative abundance of the OTUs and distribution parameters derived from a set of reference relative abundance values. In one embodiment, the multivariate analysis employs a Random Forest Classification Model. In another embodiment, the Random Forest Classification Model is a LASSO pipeline method.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Sampling

CRC-Patients: In total, 89 individuals scheduled for colonic resection at Mercy University Hospital, Cork, were recruited to the study. Exclusion criteria were a personal history of CRC, inflammatory bowel disease (IBD) or inflammatory bowel syndrome (IBS). Individuals were not treated with antibiotics in the month prior to surgery but were administered antibiotics intravenously within a few hours of the resection. Faecal samples were self-sampled prior to the start of the bowel preparation, transported to the laboratory on ice and frozen at −80° C. In total, stool samples from 69 individuals were analysed. Oral samples were obtained by rubbing the inside of both cheeks with a swab. Samples were stored at −80°. In total, oral swab samples from 45 individuals were analysed.

Polyps: In total, 29 individuals scheduled for colonoscopy at Mercy University Hospital, Cork, were recruited to the study. Exclusion criteria included IBD and IBS and the use of antibiotics 1 month prior to colonoscopy. Faecal samples were self-sampled prior to the start of the bowel preparation, or at least 4 weeks after the procedure, transported to the laboratory on ice and frozen at −80° C. In total, stool samples from 24 individuals were analysed. Oral samples were obtained by rubbing the inside of both cheeks with a swab. Samples were stored at −80°. In total, oral swab samples from 22 individuals were analysed.

Healthy Controls: In total, 31 individuals scheduled for colonoscopy at Mercy University Hospital, Cork, were recruited to the study. Exclusion criteria included IBD, IBS and CRC. Faecal samples were self-sampled prior to the start of the bowel preparation, or at least 4 weeks after the procedure, transported to the laboratory on ice and frozen at −80° C. Additional 38 stool samples were selected from a previously collected cohort of healthy elderly people[12]. In total, stool samples from 62 healthy individuals were analysed. Oral samples were obtained by rubbing the inside of both cheeks with a swab. Samples were stored at −80°. In total, oral swab samples from 26 healthy individuals were analysed.

TABLE 20

Summary of samples analysed

| | CRC | Polyp | Control |
|---|---|---|---|
| Oral swab | 45 | 22 | 26 |
| Stool | 69 | 24 | 62 |
| Total number of individuals | 89 | 29 | 69 |

The study was approved by the UCC Ethics Committee under the study number APC033.

DNA/RNA extraction, 16S rRNA amplicon sequencing and analysis of 16S amplicon sequencing data is performed according to the method of Flemer, et al[2].

Statistical Analysis

Statistical analysis was carried out in R[23]. Differential abundance of OTUs between groups was assessed using DESeq2[32]. The random forest classification model to determine OTUs suitable as biomarkers of colonic lesions is described elsewhere.[3]

Results

Oral Microbiota

Microbiota profiling by sequencing identifies bacterial taxa as sequence-based divisions or Operational Taxonomic Units (OTUs). Several oral microbiota OTUs (grouped at 97% sequence similarity) were differentially abundant between individuals with CRC and healthy controls (p<0.1), with one OTU classified as *Streptococcus* (higher abundance in CRC) and three OTUs classified as *Porphyromonas*, *Haemophilys* and *Prevotella* (lower abundance in CRC) being the most differentially abundant taxa. Almost all differentially abundant OTUs (12/15) were less abundant in individuals with CRC than in healthy individuals. Collectively, members of the phyla *Actinobacteria* and Firmicutes were significantly more abundant in the oral microbiota of individuals with CRC compared to that of healthy individuals.

Oral and Faecal Microbiota—Model

Figure 2A:
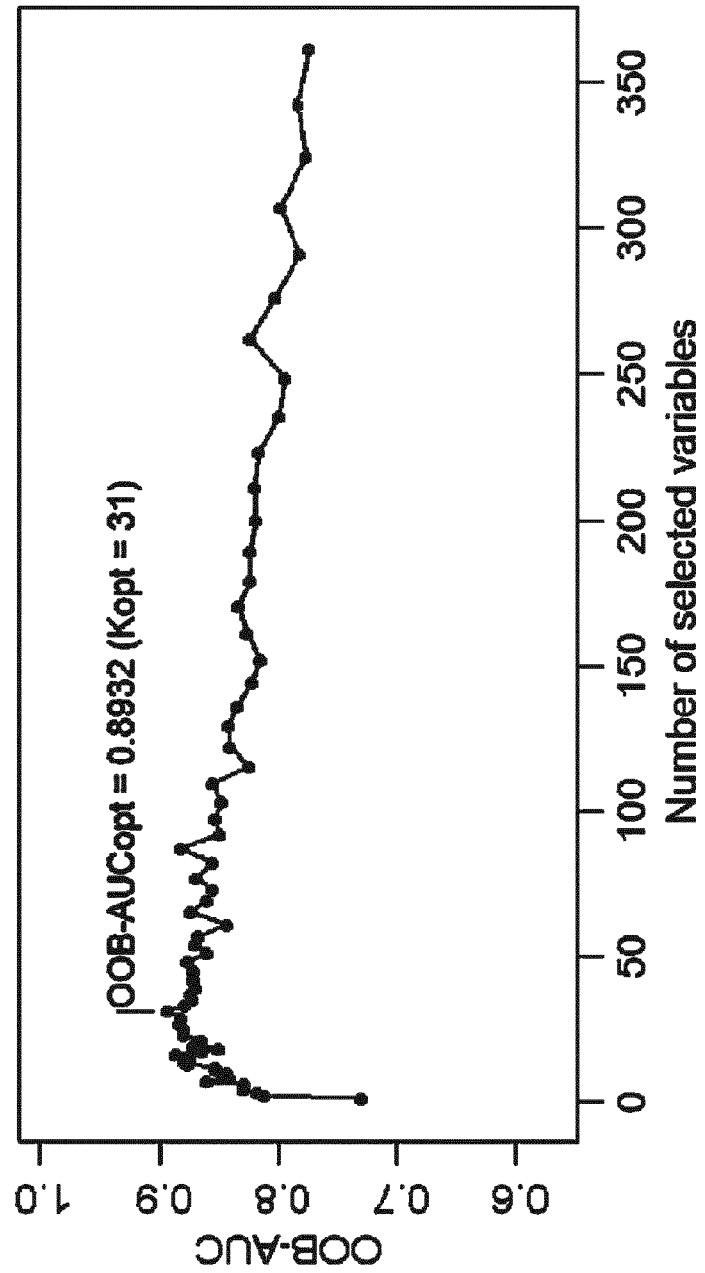
Figure 2B:
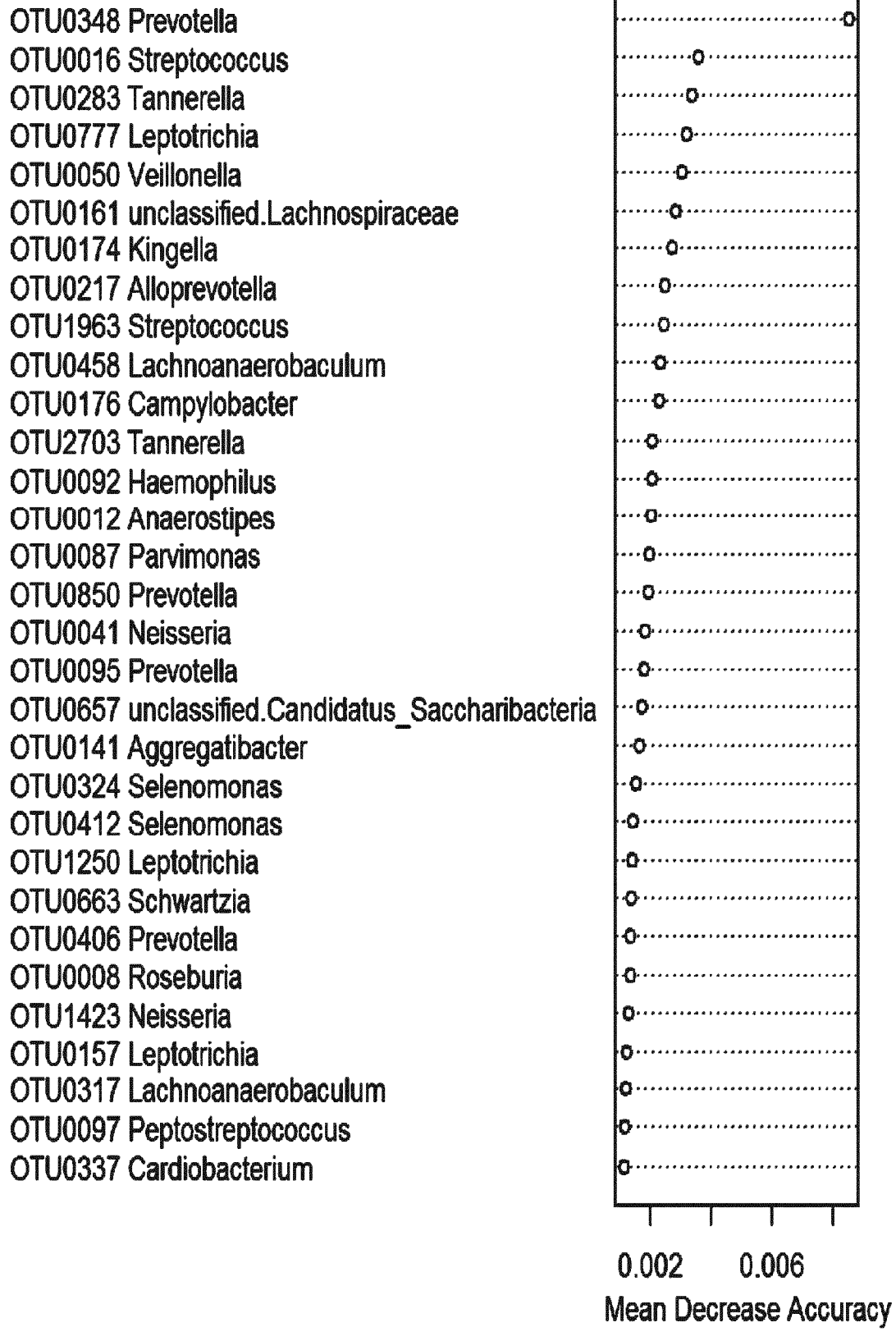
Figure 3A:
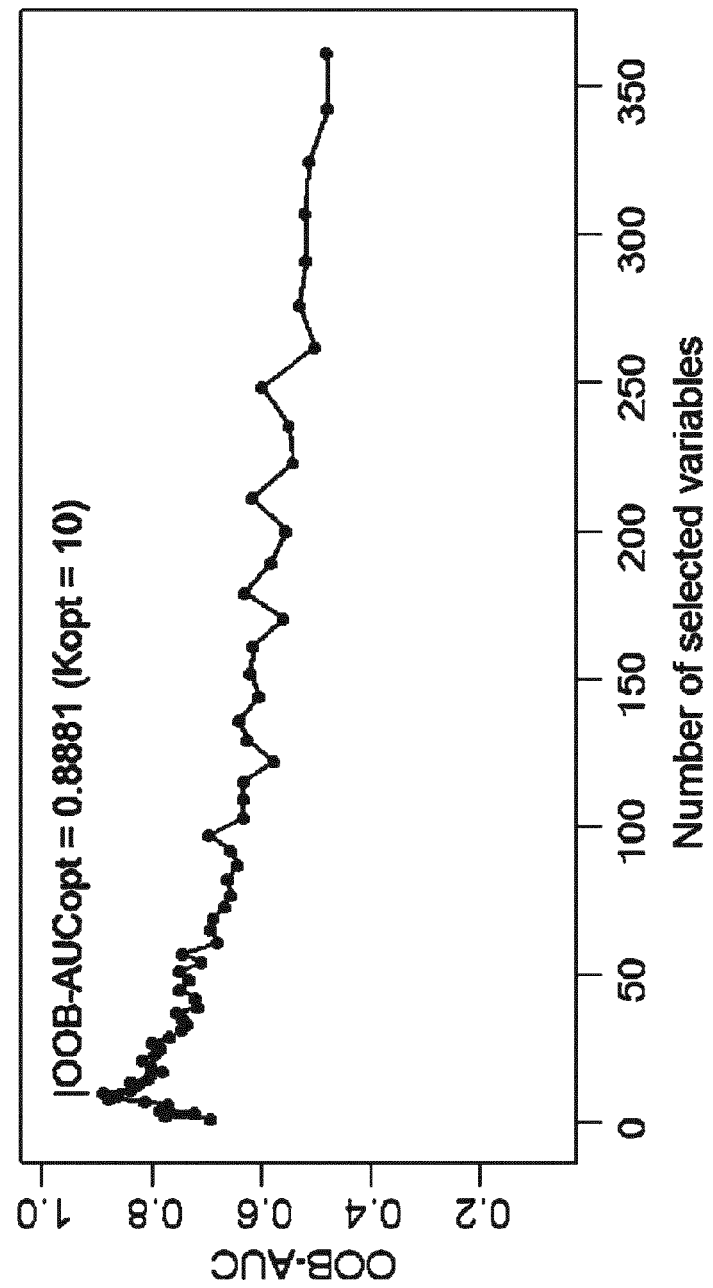
Figure 3B:
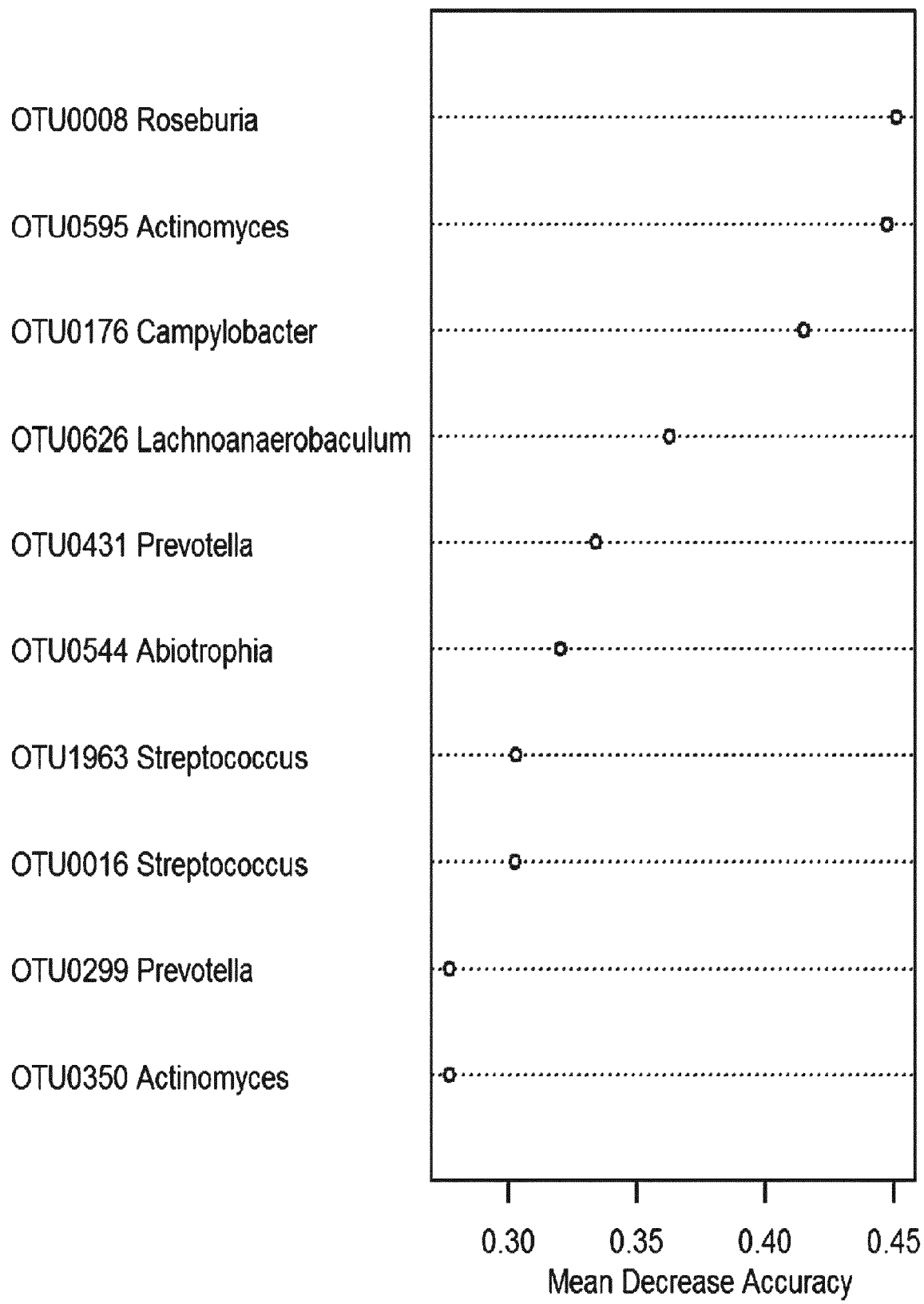

A previously established random forest classification model was employed as a screening tool for identifying subjects with polyps and CRCs[3]. The model identified 31 oral microbiota OTUs that distinguish individuals with CRC from healthy controls. The sensitivity of detection was 58% (95% CI [35.56%, 84.44%]) with a specificity of 96% (AUC: 0.893; 95% CI [0.8181, 0.9682]; Table 2 and FIGS. 2A-2C). The model could also be used to detect individuals with colorectal polyps based on the abundance of 10 oral OTUs (55%; 95% CI [31.82%, 90.91%]; AUC: 0.888; 95% CI [0.7944,0.9819]; Table 3). The results are also consistent with previous reports[3,4] in that faecal microbiota abundance of selected OTUs is able to distinguish individuals with CRC or polyps from healthy persons (FIGS. 1A-1C).

A combination of oral and stool microbiota data improved the model sensitivity to 76% for CRC (95% CI [44%, 92%], AUC: 0.916; 95% CI [0.8379,0.9936]) for the detection of CRCs and 82% for polyps (95% CI [58.82%, 100%], AUC: 0.913; 95% CI [0.7932,1]) for the detection of polyps (both: specificity 95%) (Table 7). Analysis of the abundances of 42 bacterial OTUs were optimal for the differentiation between individuals with polyps and healthy controls (for 23 OTUs the abundance in the oral cavity was used, for 19 OTUs the faecal abundance was used) (Table 9); the model for the detection of CRCs used 77 OTUs (24 oral OTUs, 53 stool OTUs) (Table 8).

Example 2

Sampling, DNA Extraction and 16S rRNA Gene Amplicon Sequencing

The samples analysed in Example 2 are the same samples as described in Example 1. A detailed description of the sampling follows: CRC patients: Individuals scheduled for colonic resection at Mercy University Hospital, Cork, were recruited to the study. These individuals had presented with altered bowel habits, rectal bleeding, or other factors, and had a conformed diagnosis of cancer prior to surgery. Exclusion criteria were a personal history of CRC, IBD or IBS. Individuals were not treated with antibiotics in the month prior to surgery but were administered antibiotics intravenously within a few hours of the resection. After surgery, two samples from up to five different sites were collected in RNAlater (Qiagen, Hilden, Germany): OFFD (off-distal; 2-5 cm towards the distal end of the colon), OFFP (off-proximal; 2-5 cm towards the proximal end of the colon), UDD (undiseased distal; as far away from the cancer as possible; distal; usually 10-30 cm) and UDP (undiseased proximal; as far away from the cancer as possible; proximal; usually 10-30 cm). Samples were placed in 3 mL RNAlater, stored at 4° C. for 12 h and then stored at −20° C. Faecal samples were self-sampled prior to the start of the bowel preparation, transported to the laboratory on ice and frozen at −80° C.

Polyps: Polyp biopsies were collected from patients presenting for routine colonoscopy [34]. Biopsy samples from individuals with polyps were obtained in RNAlater as described above. Mostly, undiseased tissue was collected from individuals with polyps because the small polyp sample was reserved for examination by a pathologist. Up to two biopsies were obtained per individual upon endoscopy, one from undiseased tissue in the descending colon and one from undiseased tissue in the ascending colon. Exclusion criteria included IBD and IBS and the use of antibiotics 1 month prior to surgery. No stool samples were sampled from individuals with polyps.

Healthy controls: These individuals had presented with altered bowel habits, rectal bleeding, or other factors. Biopsy samples from healthy controls were obtained in RNAlater as described above. Exclusion criteria included IBD, IBS and CRC and use of antibiotics 1 month prior to sampling. Up to three biopsies were obtained per individual upon endoscopy, one from the descending colon, one from the transverse and one from the ascending colon. Stool samples were collected as described above. Additional samples were selected from a previously collected cohort of healthy elderly people [35].

Oral samples were obtained by rubbing the inside of both cheeks with a swab. Oral swabs were stored at −80° C. No restrictions on tooth brushing or mouthwashes were applied. A summary of the samples analysed is provided in FIG. 13.

The study was approved by the University Ethics Committee under the study number APC033.

DNA/RNA Extraction and 16S rRNA Gene Amplicon Sequencing

The protocol for simultaneous DNA and RNA extraction from all sample types is described elsewhere [34]. Briefly, genomic DNA and total RNA was extracted using the AllPrep DNA/RNA kit from Qiagen (Hilden, Germany). Samples were homogenized using bead tubes with 250 μl of 0.1 mm sterile glass beads and several 3-4 mm sterile glass beads in a MagnaLyzer (Roche, Penzberg, Germany). The rest of the DNA extraction was carried out according to the AllPrep DNA/RNA extraction kit (Qiagen, Hilden, Germany).

16S rRNA gene amplicon sequencing was carried out employing the 16S Metagenomic Sequencing Library Preparation protocol developed by Illumina (Illumina, San Diego, USA). Briefly, 200 ng of mucosal DNA (50 ng for faecal samples, 25 ng for oral swab samples) was amplified employing primers targeting the V3/V4 variable region of the 16S rRNA gene: 16S Amplicon PCR Forward Primer (V3 region) 5'-TCGTCGGCAGCGTCA-GATGTGTATAAGAGACAGCCTACGGG-NGGCWGCAG (SEQUENCE ID NO: 189); 16S Amplicon PCR Reverse Primer (V4 region) 5'-GTCTCGTGGGCTCGGAGATGTGTATAAGA-GACAGGACTACHVGGGTATCTAATC C 13 (SEQUENCE ID NO: 190). The products were purified and forward and reverse barcodes were attached (Nextera XT v2 Index Kit set A and D, Illumina, San Diego, USA). Pools of amplicons were sequenced at GATC (Konstanz, Germany) on a MiSeq sequencing instrument (Illumina, San Diego, USA) using 2×250 bp chemistry.

Analysis of 16S Amplicon Sequencing Data 16S amplicon sequences from our Irish cohort were processed as previously described [34]. We also conducted a meta-analysis with amplicon sequencing data pertaining to Gevers et al [41] and processed data associated with this study similarly. In order to compare bacterial operational taxonomic units (OTUs) obtained in the Irish CRC cohort (sequenced region: V3-V4) with OTUs obtained in the Crohn's disease cohort (V4), we shortened the sequences of the CRC cohort to the sequenced region of the CD cohort using cutadapt [36] and then processed the sequences of the two studies together.

Briefly, adaptors were removed using cutadapt [36] and paired-end reads were merged using FLASH [37]. Libraries were split using QIIMEs [38] split_libraries_fastq.py script. An OTU (operational taxonomic unit) table was obtained using usearch [39] (open reference approach). Representative OTU-sequences were classified using mother [40] and RDP reference, version 14. We removed three OTUs from further analysis which were detected in sequenced negative controls (the OTUs were classified as *Halomonas* (2 OTUs) and *Shewanella*). Since we have previously [34] found no differences both between the four samples from OFF the cancer (OFFD, OFFP, UDD and UDP) we merged these sequences per individual and refer to this merged sample as OFF throughout this example. Similarly, we could not detect differences between left and right sided biopsy samples from healthy controls [34] and as a consequence pooled the sequences per individual. Amplicon sequencing data pertaining to Gevers et al. [41] was analysed similarly. In order to compare bacterial OTUs obtained in the Irish CRC cohort (sequenced region: V3-V4) with OTUs obtained in the Crohn's disease (CD) cohort (V4) we shortened the sequences of the CRC cohort to the sequenced region of the CD cohort using cutadapt and then processed the sequences of the two studies together as described above.

Statistical Analysis

Statistical analysis was carried out in R [42]. Standard visualizations were carried out using base R or ggplot2 [43]. Unweighted UniFrac distances were calculated in QIIME using data rarified to the lowest sequencing depth per sample (5652 sequences) [38] and were visualized using function s.class [44]. Statistical significance was established using permutational analysis of variance (PERMANOVA) using distance matrices and the function adonis of the vegan package [45]. Differential abundance of OTUs between groups was assessed using analysis of composition of microbiomes (ANCOM) [47] with an FDR<0.1 and raw read counts. Other P-values were adjusted using the function p.adjust (stats package of base R) and the method of Benjamini and Hochberg [48]. Significance was assumed for adjusted P-values equal to or below 0.05, if not stated otherwise.

CRC Classifier

The Random Forest (RF) classifier to determine OTUs suitable as biomarkers of colonic lesions was described elsewhere [49]. In brief, we used log-ratio transformed values of OTUs present in at least 5% of individuals as input to the function AUCRF of the AUCRF package [50]. Significance of difference between ROC curves was assessed using the function roc.test of the pROC package [51]. A schematic is depicted in FIG. 5. We also employed an in-house pipeline for classification which consisted of a two-step procedure—the Least Absolute Shrinkage and Selection Operator (LASSO) feature selection, followed by RF modelling. The full dataset was pre-processed (i.e. filtered to exclude features which were present in less than 5% of individuals). Ten-fold cross-validation (CV) was applied to the data. Within each iteration of the 10-fold CV, feature selection was performed using the LASSO algorithm on 90% of the dataset, which was used as a training set to generate a predictive model within each iteration. LASSO improves accuracy and interpretability of models by efficiently selecting the relevant features, a process which is tuned by the parameter lambda. The model was generated within the 10-fold CV training data by filtering the dataset to include only the features selected by the LASSO algorithm, and RF was used for subsequent modelling of this subset. Both LASSO feature selection and RF modelling were performed within the 10-fold CV, which generates an internally validated list of features and an internal 10-fold prediction in order to generate an estimate of the predictive value of the overall model. We report both the results from the default threshold selected by the model and a Youden optimized result where the threshold has been optimized to improve the sensitivity and specificity. A schematic for this protocol is presented in FIG. 6.

Results

The Oral Microbiota is Significantly Different in CRC

We analysed the microbiota from individuals with CRC, colorectal polyps and healthy controls from multiple body sites (FIG. 13) using 16S rRNA gene amplicon sequencing.

Figure 7:
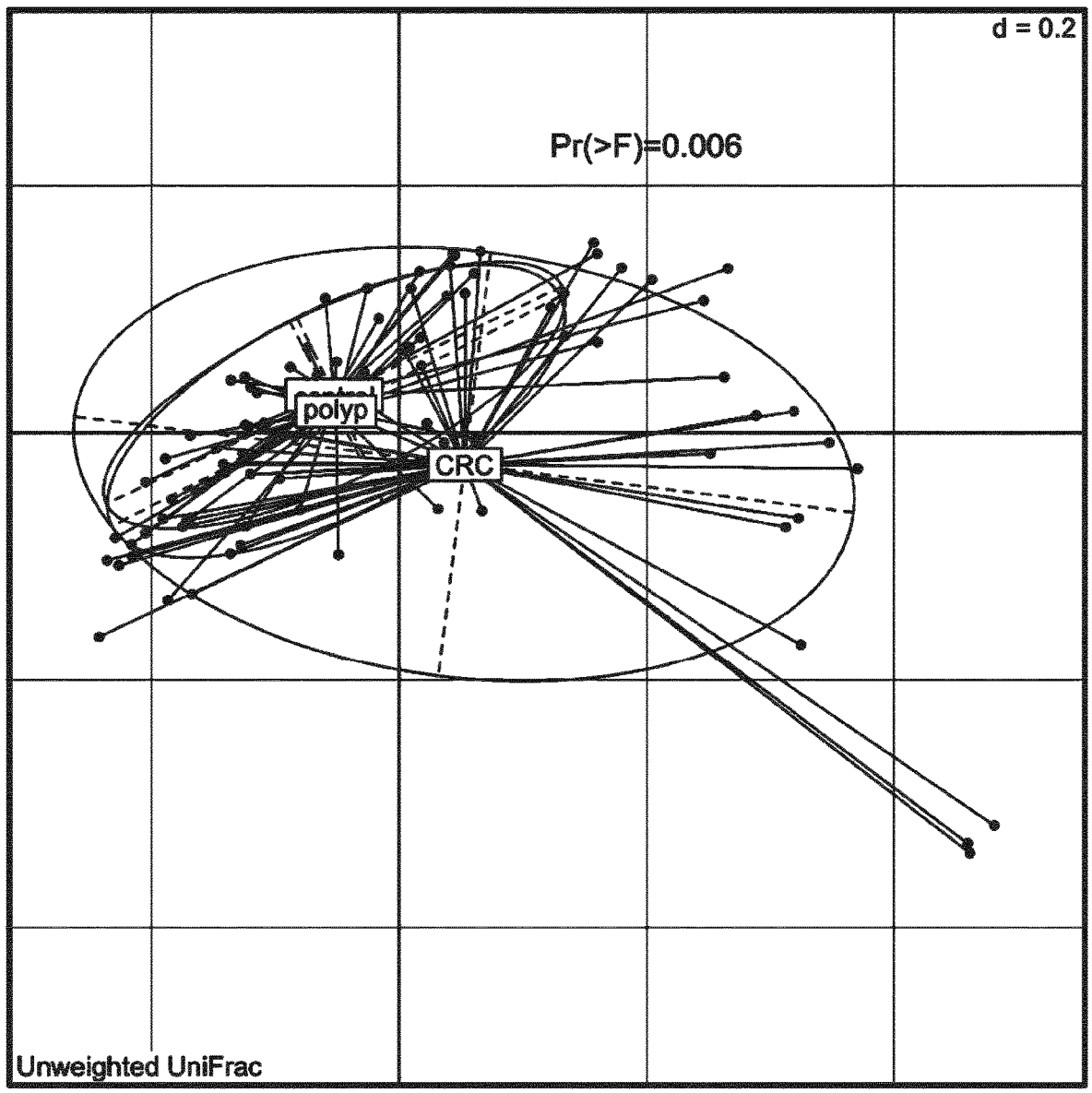
FIG. 7: The oral microbiota of individuals with CRC is statistically significantly different from that of healthy individuals. Shown is the PCoA of the unweighted UniFrac distance (significance assessed using PERMANOVA as described in Materials and Methods). CRC, colorectal cancer; PERMANOVA, permutational analysis of variance.

Microbiota profiling by sequencing identifies bacterial taxa as sequence-based divisions or OTUs. The overall oral profile of bacterial OTUs (grouped at 97% sequence similarity) was significantly different between individuals with CRC and healthy controls (permutational analysis of variance of the unweighted UniFrac distance, FIG. 7). Moreover, eight oral microbiota OTUs were differentially abundant between individuals with CRC and healthy controls (ANCOM, FDR<0.05) (FIG. 8). Differentially abundant OTUs were classified as *Haemophilus, Parvimonas, Prevotella, Alloprevotella, Lachnoanaerobaculum, Neisseria, Leptotrichia*, and *Streptococcus* (FIG. 8). Almost all differentially abundant OTUs (7/8) were less abundant in individuals with CRC than in healthy individuals. Even though the overall microbiota was similar between individuals with polyps and healthy controls, four individual bacterial OTUs were differentially abundant between the two groups (FIG. 8), three of which were also differentially abundant in CRC. The four differentially abundant OTUs for polyps were classified as *Parvimonas, Streptococcus, Leptotrichia* and *Prevotella* (FIG. 8).

Oral and Stool Microbiota as Biomarkers of CRC

Current non-invasive screening tools for CRC can reliably detect advanced carcinomas based on traces of blood in faeces released by colonic lesions, but these methods suffer from low sensitivity for detecting early lesions [22]. Motivated by the findings presented above, we assessed the suitability of oral microbiota as a screening tool for identifying subjects with polyps and CRC by employing a previously established RF classification methodology [49] (FIG. 5). The model identified 16 oral microbiota OTUs that distinguish individuals with CRC from healthy controls (Table 12). The sensitivity of detection was 53% (95% CI (31.11% to 93.33%) with a specificity of 96% (area under the curve (AUC): 0.9; 95% CI (0.83 to 0.9); FIGS. 9A-9B and FIGS. 10A-10C). The model could also be used to detect individuals with colorectal polyps based on the abundance of 12 oral OTUs (Table 13) (sensitivity 67%; 95% CI (23.81% to 90.48%); AUC: 0.89; 95% CI (0.8 to 0.89); FIGS. 9A-9B and FIGS. 11A-11C) with a specificity of 96%.

Figure 9A:
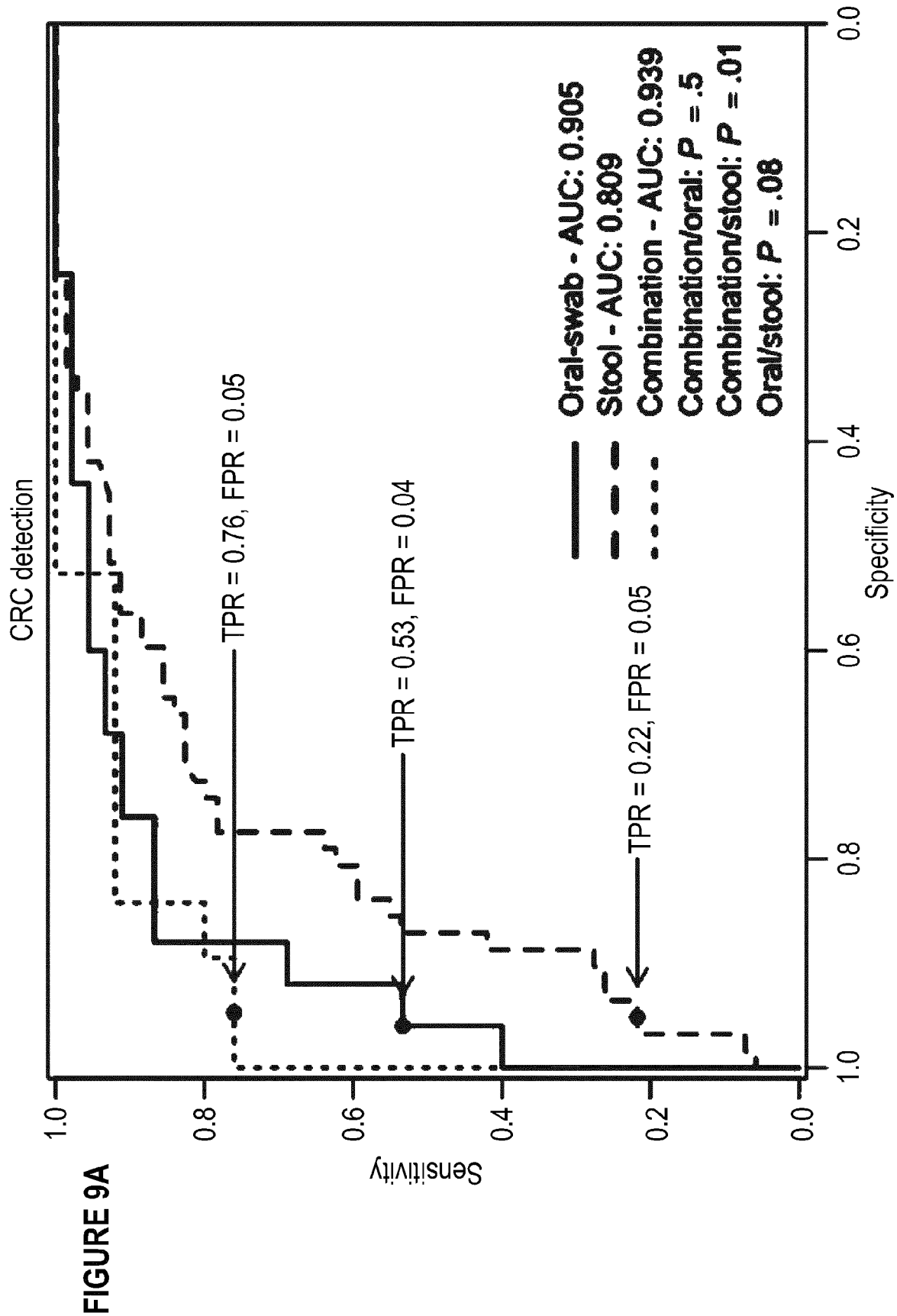
FIGS. 9A-9B: Oral and stool microbiota profiles as tools for the detection of CRC.
Figure 9B:
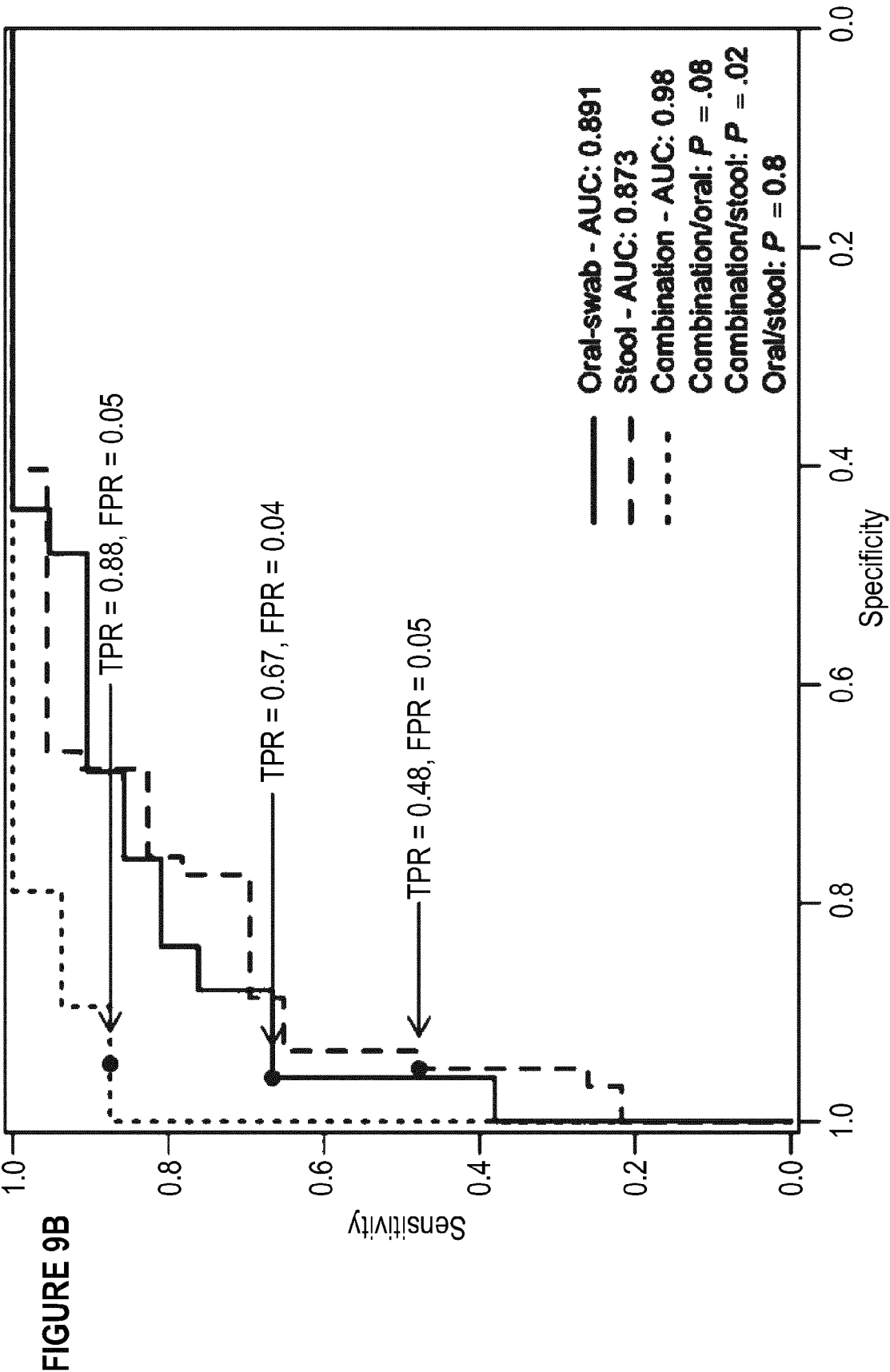
Figure 10B:
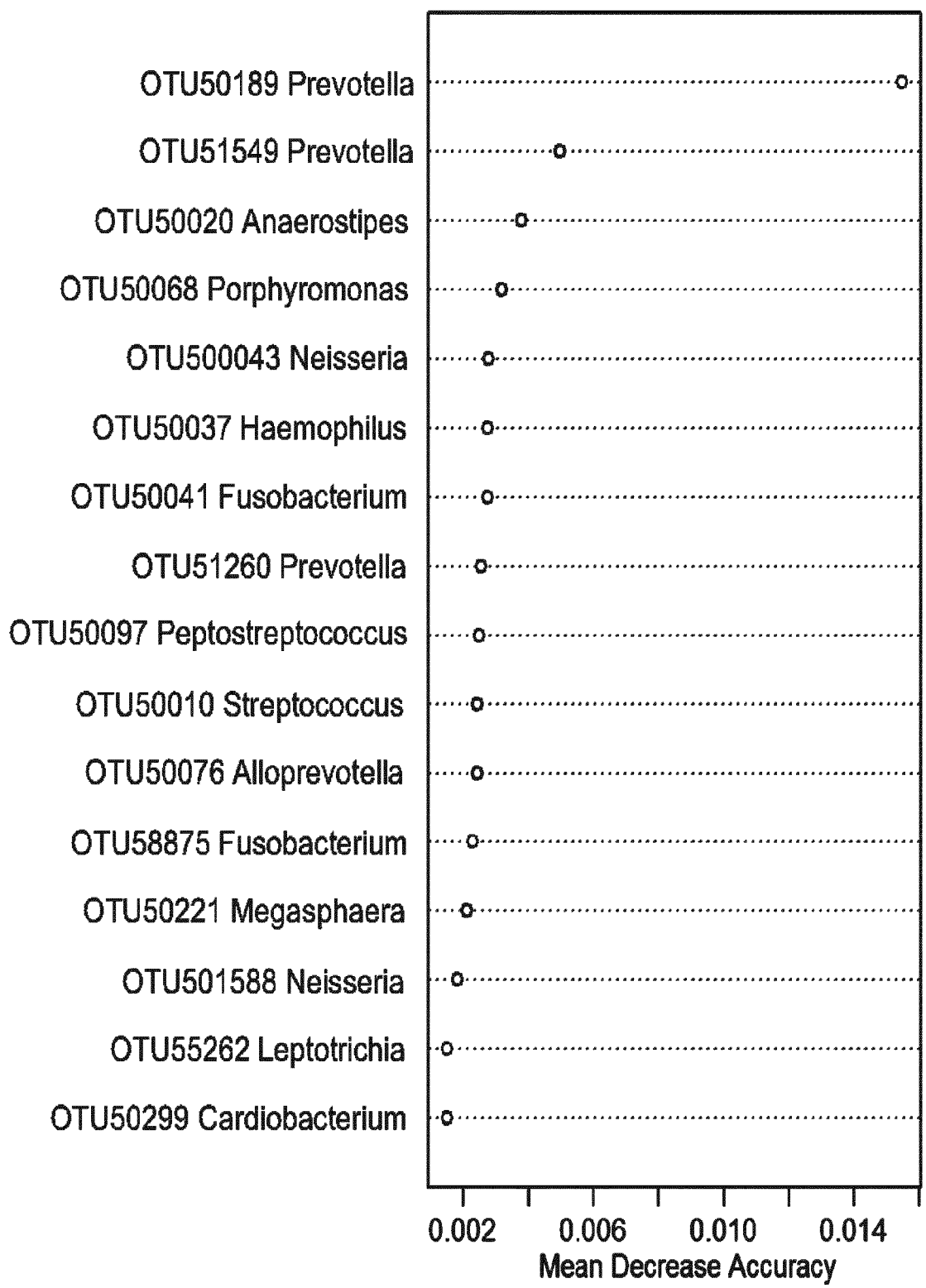
Figure 11A:
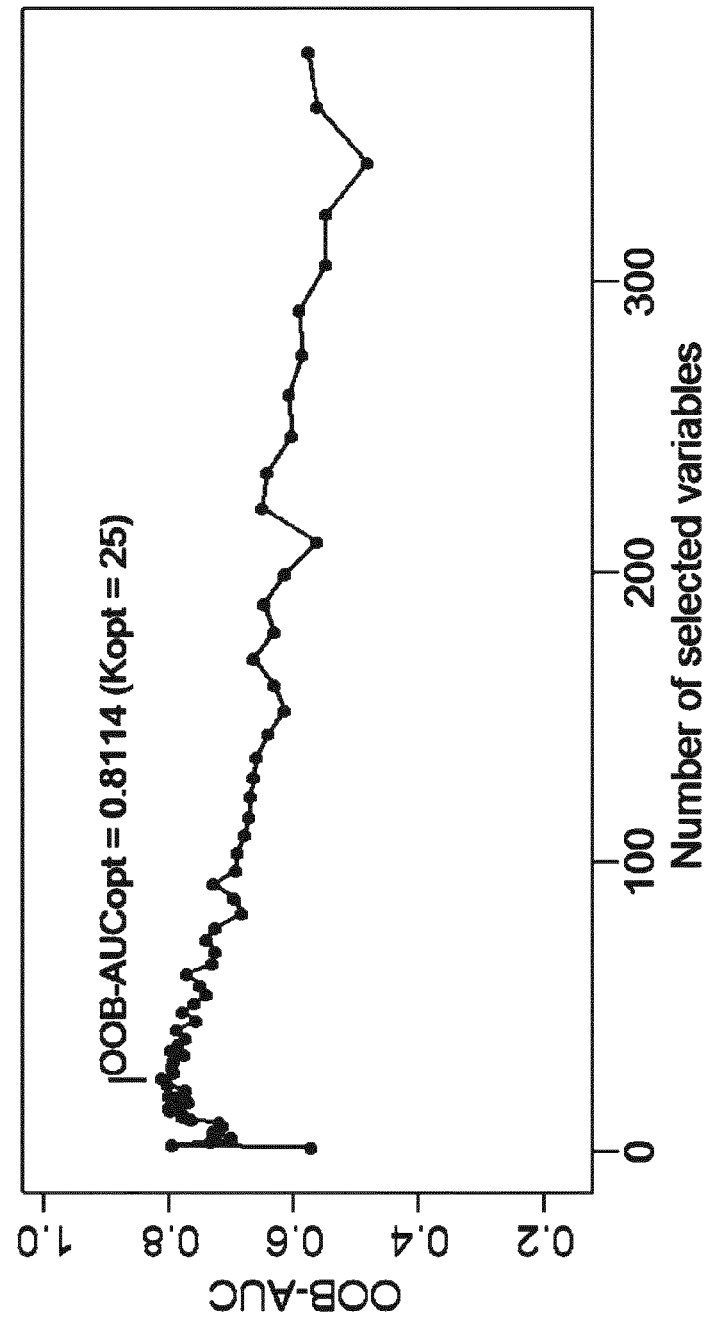
FIGS. 11A-11C: Details of the Baxter pipeline random forest classifier for distinguishing individuals with colorectal polyps from healthy persons using oral-swab microbiota (FIG. 11A). Contribution of all OTUs to the model (FIG. 11B). Strip-chart of the relative abundance of the five OTUs contributing most to the model (FIG. 11C).
Figure 11B:
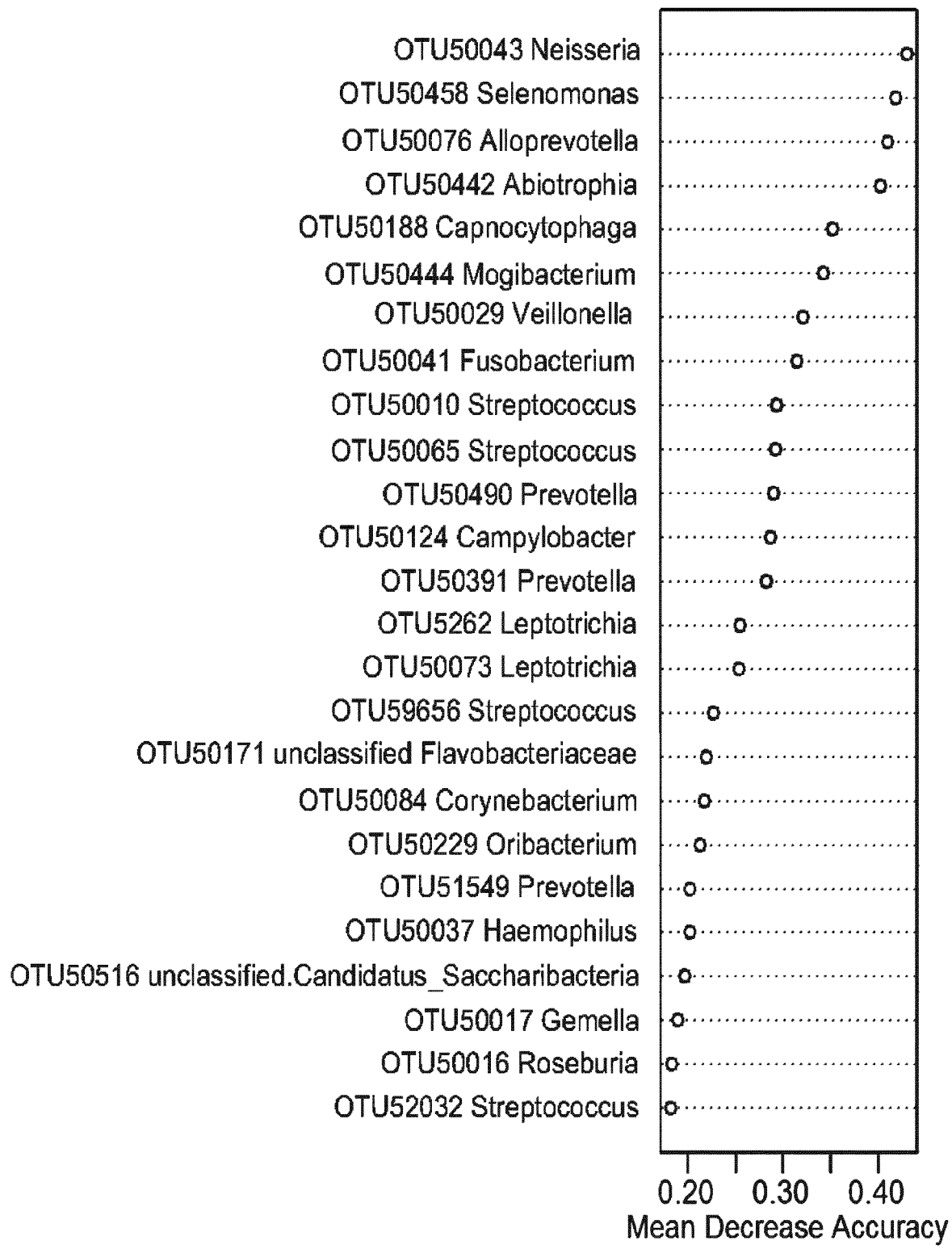
Figure 11C:
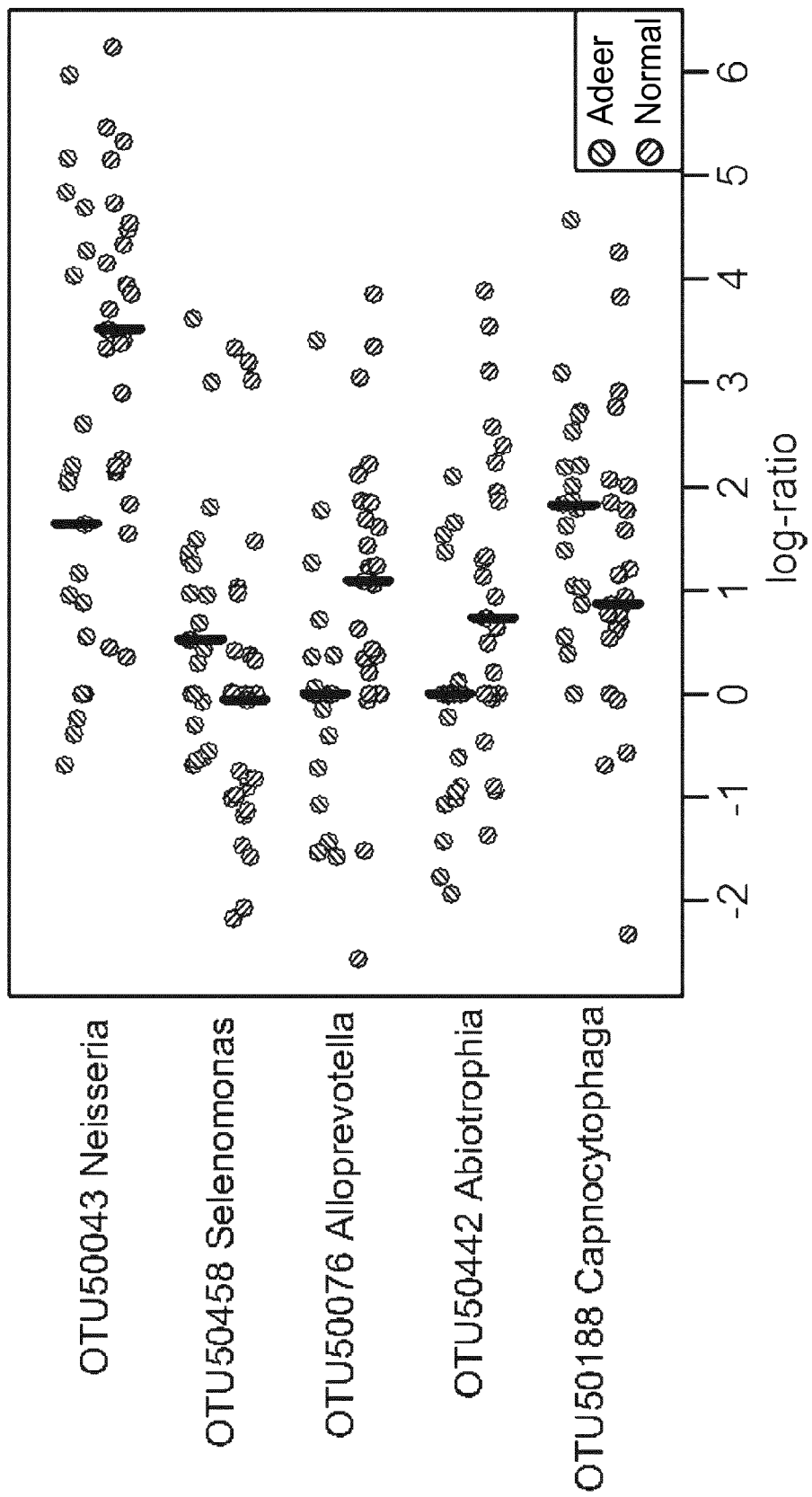

Our findings are also consistent with previous reports [3,4] in that faecal microbiota abundance of selected OTUs is able to distinguish individuals with CRC or polyps from healthy persons (FIGS. 9A-9B). However, the sensitivity of our model to use faecal microbiota to detect individuals with CRCs was considerably lower (sensitivity 22%; 95% CI (4.35% to 52.17%); specificity 95%, AUC 0.81; 95% CI (0.73 to 0.81)) than previously reported. A combination of oral and stool microbiota data improved the model sensitivity to 76% (95% CI (59.9% to 92%), AUC: 0.94; 95% CI (0.87 to 0.94) for the detection of CRCs and a sensitivity of 88% for the detection of polyps (95% CI (68.75% to 100%), AUC: 0.98; 95% CI (0.95 to 0.98) for the detection of polyps (both: specificity 95%) (FIGS. 9A-9B). Analysis of the abundances of 28 bacterial OTUs were optimal for the differentiation between individuals with polyps and healthy controls (Table 15; for 25 OTUs, the abundance in the oral cavity was used, while for 16 OTUs, the faecal abundance was used); the model for the detection of CRCs used 63 OTUs (Table 16; 29 oral OTUs and 34 stool OTUs).

Figure 6:
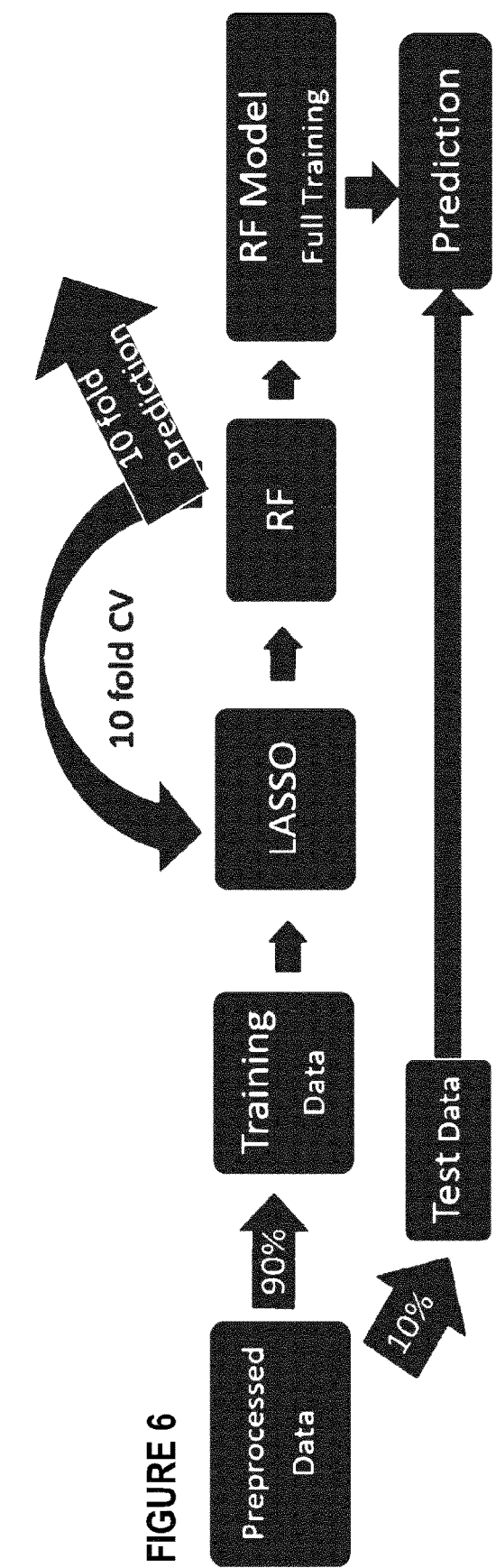
FIG. 6: The in-house LASSO pipeline schematic showing all feature selection (LASSO occurs within the 10-fold CV).

We were able to confirm the predictive value of the oral microbiota for CRC screening by employing an in-house pipeline using a LASSO feature selection step and a RF classifier within a 10-fold CV pipeline (see FIG. 6). This methodology, using the default probability threshold and when applied to the oral swab microbiota dataset (Table 12 and Table 13), yielded 74% sensitivity and 90% specificity (AUC 0.91) for the prediction of adenomas and 98% sensitivity and 70% specificity (AUC 0.96) for the prediction of CRC, respectively. A full list of values is shown in FIG. 12.

Low Colonic Abundance of Lachnospiraceae Favours Colonisation of Gut Mucosa by Oral Pathogens Linked to CRC Given the associations of oral bacteria with the altered microbiota found on CRC biopsies and our current finding that characterising oral microbiota profiles has potential for CRC detection, we hypothesised that the oral microbiota might generally be reflected in gut microbiota composition. However, bacteria typically enriched on colorectal tumours and found in both the oral cavity and the colon, such as *Porphyromonas, Parvimonas* and *Fusobacterium*, were less abundant in the oral mucosa of individuals with CRC compared with healthy controls (FIG. 8; statistically significant difference for one *Parvimonas* OTU).

The use of microbiome structure as a biomarker of health and disease is gaining momentum particularly with the development of affordable high-throughput DNA sequencing technology. It is now possible to obtain deep knowledge about the microbiota of a sample for less than $10 sequencing cost. Moreover, improved pipelines for in silico analysis of sequencing data enable researchers and clinicians to rapidly turn 16S rRNA amplicon sequencing data into clinically informative data without the need for dedicated large-scale computational facilities. Recent reports have shown the potential suitability of faecal microbiota profiles for screening for colonic lesions using 16S rRNA amplicon sequencing [3, 4, 13, 52] metagenomic sequencing [4] and qPCR [13]. In addition, diagnostic tests may be improved with a combination of microbiota information and the FIT [3,4]. The AUC values we obtained when using a combination of oral and faecal microbiota OTUs for CRC and adenoma detection (0.94 and 0.98, respectively) and the specificity (95% for both) and sensitivity (76% and 88%, respectively) were comparable or higher than those reported in the above-named studies (ranging from 0.64 to 0.93), suggesting that the inclusion of oral microbiota information has the potential to enhance the performance of current diagnostic tests. Particularly promising is the high sensitivity for the detection of adenomas (88%) because of the prognostic and therapeutic importance of early discovery of colonic disease. By comparison, Baxter et al [3] reported sensitivities below 20% for the detection of adenomas using either FIT or faecal microbiota composition alone and a sensitivity of below 40% when using a combination (specificity>90%). Our analysis significantly improves on this, and we were able to confirm the value of the oral microbiota to predict colonic lesions with an independent classification strategy employing both LASSO and RF feature selection.

Our finding that the presence and abundance of oral pathogens both in CRC and in healthy individuals is negatively associated with the abundance of Lachnospiraceae such as *Anaerostipes*, *Blautia* and *Roseburia* suggests that these bacteria also play an important protective role. The concept that the gut microbiota protects against the colonisation of the bowel with environmental bacteria, including pathogens, is well established [53] and, according to our data, is also relevant in the context of CRC and CD.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

REFERENCES

1. Polk, D. B. & Peek, R. M. *Helicobacter pylori*: gastric cancer and beyond. Nat. Rev. Cancer 10, 403-414 (2010).
2. Flemer, B. et al. Tumour-associated and non-tumour-associated microbiota in colorectal cancer. Gut gutjnl-2015-309595 (2016). doi:10.1136/gutjnl-2015-309595
3. Baxter, N. T., Ruffin, M. T., Rogers, M. A. M. & Schloss, P. D. Microbiota-based model improves the sensitivity of fecal immunochemical test for detecting colonic lesions. Genome Med. 8, 1-10 (2016).
4. Zeller, G. et al. Potential of fecal microbiota for early-stage detection of colorectal cancer. Mol Syst Biol 10, (2014).
5. Warren, R. L. et al. Co-occurrence of anaerobic bacteria in colorectal carcinomas. Microbiome 1, 16 (2013).
6. Kostic, A. D. et al. Genomic analysis identifies association of *Fusobacterium* with colorectal carcinoma. Genome Res. 22, 292-298 (2012).
7. Castellarin, M. et al. *Fusobacterium nucleatum* infection is prevalent in human colorectal carcinoma. Genome Res. 22, 299-306 (2012).
8. Wu, S. et al. A human colonic commensal promotes colon tumorigenesis via activation of T helper type 17 T cell responses. Nat Med 15, (2009).
9. Arthur, J. C. et al. Intestinal Inflammation Targets Cancer-Inducing Activity of the Microbiota. Science 338, 120-123 (2012).
10. Kostic, A. D. et al. *Fusobacterium nucleatum* Potentiates Intestinal Tumorigenesis and Modulates the Tumor-Immune Microenvironment. Cell Host Microbe 14, 207-215 (2013).
11. Rubinstein, M. R. et al. *Fusobacterium nucleatum* Promotes Colorectal Carcinogenesis by Modulating E-Cadherin/β-Catenin Signaling via its FadA Adhesin. Cell Host Microbe 14, 195-206 (2013).
12. Nakatsu, G. et al. Gut mucosal microbiome across stages of colorectal carcinogenesis. Nat. Commun. 6, 8727 (2015).
13. Liang, J. Q. et al. Fecal Bacteria Act as Novel Biomarkers for Non-Invasive Diagnosis of Colorectal Cancer. Clin. Cancer Res. clincanres.1599.2016 (2016). doi:10.1158/1078-0432.CCR-16-1599
14. Pushalkar, S. et al. Comparison of oral microbiota in tumor and non-tumor tissues of patients with oral squamous cell carcinoma. BMC Microbiol. 12, 144 (2012).
15. Schmidt, B. L. et al. Changes in Abundance of Oral Microbiota Associated with Oral Cancer. PLOS ONE 9, e98741 (2014).
16. Chen, X. et al. Oral Microbiota and Risk for Esophageal Squamous Cell Carcinoma in a High-Risk Area of China. PLOS ONE 10, e0143603 (2015).
17. Farrell, J. J. et al. Variations of oral microbiota are associated with pancreatic diseases including pancreatic cancer. Gut 61, 582-588 (2012).
18. Torres, P. J. et al. Characterization of the salivary microbiome in patients with pancreatic cancer. PeerJ 3, e1373 (2015).
19. Kato, I. et al. Oral microbiome and history of smoking and colorectal cancer. J. Epidemiol. Res. 2, (2016).
20. Segata, N. et al. Composition of the adult digestive tract bacterial microbiome based on seven mouth surfaces, tonsils, throat and stool samples. Genome Biol. 13, R42 (2012).
21. Bassis, C. M. et al. Analysis of the Upper Respiratory Tract Microbiotas as the Source of the Lung and Gastric Microbiotas in Healthy Individuals. mBio 6, e00037-15 (2015).
22. Hundt, S., Haug, U. & Brenner, H. Comparative Evaluation of Immunochemical Fecal Occult Blood Tests for Colorectal Adenoma Detection. Ann. Intern. Med. 150, 162-169 (2009).
23. Flanagan, L. et al. *Fusobacterium nucleatum* associates with stages of colorectal neoplasia development, colorectal cancer and disease outcome. Eur. J. Clin. Microbiol. Infect. Dis. 33, 1381-1390 (2014).
24. Ito, M. et al. Association of *Fusobacterium nucleatum* with clinical and molecular features in colorectal serrated pathway. Int. J. Cancer 137, 1258-1268 (2015).
25. Arumugam, M. et al. Enterotypes of the human gut microbiome. Nature 473, 174-180 (2011).
26. Heller, D. et al. Microbial Diversity in the Early In Vivo-Formed Dental Biofilm. Appl. Environ. Microbiol. 82, 1881-1888 (2016).
27. Palmer Jr, R. J. Composition and development of oral bacterial communities. Periodontol. 2000 64, 20-39 (2014).
28. Arora, N., Mishra, A. & Chugh, S. Microbial role in periodontitis: Have we reached the top? Some unsung bacteria other than red complex. J. Indian Soc. Periodontol. 18, 9-13 (2014).
29. Jover-Diáz, F., Cuadrado, J. M., Laveda, R., Andreu, L. & Merino, J. *Porphyromonas asaccharolytica* liver abscess. Anaerobe 9, 87-89 (2003).
30. Socransky, S. s., Haffajee, A. d., Cugini, M. a., Smith, C. & Kent, R. L. Microbial complexes in subgingival plaque. J. Clin. Periodontol. 25, 134-144 (1998).
31. Gevers, D. et al. The Treatment-Naive Microbiome in New-Onset Crohn's Disease. Cell Host Microbe 15, 382-392 (2014).
32. Love M I, Huber W and Anders S (2014). "Moderated estimation of fold change and dispersion for RNA-seq 33. *Helicobacter pylori*, gastric MALT lymphoma, and adenocarcinoma of the stomach. Go M F, Smoot D T. Semin Gastrointest Dis. 2000 July; 11(3):134-41.
34. Flemer B, Lynch D B, Brown J M et al. Tumour-associated and non-tumour-associated microbiota in colorectal cancer. Gut 2017; 66:633-43. doi:10.1136/gutjnl-2015-309595.
35. Claesson M J, Jeffery I B, Conde S et al. Gut microbiota composition correlates with diet and health in the elderly. Nature 2012; 488:178-84. doi:10.1038/nature11319.
36. Martin M. Cutadapt removes adapter sequences from high-throughput sequencing reads. 2011 2011; 17. doi: 10.14806/ej.17.1.200 pp. 10-12.
37. Magoc T, Salzberg SL. FLASH: Fast length adjustment of short reads to improve genome assemblies. Bioinformatics 2011; 27:2957-63. doi:10.1093/bioinformatics/btr507.
38. Caporaso J G, Kuczynski J, Stombaugh J et al. QIIME allows analysis of high-throughput community sequencing data. Nat Methods 2010; 7:335-6. doi: 10.1038/nmeth.f.303.
39. Edgar R C. Search and clustering orders of magnitude faster than blast. Bioinformatics 2010; 26:2460-1. doi: 10.1093/bioinformatics/btq461
40. Schloss P D, Westcott S L, Ryabin T et al. Introducing mothur: Open-source, platform-independent, community-supported software for describing and comparing microbial communities. Appl Environ Microbiol 2009; 75:7537-41. doi:10.1128/AEM.01541-09
41. Gevers D, Kugathasan S, Denson L A et al. The treatment-naive microbiome in new-onset crohn's disease. Cell Host Microbe 2014; 15:382-92. doi:10.1016/j.chom.2014.02.005
42. R Core Team. R: A language and environment for statistical computing. Vienna, Austria: R Foundation for Statistical Computing 2016. https://www.R-project.org/.
43. Wickham H. Ggplot2: Elegant graphics for data analysis. Springer-Verlag New York 2009. http://ggplot2.org.
44. Dray S, Dufour A-B. The ade4 package: Implementing the duality diagram for ecologists. Journal of Statistical Software 2007; 22:1-20. doi:10.18637/jss.v022.j04
45. Oksanen J, Blanchet F G, Friendly M et al. Vegan: Community ecology package. 2017. https://CRAN.R-project.org/package=vegan
46. Friedman E J Jonathan AND Alm. Inferring correlation networks from genomic survey data. PLOS Computational Biology 2012; 8:1-11. doi:10.1371/journal.pcbi.1002687
47. Mandal S, Van Treuren W, White R A et al. Analysis of composition of microbiomes: A novel method for studying microbial composition. Microb Ecol Health Dis 2015; 26:27663. doi:10.3402/mehd.v26.27663.
48. Benjamini Y, Hochberg Y. Controlling the false discovery rate: A practical and powerful approach to multiple testing.
49. Baxter N T, Ruffin M T th, Rogers M A et al. Microbiota-based model improves the sensitivity of fecal immunochemical test for detecting colonic lesions. Genome Med 2016; 8:37. doi:10.1186/s13073-016-0290-3.
50. Urrea V, Calle M. AUCRF: Variable selection with random forest and the area under the curve. 2012. https://CRAN.R-project.org/package=AUCRF.
51. Robin X, Turck N, Hainard A et al. PROC: An open-source package for r and s+ to analyze and compare roc curves. BMC Bioinformatics 2011; 12:77.
52. Shah M S, DeSantis T Z, Weinmaier T, et al, Leveraging sequence-based faecal microbial community survey data to identify a composite biomarker for colorectal cancer. Gut 2017 doi:10.1136/gutjnl-2016-313189.
53. Zhang C, Derrien M, Levenez F, et al, Ecological robustness of the gut microbiota in response to ingestion of transient food-borne microbes. Isme J 2016; 10:2235-45. doi:10.1038/ismej.2016.13.
54. Calle, M. et al. AUC-RF: A new strategy for genomic profiling with random forest, Human Heredity, 72(2): 121-132.
55. Youden, W. J. (1950). "Index for rating diagnostic tests". Cancer. 3: 32-35. doi:10.1002/1097-0142 (1950) 3:1<32::aid-cncr2820030106>3.0.co;2-3.

APPENDIX 1

```
>OTU0001 [SEQUENCE ID 1] Escherichia/Shigella
Tggggaatattgcacaatgggcgcaagcctgatgcagccatgccgcgtgtatgaagaaggccttcgggttgtaaagtactttca
gcggggaggaagggagtaaagttaataccctttgctcattgacgttacccgcagaagaagcaccggctaactccgtgccagcag
ccgcggtaatacggagggtgcaagcgttaatcggaattactgggcgtaaagcgcacgcaggcggtttgttaagtcagatgtgaa
atccccgggctcaacctgggaactgcatctgatactggcaagcttgagtctcgtagagggggggtagaattccaggtgtagcggtg
aaatgcgtagagatctggaggaataccggtggcgaaggcggcccctggacgaagactgacgctcaggtgcgaaagcgtgg
ggagcaaaca >OTU0002 [SEQUENCE ID 2] Blautia
Tggggaatattgcacaatgggggaaaccctgatgcagcgacgccgcgtgaaggaagaagtatctcggtatgtaaacttctatc
agcagggaagatagtgacggtacctgactaagaagcccggctaactacgtgccagcagccgcggtaatacgtaggggca
agcgttatccggatttactgggtgtaaagggagcgtagacggtgtggcaagtctgatgtgaaaggcatgggctcaacctgtggac
tgcattggaaactgtcatacttgagtgccggaggggtaagcggaattcctagtgtagcggtgaaatgcgtagatattaggagaa
caccagtggcgaaggcggcttactggacggtaactgacgttgaggctcgaaagcgtggggagcaaaca >OTU0003 [SEQUENCE ID 3] Faecalibacterium
Tggggaatattgcacaatgggggaaaccctgatgcagcgacgccgcgtggaggaagaaggtcttcggattgtaaactcctgtt
gttgaggaagataatgacggtactcaacaaggaagtgacggctaactacgtgccagcagccgcggtaaaacgtaggtcaca
agcgttgtccggaattactgggtgtaaagggagcgcaggcgggaagacaagttggaagtgaaatctatgggctcaacccataa
actgctttcaaaactgtttttcttgagtagtgcagaggtaggcggaattcccggtgtagcggtggaatgcgtagatatcgggaggaa
caccagtggcgaaggcggcctactgggcaccaactgacgctgaggctcgaaagtgtgggtagcaaaca >OTU0006 [SEQUENCE ID 4] Ruminococcus2
Tggggaatattgcacaatgggggaaaccctgatgcagcgacgccgcgtgagcgatgaagtatttcggtatgtaaagctctatca
gcagggaagaaaatgacggtacctgactaagaagcaccggctaaatacgtgccagcagccgcggtaatacgtatggtgcaa
gcgttatccggatttactgggtgtaaagggagcgtagacggagtggcaagtctgatgtgaaaacccggggctcaaccccggga
ctgcattggaaactgtcaatctagagtaccggagaggtaagcggaattcctagtgtagcggtgaaatgcgtagatattaggagg
aacaccagtggcgaaggcggcttactggacggtaactgacgttgaggctcgaaagcgtggggagcaaaca
```

APPENDIX 1-continued

>OTU0007 [SEQUENCE ID 5] *Streptococcus*
Tagggaatcttcggcaatggacggaagtctgaccgagcaacgccgcgtgagtgaagaaggttttcggatcgtaaagctctgttg
taagagaagaacgagtgtgagagtggaaagttcacactgtgacggtatcttaccagaaagggacggctaactacgtgccagc
agccgcggtaatacgtaggtcccgagcgttgtccggatttattgggcgtaaagcgagcgcaggcggttagataagtctgaagtta
aaggctgtggcttaaccatagtacgctttggaaactgtttaacttgagtgcaagaggggagagtggaattccatgtgtagcggtga
aatgcgtagatatatggaggaacaccggtggcgaaagcggctctctggcttgtaactgacgctgaggctcgaaagcgtgggga
gcaaaca >OTU0008 [SEQUENCE ID 6] *Roseburia*
tgggaatattgcacaatgggcgaaagcctgatgcagcgacgccgcgtgagcgaagaagtatttcggtatgtaaagctctatc
agcagggaagataatgacggtacctgactaagaagcaccggctaaatacgtgccagcagccgcggtaatacgtatggtgcaa
gcgttatccggatttactgggtgtaaagggagcgcaggcggtgcggcaagtctgatgtgaaagcccggggctcaaccccgta
ctgcattggaaactgtcgtactagagtgtcggaggggtaagcggaattcctagtgtagcggtgaaatgcgtagatattaggagga
acaccagtggcgaaggcggcttactggacgataactgacgctgaggctcgaaagcgtggggagcaaaca >OTU0012 [SEQUENCE ID 7] *Anaerostipes*
tgggaatattgcacaatgggggaaaccctgatgcagcgacgccgcgtgagtgaagaagtatctcggtatgtaaagctctatca
gcagggaagaaaatgacggtacctgactaagaagcccggctaactacgtgccagcagccgcggtaatacgtaggggggca
agcgttatccggaattactgggtgtaaagggtgcgtaggtggtatggcaagtcagaagtgaaaacccagggcttaactctggga
ctgcttttgaaactgtcagactggagtgcaggagaggtaagcggaattcctagtgtagcggtgaaatgcgtagatattaggagga
acatcagtggcgaaggcggcttactggactgaaactgacactgaggcacgaaagcgtggggagcaaaca >OTU0013 [SEQUENCE ID 8] *Roseburia*
Tgggaatattgcacaatgggggaaaccctgatgcagcgacgccgcgtgagcgaagaagtatttcggtatgtaaagctctatc
agcagggaagaagaaatgacggtacctgactaagaagcaccggctaaatacgtgccagcagccgcggtaatacgtatggtg
caagcgttatccggatttactgggtgtaaagggagcgcaggcggaaggctaagtctgatgtgaaagcccggggctcaaccccg
gtactgcattggaaactggtcatctagagtgtcggaggggtaagtggaattcctagtgtagcggtgaaatgcgtagatattaggag
gaacaccagtggcgaaggcggcttactggacgataactgacgctgaggctcgaaagcgtggggagcaaaca >OTU0015 [SEQUENCE ID 9] *Haemophilus*
Tgggaatattgcgcaatgggggcaaccctgacgcagccatgccgcgtgaatgaagaaggccttcggggttgtaaagttctttcg
gtagcgaggaaggcatttagtttaatagactaggtgattgacgttaactacagaagaagcaccggctaactccgtgccagcagc
cgcggtaatacgagggtgcgagcgttaatcggaataactgggcgtaaagggcacgcaggcggtgacttaagtgaagtgtga
aagccccgggcttaacctgggaattgcatttcatactgggtcgctagagtacttttagggagggtagaattccacgtgtagcggtg
aaatgcgtagagatgtggaggaataccgaaggcgaaggcagccccttgggaatgtactgacgctcatgtgcgaaagcgtggg
gagcaaaca >OTU0016 [SEQUENCE ID 10] *Streptococcus*
tagggaatcttcggcaatgggggcaaccctgaccgagcaacgccgcgtgagtgaagaaggttttcggatcgtaaagctctgtt
gtaagtcaagaacgagtgtgagagtggaaagttcacactgtgacggtagcttaccagaaagggacggctaactacgtgccag
cagccgcggtaatacgtaggtcccgagcgttgtccggatttattgggcgtaaagcgagcgcaggcggtttgataagtctgaagtt
aaaggctgtggctcaaccatagttcgctttggaaactgtcaaacttgagtgcagaagggggagagtggaattccatgtgtagcggt
gaaatgcgtagatatatggaggaacaccggtggcgaaagcggctctctggtctgtaactgacgctgaggctcgaaagcgtggg
gagcgaaca >OTU0018 [SEQUENCE ID 11] *Gemmiger*
tggggatattgcacaatgggggaaaccctgatgcagcgacgccgcgtggaggaagaaggttttcggattgtaaactcctgtc
gttagggacgataatgacggtacctaacaagaaagcaccggctaactacgtgccagcagccgcggtaaaacgtagggtgca
agcgttgtccggaattactgggtgtaaagggagcgcaggcggaccggcaagttggaagtgaaaactatgggctcaacccata
aattgctttcaaaactgctggccttgagtagtgcagaggtaggtggaattcccggtgtagcggtggaatgcgtagatatcggagg
aacaccagtggcgaaggcgacctactgggcaccaactgacgctgaggctcgaaagcatgggtagcaaaca >OTU0019 [SEQUENCE ID 12] *Clostridium_sensu_stricto*
tgggaatattgcacaatgggggaaaccctgatgcagcaacgccgcgtgagtgatgaaggttttcggatcgtaaagctctgtctt
tggggaagataatgacggtacccaaggaggaagccacggctaactacgtgccagcagccgcggtaatacgtaggtggcgag
cgttatccggatttactgggcgtaaagggagcgtaggcggatgattaagtgggatgtgaaatacccgggctcaacttgggtgctg
cattccaaactggttatctagagtgcaggagaggagagtggaattcctagtgtagcggtgaaatgcgtagagattaggaagaac
accagtggcgaaggcgactctctggactgtaactgacgctgaggctcgaaagcgtggggagcaaaca >OTU0020 [SEQUENCE ID 13] *Bacteroides*
tgaggaatattggtcaatgggcgcaggcctgaaccagccaagtagcgtgaaggatgactgccctatgggttgtaaacttctttat
atgggaataaagttttcacgtgtggaattttgtatgtaccatatgaataaggatcggctaactccgtgccagcagccgcggtaata
cggaggatccgagcgttatccggatttattgggtttaaagggagcgtaggcggacagttaagtcagttgtgaaagtttgcggctca
accgtaaaattgcagttgatactggctgtcttgagtacagtagaggtgggcggaattcgtggtgtagcggtgaaatgcttagatatc
acgaagaactccgattgcgaaggcagctcactggactgcaactgacactgatgctcgaaagtgtgggtatcaaaca >OTU0022 [SEQUENCE ID 14] *Parabacteroides*
Tgaggaatattggtcaatggccgagaggctgaaccagccaagtcgcgtgaaggaagaaggatctatggtttgtaaacttctttta
taggggaataaagtggaggacgtgtccttttttgtatgtaccctatgaataagcatcggctaactccgtgccagcagccgcggtaat
acggaggatgcgagcgttatccggatttattgggtttaaagggtgcgtaggtggtgatttaagtcagcggtgaaagtttgtggctca
accataaaattgccgttgaaactgggtacttgagtgtgtttgaggtaggcggaatgcgtggtgtagcggtgaaatgcatagatatc
acgcagaactccgattgcgaaggcagcttactaaaccataactgacactgaagcgaaagcgtggggatcaaaca >OTU0026 [SEQUENCE ID 15] *Dorea*
Tgggaatattgcacaatggaggaaactctgatgcagcgacgccgcgtgaaggatgaagtatttcggtatgtaaacttctatcag
cagggaagaaaatgacggtacctgactaagaagcccggctaactacgtgccagcagccgcggtaatacgtaggggggcaa
gcgttatccggatttactgggtgtaaagggagcgtagacggcacggcaagccagatgtgaaagcccggggctcaaccccggg
actgcatttggaactgctgagctagagtgtcggagaggcaagtggaattcctagtgtagcggtgaaatgcgtagatattaggagg
aacaccagtggcgaaggcggcttgctggacgatgactgacgttgaggctcgaaagcgtggggagcaaaca APPENDIX 1-continued >OTU0029 [SEQUENCE ID 16] *Bifidobacterium*
Tggggaatattgcacaatgggcgcaagcctgatgcagcgacgccgcgtgcgggatgacggccttcggggttgtaaaccgcttttg
actgggagcaagcccttcggggtgagtgtaccttcgaataagcaccggctaactacgtgccagcagccgcggtaatacgtag
ggtgcaagcgttatccggaattattgggcgtaaagggctcgtaggcggttcgtcgcgtccggtgtgaaagtccatcgcttaacggt
ggatccgcgccgggtacgggcgggcttgagtgcggtaggggagactggaattcccggtgtaacggtggaatgtgtagatatcg
ggaagaacaccaatggcgaaggcaggtctctgggccgtcactgacgctgaggagcgaaagcgtggggagcgaaca >OTU0030 [SEQUENCE ID 17] *Coprococcus*
Tggggaatattgcacaatgggggaaaccctgatgcagcgacgccgcgtgaaggaagaagtatctcggtatgtaaacttctatc
agcagggaagataatgacggtacctgactaagaagccccggctaactacgtgccagcagccgcggtaatacgtaggggggca
agcgttatccggatttactgggtgtaaagggagcgtaggcggcggagcaagtcagaagtgaaagcccggggctcaacccgg
gacggcttttgaaactgccctgcttgatttcaggagaggtaagcggaattcctagtgtagcggtgaaatgcgtagatattaggagg
aacaccagtggcgaaggcggcttactggactgacaatgacgctgaggctcgaaagcgtggggagcaaaca >OTU0031 [SEQUENCE ID 18] *Clostridium_sensu_stricto*
Tggggaatattgcacaatgggggaaaccctgatgcagcaacgccgcgtgagtgatgacggccttcggggttgtaaagctctgtct
tcagggacgataatgacggtacctgaggaggaagccacggctaactacgtgccagcagccgcggtaatacgtaggtggcga
gcgttgtccggatttactgggcgtaaagggagcgtaggcggacttttaagtgagatgtgaaatacccgggctcaacttgggtgctg
catttcaaactggaagtctagagtgcaggagaggagaatggaattcctagtgtagcggtgaaatgcgtagagattaggaagaa
caccagtggcgaaggcgattctctggactgtaactgacgctgaggctcgaaagcgtggggagcaaaca >OTU0038 [SEQUENCE ID 19] *Alistipes*
Tgaggaatattggtcaatggacgcaagtctgaaccagccatgccgcgtgcaggaagacggctctatgagttgtaaactgcttttg
tacgagggtaaaactcacctacgtgtaggtgactgaaagtatcgtacgaataaggatcggctaactccgtgccagcagccgcggt
aatacggaggattcaagcgttatccggatttattgggtttaaagggtgcgtaggcggtttgataagttagaggtgaaatcccgggg
cttaactccggaactgcctctaatactgttagactagagagtagttgcggtaggcggaatgtatggtgtagcggtgaaatgcttaga
gatcatacagaacaccgattgcgaaggcagcttaccaaactatatctgacgttgaggcacgaaagcgtggggagcaaaca >OTU0040 [SEQUENCE ID 20] *Bacteroides*
Tgaggaatattggtcaatggacgagagtctgaaccagccaagtagcgtgaaggatgaaggttctatggattgtaaacttcttttat
acgggaataaacgaatccacgtgtggatttttgcatgtaccgtatgaataaggatcggctaactccgtgccagcagccgcggtaa
tacggaggatccgagcgttatccggatttattgggtttaaagggagcgtagatggggttgttaagtcagttgtgaaagtttgcggctca
accgtaaaattgcaattgatactggcagtcttgagtacgttgaggtaggcggaattcgtggtgtagcggtgaaatgcttagatatc
acgaagaactccgattgcgaaggcagcttactaacctgtaactgacattgatgctcgaaagtgtgggtatcaaaca >OTU0041 [SEQUENCE ID 21] *Neisseria*
Tggggaattttggacaatgggcgcaagcctgatccagccatgccgcgtgtctgaagaaggccttcggggttgtaaaggacttttgt
cagggaagaaaagggcggggttaatacccctgtctgatgacggtacctgaagaataagcaccggctaactacgtgccagcag
ccgcggtaatacgtaggtgcgagcgttaatcggaattactgggcgtaaagcgggcgcagacggttacttaagcaggatgtga
aatcccgggctcaacctgggaactgcgttctgaactgggtgactagagtgtgtcagaggggaggtagaattccacgtgtagcagt
gaaatgcgtagagatgtggaggaataccgatggcgaaggcagcctcctgggataacactgacgttcatgcccgaaagcgtgg
gtagcaaaca >OTU0042 [SEQUENCE ID 22] *Clostridium_XI*
Tggggaatattgcacaatgggcgaaagcctgatgcagcaacgccgcgtgagcgatgaaggccttcggggtcgtaaagctctgtc
ctcaaggaagataatgacggtacttgaggaggaagccccggctaactacgtgccagcagccgcggtaatacgtaggggggcta
gcgttatccggaattactgggcgtaaagggtgcgtaggtggtttcttaagtcagaggtgaaaggctacggctcaaccgtagtaag
cctttgaaactgggaaacttgagtgcaggagaggagagtggaattcctagtgtagcggtgaaatgcgtagatattaggaggaac
accagttgcgaaggcggctctctggactgtaactgacactgaggcacgaaagcgtggggagcaaaca >OTU0045 [SEQUENCE ID 23] unclassified.*Lachnospiraceae*
Tggggaatattgcacaatggaggaaactctgatgcagcgacgccgcgtgagtgaagaagtatttcggtatgtaaagctctatca
gcagggaagaaaatgacggtacctgactaagaagcaccggctaaatacgtgccagcagccgcggtaatacgtatggtgcaa
gcgttatccggatttactgggtgtaaagggagcgtaggcggtggcaaggcaagccagaagtgaaaacccggggctcaaccgcg
gattgcttttggaactgtcatgctagagtgcaggaggggtgagcggaattcctagtgtagcggtgaaatgcgtagatattaggagg
aacaccggaggcgaaggcggctcactggactgtaactgacactgaggctcgaaagcgtggggagcaaaca >OTU0049 [SEQUENCE ID 24] unclassified.*Lachnospiraceae*
Tggggaatattgcacaatgggggaaaccctgatgcagcgacgccgcgtgagcgatgaagtatttcggtatgtaaagctctatca
gcagggaagataatgacggtacctgactaagaagctccggctaaatacgtgccagcagccgcggtaatacgtatggagcaag
cgttatccggatttactgggtgtaaagggagcgtaggcggtcctgcaagtctgatgtgaaaggcggggctcaacccccgggact
gcattggaaactgtaggactagagtgtcggaggggtaagtggaattcctagtgtagcggtgaaatgcgtagatattaggaggaa
caccagtggcgaaggcggcttactggacgactactgacgctgaggctcgaaagcgtggggagcaaaca >OTU0050 [SEQUENCE ID 25] *Veillonella*
Tggggaatcttccgcaatgacgaaagtctgacggagcaacgccgcgtgagtgatgacggccttcggggttgtaaagctctgtta
atcgggacgaaaggccttcttgcgaatagtgagaaggattgacggtaccggaatagaaagccacggctaactacgtgccagc
agccgcggtaatacgtaggtggcaagcgttgtccggaattattgggcgtaaagcgcgcgcaggcggataggtcagtctgtctta
aaagttcggggcttaacccgtgatgggatggaaactgccaatctagagtatcggagaggaaagtggaattcctagtgtagcgg
tgaaatgcgtagatattaggaagaacaccagtggcgaaggcgactttctggacgaaaactgacgctgaggcgcgaaagcca
ggggagcgaacg >OTU0054 [SEQUENCE ID 26] *Bacteroides*
Tgaggaatattggtcaatggacgagagtctgaaccagccaagtagcgtgaaggatgactgccctatggggttgtaaacttcttttat
acgggaataaagtgagccacgtgtggcttttttgtatgtaccgtatgaataaggatcggctaactccgtgccagcagccgcggtaat
acggaggatccgagcgttatccggatttattgggtttaaagggagcgtaggcggttgttaagtcagttgtgaaagtttgcggctca
accgtaaaattgcagttgatactggcgaccttgagtgcaacagaggtaggcggaattcgtggtgtagcggtgaaatgcttagatat
cacgaagaactccgattgcgaaggcagcttactggattgtaactgacgctgatgctcgaaagtgtgggtatcaaaca APPENDIX 1-continued >OTU0059 [SEQUENCE ID 27] *Sutterella*
Tggggaattttggacaatgggggcaaccctgatccagccatgccgcgtgcaggatgaaggtcttcggattgtaaactgcttttgtc
agggacgaaaagggatgcgataacaccgcattccgctgacggtacctgaagaataagcaccggctaactacgtgccagcag
ccgcggtaatacgtagggtgcaagcgttaatcggaattactgggcgtaaagcgtgcgcaggcggttctgtaagatagatgtgaa
atccccgggctcaacctgggaattgcatatatgactgcaggacttgagtttgtcagaggagggtggaattccacgtgtagcagtg
aaatgcgtagatatgtggaagaacaccgatggcgaaggcagccctctgggacatgactgacgctcatgcacgaaagcgtggg
gagcaaaca >OTU0061 [SEQUENCE ID 28] *Bifidobacterium*
Tggggaatattgcacaatgggcgcaagcctgatgcagcgacgccgcgtgagggatggaggccttcggggttgtaaacctctttta
tcggggagcaagcgagagtgagtttacccgttgaataagcaccggctaactacgtgccagcagccgcggtaatacgtagggtg
caagcgttatccggaattattgggcgtaaagggctcgtaggcggttcgtcgcgtccggtgtgaaagtccatcgcttaacggtggat
ccgcgccggtacgggcgggcttgagtgcggtaggggagactggaattcccggtgtaacggtggaatgtgtagatatcgggaa
gaacaccaatggcgaaggcaggtctctgggccgttactgacgctgaggagcgaaagcgtggggagcgaaca >OTU0063 [SEQUENCE ID 29] *Fusobacterium*
Tggggaatattggacaatgaccgagagtctgatccagccaattctgtgtgcacgatgaagttttcggaatgtaaagtgctttcagt
tgggaagaaataaatgacggtaccaacagaagaagtgacggctaaatacgtgccagcagccgcggtaatacgtatgtcacg
agcgttatccggatttattgggcgtaaagcgcgtctaggtggttatgtaagtctgatgtgaaaatgcagggctcaactctgtattgcgt
tggaaactgtgtaactagagtactggagaggtaagcggaactacaagtgtagaggtgaaattcgtagatatttgtaggaatgccg
atggggaagccagcttactggacagatactgacgctaaagcgcgaaagcgtgggtagcaaaca >OTU0065 [SEQUENCE ID 30] *Collinsella*
Tggggaatcttgcgcaatgggggaaccctgacgcagcgacgccgcgtgcgggacggaggccttcgggtcgtaaaccgcttt
cagcagggaagagtcaagactgtacctgcagaagaagccccggctaactacgtgccagcagccgcggtaatacgtaggggg
gcgagcgttatccggattcattgggcgtaaagcgcgcgtaggcggccccggcaggccggggtcgaagcggggggctcaacc
ccccgaagccccgggaacctccgcggcttgggtccggtaggggagggtggaacaccggtgtagcggtggaatgcgcagat
atcgggtggaacaccggtggcgaaggcggccctctgggccgagaccgacgctgaggcgcgaaagctgggggagcgaaca >OTU0067 [SEQUENCE ID 31] *Clostridium_XIVa*
Tggggaatattgcacaatgggggaaaccctgatgcagcgacgccgcgtgagtgaagaagtatttcggtatgtaaagctctatca
gcagggaagaaagtgacggtacctgaataagaagccccggctaactacgtgccagcagccgcggtaatacgtaggggca
agcgttatccggatttactgggtgtaaagggagcgtagacggcaaggcaagtctgaagtgaaagcccggtgcttaacgccggg
actgctttggaaactgtttggctgagtgccggagaggtaagcggaattcctagtgtagcggtgaaatgcgtagatattaggaag
aacaccagtggcgaaggcggcttactggacgtaactgacgttgaggctcgaaagcgtggggagcaaaca >OTU0072 [SEQUENCE ID 32] *Streptococcus*
Tagggaatcttcggcaatggacgaaagtctgaccgagcaacgccgcgtgagtgaagaaggttttcggatcgtaaagctctgttg
taagtcaagaacgtgtgtgagagtggaaagttcacacagtgacggtagcttaccagaaagggacggctaactacgtgccagc
agccgcggtaatacgtaggtcccgagcgttgtccggatttattgggcgtaaaggagcgcaggcggtcaggaaagtctggagt
aaaaggctatggctcaaccatagtgtgctctggaaactgtctgacttgagtgcagaagggagagtggaattccatgtgtagcgg
tgaaatgcgtagatatgtgaggaacaccagtggcgaaagcggctctctggtctgtcactgacgctgaggctcgaaagcgtgg
gtagcgaaca >OTU0073 [SEQUENCE ID 33] unclassified.*Firmicutes*
Tggggaatattgggcaatggaggaaactctgacccagcaacgccgcgtggaggaagaaggttttcggatcgtaaactcctgtc
cttggagacgagtagaagacggtatccaaggaggaagccccggctaactacgtgccagcagccgcggtaatacgtaggggg
caagcgttgtccggaataattgggcgtaaagggcgcgtaggcggctcggtaagtctggagtgaaagtcctgcttttaaggtggga
attgctttggatactgtcgggcttgagtgcaggagaggttagtggaattcccagtgtagcggtgaaatgcgtagagattgggagga
acaccagtggcgaaggcgactaactggactgtaactgacgctgaggcgcgaaagtgtggggagcaaaca >OTU0075 [SEQUENCE ID 34] *Clostridium_XIVa*
Tggggaatattgcacaatgggggaaaccctgatgcagcaacgccgcgtgagtgaagaagtatttcggtatgtaaagctctatca
gcagggaagaaaatgacggtacctgactaagaagccccggctaactacgtgccagcagccgcggtaatacgtagggggca
agcgttatccggatttactgggtgtaaagggagcgtagacggcgagacaagtctgaagtgaaagcccggggctcaacccccgg
gactgctttggaaactgccttgctagagtgctggagaggtaagtggaattcctagtgtagcggtgaaatgcgtagatattaggagg
aacaccagtggcgaaggcggcttactggacagtaactgacgttgaggctcgaaagcgtggggagcaaaca >OTU0080 [SEQUENCE ID 35] *Prevotella*
Tgaggaatattggtcaatggacggaagtctgaaccagccaagtagcgtgcaggatgacggccctatgggttgtaaactgcttttg
tatgggataaaagttagggacgtgtccctatttgcaggtaccatacgaataaggaccggctaattccgtgccagcagccgcggta
atacggaaggtccaggcgttatccggatttattgggtttaaagggagcgtaggctggagattaagtgtgttgtgaaatgtagacgct
caacgtctgaattgcagcgcatactggtttccttgagtacgcacaacgttggcggaattcgtcgtgtagcggtgaaatgcttagatat
gacgaagaactccgattgcgaaggcagctgacgggagcgcaactgacgcttaagctcgaaggtgcgggtatcaaaca >OTU0081 [SEQUENCE ID 36] *Neisseria*
Tggggaattttggacaatgggcgcaagcctgatccagccatgccgcgtgtctgaagaaggccttcgggttgtaaaggactttttgt
cagggaagaaaaggctgttgctaatatcgacagctgatgacggtacctgaagaataagcaccggctaactacgtgccagcag
ccgcggtaatacgtagggtgcgagcgttaatcggaattactgggcgtaaagcgagcgcagacggttacttaagcaggatgtga
aatccccgggctcaacctgggaactgcgttctgaactgggtgactagagtgtgtcagaggaggtagaattccacgtgtagcagt
gaaatgcgtagagatgtggaggaataccgatggcgaaggcagcctcctgggataacactgacgttcatgctcgaaagcgtgg
gtagcaaaca >OTU0083 [SEQUENCE ID 37] *Gemella*
Tagggaatcttccgcaatgggcgaaagcctgacggagcaacgccgcgtgagtgaagaaggatttcggttcgtaaagctctgtt
gttagggaagaatgattgtgtagtaactatacacagtagagacggtacctaaccagaaagccacggctaactacgtgccagca
gccgcggtaatacgtaggtggcaagcgttgtccggaattattgggcgtaaagcgcgcgcaggtggtttaataagtctgatgtgaa
agcccacggctcaaccgtggagggtcattggaaactgttaaacttgagtgcaggagagaaaagtggaattcctagtgtagcggt
gaaatgcgtagagattaggaggaacaccagtggcgaaggcggcttttggcctgtaactgacactgaggcgcgaaagcgtgg
ggagcaaaca APPENDIX 1-continued >OTU0085 [SEQUENCE ID 38] *Bilophila*
Tggggaatattgcgcaatgggcgaaagcctgacgcagcgacgccgcgtgagggatgaaggttctcggatcgtaaacctctgtc
aggggggaagaaaccccctcgtgtgaataatgcgagggcttgacggtaccccccaaaggaagcaccggctaactccgtgcca
gcagccgcggtaatacggagggtgcaagcgttaatcggaatcactgggcgtaaagcgcacgtaggcggcttggtaagtcagg
ggtgaaatcccacagcccaactgtggaactgcctttgatactgccaggcttgagtaccggagagggtggcggaattccaggtgt
aggagtgaaatccgtagatatctggaggaacaccggtggcgaaggcggccacctggacggtaactgacgctgaggtgcgaa
agcgtgggtagcaaaca >OTU0086 [SEQUENCE ID 39]
Tgaggaatattggtcaatggacgcgagtctgaaccagccaagtagcgtgcaggatgacggccctatgggttgtaaactgcttttg
cgcgggataacaccctccacgtgctggaggtctgcaggtaccgcgcgaataaggaccggctaattccgtgccagcagccgc
ggtaatacggaaggtccgggcgttatccggatttattgggtttaaagggagcgtaggccgtgaggtaagcgtgttgtgaaatgtag
gcgcccaacgtctgcactgcagcgcgaactgccccacttgagtgcgcgcaacgccggcggaactcgtcgtgtagcggtgaaat
gcttagatatgacgaagaaccccgattgcgaaggcagctggcgggagcgtaactgacgctgaagctcgaaagcgcgggtatc
gaaca >OTU0087 [SEQUENCE ID 40] *Parvimonas*
Tggggaatattgcacaatgggggaaccctgatgcagcgacgccgcgtgagcgaagaaggttttcgaatcgtaaagctctgtc
ctatgagaagataatgacggtatcataggaggaagccccggctaaatacgtgccagcagccgcggtaatacgtatggggcga
gcgttgtccggaattattgggcgtaaagggtacgtaggcggtttttttaagtcaggtgtgaaagcgtgaggcttaacctcattaagca
cttgaaactggaagacttgagtgaaggagaggaaagtggaattcctagtgtagcggtgaaatgcgtagatattaggaggaatac
cggtggcgaaggcgactttctggacttttactgacgctcaggtacgaaagcgtggggagcaaaca >OTU0089 [SEQUENCE ID 41] *Barnesiella*
Tgaggaatattggtcaatggtcggcagactgaaccagccaagtcgcgtgagggaagacggccctacgggttgtaaacctctttt
gtcgagagtaaagtacgctacgtgtagcgtattgcaagtatccgaagaaaaagcatcggctaactccgtgccagcagccgcg
gtaatacggaggatgcaagcgttatccggatttattgggtttaaagggtgcgtaggcggcacgccaagtcagcggtgaaatttcc
gggctcaacccggactgtgccgttgaaactggcgagctagagtgcacaagaggcaggcggaatgcgtggtgtagcggtgaa
atgcatagatatcacgcagaaccccgattgcgaaggcagcctgctagggtgcgacagacgctgaggcacgaaagcgtgggt
atcgaaca >OTU0092 [SEQUENCE ID 42] *Haemophilus*
Tggggaatattgcgcaatggggggaaccctgacgcagccatgccgcgtgaatgaagaaggccttcggggttgtaaagttctttcg
gtattgaggaaggagtgtatgttaatagcatacattattgacgttaaatacagaagaagcaccggctaactccgtgccagcagcc
gcggtaatacggagggtgcgagcgttaatcggaataactgggcgtaaagggcacgcaggcggttatttaagtgaggtgtgaaa
gccccgggcttaacctgggaattgcatttcagactgggtaactagagtactttagggaggggtagaattccacgtgtagcggtga
aatgcgtagagatgtggaggaataccgaaggcgaaggcagcccccttgggaatgtactgacgctcatgtgcgaaagcgtgggg
agcaaaca >OTU0093 [SEQUENCE ID 43] *Clostridium_IV*
Tgagggatattgggcaatggggggaaccctgacccagccaacgccgcgtgagggatgacggttttcggattgtaaacctctgtcc
tctgtgaagatagtgacggtagcagaggaggaagctccggctaactacgtgccagcagccgcggtaatacgtagggagcaa
gcgttgtccggatttactgggtgtaaagggtgcgtaggcggattgcaagtcagaagtgaaatccatgggcttaacccatgaact
gcttttgaaactgttagtcttgagtgaagtagaggtaggcggaattcccggtgtagcggtgaaatgcgtagagatcgggaggaac
accagtggcgaaggcggcctactgggctttaactgacgctgaggcacgaaagtgtgggtagcaaaca >OTU0095 [SEQUENCE ID 44] *Prevotella*
Tgaggaatattggtcaatggacgcaagtctgaaccagccaagtagcgtgcaggatgacggccctatgggttgtaaactgcttttta
tgtgggaataaattggcgcacgtgtgcgccattgcatgtacctcatgaataaggaccggctaattccgtgccagcagccgcggta
atacggaaggtccgggcgttatccggatttattgggtttaaagggagtgtaggcggtctgttaagcgtgttgtgaaatttaggtgctc
aacatttaacttgcagcgcgaactgtcagacttgagtacacgcagcgcaggcggaattcatggtgtagcggtgaaatgcttagat
atcatgaggaactccgatcgcgaaggcagcctgcgggagtgttactgacgcttaagctcgaaggtgcgggtatcgaaca >OTU0097 [SEQUENCE ID 45] *Peptostreptococcus*
Tggggaatattgcacaatgggcgaaagcctgatgcagcaacgccgcgtgaacgatgaaggtcttcggatcgtaaagttctgttg
cagggggaagataatgacggtaccctgtgaggaagccccggctaactacgtgccagcagccgcggtaatacgtaggggcta
gcgttatccggatttactgggcgtaaagggtgcgtaggtggtccttcaagtcggtggttaaaggctacggctcaaccgtagtaagc
cgccgaaactggaggacttgagtgcaggagaggaaagtggaattcccagtgtagcggtgaaatgcgtagatattgggaggaa
caccagtagcgaaggcggctttctggactgcaactgacactgaggcacgaaagcgtgggtagcaaaca >OTU0105 [SEQUENCE ID 46] *Clostridium_IV*
Tggggatattgcgcaatggggaaaccctgacgcagcaacgccgcgtgaaggaagaaggtcttcggattgtaaacttcttttg
tcagggacgaagaaagtgacggtacctgacgaataagctccggctaactacgtgccagcagccgcggtaatacgtagggag
cgagcgttgtccggatttactgggtgtaaagggtgcgtaggcggccgagcaagtcagttgtgaaaactatgggcttaacccataa
cgtgcaattgaaactgtccggcttgagtgaagtagaggtaggcggaattcccggtgtagcggtgaaatgcgtagagatcgggag
gaacaccagtggcgaaggcggcctactgggctttaactgacgctgaggcacgaaagcatgggtagcaaaca >OTU0109 [SEQUENCE ID 47] *Porphyromonas*
Tgaggaatattggtcaatgggcgagagcctgaaccagccaagtcgcgtgaaggaagactgcccgcaagggttgtaaacttctt
ttgtatgggattaaagtcgtctacgtgtagacgtttgcagttaccatacgaataagcatcggctaactccgtgccagcagccgcggt
aatacggaggatgcgagcgttatccggaattattgggtttaaagggtgcgtaggttgcaagggaagtcagggtgaaaagctgt
agctcaactatggtcttgccttgaaactctagctagagtgtactggaggtacgtggaacgtgtggtgtagcggtgaaatgcata
gatatcacacagaactccgattgcgcaggcagcgtactacattacaactgacactgaagcacgaaagcgtgggtatcaaaca >OTU0112 [SEQUENCE ID 48] *Clostridium_XIVa*
Tggggaatattgcacaatgggcgaaagcctgatgcagcgacgccgcgtgagtgaagaagtatttcggtatgtaaagctctatca
gcagggaagaaaatgacggtacctgactaagaagcccggctaactacgtgccagcagccgcggtaatacgtaggggca APPENDIX 1-continued agcgttatccggatttactgggtgtaaagggagcgtagacggcgaagcaagtctgaagtgaaaacccagggctcaaccctgg
gactgctttggaaactgttttgctagagtgtcggagaggtaagtggaattcctagtgtagcggtgaaatgcgtagatattaggagga
acaccagtggcgaaggcggcttactggacgataactgacgttgaggctcgaaagcgtggggagcaaaca >OTU0114 [SEQUENCE ID 49] *Parasutterella*
Tgggaattttggacaatgggcgcaagcctgatccagctattccgcgtgtgggatgaaggcccctcggggttgtaaaccacttttgta
gagaacgaaaagacaccttcgaataaagggtgttgctgacggtactctaagaataagcaccggctaactacgtgccagcagc
cgcggtaatacgtagggtgcgagcgttaatcggaattactgggcgtaaagggtgcgcaggcggttgagtaagacagatgtgaa
atccccgagcttaactcgggaatggcatatgtgactgctcgactagagtgtgtcagagggaggtggaattccacgtgtagcagtg
aaatgcgtagatatgtggaagaacaccgatggcgaaggcagcctcctgggacataactgacgctcaggcacgaaagcgtgg
ggagcaaaca >OTU0115 [SEQUENCE ID 50] *Clostridium_XIVa*
Tgggaatattgcacaatggggggaaaccctgatgcagcgacgccgcgtgagtgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgtagacggcaagcaagtcagaagtgaaaggctggggctcaacccccgg
gactgcttttgaaactgtttgactggagtgctggagaggtaagcggaattcctagtgtagcggtgaaatgcgtagatattaggagg
aacaccagtggcgaaggcggcttactggacagtaactgacgttgaggctcgaaagcgtggggagcaaaca >OTU0120 [SEQUENCE ID 51] *Bifidobacterium*
Tgggaatattgcacaatgggcgcaagcctgatgcagcgacgccgcgtgagggatgaggccttcggggttgtaaacctcttttg
tttgggagcaagccttcggggtgagtgtaccttttcgaataagcgccggctaactacgtgccagcagccgcggtaatacgtagggc
gcaagcgttatccggatttattgggcgtaaagggctcgtaggcggctcgtcgcgtccggtgtgaaagtccatcgcttaacggtgga
tctgcgccgggtacgggcgggctgagtgcggtaggggagactgaattcccggtgtaacggtgaatgtgtagatatcggga
agaacaccgatggcgaaggcaggtctctgggccgtcactgacgctgaggagcgaaagcgtggggagcgaaca >OTU0130 [SEQUENCE ID 52] *Solobacterium*
Tagggaattttcggcaatggggggcaacccctgaccgagcaacgccgcgtgagtgaagacggccttcggggttgtaaagctctgttg
taagggaagaacggtagatagagaatatctaagtgacggtaccttaccagaaagccacggctaactacgtgccagcagccgc
ggtaatacgtaggtggcgagcgttatccggaattattgggcgtaaagggtgcgtaggcggccgtgttaagtaagtggttaaattgttg
ggctcaacccaatccagccacttaaactggcaggctagagtattggagaggcaagtggaattccatgtgtagcggtaaaatgcg
tagatatatggaggaacaccagtggcgaaggcggcttgctagccaaagactgacgctcatgcacgaaagcgtggggagcaa
ata >OTU0134 [SEQUENCE ID 53] *Phascolarctobacterium*
Tgggaatcttccgcaatgggcgaaagcctgacggagcaatgccgcgtgagtgatgaaggaattcgttccgtaaagctcttttgt
ttatgacgaatgtgcaggttgtgaataatgacttgtaatgacggtagtaaacgaataagccacggctaactacgtgccagcagcc
gcggtaatacgtaggtggcgagcgttgtccggaattattgggcgtaaagagcatgtaggcggttttttaagtctggagtgaaaatg
cggggctcaacccccgtatggctctggatactggaagacttgagtgcaggagaggaaagggaattcccagtgtagcggtgaa
atgcgtagatattgggaggaacaccagtggcgaaggcgccttttctggactgtgtctgacgctgagatgcgaaagccagggtag
cgaacg >OTU0135 [SEQUENCE ID 54] *Hespellia*
Tgggaatattgcacaatggggggaaaccctgatgcagcgacgccgcgtgaaggatgaagtatttcggtatgtaaacttctatca
gcagggaagaaaatgacggtacctgactaagaagccccggctaactacgtgccagcagccgcggtaatacgtaggggggca
agcgttatccggatttactgggtgtaaagggagcgtagacggtatggcaagtctgatgtgaaaggccagggctcaaccctggga
ctgcattggaaactgtcgaactagagtgtcggagaggcaagtggaattcctagtgtagcggtgaaatgcgtagatattaggagg
aacaccagtggcgaaggcggcttgctggacgatgactgacgttgaggctcgaaagcgtggggagcaaaca >OTU0141 [SEQUENCE ID 55] *Aggregatibacter*
Tgggaatattgcgcaatggggggcaacccctgacgcagccatgccgcgtgaatgaagaaggccttcggggttgtaaagttctttcg
gtgacgaggaaggcgtgatgtttaataggcatcacgattgacgttaatcacagaagaagcacggctaactccgtgccagcag
ccgcggtaatacggagggtgcgagcgttaatcggaataactgggcgtaaagggcacgcaggcggctatttaagtgaggtgtga
aatccccgggcttaacctgggaattgcatttcagactgggtagctagagtactttagggaggggtagaattccacgtgtagcggtg
aaatgcgtagagatgtggaggaataccgaaggcgaaggcagccccttgggaatgtactgacgctcatgtgcgaaagcgtggg
gagcaaaca >OTU0142 [SEQUENCE ID 56] *Dialister*
Tgggaatcttccgcaatggacgaaagtctgacggagcaacgccgcgtgaacgaagaaggtcttcggattgtaaagttctgtg
attcgggacgaaagggtttgtggtgaataatcatagacattgacggtaccgaaaaagcaagccacggctaactacgtgccagc
agccgcggtaatacgtaggtggcaagcgttgtccggaattattgggcgtaaagcgcgcgcaggcggtttcttaagtccatcttaaa
agcgtggggctcaacccccatgaggggatgaaactgggaagctggagtatcggagaggaaagtggaattcctagtgtagcgg
tgaaatgcgtagagattaggaagaacaccggtggcgaaggcgactttctagacgaaaactgacgctgaggcgcgaaagcgt
ggggagcaaaca >OTU0148 [SEQUENCE ID 57] *Flavonifractor*
Tgggaatattgggcaatgggcgcaagcctgacccagcaacgccgcgtgaaggaagaaggctttcgggttgtaaacttcttttg
tcggggacgaaacaaatgacggtacccgacgaataagccacggctaactacgtgccagcagccgcggtaatacgtaggtgg
caagcgttatccggatttactgggtgtaaagggcgtgtaggcgggattgcaagtcagatgtgaaaactgggggctcaacctcca
gcctgcatttgaaactgtagttcttgagtgctggagaggcaatcggaattccgtgtgtagcggtgaaatgcgtagatatacggagg
aacaccagtggcgaaggcggattgctggacagtaactgacgctgaggcgcgaaagcgtggggagcaaaca >OTU0149 [SEQUENCE ID 58] *Blautia*
Tgggaatattgcacaatggggggaaaccctgatgcagcgacgccgcgtgaaggaagaagtatctcggtatgtaaacttctatc
agcagggaagaaaatgacggtacctgactaagaagccccggctaactacgtgccagcagccgcggtaatacgtaggggggc
aagcgttatccggatttactgggtgtaaagggagcgtagacggcataacaagtctgatgtgaaaggctgggcttaaccccggg
actgcattggaaactgtaagcttgagtgccggagggtaagcggaattcctagtgtagcggtgaaatgcgtagatattaggagg
aacaccagtggcgaaggcggcttactggacggtaactgacgttgaggctcgaaagcgtggggagcaaaca APPENDIX 1-continued >OTU0155 [SEQUENCE ID 59] *Lactobacillus*
tagggaatcttccacaatggacgcaagtctgatggagcaacgccgcgtgagtgaagaaggttttcggatcgtaaagctctgttgtt
ggtgaagaaggatagaggcagtaactggtctctttatttgacggtaatcaaccagaaagtcacggctaactacgtgccagcagcc
gcggtaatacgtaggtggcaagcgttgtccggatttattgggcgtaaagcgagcgcaggcggaatgataagtctgatgtgaaag
cccacggctcaaccgtggaactgcatcggaaactgtcattcttgagtgcagaagaggagagtggaattccatgtgtagcggtgg
aatgcgtagatatatggaagaacaccagtggcgaaggcggctctctggtctgcaactgacgctgaggctcgaaagcatgggta
gcgaaca >OTU0157 [SEQUENCE ID 60] *Leptotrichia*
tggggaatattggacaatgggggcaaccctgatccagcaattctgtgtgcacgaagaaggttttcggattgtaaagtgctttcagc
agggaagaagaaagtgacggtacctgcagaagaagcgacggctaaatacgtgccagcagccgcggtaatacgtatgtcgc
aagcgttatccggaattattgggcataaagggcatctaggcggccctgtaagtctagggtgaaaacctgcggctcaaccgcagg
cctgccccggaaactacagggctagagtatcggagaggtggacggaactgcacgagtagaggtgaaattcgtagatatgtgc
aggaatgccgatgatgaagatagttcactggacggtaactgacgctgaagtgcgaaagctaggggagcaaaca >OTU0158 [SEQUENCE ID 61] Unknown
tggggaatattgcacaatggaggcaactctgatgcagcgacgccgcgtgagtgaagaagtatttcggtatgtaaagctctatcag
taggaagataatgacggtacctacagaagaagcccccggctaaatacgtgccagcagccgcggtaatacgtatggggcaag
cgttatccggatttactgggtgtaaagggagtgtaggcggcagtacaagtcaggagtgaaaacttggggctcaaccccaagact
gcttttgaaactgtacagctagagtgtaggaagggcaagcggaattcctggtgtagcggtgaaatgcgtagatatcaggaagaa
caccggtggcgaaggcggcttgctggactataactgacgctgagactcgaaagcgtggggagcgaaca >OTU0161 [SEQUENCE ID 62] unclassified.*Lachnospiraceae*
tggggaatattgcacaatggggggaaaccctgatgcagcgacgccgcgtgagcgaagaagtatttcggtatgtaaagctctatca
gcagggaagataatgacggtacctgactaagaagcccccggctaactacgtgccagcagccgcggtaatacgtaggggggcaa
gcgttatccggatttactgggtgtaaagggagcgtagacggcaaggcaagtctgatgtgaaaacccagggcttaaccctggga
ctgcattggaaactgtctggctcgagtgccggagaggtaagcggaattcctagtgtagcggtgaaatgcgtagatattaggagga
acaccagtggcgaaggcggcttactggacggtaactgacgttgaggctcgaaagcgtggggagcaaaca >OTU0167 [SEQUENCE ID 63] *Streptococcus*
tagggaatcttcggcaatgggggggaaccctgaccgagcaacgccgcgtgagtgaagaaggttttcggatcgtaaagctctgttg
ttaaggaagaacgtgtgtgagagtggaaagttcacacagtgacggtacttaaccagaaagggacggctaactacgtgccagc
agccgcggtaatacgtaggtcccgagcgttgtccggatttattgggcgtaaagcgagcgcaggcggtttagataagtctgaagtg
aaaggcagtggctcaaccattgtaggctttggaaactgtttaacttgagtgcagaagggggagtggaattccatgtgtagcggt
gaaatgcgtagatatatggaggaacaccggtggcgaaagcggctctctggtctgtaactgacgctgaggctcgaaagcgtggg
gagcgaaca >OTU0171 [SEQUENCE ID 64] UNKNOWN
tggggaatcttccgcaatgacgaaagtctgacggagcaacgccgcgtgagtgatgaaggtcttcggattgtaaaactctgttgtt
agggacgaaagcaccgtgttcgaacaggtcatggtgttgacggtacctaacgaggaagccacggctaactacgtgccagcag
ccgcggtaatacgtaggtggcaagcgttgtccggaattattgggcgtaaagcagcatgtaggcgggctttaagtctgacgtgaaa
atgcggggcttaaccccgtatggcgttggatactggaagtcttgagtgcaggagaggaaagggggaattcccagtgtagcggtga
aatgcgtagatattgggaggaacaccagtggcgaaggcgcctttctggactgtgtctgacgctgagatgcgaaagccagggta
gcaaacg >OTU0173 [SEQUENCE ID 65] UNKNOWN
tggggaatattgggcaatgggcgaaagcctgacccagcaacgccgcgtgaaggaagaaggccttcgggttgtaaacttcttttta
agagggacgaagaagtgacggtacctcttgaataagccacggctaactacgtgccagcagccgcggtaatacgtaggtggcg
agcgttatccggatttactgggtgtaaagggcgcgtaggcgggaatgcaagtcagatgtgaaatccaagggctcaacccttgaa
ctgcatttgaaactgtatttcttgagtgtcggagaggttgacggaattcctagtgtagcggtgaaatgcgtagatattaggaggaac
accaggtggcgaaggcggtcaactggacgataactgacgctgaggcgcgaaagcgtggggagcaaaca >OTU0174 [SEQUENCE ID 66] *Kingella*
tggggaattttggacaatgggcgcaagcctgatccagccatgccgcgtgtctgaagaaggccttcgggttgtaaaggacttttgtt
agggaagaaaaggatagtgttaataccattatctgctgacggtacctaaagaataagcaccggctaactacgtgccagcagcc
gcggtaatacgtagggtgcgagcgttaatcggaattactgggcgtaaagcgagcgcagacggtttattaagcaagatgtgaaat
ccccgagcttaacttgggaactgcgttttgaactggtaagctagagtatgtcagagggggtagaattccacgtgtagcagtgaa
atgcgtagagatgtggaggaataccgatggcgaaggcagccccctgggataatactgacgttcatgctcgaaagcgtgggtag
caaaca >OTU0175 [SEQUENCE ID 67] *Aggregatibacter*
tggggaatattgcgcaatgggggcaaccctgacgcagccatgccgcgtgaatgaagaaggccttcgggttgtaaagttctttcgg
tgacgaggaaggttgttgtgttaatagcgcaacaaattgacgttaatcacagaagaagcaccggctaactccgtgccagcagcc
gcggtaatacgagggtgcgagcgttaatcggaataactgggcgtaaagggcacgcaggcggctatttaagtgaggtgtgaa
atccccgggcttaacctgggaattgcatttcagactgggtagctagagtactttagggaggggtagaattccacgtgtagcggtga
aatgcgtagagatgtggaggaataccgaaggcgaaggcagcccccttgggaatgtactgacgctcatgtgcgaaagcgtgggg
agcaaaca >OTU0176 [SEQUENCE ID 68] *Campylobacter*
tagggaatattgcgcaatgggggaaaccctgacgcagcaacgccgcgtggaggatgacacttttcggagcgtaaactccttttgt
tagggaagaataatgacgttacctaacgaataagcaccggctaactccgtgccagcagccgcggtaatacgagggtgcaa
gcgttactcggaatcactgggcgtaaaggacgcgtaggcggattatcaagtctcttgtgaaatcaacggcttaaccgttaaactg
cttgggaaactgataatctagagtaagggagaggcagatggaattcttggtgtaggggtaaaatccgtagatatcaagaagaat
acctattgcgaaggcgatctgctggaacttaactgacgctaatgcgtgaaagcgtggggagcaaaca >OTU0187 [SEQUENCE ID 69] *Paraprevotella*
Tgaggaatattggtcaatgggcgggagcctgaaccagccaagtagcgtgaaggacgacggccctacgggttgtaaacttcttttt
ataagggaataaagttcgccacgtgtggtgttttgtatgtaccttatgaataagcatcggctaattccgtgccagcagccgcggtaa
tacggaagatgcgagcgttatccggatttattgggtttaaagggagcgtaggcgggcttttaagtcagcggtcaaatgtcgtggctc APPENDIX 1-continued

```
aaccatgtcaagccgttgaaactgtaagccttgagtctgcacagggcacatggaattcgtggtgtagcggtgaaatgcttagatat
cacgaagaactccgatcgcgaaggcattgtgccggggcataactgacgctgaggctcgaaagtgcgggtatcaaaca >OTU0194 [SEQUENCE ID 70] Bacteroides
tgaggaatattggtcaatggacgagagtctgaaccagccaagtagcgtgaaggatgactgccctatgggttgtaaacttcttttata
cgggaataaagtggagtatgcatactcctttgtatgtaccgtatgaataaggatcggctaactccgtgccagcagccgcggtaata
cggaggatccgagcgttatccggatttattgggtttaaagggagcgtaggcgggtgcttaagtcagttgtgaaagtttgcggctcaa
ccgtaaaattgcagttgatactgggcgccttgagtgcagcataggtaggcggaattcgtggtgtagcggtgaaatgcttagatatc
acgaagaactcctattgcgaaggcagcttactggactgtaactgacgctgatgctcgaaagtgtgggtatcaaaca >OTU0206 [SEQUENCE ID 71] Clostridium_IV
tgggggatattgcacaatggggaaaccctgatgcagcaacgccgcgtgaaggaagaaggtcttcggattgtaaacttctgtcc
tcagggaagataatgacggtaccttgaggaggaagctccggctaactacgtgccagcagccgcggtaataggggagcga
gcgttgtccggatttactgggtgtaaagggtgcgtaggcggatctgcaagtcagtagtgaaatcccagggcttaaccctggaact
gctattgaaactgtgggtcttgagtgaggtagaggcaggcggaattcccggtgtagcggtgaaatgcgtagagatcgggagga
acaccagtggcgaaggcggcctgctgggccttaactgacgctgaggcacgaaagcatgggtagcaaaca >OTU0210 [SEQUENCE ID 72] UNKNOWN
tgggggaatattgcacaatggggaaaccctgatgcagcaacgccgcgtgaaggatgaaggcctttgggtcgtaaacttctgttct
aagggaagatagtgacggtaccttaggagcaagtcccggctaactacgtgccagcagccgcggtaatacgtaggggggcaag
cgttatccggaattattgggcgtaaagagtacgtaggtggttttctaagcacggggtttaaggcaatggcttaaccattgttcgccttg
tgaactggaagacttgagtgcaggagaggaaagcggaattcctagtgtagcggtgaaatgcgtagatattaggaggaacacc
agtggcgaaggcggctttctggactgtaactgacactgaggtacgaaagcgtggggagcaaaca >OTU0217 [SEQUENCE ID 73] Alloprevotella
tgaggaatattggtcaatggacgaaagtctgaaccagccaagtagcgtgcaggatgacggccctctgggttgtaaactgcttttta
gttgggaataaaaaagaggacgtgtcctctattgtatgtaccttcagaaaaaggaccggctaattccgtgccagcagccgcggta
atacggaaggtccaggcgttatccggatttattgggtttaaagggagcgtaggcggattattaagtcagtggtgaaagacggtgg
ctcaaccatcgttagccattgaaactggtagtcttgagtgcagacagggatgctggaactcgtggtgtagcggtgaaatgcttaga
tatcacgatgaactccgatcgcgaaggcaggtgtccgggctgcaactgacgctgaggctcgaaagtgtgggtatcaaaca >OTU0228 [SEQUENCE ID 74] UNKNOWN
tgaggaatattggtcaatggacggaagtctgaaccagccatgccgcgtgcaggatgaatgtgctatgcattgtaaactgcttttgta
cgagggtaaacacagatacgcgtatctgcttgaaagtatcgtacgaataaggatcggctaactccgtgccagcagccgcggta
atacggaggatccgagcgttatccggatttattgggtttaaagggtgcgtaggctgtttttttaagttagaggtgaaagctcgacgctc
aacgtcgaaattgcctctgatactgagagactagagtgtagttgcggaaggcggaatgtgtggtgtagcggtgaaatgcttagat
atcacacagaacaccgattgcgaaggcagcttccaagctattactgacgctgaggcacgaaagcgtggggagcgaaca >OTU0233 [SEQUENCE ID 75] Capnocytophaga
tgaggaatattggtcaatggtcggaagactgaaccagccatgccgcgtgcaggaagaatgccttatgggttgtaaactgctttttat
atgggaagaataaggagtacgtgtactttgatgacggtaccatatgaataagcatcggctaactccgtgccagcagccgcggta
atacggaggatgcgagcgttattcggaatcattgggtttaaagggtcgtaggcgggctattaagtcagggtgaaagtttcagc
ttaactgagaaattgcctttgatactgtagtcttgaatatctgtgaagttcttggaatgtgtagtgtagcggtgaaatgcttagatatta
cacagaacaccgattgcggaggcagggagactaacagacgattgacgctgagagacgaaagcgtggggagcgaaca >OTU0244 [SEQUENCE ID 76] Capnocytophaga
tgaggaatattggacaatggtcggaagactgatccagccatgccgcgtgcaggaagacggccttatgggttgtaaactgcttttg
caggggaagaataaggagtacgtgtactttgatgacggtactctgcgaataagcatcggctaactccgtgccagcagccgcggt
aatacggaggatgcgagcgttatccggaatcattgggtttaaagggtccgtaggcgggctaataagtcagaggtgaaagcgctc
agctcaactgagcaactgcctttgaaactgttagtcttgaatggttgtgaagtagttggaatgtgtagtgtagcggtgaaatgcttag
atattacacagaacaccgatagcgaaggcatattactaacaattaattgacgctgatggacgaaagcgtggggagcgaaca >OTU0251 [SEQUENCE ID 77] Pseudoflavonifractor
tgggggaatattgggcaatgggcgcaagcctgacccagcaacgccgcgtgaaggaagaaggctttcgggttgtaaacttcttttcTt
agggacgaagcaagtgacggtacctaaggaataagccacggctaactacgtgccagcagccgcggtaatacgtaggtggca
agcgttatccggatttactgggtgtaaagggcgtgtaggcgggatttgcaagtcagatgtgaaaaccacgggctcaacctgtggc
ctgcatttgaaactgtagttcttgagtactggagaggcagacggaattcctagtgtagcggtgaaatgcgtagatattaggaggaa
caccagtggcgaaggcggtctgctggacagcaactgacgctgaggcgcgaaagcgtggggagcaaaca >OTU0261 [SEQUENCE ID 78] UNKNOWN
tgggggaatattgggcaatgggcgaaagcctgacccagcaacgccgcgtgaaggaagaaggttttcggatcgtaaacttctatcc
ttggtgaagataatgacggtagccaagaaggaagccccggctaactacgtgccagcagccgcggtaatacgtaggggggcaa
gcgttgtccggaatgattgggcgtaaagggcgcgtaggcggcaactaagtctgacgtgaaaggtcctgcttttaaggtgggaatt
gctttggaaactgtgatggcttgagtgcaggagaggtaagcggaattcccggtgtagcggtgaaatgcgtagagatcgggagga
acaccagtggcgaaggcggcttactggactgtaactgacgctgaggcgcgaaagtgtggggagcaaaca >OTU0277 [SEQUENCE ID 79] Eikenella
tggggaattttggacaatgggggcaaccctgatccagccatgccgcgtgtatgaagaaggccttcgggttgtaaagtacttttgtta
gggaagaaaagggaagtgctaataccactttttgctgacggtacctaaagaataagcaccggctaactacgtgccagcagccg
cggtaatacgtagggtgcgagcgttaatcggaattactgggcgtaaagcgagcgcagacggttatttaagcaggatgtgaaatc
cccggggcttaacctgggaactgcgttctgaactggatagctagagtgtgtcagagggggtagaattccacgtgtagcagtgaa
atgcgtagagatgtggaggaataccgatggcgaaggcagcccctgggataacactgacgttcatgctcgaaagcgtgggta
gcaaaca >OTU0283 [SEQUENCE ID 80] Tannerella
tgaggaatattggtcaatgggcgagagcctgaaccagccaagtcgcgtgaaggatgacggccctatgggttgtaaacttctttg
caggggaataaagatattcacgtgtgggtagttgtatgtaccctgcgaataagcatcggctaactccgtgccagcagccgcggta
atacggaggatgcgagcgttatccggatttattgggtttaaagggtgcgtaggtgggctattaagtcagtggtgaaagtttgtcgctc
aacgataaaattgccgttgaaactggtggtcttgagtatggatgaagtaggcggaatgcgtggtgtagcggtgaaatgcatagag
atcacgcagaactccgattgcgaaggcagcttactaaggcataactgacactgaagcacgaaagcgtgggtatcaaaca
```

APPENDIX 1-continued

>OTU0290 [SEQUENCE ID 81] Neisseria
tggggaattttggacaatgggggcaaccctgatccagccatgccgcgtgtctgaagaaggccttcgggttgtaaaggacttttgtc
cggaagaaaagcgcgatgttaataccattgcgtgctgacggtaccggaagaataagcaccggctaactacgtgccagcagc
cgcggtaatacgtagggtgcgagcgttaatcggaattactgggcgtaaagcgggcgcagacggttacttaagcaggatgtgaa
atccccgggctcaacctgggaattgcgttctgaactgggtggctagagtgtgtcagaggggggtagaattccacgtgtagcagtg
aaatgcgtagagatgtggaggaataccgatggcgaaggcagccccctgggatagcactgacgttcatgcccgaaagcgtggg
tagcaaaca >OTU0299 [SEQUENCE ID 82] Prevotella
tgaggaatattggtcaatgggcgagagcctgaaccagccaagtagcgtgcaggacgacggccctatgggttgtaaactgctttt
gtatggggataaagtcaatcacgtgtgattgtttgcaggtaccatacgaataaggaccggctaattccgtgccagcagccgcggt
aatacggaaggttcgggcgttatccggatttattgggtttaaagggagcgtaggccggagattaagtgtgttgtgaaatgtagacg
ctcaacgtctgacttgcagcgcatactggtttccttgagtacgcacaacgttggcggaattcgtcgtgtagcggtgaaatgcttagat
atgacgaagaactccgattgcgaaggcagctgacgggagcgccactgacgcttaagctcgaaggtgcgggtatcgaaca >OTU0303 [SEQUENCE ID 83] unclassified.Flavobacteriaceae
tgaggaatattggacaatgggtggaagcctgatccagccatcccgcgtgcaggacgactgccctatgggttgtaaactgcttttat
ataggataaaacctactctcgtgagagtagctgaaggtactatatgaataagcaccggctaactccgtgccagcagccgcggta
atacggagggtgcaagcgttatccggatttattgggtttaaagggtccgtaggtgggctgataagtcagcggtgaaatcctgcagc
ttaactgtagaactgccgttgatactgttagtcttgagtgtatttgaagtggctggaataagtagtgtagcggtgaaatgcatagatatt
acttagaacaccaattgcgaaggcaggtcactaagatacaactgacgctgagggacgaaagcgtggggagcgaaca >OTU0306 [SEQUENCE ID 84] UNKNOWN
tggggaatattgcacaatgggggaaaccctgatgcagcaacgccgcgtgagggaagaaggttttcggattgtaaacctctgttct
tagtgacgataatgacggtagctaaggagaaagctccggctaactacgtgccagcagccgcggtaatacgtagggagcgagc
gttgtccggatttactgggtgtaaagggtgcgtaggcggcgaggcaagtcaggcgtgaaatctatgggcttaacccataaactgc
gcttgaaactgtcttgcttgagtgaagtagaggtaggcggaattcccggtgtagcggtgaaatgcgtagagatcgggaggaaca
ccagtggcgaaggcggcctactgggctttaactgacgctgaagcacgaaagcatgggtagcaaaca >OTU0317 [SEQUENCE ID 85] Lachnoanaerobaculum
tggggaatattggacaatgggggaaaccctgatccagcgacgccgcgtgagtgaagaagtatttcggtatgtaaagctctatca
gcagggaagaaaatgacggtacctgactaagaagccccggctaactacgtgccagcagccgcggtaatacgtagggggca
agcgttatccggatttactgggtgtaaagggagcgcagacggccaagcaagtctgaagtgaaatgcatgggctcaacccatga
attgctttggaaactgttaggcttgagtgtcggagggtaagcgaattcctagtgtagcggtgaaatgcgtagatattaggagga
acaccggaggcgaaggcggcttactggacgacaactgacgttgaggctcgaaggcgtgggagcaaaca >OTU0324 [SEQUENCE ID 86] Selenomonas
tggggaatcttccgcaatgggcgcaagcctgacggagcaacgccgcgtgagtgaagaaggtcttcggatcgtaaagctctgttg
atggggacgaacgtgcctaatgcgaatagttttaggcaatgacggtacccatcgaggaagccacggctaactacgtgccagca
gccgcggtaatacgtaggtggcgagcgttgtccgaatcattgggcgtaaagggagcgcaggcgggcatgtaagtctttcttaa
aagtgcgggctcaaccccgtgatgggaaagaaactatgtgtcttgagtacaggagaggaaagcggaattcccagtgtagcg
gtgaaatgcgtagatattgggaggaacaccagtggcgaaggcggctttctggactgcaactgacgctgaggctcgaaagcca
ggggagcgaacg >OTU0337 [SEQUENCE ID 87] Cardiobacterium
tggggaatattggacaatgggggaaccctgatccagcaatgccgcgtgtgtgaagaaggccttcgggttgtaaagcactttca
gcagggaggaaaggtgcgtagttaatagctgcgcaattgacgttacctgcagaagaagcaccggctaactccgtgccagcag
ccgcggtaatacggagggtgcaagcgttattcggaattactgggcgtaaagcgcacgcaggcggttgcccaagtcagatgtga
aagccccgggcttaacctgggaactgcatttgaaactgggcgactagagtatgaaagaggaaagcggaatttccagtgtagca
gtgaaatgcgtagatattggaaggaacaccgatggcgaaggcagctttctgggtcgatactgacgctcatgtgcgaaagcgtgg
ggagcaaaca >OTU0348 [SEQUENCE ID 88] Prevotella
tgaggaatattggtcaatggatggaaatctgaaccagccaagtagcgtgcaggatgacggccctatgggttgtaaactgcttttat
gtgagaataaagttaggtatgtatacttatttgcatgtatcacatgaataaggaccggctaattccgtgccagcagccgcggtaata
cggaaggtccaggcgttatccggatttattgggtttaaagggtgcgtaggccgtttgataagcgtgctgtgaaatatagtggctcaa
cctctatcgtgcagcgcgaactgtcgaacttgagtgcgtagtaggtaggcggaattcgtggtgtagcggtgaaatgcttagatatc
acgaagaactccgattgcgaaggcagcttaccgtaacgttactgacgcttaagcacgaaggtgcgggtatcgaaca >OTU0350 [SEQUENCE ID 89] Actinomyces
tgggggattttgcacaatgggcgcaagcctgatgcagcgacgccgcgtgagggatggaggcctcgggttgtgaacctctgtcg
ccggtgatgtaggctctgctttgtgggtggggttgacggtagcggggtatgaagtgccggctaactacgtgccagcagccgcgg
taatacgtagggcgcgagcgttgtccggaattattgggcgtaaagagctcgtaggcggcttggtcgcgtctgtcgtgaaatcctctg
gcttaactggggcgtgcggtgggtacgggccggcttgagtgcgtagggaggctggaattcctggtgtagcggtggaatgcg
cagatatcaggaggaacaccggtggcgaaggcgggctctctgggccgtgtactgacgctgagagcgaaagcgtggggagc
gaaca >OTU0351 [SEQUENCE ID 90] UNKNOWN
tggggaatattgcacaatgggggaaccctgatgcagcgacgccgcgtgagggaagaaggttttcggattgtaaacctctgtcc
ttggtgacgataatgacggtagccaaggaggaagccacggctaactacgtgccagcagccgcggtaatacgtaggtggcaag
cgttgtccggaattactgggtgtaaagggagcgtaggcgggaagacaagttgggagtgaaatgtatgggcttaacccataaact
gctttcaaaactgtttttcttgagtgaagtagaggcaggcggaattcctagtgtagcggtgaaatgcgtaaatattaggaggaaca
ccagtggcgaaggcggcctgctgggctttaactgacgctgaggctcgaaagcgtgggtagcaaaca >OTU0358 [SEQUENCE ID 91] UNKNOWN
tgagggatattgggcaatgggggaaaccctgacccagcgacgccgcgtgagggaagaacggtcttcggattgtaaacctctgtct
ttggggacgaaaaggacggtacccaaggaggaagctccggctaactacgtgccagcagccgcggtaatacgtagggagc
gagcgttgtccggaattactgggtgtaaagggagcgtaggcgggaaggcaagttggatgtgaaaactgtgggcttaaccgaca APPENDIX 1-continued gactgcattcaaaactgtttttcttgagtgaagtagaggcaagcggaattcctagtgtagcggtgaaatgcgtagatattaggagg
aacaccagtggcgaaggcggcttgctgggcttttactgacgctgaggctcgaaagtgtggggagcaaaca >OTU0359 [SEQUENCE ID 92] UNKNOWN
tagggaattttcggcaatgggcgaaagcctgaccgagcaacgccgcgtgagtgaagaaggccttcggggtgtaaagctctgttg
tgaaggaagaacggctcatacaggaatggtatgggagtgacggtactttaccagaaagccacggctaactacgtgccagca
gccgcggtaatacgtaggtggcgagcgttatccggaattattgggcgtaaagggtgcgcaggcggtttgttaagtttaaggtgaa
agcgtggggcttaaccccatatagccttagaaactgacagactagagtacaggagagggcaatgaattccatgtgtagcggt
aaaatgcgtagatatatggaggaacaccagtggcgaaggcggttgcctggcctgtaactgacgctcatgcacgaaagcgtgg
ggagcaaata >OTU0361 [SEQUENCE ID 93] Butyricimonas
tgaggaatattggtcaatgggcgagagcctgaaccagccaagtcgcgtgagggaagaatggtctatggcctgtaaacctcttttg
ccagggaagaataaaaggtacgtgtaccttcttgccagtacctgacgaataagcatcggctaactccgtgccagcagccgcggt
aatacggggatgcgagcgttatccggatttattgggtttaaagggcgcgtaggcgggacgccaagtcagcggtaaaagactg
cagctaaactgtagcacgccgttgaaactggcgacctggagacgagacgagggaggcggaacaagtgaagtagcggtgaa
atgcttagatatcacttggaacccgatagcgaaggcagcttcccaggctcgatctgacgctgatgcgcgagagcgtgggtagc
gaaca >OTU0362 [SEQUENCE ID 94] UNKNOWN
tagggaattttcggcaatggacggaagtctgaccgagcaacgccgcgtgaatgatgaagtatttcggtatgtaaagttcttttatttg
ggaagaaaaaacaaattgacggtaccaaatgaataagcccccggctaactacgtgccagcagccgcggtaatacgtaggggg
caagcgttatccggaattattgggcgtaaagggtgcgtaggcggttatcaagtctttgttaaaatgcggtgctcaacgccgtagt
gccaaagaaactgatagtctagagtatggtagaagtgagtggaactccatgtgtagcggtaaaatgcgtaaatatatggaagaa
caccagtggcgaaggcggctcactaggccaatactgacgctgagacacgaaagcgtggggagcaaaca >OTU0364 [SEQUENCE ID 95] unclassified.Clostridiales
tggggaatattgggcaatggggaaaccctgacccagcaacgccgcgtgaggaagaaggtcttcggattgtaaactcctgtc
cttagggaagaaacaaatgacggtacctgagggaggaagctccggctaactacgtgccagcagccgcggtaatacgtaggga
gcgagcgttgtccggaattactgggcgtaaagggtgcgtaggcggtctgaaaagtcggatgtgaaatccccgtgcttaacatgg
gagctgcattcgaaactttcggactgtgagtgtcggagaggtaagcggaattcccggtgtagcggtgaaatgcgtagatatcggga
ggaacaccagtggcgaaggcggcttactgacgacaactgacgctgaggcacgaaagcgtggggagcaaaca >OTU0366 [SEQUENCE ID 96] UNKNOWN
tggggaatattgggcaatggagggaactctgacccagcaacgccgcgtgagtgaagaaggttttcggattgtaaaactctttaag
cggggacgaagaaagtgactgtacccgcagaataagcatcggctaactacgtgccagcagccgcggtaatacgtaggatgc
aagcgttatccggaatgactgggcgtaaagggtgcgtaggtggtttgccaagttggcagcgtaattccgtggcttaaccgcggaa
ctactgccaaaactggtaggcttgagtgcggcaggggtatgtggaattcctagtgtagcggtggaatgcgtagatattaggagga
acaccggtggcgaaagcgacatactgggccgtaactgacactgaggcacgaaagcgtggggagcaaaca >OTU0369 [SEQUENCE ID 97] UNKNOWN
tggggaatattgggcaatggacgcaagtctgacccagcaacgccgcgtgaaggaagaaggctttcggggtgtaaacttcttttgt
cagggaacagtagaagaggggtacctgacgaataagccacggctaactacgtgccagcagccgcggtaatacgtaggtggca
agcgttgtccggatttactgggtgtaaagggcgtgcagccgggctggcaagtcaggcgtgaaatcccagggctcaaccctgga
actgcgtttgaaactgctggtcttgagtaccggagaggtcatcggaattccttgtgtagcggtgaaatgcgtagatataaggaaga
acaccagtggcgaaggcggatgactggacggcaactgacggtgaggcgcgaaagcgtggggagcaaaca >OTU0371 [SEQUENCE ID 98] UNKNOWN
tgggggatattgcacaatggaggaaactctgatgcagcaacgccgcgtgagggaagaaggttttcggattgtaaacctctgttttt
agtgaagaaacaaatgacggtagctaaagaggaagccacggctaactacgtgccagcagccgcggtaatacgtaggtggc
aagcgttgtccggaattactgggtgtaaagggtgcgcaggcgggattgcaagttggatgtgaaataccggggcttaaccccgga
gctgcatccaaaactgtagttcttgagtggagtagaggtaagcggaattccgagtgtagcggtgaaatgcgtagatattcggagg
aacaccagtggcgaaggcggcttactgggctctaactgacgctgaggcacgaaagcatgggtagcaaaca >OTU0380 [SEQUENCE ID 99] UNKNOWN
tggggaattttgcgcaatggggcaaccctgacgcagcgacgccgcgtgcgggacgaagtcattcgtgacgtaaaccgctttc
agcgaggaagaaccatgacggtactcgcagaagaagccccggctaactacgtgccagcagccgcggtaatacgtagggg
cgagcgttatccggaatcattgggcgtaaagcgcgcgcaggcgggctttcaagcggcggcgtcgaagccgggggctcaaccc
ccggaagcgccccgaactggaagcctcggatgcggcaggggaggcggaattcccggtgtagcggtgaaatgcgcagatat
cgggaagaacaccgacggcgaaggcagcctcctgggccggcatcgacgctgaggcgcgaaagcgtggggagcgaaca >OTU0389 [SEQUENCE ID 100] Prevotella
tgaggaatattggtcaatgggcgtgagcctgaaccagccaagtagcgtgcaggatgacggccctatgggttgtaaactgcttttat
acggggataaaagggtgaacgtgttctcctttgcaggtacctgtgaataagaccggctaattccgtgccagcagccgcgta
atacggaaggtcctggcgttatccggatttattgggtttaaagggagcgcaggctgcactttaagcgtgttgtgaaatgtaccggct
caaccggtaacgtgcagcgcgaactggggtgcttgagtacgaagagggaaggcggaactcgtggtgtagcggtgaaatgctt
agatatcacgaggaactccgatcgcgaaggcagctttccgtttcggaactgacgctgaggctcgaaagtgcgggtatcgaaca >OTU0395 [SEQUENCE ID 101] UNKNOWN
tgggggatattgcacaatgggcgaaagcctgatgcagcgacgccgcgtgagggaagacgccttcggggtgtaaacctctgtc
attcgggacgaattagatgacggtaccgaagaaggaagctccggctaactacgtgccagcagccgcggtaatacgtagggag
cgagcgttgtccggaattactgggtgtaaagggagcgtaggcgggaaagcaagttggaagtgaaatgcatgggcttaacccat
gagctgcttcaaaactgtttttcttgagtgaagtagaggcaggcggaattcctagtgtagcggtgaaatgcgtagatattaggagg
aacaccagtggcgaaggcggcctgctgggcttaactgacgctgaggctcgaaagcgtgggtagcaaaca >OTU0397 [SEQUENCE ID 102] Gemmiger
tgggggatattgcacaatggggaaaccctgatgcagcgacgccgcgtgagggaagaaggttttcggattgtaaactcctgtcg
ttagggacgataatgacggtacctaacaagaaagcaccggctaactacgtgccagcagccgcggtaaaacgtagggtgcaa APPENDIX 1-continued gcgttgtccggaattactgggtgtaaaggagcgcaggcgggaagacaagttggaagtgaaaaccatgggctcaacccatga
attgctttcaaaactgttttgcttgagtagtgcagaggtagatggaattcccggtgtagcggtggaatgcgtagatatcgggaggaa
caccagtggcgaaggcggtctactgggcaccaactgacgctgaggctcgaaagcatgggtagcaaaca >OTU0406 [SEQUENCE ID 103] *Prevotella*
tgaggaatattggtcaatgggcgagagcctgaaccagccaagtagcgtgcaggatgacggcccctatgggttgtaaactgcttttta
tgcggggataaagtgagggacgtgtccttcattgcaggtaccgcatgaataaggaccggctaattccgtgccagcagccgcggt
aatacgaaggtccgggcgttatccggatttattgggtttaaagggagcgtaggccgtggattaagcgtgttgtgaaatgcaggtg
ctcaacgtctgcactgcagcgcgaactggtccacttgagtgtgcgcaacgcaggcggaattcgtcgtgtagcggtgaaatgctta
gatatgacgaagaactccgattgcgaaggcacttgcgggagcacaactgacgctgaagctcgaaagtgcgggtatcgaaca >OTU0412 [SEQUENCE ID 104] *Selenomonas*
tggggaatcttccgcaatgggcgcaagcctgacggagcaacgccgcgtgagtgaagaaggtcttcggatcgtaaagctctgttg
atggggacgaacgtgcgaagggtgaataatcctttgcaatgacggtacctatcgaggaagccacggctaactacgtgccagca
gccgcggtaatacgtaggtggcgagcgttgtccggaatcattgggcgtaaagggagcgcaggcgggcatgtaagtctttcttaa
aagttcggggctcaaccccgtgatgggaaagaaactacatgtcttgagtacaggagaggaaagcggaattcccagtgtagcg
gtgaaatgcgtagatattgggaggaacaccagtggcgaaggcggctttctggactgcaactgacgctgaggctcgaaagcca
ggggagcgaacg >OTU0424 [SEQUENCE ID 105] *Veillonella*
tggggaatcttccgcaatggacgaaagtctgacggagcaacgccgcgtgagtgatgacggccttcgggttgtaaagctctgttaa
tcgggacgaatggttcttgtgcgaatagtgcgaggatttgacggtaccggaatagaaagccacggctaactacgtgccagcagc
cgcggtaatacgtaggtggcaagcgttgtccggaattattgggcgtaaagcgcgcgcaggcggatcagttagtctgtcttaaaag
ttcggggcttaaccccgtgatgggatggaaactgctgatctagagtatcggagaggaaagtggaattcctagtgta
gcggtgaaa
tgcgtagatattaggaagaacaccagtggcgaaggcgactttctggacgaaaactgacgctgaggcgcgaaagccagggga
gcgaacg >OTU0427 [SEQUENCE ID 106] *Dorea*
tggggaatattgcacaatgggcgaaagcctgatgcagcgacgccgcgtgaaggatgaagtatttcggtatgtaaacttctatcag
cagggaagaaaatgacggtacctgactaagaagcccggctaactacgtgccagcagccgcggtaatacgtaggggggcaa
gcgttatccggatttactgggtgtaaaggagcgtagacggctgtgcaagtctgaagtgaaaggcatgggcgcaacctgtggac
tgctttggaaactgtgcagctagagtgtcggagaggtaagtggaattcctagtgtagcggtgaaatgcgtagatattaggaggaa
caccagtggcgaaggcggcttactggacgatgactgacgttgaggctcgaaagcgtggggagcaaaca >OTU0431 [SEQUENCE ID 107] *Prevotella*
tgaggaatattggtcaatgggcggaagcctgaaccagccaagtagcgtgcaggatgacggcccctacggggttgtaaactgctttt
atgcggggataaagtgagggacgcgtccctttttgcaggtaccgcatgaataaggaccggctaattccgtgccagcagccgcg
gtaatacgaaggtccgggcgttatccggatttattgggtttaaagggagcgtaggccggggattaagtgtgttgtgaaatgtagg
cgcccaacgtctgacttgcagcgcatactggttcccttgagtacgcgcaacgccggcggaattcgtcgtgtagcggtgaaatgctt
agatatgacgaagaaccccgattgcgaaggcagccggcgggagcgcaactgacgctgaagctcgaaggtgcgggtatcga
aca >OTU0433 [SEQUENCE ID 108] *Selenomonas*
tggggaatcttccgcaatgggcgcaagcctgacggagcaacgccgcgtgagtgaagaaggtcttcggatcgtaaagctctgttg
aaggggacgaacgatcgaggggcgaacaggctctcggtatgacggtaccttttgaggaagccacggctaactacgtgccagc
agccgcggtaatacgtaggtggcgagcgttgtccggaatcattgggcgtaaagggagcgcaggcggcatgtaagtcttgctta
aaagttcggggctcaaccccgtgatgggcaagaaactatatggcttgagtgcaggagaggaaagcggaattcccagtgtagc
ggtgaaatgcgtagatattgggaggaacaccagtggcgaaggcggctttctggactgcaactgacgctgaggctcgaaagcc
aggggagcgaacg >OTU0436 [SEQUENCE ID 109] UNKNOWN
tggggaatattgggcaatgggcgaaagcctgacccagcgacgccgcgtgaaggatgaaggtcttcggattgtaaacttctgtct
acagggacgaacaaatgacggtacctgtaaagaaagccacggctaactacgtgccagcagccgcggtaatacgtaggtggc
aagcgttatccggatttactgggtgtaaagggtgtgtaggcgggaagccaagtcagatgtgaaaatcatgggctcaactcatgac
ttgcatttgaaactggttttcttgagtatgggagaggtaaatggaattcccggtgtagcggtgaaatgcgtagatatcgggaggaac
accagtggcgaaggcggtttactggaccacaactgacgctgatacacgaaagcgtggggagcaaaca >OTU0458 [SEQUENCE ID 110] *Lachnoanaerobaculum*
tggggaatattggacaatgggggcaaccctgatccagcgacgccgcgtgagtgaagaagtatttcggtatgtaaagctctatcg
ataacggaagaagatgacaagccgttaaggaagaagcccggctaactacgtgccagcagccgcggtaatacgtaggggg
caagcgttatccggatttactgggtgtaaaggagcgtagacggcgaataaagtctgaagtgaaacccgcagctcaactgcg
gagttgctttggaaacttataagctggagtgtcggaggggtaagcggaattcccagtgtagcggtgaaatgcgtagatattggga
ggaacaccggaggcgaaggcggcttactggaagataactgacgttgaggctcgaaggcgtgggtagcaaaca >OTU0472 [SEQUENCE ID 111] UNKNOWN
tggggatattgcacaatgggggaaaccctgatgcagcaacgccgcgtgaaggaagaaggtcttcggattgtaaactttgtcct
cagtgaagataatgacggtagctgaggaggaagctccggctaactacgtgccagcagccgcggtaatacgtagggagcgag
cgttgtccggatttactgggtgtaaagggtgcgtaggcggactggcaagtcagtggtgaaaactatgggcttaacccatagactg
ccattgaaactgttggtcttgagtgaagtagaggtaggcggaattcccggtgtagcggtgaaatgcgtagagatcgggaggaac
accagtggcgaaggcggcctactgggctttaactgacgctgaggcacgaaagtgtgggtagcaaaca >OTU0473 [SEQUENCE ID 112] *Tannerella*
tgaggaatattggtcaatgggcgagagcctgaaccagccaagtcgcgtgaaggatgactgccctatgggttgtaaacttcttttac
aggggaataaaatgagatacgtgtatttattgcatgtaccttgtgaataagcatcggctaactccgtgccagcagccgcgtaat
acgaggatgcgagcgttatccggatttattgggtttaaagggtgcgtaggtggctgttaagtccgcggtgaaagtttgtcgctta
acgataaaattgccgttgaaactggtagtcttgagtatagatgaagtaggcggaatgcgtggtgtagcggtgaaatgcatagaga
tcacgcagaactccgattgcgaaggcagcttactaaggtataactgacactgaagcacgaaagcgtgggtatcaaaca APPENDIX 1-continued >OTU0476 [SEQUENCE ID 113] UNKNOWN
tggggaatcttgcacaatgggcgaaagcctgatgcagcaacgccgcgtgagcgaagaaggcctttgggtcgtaaagctctgtc
ggtagggaagaaggaagtgacggtacctaccgaggaagccccggctaactacgtgccagcagccgcggtaatacgtaggg
ggcgagcgttatccggaattattgggcgtaaagagtacgtaggcggttttttaagcgaggggtataaggcagcggcttaactgctg
ttggcccctcgaactggaggacttgagtgtcggagaggaaagcggaattcctagtgtagcggtgaaatgcgtagagattaggag
gaacaccagtggcgaaggcggcttctggacgacaactgacgctgaggtacgaaagcgtggggagcaaaca >OTU0511 [SEQUENCE ID 114] unclassified.Porphyromonadaceae
tgaggaatattggtcaatggacgagagtctgaaccagccaagtcgcgtgaaggaagacggatctatggtttgtaaacttctttagt
gcgggaacaaagcggcgtcgtgacgccggatgagtgtaccgcaagaataagcatcggctaactccgtgccagcagccgcgg
taatacggaggatgcgagcgttatccggatttattgggtttaaagggagcgcaggctgcgaggcaagtcagcggtcaaatgtcg
gggctcaaccccggcctgccgttgaaactgtcctgctagagttcgagtgaggtatgcggaatgcgttgtgtagcggtgaaatgcat
agatatgacgcagaactccgattgcgaaggcagcataccaactcgcgactgacgctgaggctcgaaagcgtgggtatcgaac
a >OTU0512 [SEQUENCE ID 115] UNKNOWN
tagggaatattgggcaatgggcgaaagcctgacccagcaacgccgcgtgaaggaagaaggtcttcggattgtaaacttttgttgt
cagggaagaagaaggacagtacctgacgaggaagccccggctaactacgtgccagcagccgcggtaatacgtaggggggc
gagcgttgtccggaattactgggcgtaaagggcgcgtaggcggcatattaagttagatgtgaaattcccgggcttaacctgggcg
ttgcatttaaaactgataagcttgagtgccggagaggaaagcggaattcctagtgtagcggtgaaatgcgtagatattaggagga
acatcagtggcgaaggcggcttctggacggtaactgacgctgaggcgcgaaagcgtgggtagcaaaca >OTU0543 [SEQUENCE ID 116] UNKNOWN
tggggaatattgcacaatggggaaaccctgatgcagcgacgccgcgtgaaggaagaagtatttcggtatgtaaacttctatca
gcagggaagaaagtgacagtacctgactaagaagccccggctaactacgtgccagcagccgcggtaatacgtaggggggca
agcgttatccggatttactgggtgtaaagggagcgtaggtggcgatgcaagccagaagtgaaaacccggggctcaacccccga
ggactgcttttggaactgtgttgctggagtgcaggagaggtaagtggaattcctagtgtagcggtgaaatgcgtagatattaggag
gaacaccggtggcgaaggcggcttactggactgtaactgacactgaggctcgaaagcgtggggagcaaaca >OTU0544 [SEQUENCE ID 117] Abiotrophia
tagggaatcttccgcaatgacgcaagtctgacggagcaacgccgcgtgagtgaagaaggtcttcggatcgtaaagctctgttgt
tagagaagaacagcgcatagagtaactgctatgcgtgtgacggtatctaaccagaaagccacggctaactacgtgccagcag
ccgcggtaatacgtaggtggcgagcgttgtccggatttattgggcgtaaagggagtgtaggcggctctttaagtctgatgtgaaagc
ccacggctcaaccgtggaggtcattggaaactgggagacttgagtgcagaagaggagagcggaattccatgtgtagcggtg
aaatgcgtagatatatggaggaacaccagtggcgaaggcggctctctggtctgtaactgacgctgaggctcgaaagcgtgggg
agcaaaca >OTU0571 [SEQUENCE ID 118] Treponema
ctaagaatattccgcaatgacggaagtctgacggagcgacgccgcgtggatgaagaaggctgaaaagttgtaaaatcctttg
ttgatgaagaataagggtgagagggaatgctcatctgatgacggtaatcgacgaataagccccggctaattacgtgccagcag
ccgcggtaacacgtaaggggcgagcgttgttcggaattattgggcgtaaagggcatgtaggcggctatgtaagcctgatgtgaa
atcctgggcttaacccctagaatagcattgggtactgtatagcttgaattacggaagggaaactggaattccaagtgtaggggtgg
aatctgtagatatttggaagaacaccggtggcgaaggcgggtttctggccgataattgacgctgagatgcgaaagtgtgggatc
gaaca >OTU0588 [SEQUENCE ID 119] UNKNOWN
tggggaatattaggcaatgggcgaaagcctgacctagcgacgccgcgtgagggaagacggtcttcggattgtaaacctctgtctt
cagggacgaagaagatgacggtacctgaagaggaagccacggctaactacgtgccagcagccgcggtaatacgtaggtgg
cgagcgttgtccggaattactgggtgtaaagggagcgtaggcgggtacgcaagttgaatgtgaaaactaacggctcaaccgat
agttgcgttcaaaactgcggatcttgagtgaagtagaggcaggcggaattcctagtgtagcggtaaaatgcgtagatattaggag
gaacaccagtggcgaaggcggcctgctgggctttaactgacgctgaggctcgaaagtgtggggagcaaaca >OTU0595 [SEQUENCE ID 120] Actinomyces
tggggaatattgcacaatgggcgcaagcctgatgcagcgacgccgcgtgagggatgagggccttcggggttgtgaacctcttcg
cccgtggtcaagccgcgacgtgggtcgtggtgagggtagtgggtaaagaagcgccggctaactacgtgccagcagccgcggt
aatacgtaggggcgcgagcgttgtccggaattattgggcgtaaagggcttgtaggcggctggtcgcgtctgccgtgaaatcctctgg
ctcaactggggcgtgcggtgggtacgggctggcttgagtgcggtaggggaggctggaactcctggtgtagcggtggaatgcg
cagatatcaggaagaacaccggtggcgaaggcgggtctctgggccgttactgacgctgaggagcgaaagcgtggggagcg
aaca >OTU0599 [SEQUENCE ID 121] unclassified.Lachnospiraceae
tggggaatattgcacaatgggggaaccctgatgcagcaacgccgcgtgagtgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgcaggcggtctgcaagtctgatgtgaaatcccggggctcaactccggaat
tgcattggaaactgtcagactagagtgccggagaggtaagtggaattcctagtgtagcggtgaaatgcgtagatattaggagga
acaccagtggcgaaggcggcttactggacggtaactgacgctgaggctcgaaagcgtggggagcaaaca >OTU0618 [SEQUENCE ID 122] UNKNOWN
taggaatttttcggcaatgggcgaaagcctgaccgagcaacgccgcgtgaaggaagaagtcattcgtgatgtaaacttctgttat
gaaggaagaacggcagatggaggaatgccatgtgcgtgacggtacttcatgaggaagccacggctaactacgtgccagca
gccgcggtaatacgtaggtgcgagcgttatccggaatcattgggcgtaaagggagcaggcggcagtgcaggtctgcgt
gaaagaccggagctaaaacttcggtaagccgtggaaaccgcacagtctagagagcatcagaggatcgcggaattccatgtgtag
cggtgaaatgcgtagatatatggaggaacaccagtggcgaaggcggcggtctggggtgcagctgacgctcagtcccgaaagc
gtggggagcaaata >OTU0626 [SEQUENCE ID 123] Lachnoanaerobaculum
tggggaatattggacaatgggggaaaccctgatccagcgacgccgcgtgagtgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgtagacggcgatgtaagtctgaagtgaaagcccacggctcaactgtggga APPENDIX 1-continued ctgctttggaaactatatagctagagtatcggaggggcaagcggaattcctagtgtagcggtgaaatgcgtagatattaggaga
acaccggaggcgaaggcggcttgctggacgaagactgacgttgaggctcgaaggcgtggggagcaaaca >OTU0657 [SEQUENCE ID 124] unclassified.*Candidatus_Saccharibacteria*
tgaggaatcttccacaatgggcgaaagcctgatggagcaacgccgcgtgcaggacgaaggccttcgggttgtaaactgcttttat
aagtgaggaatatgacggtaacttatgaataaggatcggctaactacgtgccagcagccgcggtcatacgtaggatccgagcg
ttatccggagtgactgggcgtaaagagttgcgtaggcggttgtataagtgaatagtgaaatctggtggctcaaccatacaggctatt
gttcaaactgtacaacttgagagtggtagaggtcactggaatttcttgtgtaggagtgaaatccgtagatataagaaggaacacc
aatggcgtaggcaggtgactggaccatttctgacgctaaggcacgaaagcgtggggagcgaacc >OTU0663 [SEQUENCE ID 125] *Schwartzia*
tgggaatcttccgcaatgggcgaaagcctgacggagcaacgccgcgtgagtgaagaaggtcttcggatcgtaaagctctgttg
tcggggacgaaagagtagacgaggaaatgcgtctactaagacggtacctgacgaggaagccacggctaactacgtgccagc
agccgcggtaatacgtaggcggcaagcgttgtccggaattattgggcgtaaagggagcgcaggtgggacggtaagtccgtctt
aaaaggcaggggctcagcccctgtaagggatggaaactatcgatcttgagtgccggagaggaaagcggaattcccagtgtag
cggtgaaatgcgtagatattgggaagaacaccagtggcgaaggcggctttctggacggcaactgacactgaggctcgaaagc
caggggagcgaacg >OTU0664 [SEQUENCE ID 126] UNKNOWN
tgggaatattgggcaatggggggaaaccctgacccagcaacgccgcgtgaaggaagaaggcccctcgggttgtaaacttcttttta
ccagggacgaaggaagtgacggtacctggagaaaaagccaggctaactactgccagcagccgcggtaatacgtaggtg
gcaagcgttgtccggatttactgggtgtaaagggcgtgtaggcgggactgcaagtctgatgtgtaatctggtggctcaaccacca
aactgcattggaaactgtagttcttgagtatcggagaggcaggcggaattcctagtgtagcggtgaaatgcgtagatattaggaa
gaacaccagtggcgaaggcggcctgctggacgacaactgacgctgaggcgcgaaagcgtggggagcaaaca >OTU0666 [SEQUENCE ID 127] *Leptotrichia*
tgggaatattggacaatggagggaactctgatccagcaattctgtgtgcatgaagaaggttttcggattgtaaagtgctttcagca
gggaagaagaaagtgacggtacctgcagaagaagcgacggctaaatacgtgccagcagccgcggtaatacgtatgtcgcg
agcgttatccggaattattgggcataaagggcatctaggcggcacgacaagtcagggtgaaaacttgcggctcaactgcaag
cttgcctttgaaactgtagtgctagagtattggaaggtgggcggaactacacgagtagaggtgaaattcgtagatatgtgtagga
atgccgatgatgaagatagctcactggacgataactgacgctgaagtgcgaaagctagggagcgaaca >OTU0675 [SEQUENCE ID 128] UNKNOWN
tgggaatattgcacaatgggggaaaccctgatgcagcgacgccgcgtgagggaagaaggttttcggattgtaaacctctgtctt
cagggacgatagtgacggtacctgaggaggaagctccggctaactacgtgccagcagccgcggtaatacgtagggagcgag
cgttgtccggaattactgggtgtaaagggagcgtaggcgggacagcaagttgaatgtgaaatctatgggctcaacccataaact
gcgttcaaaactgttgttcttgagtgaagtagaggtaggcggaattcctagtgtagcggtgaaatgcgtagatattaggaggaaca
ccagtggcgaaggcggcctactgggctttaactgacgctgaggctcgaaagcgtgggtagcaaaca >OTU0707 [SEQUENCE ID 129] UNKNOWN
tgggaatattgggcaatgggcgcaagcctgacccagcaacgccgcgtgaaggaagaaggctttcgggttgtaaacttctttttct
cagggacgaaacaaatgacggtacctgaggaataagctacggctaactacgtgccagcagccgcggtaatacgtaggtggc
aagcgttatccggatttactgggtgtaaagggcgtgtaggcgggcgagcaagtcagatgtgaaattccagggctcaaccctgga
actgcatttgaaactgttggtcttgagtgctggagaggcaatcggaattccgtgtgtagcggtgaaatgcgtagatatacggagga
acaccagtggcgaaggcggattgctggacagtaactgacgctgaggcgcgaaagcgtggggagcaaaca >OTU0726 [SEQUENCE ID 130] UNKNOWN
tgaggaatattggtcaatggacgagagtctgaaccagccaagtagcgtgcaggaagacggccctatgggttgtaaactgcttttta
taagggaataaagtgagtctcgtgagacttttttgcatgtaccttatgaataaggaccggctaattccgtgccagcagccgcggtaa
tacggaaggtccgggcgttatccggatttattgggtttaaagggagcgtagatgatgtttaagtcagttgtgaaagtttgcggctca
accgtaaaattgcagttgatactggatatcttgagtgcagttgaggcaggcggaattcgtggtgtagcggtgaaatgcttagatatc
acgaagaacctccgattgcgaaggcagctcactggagcgcaactgacgctgaagctcgaaagtgcgggtatcgaaca >OTU0731 [SEQUENCE ID 131] *Clostridium_XIVa*
tgggaatattgcacaatggggaaaccctgatgcagcaacgccgcgtgagtgaagaagtatttcggtatgtaaagctctatca
gcaggaaagaaaatgacggtacctgactaagaagcccggctaactacgtgccagcagccgcggtaatacgtaggggca
agcgttatccggatttactgggtgtaaagggagcgtagacggcatgcaagtctgaagtgaaatgcgggggctcaacccctga
actgctttggaaactgtcaggctggagtgcaggagaggtaagtggaattcctagtgtagcggtgaaatgcgtagatattaggag
aacaccagtggcgaaggcggcttactggactgtaactgacgttgaggctcgaaagcgtggggagcaaaca >OTU0773 [SEQUENCE ID 132] UNKNOWN
tgggaatattgcacaatggggggaaaccctgatgcagcgacgccgcgtgagtgaagaagtatttcggtatgtaaagctctatca
gcagggaagaaaatgacggtacctgactaagaagcccggctaactacgtgccagcagccgcggtaatacgtaggggca
agcgttatccggatttactgggtgtaaagggagcgtaggtggtagtgcaagtcagaagtgaaaacccaaggcttaaccatggga
ttgcttttgaaactgcataactagagtgctggagaggtaagtggaattcctagtgtagcggtgaaatgcgtagatattaggaggaa
caccggtggcgaaggcggcttactggacagtaactgacactgaggctcgaaagcgtggggagcaaaca >OTU0777 [SEQUENCE ID 133] *Leptotrichia*
tgggaatattggacaatgggggcaaccctgatccagcaattctgtgtgcacgatgaagtcttcggattgtaaagtgctttcagc
agggaagaaagaaatgacggtacctgcagaagaagcgacggctaaatacgtgccagcagccgcggtaatacgtatgtcgc
gagcgttatccggaattattgggcataaagggcatctaggcggccggataagtcggggtgaaaacttgcggctcaaccgcaa
gcctgccctgaaactatgcgcgtagagtactggagaggtggacggaactgcacgagtagaggtgaaattcgtagatatgtgc
aggaatgccgatgatgaagatagttcactggacggtaactgacgctgaagtgcgaaagctaggggagcaaaca >OTU0831 [SEQUENCE ID 134] unclassified.*Lachnospiraceae*
tgggaatattgcacaatgggggaaaccctgatgcagcaacgccgcgtgagtgaagaagtatttcggtatgtaaagctctatca
gcagggaagaaagtgacggtacctgactaagaagcccggctaactacgtgccagcagccgcggtaatacgtaggggca
agcgttatccggatttactgggtgtgaagggagcgtagacggcacagcaagtctgaagtgaaatccccgggctcaacccggga
actgctttggaaactgtgggctggagtgctggagaggcaagcggaattcctagtgtagcggtgaaatgcgtagatattaggagg
aacaccagtggcgaaggcggcttgctggacagtaactgacgttgaggctcgaaagcgtggggagcaaaca APPENDIX 1-continued >OTU0850 [SEQUENCE ID 135] *Prevotella*
tgaggaatattggtcaatgggcggaagcctgaaccagccaagtagcgtgcaggatgacggccctatgggttgtaaactgcttttta
cagggaataaaaaggagcacgtgtgctctgttgcatgtaccctgccgataaggaccggctaattccgtgccagcagccgcgg
taatacggaaggtcctggtgttatccggatttattgggtttaaagggagcgtaggccgtagattaagtgtgttgtgaaatgtaggcgc
ccaacgtctgccttgcagcgcaaactggtttacttgagtacgcgcaacgcaggcggaattcgtcgtgtagcggtgaaatgcttag
atatgacgaagaactcctattgcgaaggcagcttgcgggagcgttactgacgctgaagctcgaaagtgcgggtatcgaaca >OTU0865 [SEQUENCE ID 136] *Blautia*
tggggaatattgcacaatgggggaaaccctgatgcagcgacgccgcgtgaaggaagaagtatctcggtatgtaaacttctatca
gcagggaagataatgacggtacctgactaagaagccccggctaactacgtgccagcagccgcggtaatacgtaggggggcaa
gcgttatccggatttactgggtgtaaagggagcgtagacggcgcagcaagtctgatgtgaaaggcaggggcttaaccctgga
ctgcattggaaactgctgtgcttgagtgccggaggggtaagcggaattcctagtgtagcggtgaaatgcgtagatattaggagga
acaccagtggcgaaggcggcttactggacgaccactgacgctgaggctcgaaagcgtggggagcaaaca >OTU0876 [SEQUENCE ID 137] *Ruminococcus*2
tggggaatattgcacaatgggcgaaagcctgatgcagcgacgccgcgtgagcgaagaagtatttcggtatgtaaagctctatca
gcagggaagataatgacggtacctgactaagaagcaccggctaaatacgtgccagcagccgcggtaatacgtatggtgcaag
cgttatccggatttactgggtgtaaagggagcgtagacggcaagcaagtctgatgtgaaaacccagggcttaaccctgggact
gcattggaaactgtctggctcgagtgccgagaggtaagcggaattcctagtgtagcggtgaaatgcgtagatattaggaggaa
caccagtggcgaaggcggcttactggacgataactgacgctgaggctcgaaagcgtggggagcaaaca >OTU0892 [SEQUENCE ID 138] UNKNOWN
tggggaatattgcacaatgggcggaagcctgatgcagcgacgccgcgtgagtgaagaagtatctcggtatgtaaagctctatca
gcagggaagaaaatgacggtacctgactaagaagccccggctaactacgtgccgcgcggtaatacgtaggggggca
agcgttatccggatttactgggtgtaaagggagcgtagacggcgacgcaagtctggagtgaaagcccggggcccaaccccgg
gactgctttggaaactgtgctgctggagtgcaggagaggtaagtggaattcctagtgtagcggtgaaatgcgtagatattaggag
gaacaccagtggcgaaggcggcttactggacggtaactgacgttgaggctcgaaagcgtggggagcaaaca >OTU0903 [SEQUENCE ID 139] *Prevotella*
tgaggaatattggtcaatgggcgagagcctgaaccagccaagtagcgtgcaggatgacggccttatgggttgtaaactgcttttat
gcgaggataaagttacccacgtgtgggtgtttgcaggtatcgcatgaataaggaccggctaattccgtgccagcagccgcggta
atacggaaggttctggcgttatccggatttattgggtttaaagggagcgtaggctgttttttaagcgtgttgtgaaatgtaccggctca
accggtgatgtcagcgcgaactggaagacttgagtgtgttgtaagtaggcggaattcgtggtgtagcggtgaaatgcttagatat
cacgaggaactccgattgcgtaggcagcttactgtctcactactgacgctgatgctcgaaagcgcgggtatcgaaca >OTU0943 [SEQUENCE ID 140] UNKNOWN
tgaggaatattggtcaatgggcgcaggcctgaaccagccaagtagcgtgaaggatgactgccctatgggttgtaaacttcttttat
aaaggaataaagtcgggtatgtataccgtttgcatgtactttatgaataaggatcggctaactccgtgccagcagccgcggtaat
acggaggatccgagcgttatccggatttattgggtttaaagggagcgtaggcgggttgttaagtcagttgtgaaagtttgcggctca
accgtaaaattgcagttgatactggcgaccttgagtgcaacagaggtaggcggaattcgtggtgtagcggtgaaatgcttagatat
cacgaagaactccgattgcgaaggcagcctgctaagctgcaactgacattgaggctcgaaagtgtgggtatcaaaca >OTU0951 [SEQUENCE ID 141] UNKNOWN
tggggaatattgcacaatgggggaaaccctgatgcagcgacgccgcgtgattgaagaagtatttcggtatgtaaagatctatcag
caaggaagaaaatgacggtacttgactaagaagccccggctaactacgtgccagcagccgcggtaatacgtaggggggcaag
cgttatccggatttactgggtgtaaagggagcgtaggcggtctggcaagccagaagtgaaagcccggggcttaaccccgggac
tgcttttggaactgttagactagagtgtcggagaggtaagtggaattcctagtgtagcggtgaaatgcgtagatattaggaggaac
accagtggcgaaggcggcttactggacggtaactgacgttgaggctcgaaagcgtggggagcaaaca >OTU0963 [SEQUENCE ID 142] UNKNOWN
tggggaatattgcacaatgggggaaaccctgatgcagcaacgccgcgtgaaggaagaaggtctttgggtcgtaaacttctgttct
gagggaagaaagtgacggtacctcaggagcaagtcccggctaactacgtgccagcagccgcggtaatacgtaggggggcaa
gcgttatccggaattattgggcgtaaagagtacgtaggtggttacctaagcacggggtataaggcaatggctcaaccattgtttgc
cttgtgaactgggctacttgagtgcaggagaggaaagcggaattcctagtgtagcggtgaaatgcgtagatattaggaggaaca
ccagtggcgaaggcggctttctggactgtaactgacactgaggtacgaaagcgtggggagcaaaca >OTU0976 [SEQUENCE ID 143] *Clostridium_XIVa*
tggggaatattgcacaatgggggaaaccctgatgcagcgacgccgcgtgagtgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgtagacggcatggcaagccagatgtgaaaacccagggctcaaccttggg
attgcatttggaactgccaggctggagtgcaggagaggtaagcggaattcctagtgtagcggtgaaatgcgtagatattaggag
gaacaccagtggcgaaggcggcttactggacgatgactgacgttgaggctcgaaagcgtggggagcaaaca >OTU0978 [SEQUENCE ID 144] UNKNOWN
tggggaatattgcacaatgggggaaaccctgatgcagcgacgccgcgtggaggaagaaggtcttcggattgtaaactcctgttg
ttgaggaagataatgacggtactcaacaaggaagtgacggctaactacgtgccagcagccgcggtaataggtaggtcacaa
gcgttgtccggaattactgggtgtaaagggagcgtagacggcaaggcaagtctgatgtgaaaacccagggcttaaccctggga
ctgcattggaaactgtctggctcgagtgccggagaggtaagcggaattcctagtgtagcggtgaaatgcgtagatatcggagg
aacaccagtggcgaaggcggcctactgggcaccaactgacgctgaggctcgaaagtgtgggtagcaaaca >OTU0989 [SEQUENCE ID 145] unclassified.*Lachnospiraceae*
tggggaatattgcacaatgggggaaaccctgatgcagcaacgccgcgtgagtgaagaaatattcggtatgtaaagctctatca
gcagggaagaaaatgacggtacctgagtaagaagccccggctaactacgtgccagcagccgcggtaatacgtaggggggca
agcgttatccggatttactgggtgtaaagggagcgtagacggcgaggcaagtctgatgtgaaagcctggggcttaaccccgga
actgcattggaaactgctttgctgagtgccggagaggtaagcggaattcctagtgtagcggtgaaatgcgtagatattaggagg
aacaccagtggcgaaggcggcttactggacggtaactgacgttgaggctcgaaagcgtggggagcaaaca >OTU1011 [SEQUENCE ID 146] UNKNOWN
tgaggaatattggtcaatggacgagagtctgaaccagccaagtagcgtgcaggatgacggccctatgggttgtaaactgcttttg APPENDIX 1-continued

```
cgcggggataacaccctccacgtgctggaggtctgcaggtaccgcgcgaataaggaccggctaattccgtgccagcagccgc
ggtaatacgaaggtccggcgcttatccggatttattgggtttaaagggagcgtaggccggagattaagcgtgttgtgaaatgtag
acgctcaacgtctgcactgcagcgcgaactggttccttgagtacgcacaaagtgggcggaattcgtggtgtagcggtgaaatgc
ttagatatgacgaagaaccccgattgcgaaggcagctggcggagcgtaactgacgctgaagctcgaaagcgcgggtatcga
aca
```

>OTU1080 [SEQUENCE ID 147] UNKNOWN
```
tggggaatattgcacaatgggggaaaccctgatgcagcgacgccgcgtgaaggaagaagtatctcggtatgtaaacttctatca
gcagggaagatagtgacggtacctgactaagaagccccggctaactacgtgccagcagccgcggtaatacgtaggggggcaa
gcgttatccggatttactgggtgtaaagggcgtgcagccgggtctgcaagtcagatgtgaaatccatgggctcaacccatgaact
gcatttgaaactgtagatcttgagtgtcggagggggcaatcggaattcctagtgtagcggtgaaatgcgtagatattaggaggaac
accagtggcgaaggcggcttactggacggtaactgacgttgaggctcgaaagcgtggggagcaaaca
```

>OTU1128 [SEQUENCE ID 148] UNKNOWN
```
ttaggaatattcgtcaatgggggaaaccctgaacgagcaatgccgcgtgaacgatgaaggccctatgggttgtaaagttctgttg
catgggacgaacgattaggataggaaatgatcttaatgtgacggtaccatgccagaaagctccggctaactacgtgccagcag
ccgcggtaatacgtagggagcaagcgttatccggatttattgggcgtaaagggtgcgtaggcggcttgttaagtatgagattaaa
gcccgaggcttaacctcggttcgtttcataaactggcaggcttgagtgtggcagaggtaaacggaatttctagtgtagcggttaaat
gcgtagatattagaaggaacaccagtggcgaaggcggtttactgggccataactgacgctgaggcacgaaagcgtggggag
caaata
```

>OTU1175 [SEQUENCE ID 149] unclassified.*Lachnospiraceae*
```
tggggaatattgcacaatgggggaaaccctgatgcagcgacgccgcgtgagtgaagaagtaattcgttatgtaaagctctatca
gcagggaagaaaatgacggtacctgactaagaagccccggctaactacgtgccagcagccgcggtaatacgtaggggggca
agcgttatccggatttactgggtgtaaagggagcgtagacggccgtgcaagtctgatgtgaaaggctgggctcaacccccggg
actgcattggaaactgtatggctggagtgccggagaggtaagcggaattcctagtgtagcggtgaaatgcgtagatattaggag
gaacaccagtggcgaaggcggtttactggactgtaactgacgttgaggctcgaaagcgtggggagcaaaca
```

>OTU1197 [SEQUENCE ID 150] *Escherichia/Shigella*
```
tggggaatattgcacaatgggcgcaagcctgatgcagccatgccgcgtgtatgaagaaggccttcgggttgtaaagtactttcag
cggggaggaagggagtaaagttaatacctttgctcattgacgttacccgcagaagaagcaccggctaactccgtgccagcagc
cgcggtaatacggagggtgcaagcgttaatcggaattactgggcgtaaagcgcacgcaggcggtttgttaagtcagatgtgaaa
tccccgggctcaacctgggaactgcatctgatactggcaagcttgagtctcgtagaggggggtagaattccaggtgtagcggtga
aatgcgtagagatctggaggaataccggtggcgaaggcggccccctggacattaactgacgctgaggcacgaaggccaggg
gagcgaaag
```

>OTU1239 [SEQUENCE ID 151] UNKNOWN
```
tgaggaatattggtcaatggacgagagtctgaaccagccaagtagcgtgaaggatgactgccctatgggttgtaaacttcttttata
cgggaataaagtgaggcacgtgtgcctttttgtatgtaccgtatgaataaggatcggctaactccgtgccagcagccgcggtaata
cggaggatccgagcgttatccggatttattgggtttaaagggtgcgtaggcggcacgccaagtcagcggtgaaatttccgggctc
aacccggagtgtgccgttgaaactggcgagctagagtacacaagaggcaggcggaatgcgtggtgtagcggtgaaatgcata
gatatcacgaagaactccgattgcgaaggcagcctgctaagctgcaactgacattgaggctcgaaagtgtgggtatcaaaca
```

>OTU1250 [SEQUENCE ID 152] *Leptotrichia*
```
tggggaatattggacaatgggggcaacccctgatccagcaattctgtgtgcacgaagaaggctttcgggctgtaaagtgctttcag
cagagaagaagcaagtgacggtacctgcagaagaagcgacggctaaatacgtgccagcagccgcggtaatacgtatcgc
aagcgttatccggaattattgggcataaagggcatctaggcggccaggcaagtctggggtgaaaacctgcggctcaaccgcag
gcctgccctggaaactgcgtggctagagtactggagaggtggacggaactgcacgagtagaggtgaaattcgtagatatgtgc
aggaatgccgatgatgaagatagttcactggacggcaactgacgctgaagtgcgaaagccggggggagcgaaca
```

>OTU1254 [SEQUENCE ID 153] *Blautia*
```
tggggaatattgcacaatgggggaaaccctgatgcagcgacgccgcgtgaaggaagaagtatctcggtatgtaaacttctatca
gcagggaagaaaatgacggtacctgactaagaagccccggctaactacgtgccagcagccgcggtaatacgtaggggggca
agcgttatccggatttactgggtgtaaagggagcgtagacggttgcaagtctgatgtgaaaggcgggggctcaacccctgga
ctgcattggaaactgtgatactcgagtgccggagaggtaagcggaattcctagtgtagcggtgaaatgcgtagatattaggagg
aacaccagtggcgaaggcggcttctggacgatgactgacgttgaggctcgaaagcgtggggagcaaaca
```

>OTU1280 [SEQUENCE ID 154] unclassified.*Lachnospiraceae*
```
tggggaatattgcacaatgggggaaaccctgatgcagcaacgccgcgtgagtgaagaagtatttcggtatgtaaagctctatca
gcagggaagataatgacggtacctgactaagaagctccggctaaatacgtgccagcagccgcggtaatacgtatggagcaag
cgttatccggatttactgggtgtaaagggagcgtagacggcaaggcaagtctgatgtgaaaacccagggcttaaccctgggact
gcattggaaactgtctggctcgagtgccggagaggtaagcggaattcctagtgtagcggtgaaatgcgtagatattaggaggaa
catcagtggcgaaggcggcttactggactgaaactgacactgaggcacgaaagcgtggggagcaaaca
```

>OTU1292 [SEQUENCE ID 155] UNKNOWN
```
tggggaatattgcacaatgggggaaaccctgatgcagcgacgccgcgtgagcgatgaagtatttcggtatgtaaagctctatca
gcagggaagaaaatgacggtacctgactaagaagcaccggctaaatacgtgccagcagccgcggtaatacgtatgtgcaa
gcgttatccggatttactgggtgtaaagggagcgtaggcggcggagcaagtcagaagtgaaagcccggggctcaacccccggg
acggcttttgaaactgccctgcttgatttcaggagaggtaagcggaattcctagtgtagcggtgaaatgcgtagatattaggagga
acaccagtggcgaaggcggcttactggacggtaactgacgttgaggctcgaaagcgtggggagcaaaca
```

>OTU1339 [SEQUENCE ID 156] *Roseburia*
```
tggggaatattgggcaatgggcgcaagcctgacccagcaacgccgcgtgagcgaagaagtatttcggtatgtaaagctctatca
gcagggaagaagaaatgacggtacctgactaagaagcaccggctaaatacgtgccagcagccgcggtaatacgtatggtgc
aagcgttatccggatttactgggtgtaaagggagcgcaggcggtacggcaagtctgatgtgaaagcccggggctcaacccccgg
tactgcattggaaactgtcggactagagtgtcggaggggtaagtggaattcctagtgtagcggtgaaatgcgtagatattaggag
gaacaccagtggcgaaggcggcttactggacgattactgacgctgaggctcgaaagcgtggggagcaaaca
```

>OTU1376 [SEQUENCE ID 157] *Faecalibacterium*
```
tggggaatattgcacaatgggggaaaccctgatgcagcgacgccgcgtggaggaagaaggtcttcggattgtaaactcctgttg
```

APPENDIX 1-continued

```
ttgaggaagataatgacggtactcaacaaggaagtgacggctaactacgtgccagcagccgcggtaaaacgtaggtcacaa
gcgttgtccggaattactgggtgtaaagggagcgcaggcgggcgatcaagttggaagtgaaatccatgggctcaacccatgaa
ctgctttcaaaactggtcgtcttgagtagtgcagaggtaggcggaattcccggtgtagcggtggaatgcgtagatatcgggagga
acaccagtggcgaaggcggcctgctaagctgcaactgacattgaggctcgaaagtgtgggtatcaaaca
```

>OTU1395 [SEQUENCE ID 158] UNKNOWN
```
tggggaatattgcacaatgggggaaaccctgatgcagcgacgccgcgtgagcgaagaagtatttcggtatgtaaagctctatca
gcagggaagaaaatgacggtacctgactaagaagccccggctaactacgtgccagcagccgcggtaatacgtagggggca
agcgttatccggatttactgggtgtaaagggagcgtagacggataggcaagtctggagtgaaaacccagggctcaaccctggg
actgcttttggaaactgcagatctggagtgccggagaggtaagcggaattcctagtgtagcggtgaaatgcgtagatattaggag
gaacaccagtggcgaaggcggcttactggacggtaactgacgttgaggctcgaaagcgtggggagcaaaca
```

>OTU1423 [SEQUENCE ID 159] *Neisseria*
```
tggggaattttggacaatgggcgcaagcctgatccagccatgccgcgtgtctgaagaaggccttcgggttgtaaaggacttttgtc
agggaagaaaaggagttggttaatacccgactctgatgacggtacctgaagaataagcaccggctaactacgtgccagcagc
cgcggtaatacgtagggtgcgagcgttaatcggaattactgggcgtaaagcgagcgcagacggtttgttaagcaggatgtgaaa
tccccgggctcaacctgggaactgcgttctgaactggcaggctagagtgtgtcagagggggtagaattccacgtgtagcagtg
aaatgcgtagagatgtggaggaataccgatggcgaaggcagcctcctgggataacactgacgttcatgctcgaaagcgtgggt
agcaaaca
```

>OTU1487 [SEQUENCE ID 160] *Clostridium_XIVa*
```
tggggaatattggacaatgggcgaaagcctgatccagcgacgccgcgtgagtgaagaagtatttcggtatgtaaagctctatca
gcagggaagaaaatgacggtacctgactaagaagccccggctaactacgtgccagcagccgcggtaatacgtagggggca
agcgttatccggatttactgggtgtaaagggagcgtagacggttaagcaagtctgaagtgaaagcccggggctcaacccggt
actgcttttggaaactgtttgacttgagtgcaggagagtaagtggaattcctagtgtagcggtgaaatgcgtagatattaggagga
acaccagtggcgaaggcggcttactggacgataactgacgttgaggctcgaaagcgtggggagcaaaca
```

>OTU1494 [SEQUENCE ID 161] UNKNOWN
```
tggggaatattgcacaatgggggaaaccctgatgcagcgacgccgcgtgagggaagaaggtcttcggattgtaaactcctgttg
ttgaggaagataatgacggtactcaacaaggaagtgacggctaactacgtgccagcagccgcggtaaaacgtaggtcacaa
gcgttgtccggaattactgggtgtaaagggcgtgtaggcggagaagcaagtcagaagtgaaatccatgggcttaacccatgaa
ctgcttttgaaactgtttcccttgagtatcggagaggcaggcggaattcctagtgtagcggtgaaatgcgtagatattaggaggaac
accagtggcgaaggcggtctactgggcaccaactgacgctgaggctcgaaagcatgggtagcaaaca
```

>OTU1550 [SEQUENCE ID 162] *Coprococcus*
```
tggggaatattgcacaatgggggaaaccctgatgcagcgacgccgcgtgaaggaagaagtatctcggtatgtaaacttctatca
gcagggaagatagtgacggtacctgactaagaagccccggctaactacgtgccagcagccgcggtaatacgtagggggcaa
gcgttatccggatttactgggtgtaaagggagcgtaggtggcaaggcaagccagaagtgaaaacccagggctcaaccgcgg
gattgcttttggaactgtcatgctagagtgcaggaggggtgagcggaattcctagtgtagcggtgaaatgcgtagatattaggagg
aacaccagtggcgaaggcgacttactggactgctactgacactgaggcacgaaagcgtggggagcaaaca
```

>OTU1571 [SEQUENCE ID 163] UNKNOWN
```
tggagaatattgcgcaatgggggcaaccctgacgcagcaacgccgcgtgcaggaagaaggtcttcggattgtaaactgttgtcg
caagggaagaagacagtgacggtaccttgtgagaaagtcacggctaactacgtgccagcagccgcggtaatacgtaggtgac
aagcgttgtccggatttactgggtgtaaagggcgcgtaggcggactgtcaagtcagtcgtgaaataccggggcttaacccccggta
ctgcattggaaactgtcgtactagagtgtcggaggggtaagcggaattcctagtgtagcggtgaaatgcgtagatattaggagga
acaccagtggcgaaggcgacttactggactgaaactgacgttgaggcacgaaagtgtggggagcaaaca
```

>OTU1582 [SEQUENCE ID 164] *Blautia*
```
tggggatattgcacaatggaggaaactctgatgcagcgacgccgcgtgagtgaagaagtatttcggtatgtaaagctctatcag
cagggaagacagtgacggtacctgactaagaagccccggctaactacgtgccagcagccgcggtaatacgtagggggcaa
gcgttatccggatttactgggtgtaaagggagcgtagacggatggacaagtctgatgtgaaaggctgggctcaaccccggga
ctgcattggaaactgcccgtcttgagtgccggagaggtaagcggaattcctagtgtagcggtgaaatgcgtagatattaggagga
acaccagtggcgaaggcggcttactggacggtaactgacgttgaggctcgaaagcgtggggagcaaaca
```

>OTU1584 [SEQUENCE ID 165] *Parabacteroides*
```
tgaggaatattggtcaatgggcgtaagcctgaaccagccaagtcgcgtgagggatgaaggttctatggatcgtaaacctctttat
aagggaataaagtgcgggacgtgtcctgttttgtatgtaccttatgaataaggatcggctaactccgtgccagcagccgcggtaat
acggaggatccgagcgttatccggatttattgggtttaaagggtgcgtaggcggcctttaagtcagcggtgaaatctgtggctca
cccatagaattgccgttgaaactggggggcttgagtatgtttgaggcaggcggaatgcgtggtgtagcggtgaaatgcttagatat
cacgcagaaccccgattgcgaaggcagcctgccaagccatgactgacgctgatgcacgaaagcgtgggatcaaaca
```

>OTU1610 [SEQUENCE ID 166] *Blautia*
```
tggggaatattgcacaatgggggaaaccctgatgcagcgacgccgcgtgaaggaagaagtatctcggtatgtaaacttctatca
gcagggaagataatgacggtacctgactaagaagccccggctaactacgtgccagcagccgcggtaatacgtagggggcaa
gcgttatccggatttactgggtgtaaagggagcgtagacggcaaggcaagtctgaagtgaaagcccggtgcttaacgccggga
ctgctttggaaactgctgtgcttgagtgccggagggtaagcggaattcctagtgtagcggtgaaatgcgtagatattaggagga
acaccagtggcgaaggcggcttactggacggtaactgacgttgaggctcgaaagcgtggggagcaaaca
```

>OTU1640 [SEQUENCE ID 167] UNKNOWN
```
tggggatattgcacaatgggggaaaccctgatgcagcgacgccgcgtgagggaagaaggttttcggattgtaaactcctgtcg
ttagggacgataatgacggtacctaacaagaaagcaccggctaactacgtgccagcagccgcggtaaaacgtaggtcacaa
gcgttgtccggaattactgggtgtaaagggagcgcaggcgggcgatcaagttggaagtgaaatccatgggctcaacccatgaa
ctgctttcaaaactggtcgtcttgagtagtgcagaggtaggtggaattcccggtgtagcggtggaatgcgtagatatcgggaggaa
caccagtggcgaaggcgacctactgggcaccaactgacgctgaggctcgaaagcatgggtagcaaaca
```

>OTU1645 [SEQUENCE ID 168] unclassified.*Lachnospiraceae*
```
tggggaatattgcacaatgggggaaaccctgatgcagcgacgccgcgtgagcgaagaagtatttcggtatgtaaagctctatca
gcagggaagaaaatgacggtacctgactaagaagccccggctaactacgtgccagcagccgcggtaatacgtagggggca
agcgttatccggatttactgggtgtaaagggagcgtaggcggcacgccaagccagatgtgaaagcccgaggcttaacctcgcg
```

APPENDIX 1-continued gattgcatttggaactggcgagctagagtacaggagaggaaagcggaattcctagtgtagcggtgaaatgcgtagatattagga
ggaacaccagtggcgaaggcggcttactggacggtaactgacgttgaggctcgaaagcgtggggagcaaaca >OTU1682 [SEQUENCE ID 169] UNKNOWN
tggggaatattgcacaatgggggaaccctgatgcagcaacgccgcgtgaaggaagacggttttcggattgtaaacttctatca
atagggacgaagaaagtgacggtacctaaataagaagccccggctaactacgtgccagcagccgcggtaatacgtaggggg
caagcgttatccggaattactgggtgtaaagggtgagtaggcggcacggcaagtaagatgtgaaagcccacggcttaactgtg
ggattgcattttaaactgttgagctagagtacaggagaggaaagcggaattcctagtgtagcggtgaaatgcgtagatattagga
agaacaccagtggcgaaggcggctttctggacgggaaactgacgctgaggcacgaaagcgtggggagcgaaca >OTU1699 [SEQUENCE ID 170] Lachnoanaerobaculum
tggggaatattggacaatgggggaaccctgatccagcgacgccgcgtgagtgaagaagtatttcggtatgtaaagctctatca
gcagggaagaaaatgacggtacctgactaagaagccccggctaactacgtgccagcagccgcggtaatacgtaggggca
agcgttatccggatttactgggtgtaaagggagcgcagacggttgccaagtctgaagtgaaatcccgaggcttaaccacggg
actgctttggaaactgtgcgacttgagtatcggaggggcaggcggaattcctagtgtagcggtgaaatgcgtagatattaggaag
aacaccggtggcgaaggcggcctgctggacgaaaactgacgttgaggctcgaaggcgtggggagcaaaca >OTU1963 [SEQUENCE ID 171] Streptococcus
tagggaatcttcggcaatggacggaagtctgaccgagcaacgccgcgtgagtgaagaaggttttcggatcgtaaagctctgttgt
tagagaagaacagcgcatagagtaactgttatgcgtgtgacggtatcttaccagaaagggacggctaactacgtgccagcagc
cgcggtaatacgtaggtcccgagcgttgtccggatttattgggcgtaaagcgagcgcaggcggttagataagtctgaagttaaag
gctgtggcttaaccatagtacgctttggaaactgtttaacttgagtgcaagaggggagagtgaattccatgtgtagcggtgaaat
gcgtagatatatggaggaacaccggtggcgaaagcggctctctggcttgtaactgacgctgaggctcgaaagcgtggggagc
aaaca >OTU1999 [SEQUENCE ID 172] UNKNOWN
tggggaatattgcacaatggggggaaccctgatgcagcgacgccgcgtgaaggaagaagtatctcggtatgtaaacttctatca
gcagggaagaaaatgacggtacctgactaagaagccccggctaactacgtgccagcagccgcggtaatacgtaggggca
agcgttatccggatttactgggtgtaaagggcgcgtaggcggctcggtaagtctggagtgaaagtcctgcttttaaggtgggaattg
ctttggatactgtcgggcttgagtgcaggagaggtaagcggaattcctagtgtagcggtgaaatgcgtagatattaggaggaaca
ccagtgcgaaggcggcttactggactgtaactgacgttgaggctcgaaagcgtggggagcaaaca >OTU2036 [SEQUENCE ID 173] unclassified.Lachnospiraceae
tagggaatcttcggcaatgggggcaaccctgaccgagcaacgccgcgtgagtgaagaagtatttcggtatgtaaagctctatca
gcagggaagataatgacggtacctgactaagaagctccggctaaatacgtgccagcagccgcggtaatacgtatggagcaag
cgttatccggatttactgggtgtaaagggcgcgtaggtggcagtgcaagtcagatgtgaaaggccggggctcaaccccggagct
gcatttgaaactgcatagctggagtacaggagaggcaggcggaattcctagtgtagcggtgaaatgcgtagatattaggagga
acaccagtggcgaaggcggcctgctggactgttactgacactgaggcacgaaagcgtggggagcaaaca >OTU2137 [SEQUENCE ID 174] UNKNOWN
tgaggaatattggtcaatgggcgagagcctgaaccagccaagtagcgtgaaggatgactgccctatgggttgtaaacttcttttat
aaaggaataaagtcgggtatggatacccgtttgcatgtactttatgaataaggatcggctaactccgtgccagcagccgcgtaa
tacggaggatccgagcgttatccggatttattgggtttaaagggtgcgtaggtggtgatttaagtcagcggtgaaagtttgtggctca
accataaaattgccgttgaaactgggttacttgagtgcagttgaggcaggcggaattcgtggtgtagcggtgaaatgcttagatatc
acgaagaactccgattgcgaaggcagcctgctaagctgcaactgacattgaggctcgaaagtgtgggtatcaaaca >OTU2176 [SEQUENCE ID 175] Bacteroides
tgaggaatattggtcaatgggcgcaggcctgaaccagccaagtagcgtgaaggatgactgccctatgggttgtaaacttcttttat
aaaggaataaagtcgggtatggatacccgtttgcatgtactttatgaataaggatcggctaactccgtgccagcagccgcgtaa
tacggaggatccgagcgttatccggatttattgggtttaaagggagcgtagatggatgtttaagtcagttgtgaaagtttgcggctca
accgtaaaattgcagttgatactgggcgccttgagtgcagcataggtaggcggaattcgtggtgtagcggtgaaatgcttagatat
cacgaagaactccgattgcgaaggcagcctgctggactgtaactgacattgaggctcgaaagtgtgggtatcaaaca >OTU2203 [SEQUENCE ID 176] UNKNOWN
tggggaatattgcacaatgggcgaaagcctgatgcagcgacgccgcgtgagcgaagaagtatttcggtatgtaaagctctatca
gcagggaagataatgacggtacctgactaagaagcaccggctaaatacgtgccagcagccgcggtaatacgtatggtgcaag
cgttatccggatttactgggtgtaaagggtgcgtaggtggcagtgcaagtcagatgtgaaaggccggggctcaaccccggagct
gcatttgaaactgcatagctagagtacaggagaggcaggcggaattcctagtgtagcggtgaaatgcgtagatattaggagga
acaccagtggcgaaggcggcctactgggcaccaactgacgctgaggctcgaaagtgtgggtagcaaaca >OTU2229 [SEQUENCE ID 177] unclassified.Clostridiales
tcgggaatattgcgcaatggaggaaactctgacgcagtgacgccgcgtgcaggaagaaggttttcggattgtaaactgctttaga
cagggaagaacaaagacagtacctgtagaataagctccggctaactacgtgccagcagccgcggtaatacgtagggagcga
gcgttatccggatttattgggtgtaaagggtgcgtagacgggaagtcaagttagttgtgaaatccctcggcttaactgaggaactgc
aactaaaactgattttcttgagtactggagaggaaagtggaattcctagtgtagcggtgaaatgcgtagatattaggaggaacac
cagtggcgaaggcggcttactggactgtaactgacgttgaggcgcgaaagtgtggggagcaaaca >OTU2397 [SEQUENCE ID 178] UNKNOWN
tggggaatattgggcaatgggggaaccctgacccagcaacgccgcgtgaaggaagaaggctttcggttgtaaacttcttttta
ccagggacgaaggacgtgacggtacctggagaaaaagccacggctaactacgtgccagcagccgcggtaatacgtaggtg
gcaagcgttgtccggatttactgggtgtaaagggagctagacggctttgcaagtctgacgtgaaactccggggctcaactccgg
aactgcgttggaaactgtaaggcttgagtgccggagaggtaagcggaattcctagtgtagcggtgaaatgcgtagatattagga
ggaacaccagtggcgaaggcggcttactggactaactgacgttgaggctcgaaagcgtggggagcaaaca >OTU2689 [SEQUENCE ID 179] UNKNOWN
tggggtatattgggcaatggaggaaactctgacccagcaacgccgcgtggaggaagaaggttttcggatcgtaaactcctgtcct
tggagacgagtagaagacggtatccaaggaggaagccccggctaactacgtgccagcagccgcggtaatacgtaggggc
aagcgttatccggatttactgggtgtaaagggagcgtagacggcaaggcaagtctgatgtgaaaacccagggcttaaccctgg
gactgcattggaaactgtctggctcgagtgccggagaggtaagcggaattcctagtgtagcggtgaaatgcgtagagattggga
ggaacaccagtggcgaaggcggattgctggacgataactgacggtgaggcgcgaaagtgtggggagcaaaca APPENDIX 1-continued

```
>OTU2703 [SEQUENCE ID 180] Tannerella
tgaggaatattggtcaatgggcgagagcctgaaccagccaagtcgcgtgaaggatgactgtcttatggattgtaaacttcttttata
cgggaataacaagagtcacgtgtgactccctgcatgtaccgtatgaataagcatcggctaactccgtgccagcagccgcggtaa
tacggaggatgcgagcgttatccggatttattgggtttaaagggtgcgtaggtgggctattaagtcagtggtgaaagtttgtcgctca
acgataaaattgccgttgaaactggtggtcttgagtgtagatgaggtaggcggaatgcgtggtgtagcggtggaatgcatagatat
cacgcagaactccgattgcgaaggcagcttactaaggtacaactgacgctgaagcacgaaagcgtgggtatcaaaca >OTU2738 [SEQUENCE ID 181] UNKNOWN
tggggaatattgcacaatgggggaaaccctgatgcagcgacgccgcgtgagcgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgtagacggaatggcaagtctgatgtgaaagaccggggctcaaccccggg
actgcattggaaactgtcaatctagagtaccggagggtaagtggaattcctagtgtagcggtgaaatgcgtagatattaggagg
aacaccagtggcgaaggcggcttaccaaactatatctgacgttgaggcacgaaagcgtggggagcaaaca >OTU2762 [SEQUENCE ID 182] UNKNOWN
tggggaatattgcacaatgggggaaaccctgatgcagcgacgccgcgtgaaggaagaagtatctcggtatgtaaacttctatca
gcagggaagaagaatgacggtacctgactaagaagcaccggctaaatacgtgccagcagccgcggtaatacgtaggggggc
aagcgttatccggatttactgggtgtaaagggagcgtagacggcaaggcaagtctgatgtgaaaggctgggctcaaccccgg
gactgcattggaaactgtcctgctggagtgccggagaggtaagcggaattcctagtgtagcggtgaaatgcgtagatattaggag
gaacaccagtggcgaaggcggcttgctggacgatgactgacgttgaggctcgaaagcgtggggagcaaaca >OTU2771 [SEQUENCE ID 183] UNKNOWN
tggggaatattgcacaatgggggaaaccctgatgcagcgacgccgcgtgagtgaagaagtatctcggtatgtaaagctctatca
gcagggaagaaaatgacggtacctgactaagaagccccggctaactacgtgccagcagccgcggtaatacgtaggggggca
agcgttatccggatttactgggtgtaaagggagcgtagacggcggagcaagtctgaagtgaaagcccggggctcaaccccgg
gactgctttggaaactgttctgctagagtgctggagaggcaagcggaattcctagtgtagcggtgaaatgcgtagatattaggaa
gaacaccagtggcgaaggcggctttctggacgatgactgacgttgaggctcgaaagcgtggggagcaaaca >OTU3092 [SEQUENCE ID 184] UNKNOWN
tggggaatattgcacaatgggggaaaccctgatgcagcgacgccgcgtgagcgatgaagtatttcggtatgtaaagctctatca
gcagggaagaaaatgacggtacctgactaagaagcaccggctaaatacgtgccagcagccgcggtaatacgtatggtgcaa
gcgttatccggatttactgggtgtaaagggagcgcaggcggtctggcaagtctgatgtgaaaatccggggctcaactccggaact
gcattggaaactgtcagactagagtgtcggaggggtaagcggaattcctagtgtagcggtgaaatgcgtagatattaggaggaa
caccagtggcgaaggcggcttactggacagtaactgacgttgaggctcgaaagcgtggggagcaaaca >OTU3180 [SEQUENCE ID 185] UNKNOWN
tggggaatattgcacaatggaggaaactctgatgcagcgatgccgcgtgaaggatgaagtatttcggtatgtaaacttctatcagc
agggaagaaaatgacggtacctgactaagaagccccggctaactacgtgccagcagccgcggtaatacgtatggtgcaagc
gttatccggatttactgggtgtaaagggagcgtagacggagtggcaagtctgatgtgaaaacccggggctcaaccccgggact
gcattggaaactgtcaatctagagtaccggagaggtaagcggaattcctagtgtagcggtgaaatgcgtagatattaggaggaa
caccagtggcgaaggcggctttctggacgatgactgacgttgaggctcgaaagcgtgggaagcaaaca >OTU3273 [SEQUENCE ID 186] UNKNOWN
tggggaatattgcacaatgggggaaaccctgatgcagcgacgccgcgtgaaggatgaagtatttcggtatgtaaacttctatcag
cagggaagaaagtgacggtacctgagtaagaagccccggctaactacgtgccagcagccgcggtaatacgtaggggggcaa
gcgttatccggatttactgggtgtaaagggagcgtagacggcggagcaagtctgatgtgaaaggcaggggcttaaccccctgga
ctgcattggaaactgtttagctggagtgccggagaggtaagcggaattcctagtgtagcggtgaaatgcgtagatattaggaaga
acaccagtggcgaaggcggcttactggacggtaactgacgttgaggctcgaaagcgtggggagcaaaca >OTU3755 [SEQUENCE ID 187] UNKNOWN
tggggaatattgcacaatggggggaaccctgatgcagcaacgtcgcgtgagtgaagaagtatttcggtatgtaaacttctatcag
cagggaagaaaatgacggtacctgactaagaagccccggctaactacgtgccagcagccgcggtaatacgtaggggggcaa
gcgttatccggatttactgggtgtaaagggagcgtagacggagcagcaagtctgatgtgaaaggcggggctcaaccccggg
actgcattggaaactgttgatcttgagtaccggagaggtaagcggaattcctagtgtagcggtgaaatgcgtagatattaggagg
aacaccagtggcgaaggcggcttactggacgtaactgacgttgaggctcgaaagcgtggggagcaaaca >OTU3831 [SEQUENCE ID 188] UNKNOWN
tggggaatattgcacaatgggggaaaccctgatgcagcgacgccgcgtggaggaagaaggtcttcggattgtaaactcctgttg
ttggggaagataatgacggtacccaacaaggaagtgacggctaactacgtgccagcagccgcggtaaaacgtaggtcacaa
gcgttgtccggaattactgggtgtaaagggagcgcaggcgggatagcaagtcagctgtgaaaactatgggctcaacccataaa
ctgcagttgaaactgttattcttgagtggagtagaggcaagcggaattccgagtgtagcggtgaaatgcgtagatattaggagga
acaccagtggcgaaggcggccaactgggctttactgacgctgaggctcgaaagtgtggggagcaaaca >16S Amplicon PCR Forward Primer 5' (V3 region) [SEQUENCE ID 189]
5'-TCGTCGGCAGCGTCAGATGTGTATAAGAGACAGCCTACGGGNGGCWGCAG-3'

>16S Amplicon PCR Reverse Primer 5' (V4 region) [SEQUENCE ID 190]
5'-GTCTCGTGGGCTCGGAGATGTGTATAAGAGACAGGACTACHVGGGTATCTAATCC-3'

>OTU50001 [SEQUENCE ID 191] Streptococcus
tagggaatcttcggcaatggacggaagtctgaccgagcaacgccgcgtgagtgaagaaggttttcggatcgtaaagctctgttgt
aagagaagaacgagtgtgagagtggaaagttcacactgtgacggtatcttaccagaaagggacggctaactacgtgccagca
gccgcggtaatacgtaggtcccgagcgttgtccggatttattgggcgtaaagcgagcgcaggcggttagataagtctgaagttaa
aggctgtggcttaaccatagtacgctttggaaactgtttaacttgagtgcaagaggggagagtggaattccatgtgtagcggtgaa
atgcgatagatatatggaggaacaccggtggcgaaagcggctctctggcttgtaactgacgctgaggctcgaaagcgtgggag
caaaca >OTU50010 [SEQUENCE ID 192] Streptococcus
tagggaatcttcggcaatgggggcaaccctgaccgagcaacgccgcgtgagtgaagaaggttttcggatcgtaaagctctgttgt
```

APPENDIX 1-continued

```
aagtcaagaacgagtgtgagagtggaaagttcacactgtgacggtagcttaccagaaagggacggctaactacgtgccagca
gccgcggtaatacgtaggtcccgagcgttgtccggatttattgggcgtaaagcgagcgcaggcggtttgataagtctgaagttaa
aggctgtggctcaaccatagttcgctttggaaactgtcaaacttgagtgcagaaggggagagtggaattccatgtgtagcggtga
aatgcgtagatatgtgaggaacaccggtggcgaaagcggctctctggtctgtaactgacgctgaggctcgaaagcgtgggga
gcgaaca
```

>OTU50012 [SEQUENCE ID 193] *Ruminococcus*
```
tggggaatattgcacaatgggggaaaccctgatgcagcgacgccgcgtgagcgatgaagtatttcggtatgtaaagctctatca
gcagggaagaaaatgacggtacctgactaagaagcaccggctaaatacgtgccagcagccgcggtaatacgtatggtgcaa
gcgttatccggatttactgggtgtaaaggggagcgtagacggagtggcaagtctgatgtgaaaacccggggctcaaccccggga
ctgcattggaaactgtcaatctagagtaccggagaggtaagcggaattcctagtgtagcggtgaaatgcgtagatattaggagg
aacaccagtggcgaaggcggcttactggacggtaactgacgttgaggctcgaaagcgtggggagcaaaca
```

>OTU50016 [SEQUENCE ID 194] *Roseburia*
```
tggggaatattgcacaatgggcgaaagcctgatgcagcgacgccgcgtgagcgaagaagtatttcggtatgtaaagctctatca
gcagggaagataatgacggtacctgactaagaagcaccggctaaatacgtgccagcagccgcggtaatacgtatggtgcaag
cgttatccggatttactgggtgtaaagggagcgcaggcggtgcgcaagtctgatgtgaaagcccggggctcaaccccggtact
gcattggaaactgtcgtactagagtgtcggagggtaagcggaattcctagtgtagcggtgaaatgcgtagatattaggaggaa
caccagtggcgaaggcggcttactggacgataactgacgctgaggctcgaaagcgtggggagcaaaca
```

>OTU50017 [SEQUENCE ID 195] *Gemella*
```
tagggaatcttccgcaatgggcgaaagcctgacggagcaacgccgcgtgagtgaagaaggatttcggttcgtaaagctctgttg
ttagggaagaatgattgtgtagtaactatacacagtagagacggtacctaaccagaaagccacggctaactacgtgccagcag
ccgcggtaatacgtaggtggcaagcgttgtccggaattattgggcgtaaagcgcgcgcaggtggtttaataagtctgatgtgaaa
gcccacggctcaaccgtggagggtcattggaaactgttaaacttgagtgcaggagaagaaagtgaattcctagtgtagcggtg
aaatgcgtagagattaggaggaacaccagtggcgaaggcggctttttggcctgtaactgacactgaggcgcgaaagcgtggg
gagcaaaca
```

>OTU50018 [SEQUENCE ID 196] *Bacteroides*
```
tgaggaatattggtcaatgggcgctagcctgaaccagccaagtagcgtgaaggatgaaggctctatgggtcgtaaacttctttat
ataagaataaagtgcagtatgtatactgttttgtatgtattatatgaataaggatcggctaactccgtgccagcagccgcggtaatac
ggaggatccgagcgttatccggatttattgggtttaaagggagcgtaggtggactggtaagtcagttgtgaaagtttgcggctcaa
ccgtaaaattgcagttgatactgtcagtcttgagtacagtagaggtgggcggaattcgtggtgtagcggtgaaatgcttagatatca
cgaagaactccgattgcgaaggcagctcactggactgcaactgacactgatgctcgaaagtgtgggtatcaaaca
```

>OTU50020 [SEQUENCE ID 197] *Anaerostipes*
```
tggggaatattgcacaatgggggaaaccctgatgcagcgacgccgcgtgagtgaagaagtatctcggtatgtaaagctctatca
gcagggaagaaaatgacggtacctgactaagaagccccggctaactacgtgccagcagccgcggtaatacgtagggggca
agcgttatccggaattactgggtgtaaagggtgcgtaggtggtatggcaagtcagaagtgaaaacccagggctcaactctggga
ctgcttttgaaactgtcagactggagtgcaggagaggtaagcggaattcctagtgtagcggtgaaatgcgtagatattaggagga
acatcagtggcgaaggcggcttactggactgaaactgacactgaggcacgaaagcgtggggagcaaaca
```

>OTU50023 [SEQUENCE ID 198] *Prevotella*
```
tggggaatattgcacaatgggggaaaccctgatgcagcgacgccgcgtgagcgaagaagtatttcggtatgtaaagctctatca
gcagggaagaagaaatgacggtacctgactaagaagcaccggctaaatacgtgccagcagccgcggtaatacgtatggtgc
aagcgttatccggatttactgggtgtaaagggagcgcaggcggaaggctaagtctgatgtgaaagcccggggctcaaccccgg
tactgcattggaaactgtcatctagagtgtcggagggtaagcggaattcctagtgtagcggtgaaatgcgtagatattaggagg
aacaccagtggcgaaggcggcttactggacgataactgacgctgaggctcgaaagcgtggggagcaaaca
```

>OTU50032 [SEQUENCE ID 199] *Bacteroides*
```
tgaggaatattggtcaatgggcgcaggcctgaaccagccaagtagcgtgaaggatgactgccctatgggttgtaaacttctttat
atgggaataaagttttccacgtgtggaattttgtatgtaccatatgaataaggatcggctaactccgtgccagcagccgcggtaata
cggaggatccgagcgttatccggatttattgggtttaaagggagcgtaggtggacagttaagtcagttgtgaaagtttgcggctca
accgtaaaattgcagttgatactggctgtcttgagtacagtagaggtgggcggaattcgtggtgtagcggtgaaatgcttagatatc
acgaagaactccgattgcgaaggcagctcactggactgcaactgacactgatgctcgaaagtgtgggtatcaaaca
```

>OTU50037 [SEQUENCE ID 200] *Haemophilus*
```
tggggaatattgcgcaatgggggaaccctgacgcagccatgccgcgtgaatgaagaaggccttcgggttgtaaagttctttcg
gtattgaggaaggagtgtatgttaatagcatacattattgacgttaaatacagaagaagcaccggctaactccgtgccagcagcc
gcggtaatacgagggtgcgagcgttaatcggaataactgggcgtaaagggcacgcaggcggtttatttaagtgaggtgtgaaa
gccccgggcttaacctgggaattgcatttcagactgggtaactagagtactttagggaggggtagaattccacgtgtagcggtga
aatgcgtagagatgtggaggaataccgaaggcgaaggcagccccttgggaatgtactgacgctcatgtgcgaaagcgtgggg
agcaaaca
```

>OTU50038 [SEQUENCE ID 201] unclassified.*Lachnospiraceae*
```
tggggaatattgcacaatgggggaaaccctgatgcagcaacgccgcgtgagtgaagaagtatttcggtatgtaaagctctatca
gcagggaagataatgacggtacctgactaagaagctccggctaaatacgtgccagcagccgcggtaatacgtatggagcaag
cgttatccggatttactgggtgtaaagggtgcgtaggtggcagtgcaagtcagatgtgaaaggccggggctcaaccccggagct
gcatttgaaactgctcggctagagtacaggagaggcaggcggaattcctagtgtagcggtgaaatgcgtagatattaggagga
acaccagtggcgaaggcggcctgctggactgttactgacactgaggcacgaaagcgtggggagcaaaca
```

>OTU50041 [SEQUENCE ID 202] *Fusobacterium*
```
tggggaatattggacaatggaccaaaagtctgatccagcaattctgtgtgcacgatgacgttttcggaatgtaaagtgctttcagtt
gggaagaaaaaaatgacggtaccaacagaagaagtgacggctaaatacgtgccagcagccgcggtaatacgtatgtcaca
agcgttatccggatttattgggcgtaaagcgcgtctaggtggtatgtaagtctgatgtgaaaatgcagggctcaactctgtattgcgt
tggaaactgcatgactagagtactggagaggtaagcggaactacaagtgtagaggtgaaattcgtagatatttgtaggaatgcc
gatggggaagccagcttactggacagatactgacgctaaagcgcgaaagcgtgggtagcaaaca
```

>OTU50043 [SEQUENCE ID 203] *Neisseria*
```
tggggaattttggacaatgggcgcaagcctgatccagccatgccgcgtgtctgaagaaggccttcgggttgtaaaggacttttgtc
```

APPENDIX 1-continued agggaagaaaagggcggggttaatacccctgtctgatgacggtacctgaagaataagcaccggctaactacgtgccagcagc
cgcggtaatacgtagggtgcgagcgttaatcggaattactgggcgtaaagcgggcgcagacggttacttaagcaggatgtgaa
atccccgggctcaacctgggaactgcgttctgaactgggtgactagagtgtgtcagagggaggtagaattccacgtgtagcagtg
aaatgcgtagagatgtggaggaataccgatggcgaaggcagcctcctgggataacactgacgttcatgcccgaaagcgtggg
tagcaaaca >OTU50046 [SEQUENCE ID 204] *Clostridium_sensu_stricto*
tggggaatattgcacaatgggggaaaccctgatgcagcaacgccgcgtgagtgatgacggccttcgggttgtaaagctctgtctt
cagggacgataatgacggtacctgaggaggaagccacggctaactacgtgccagcagccgcggtaatacgtaggtggcgag
cgttgtccggatttactgggcgtaaagggagcgtaggcggacttttaagtgagatgtgaaatacccgggctcaacttgggtgctgc
atttcaaactggaagtctagagtgcaggagaggagaatggaattcctagtgtagcggtgaaatgcgtagagattaggaagaac
accagtggcgaaggcgattctctggactgtaactgacgctgaggctcgaaagcgtggggagcaaaca >OTU50048 [SEQUENCE ID 205] *Coprococcus*
tggggaatattgcacaatgggggaaaccctgatgcagcgacgccgcgtgaaggaagaagtatctcggtatgtaaacttctatca
gcagggaagataatgacggtacctgactaagaagccccggctaactacgtgccagcagccgcggtaatacgtaggggggcaa
gcgttatccggatttactgggtgtaaagggagcgtaggcgggcaagtcagaagtgaaagcccggggctcaaccccggg
acggcttttgaaactgccctgcttgatttcaggagaggtaagcggaattcctagtgtagcggtgaaatgcgtagatattaggagga
acaccagtggcgaaggcggcttactggactgacaatgacgctgaggctcgaaagcgtggggagcaaaca >OTU50053 [SEQUENCE ID 206] *Clostridium_XIVa*
tggggaatattgcacaatgggcgaaagcctgatgcagcaacgccgcgtgagtgaagaagtatctcggtatgtaaagctctatca
gcagggaagaaaatgacggtacctgactaagaagccccggctaactacgtgccagcagccgcggtaatacgtaggggggca
agcgttatccggatttactgggtgtaaagggagcgcagacggcactgcaagtctgaagtgaaagcccggggctcaacccgg
gactgctttggaaactgtagagctagagtgctggagaggcaagcggaattcctagtgtagcggtgaaatgcgtagatattagga
agaacaccagtggcgaaggcggcttgctggacagtaactgacgttcaggctcgaaagcgtggggagcaaaca >OTU50059 [SEQUENCE ID 207] *Prevotella*
tgaggaatattggtcaatgggcgcgagcctgaaccagccaagtagcgtgcaggatgacggccctatgggttgtaaactgcttttg
tatgggaataaagtcaatcacgtgtgattgtttgcaggtaccatacgaataaggaccggctaattccgtgccagcagccgcggta
atacggaaggtccgggcgttatccggatttattgggtttaaagggagcgtaggccggagattaagtgtgttgtgaaatgtagacgc
tcaacgtctgacttgcagcgcatactggtttccttgagtacgcacaacgttggcggaattcgtcgtgtagcggtgaaatgcttagata
tgacgaagaactccgattgcgaaggcagctgacgggagcgcaactgacgcttaagctcgaaggtgcgggtatcgaaca >OTU50062 [SEQUENCE ID 208] *Bacteroides*
tgaggaatattggtcaatggacgagagtctgaaccagccaagtagcgtgaaggatgaaggttctatggattgtaaacttctttata
cgggaataaacgaatccacgtgtggattttgcatgtaccgtatgaataaggatcggctaactccgtgccagcagccgcggtaat
acggaggatccgagcgttatccggatttattgggtttaaagggagcgtagatgggttgttaagtcagttgtgaaagtttgcggctca
accgtaaaattgcaattgatactggcagtcttgagtacagttgaggtaggcggaattcgtggtgtagcggtgaaatgcttagatatc
acgaagaactccgattgcgaaggcagcttactaacctgtaactgacattgatgctcgaaagtgtgggtatcaaaca >OTU50064 [SEQUENCE ID 209] *Clostridium_XVIII*
tagggaattttcggcaatgggggaaaccctgaccgagcaacgccgcgtgaaggaagaagtaattcgttatgtaaacttctgtcat
agaggaagaacggtggatataggaatgatatccaagtgacggtactctataagaaagccacggctaactacgtgccagcag
ccgcggtaatacgtaggtggcgagcgttatccggaattattgggcgtaaagagggagcaggcggcactaagggtctgtggtga
aagatcgaagcttaacttcggtaagccatggaaaccgtagagctagagtgtgtgagaggatcgtggaattccatgtgtagcggtg
aaatgcgtagatatatggaggaacaccagtggcgaaggcgacgatctggcgcataactgacgctcagtcccgaaagcgtggg
gagcaaata >OTU50065 [SEQUENCE ID 210] *Streptococcus*
tagggaatcttcggcaatggacgaaagtctgaccgagcaacgccgcgtgagtgaagaaggttttcggatcgtaaagctctgttgt
aagtcaagaacgtgtgtgagagtggaaagttcacacagtgacggtagcttaccagaaagggacggctaactacgtgccagca
gccgcggtaatacgtaggtcccgagcgttgtccggatttattgggcgtaaagggagcgcaggcggtcaggaaagtctggagta
aaaggctatggctcaaccatagtgtgctctggaaactgtctgacttgagtgcagaaggggagagtggaattccatgtgtagcggt
gaaatgcgtagatatatggaggaacaccagtggcgaaagcggctctctggtctgtcactgacgctgaggctcgaaagcgtggg
tagcgaaca >OTU50066 [SEQUENCE ID 211] unclassified.*Lachnospiraceae*
tggggaatattgcacaatggaggaaactctgatgcagcgacgccgcgtgagtgaagaagtatttcggtatgtaaagctctatcag
cagggaagaaaatgacggtacctgactaagaagcaccggctaaatacgtgccagcagccgcggtaatacgtatggtgcaag
cgttatccggatttactgggtgtaaagggagcgtaggtggcaaggcaagccagaagtgaaaacccggggctcaaccgcggg
attgcttttggaactgtcatgctagagtgcaggagggtgagcggaattcctagtgtagcggtgaaatgcgtagatattaggagga
acaccggaggcgaaggcggctcactggactgtaactgacactgaggctcgaaagcgtggggagcaaaca >OTU50068 [SEQUENCE ID 212] *Porphyromonas*
tgaggaatattggtcaatgggcgagagcctgaaccagccaagtcgcgtgaaggatgactgtcttatggattgtaaacttctttata
cgggaataacaagagtcacgtgtggctccctgcatgtaccgtatgaataaggatcctaactccgtgccagcagccgcggtaa
tacggaggatgcgagcgttatccggatttattgggtttaaagggtgcgtaggcggcctgttaagtcagcggttgaaatctaggagctt
aactcctaaattgccattgatactggcgggcttgagtgtagatgaggtaggcggaatgcgtggtgtagcggtggaatgcatagat
atcacgcagaactccgattgcgaaggcagcttactaaggtacaactgacgctgaagcacgaaagcgtgggtatcaaaca >OTU50076 [SEQUENCE ID 213] *Alloprevotella*
tgaggaatattggtcaatgggcgagagcctgaaccagccaagtagcgtgcaggatgacgcctccgggttgtaaactgctttta
gttgggaataaaaaagggacttgtccttcttgtatgtaccttcagaaaaggaccggctaattccgtgccagcagccgcggta
atacggaaggtccaggcgttatccggatttattgggtttaaagggagcgtaggcggattgttaagtcagcggttaaagggtgtggc
tcaacgtcattgccgttgaaactggcgatcttgagtgcagacagggatgccggaattcgtggtgtagcggtgaaatgcttagat
atcacgaagaactccgatcgcgaaggcaggtgtccgggctgcaactgacgctgaggctcgaaagtgtgggtatcaaaca >OTU50080 [SEQUENCE ID 214] *Clostridium_XIVb*
tggggaatattgcacaatgggggaaaccctgatgcagcaacgccgcgtgaaggaagaaggttttcggatcgtaaacttctatca APPENDIX 1-continued

```
acagggacgaagaaagtgacggtacctgaataagaagccccggctaactacgtgccagcagccgcggtaatacgtaggggg
gcaagcgttatccggaattactgggtgtaaagggagcgtaggcggcacgccaagccagatgtgaaagcccgaggcttaacct
cgcggattgcatttggaactggcgagctagagtacaggagaggaaagcggaattcctagtgtagcggtgaaatgcgtagatatt
aggaagaacaccagtggcgaaggcggctttctggactgaaactgacgctgaggctcgaaagcgtggggagcaaaca >OTU50086 [SEQUENCE ID 215] Sutterella
tgggaattttggacaatgggggcaaccctgatccagccatgccgcgtgcaggatgaaggtcttcggattgtaaactgcttttgtca
gggacgaaaagggatgcgataacaccgcattccgctgacggtacctgaagaataagcaccggctaactacgtgccagcagc
cgcggtaatacgtagggtgcaagcgttaatcggaattactgggcgtaaagcgtgcgcaggcggttctgtaagatagatgtgaaat
ccccgggctcaacctgggaattgcatatatgactgcaggacttgagtttgtcagaggagggtggaattccacgtgtagcagtgaa
atgcgtagatatgtggaagaacaccgatggcgaaggcagccctctgggacatgactgacgctcatgcacgaaagcgtgggga
gcaaaca >OTU50087 [SEQUENCE ID 216] Clostridium_XIVa
tgggaatattgcacaatgggcgaaagcctgatgcagcgacgccgcgtgagtgaagaagtatttcggtatgtaaagctctatca
gcagggaagaaaatgacggtacctgactaagaagccccggctaactacgtgccagcagccgcggtaatacgtaggggcga
agcgttatccggatttactgggtgtaaagggagcgtagacggcgaagcaagtctgaagtgaaaacccagggctcaacctgg
gactgctttggaaactgtttgctagagtgtcggagaggtaagtggaattcctagtgtagcggtgaaatgcgtagatattaggagga
acaccagtggcgaaggcggcttactgacgataactgacgttgaggctcgaaagcgtggggagcaaaca >OTU50091 [SEQUENCE ID 217] Collinsella
tgggaatcttgcgcaatgggggaaccctgacgcagcgacgccgcgtgcgggacggaggccttcgggtcgtaaaccgctttc
agcagggaagagtcaagactgtacctgcagaagaagccccggctaactacgtgccagcagccgcggtaatacgtaggggg
cgagcgttatccggattcattgggcgtaaagcgcgcgtaggcggcccggcaggccgggggtcgaagcgggggctcaaccc
cccgaagcccccggaacctccgcggcttgggtccggtaggggagggtggaacaccggtgtagcggtggaatgcgcagatat
cggtggaacaccggtggcgaaggcggccctctgggccgagaccgacgctgaggcgcgaaagctggggagcgaaca >OTU50092 [SEQUENCE ID 218] Clostridium_XIVa
tgggaatattgcacaatgggggaaccctgatgcagcgacgccgcgtgagtgaagaagtatttcggtatgtaaagctctatca
gcagggaagaaagtgacggtacctgaataagaagccccggctaactacgtgccagcagccgcggtaatacgtaggggca
agcgttatccggatttactgggtgtaaagggagcgtagacggcaaggcaagtctgaagtgaaagcccggtgcttaacgccggg
actgctttggaaactgtttggctggagtgccggagaggtaagcggaattcctagtgtagcggtgaaatgcgtagatattaggaag
aacaccagtggcgaaggcggcttactggacgtaactgacgttgaggctcgaaagcgtggggagcaaaca >OTU50095 [SEQUENCE ID 219] Oscillibacter
tgggaatattgggcaatgggcgcaagcctgacccagcaacgccgcgtgaaggaagaaggctttcgggttgtaaacttcttttta
agtgggaagagtagaagacggtaccacttgaataagccacggctaactacgtgccagcagccgcggtaatacgtaggtggca
agcgttgtccggatttactgggtgtaaagggcgtgcagccgggcatgcaagtcagatgtgaaatctcagggcttaaccctgaaac
tgcatttgaaactgtatgtcttgagtgccggagaggtaatcggaattccttgtgtagcggtgaaatgcgtagatataaggaagaac
accagtggcgaaggcggattactggacggtaactgacggtgaggcgcgaaagcgtggggagcgaaca >OTU50097 [SEQUENCE ID 220] Peptostreptococcus
tgggaatattgcacaatgggcgaaagcctgatgcagcaacgccgcgtgaacgatgaaggtcttcggatcgtaaagttctgttg
cagggggaagataatgacggtaccctgtgaggaagccccggctaactacgtgccagcagccgcggtaatacgtagggggcta
gcgttatccggatttactgggcgtaaagggtgcgtaggtggtccttcaagtcggtggttaaaggctacggctcaaccgtagtaagc
cgccgaaactggaggacttgagtgcaggagggaaagtgaattcccagtgtagcggtgaaatgcgtagatattgggaggaa
caccagtagcgaaggcggctttctggactgcaactgacactgaggcacgaaagcgtgggtagcaaaca >OTU50100 [SEQUENCE ID 221] unclassified.Firmicutes
tgggaatattgggcaatggaggaaactctgacccagcaacgccgcgtggaggaagaaggttttcggatcgtaaactcctgtcc
ttggagacgagtagaagacggtatccaaggaggaagccccggctaactacgtgccagcagccgcggtaatacgtaggggc
aagcgttgtccggaataattgggcgtaaagggcgcgtaggcggctcggtaagtctgagtgaaagtcctgcttttaaggtgggaa
ttgctttggatactgtcgggcttgagtgcaggagaggttagtggaattcccagtgtagcggtgaaatgcgtagagattgggaggaa
caccagtggcgaaggcgactaactggactgtaactgacgctgaggcgcgaaagtgtggggagcaaaca >OTU50101 [SEQUENCE ID 222] Clostridium_XIVa
tgggaatattgcacaatgggggaaccctgatgcagcaacgccgcgtgagtgaagaagtatttcggtatgtaaagctctatca
gcagggaagaaaatgacggtacctgactaagaagccccggctaactacgtgccagcagccgcggtaatacgtaggggca
agcgttatccggatttactgggtgtaaagggagcgtagacggcgagacaagtctgaagtgaaagcccggtgcttaacccgg
gactgctttggaaactgccttgctagagtgctggagaggtaagtggaattcctagtgtagcggtgaaatgcgtagatattaggagg
aacaccagtggcgaaggcggcttactggacagtaactgacgttgaggctcgaaagcgtggggagcaaaca >OTU50108 [SEQUENCE ID 223] Bilophila
tgggaatattgcgcaatgggcgaaagcctgacgcagcgacgccgcgtgagggatgaaggttctcggatcgtaaacctctgtc
aggggggaagaaaaccccctcgtgtgaataatgcgagggcttgacggtaccccaaaggaagcaccggctaactccgtgcca
gcagccgcggtaatacggagggtgcaagcgttaatcggaatcactgggcgtaaagcgcacgtaggcggcttggtaagtcagg
ggtgaaatcccacagcccaactgtggaactgcctttgatactgccaggcttgagtaccggagagggtggcggaattccaggtgt
aggagtgaaatccgtagatatctgcgaggaacaccggtggcgaaggcggccacctggacggtaactgacgctgaggtgcgaa
agcgtgggtagcaaaca >OTU50112 [SEQUENCE ID 224] Clostridium_IV
tgagggatattgggcaatgggggaaccctgacccagcaacgccgcgtgagggatgacggttttcggattgtaaacctctgtcct
ctgtgaagatagtgacggtagcagaggaggaagctccggctaactacgtgccagcagccgcggtaatacgtagggagcaag
cgttgtccggatttactgggtgtaaagggtgcgtaggcggattggcaagtcagaagtgaaatccatgggcttaacccatgaactg
cttttgaaactgttagtcttgagtgaagtagaggtaggcggaattcccggtgtagcggtgaaatgcgtagagatcggaggaaca
ccagtggcgaaggcggcctactgggctttaactgacgctgaggcacgaaagtgtgggtagcaaaca >OTU50122 [SEQUENCE ID 225] unclassified.Erysipelotrichaceae
tagggaattttcgtcaatgggggaaccctgaacgagcaatgccgcgtgagtgaggaaggtcttcggatcgtaaagctctgttgt
aagagaaaaacggcactcatagggaatgatgagtgagtgatggtatcttaccagaaagtcacggctaactacgtgccagcag
```

APPENDIX 1-continued ccgcggtaatacgtaggtggcgagcgttatccggaatgattgggcgtaaagggtgcgtaggtggcagatcaagtctggagtaaa
aggtatgggctcaacccgtactggctctggaaactgatcagctagagaacagaagaggacggcggaactccatgtgtagcggt
aaaatgcgtagatatggaagaacaccggtggcgaaggcggccgtctggtctggattctgacactgaagcacgaaagcgtg
gggagcaaata >OTU50124 [SEQUENCE ID 226] Campylobacter
tagggaatattgcgcaatgggggaaaccctgacgcagcaacgccgcgtggaggatgacacttttcggagcgtaaactcctttgt
tagggaagaataatgacggtacctaacgaataagcaccggctaactccgtgccagcagccgcggtaatacgaggggtgcaa
gcgttactcggaatcactgggcgtaaagggacgcgtaggcggattatcaagtctcttgtgaaatctaacggcttaaccgttaaactg
cttgggaaactgataatctagagtaagggagaggcagatggaattcttggtgtaggggtaaaatccgtagatatcaagaagaat
acctattgcgaaggcgatctgctggaacttaactgacgctaatgcgtgaaagcgtggggagcaaaca >OTU50128 [SEQUENCE ID 227] Prevotella
tgaggaatattggtcaatgggcgcaagcctgaaccagccaagtagcgtgcaggaagacgccctatgggttgtaaactgctttt
atacgagaataatttgatgcacgtgtgcgttattgcatgtatcgtatgaataaggaccggctaattccgtgccagcagccgcggta
atacggaaggtccaggcgttatccggatttattgggtttaaagggagtgtaggcggtttgttaagcgtgttgtgaaatttagatgctca
acatttaacttgcagcgcgaactgtcagacttgagtacacgcaacgtatgcggaattcatggtgtagcggtgaaatgcttagatat
catgaagaactccgattgcgaaggcagcatacgggagtgtaactgacgcttaagctcgaaggtgcgggtatcgaaca >OTU50138[ SEQUENCE ID 228] Atopobium
tgggggaatcttgcacaatgggcgaaagcctgatgcagcgacgccgcgtgcgggatgaaggccttcgggttgtaaaccgctttca
gcagggacgaggcgaaagtgacggtacctgcagaagaagccccggctaactacgtgccagcagccgcggtaatacgtagg
gggcaagcgttatccggattcattgggcgtaaagcgctcgtaggcggtctgttaggtcgggagtaaatccgggggctcaacccc
cgttcgctcccgataccggcagacttgagtttggtaggggaaggtggaattcctagtgtagcggtggaatgcgcagatattagga
agaacaccagtggcgaaggcggccttctgggccataactgacgctgaggagcgaaagctaggggagcaaaca >OTU50143 [SEQUENCE ID 229] Acetanaerobacterium
tgggggatattgcacaatgggggaaaccctgatgcagcgacgccgcgtgagggaagacggtcctctggattgtaaacctctgtc
ttcggggacgaaacgagacggtacccgaggaggaagccacggctaactacgtgccagcagccgcggtaatacgtaggtgg
caagcgttgtccggaattactgggtgtaaagggagcgtaggcggcaagtcaggcgtgaaatatccggctcaaccggt
aacgcgcttgaaactgcaggtcttgagtgaagtagaggttggcggaattcctagtgtagcggtgaaatgcgtagatattaggag
gaacaccagtggcgaaggcggccaactgggctttactgacgctgaggctcgaaagtgtggggagcaaaca >OTU50150 [SEQUENCE ID 230] Parabacteroides
tgaggaatattggtcaatgggcgtaagcctgaaccagccaagtcgcgtgagggatgaaggttctatggatcgtaaacctcttttat
aagggaataaagtgcgggacgtgtcccgttttgtatgtaccttatgaataaggatcggctaactccgtgccagcagccgcggtaat
acggaggatccgagcgttatccggatttattgggtttaaagggtgcgtaggcggcttttaagtcagcggtgaaagtctgtggctca
accatagaattgccgttgaaactgggaggcttgagtatgtttgaggcaggcggaatgcgtggtgtagcggtgaaatgcttagatat
cacgcagaaccccgattgcgaaggcagcctgccaagccatgactgacgctgatgcacgaaagcgtggggatcaaaca >OTU50168 [SEQUENCE ID 231] Veillonella
tggggaatcttccgcaatggacgaaagtctgacggagcaacgccgcgtgagtgatgacggccttcgggttgtaaagctctgttaa
tcgggacgaatggttcttgtgcgaatagtgcgaggatttgacggtaccggaatagaaagccacggctaactacgtgccagcagc
cgcggtaatacgtaggtggcaagcgttgtccggaattattgggcgtaaagcgcgcgcaggcggatcagttagtctgtcttaaaag
ttcgggcttaaccccgtgatgggatggaaactgctgatctagagtatcggagaggaaagtggaattcctagtgtagcggtgaaa
tgcgtagatattaggaagaacaccagtggcgaaggcgactttctggacgaaaactgacgctgaggcgcgaaagccaggggga
gcgaacg >OTU50171 [SEQUENCE ID 232] unclassified.Flavobacteriaceae
tgaggaatattggacaatgggtgagagcctgatccagccatcccgcgtgcaggacgactgccctatgggttgtaaactgcttttat
atagggataaaacctactctcgtgagagtagctgaaggtactatatgaataagcaccggctaactccgtgccagcagccgcggta
atacggagggtgcaagcgttatccggatttattgggtttaaagggtccgtaggtgggctgataagtcagcggtgaaatcctgcagc
ttaactgtagaactgccgttgatactgttagtcttgagtgtatttgaagtggctggaataagtagtgtagcggtgaaatgcatagatatt
acttagaacaccaattgcgaaggcaggtcactaagatacaactgacgctgagggacgaaagcgtggggagcgaaca >OTU50172 [SEQUENCE ID 233] unclassified.Lachnospiraceae
tggggaatattgcacaatgggggaaaccctgatgcagcgacgccgcgtgaaggatgaagtatttcggtatgtaaacttctatcag
cagggaagaaaatgacggtacctgactaagaagcccggctaactacgtgccagcagccgcggtaatacgtaggggcaa
gcgttatccggatttactgggtgtaaagggtgcgtaggtgatgtgaaagcctgaaggctcaaccctgggac
tgcattggaaactgtcgaactagagtgtcggagaggcaagtggaattcctagtgtagcggtgaaatgcgtagatattaggagga
acaccagtggcgaaggcggcttgctggacgatgactgacgttgaggctcgaaagcgtggggagcaaaca >OTU50177 [SEQUENCE ID 234] Dialister
tggggaatcttccgcaatggacgaaagtctgacggagcaacgccgcgtgaacgaagaaggtcttcggattgtaaagttctgtga
ttcgggacgaaagggtttgtggtgaataatcatagacattgacggtaccgaaaaagcaagccacggctaactacgtgccagca
gccgcggtaatacgtaggtggcaagcgttgtccggaattattgggcgtaaagcgcgcgcaggcggtttcttaagtccatcttaaaa
gcgtgggctcaacccatgaggggatggaaactggaagctggagtatcggagaggaaagtggaattcctagtgtagcggt
gaaatgcgtagagattaggaagaacaccggtggcgaaggcgactttctagacgaaaactgacgctgaggcgcgaaagcgtg
gggagcaaaca >OTU50188 [SEQUENCE ID 235] Capnocytophaga
tgaggaatattggtcaatggtcggaagactgaaccagccatgccgcgtgcaggaagaatgccttatgggttgtaaactgcttttat
atgggaagaataaggagtacgtgtactttgatgacggtaccatatgaataagcatcggctaactccgtgccagcagccgcggta
atacggaggatgcgagcgttatcggaatcattgggtttaaagggtctgtaggcgggctattaagtcaggggtgaaaggtttcagc
ttaactgagaaattgcctttgatactggtagtcttgaatatctgtgaagttcttggaatgtgtagtgagcggtgaaatgcttagatatta
cacagaacaccgattgcggaggcaggggactaacagacgattgacgctgagagacgaaagcgtggggagcgaaca >OTU50189 [SEQUENCE ID 236] Prevotella
tgaggaatattggtcaatggatggaaatctgaaccagccaagtagcgtgcaggatgacggccctatgggttgtaaactgcttttat
gtgagaataaagttaggtatgtatacttatttgcatgtatcacatgaataaggaccggctaattccgtgccagcagccgcggtaata APPENDIX 1-continued cggaaggtccaggcgttatccggatttattgggtttaaagggtgcgtaggccgtttgataagcgtgctgtgaaatatagtggctcaa
cctctatcgtgcagcgcgaactgtcgaacttgagtgcgtagtaggtaggcggaattcgtggtgtagcggtgaaatgcttagatatc
acgaagaactccgattgcgaaggcagcttaccgtaacgttactgacgcttaagcacgaaggtgcgggtatcgaaca >OTU50208 [SEQUENCE ID 237] *Tannerella*
tgaggaatattggtcaatgggcgagagcctgaaccagccaagtcgcgtgaaggatgacggccctatgggttgtaaacttcttttg
caggggaataaagatattcacgtgtgggtagttgtatgtaccctgcgaataagcatcggctaactccgtgccagcagccgcggta
atacggaggatgcgagcgttatccggatttattgggtttaaagggtgcgtaggtgggctattaagtcagtggtgaaagtttgtcgctc
aacgataaaattgccgttgaaactggtggtcttgagtatggatgaagtaggcggaatgcgtggtgtagcggtgaaatgcatagag
atcacgcagaactccgattgcgaaggcagcttactaaggcataactgacactgaagcacgaaagcgtgggtatcaaaca >OTU50211 [SEQUENCE ID 238] UNKNOWN
tggggaatattgcacaatggaggcaactctgatgcagcgacgccgcgtgagtgaagaagtatttcggtatgtaaagctctatcag
tagggaagataatgacggtacctacagaagaagccccggctaaatacgtgccagcagccgcggtaatacgtatggggcaag
cgttatccggatttactgggtgtaaagggagtgtaggcggcagtacaagtcaggagtgaaaacttggggctcaaccccaagact
gcttttgaaactgtacagctagagtgtaggaagggcaagcggaattcctggtgtagcggtgaaatgcgtagatatcaggaagaa
caccggtggcgaaggcggcttgctggactataactgacgctgagactcgaaagcgtggggagcgaaca >OTU50213 [SEQUENCE ID 239] UNKNOWN
tggggaatattgggcaatgggcgaaagcctgacccagcaacgccgcgtgaaggaagaaggccttcgggttgtaaacttctttta
agagggacgaagaagtgacggtacctcttgaataagccacggctaactacgtgccagcagccgcggtaatacgtaggtggcg
agcgttatccggatttactgggtgtaaagggcgcgtaggcgggaatgcaagtcagatgtgaaatccaagggctcaaccccttgaa
ctgcatttgaaactgtatttcttgagtgtcggagaggttgacggaattcctagtgtagcggtgaaatgcgtagatattaggaggaac
accagtggcgaaggcggtcaactggacgataactgacgctgaggcgcgaaagcgtggggagcaaaca >OTU50214 [SEQUENCE ID 240] UNKNOWN
tgaggaatattggtcaatggacggaagtctgaaccagccatgccgcgtgcaggaagacggctctatgagttgtaaactgcttttgt
acgagggtaaacgcagatacgtgtatctgcctgaaagtatcgtacgaataaggatcggctaactccgtgccagcagccgcggt
aatacggaggatccaagcgttatccggatttattgggtttaaagggtgcgtaggcggtttagtaagtcagcggtgaaattttggtgct
taacaccaaacgtgccgttgatactgctgggctagagagtagttgcggtaggcggaatgtatggtgtagcggtgaaatgcttaga
gatcatacagaacaccgattgcgaaggcagcttaccaaactatatctgacgttgaggcacgaaagcgtggggagcaaaca >OTU50220 [SEQUENCE ID 241] unclassified.*Lachnospiraceae*
tagggaatattgcacaatggggaaccctgatgcagcgacgccgcgtgaaggaagaagtatttcggtatgtaaacttctatca
gcaaggaagaaaatgacggtacttgactaagaagccccggctaaatacgtgccagcagccgcggtaatacgtatggggcaa
gcgttatccggatttactgggtgtaaagggagcgtaggcggcatggcaagtcagaagtgaaagcctgggctcaaccccgga
attgcttttgaaactgtcaggctagagtgtcggagggtaagcggaattcctagtgtagcggtgaaatgcgtagatattaggagga
acaccggtggcgaaggcggcttactggacgattactgacgctgaggctcgaaagcgtggggagcaaaca >OTU50221 [SEQUENCE ID 242] *Megasphaera*
tggggaatcttccgcaatgggcgaaagcctgacggagcaacgccgcgtgagtgaagacggccttcgggttgtaaagctctgtta
tacgggacgaataatcttgtggttaatacccatgagaagtgacggtaccgtaagagaaagccacggctaactacgtgccagca
gccgcggtaatacgtaggtggcaagcgttgtccggaattattgggcgtaaagggcgcgcaggcggcttcttaagtctgtcttaaa
agtgcgggcttaacccccgtgatgggatgaaactgggaagctcagagtatcggagaggaaagcggaattcctagtgtagcg
gtgaaatgcgtagatattaggaggaacaccagtggcgaaagcggcttttctggacgaaaactgacgctgaggcgcgaaagcc
aggggagcgaacg >OTU50223 [SEQUENCE ID 243] *Alistipes*
tgaggaatattggtcaatggacgcaagtctgaaccagccatgccgcgtgcaggaagacggctctatgagttgtaaactgctttgt
acgagagtaaacgctcttacgtgtaagagcctgaaagtatcgtacgaataaggatcggctaactccgtgccagcagccgcggt
aatacggaggatccaagcgttatccggatttattgggtttaaagggtgcgtaggcggtttgataagttagaggtgaaataccggtg
cttaacaccggaactgcctctaatactgttgaactagagagtagttgcggtaggcggaatgtatggtgtagcggtgaaatgcttag
agatcatacagaacaccgattgcgaaggcagcttaccaaactatatctgacgttgaggcacgaaagcgtggggagcaaaca >OTU50233 [SEQUENCE ID 244] UNKNOWN
tggggaatcttccgcaatggacgaaagtctgacggagcaacgccgcgtgagtgatgaaggtcttcggattgtaaaactctgttgtt
agggacgaaagcaccgtgttcgaacaggtcatggtgttgacggtacctaacgaggaagccacggctaactacgtgccagcag
ccgcggtaatacgtaggtggcaagcgttgtccggaattattgggcgtaaagagcatgtaggcgggcttttaagtctgacgtgaaa
atgcgggcttaacccccgtatggcgttggatactggaagtcttgagtgcaggagaggaaggggaattcccagtgtagcggtga
aatgcgtagatattgggaggaacaccagtggcgaaggcgcctttctggactgtgtctgacgctgagatgcgaaagccagggta
gcaaacg >OTU50255 [SEQUENCE ID 245] UNKNOWN
tgaggaatattggtcaatgggcgggagcctgaaccagccaagtagcgtgaaggacgacggccctacgggttgtaaacttctttt
ataagggaataaagttcgccacgtgtggtgttttgtatgtaccttatgaataagcatcggctaattccgtgccagcagccgcggtaa
tacggaagatgcgagcgttatccggatttattgggtttaaagggagcgtaggcgggcttttaagtcagcggtcaaatgtcgtggctc
aaccatgtcaagccgttgaaactaagccttgagtctgcacagggcacatggaattcgtggtgtagcggtgaaatgcttagatat
cacgaagaactccgatcgcgaaggcattgtgccggggcataactgacgctgaggctcgaaagtgcgggtatcaaaca >OTU50270 [SEQUENCE ID 246] *Porphyromonas*
tgaggaatattggtcaatgggcgagagcctgaaccagccaagtcgcgtgaaggatgactgtcttatggattgtaaacttcttttgta
ggggaataaagaacggtacgtgtaccgtagtgaatgtaccctacgaataagcatcggctaactccgtgccagcagccgcggta
atacggaggatgcgagcgttatccggatttattgggtttaaagggtgcgtaggcggcctgttaagtcagcggtgaaatctaggagc
ttaactcctaaattgccattgatactggcgggcttgagtgtagatgaggtaggcggaatgcgtggtgtagcggtggaatgcataga
tatcacgcagaactccgattgcgaaggcagcttactaaggtacaactgacgctgaagcacgaaagcgtgggtatcaaaca >OTU50299 [SEQUENCE ID 247] *Cardiobacterium*
tggggaatattggacaatgggggaaccctgatccagcaatgccgcgtgtgtgaagaaggccttcgggttgtaaagcactttca
gtagggaggaaaggtgcgtagttaatacctgcgcaattgacgttacctacagaagaagcaccggctaactccgtgccagcagc
cgcggtaatacggagggtgcgagcgttattcggaattactgggcgtaaagcgcacgcaggcggttgcccaagtcagatgtgaa APPENDIX 1-continued agccccgggcttaacctgggaactgcatttgaaactgggcgactagagtatgaaagaggaaagcggaatttccagtgtagcag
tgaaatgcgtagatattggaaggaacaccgatggcgaaggcagctttctgggtcgatactgacgctcatgtgcgaaagcgtggg
gagcaaaca >OTU50358 [SEQUENCE ID 248] *Capnocytophaga*
tgaggaatattggacaatggtcggaagactgatccagccatgccgcgtgcaggatgaaggtcttatggattgtaaactgcttttgc
aggggaagaataaggactacgcgtagtttgatgacggtactctgtgaataagcatcggctaactccgtgccagcagccgcggta
atacggaggatgcgagcgttatccggaatcattgggtttaaagggtctgtaggcgggctggtaagtcagaggtgaaagcgctta
gctcaactaagcaactgcctttgaaactgctggtcttgaatggttgtgaagtagttggaatgtgtagtgtagcggtgaaatgcttaga
tattacacagaacaccgatagcgaaggcatattactaacaattaattgacgctgatggacgaaagcgtggggagcgaaca >OTU50365 [SEQUENCE ID 249] unclassified.*Ruminococcaceae*
tggggaatattgggcaatgggcgaaagcctgacccagccaacgccgcgtgaaggaagaaggtcttcggattgtaaacttcttttat
cagggacgaagtaagtgacggtacctgatgaataagccacggctaactacgtgccagcagccgcggtaatacgtaggtggca
agcgttatccggatttactgggtgtaaagggcgcgtaggcgggatacaagtcagatgtgaaatctatgggcttaacccataaac
tgcatttgaaactgtatctcttgagtgtcggagaggtagacggaattcctagtgtagcggtgaaatgcgtagatattaggaggaac
accagtggcgaaggcggtctactggacgataactgacgctgaggcgcgaaagcgtggggagcaaaca >OTU50367 [SEQUENCE ID 250] UNKNOWN
tgggggatattgcacaatggggaaaccctgatgcagcaacgccgcgtgagggaagaaggttttcggattgtaaacctctgttct
tagtgacgataatgacggtagctaaggagaaagctccggctaactacgtgccagcagccgcggtaatacgtagggagcgagc
gttgtccggatttactgggtgtaaagggtgcgtaggcggcgaggcaagtcaggcgtgaaatctatgggcttaacccataaactgc
gcttgaaactgtcttgcttgagtgaagtagaggtaggcggaattcccggtgtagcggtgaaatgcgtagagatcgggaggaaca
ccagtggcgaaggcggcctactgggctttaactgacgctgaagcacgaaagcatgggtagcaaaca >OTU50383 [SEQUENCE ID 251] *Tannerella*
tgaggaatattggtcaatgggcgagagcctgaaccagccaagtcgcgtgaaggatgactgccctatgggttgtaaacttcttttac
aggggaataaaatgagatacgtgtattttattgcatgtaccttgtgaataagcatcggctaactccgtgccagcagccgcggtaat
acgaggatgcgagcgttatccggatttattgggtttaaagggtgcgtaggtggctgttaagtccgcggtgaaagtttgtcgctta
acgataaaattgccgttgaaactggtagtcttgagtatagatgaagtaggcggaatgcgtggtgtagcggtgaaatgcatagaga
tcacgcagaactccgattgcgaaggcagcttactaaggtataactgacactgaagcacgaaagcgtgggtatcaaaca >OTU50412 [SEQUENCE ID 252] *Prevotella*
tgaggaatattggtcaatgggcgagagcctgaaccagccaagtagcgtgcaggatgacggccctatgggttgtaaactgcttttta
taggggaataaagtgatctacgtgtagtttattgtatgtaccctatgaataaggaccggctaattccgtgccagcagccgcggtaat
acgaaggttcgggcgttatccggatttattgggtttaaagggagcgtaggccgtagattaagcgtgttgtgaaatgtagatgctca
acatctgacttgcagcgcgaactggtttactagagtgtgcgcaacgtaggcggaattcgtcgtgtagcggtgaaatgcttagatat
gacgaagaactccgattgcgaaggcagcttacgggagcacaactgacgctgaagctcgaaggtgcgggtatcaaaca >OTU50413 [SEQUENCE ID 253] *Bacteroides*
tgaggaatattggtcaatggacgtaagtctgaaccagccaagtagcgtgaaggatgactgccctatgggttgtaaacttcttttatat
gggaataaagtattccacgtgtgggattttgtatgtaccatagtaagaatcggctaactccgtgccagcagccgcggtaatac
ggaggatccgagcgttatccggatttattgggtttaaagggagcgtaggtggattgttaagtcagttgtgaaagtttgcggctcaac
cgtaaaattgcagttgaaactggcagtcttgagtacagtagaggtgggcggaattcgtggtgtagcggtgaaatgcttagatatca
cgaagaactccgattgcgaaggcagctcactagactgtcactgacactgatgctcgaaagtgtgggtatcaaaca >OTU50442 [SEQUENCE ID 254] *Abiotrophia*
tagggaatcttccgcaatggacgcaagtctgacggagcaacgccgcgtgagtgaagaaggtcttcggatcgtaaagctctgttgt
tagagaagaacagcgcatagagtaactgctatgcgtgtgacggtatctaaccagaaagccacggctaactacgtgccagcag
ccgcggtaatacgtaggtggcgagcgttgtccggatttattgggcgtaaagggagtgtaggcggtctttttaagtctgatgtgaaagc
ccacggctcaaccgtggagggtcattggaaactgggagacttgagtgcagaagaggagagcggaattccatgtgtagcggtg
aaatgcgtagatatgtgaggaacaccagtggcgaaggcggctctctggtctgtaactgacgctgaggctcgaaagcgtgggg
agcaaaca >OTU50444 [SEQUENCE ID 255] *Mogibacterium*
tagggaatcttgcacaatgggcgaaagcctgatgcagcaacgccgcgtgaaggatgaaggccttcgggttgtaaacttctgttct
aagggaagaaacaaatgacggtaccttaggagcaagcccggctaactacgtgccagcagccgcggtaatacgtagggggg
caagcgttatccggaattattgggcgtaaagagtgcgtaggtggttacctaagcgcaaggtttaatttagaggctcaacctctactt
gccttgcgaactgggctacttgagtgcaggaggggaaagcggaattcctagtgtagcggtgaaatgcgtagatattaggagga
acaccagcggcgaaggcggcttctggactgtaactgacactgaggcacgaaagcgtgggtagcaaaca >OTU50458 [SEQUENCE ID 256] *Selenomonas*
tggggaatcttccgcaatgggcgcaagcctgacggagcaacgccgcgtgagtgaagaaggtcttcggatcgtaaagctctgttg
atggggacgaacgtgcgaagggtgaataatccttttgcaatgacggtacctatcgaggaagccacggctaactacgtgccagca
gccgcggtaatacgtaggtggcgagcgttgtccggaatcattgggcgtaaagggagcgcaggcgggcatgtaagtctttcttaa
aagttcgggctcaaccccgtgatgggaaagaaactacatgtcttgagtacaggagaggaaagcggaattcccagtgtagcg
gtgaaatgcgtagatattggaggaacaccagtggcgaaggcggcttctggactgcaactgacgctgaggctcgaaagcca
ggggagcgaacg >OTU50466 [SEQUENCE ID 257] unclassified.*Ruminococcaceae*
tggggaatattgggcaatgggcgaaagcctgacccagccaacgccgcgtgaaggaagaaggtcttcggattgtaaacttcttttat
gagggacgaaggacgtgacggtacctcatgaataagccacggctaactacgtgccagcagccgcggtaatacgtaggtggc
aagcgttatccggatttactgggtgtaaagggcgcgtaggcgggatgcaagtcagatgtgaaatctatgggcttaacccataaa
ctgcatttgaaactgtatctcttgagtgctggagaggtagacggaattccttgtgtagcggtgaaatgcgtagatataaggaagaa
caccagtggcgaaggcggtctactggacagtaactgacgctgaggcgcgagagcgtggggagcaaaca >OTU50479 [SEQUENCE ID 258] *Blautia*
tggggaatattgcacaatgggggaaaccctgatgcagcgacgccgcgtgagcgaagaagtatttcggtatgtaaacttctatca
gcagggaagatagtgacggtacctgactaagaagccccggctaactacgtgccagcagccgcggtaatacgtaggggcaa
gcgttatccggatttactgggtgtaaagggagcgtagacggactggcaagtctgatgtgaaaggcgggggctcaaccctgga APPENDIX 1-continued ctgcattggaaactgttagtcttgagtgccggagaggtaagcggaattcctagtgtagcggtgaaatgcgtagatattaggagga
acaccagtggcgaaggcggcttactggacggtaactgacgttgaggctcgaaagcgtggggagcaaaca >OTU50492 [SEQUENCE ID 259] *Treponema*
gtaagaatattccgcaatgggggaaccctgacggagcgacgccgcgtgaacgaagaaggccggaaggttgtaaagttcttttt
ctgtccgaggaataagtgtaggaggaaatgcctgcatggtgacggtagggcaggaataagcaccggctaattacgtgccagc
agccgcggtaacacgtaaggtgcgagcgttgttcggaattattgggcgtaaagggcatgcaggcgggtcgccaagcttggtaa
gaaataccggggctcaactccggagctatattgagaactggcgagctagagttgccgaagggtatccggaattccgcgtgaag
gggtgaaatctgtagatatgcggaagaacaccgatggcgaaggcaggataccggcggacgactgacgctgaggtgcgaag
gtgcggggagcaaaca >OTU50500 [SEQUENCE ID 260] *Gemmiger*
tggggatattgcacaatgggggaaccctgatgcagcgacgccgcgtggaggaagaaggttttcggattgtaaactcctgtcg
ttagggacgataatgacggtacctaacaagaaagcaccggctaactacgtgccagcagccgcggtaaaacgtagggtgcaa
gcgttgtccggaattactgggtgtaaagggagcgcaggcgggaagacaagttggaagtgaaaaccatgggctcaacccatga
attgctttcaaaactgttttgcttgagtagtgcagaggtagatgaattcccggtgtagcggtggaatgcgtagatatcgggaggaa
caccagtggcgaaggcggtctactgggcaccaactgacgctgaggctcgaaagcatgggtagcaaaca >OTU50501 [SEQUENCE ID 261] UNKNOWN
tggggatattgcacaatgggcgaaagcctgatgcagcgacgccgcgtgagggaagacggccttcgggttgtaaacctctgtc
attcgggacgaattagatgacggtaccgaagaaggaagctccggctaactacgtgccagcagccgcggtaatacgtagggag
cgagcgttgtccggaattactgggtgtaaagggagcgtaggcgggaaagcaagttggaagtgaaatgcatgggcttaacccat
gagctgcttcaaaactgtttttcttgagtgaagtagaggcaggcggaattcctagtgtagcggtgaaatgcgtagatattaggagg
aacaccagtggcgaaggcggcctgctgggcttaactgacgctgaggctcgaaagcgtgggtagcaaaca >OTU50523 [SEQUENCE ID 262] UNKNOWN
tggggaatattgcacaatgggcgaaagcctgatgcagcaacgccgcgtgaaggaagaaggccttcgggtcgtaaacttctgtc
ctatgggaagaaaaaaatgacggtaccataggaggaagcccggctaactacgtgccagcagccgcggtaatacgtagggg
gcgagcgttatccggaattattgggcgtaaagagtgcgtaggtggtaacttaagcgcggggtttaaggcaatggcttaaccattgtt
cgccctgcgaactgggatacttgagtgcaggagaggaaagcggaattcctagtgtagcggtgaaatgcgtagatattaggagg
aacaccagtggcgaaggcggcttctggactgaaactgacactgaggcacgaaagtgtggggagcaaaca >OTU50529 [SEQUENCE ID 263] UNKNOWN
tggggaatattgggcaatgggggaaaccctgacccagcaacgccgcgtgaaggaagaaggtcttcggatcgtaaacttctatc
ctcggtgaagaggagaagacggtagccgagaaggaagccccggctaactacgtgccagcagccgcggtaatacgtaggggg
gcaagcgttgtccggaatgattgggcgtaaagggcgtgtaggcggctaagtaagtctggagtgaaagtcctgcttttaaggtggg
aattgctttggatactgcatagctagagtgcaggagaggtaagtggaattcccagtgtagcggtgaaatgcgtagagattgggag
gaacaccagtggcgaaggcgacttactggactgtaactgacgctgaggcgcgaaagtgtggggagcaaaca >OTU50547 [SEQUENCE ID 264] *Olsenella*
tggggaatcttgcacaatgggcgaaagcctgatgcagcgacgccgcgtgcgggacgaaggccttcgggtcgtaaaccgctttc
agcagggacgaggccgcgaggtgacggtacctgcagaagaagcccggctaactacgtgccagcagccgcggtaatacgt
aggggcgagcgttatccggattcattgggcgtaaagcgcgcgcaggcggcctgctcggtcgggagtcaaatccgggggctc
aaccccgcccgctcccgataccggcgggcttgagtctggtaggggaaggcggaattcccagtgtagcggtggaatgcgcag
atattgggaagaacaccggtggcgaaggcggccttctgggccacgactgacgctgaggcgcgaaagctaggggagcgaac
a >OTU50552 [SEQUENCE ID 265] *Lachnoanaerobaculum*
tggggaatattggacaatgggggaaaccctgatccagcgacgccgcgtgagtgaagaagtatttcggtatgtaaagctctatca
gcaggagaaaaatgacggtacctgactaagaagccccggctaactacgtgccagcagccgcggtaatacgtagggggca
agcgttatccggatttactgggtgtaaagggagcgtagacggcgatgtaagtctgaagtgaaagcccacggctcaactgtggga
ctgctttggaaactatatagctagagtatcggaggggcaagcggaattcctagtgtagcggtgaaatgcgtagatattaggagga
acaccggaggcgaaggcggcttgctggacgaagactgacgttgaggctcgaaggcgtggggagcaaaca >OTU50593 [SEQUENCE ID 266] *Alloprevotella*
tgaggaatattggtcaatggacgagagtctgaaccagccaagtagcgtgcaggatgacggccctctgggttgtaaactgcttttta
gttgggaacaaaaaaggcgacgtgtcgcctctggagtgtaccatcagaaaaaggaccggctaattccgtgccagcagccgcg
gtaatacggaaggtccaggcgttatccggatttattgggtttaaagggagcgtaggcggacgattaagtcagctgtgaaagtttgc
ggctcaaccgtaaaattgcagttgaaactggttgtcttgagtgcacgcagggatgttggaattcatggtgtagcggtgaaatgctta
gatatcatgaagaactccgatcgcgaaggcatatgtctggagtgcaactgacgctgaggctcgaaagtgcgggtatcgaaca >OTU50630 [SEQUENCE ID 267] UNKNOWN
tgaggaatattggtcaatggacgcaagtctgaaccagccatgccgcgtgcaggaagacggctctatgagttgtaaactgcttttgt
attagggtaaactcaggtacgtgtacctgactgaaagtataatacgaataaggatcggctaactccgtgccagcagccgcgta
atacggaggatccaagcgttatccggatttattgggtttaaagggtgcgtaggcggtttgataagttagaggtgaaagaccgggg
cttaactccggaactgcctctaatactgttgaactagagagtagttgcggtaggcggaatgtatggtgtagcggtgaaatgcttaga
gatcatacagaacaccgattgcgaaggcagccttaccaaactatatctgacgttgaggcacgaaagcgtggggagcaaaca >OTU50726 [SEQUENCE ID 268] UNKNOWN
tggggaatattgggcaatgggcgcaagcctgacccagcaacgccgcgtgaaggaagaaggctttcgggttgtaaacttcttttct
ggggacgaacaaatgacggtaccccaggaataagccacggctaactacgtgccagcagccgcggtaatacgtaggtggc
aagcgttatccggatttattgggtgtaaagggcgtgtaggcgggaatgcaagtcagatgtgaaaactcagggctcaaccctgag
cctgcatttgaaactgtgtttcttgagtgctggagaggcaatcggaattccgtgtgtagcggtgaaatgcgtagatatacggaggaa
caccagtggcgaaggcggattgctggacagtaactgacgctgaggcgcgaaagcgtggggagcaaaca >OTU50735 [SEQUENCE ID 269] UNKNOWN
tggggaatattgggcaatgggcgaaagcctgacccagcaacgccgcgtgagggaagaaggttttcggattgtaaacctctgtcc
tcagggacgaaggaagtgacggtacctgaggaggaagcccggctaactacgtgccagcagccgcggtaatacgtagggg
gcaagcgttgtccggaatgactgggcgtaaagggcgtgtaggcggcctgataagtatgaagtgaaagtcctgcttttcaaggtgg APPENDIX 1-continued gaattgctttgtagactgtcgggcttgagtgcggaagaggtaagtggaattcccagtgtagcggtgaaatgcgtagagattggga
ggaacaccagtggcgaaggcgacttactgggccgtaactgacgcgtgaggcgcgaaagcgtggggagcgaaca >OTU50743 [SEQUENCE ID 270] *Bacteroides*
tgaggaatattggtcaatgggcgatggcctgaaccagccaagtagcgtgaaggatgactgccctatgggttgtaaacttcttttata
aaggaataaagtcgggtatgcatacccgtttgcatgtactttatgaataaggatcggctaactccgtgccagcagccgcggtaata
cggaggatccgagcgttatccggatttattgggtttaaagggagcgtaggtggattgttaagtcagttgtgaaagtttgcggctcaa
ccgtaaaattgcagttgaaactggcagtcttgagtacagtagaggtgggcggaattcgtggtgtagcggtgaaatgcttagatatc
acgaagaactccgattgcgaaggcagcctgctaagctgcaactgacattgaggctcgaaagtgtgggtatcaaaca >OTU50759 [SEQUENCE ID 271] *Prevotella*
tgaggaatattggtcaatgggcgagagcctgaaccagccaagtagcgtgcaggatgacggcccttatgggttgtaaactgcttttat
gcgaggataaagttacccacgtgtgggtgtttgcaggtatcgcatgaataaggaccggctaattccgtgccagcagccgcggta
atacggaaggttctggcgttatccggatttattgggtttaaagggagcgtaggctgtttttttaagcgtgttgtgaaatgtaccggctca
accggtgatgtgcagcgcgaactggaagacttgagtgtgttgtaagtaggcggaattcgtggtgtagcggtgaaatgcttagatat
cacgaggaactccgattgcgtaggcagcttactgtctcactactgacgctgatgctcgaaagcgcgggtatcgaaca >OTU50833 [SEQUENCE ID 272] UNKNOWN
tggggaatattgcacaatgggggaaaccctgatgcagcaacgccgcgtgagtgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgcaggcggtacggcaagtcagatgtgaaaacccgggggctcaacccgg
gactgcatttgaaactgtcggactagagtgccggagaggtaagtggaattcctagtgtagcggtgaaatgcgtagatattaggag
gaacaccagtggcgaaggcggcttactggacggtaactgacgctgaggctcgaaagcgtggggagcaaaca >OTU50880 [SEQUENCE ID 273] UNKNOWN
tggggaatattgggcaatgggggcaaccctgacccagcaacgccgcgtgagggaagaaggttttcggattgtaaacctctgtcc
ttggggacgaagaagtgacggtacccaaggaggaagctccggctaactacgtgccagcagccgcggtaatacgtagggagc
gagcgttgtccggaattactgggcgtaaagggtgcgtaggcggtttggtaagtcagatgtgaaataccccgggcttaacccgggg
gctgcatctgatactgtcagacttgagtgcaggagaggaaagcggaattcctagtgtagcggtgaaatgcgtagatattaggag
gaacaccagtggcgaaggcggctttctggactgtaactgacgctgaggcacgaaagcgtggggagcaaaca >OTU50944 [SEQUENCE ID 274] *Rothia*
tagggaatcttcggcaatggacggaagtctgaccgagcaacgccgcgtgagggatgacggccttcgggttgtaaacctctgtta
gcagggaagaagagaaattgacggtacctgcagagaaagcgccggctaactacgtgccagcagccgcggtaatacgtagg
gcgcgagcgttgtccggaattattgggcgtaaagagcttgtaggcggtttgtcgcgtctgctgtgaaaggccggggcttaaccccg
tgtattgcagtgggtacggcagactagagtgcagtaggggagactggaactcctggtgtagcggtggaatgcgcagatatcag
gaagaacaccgatggcgaaggcaggtctctgggctgtaactgacgctgagaagcgaaagcatggggagcgaaca >OTU51014 [SEQUENCE ID 275] unclassified.*Lachnospiraceae*
tggggaatattgcacaatgggggaaaccctgatgcagcgacgccgcgtgaaggaagaagtatctcggtatgtaaacttctatca
gcagggaagatagtgacggtacctgactaagaagccccggctaactacgtgccagcagccgcggtaatacgtaggggggcaa
gcgttatccggatttactgggtgtaaagggtgcgtaggtggcagtgcaagtcagatgtgaaaggccggggctcaacccccggag
ctgcatttgaaactgctcggctagagtacaggagaggcaggcggaattcctagtgtagcggtgaaatgcgtagatattaggagg
aacaccagtggcgaaggcggcttactggacggtaactgacgttgaggctcgaaagcgtggggagcaaaca >OTU51026 [SEQUENCE ID 276] unclassified.*Lachnospiraceae*
tggggaatattgcacaatgggggaaaccctgatgcagcaacgccgcgtgagtgaagaagtatttcggtatgtaaagctctatca
gcagggaagaaaatgacggtacctgactaagaagcaccggctaaatacgtgccagcagccgcggtaatacgtatggtgcaa
gcgttatccggatttactgggtgtaaagggagcgcaggcggtctggcaagtctgatgtgaaaatccggggctcaactccggaact
gcattggaaactgtcagactagagtgtcggagaggtaagtggaattcctagtgtagcggtgaaatgcgtagatattaggaggaa
caccagtggcgaaggcggcttactggacggtaactgacgttgaggctcgaaagcgtggggagcaaaca >OTU51130 [SEQUENCE ID 277] *Clostridium_XIVa*
tggggaatattgcacaatgggggaaaccctgatgcagcaacgccgcgtgagtgaagaagtatttcggtatgtaaagctctatca
gcagggaagaaaatgacggtacctgactaagaagccccggctaactacgtgccagcagccgcggtaatacgtaggggggca
agcgttatccggatttactgggtgtaaagggagcgtagacgcatgcaagtctgaagtgaaatgcgggggctcaaccctga
actgctttgaaactgtcaggctggagtgcaggagaggtaagtggaattcctagtgtagcggtgaaatgcgtagatattaggaag
aacaccagtggcgaaggcggcttactggacggtaactgacgttgaggctcgaaagcgtggggagcaaaca >OTU51260 [SEQUENCE ID 278] *Prevotella*
tgaggaatattggtcaatgggcgcaagcctgaaccagccaagtagcgtgcaggatgacggcccctatgggttgtaaactgctttta
tgcggggataaagtgacccacgtgtgggttttgcaggtaccgcatgaataaggaccggctaattccgtgccagcagccgcggt
aatacggaaggtccgggcgttatccggatttattgggtttaaagggagcgtaggccgccttaagcgtgttgtgaaatccggttg
ctcaacatccgttgcagcgcgaactggggcgcttgagtgcgctgaaagtaggcggaattcgtggtgtagcggtgaaatgcttta
gatatcacgaggaactccgattgcgaaggcagcctactgtagcgctactgacgctgatgctcgaaagcgtgggtatcgaaca >OTU51288 [SEQUENCE ID 279] UNKNOWN
tggggaatattgcacaatggaggaaactctgatgcagcgacgccgcgtgagtgaagaagtatttcggtatgtaaagctctatcag
cagggaagacagtgacggtacctgactaagaagctccggctaaatacgtgccagcagccgcggtaatacgtatggagcaag
cgttatccggatttactgggtgtaaagggagtgtaggtggtatcacaagtcagaagtgaaagcccggggcgcaacccccgggac
tgcttttgaaactgtggaactggagtgcaggagaggtaagtggaattcctagtgtagcggtgaaatgcgtagatattaggaggaa
caccagtggcgaaggcggcttactggactgtaactgacactgaggctcgaaagcgtggggagcaaaca >OTU51340 [SEQUENCE ID 280] UNKNOWN
tggggaatattgcacaatgggggaaaccctgatgcagcaacgccgcgtgaaggaagaaggtctttgggtcgtaaacttctgttct
gagggaagaaagtgacggtacctcaggagcaagtcccggctaactacgtgccagcagccgcggtaatacgtaggggggcaa
gcgttatccggaattattgggcgtaaagagtacgtaggtggttacctaagcacggggtataaggcaatggctcaaccattgtttgc
cttgtgaactgggctacttgagtgcaggagaggaaagcggaattcctagtgtagcggtgaaatgcgtagatattaggaggaaca
ccagtggcgaaggcggctttctggactgtaactgacactgaggtacgaaagcgtggggagcaaaca APPENDIX 1-continued >OTU51343 [SEQUENCE ID 281] UNKNOWN
tggggaatattgcacaatgggggaaaccctgatgcagcgacgccgcgtgaggaagaaggtcttcggattgtaaactcctgttg
ttgaggaagataatgacggtactcaacaaggaagtgacggctaactacgtgccagcagccgcggtaaaacgtaggtcacaa
gcgttgtccggaattactgggtgtaaagggagcgcaggcgggagaacaagttggaagtgaaatccatgggctcaacccatga
actgctttcaaaactgttttttcttgagtagtgcagaggtaggcggaattcccggtgtagcggtggaatgcgtagatatcggaggaa
caccagtggcgaaggcggcctactgggcaccaactgacgctgaggcacgaaggccaggggagcgaaag >OTU51401 [SEQUENCE ID 282] UNKNOWN
tggggatattggtcaatgggggaaaccctgaaccagcaatgccgcgtgagggaagaaggtcttcggattgtaaaccctaagta
gtcagggacgaaggaagtgacggtacctgaagagtaagctccggctaactacgtgccagcagccgcggtaatacgtaggga
gcgagcgttgtccggaattactgggtgtaaagggtgcgtaggcgggcttgcaagtcagatgtgaaataccggggcttaaccccg
gggctgcatttgaaactgtaggtcttgagtgaagtagaggcaggcggaattcctagtgtagcggtgaaatgcgtagatattagga
ggaacaccagtggcgaaggcggcctgctgggctttaactgacgctgaggcacgaaagcatggggagcaaaca >OTU51411 [SEQUENCE ID 283]UNKNOWN
tggggaatattgcacaatgggggaaaccctgatgcagcaacgccgcgtgaaggaagaaggcctttgggtcgtaaacttctgtcc
taagggaagataatgacggtaccttttggaggaagccccggctaactacgtgccagcagccgcggtaatacgtaggggcgag
cgttatccggaattattgggcgtaaagagtgcgtaggcggttttttaagcgcggggtgaaaggcaatggcttaaccattgttagccc
tgcgaactgggagacttgagtgcaggagaggaaagcggaattcctagtgtagcggtgaaatgcgtagatattaggaggaaca
ccagtggcgaaggcggctttctggactgtaactgacgctgaggcacgaaagtgtggggagcaaaca >OTU51546 [SEQUENCE ID 284] UNKNOWN
tcgagaatcattcacaatgggggaaaccctgatggtgcgacgccgcgtggggaatgaaggtcttcggattgtaaacccctgtc
atgtggggagcaaattaaaaagatagtaccacaagaggaagagacggctaactctgtgccagcagccgcggtaatacagagg
tctcaagcgttgttcggaatcactgggcgtaaagcgtgcgtaggcggtttcgtaagtcgtgtgtgaaaggcgggggctcaacccc
cggactgcacatgatactgcgagactagagtaatggaggggaaccggaattctcggtgtagcagtgaaatgcgtagatatcg
agaggaacactcgtggcgaaggcgggttcctggacattaactgacgctgatgctcgaaagtgtgggtatcaaaca >OTU51549 [SEQUENCE ID 285] Prevotella
tgaggaatattggtcaatggacgaagtctgaaccagccaagtagcgtgcaggatgacggccctatgggttgtaaactgcttttgt
atggggataaagttagggacgtgtccctatttgcaggtaccatacgaataaggaccggctaattccgtgccagcagccgcggta
atacggaaggtccaggcgttatccggatttattgggtttaaagggagcgtaggcggattgttaagtcagcggttaaagggtgtggc
tcaaccatgcattgccgttgaaactggcgatcttgagtgcagacagggatgccggaattcgtggtgtagcggtgaaatgcttagat
atgacgaagaactccgattgcgaaggcagctgacgggagcgcaactgacgcttaagctcgaaggtgcgggtatcaaaca >OTU51588 [SEQUENCE ID 286] Neisseria
tggggaattttggacaatgggcgcaagcctgatccagccatgccgcgtgtctgaagaaggccttcggggttgtaaaggacttttgtc
agggaagaaaaggagttggttaataccccgactctgatgacggtacctgaagaataagcaccggctaactacgtgccagcagc
cgcggtaatacgtagggtgcgagcgttaatcggaattactgggcgtaaagcgagcgcagacggtttgttaagcaggatgtgaaa
tccccgggctcaacctgggaactgcgttctgaactggcaggctagagtgtgtcagaggggggtagaattccacgtgtagcagtg
aaatgcgtagagatgtggaggaataccgaaggcgaaggcagcccccttgggaatgtactgacgctcatgtgcgaaagcgtggg
gagcaaaca >OTU51727 [SEQUENCE ID 287] Ruminococcus
tgggggatattgcgcaatgggggcaacccctgacgcagcaacgccgcgtgaaggatgaaggttttcggattgtaaacttcttttatt
aaggacgaaaaatgacggtacttaatgaataagctccggctaactacgtgccagcagccgcggtaatacgtagggagcaagc
gttgtccggatttactgggtgtaaagggtgcgtaggcggtttgcaagtcagatgtgaaatctatgggctcaacccataaactgcat
ttgaaactgtagagcttgagtgaagtagaggcaggcggaattcccgtgtagcggtgaaatgcgtagagatggggaggaaca
ccagtggcgaaggcggcctgctgggctttaactgacgctgaggcacgaaggccaggggagcgaaag >OTU51883 [SEQUENCE ID 288] UNKNOWN
tgaggaatattggtcaatggacgagagtctgaaccagccaagtagcgtgcaggatgacggccctatgggttgtaaactgcttttg
cgcggggataacaccctccacgtgctggaggtctgcaggtaccgcgcgaataaggaccggctaattccgtgccagcagccgc
ggtaatacggaaggtccgggcgttatccggatttattgggtttaaagggagcgtagatggatgtttaagtcagttgtgaaagtttgcg
gctcaaccgtaaaattgcagttgatactggatatcttgagtgcagttgaggcaggcggaattcgtggtgtagcggtgaaatgcttag
atatgacgaagaaccccgattgcgaaggcagctggcgggagcgtaactgacgctgaagctcgaaagcgcgggtatcgaaca >OTU51970 [SEQUENCE ID 289] UNKNOWN
tgaggaatattggtcaatgggcgagagcctgaaccagccaagtagcgtgaaggatgaaggtcctacggattgtaaacttcttttat
acgggaataaagtatcctacgtgtaggattttgtatgtaccgtatgaataagcatcggctaactccgtgccagcagccgcggtaat
acggaggatgcgagcgttatccggatttattgggtttaaagggagcgtaggtggattgttaagtcagttgtgaaagtttgcggctca
accgtaaaattgcagttgaaactggcagtcttgagtacagtagaggtgggcggaattcgtggtgtagcggtgaaatgcttagatat
cacgaagaaccccgattgcgaaggcagcttgctaaactgtaactgacgttcatgctcgaaagtgtgggtatcaaaca >OTU52070 [SEQUENCE ID 290] Haemophilus
tgaggaatattggtcaatggtcggaagactgaaccagccatgccgcgtgaatgaagaaggccttcggggttgtaaagttctttcggt
agcgaggaaggcatttagtttaataaaactggatgattgacgttaactacagaagaagcaccggctaactccgtgccagcagccg
cggtaatacggagggtgcgagcgttaatcggaataactgggcgtaaagggcacgcaggcggtgacttaagtgaggtgtgaaa
gccccgggcttaacctgggaattgcatttcatactgggtcgctagagtacttagggaggggtagaattccacgtgtagcggtgaa
atgcgtagagatgtggaggaataccgaaggcgaaggcagcccccttgggaatgtactgacgctcatgtgcgaaagcgtgggga
gcaaaca >OTU52086 [SEQUENCE ID 291] Clostridium_XIVa
tggggaatattgcacaatgggggaaaccctgatgcagcgacgccgcgtgagcgaagaagtatttcggtatgtaaagctctatca
gcagggaagaaaatgacggtacctgactaagaagcccggctaactacgtgccagcagccgcggtaatacgtaggggca
agcgttatccggatttactgggtgtaaagggagcgtagacggataggcaagtctggagtgaaaacccagggctcaaccctggg
actgctttgaaactgcagatctggagtgccggagaggtaagcggaattcctagtgtagcggtgaaatgcgtagatattaggag
gaacaccagtggcgaaggcggcttactggacggtaactgacgttgaggctcgaaagcgtggggagcaaaca >OTU52183 [SEQUENCE ID 292] *Selenomonas*
tggggaatcttccgcaatgggcgcaagcctgacggagcaacgccgcgtgagtgaagaaggtcttcggatcgtaaagctctgttg
aaggggggcgaacgtacgcagtgcgaatagtgctgcgcagtgacggtacctttcgaggaagccacggctaactacgtgccagc
agccgcggtaatacgtaggtggcgagcgttgtccggaatcattgggcgtaaagggagcgcaggcggtgatgtaagtcttgctta
aaagttcggggctcaacccgtgatgggcaagaaactatatgacttgagtgcaggagaggaaagcggaattcccagtgtagc
ggtgaaatgcgtagatattgggaggaacaccagtggcgaaggcggctttctggactgcaactgacgctgaggctcgaaagcc
agggggagcgaacg >OTU52345 [SEQUENCE ID 293] *Neisseria*
tggggaattttggacaatgggcgcaagcctgatccagccatgccgcgtgtctgaagaaggccttcgggttgtaaaggacttttgtc
agggaagaaaagggcggggttaataccctgtctgatgacggtacctgaagaataagcaccggctaactacgtgccagcagc
cgcggtaatacgtagggtgcgagcgttaatcggaattactgggcgtaaagagtgcgcaggcggttttgcaagaccgatgtgaaa
tccccgggcttaacctgggaactgcattggtgactgcaaggctagagtgtgtcagagggaggtggaattccgcatgtagcagtg
aaatgcgtagagatgtggaggaataccgatggcgaaggcagcctcctgggataacactgacgttcatgcccgaaagcgtggg
tagcaaaca >OTU52529 [SEQUENCE ID 294] unclassified.*Actinomycetales*
tggggaatattgcacaatgggcgcaagcctgatgcagcgacgccgcgtggggatgacggccttcgggttgtaaactcctttcgt
tagggacgaagccacacttttttgggtgtggtgacggtacctttgttaagaagcaccggctaactacgtgccagcagccgcggtaa
tacgtagggcgcgagcgttgtccggaattattgggcgtaaagggctcgtaggcggcttgtcgcgtctgctgtgaaaatgcggggc
ttaactccgtacgtgcagtgggtacgggcaggctagagtgcggtaggggtgactggaattcctggtgtagccggtggaatgcgca
gatatcaggaggaacaccgatggcgaaggcaggtctctgggcagtaactgacgctgaggagcgaaagcatggggagcgaa
ca >OTU52704 [SEQUENCE ID 295] UNKNOWN
tggggaatattgcacaatggggggaaaccctgatgcagcgacgccgcgtgaaggaagaaggttttcggattgtaaaactcctgtcg
ttagggacgataatgacggtacctaacaagaaagcaccggctaactacgtgccagcagccgcggtaaaacgtaggtcacaa
gcgttgtccggaattactgggtgtaaagggagcgcaggcgggcgatcaagttggaagtgaaatccatgggctcaacccatgaa
ctgcttttcaaaactggtcgtcttgagtagtgcagaggtaggtggaattcccggtgtagcggtggaatgcgtagatatcgggaggaa
caccagtggcgaaggcgacctactgggcaccaactgacgctgaggctcgaaagcatgggtagcaaaca >OTU53156 [SEQUENCE ID 296] unclassified.*Lachnospiraceae*
tggggaatattgcacaatggggggaaaccctgatgcagcgacgccgcgtgaaggaagaagtatctcggtatgtaaagctctatc
agcagggaagaaaatgacggtacctgactaagaagccccggctaactacgtgccagcagccgcggtaatacgtaggggggc
aagcgttatccggatttactgggtgtaaagggagcgtagacggaatggcaagtctgatgtgaaagaccggggctcaacccccgg
gactgcattggaaactgtcaatctagagtaccggagaggtaagcggaattcctagtgtagcggtgaaatgcgtagatattagga
agaacaccagtggcgaaggcggcttactggacggtaactgacgttgaggctcgaaagcgtggggagcaaaca >OTU53349 [SEQUENCE ID 297] UNKNOWN
tgaggaatattggtcaatggccgagaggctgaaccagccaagtcgcgtgaaggaagaaggatctatggtttgtaaacttcttttat
aggggaataaagtggaggacgtgtcctttttgtatgtaccctatgaataagcatcggctaactccgtgccagcagccgcggtaat
acggaggatgcgagcgttatccggatttattgggtttaaagggtgcgtaggcggcacgccaagtcagcggtgaaatttccgggct
caacccggactgtgccgttgaaactggcgagctagagtgcacaagaggcaggcgaatgcgtggtgtagcggtgaaatgcat
agatatcacgcagaactccgattgcgaaggcagcttactaaaccataactgacactgaagcacgaaagcgtggggatcaaac
a >OTU53421 [SEQUENCE ID 298] UNKNOWN
tgaggaatattggtcaatgggcgcaggcctgaaccagccaagtagcgtgaaggatgactgccctatgggttgtaaacttcttttat
aaaggaataaagtcgggtatggataccgtttgcatgtactttatgaataaggatcggctaactccgtgccagcagccgcggtaa
tacgaggatccgagcgttatccggatttattgggtttaaagggagcgtagatggatgtttaagtcagttgtgaaagtttgcggctca
accgtaaaattgcagttgatactgggcgccttgagtgcagcataggtaggcggaattcgtggtgtagcggtgaaatgcttagatat
cacgaagaactccgattgcgaaggcagcctgctggactgtaactgacattgaggctcgaaagtgtgggtatcaaaca >OTU53463 [SEQUENCE ID 299] *Clostridium_XIVa*
tggggaatattgcacaatggggggaaaccctgatgcagcaacgccgcgtgagtgaagaagtatttcggtatgtaaagctctatca
gcaggaaagaaaatgacggtacctgactaagaagccccggctaactacgtgccagcagccgcggtaatacgtaggggggca
agcgttatccggatttactgggtgtaaagggagcgtaggtggtatggcaagtcagaagtgaaaacccagggcttaactctggga
ctgcttttgaaactgtcagactggagtgcaggagaggtaagcggaattcctagtgtagcggtgaaatgcgtagatattaggagga
acaccagtggcgaaggcggcttactggacggtaactgacgttgaggctcgaaagcgtggggagcaaaca >OTU53501 [SEQUENCE ID 300] UNKNOWN
tggggaatattgcacaatggggggaaaccctgatgcagcgacgccgcgtgaaggaagaagtatctcggtatgtaaacttctatca
gcagggaagaaaatgacggtacctgactaagaagccccggctaactacgtgccagcagccgcggtaatacgtaggggggca
agcgttatccggatttactgggtgtaaagggcgcgtaggcggctcggtaagtctggagtgaaagtcctgcttttaaggtgggaattg
ctttggatactgtcgggcttgagtgcaggagaggtaagcggaattcctagtgtagcggtgaaatgcgtagatattaggaggaaca
ccagtggcgaaggcggcttactggactgtaactgacgttgaggctcgaaagcgtggggagcaaaca >OTU53631 [SEQUENCE ID 301] UNKNOWN
tggggaatattgcacaatggggggaaaccctgatgcagcgacgccgcgtgagcgaagaagtatttcggtatgtaaagctctatca
gcagggaagaagaatgacggtacctgactaagaagcaccggctaaatacgtgccagcagccgcggtaatacgtatggtgca
agcgttatccggatttactgggtgtaaagggagcgcaggcggtgcggcaagtctgaagtgaaaatccggggcttaacccccgga
actgctttgaaactgcctgactagatacaggagaggtaagtggaattcctagtgtagcggtgaaatgcgtagatattaggagg
aacaccagtggcgaaggcggcttactggacggtaactgacgttgaggctcgaaagcgtggggagcaaaca >OTU53773 [SEQUENCE ID 302] UNKNOWN
tggggaatattgggcaatgggcgaaagcctgacccagcaacgccgcgtgaaggaagaaggccctcgggttgtaaacttcttttg
tcagggacgaagcaagtgacggtacctgacgaataagccacggctaactacgtgccagcagccacggtaatacgtaggtgg APPENDIX 1-continued

```
caagcgttatccggatttactgggtgtaaagggcgtgtaggcgggagtgcaagtcagatgtgaaaactatgggctcaacccata
gcctgcatttgaaactgtacttcttgagtgatggagaggcaggcggaattccctgtgtagcggtgaaatgcgtagatatagggagg
aacaccagtggcgaaggcgatctgctggacagcaactgacgctgaggcgcgaaagcgtggggagcaaaca
```

>OTU54003 [SEQUENCE ID 303] unclassified.*Lachnospiraceae*
```
gactacacgggtatctaatcctgtttgctccccacgctttcgtgcctcagtgtcagtaacagtccagcaggccgccttcgccactggt
gttcctcctaatatctacgcatttcaccgctacactaggaattccgcctgcctctcctgtactctagccgcgcagtttcaaatgcagct
ccggggttgagcccggcctttcacatctgacttgcactgccacctacgcacccttacacccagtaaatccggataacgcttgctc
catacgtattaccgcggctgctggcacgtatttagccggagcttcttagtcaggtaccgtcattatcttccctgctgatagagctttaca
taccgaaatacttcttcactcacgcggcgttgctgcatcagggttcccccattgtgcaatattccccactgcagcccccgtagg
```

>OTU54023 [SEQUENCE ID 304] UNKNOWN
```
tggggaatattgcacaatgggggaaaccctgatgcagcgacgccgcgtgagcgatgaagtatttcggtatgtaaagctctatca
gcagggaagaaaatgacggtacctgactaagaagcaccggctaaatacgtgccagcagccgcggtaatacgtatggtgcaa
gcgttatccggatttactgggtgtaaagggagcgtagacggcaaggcaagtctgaagtgaaagcccggtgcttaacgccggga
ctgctttggaaactgtttagctggagtgccggagaggtaagcggaattcctagtgtagcggtgaaatgcgtagatattaggagga
acaccagtggcgaaggcggcttactggactgcaactgacactgaggcacgaaagcgtgggtagcaaaca
```

>OTU54670 [SEQUENCE ID 305] UNKNOWN
```
tggggaatattgcacaatgggggaaaccctgatgcagcaacgccgcgtgagtgaagaagtatttcggtatgtaaagctctatca
gcagggaaagaaaatgacggtacctgactaagaagccccggctaactacgtgccagcagccgcggtaatacggaggatgcg
agcgttatccggatttactgggtgtaaagggagcgtagacggaatgcaagtctgatgtgaaaggccggggctcaaccccggg
actgcattggaaactgtcaatctagagtaccggaggggtaagtggaattcctagtgtagcggtgaaatgcgtagatattaggagg
aacaccagtggcgaaggcggcttactggactgtaactgacactgaggctcgaaagcgtggggagcaaaca
```

>OTU54910 [SEQUENCE ID 306] UNKNOWN
```
tggggaatattgcacaatgggggaaaccctgatgcagcgacgccgcgtgaaggaagaagtatctcggtatgtaaacttctatca
gcagggaagaaaatgacggtacctgactaagaagccccggctaactacgtgccagcagccgcggtaatacgtaggggca
agcgttatccggatttactgggtgtaaagggagcgtagacggtaatgcaagtctggagtgaaaacccggggctcaaccccggg
actgctttggaaactgtgtaactagagtgtcggagaggcaagtggaattcctagtgtagcggtgaaatgcgtagatattaggaag
aacaccagtggcgaaggcggcttactggactaactgacgttgaggctcgaaagcgtggggagcaaaca
```

>OTU54957 [SEQUENCE ID 307] UNKNOWN
```
tggggaatattgcacaatgggggaaaccctgatgcagcgacgccgcgtgaaggaagaagtatctcggtatgtaaagctctatc
agcagggaagaagaaatgacggtacctgactaagaagcaccggctaaatacgtgccagcagccgcggtaatacgtatggtg
caagcgttattcggatttactgggtgtaaagggagcgtagacggttttgcaagtctgaagtgaaagcccagggcttaacccggg
actgctttggaaactgtaggactagagtgcaggagaggtaagtggaattcctagtgtagcggtgaaatgcgtagatattaggagg
aacaccagtggcgaaggcggcttactggacgataactgacgctgaggctcgaaagcgtggggagcaaaca
```

>OTU54992 [SEQUENCE ID 308] UNKNOWN
```
tggggaatattgcacaatggaggaaactctgatgcagcgacgccgcgtgagtgaagaagtaattcgttatgtaaagctctatcag
cagggaagatagtgacggtacctgactaagaagctccggctaaatacgtgccagcagccgcggtaatacgtaggggcaag
cgttatccggatttactgggtgtaaagggagcgcaggcggcagggcaagtcagatgtgaaatactgggctcaaccccgggac
tgcatttgaaactgtccggctagagtgcaggagaggcaggcggaattcctagtgtagcggtgaaatgcgtagatattaggagga
acaccagtggcgaaggcggctcactggactgtaactgacactgaggctcgaaagcgtggggagcaaaca
```

>OTU55262 [SEQUENCE ID 309] *Leptotrichia*
```
tggggaatattggacaatgggggcaaccctgatccagcaattctgtgtgcacgaagaaggttttcggattgtaaagtgctttcagc
agggaagaagagagtgacggtacctgcagaagaagcgacggctaaatacgtgccagcagccgcggtaatacgtatgtcgc
gagcgttatccggaattattgggcataaagggcatctaggcggcctaacaagtcaggggtgaaaacctgcggctcaaccgcag
gcctgcctttgaaactgtgaggctggagtaccggagaggtggacggaactgcacgagtagaggtgaaattcgtagatatgtgca
ggaatgccgatgatgaagatagtccactggacggaaactgacgctgaggagcgaaagcatggggagcgaaca
```

>OTU55394 [SEQUENCE ID 310] UNKNOWN
```
tgaggaatattggtcaatggacgagagtctgaaccagccaagtagcgtgaaggatgactgccctatgggttgtaaacttcttttata
tgggaataaagtattccacgtgtgggattttgtatgtaccatatgaataaggatcggctaactccgtgccagcagccgcggtaata
cggaggatccgagcgttatccggatttattgggtttaaagggagcgtaggcggacgcttaagtcagttgtgaaagtttgcggctca
accgtaaaattgcagttgatactggggtgtcttgagtacagtagaggcaggcggaattcctagtgtagcggtgaaatgcttagatatc
acgaagaactccgattgcgaaggcagctcactagactgcaactgacgctgaggctcgaaagtgtgggtagcaaaca
```

>OTU55821 [SEQUENCE ID 311] UNKNOWN
```
tgaggaatattggtcaatggtcggcagactgaaccagccaagtcgcgtgagggaagacggccctacggggttgtaaacctcttttg
tcggagagtaaaagtacgctacgtgtagcgtattgcaagtatccgagaaaaagcatccgctaactccgtgccagcagccgcgg
taatacggaggatgcaagcgttatccggatttattgggtttaaagggagcgtagggatgtttaagtcagttgtgaaagtttgcggc
tcaaccgtaaaattgcagttgatactggatatcttgagtgcagttgaggcaggcggaatgcgtggtgtagcggtgaaatgcatag
atatcacgcagaaccccgattgcgaaggcagcctgctagggtgcgacagacgctgaggcacgaaagcgtgggtatcgaaca
```

>OTU56073 [SEQUENCE ID 312] UNKNOWN
```
tgaggaatattggtcaatgggcgtaagcctgaaccagccaagtcgcgtgagggatgaaggttctatggatcgtaaacctcttttataag
ggaataaagtgcgggacgtgtcctgttttgtatgtaccttatgaataaggatcggctaactccgtgccagcagccgcggtaatacggag
gatccgagcgttatccggatttattgggtttaaagggtgcgtaggcggcacgccaagtcagcggtgaaatttccgggctcaacccgga
gtgtgccgttgaaactggcgagctagagtacaaagaggcaggcggaatgcgtggtgtagcggtgaaatgcatagatatcacgcag
aacccgattgcgaaggcagcatactgggctataactgacgctgaagcacgaaagcgtgggtatcgaaca
```

>OTU56301 [SEQUENCE ID 313] UNKNOWN
```
tggggaatattgcacaatgggggaaaccctgatgcagcgacgccgcgtgagtgaagaagtatctcggtatgtaaagctctatca
gcagggaagaaaatgacggtacctgactaagaagccccggctaactacgtgccagcagccgcggtaatacgtaggggca
agcgttatccggaattactgggtgtaaagggtgcgtagacggatggacaagtctgatgtgaaaggctgggctcaaccccggg
actgcattggaaactgcccgtcttgagtgccggagaggtaagcggaattcctagtgtagcggtgaaatgcgtagagatcgggag
gaacaccagtggcgaaggcggcctactgggctttaactgacgctgaggcacgaaagtgtgggtagcaaaca
```

APPENDIX 1-continued

>OTU56581 [SEQUENCE ID 314] UNKNOWN
tggggaatattgcacaatggaggaaactctgatgcagcgacgccgcgtgaaggatgaagtatttcggtatgtaaacttctatcag
cagggaagaaaatgacggtacctgactaagaagcccggctaactacgtgccagcagccgcggtaatacgtaggggcaa
gcgttatccggatttactgggtgtaaaggcgcgtgtaggcggggaagcaagtcagatgtgaaaaccagtggctcaaccactggc
ctgcatttgaaactgttttcttgagtgatggagaggcaggcggaattccgtgtgtagcggtgaaatgcgtagatattaggaggaac
accagtggcgaaggcggcttactgacggtaactgacgttgaggctcgaaagcgtggggagcaaaca >OTU56772 [SEQUENCE ID 315] Corynebacterium
tggggaatattgcacaatgggcgcaagcctgatgcagcgacgccgcgtgggggatgacggccttcggggttgtaaactcctttcgt
tagggacgaagccacacttttgggtgtggtgacggtaccttgttaagaagcaccggctaactacgtgccagcagccgcggtaa
tacgtagggtgcgagcgttgtccggaattactgggcgtaaagagctcgtaggtggtgtgtcgcgtcgtctgtgaaattccggggctt
aactccgggcgtgcaggcgatacgggcacgactagagtgctgtaggggtaactggaattcctggtgtagcggtgaatgcgca
gatatcaggaggaacaccgatggcgaaggcaggtctctgggcagtaactgacgctgaggagcgaaagcatggggagcgaa
cc >OTU56780 [SEQUENCE ID 316] Faecalibacterium
gactacaggggtatctaatcctgtttgctacccacactttcgagcctcagcgtcagttggtgcccagtaggccgccttcgccactggt
gttcctcccgatatctacgcattccaccgctacaccgggaattccgcctacctctgcactactcaagaaaaacagttttgaaagca
gttcatgggttgagcccatggatttcacttccaacttgttctcccgcctgcgctccctttacacccagtaattccggacaacgcttgtga
cctacgttttaccgcggctgctggcacgtagttagccgtcacttccttgttgagtaccgtcattatcttcctcaacaacaggagtttaca
atccgaagaccttcttcctccacgcggcgtcgctgcatcagggttcccccattgtgcaatattcccactgcagcccccgtagg >OTU56933 [SEQUENCE ID 317] UNKNOWN
tggggaatattgggcaatggggggaaccctgacccagcaacgccgcgtgaaggaagaaggttttcggatcgtaaactcctgtc
cttggagacgagtagaagacggtatccaaggaggaagccccggctaactacgtgccagcagccgcggtaatacgtaggggg
caagcgttgtccggatttactgggtgtaaagggcgtgcagcggggtttgcaagtcagatgtgaaatccatgggctcaacccatga
actgcatttgaaactgtagatcttgagtgtcggagggcaatcggaattcctagtgtagcggtgaaatgcgtagatataaggaag
aacaccagtggcgaaggcggattactggacgtaactgacggtgaggcgcgaaagcgtggggagcgaaca >OTU57157 [SEQUENCE ID 318] Veillonella
gactactagggtatctaatcccgttcgctcccctggctttcgcgcctcagcgtcagttttcgtccagaaagtcgccttcgccactggtg
ttcttcctaatatctacgcatttcaccgctacactaggaattccactttcctctccgatactctagattggcagtttccatcccatcacgg
ggttaagccccgaacttttaagacagactgactacgccaatccgcctgcgcggcgctttacgcccaataattccggacaacgcttgccacc
tacgtattaccgcggctgctggcacgtagttagccgtggcttctctattccggtaccgtcaatccttctaactgttcgcaagaaggcctttt
cgtcccgattaacagagctttacaaccccgaaggccgtcatcactcacgcggcgttgctccgtcagactttcgtccattgcggaaga
ttccccactgcagcccccgtagg >OTU57512 [SEQUENCE ID 319] unclassified.Lachnospiraceae
tggggaatattgcacaatgggcgaaagcctgatgcagcgacgccgcgtgagcgaagaagtatttcggtatgtaaagctctatca
gcagggaagataatgacggtacctgactaagaagcaccggctaaatacgtgccagcagccgcggtaatacgtatggtacaag
cgttatccggatttactgggtgtaaagggagcgtagacggcgacgcaagtctgaagtgaaatacccgggctcaacctgggaact
gctttggaaactgtgttgctggagtgctggagaggtaagcggaattcctagtgtagcggtgaaatgcgtagatattaggaggaac
accagtggcgaaggcggcttactggacgataactgacgctgaggctcgaaagcgtggggagcaaaca >OTU57750 [SEQUENCE ID 320] UNKNOWN
tgaggaatattggtcaatggacgagagtctgaaccagccaagtagcgtgaaggatgactgccctatgggttgtaaacttcttttata
cgggaataaagtggtccacgtgtggattttttgtatgtaccgtatgaataaggatcggctaactccgtgccagcagccgcggtaata
cggaggatccgagcgttatccggatttattgggtttaaagggagcgtaggtggacatgtaagtcagttgtgaaagtttgcggctca
accgtaaaattgcagttgatactgcgtgtcttgagtacagtagaggtgggcggaattcgtggtgtagcggtgaaatgcttagatatc
acgaagaactccgattgcgaaggcagctcactggagtgtaactgacgctgatgctcgaaagtgtgggtatcaaaca >OTU58020 [SEQUENCE ID 321] Blautia
tggggaatattgcacaatgggggaaaccctgatgcagcgacgccgcgtgagtgaagaagtatttcggtatgtaaagctctatca
gcagggaagaactaggacggtacctgactaagaagcccccggctaactacgtgccagcagccgcggtaatacgtagggggc
aagcgttatccggatttactgggtgtaaagggagcgtagacggcgtatcaagtctgatgtgaaaggcaggggcttaaccctgg
actgcattggaaactggtatgcttgagtgccggagggtaagcggaattcctagtgtagcggtgaaatgcgtagatattaggagg
aacaccagtggcgaaggcggcttactggacgtaactgacgttgaggctcgaaagcgtggggagcaaaca >OTU58875 [SEQUENCE ID 322] Fusobacterium
gactactggggtatctaatcctgtttgctacccacgctttcgcgcttcagcgtcagtatctgtccagtaagctggcttcccatcggcat
tcctacaaatatctacgaatttcacctctacacttgtagttccgcttacctctccagtactctagttacacagtttccaacgcaatacag
agttgagccctgcattttcacatcagacttacataaccacctagacgcgctttacgcccaataaatccggataacgcttgtgacata
cgtattaccgcggctgctggcacgtatttagccgtcacttcttctgttggtaccgtcatttttttcttcccaactgaaagcactttacat
tcc
gaaaaacttcatcgtgcacacagaattgctggatcagactcttggtccattgtccaatattcccactgcagcctcccgtagg >OTU59239 [SEQUENCE ID 323] UNKNOWN
tggggaatattgcacaatgggggaaaccctgatgcagcgacgccgcgtgaaggaagaagtatttcggtatgtaaacttctatca
gcagggaagaaaatgacggtacctgactaagaagcccggctaactacgtgccagcagccgcggtaatacgtaggtggcaa
gcgttgtccggaattactgggtgtaaagggagcgtagacgccgtgcaagtctgatgtgaaaggctgggcgtcaaccccggga
ctgcattggaaactgtatgctggagtgccggagaggtaagcggaattcctagtgtagcggtgaaatgcgtagatattaggagg
aacaccagtggcgaaggcggcttactggacgtaactgacgttgaggctcgaaagcgtggggagcaaaca >OTU59581 [SEQUENCE ID 324] UNKNOWN
tggggaatattgcacaatgggggaaaccctgatgcagcgacgccgcgtgagcgaagaagtatttcggtatgtaaagctctatca
gcagggaagaagaaatgacggtacctgactaagaagcaccggctaaatacgtgccagcagccgcggtaatacgtatggtgc
aagcgttgtccggaattactgggtgtaaagggagcgtaggcgggcaggcaagtcaggcgtgaaatatatcggctcaaccggta
acggcgcttgaaactgcaggtcttgagtgaagtagaggttggcggaattcctagtgtagcggtgaaatgcgtagatattaggagg
aacaccagtggcgaaggcggcttactggacgataactgacgctgaggctcgaaagcgtggggagcaaaca APPENDIX 1-continued >OTU59656 [SEQUENCE ID 325] *Streptococcus*
gactactcgggtatctaatcctgtttgctccccacgctttcgagcctcagcgtcagttacaagccagagagccgctttcgccaccgg
tgttcctccatatatctacgcatttcaccgctacacatggaattccactctccctcttgcactcaagttaaacagtttccaaagcgtac
tatggttaagccacagcctttaacttcagacttatctaaccgcctgcgctcgctttacgcccaataaatccggacaacgctcgggac
ctacgtattaccgcggctgctggcacgtagttagccgtcccttctggtaagataccgtcacagtgtgaactttccactctcacactcg
ttcttctcttacaacagagctttacgatccgaaaaccttcttcactcacgcggcgttgctcggtcagacttccgtccattgccgaagatt
ccctactgcagcccccgtagg >OTU510131 [SEQUENCE ID 326] *Parabacteroides*
gactactagggtatctaatcctgtttgatccccacgctttcgtgcttcagtgtcagttatggtttagtaagctgccttcgcaatcggagtt
ctgcgtgatatctatgcatttcaccgctacaccacgcattccgcctacctcaaacacactcaagtaacccagtttcaacggcaattt
atggttgagccacaaactttcaccgctgacttaaatcaccacctacgcacccttttaaacccaataaatccggataacgctcgcatc
ctccgtattaccgcggctgctggcacggagttagccgatgcttattcatagggtacatacaaaaaaggacacgtcctccactttatt
ccctataaaagaagtttacaaaccatagatccttcttccttcacgcgacttggctggttcagcctctcggccattgaccaatattcct
cactgctgccgcccgtagg

TABLE 21

Relative abundance of OTUs in oral swab samples

| | mean CRCs [%] | mean Polyps [%] | mean HCs [%] | mean CRCs vs mean HCs | mean Polyps vs mean HCs | Genus |
|---|---|---|---|---|---|---|
| OTU0001 | 0.055028579 | 0.014105697 | 0.010194467 | 5.397886894 | 1.383662046 | *Escherichia*/Shigella |
| OTU0002 | 0.011313131 | 0.031528782 | 0.006463083 | 1.75042325 | 4.878288403 | *Blautia* |
| OTU0003 | 0.042047399 | 0.064836386 | 0.013972091 | 3.00938491 | 4.640421175 | *Faecalibacterium* |
| OTU0006 | 0.011843836 | 0.019889543 | 0.002543013 | 4.657403273 | 7.821251919 | *Ruminococcus* 2 |
| OTU0007 | 33.73916301 | 33.82241781 | 38.64171217 | 0.873128056 | 0.875282588 | *Streptococcus* |
| OTU0008 | 0.005045105 | 0.032319853 | 0.007460596 | 0.676233529 | 4.332073598 | *Roseburia* |
| OTU0012 | 0.005244229 | 0.006455044 | 0.001224844 | 4.281548491 | 5.270094833 | *Anaerostipes* |
| OTU0013 | 0.00160735 | 0.006843728 | 0.000462443 | 3.475782212 | 14.79908066 | *Roseburia* |
| OTU0015 | 11.58659408 | 18.79786928 | 20.8398448 | 0.555982743 | 0.9020158 | *Haemophilus* |
| OTU0016 | 7.803114169 | 2.853514964 | 1.158931364 | 6.73302528 | 2.462194961 | *Streptococcus* |
| OTU0018 | 0.002781471 | 0.006453046 | 0.001352832 | 2.056036123 | 4.770027853 | *Gemmiger* |
| OTU0019 | 0.00037326 | 0.002545332 | 0.002612474 | 0.142875901 | 0.974299339 | Clostridium_sensu_stricto |
| OTU0020 | 0.000633712 | 0.007600077 | 0.000694078 | 0.913027092 | 10.9498842 | *Bacteroides* |
| OTU0022 | 0.00165728 | 0.012154165 | 0.000808567 | 2.049649302 | 15.03172735 | *Parabacteroides* |
| OTU0026 | 0.004477528 | 0.003593469 | 0.001549276 | 2.890047049 | 2.319451203 | *Dorea* |
| OTU0029 | 0.027353094 | 0.003357279 | 0.001758499 | 15.55479279 | 1.909172914 | *Bifidobacterium* |
| OTU0030 | 0.000771882 | 0.003238598 | 9.17E−05 | 8.413097288 | 35.2989642 | *Coprococcus* |
| OTU0031 | 0.000628651 | 0.005239441 | 0.001064259 | 0.590693847 | 4.923089057 | Clostridium_sensu_stricto |
| OTU0038 | 0 | 0.002861829 | 0.000143712 | 0 | 19.91369262 | *Alistipes* |
| OTU0039 | 0.000886054 | 0.000753682 | 0.0001835 | 4.82863725 | 4.107263985 | *Sutterella* |
| OTU0040 | 0.004321983 | 0.009315496 | 0.00058963 | 7.329993156 | 15.79888823 | *Bacteroides* |
| OTU0041 | 2.654757689 | 2.104393832 | 3.693940239 | 0.718679112 | 0.56968811 | *Neisseria* |
| OTU0042 | 0 | 0.002390496 | 0.000353571 | 0 | 6.761008134 | Clostridium_XI |
| OTU0045 | 0.000317687 | 0.002214254 | 0.001101617 | 0.288382711 | 2.010004109 | unclassified. Lachnospiraceae |
| OTU0049 | 0.001930951 | 0.004852475 | 0.000791039 | 2.44103062 | 6.134305378 | unclassified. Lachnospiraceae |
| OTU0050 | 4.769386038 | 4.549775391 | 2.287302904 | 2.085157165 | 1.989144238 | *Veillonella* |
| OTU0054 | 0.000531145 | 0.003062356 | 0.000348208 | 1.525366667 | 8.794606818 | *Bacteroides* |
| OTU0059 | 0.000863112 | 0.00124379 | 0.000598796 | 1.441412586 | 2.077151364 | *Sutterella* |
| OTU0061 | 0.014257184 | 0.005291664 | 0.000353313 | 40.35289611 | 14.97728837 | *Bifidobacterium* |
| OTU0063 | 0.688193755 | 0.908334443 | 1.018833514 | 0.675472239 | 0.891543545 | *Fusobacterium* |
| OTU0065 | 0.000306519 | 0 | 0.000495544 | 0.618551291 | 0 | *Collinsella* |
| OTU0067 | 0.000548303 | 0.009827817 | 0.000737642 | 0.743319638 | 13.32329666 | Clostridium_XIVa |
| OTU0072 | 1.489165157 | 0.880552938 | 0.091889714 | 16.20600487 | 9.582714947 | *Streptococcus* |
| OTU0073 | 0 | 0.001130523 | 8.73E−05 | 0 | 12.94669963 | unclassified. Firmicutes |
| OTU0075 | 0.000293336 | 0.001323675 | 0.000208633 | 1.405990117 | 6.344506476 | Clostridium_XIVa |
| OTU0080 | 1.869768835 | 1.17900244 | 3.338234784 | 0.560107049 | 0.353181402 | *Prevotella* |
| OTU0081 | 3.157758282 | 3.704552273 | 4.306064669 | 0.733328114 | 0.860310413 | *Neisseria* |
| OTU0083 | 1.202425676 | 1.329970753 | 1.314242906 | 0.914918902 | 1.01196723 | *Gemella* |
| OTU0085 | 0 | 0.00265949 | 7.61E−05 | 0 | 34.9377691 | *Bilophila* |
| OTU0087 | 0.052442878 | 0.089438373 | 0.089882372 | 0.583461213 | 0.995060224 | *Parvimonas* |
| OTU0089 | 0.000453029 | 0.003589067 | 8.73E−05 | 5.188066725 | 41.10185702 | *Barnesiella* |
| OTU0092 | 0.693624501 | 1.365167151 | 2.239622004 | 0.309706057 | 0.609552482 | *Haemophilus* |
| OTU0093 | 0.000106284 | 0.000852499 | 8.41E−05 | 1.263474957 | 10.13426446 | Clostridium_IV |
| OTU0095 | 0.27306594 | 0.252286548 | 0.201819871 | 1.353031093 | 1.250058022 | *Prevotella* |
| OTU0097 | 0.025064766 | 0.069342204 | 0.074564375 | 0.336149341 | 0.929964252 | *Peptostreptococcus* |
| OTU0105 | 0.00020414 | 0.000612471 | 0 | Inf | Inf | Clostridium_IV |
| OTU0109 | 0.002091331 | 0.000773475 | 0.001029182 | 2.032032848 | 0.751543594 | *Porphyromonas* |
| OTU0112 | 0.000147676 | 0.000376841 | 0 | Inf | Inf | Clostridium_XIVa |
| OTU0114 | 0 | 0.001366153 | 0.000735348 | 0 | 1.857832508 | *Parasutterella* |
| OTU0115 | 0.001037434 | 0.001884204 | 0.000100922 | 10.27952129 | 18.66982711 | Clostridium_XIVa |
| OTU0120 | 0.000465363 | 0.000376841 | 0 | Inf | Inf | *Bifidobacterium* |
| OTU0130 | 0.017416935 | 0.00768718 | 0.021436689 | 0.812482509 | 0.358599243 | *Solobacterium* |
| OTU0134 | 0.00174728 | 0.004245044 | 0 | Inf | Inf | *Phascolarctobacterium* |

TABLE 21-continued

Relative abundance of OTUs in oral swab samples

| | mean CRCs [%] | mean Polyps [%] | mean HCs [%] | mean CRCs vs mean HCs | mean Polyps vs mean HCs | Genus |
|---|---|---|---|---|---|---|
| OTU0135 | 0 | 0 | 0.000100922 | 0 | 0 | *Hespellia* |
| OTU0141 | 0.533517108 | 0.811016085 | 0.312968554 | 1.704698764 | 2.591366043 | *Aggregatibacter* |
| OTU0142 | 0.019809765 | 0.030660762 | 0.03662766 | 0.540841685 | 0.837093121 | *Dialister* |
| OTU0148 | 9.04E−05 | 0 | 0 | Inf | NA | *Flavonifractor* |
| OTU0149 | 0.001174109 | 0.002760488 | 0.000538483 | 2.18040284 | 5.126419493 | *Blautia* |
| OTU0155 | 0.141808032 | 0.00075096 | 0.000110898 | 1278.728408 | 6.771646534 | *Lactobacillus* |
| OTU0157 | 1.072733542 | 0.639610337 | 0.233559062 | 4.592986165 | 2.738537867 | *Leptotrichia* |
| OTU0161 | 0.002262355 | 0.010408181 | 0.002395009 | 0.944612122 | 4.345778865 | unclassified. Lachnospiraceae |
| OTU0167 | 0.462851223 | 0.113080854 | 0.11001215 | 4.207273668 | 1.027894224 | *Streptococcus* |
| OTU0174 | 0.477022962 | 0.200613252 | 0.084959629 | 5.614701533 | 2.36127739 | *Kingella* |
| OTU0175 | 0.682934991 | 0.681454333 | 0.771791717 | 0.884869552 | 0.882951084 | *Aggregatibacter* |
| OTU0176 | 0.812901048 | 0.563723862 | 0.302762109 | 2.684949743 | 1.861936631 | *Campylobacter* |
| OTU0187 | 0.000158844 | 0 | 9.17E−05 | 1.731309666 | 0 | *Paraprevotella* |
| OTU0194 | 0.00038116 | 0.000753682 | 0.00066238 | 0.575439419 | 1.137838873 | *Bacteroides* |
| OTU0206 | 5.69E−05 | 0 | 0 | Inf | NA | Clostridium__IV |
| OTU0217 | 0.173940699 | 0.552503832 | 0.298141163 | 0.583417255 | 1.853161859 | *Alloprevotella* |
| OTU0233 | 0.473992363 | 0.834089039 | 0.421968287 | 1.123289066 | 1.976662853 | *Capnocytophaga* |
| OTU0244 | 0.254097015 | 0.523957734 | 0.487802565 | 0.52090135 | 1.074118449 | *Capnocytophaga* |
| OTU0251 | 0 | 0.001130523 | 0 | NA | Inf | *Pseudoflavonifractor* |
| OTU0277 | 0.168120603 | 0.203317801 | 0.099617976 | 1.687653281 | 2.040975034 | *Eikenella* |
| OTU0283 | 0.232442931 | 0.341748279 | 0.183238807 | 1.268524584 | 1.865043142 | *Tannerella* |
| OTU0290 | 0.228101707 | 0.054594393 | 0.185481149 | 1.229783774 | 0.294339307 | *Neisseria* |
| OTU0299 | 1.20335511 | 0.521066657 | 0.243505571 | 4.941797041 | 2.13985518 | *Prevotella* |
| OTU0303 | 0.09118412 | 0.121009003 | 0.046043996 | 1.980369378 | 2.628116878 | unclassified. Flavobacteriaceae |
| OTU0317 | 0.296085045 | 0.361852645 | 0.215340696 | 1.374960939 | 1.680372789 | *Lachnoanaerobaculum* |
| OTU0324 | 0.275570054 | 0.393758147 | 0.196297365 | 1.403839801 | 2.005926812 | *Selenomonas* |
| OTU0337 | 0.062435163 | 0.090744167 | 0.097650162 | 0.63937593 | 0.929278209 | *Cardiobacterium* |
| OTU0348 | 0.037647895 | 0.240380645 | 0.200407737 | 0.187008226 | 1.199457908 | *Prevotella* |
| OTU0350 | 0.11900781 | 0.107895953 | 0.163935932 | 0.725940972 | 0.658159268 | *Actinomyces* |
| OTU0361 | 0 | 0.000376841 | 0 | NA | Inf | *Butyricimonas* |
| OTU0363 | 0.083378244 | 0.03373667 | 0.049271949 | 1.692205112 | 0.684703389 | *Oribacterium* |
| OTU0364 | 0 | 0.000376841 | 0 | NA | Inf | unclassified. Clostridiales |
| OTU0389 | 0.038768743 | 0.23574301 | 0.250803326 | 0.154578264 | 0.939951691 | *Prevotella* |
| OTU0397 | 0.001575529 | 0.005804057 | 0.000626866 | 2.513343393 | 9.258851766 | *Gemmiger* |
| OTU0406 | 0.343391928 | 0.248267395 | 0.216522591 | 1.585940417 | 1.14661197 | *Prevotella* |
| OTU0412 | 0.267951749 | 0.397492533 | 0.287852363 | 0.930865206 | 1.380890289 | *Selenomonas* |
| OTU0424 | 0.797135207 | 0.328470004 | 0.415055202 | 1.920552262 | 0.791388717 | *Veillonella* |
| OTU0427 | 0.000895043 | 0.001281858 | 0.00035023 | 2.555588079 | 3.660049447 | *Dorea* |
| OTU0431 | 0.203285894 | 0.057040608 | 0.129882142 | 1.565156619 | 0.439172065 | *Prevotella* |
| OTU0433 | 0.092221252 | 0.050212653 | 0.024600565 | 3.748745249 | 2.041117864 | *Selenomonas* |
| OTU0458 | 0.056107916 | 0.170636095 | 0.074128238 | 0.756895364 | 2.301904116 | *Lachnoanaerobaculum* |
| OTU0473 | 0.027486635 | 0.013214742 | 0.045941405 | 0.598297648 | 0.287643393 | *Tannerella* |
| OTU0511 | 0 | 0.001507363 | 0 | NA | Inf | unclassified. Porphyromonadaceae |
| OTU0544 | 0.144520571 | 0.066486672 | 0.249533257 | 0.579163566 | 0.266444132 | *Abiotrophia* |
| OTU0571 | 0.064922957 | 0.05913134 | 0.039506153 | 1.643363187 | 1.496762794 | *Treponema* |
| OTU0595 | 0.036101131 | 0.092780036 | 0.029097482 | 1.240696063 | 3.188593347 | *Actinomyces* |
| OTU0599 | 4.80E−05 | 0.000376841 | 0 | Inf | Inf | unclassified.Lachnospiraceae |
| OTU0626 | 0.035016581 | 0.020778052 | 0.005805661 | 6.031454879 | 3.578929818 | *Lachnoanaerobaculum* |
| OTU0657 | 0.056277199 | 0.02423338 | 0.003927706 | 14.32826221 | 6.169856241 | unclassified. Candidatus_Saccharibact |
| OTU0663 | 0.027898051 | 0.030348757 | 0.010965852 | 2.5440841 | 2.767569317 | *Schwartzia* |
| OTU0666 | 0.029173949 | 0.009269634 | 0.032051152 | 0.910230889 | 0.289213746 | *Leptotrichia* |
| OTU0731 | 0 | 0.000284286 | 0.000427856 | 0 | 0.664444383 | Clostridium_XIVa |
| OTU0777 | 0.118155447 | 0.116444246 | 0.079938235 | 1.478084268 | 1.456677717 | *Leptotrichia* |
| OTU0831 | 0 | 0.001658699 | 0 | NA | Inf | unclassified. Lachnospiraceae |
| OTU0850 | 0.004991521 | 0.003444236 | 0.018198321 | 0.274284716 | 0.189261185 | *Prevotella* |
| OTU0853 | 0.005209619 | 0.000657267 | 0.001631715 | 3.19272562 | 0.402807614 | unclassified. Clostridiales |
| OTU0856 | 0.006616405 | 0.001235479 | 0.00063469 | 10.42462876 | 1.946586793 | *Capnocytophaga* |
| OTU0857 | 0 | 0.000633844 | 0 | NA | Inf | *Corynebacterium* |
| OTU0860 | 0.004069615 | 0.00536147 | 0.007037842 | 0.578247495 | 0.761805984 | *Prevotella* |
| OTU0863 | 0.00078305 | 0 | 0 | Inf | NA | unclassified. Erysipelotrichaceae |
| OTU0865 | 0.000295351 | 0 | 0.000208633 | 1.415647705 | 0 | *Blautia* |
| OTU0876 | 0 | 0.000428918 | 0 | NA | Inf | Ruminococcus 2 |
| OTU0903 | 0.005111622 | 0.004020325 | 0.004336327 | 1.178790847 | 0.927126775 | *Prevotella* |
| OTU0976 | 0 | 0 | 0.000279139 | 0 | 0 | Clostridium_XIVa |
| OTU0989 | 7.94E−05 | 0.000284286 | 0 | Inf | Inf | unclassified. Lachnospiracea |
| OTU1175 | 7.94E−05 | 0.001152126 | 0.000108737 | 0.730399492 | 10.59548259 | unclassified. Lachnospiracea |
| OTU1197 | 0.000177565 | 0 | 0 | Inf | NA | *Escherichia*/*Shigella* |
| OTU1250 | 0.11862174 | 0.287238281 | 0.034676121 | 3.420848082 | 8.283460693 | *Leptotrichia* |
| OTU1254 | 7.94E−05 | 0 | 8.07E−05 | 0.984411087 | 0 | *Blautia* |
| OTU1280 | 7.94E−05 | 0 | 0 | Inf | NA | unclassified. Lachnospiracea |
| OTU1339 | 0.000147676 | 0.000306236 | 0 | Inf | Inf | *Roseburia* |
| OTU1376 | 0.001032484 | 0.001863368 | 0 | Inf | Inf | *Faecalibacterium* |
| OTU1423 | 0.002457565 | 0.003027167 | 0.02354508 | 0.104376998 | 0.128568974 | *Neisseria* |
| OTU1487 | 0.000114565 | 0.00219044 | 0 | Inf | Inf | Clostridium_XIVa |
| OTU1550 | 0 | 8.41E−05 | 0 | NA | Inf | *Coprococcus* |

TABLE 21-continued

Relative abundance of OTUs in oral swab samples

| | mean CRCs [%] | mean Polyps [%] | mean HCs [%] | mean CRCs vs mean HCs | mean Polyps vs mean HCs | Genus |
|---|---|---|---|---|---|---|
| OTU1582 | 7.94E−05 | 0 | 8.73E−05 | 0.909535382 | 0 | *Blautia* |
| OTU1584 | 0.000306519 | 0 | 0 | Inf | NA | *Parabacteroides* |
| OTU1610 | 0 | 0 | 0.000108737 | 0 | 0 | *Blautia* |
| OTU1645 | 0.000238265 | 0 | 0 | Inf | NA | unclassified. Lachnospiracea |
| OTU1699 | 0.053937091 | 0.016015973 | 0.03903795 | 1.381657873 | 0.410266751 | *Lachnoanaerobaculum* |
| OTU1963 | 0.026871627 | 0.015762581 | 0.035098745 | 0.765600792 | 0.449092457 | *Streptococcus* |
| OTU2036 | 0.000158844 | 0 | 0 | Inf | NA | unclassified. Lachnospiracea |
| OTU2176 | 0 | 0 | 8.73E−05 | 0 | 0 | *Bacteroides* |
| OTU2229 | 7.94E−05 | 0 | 0 | Inf | NA | unclassified. Clostridiales |
| OTU2703 | 0.002604229 | 0.017457127 | 0.00690751 | 0.377014141 | 2.527267895 | *Tannerella* |
| OTU3273 | 0.000141417 | 0.000275649 | 0 | Inf | Inf | *Blautia* |

TABLE 22

Relative abundance of OTUs in stool samples

| | mean CRCs [%] | mean Polyps [%] | mean HCs [%] | mean CRCs vs mean HCs | mean Polyps vs mean HCs | Genus |
|---|---|---|---|---|---|---|
| OTU0001 | 3.211285752 | 0.34401564 | 1.300582054 | 2.469114303 | 0.264508986 | *Escherichia*/Shigella |
| OTU0002 | 4.175836992 | 3.545598568 | 5.063276298 | 0.824730223 | 0.70025777 | *Blautia* |
| OTU0003 | 9.151664828 | 8.902380689 | 9.359696463 | 0.977773677 | 0.951139893 | *Faecalibacterium* |
| OTU0006 | 1.333268323 | 0.627345368 | 0.963193385 | 1.384216652 | 0.651318186 | *Ruminococcus 2* |
| OTU0007 | 0.199801213 | 0.149625584 | 0.180862538 | 1.104713091 | 0.827288976 | *Streptococcus* |
| OTU0008 | 3.078229131 | 2.806782731 | 4.863450766 | 0.632931077 | 0.577117538 | *Roseburia* |
| OTU0012 | 1.114557442 | 1.091720631 | 1.272105883 | 0.876151472 | 0.858199499 | *Anaerostipes* |
| OTU0013 | 0.450276595 | 0.555452231 | 0.460551015 | 0.977691026 | 1.206060159 | *Roseburia* |
| OTU0015 | 0.278866337 | 0.54895857 | 0.129638265 | 2.151111306 | 4.234541175 | *Haemophilus* |
| OTU0016 | 0.581993271 | 0.622356315 | 0.602204661 | 0.966437673 | 1.033463131 | *Streptococcus* |
| OTU0018 | 0.757069415 | 0.668514709 | 0.945993355 | 0.800290416 | 0.706680132 | *Gemmiger* |
| OTU0019 | 0.256712085 | 0.029798471 | 0.039640085 | 6.476072996 | 0.751725718 | Clostridium_sensu_stricto |
| OTU0020 | 1.087384521 | 0.570821752 | 0.408902828 | 2.659273666 | 1.395983871 | *Bacteroides* |
| OTU0022 | 0.835166523 | 1.059116276 | 0.465269146 | 1.795018066 | 2.276351839 | *Parabacteroides* |
| OTU0026 | 0.618364346 | 0.501800077 | 0.668496558 | 0.925007525 | 0.750639732 | *Dorea* |
| OTU0029 | 1.520885754 | 0.867867295 | 1.081563377 | 1.406191987 | 0.802419269 | *Bifidobacterium* |
| OTU0030 | 0.182555219 | 0.150549384 | 0.201351818 | 0.906647983 | 0.747693197 | *Coprococcus* |
| OTU0031 | 0.310187135 | 0.227738853 | 0.610341037 | 0.508219366 | 0.373133772 | Clostridium_sensu_stricto |
| OTU0038 | 0.653139136 | 1.995782947 | 0.602149801 | 1.084678821 | 3.314429303 | *Alistipes* |
| OTU0040 | 0.259137869 | 0.54103813 | 0.601163821 | 0.43106032 | 0.899984515 | *Bacteroides* |
| OTU0041 | 0.000332006 | 0.000187553 | 0.00036211 | 0.916866229 | 0.517943611 | *Neisseria* |
| OTU0042 | 0.448024277 | 0.377417849 | 0.861502801 | 0.520049704 | 0.438092423 | Clostridium_XI |
| OTU0045 | 0.34689414 | 0.317517594 | 0.488611418 | 0.709959137 | 0.649836623 | unclassified. Lachnospiracea |
| OTU0049 | 0.211284454 | 0.16199492 | 0.242710465 | 0.870520576 | 0.667441021 | unclassified. Lachnospiracea |
| OTU0050 | 0.083503628 | 0.034405767 | 0.034936539 | 2.390151671 | 0.984807542 | *Veillonella* |
| OTU0054 | 0.54673851 | 0.415548302 | 0.595151863 | 0.918653781 | 0.698222299 | *Bacteroides* |
| OTU0059 | 0.124200227 | 0.451922185 | 0.107747601 | 1.152695988 | 4.194266799 | *Sutterella* |
| OTU0061 | 0.486654589 | 0.202476023 | 0.282635379 | 1.721845972 | 0.71638598 | *Bifidobacterium* |
| OTU0063 | 0.007081712 | 0 | 0.000877345 | 8.071757262 | 0 | *Fusobacterium* |
| OTU0065 | 0.212936858 | 0.152745317 | 0.145510657 | 1.463376372 | 1.049719104 | *Collinsella* |
| OTU0067 | 0.304083389 | 0.205661215 | 0.246332688 | 1.23444189 | 0.834892098 | Clostridium_XIVa |
| OTU0072 | 0.030768287 | 0.002694371 | 0.031227401 | 0.983720428 | 0.086144156 | *Streptococcus* |
| OTU0073 | 0.373495649 | 0.80649422 | 0.909906321 | 0.410477035 | 0.886348628 | unclassified. Firmicute |
| OTU0075 | 0.08654399 | 0.064407714 | 0.103528672 | 0.835942241 | 0.622124411 | Clostridium_XIVa |
| OTU0080 | 0.00136181 | 0.000187553 | 0.001026266 | 1.32695582 | 0.182752344 | *Prevotella* |
| OTU0081 | 0.000311188 | 0.000780275 | 0.000421105 | 0.739115615 | 1.853260971 | *Neisseria* |
| OTU0083 | 0.003805249 | 0 | 0.000871967 | 4.363982035 | 0 | *Gemella* |
| OTU0085 | 0.1374355 | 0.132688115 | 0.098631661 | 1.39342173 | 1.345289265 | *Bilophila* |
| OTU0086 | 0.68191011 | 0.438288097 | 0.184064769 | 3.704729123 | 2.381162346 | *Prevotella* |
| OTU0087 | 0.021244221 | 0.000276066 | 0.001415445 | 15.00886734 | 0.195038479 | *Parvimonas* |
| OTU0089 | 0.581815423 | 1.250251973 | 0.795449505 | 0.731429738 | 1.571755297 | *Barnesiella* |
| OTU0092 | 0.000136652 | 0.000268367 | 0.00240201 | 0.056890761 | 0.111726008 | *Haemophilus* |
| OTU0093 | 0.133015129 | 0.134729439 | 0.117829792 | 1.128875194 | 1.143424232 | Clostridium_IV |
| OTU0095 | 0.001141419 | 0 | 0.000233357 | 4.891305175 | 0 | *Prevotella* |
| OTU0097 | 0.079214441 | 0.002415303 | 0.000726563 | 109.0262668 | 3.324286635 | *Peptostreptococcus* |
| OTU0105 | 0.04769277 | 0.119160782 | 0.055868512 | 0.853661004 | 2.132879104 | Clostridium_IV |
| OTU0109 | 0.144305249 | 0 | 0.000864187 | 166.9837774 | 0 | *Porphyromonas* |
| OTU0112 | 0.106899514 | 0.076292686 | 0.027225364 | 3.926467717 | 2.802265005 | Clostridium_XIVa |
| OTU0114 | 0.125029093 | 0.091648428 | 0.121727407 | 1.027123605 | 0.752898881 | *Parasutterella* |
| OTU0115 | 0.10349916 | 0.112807878 | 0.130129674 | 0.795354021 | 0.86688819 | Clostridium_XIVa |
| OTU0120 | 0.079984848 | 0.103340718 | 0.078176696 | 1.023129037 | 1.321886487 | *Bifidobacterium* |
| OTU0130 | 0.001131747 | 0 | 0.000369923 | 3.059416948 | 0 | *Solobacterium* |
| OTU0134 | 0.309981742 | 0.5020991 | 0.209650153 | 1.478566732 | 2.39493791 | *Phascolarctobacteriu* |

TABLE 22-continued

Relative abundance of OTUs in stool samples

| | mean CRCs [%] | mean Polyps [%] | mean HCs [%] | mean CRCs vs mean HCs | mean Polyps vs mean HCs | Genus |
|---|---|---|---|---|---|---|
| OTU0135 | 0.071745568 | 0.055713794 | 0.079616109 | 0.901143858 | 0.699780414 | Hespellia |
| OTU0141 | 0.000587876 | 0 | 0.000149227 | 3.939478152 | 0 | Aggregatibacter |
| OTU0142 | 0.019361264 | 0 | 0.000200402 | 96.61200739 | 0 | Dialister |
| OTU0148 | 0.053381942 | 0.023531236 | 0.026116639 | 2.043982085 | 0.901005526 | Flavonifractor |
| OTU0149 | 0.36988581 | 0.282628057 | 0.352056523 | 1.050643252 | 0.802791706 | Blautia |
| OTU0155 | 0.088961758 | 0.002998193 | 0.014219803 | 6.256187595 | 0.210846335 | Lactobacillus |
| OTU0157 | 7.51E-05 | 0 | 0.000352207 | 0.213123116 | 0 | Leptotrichia |
| OTU0158 | 0.025674876 | 0.012413642 | 0.019175747 | 1.338924401 | 0.647361578 | Howardella |
| OTU0161 | 1.244420347 | 1.342848847 | 1.41677844 | 0.878345062 | 0.947818522 | unclassified. Lachnospiraceae |
| OTU0167 | 0.009685521 | 0.003403325 | 0.001628561 | 5.947289395 | 2.089774907 | Streptococcus |
| OTU0171 | 0.038868079 | 0.321545487 | 0.001475251 | 26.34674952 | 217.9597918 | Acidaminococcus |
| OTU0173 | 0.08219383 | 0.065674078 | 0.144137571 | 0.5702457 | 0.455634692 | unclassified. Ruminococcacea |
| OTU0174 | 5.48E-05 | 0 | 8.02E-05 | 0.683832905 | 0 | Kingella |
| OTU0175 | 0.000531912 | 0 | 0 | Inf | NA | Aggregatibacter |
| OTU0176 | 0.00080533 | 0.000187553 | 0 | Inf | Inf | Campylobacter |
| OTU0187 | 0.101563868 | 0.207703754 | 0.078402618 | 1.295414231 | 2.6491941 | Paraprevotella |
| OTU0194 | 0.257647979 | 0.712477019 | 0.227053886 | 1.134743753 | 3.137920385 | Bacteroides |
| OTU0206 | 0.028112117 | 0.021201925 | 0.009377139 | 2.997941729 | 2.261022714 | Clostridium_IV |
| OTU0210 | 0.026864361 | 0.024069306 | 0.032637434 | 0.823114992 | 0.737475428 | Eubacterium |
| OTU0228 | 0.041589056 | 0.051993555 | 0.061059304 | 0.681125612 | 0.851525515 | Alistipes |
| OTU0233 | 4.95E-05 | 0 | 0 | Inf | NA | Capnocytophaga |
| OTU0244 | 0 | 0.000375105 | 0.000120294 | 0 | 3.118233105 | Capnocytophaga |
| OTU0251 | 0.025974015 | 0.021145388 | 0.014872633 | 1.746430134 | 1.42176489 | Pseudoflavonifractor |
| OTU0261 | 0.01957638 | 0.027284068 | 0.043765316 | 0.447303521 | 0.623417591 | unclassified. Clostridiales |
| OTU0277 | 0.000160937 | 0.00045592 | 8.67E-05 | 1.855924695 | 5.257664308 | Eikenella |
| OTU0283 | 0 | 0 | 4.76E-05 | 0 | 0 | Tannerella |
| OTU0290 | 5.67E-05 | 0 | 4.08E-05 | 1.390185278 | 0 | Neisseria |
| OTU0299 | 0.000241926 | 0 | 5.14E-05 | 4.710258284 | 0 | Prevotella |
| OTU0306 | 0.015059251 | 0.010074865 | 0.029841655 | 0.504638599 | 0.337610809 | Clostridium_IV |
| OTU0317 | 0.000193568 | 0 | 0.000161394 | 1.199350965 | 0 | Lachnoanaerobaculum |
| OTU0324 | 0.000266354 | 0 | 6.56E-05 | 4.063244483 | 0 | Selenomonas |
| OTU0337 | 1.01E-05 | 0.000562658 | 4.24E-05 | 0.238675675 | 13.28132877 | Cardiobacterium |
| OTU0350 | 0.000171148 | 0 | 4.01E-05 | 4.268230784 | 0 | Actinomyces |
| OTU0351 | 0.00506436 | 0.000995426 | 0.004135951 | 1.224472922 | 0.240676436 | Clostridium_IV |
| OTU0358 | 0.024369741 | 0.016091515 | 0.018882098 | 1.290626738 | 0.852210112 | unclassified. Ruminococcaceae |
| OTU0359 | 0.008778972 | 0.01093994 | 0.007173404 | 1.223822227 | 1.525069509 | Holdemania |
| OTU0361 | 0.025565079 | 0.024395722 | 0.016864571 | 1.515903942 | 1.44656587 | Butyricimonas |
| OTU0362 | 0.00168539 | 0.000237661 | 0.04877449 | 0.034554744 | 0.004872643 | Anaeroplasma |
| OTU0364 | 0.0139379 | 0.009728952 | 0.004047646 | 3.443458056 | 2.40360738 | unclassified. Clostridiales |
| OTU0366 | 0.009568833 | 0.062725317 | 0.024157274 | 0.396105661 | 2.596539566 | unclassified. Clostridiales |
| OTU0369 | 0.011852956 | 0.011008217 | 0.007214923 | 1.642838917 | 1.525756708 | Oscillibacter |
| OTU0371 | 0.004571427 | 0.010172002 | 0.014149646 | 0.323077144 | 0.718887413 | Clostridium_IV |
| OTU0380 | 0.017126685 | 0.000945197 | 0.010860135 | 1.57702317 | 0.087033673 | Slackia |
| OTU0395 | 0.015250711 | 0.010400307 | 0.009094617 | 1.676894301 | 1.1435674 | Anaerotruncus |
| OTU0397 | 1.134424006 | 1.562557072 | 1.081057836 | 1.049364768 | 1.445396369 | Gemmiger |
| OTU0406 | 0.000325833 | 0 | 2.57E-05 | 12.68782802 | 0 | Prevotella |
| OTU0412 | 0.000100023 | 0 | 0 | Inf | NA | Selenomonas |
| OTU0424 | 0.056082448 | 0.020538357 | 0.021358274 | 2.625794972 | 0.961611271 | Veillonella |
| OTU0427 | 0.289420586 | 0.1604246 | 0.294722631 | 0.982010054 | 0.544323994 | Dorea |
| OTU0431 | 7.07E-05 | 0 | 0 | Inf | NA | Prevotella |
| OTU0433 | 0.00029075 | 0 | 0 | Inf | NA | Selenomonas |
| OTU0436 | 0.006391586 | 0.010330345 | 0.011747231 | 0.544092955 | 0.879385551 | unclassified. Ruminococcaceae |
| OTU0458 | 2.88E-05 | 0.000187553 | 0 | Inf | Inf | Lachnoanaerobaculum |
| OTU0472 | 0.003074672 | 0.005677971 | 0.001944143 | 1.581504825 | 2.92055188 | Clostridium_IV |
| OTU0476 | 0.011919376 | 0.006630953 | 0.002922045 | 4.079121751 | 2.269285239 | unclassified. Clostridiales |
| OTU0511 | 0.183066557 | 0.122639369 | 0.016423274 | 11.14677597 | 7.467412936 | unclassified. Porphyromonadacea |
| OTU0512 | 0.002043934 | 0.00933899 | 0.000167215 | 12.22341023 | 55.85028915 | unclassified. Ruminococcaceae |
| OTU0543 | 0.003976309 | 0.006085726 | 0.001561866 | 2.545871073 | 3.896446369 | Clostridium_XIVa |
| OTU0544 | 0.000194717 | 0.00035101 | 0.000260248 | 0.748195827 | 1.348750998 | Abiotrophia |
| OTU0571 | 2.70E-05 | 0 | 0 | Inf | NA | Treponema |
| OTU0588 | 0.00163061 | 0.008128588 | 0.001950584 | 0.835959934 | 4.167258016 | unclassified. Ruminococcaceae |
| OTU0595 | 2.93E-05 | 0 | 0 | Inf | NA | Actinomyces |
| OTU0599 | 0.041036939 | 0.028639768 | 0.138550511 | 0.296187567 | 0.206709944 | unclassified. Lachnospiraceae |
| OTU0618 | 0.005188253 | 0.002683098 | 0.002694146 | 1.925750305 | 0.995899143 | unclassified. Erysipelotrichaceae |
| OTU0657 | 2.02E-05 | 0 | 0 | Inf | NA | unclassified. Candidatus_Saccharibacteri |
| OTU0663 | 0.001074165 | 0.000108335 | 0 | Inf | Inf | Schwartzia |
| OTU0664 | 0.002083273 | 0.001572845 | 0.001646293 | 1.26543298 | 0.955386277 | unclassified. Ruminococcaceae |
| OTU0675 | 0.000359404 | 0.000281855 | 0.000270813 | 1.327128955 | 1.040773519 | Clostridium_IV |
| OTU0707 | 0.001203105 | 0.000581651 | 0.000326579 | 3.68396021 | 1.781040454 | Flavonifractor |
| OTU0726 | 0.028216011 | 0.021670395 | 0.028964577 | 0.974273035 | 0.748258892 | Prevotella |
| OTU0731 | 0.503018832 | 0.140634571 | 0.215620254 | 2.332892314 | 0.652232657 | Clostridium_XIVa |
| OTU0773 | 0.001025112 | 0.00231485 | 0.00054234 | 1.890162842 | 4.268260197 | unclassified. Lachnospiraceae |
| OTU0777 | 1.01E-05 | 0 | 0.00015222 | 0.066425943 | 0 | Leptotrichia |
| OTU0831 | 0.052095577 | 0.011222974 | 0.046565968 | 1.118747847 | 0.241012362 | unclassified. Lachnospiraceae |
| OTU0865 | 0.178720257 | 0.15846198 | 0.175602112 | 1.017756876 | 0.902392222 | Blautia |

TABLE 22-continued

Relative abundance of OTUs in stool samples

| | mean CRCs [%] | mean Polyps [%] | mean HCs [%] | mean CRCs vs mean HCs | mean Polyps vs mean HCs | Genus |
|---|---|---|---|---|---|---|
| OTU0876 | 0.084444502 | 0.126284047 | 0.109797077 | 0.769096083 | 1.150158559 | *Ruminococcus* 2 |
| OTU0892 | 0.012098197 | 0.009701474 | 0.008080342 | 1.497238225 | 1.200626626 | *Clostridium_XIVa* |
| OTU0943 | 0.015684865 | 0.027074831 | 0.007844012 | 1.999597322 | 3.451656039 | *Bacteroides* |
| OTU0951 | 0.010696751 | 0.010602272 | 0.011365795 | 0.94113526 | 0.93282275 | *Clostridium_XIVa* |
| OTU0963 | 0.016682851 | 0.011671709 | 0.017323091 | 0.96304128 | 0.673765997 | unclassified. Clostridiales |
| OTU0976 | 0.031161209 | 0.029718196 | 0.026280874 | 1.185699084 | 1.130791767 | *Clostridium_XIVa* |
| OTU0978 | 0.016335062 | 0.020876105 | 0.016734621 | 0.976123824 | 1.247480059 | *Faecalibacterium* |
| OTU0989 | 0.027170881 | 0.022826651 | 0.033989825 | 0.799382766 | 0.671573074 | unclassified. Lachnospiraceae |
| OTU1011 | 0.102309177 | 0.03725283 | 0.018732957 | 5.461453626 | 1.988625141 | *Prevotella* |
| OTU1080 | 0.052083737 | 0.039545556 | 0.052157535 | 0.99858509 | 0.758194504 | *Blautia* |
| OTU1128 | 0.000335652 | 0.003032164 | 0.002778437 | 0.120805949 | 1.09132001 | unclassified. Clostridiales |
| OTU1175 | 0.071441433 | 0.070904554 | 0.128932737 | 0.554098479 | 0.549934452 | unclassified. Lachnospiraceae |
| OTU1197 | 0.005707031 | 0.002970093 | 0.00259441 | 2.199741041 | 1.144804861 | *Escherichia/Shigella* |
| OTU1239 | 0.014246146 | 0.030872609 | 0.020094669 | 0.708951497 | 1.536358175 | *Bacteroides* |
| OTU1250 | 0 | 0 | 3.61E−05 | 0 | 0 | *Leptotrichia* |
| OTU1254 | 0.01078096 | 0.008252692 | 0.016372673 | 0.658472799 | 0.504052794 | *Blautia* |
| OTU1280 | 0.01927452 | 0.026004349 | 0.021157874 | 0.910985688 | 1.229062463 | unclassified. Lachnospiraceae |
| OTU1292 | 0.009856594 | 0.005342355 | 0.009477227 | 1.040029336 | 0.563704464 | *Coprococcus* |
| OTU1339 | 0.027980812 | 0.027337849 | 0.035566118 | 0.78672661 | 0.768648659 | *Roseburia* |
| OTU1376 | 0.19279916 | 0.130173728 | 0.234391216 | 0.822552838 | 0.555369483 | *Faecalibacterium* |
| OTU1395 | 0.019027113 | 0.010717949 | 0.020710611 | 0.91871328 | 0.51751004 | *Clostridium_XIVa* |
| OTU1487 | 0.069064957 | 0.057925078 | 0.044710297 | 1.544721503 | 1.295564601 | *Clostridium_XIVa* |
| OTU1494 | 0.005886456 | 0.003626207 | 0.005824551 | 1.010628334 | 0.622572793 | *Faecalibacterium* |
| OTU1550 | 0.010870332 | 0.01172642 | 0.019687692 | 0.552138432 | 0.595621892 | *Coprococcus* |
| OTU1571 | 0.000434132 | 0.000740968 | 0.001069421 | 0.405950465 | 0.692868705 | unclassified. Clostridiales |
| OTU1582 | 0.077291415 | 0.08971798 | 0.119937684 | 0.644429776 | 0.748038288 | *Blautia* |
| OTU1584 | 0.098835479 | 0.246980073 | 0.049050465 | 2.014975356 | 5.035223858 | *Parabacteroides* |
| OTU1610 | 0.032786178 | 0.022214653 | 0.036331309 | 0.902422156 | 0.611446543 | *Blautia* |
| OTU1640 | 0.013385861 | 0.016297939 | 0.017706543 | 0.755983899 | 0.920447284 | *Gemmiger* |
| OTU1645 | 0.028328338 | 0.025791792 | 0.019568681 | 1.447636554 | 1.318013851 | unclassified. Lachnospiracea |
| OTU1682 | 0.004556604 | 0.000736751 | 0.002280979 | 1.997653072 | 0.322997635 | *Clostridium_XIVb* |
| OTU1699 | 2.74E−05 | 0.000373941 | 0.000128404 | 0.213548177 | 2.907554918 | *Lachnoanaerobaculum* |
| OTU1999 | 0.001069788 | 0.000788582 | 0.004423592 | 0.24183693 | 0.178267336 | unclassified. Lachnospiraceae |
| OTU2036 | 0.00674278 | 0.01014812 | 0.004812588 | 1.401071466 | 2.10866166 | unclassified. Lachnospiraceae |
| OTU2137 | 0.005119753 | 0.007891097 | 0.001360842 | 3.762196095 | 5.798688243 | *Bacteroides* |
| OTU2176 | 0.049998519 | 0.11234441 | 0.048320697 | 1.03472263 | 2.324974927 | *Bacteroides* |
| OTU2203 | 0.025764052 | 0.015898353 | 0.034564156 | 0.745397995 | 0.459966495 | *Coprococcus* |
| OTU2229 | 0.017181618 | 0.015852027 | 0.04881377 | 0.351983008 | 0.324744992 | unclassified. Clostridiales |
| OTU2397 | 0.000484199 | 0.00202951 | 0.000978857 | 0.49465764 | 2.073345998 | unclassified. Lachnospiracea |
| OTU2689 | 0.000283958 | 0.004932491 | 0.002718366 | 0.104459229 | 1.814505916 | unclassified. Lachnospiracea |
| OTU2738 | 0.031419991 | 0.029016053 | 0.031980899 | 0.982461152 | 0.907293231 | *Ruminococcus* 2 |
| OTU2762 | 0.007048779 | 0.002907344 | 0.011317076 | 0.622684595 | 0.256898903 | *Blautia* |
| OTU2771 | 0.008927642 | 0.003685251 | 0.020994935 | 0.425228359 | 0.175530461 | *Clostridium_XIVa* |
| OTU3092 | 0.012193574 | 0.015422603 | 0.050623835 | 0.240866254 | 0.304651027 | *Ruminococcus* 2 |
| OTU3180 | 0.001901509 | 0.00018667 | 0.000394668 | 4.817995053 | 0.472980396 | *Ruminococcus* 2 |
| OTU3273 | 0.004862317 | 0.005418724 | 0.005751151 | 0.845450984 | 0.942198063 | *Blautia* |
| OTU3755 | 0.012497477 | 0.043346058 | 0.031548937 | 0.396129892 | 1.373930836 | *Blautia* |
| OTU3831 | 0.004059604 | 0.009017368 | 0.007989927 | 0.508090216 | 1.128592001 | *Faecalibacterium* |

The invention claimed is:

1. A method comprising: determining a level of at least one or more bacterial taxa associated with colorectal cancer in a faecal sample and at least one or more bacterial taxa associated with colorectal cancer in an oral cavity sample obtained from a test subject, and comparing the level of the at least one or more bacterial taxa to a reference level derived from a faecal sample and an oral cavity sample obtained from a subject who does not have colorectal cancer; wherein the one or more bacterial taxa associated with the colorectal cancer is selected from the group consisting of: *Prevotella, Parviomonas, Streptococcus*, Leptotrichiaa, *Tannerella*, Lachnospiraceae, *Kingella, Alloprevotella, Lachnoanaerobaculum, Campylobacter, Anaerostipes, Parvimonas, Candidatus, Saccharibacteria, Aggregatibacter, Selenomonas, Schwartzia, Roseburia, Peptostreptococcus, Cardiobacterium,* and *Abiotrophia*, wherein if the level of the one or more bacterial taxa associated with the colorectal cancer in the faecal sample and the sample obtained from the oral cavity of the test subject is higher than the reference level of the one or more bacterial taxa derived from the sample from the subject who does not have colorectal cancer, the test subject is determined to have a positive colorectal cancer status.

2. The method of claim 1, further comprising performing a biopsy on the subject if the level of the bacterial taxon associated with the colorectal cancer in the faecal and oral cavity sample from the test subject is determined to be present at a higher level when compared to the reference level of the bacterial taxon from the sample from the subject who does not have colorectal cancer.

3. The method of claim 1, wherein the determining comprises amplifying a 16s rRNA gene sequence of the bacterial taxon associated with colorectal cancer.

4. The method of claim 1, further comprising administering a pharmaceutical agent selected from the group consisting of Avastin, Bevacizumab, Camptosar, Capacitibine, Cyramza, Oxamiplatin, Erbitux, %-fluorouracil, Irinotecan, Leucovorin calcium, Lonsurf, Panitumumab, Ramucirumab, Regorafenib, Stivarga, Wellcovorin and Xeloda to the test subject if the level of the bacterial taxon associated with colorectal cancer in the faecal sample and the sample obtained from the oral cavity of the test subject is higher when compared to the reference level of the bacterial taxon derived from the sample from the subject who does not have colorectal cancer.

5. The method of claim 1, further comprising assessing a risk of colorectal cancer in the test subject, wherein the assessment of risk is determined by comparing the level of the bacterial taxon associated with colorectal cancer in the faecal sample and the sample obtained from the oral cavity of the test subject against the levels the reference level of the bacterial taxon derived from the sample from the subject who does not have colorectal cancer, wherein the risk of having a positive colorectal cancer status is increased if the level of the bacterial taxon associated with the colorectal cancer in the faecal sample and the sample obtained from the oral cavity of the test subject is higher than the reference level of the bacterial taxon derived from the sample from the subject who does not have colorectal cancer.

6. The method of claim 4, wherein the assessing is performed with a sensitivity of at least 40%.

7. The method of claim 4, wherein the assessing is performed with a specificity of at least 90%.

8. The method of claim 1, wherein the determining further comprises determining a level of at least five faecal bacterial taxa and at least five oral bacterial taxa from the faecal and oral cavity samples, respectively, wherein at least five faecal bacterial taxa are selected from Lachnospiraceae, *Peptostreptococcus, Parabacteroides, Roseburia, Blautia, Clostridium* XIVa, Clostridiales, *Flavonifractor, Escherichia/Shigella, Porphyromonas, Anaerostipes, Faecalibacterium, Coprococcus*, Clostridiales, Firmicutes, *Dialister, Clostridium* IV, *Gemmiger, Collinsella, Bacteroides, Clostridium* sensu stricto, *Fusobacterium, Ruminococcus*, Porphyromonadaceae, *Alistipes, Sutterella, Dorea, Barnesiella, Pseudoflavonifractor, Parasutterella, Haemophilus, Bifidobacterium, Phascolarctobacterium* and *Streptococcus* and the at least five oral bacterial taxa are selected from *Prevotella, Streptococcus, Tannerella, Leptotrichia, Veillonella*, Lachnospiraceae, *Kingella, Alloprevotella, Lachnoanaerobaculum, Campylobacter, Haemophilus, Anaerostipes, Parvimonas, Neisseria, Candidatus, Saccharibacteria, Aggregatibacter, Selenomonas, Schwartzia, Roseburia, Peptostreptococcus, Cardiobacterium, Actinomyces*, and *Abiotrophia*, which are associated with the colorectal cancer.

9. A method comprising: determining a level of at least one bacterial taxon associated with colorectal cancer in a sample obtained by an oral swab from an oral cavity of a test subject and comparing the level of the at least one bacterial taxon to a reference level derived from a sample from a subject who does not have colorectal cancer; wherein the at least one bacterial taxon associated with the colorectal cancer is selected from the group consisting of:

*Prevotella, Parviomonas, Streptococcus*, Leptotrichiaa, *Tannerella*, Lachnospiraceae, *Kingella, Alloprevotella, Lachnoanaerobaculum, Campylobacter, Anaerostipes, Parvimonas, Candidatus, Saccharibacteria, Aggregatibacter, Selenomonas, Schwartzia, Roseburia, Peptostreptococcus, Cardiobacterium,* and *Abiotrophia*, wherein if the level of the at least one bacterial taxon associated with the colorectal cancer in the sample obtained from the oral cavity of the test subject is higher than the reference level of the bacterial taxon derived from the sample from the subject who does not have colorectal cancer, the test subject is determined to have a positive colorectal cancer status.

10. A method comprising: determining a level of at least one bacterial taxon associated with colorectal cancer in a faecal sample obtained from a test subject and determining a level of at least one bacterial taxon associated with colorectal cancer in a sample obtained by an oral swab from an oral cavity of the test subject and comparing the level of the at least one bacterial taxon to a reference bacterial taxon level derived from a sample from a subject who does not have colorectal cancer; wherein the at least one bacterial taxon associated with the colorectal cancer is selected from the group consisting of: *Prevotella, Parviomonas, Streptococcus*, Leptotrichiaa, *Tannerella*, Lachnospiraceae, *Kingella, Alloprevotella, Lachnoanaerobaculum, Campylobacter, Anaerostipes, Parvimonas, Candidatus, Saccharibacteria, Aggregatibacter, Selenomonas, Schwartzia, Roseburia, Peptostreptococcus, Cardiobacterium,* and *Abiotrophia*, wherein if the level of the at least one bacterial taxon associated with the colorectal cancer in the faecal sample and in the sample obtained from the oral cavity of the test subject is higher than the reference level of the bacterial taxon derived from the sample from the subject who does not have colorectal cancer, the test subject is determined to have a positive colorectal polyp status.

\* \* \* \* \*

SEQUENCE LISTING

<160> NUMBER OF SEQ ID NOS: 326

<210> SEQ ID NO 1
<211> LENGTH: 427
<212> TYPE: DNA
<213> ORGANISM: Escherichia sp.

<400> SEQUENCE: 1

```
tggggaatat tgcacaatgg gcgcaagcct gatgcagcca tgccgcgtgt atgaagaagg    60
ccttcgggtt gtaaagtact ttcagcgggg aggaagggag taaagttaat acctttgctc   120
attgacgtta cccgcagaag aagcaccggc taactccgtg ccagcagccg cggtaatacg   180
gagggtgcaa gcgttaatcg gaattactgg gcgtaaagcg cacgcaggcg gtttgttaag   240
tcagatgtga aatccccggg ctcaacctgg gaactgcatc tgatactggc aagcttgagt   300
```

```
ctcgtagagg ggggtagaat tccaggtgta gcggtgaaat gcgtagagat ctggaggaat    360
accggtggcg aaggcggccc cctggacgaa gactgacgct caggtgcgaa agcgtgggga    420
gcaaaca                                                             427
```

<210> SEQ ID NO 2
<211> LENGTH: 402
<212> TYPE: DNA
<213> ORGANISM: Blautia sp.

<400> SEQUENCE: 2

```
tggggaatat tgcacaatgg gggaaaccct gatgcagcga cgccgcgtga aggaagaagt     60
atctcggtat gtaaacttct atcagcaggg aagatagtga cggtacctga ctaagaagcc    120
ccggctaact acgtgccagc agccgcggta atacgtaggg ggcaagcgtt atccggattt    180
actgggtgta aagggagcgt agacggtgtg gcaagtctga tgtgaaaggc atgggctcaa    240
cctgtggact gcattggaaa ctgtcatact tgagtgccgg aggggtaagc ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 3
<211> LENGTH: 402
<212> TYPE: DNA
<213> ORGANISM: Faecalibacterium sp.

<400> SEQUENCE: 3

```
tggggaatat tgcacaatgg gggaaaccct gatgcagcga cgccgcgtgg aggaagaagg     60
tcttcggatt gtaaactcct gttgttgagg aagataatga cggtactcaa caaggaagtg    120
acggctaact acgtgccagc agccgcggta aaacgtaggt cacaagcgtt gtccggaatt    180
actgggtgta aagggagcgc aggcgggaag acaagttgga agtgaaatct atgggctcaa    240
cccataaact gctttcaaaa ctgttttttct tgagtagtgc agaggtaggc ggaattcccg    300
gtgtagcggt ggaatgcgta gatatcggga ggaacaccag tggcgaaggc ggcctactgg    360
gcaccaactg acgctgaggc tcgaaagtgt gggtagcaaa ca                       402
```

<210> SEQ ID NO 4
<211> LENGTH: 402
<212> TYPE: DNA
<213> ORGANISM: Ruminococcus sp.

<400> SEQUENCE: 4

```
tggggaatat tgcacaatgg gggaaaccct gatgcagcga cgccgcgtga gcgatgaagt     60
atttcggtat gtaaagctct atcagcaggg aagaaaatga cggtacctga ctaagaagca    120
ccggctaaat acgtgccagc agccgcggta atacgtatgg tgcaagcgtt atccggattt    180
actgggtgta aagggagcgt agacggagtg gcaagtctga tgtgaaaacc cggggctcaa    240 cccccgggact gcattggaaa ctgtcaatct agagtaccgg agaggtaagc ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 5
<211> LENGTH: 427
<212> TYPE: DNA
<213> ORGANISM: Streptococcus sp.

<400> SEQUENCE: 5

```
tagggaatct tcggcaatgg acggaagtct gaccgagcaa cgccgcgtga gtgaagaagg    60
ttttcggatc gtaaagctct gttgtaagag aagaacgagt gtgagagtgg aaagttcaca   120
ctgtgacggt atcttaccag aaagggacgg ctaactacgt gccagcagcc gcggtaatac   180
gtaggtcccg agcgttgtcc ggatttattg ggcgtaaagc gagcgcaggc ggttagataa   240
gtctgaagtt aaaggctgtg gcttaaccat agtacgcttt ggaaactgtt taacttgagt   300
gcaagagggg agagtggaat tccatgtgta gcggtgaaat gcgtagatat atggaggaac   360
accggtggcg aaagcggctc tctggcttgt aactgacgct gaggctcgaa agcgtgggga   420
gcaaaca                                                             427
```

<210> SEQ ID NO 6
<211> LENGTH: 402
<212> TYPE: DNA
<213> ORGANISM: Roseburia sp.

<400> SEQUENCE: 6

```
tggggaatat tgcacaatgg gcgaaagcct gatgcagcga cgccgcgtga gcgaagaagt    60
atttcggtat gtaaagctct atcagcaggg aagataatga cggtacctga ctaagaagca   120
ccggctaaat acgtgccagc agccgcggta atacgtatgg tgcaagcgtt atccggattt   180
actgggtgta aagggagcgc aggcggtgcg gcaagtctga tgtgaaagcc cggggctcaa   240
ccccggtact gcattggaaa ctgtcgtact agagtgtcgg aggggtaagc ggaattccta   300
gtgtagcggt gaaatgcgta gatattagga ggaacaccag tggcgaaggc ggcttactgg   360
acgataactg acgctgaggc tcgaaagcgt ggggagcaaa ca                      402
```

<210> SEQ ID NO 7
<211> LENGTH: 402
<212> TYPE: DNA
<213> ORGANISM: Anaerostipes sp.

<400> SEQUENCE: 7

```
tggggaatat tgcacaatgg gggaaaccct gatgcagcga cgccgcgtga gtgaagaagt    60
atctcggtat gtaaagctct atcagcaggg aagaaaatga cggtacctga ctaagaagcc   120
ccggctaact acgtgccagc agccgcggta atacgtaggg ggcaagcgtt atccggaatt   180
actgggtgta aagggtgcgt aggtggtatg gcaagtcaga agtgaaaacc cagggcttaa   240
ctctgggact gcttttgaaa ctgtcagact ggagtgcagg agaggtaagc ggaattccta   300
gtgtagcggt gaaatgcgta gatattagga ggaacatcag tggcgaaggc ggcttactgg   360
actgaaactg acactgaggc acgaaagcgt ggggagcaaa ca                      402
```

<210> SEQ ID NO 8
<211> LENGTH: 404
<212> TYPE: DNA
<213> ORGANISM: Roseburia sp.

<400> SEQUENCE: 8

```
tggggaatat tgcacaatgg gggaaaccct gatgcagcga cgccgcgtga gcgaagaagt    60
atttcggtat gtaaagctct atcagcaggg aagaagaaat gacggtacct gactaagaag   120
caccggctaa atacgtgcca gcagccgcgg taatacgtat ggtgcaagcg ttatccggat   180
ttactgggtg taaagggagc gcaggcggaa ggctaagtct gatgtgaaag cccgggctc   240 aaccccggta ctgcattgga aactggtcat ctagagtgtc ggagggtaa gtggaattcc   300
```

```
tagtgtagcg gtgaaatgcg tagatattag gaggaacacc agtggcgaag gcggcttact    360
ggacgataac tgacgctgag gctcgaaagc gtggggagca aaca                      404
```

<210> SEQ ID NO 9
<211> LENGTH: 427
<212> TYPE: DNA
<213> ORGANISM: Haemophilus sp.

<400> SEQUENCE: 9

```
tggggaatat tgcgcaatgg gggcaaccct gacgcagcca tgccgcgtga atgaagaagg     60
ccttcgggtt gtaaagttct ttcggtagcg aggaaggcat ttagtttaat agactaggtg    120
attgacgtta actacagaag aagcaccggc taactccgtg ccagcagccg cggtaatacg    180
gagggtgcga gcgttaatcg gaataactgg gcgtaaaggg cacgcaggcg gtgacttaag    240
tgaggtgtga agccccgggg cttaacctgg gaattgcatt tcatactggg tcgctagagt    300
actttaggga ggggtagaat tccacgtgta gcggtgaaat gcgtagagat gtggaggaat    360
accgaaggcg aaggcagccc cttgggaatg tactgacgct catgtgcgaa agcgtgggga    420
gcaaaca                                                              427
```

<210> SEQ ID NO 10
<211> LENGTH: 427
<212> TYPE: DNA
<213> ORGANISM: Streptococcus sp.

<400> SEQUENCE: 10

```
tagggaatct tcggcaatgg gggcaaccct gaccgagcaa cgccgcgtga gtgaagaagg     60
ttttcggatc gtaaagctct gttgtaagtc aagaacgagt gtgagagtgg aaagttcaca    120
ctgtgacggt agcttaccag aaagggacgg ctaactacgt gccagcagcc gcggtaatac    180
gtaggtcccg agcgttgtcc ggatttattg ggcgtaaagc gagcgcaggc ggtttgataa    240
gtctgaagtt aaaggctgtg gctcaaccat agttcgcttt ggaaactgtc aaacttgagt    300
gcagaagggg agagtggaat tccatgtgta gcggtgaaat gcgtagatat atggaggaac    360
accggtggcg aaagcggctc tctggtctgt aactgacgct gaggctcgaa agcgtgggga    420
gcgaaca                                                              427
```

<210> SEQ ID NO 11
<211> LENGTH: 402
<212> TYPE: DNA
<213> ORGANISM: Gemmiger sp.

<400> SEQUENCE: 11

```
tgggggatat tgcacaatgg gggaaaccct gatgcagcga cgccgcgtgg aggaagaagg     60
ttttcggatt gtaaactcct gtcgttaggg acgataatga cggtacctaa caagaaagca    120
ccggctaact acgtgccagc agccgcggta aaacgtaggg tgcaagcgtt gtccggaatt    180
actgggtgta aagggagcgc aggcggaccg gcaagttgga agtgaaaact atgggctcaa    240
cccataaatt gctttcaaaa ctgctggcct tgagtagtgc agaggtaggt ggaattcccg    300
gtgtagcggt ggaatgcgta gatatcggga ggaacaccag tggcgaaggc gacctactgg    360
gcaccaactg acgctgaggc tcgaaagcat gggtagcaaa ca                        402
```

<210> SEQ ID NO 12
<211> LENGTH: 402
<212> TYPE: DNA
<213> ORGANISM: Clostridium sp.

```
<400> SEQUENCE: 12
tggggaatat tgcacaatgg gggaaaccct gatgcagcaa cgccgcgtga gtgatgaagg      60
ttttcggatc gtaaagctct gtctttgggg aagataatga cggtacccaa ggaggaagcc     120
acggctaact acgtgccagc agccgcggta atacgtaggt ggcgagcgtt atccggattt     180
actgggcgta aagggagcgt aggcggatga ttaagtggga tgtgaaatac ccgggctcaa     240
cttgggtgct gcattccaaa ctggttatct agagtgcagg agaggagagt ggaattccta     300
gtgtagcggt gaaatgcgta gagattagga agaacaccag tggcgaaggc gactctctgg     360
actgtaactg acgctgaggc tcgaaagcgt ggggagcaaa ca                        402

<210> SEQ ID NO 13
<211> LENGTH: 422
<212> TYPE: DNA
<213> ORGANISM: Bacteroides sp.

<400> SEQUENCE: 13
tgaggaatat tggtcaatgg gcgcaggcct gaaccagcca gtagcgtgaa ggatgactg       60 ccctatgggt tgtaaacttc ttttatatgg gaataaagtt ttccacgtgt ggaattttgt     120
atgtaccata tgaataagga tcggctaact ccgtgccagc agccgcggta atacggagga     180
tccgagcgtt atccggattt attgggttta aagggagcgt aggtggacag ttaagtcagt     240
tgtgaaagtt tgcggctcaa ccgtaaaatt gcagttgata ctggctgtct tgagtacagt     300
agaggtgggc ggaattcgtg gtgtagcggt gaaatgctta gatatcacga agaactccga     360
ttgcgaaggc agctcactgg actgcaactg acactgatgc tcgaaagtgt gggtatcaaa     420
ca                                                                    422

<210> SEQ ID NO 14
<211> LENGTH: 422
<212> TYPE: DNA
<213> ORGANISM: Parabacteroides sp.

<400> SEQUENCE: 14
tgaggaatat tggtcaatgg ccgagaggct gaaccagcca gtcgcgtgaa ggaagaagg       60 atctatggtt tgtaaacttc ttttataggg gaataaagtg gaggacgtgt ccttttttgt     120
atgtacccta tgaataagca tcggctaact ccgtgccagc agccgcggta atacggagga     180
tgcgagcgtt atccggattt attgggttta aagggtgcgt aggtggtgat ttaagtcagc     240
ggtgaaagtt tgtggctcaa ccataaaatt gccgttgaaa ctgggttact tgagtgtgtt     300
tgaggtaggc ggaatgcgtg gtgtagcggt gaaatgcata gatatcacgc agaactccga     360
ttgcgaaggc agcttactaa accataactg acactgaagc acgaaagcgt ggggatcaaa     420
ca                                                                    422

<210> SEQ ID NO 15
<211> LENGTH: 402
<212> TYPE: DNA
<213> ORGANISM: Dorea sp.

<400> SEQUENCE: 15
tggggaatat tgcacaatgg aggaaactct gatgcagcga cgccgcgtga aggatgaagt      60
atttcggtat gtaaacttct atcagcaggg aagaaaatga cggtacctga ctaagaagcc     120
ccggctaact acgtgccagc agccgcggta atacgtaggg ggcaagcgtt atccggattt     180
```

```
actgggtgta aagggagcgt agacggcacg gcaagccaga tgtgaaagcc cggggctcaa      240
ccccgggact gcatttggaa ctgctgagct agagtgtcgg agaggcaagt ggaattccta      300
gtgtagcggt gaaatgcgta gatattagga ggaacaccag tggcgaaggc ggcttgctgg      360
acgatgactg acgttgaggc tcgaaagcgt ggggagcaaa ca                        402
```

```
<210> SEQ ID NO 16
<211> LENGTH: 411
<212> TYPE: DNA
<213> ORGANISM: Bifidobacterium sp.

<400> SEQUENCE: 16 tgggaatat tgcacaatgg gcgcaagcct gatgcagcga cgccgcgtgc gggatgacgg      60
ccttcgggtt gtaaaccgct tttgactggg agcaagccct cgggggtgag tgtacctttc     120
gaataagcac cggctaacta cgtgccagca gccgcggtaa tacgtagggt gcaagcgtta     180
tccggaatta ttgggcgtaa agggctcgta ggcggttcgt cgcgtccggt gtgaaagtcc     240
atcgcttaac ggtggatccg cgccgggtac gggcgggctt gagtgcggta ggggagactg     300
gaattcccgg tgtaacggtg gaatgtgtag atatcgggaa gaacaccaat ggcgaaggca     360
ggtctctggg ccgtcactga cgctgaggag cgaaagcgtg gggagcgaac a              411
```

```
<210> SEQ ID NO 17
<211> LENGTH: 402
<212> TYPE: DNA
<213> ORGANISM: Coprococcus sp.

<400> SEQUENCE: 17 tgggaatat tgcacaatgg gggaaaccct gatgcagcga cgccgcgtga aggaagaagt      60
atctcggtat gtaaacttct atcagcaggg aagataatga cggtacctga ctaagaagcc     120
ccggctaact acgtgccagc agccgcggta atacgtaggg ggcaagcgtt atccggattt     180
actgggtgta aagggagcgt aggcggcgga gcaagtcaga agtgaaagcc cggggctcaa     240
ccccgggacg gcttttgaaa ctgccctgct tgatttcagg agaggtaagc ggaattccta     300
gtgtagcggt gaaatgcgta gatattagga ggaacaccag tggcgaaggc ggcttactgg     360
actgacaatg acgctgaggc tcgaaagcgt ggggagcaaa ca                        402
```

```
<210> SEQ ID NO 18
<211> LENGTH: 402
<212> TYPE: DNA
<213> ORGANISM: Clostridium sp.

<400> SEQUENCE: 18 tgggaatat tgcacaatgg gggaaaccct gatgcagcaa cgccgcgtga gtgatgacgg      60
ccttcgggtt gtaaagctct gtcttcaggg acgataatga cggtacctga ggaggaagcc     120
acggctaact acgtgccagc agccgcggta atacgtaggt ggcgagcgtt gtccggattt     180
actgggcgta aagggagcgt aggcggactt ttaagtgaga tgtgaaatac ccgggctcaa     240
cttgggtgct gcatttcaaa ctggaagtct agagtgcagg agaggagaat ggaattccta     300
gtgtagcggt gaaatgcgta gagattagga agaacaccag tggcgaaggc gattctctgg     360
actgtaactg acgctgaggc tcgaaagcgt ggggagcaaa ca                        402
```

```
<210> SEQ ID NO 19
<211> LENGTH: 422
<212> TYPE: DNA
<213> ORGANISM: Alistipes sp.
```

<400> SEQUENCE: 19

```
tgaggaatat tggtcaatgg acgcaagtct gaaccagcca tgccgcgtgc aggaagacgg      60
ctctatgagt tgtaaactgc ttttgtacga gggtaaactc acctacgtgt aggtgactga     120
aagtatcgta cgataagga tcggctaact ccgtgccagc agccgcggta atacggagga     180
ttcaagcgtt atccggattt attgggttta aagggtgcgt aggcggtttg ataagttaga     240
ggtgaaatcc cggggcttaa ctccggaact gcctctaata ctgttagact agagagtagt     300
tgcggtaggc ggaatgtatg gtgtagcggt gaaatgctta gagatcatac agaacaccga     360
ttgcgaaggc agcttaccaa actatatctg acgttgaggc acgaaagcgt ggggagcaaa     420
ca                                                                    422
```

<210> SEQ ID NO 20
<211> LENGTH: 422
<212> TYPE: DNA
<213> ORGANISM: Bacteroides sp.

<400> SEQUENCE: 20

```
tgaggaatat tggtcaatgg acgagagtct gaaccagcca agtagcgtga aggatgaagg      60
ttctatggat tgtaaacttc ttttatacgg gaataaacga atccacgtgt ggattttgc     120
atgtaccgta tgaataagga tcggctaact ccgtgccagc agccgcggta atacggagga     180
tccgagcgtt atccggattt attgggttta aagggagcgt agatgggttg ttaagtcagt     240
tgtgaaagtt tgcggctcaa ccgtaaaatt gcaattgata ctggcagtct tgagtacagt     300
tgaggtaggc ggaattcgtg gtgtagcggt gaaatgctta gatatcacga agaactccga     360
ttgcgaaggc agcttactaa cctgtaactg acattgatgc tcgaaagtgt gggtatcaaa     420
ca                                                                    422
```

<210> SEQ ID NO 21
<211> LENGTH: 427
<212> TYPE: DNA
<213> ORGANISM: Neisseria sp.

<400> SEQUENCE: 21

```
tggggaattt tggacaatgg gcgcaagcct gatccagcca tgccgcgtgt ctgaagaagg      60
ccttcgggtt gtaaaggact tttgtcaggg aagaaaaggg cggggttaat accctgtct     120
gatgacggta cctgaagaat aagcaccggc taactacgtg ccagcagccg cggtaatacg     180
tagggtgcga gcgttaatcg gaattactgg gcgtaaagcg ggcgcagacg gttacttaag     240
caggatgtga aatccccggg ctcaacctgg gaactgcgtt ctgaactggg tgactagagt     300
gtgtcagagg gaggtagaat tccacgtgta gcagtgaaat gcgtagagat gtggaggaat     360
accgatggcg aaggcagcct cctgggataa cactgacgtt catgcccgaa agcgtgggta     420
gcaaaca                                                               427
```

<210> SEQ ID NO 22
<211> LENGTH: 401
<212> TYPE: DNA
<213> ORGANISM: Clostridium sp.

<400> SEQUENCE: 22

```
tggggaatat tgcacaatgg gcgaaagcct gatgcagcaa cgccgcgtga gcgatgaagg      60
ccttcgggtc gtaaagctct gtcctcaagg aagataatga cggtacttga ggaggaagcc     120
```

```
ccggctaact acgtgccagc agccgcggta atacgtaggg ggctagcgtt atccggaatt    180
actgggcgta aagggtgcgt aggtggtttc ttaagtcaga ggtgaaaggc tacggctcaa    240
ccgtagtaag cctttgaaac tgggaaactt gagtgcagga gaggagagtg gaattcctag    300
tgtagcggtg aaatgcgtag atattaggag gaacaccagt tgcgaaggcg gctctctgga    360
ctgtaactga cactgaggca cgaaagcgtg gggagcaaac a                        401
```

<210> SEQ ID NO 23
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 23

```
tggggaatat tgcacaatgg aggaaactct gatgcagcga cgccgcgtga gtgaagaagt     60
atttcggtat gtaaagctct atcagcaggg aagaaaatga cggtacctga ctaagaagca    120
ccggctaaat acgtgccagc agccgcggta atacgtatgg tgcaagcgtt atccggattt    180
actgggtgta aagggagcgt aggtggcaag gcaagccaga agtgaaaacc cggggctcaa    240
ccgcgggatt gcttttggaa ctgtcatgct agagtgcagg aggggtgagc ggaattccta    300
gtgtagcggt gaaatgcgta gatattagga ggaacaccgg aggcgaaggc ggctcactgg    360
actgtaactg acactgaggc tcgaaagcgt ggggagcaaa ca                       402
```

<210> SEQ ID NO 24
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 24

```
tggggaatat tgcacaatgg gggaaaccct gatgcagcga cgccgcgtga gcgatgaagt     60
atttcggtat gtaaagctct atcagcaggg aagataatga cggtacctga ctaagaagct    120
ccggctaaat acgtgccagc agccgcggta atacgtatgg agcaagcgtt atccggattt    180
actgggtgta aagggagcgt aggcggtcct gcaagtctga tgtgaaaggc cggggctcaa    240
ccccgggact gcattggaaa ctgtaggact agagtgtcgg aggggtaagt ggaattccta    300
gtgtagcggt gaaatgcgta gatattagga ggaacaccag tggcgaaggc ggcttactgg    360
acgactactg acgctgaggc tcgaaagcgt ggggagcaaa ca                       402
```

<210> SEQ ID NO 25
<211> LENGTH: 427
<212> TYPE: DNA
<213> ORGANISM: Veillonella sp.

<400> SEQUENCE: 25

```
tggggaatct tccgcaatgg acgaaagtct gacggagcaa cgccgcgtga gtgatgacgg     60
ccttcgggtt gtaaagctct gttaatcggg acgaaaggcc ttcttgcgaa tagtgagaag    120
gattgacggt accggaatag aaagccacgc taactacgt gccagcagcc gcggtaatac    180
gtaggtggca agcgttgtcc ggaattattg ggcgtaaagc gcgcgcaggc ggataggtca    240
gtctgtctta aaagttcggg gcttaacccc gtgatgggat ggaaactgcc aatctagagt    300
```

-continued

| | |
|---|---|
| atcggagagg aaagtggaat tcctagtgta gcggtgaaat gcgtagatat taggaagaac | 360 |
| accagtggcg aaggcgactt tctggacgaa aactgacgct gaggcgcgaa agccagggga | 420 |
| gcgaacg | 427 |

<210> SEQ ID NO 26
<211> LENGTH: 422
<212> TYPE: DNA
<213> ORGANISM: Bacteroides sp.

<400> SEQUENCE: 26

| | |
|---|---|
| tgaggaatat tggtcaatgg acgagagtct gaaccagcca agtagcgtga aggatgactg | 60 |
| ccctatgggt tgtaaacttc ttttatacgg gaataaagtg agccacgtgt ggcttttttgt | 120 |
| atgtaccgta tgaataagga tcggctaact ccgtgccagc agccgcggta atacggagga | 180 |
| tccgagcgtt atccggattt attgggttta aagggagcgt aggcgggttg ttaagtcagt | 240 |
| tgtgaaagtt tgcggctcaa ccgtaaaatt gcagttgata ctggcgacct tgagtgcaac | 300 |
| agaggtaggc ggaattcgtg gtgtagcggt gaaatgctta gatatcacga agaactccga | 360 |
| ttgcgaaggc agcttactgg attgtaactg acgctgatgc tcgaaagtgt gggtatcaaa | 420 |
| ca | 422 |

<210> SEQ ID NO 27
<211> LENGTH: 427
<212> TYPE: DNA
<213> ORGANISM: Sutterella sp.

<400> SEQUENCE: 27

| | |
|---|---|
| tggggaattt tggacaatgg gggcaaccct gatccagcca tgccgcgtgc aggatgaagg | 60 |
| tcttcggatt gtaaactgct tttgtcaggg acgaaaaggg atgcgataac accgcattcc | 120 |
| gctgacggta cctgaagaat aagcaccggc taactacgtg ccagcagccg cggtaatacg | 180 |
| tagggtgcaa gcgttaatcg gaattactgg gcgtaaagcg tgcgcaggcg gttctgtaag | 240 |
| atagatgtga aatccccggg ctcaacctgg gaattgcata tatgactgca ggacttgagt | 300 |
| ttgtcagagg agggtggaat tccacgtgta gcagtgaaat gcgtagatat gtggaagaac | 360 |
| accgatggcg aaggcagccc tctgggacat gactgacgct catgcacgaa agcgtgggga | 420 |
| gcaaaca | 427 |

<210> SEQ ID NO 28
<211> LENGTH: 407
<212> TYPE: DNA
<213> ORGANISM: Bifidobacterium sp.

<400> SEQUENCE: 28

| | |
|---|---|
| tggggaatat tgcacaatgg gcgcaagcct gatgcagcga cgccgcgtga gggatggagg | 60 |
| ccttcgggtt gtaaacctct tttatcgggg agcaagcgag agtgagttta cccgttgaat | 120 |
| aagcaccggc taactacgtg ccagcagccg cggtaatacg tagggtgcaa gcgttatccg | 180 |
| gaattattgg gcgtaaaggg ctcgtaggcg gttcgtcgcg tccggtgtga aagtccatcg | 240 |
| cttaacggtg gatccgcgcc gggtacgggc gggcttgagt gcggtagggg agactggaat | 300 |
| tcccggtgta acgtggaat gtgtagatat cgggaagaac accaatggcg aaggcaggtc | 360 |
| tctgggccgt tactgacgct gaggagcgaa agcgtgggga gcgaaca | 407 |

<210> SEQ ID NO 29

```
<211> LENGTH: 405
<212> TYPE: DNA
<213> ORGANISM: Fusobacterium sp.

<400> SEQUENCE: 29
tggggaatat tggacaatgg accgagagtc tgatccagca attctgtgtg cacgatgaag      60
tttttcggaa tgtaaagtgc tttcagttgg gaagaaataa atgacggtac caacagaaga     120
agtgacggct aaatacgtgc cagcagccgc ggtaatacgt atgtcacgag cgttatccgg     180
atttattggg cgtaaagcgc gtctaggtgg ttatgtaagt ctgatgtgaa aatgcagggc     240
tcaactctgt attgcgttgg aaactgtgta actagagtac tggagaggta agcggaacta     300
caagtgtaga ggtgaaattc gtagatattt gtaggaatgc cgatgggaa gccagcttac      360 tggacagata ctgacgctaa agcgcgaaag cgtgggtagc aaaca                    405

<210> SEQ ID NO 30
<211> LENGTH: 403
<212> TYPE: DNA
<213> ORGANISM: Collinsella sp.

<400> SEQUENCE: 30
tggggaatct tgcgcaatgg ggggaaccct gacgcagcga cgccgcgtgc gggacggagg      60
ccttcgggtc gtaaaccgct ttcagcaggg aagagtcaag actgtacctg cagaagaagc     120
cccggctaac tacgtgccag cagccgcggt aatacgtagg gggcgagcgt tatccggatt     180
cattgggcgt aaagcgcgcg taggcggccc ggcaggccgg ggtcgaagc ggggggctca      240 acccccgaa gccccggaa cctccgcggc ttgggtccgg taggggaggg tggaacaccc       300
ggtgtagcgg tggaatgcgc agatatcggg tggaacaccg gtggcgaagg cggccctctg     360
ggccgagacc gacgctgagg cgcgaaagct gggggagcga aca                      403

<210> SEQ ID NO 31
<211> LENGTH: 402
<212> TYPE: DNA
<213> ORGANISM: Clostridium sp.

<400> SEQUENCE: 31
tggggaatat tgcacaatgg gggaaaccct gatgcagcga cgccgcgtga gtgaagaagt      60
atttcggtat gtaaagctct atcagcaggg aagaaagtga cggtacctga ataagaagcc     120
ccggctaact acgtgccagc agccgcggta atacgtaggg ggcaagcgtt atccggattt     180
actgggtgta aagggagcgt agacggcaag gcaagtctga agtgaaagcc cggtgcttaa     240
cgccgggact gctttggaaa ctgtttggct ggagtgccgg agaggtaagc ggaattccta     300
gtgtagcggt gaaatgcgta gatattagga agaacaccag tggcgaaggc ggcttactgg     360
acggtaactg acgttgaggc tcgaaagcgt ggggagcaaa ca                       402

<210> SEQ ID NO 32
<211> LENGTH: 427
<212> TYPE: DNA
<213> ORGANISM: Streptococcus sp.

<400> SEQUENCE: 32
tagggaatct tcggcaatgg acgaaagtct gaccgagcaa cgccgcgtga gtgaagaagg      60
ttttcggatc gtaaagctct gttgtaagtc aagaacgtgt gtgagagtgg aaagttcaca     120
cagtgacggt agcttaccag aaagggacgg ctaactacgt gccagcagcc gcggtaatac     180
gtaggtcccg agcgttgtcc ggatttattg ggcgtaaagg gagcgcaggc ggtcaggaaa     240
```

```
gtctggagta aaaggctatg gctcaaccat agtgtgctct ggaaactgtc tgacttgagt    300
gcagaagggg agagtggaat tccatgtgta gcggtgaaat gcgtagatat atggaggaac    360
accagtggcg aaagcggctc tctggtctgt cactgacgct gaggctcgaa agcgtgggta    420
gcgaaca                                                              427
```

```
<210> SEQ ID NO 33
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      unclassified.Firmicutes"

<400> SEQUENCE: 33
```

```
tggggaatat tgggcaatgg aggaaactct gacccagcaa cgccgcgtgg aggaagaagg     60
ttttcggatc gtaaactcct gtccttggag acgagtagaa gacggtatcc aaggaggaag    120
ccccggctaa ctacgtgcca gcagccgcgg taatacgtag ggggcaagcg ttgtccggaa    180
taattgggcg taaagggcgc gtaggcggct cggtaagtct ggagtgaaag tcctgctttt    240
aaggtgggaa ttgctttgga tactgtcggg cttgagtgca ggagaggtta gtggaattcc    300
cagtgtagcg gtgaaatgcg tagagattgg gaggaacacc agtggcgaag gcgactaact    360
ggactgtaac tgacgctgag gcgcgaaagt gtgggagca aaca                      404
```

```
<210> SEQ ID NO 34
<211> LENGTH: 402
<212> TYPE: DNA
<213> ORGANISM: Clostridium sp.

<400> SEQUENCE: 34
```

```
tggggaatat tgcacaatgg gggaaaccct gatgcagcaa cgccgcgtga gtgaagaagt     60
atttcggtat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggcgag acaagtctga agtgaaagcc cggggctcaa    240
ccccgggact gctttggaaa ctgccttgct agagtgctgg agaggtaagt ggaattccta    300
gtgtagcggt gaaatgcgta gatattagga ggaacaccag tggcgaaggc ggcttactgg    360
acagtaactg acgttgaggc tcgaaagcgt ggggagcaaa ca                        402
```

```
<210> SEQ ID NO 35
<211> LENGTH: 422
<212> TYPE: DNA
<213> ORGANISM: Prevotella sp.

<400> SEQUENCE: 35
```

```
tgaggaatat tggtcaatgg acggaagtct gaaccagcca agtagcgtgc aggatgacgg     60
ccctatgggt tgtaaactgc ttttgtatgg ggataaagtt agggacgtgt ccctatttgc    120
aggtaccata cgaataagga ccggctaatt ccgtgccagc agccgcggta atacggaagg    180
tccaggcgtt atccggattt attgggttta aaggagcgta ggctggaga ttaagtgtgt    240 tgtgaaatgt agacgctcaa cgtctgaatt gcagcgcata ctggtttcct tgagtacgca    300
caacgttggc ggaattcgtc gtgtagcggt gaaatgctta gatatgacga agaactccga    360
ttgcgaaggc agctgacggg agcgcaactg acgcttaagc tcgaaggtgc gggtatcaaa    420
```

```
ca                                                                           422

<210> SEQ ID NO 36
<211> LENGTH: 427
<212> TYPE: DNA
<213> ORGANISM: Neisseria sp.

<400> SEQUENCE: 36
tggggaattt tggacaatgg gcgcaagcct gatccagcca tgccgcgtgt ctgaagaagg    60
ccttcgggtt gtaaaggact tttgtcaggg aagaaaaggc tgttgctaat atcgacagct   120
gatgacggta cctgaagaat aagcaccggc taactacgtg ccagcagccg cggtaatacg   180
tagggtgcga gcgttaatcg gaattactgg gcgtaaagcg agcgcagacg gttacttaag   240
caggatgtga atccccggg ctcaacctgg gaactgcgtt ctgaactggg tgactagagt    300
gtgtcagagg gaggtagaat tccacgtgta gcagtgaaat gcgtagagat gtggaggaat   360
accgatggcg aaggcagcct cctgggataa cactgacgtt catgctcgaa agcgtgggta   420
gcaaaca                                                             427

<210> SEQ ID NO 37
<211> LENGTH: 427
<212> TYPE: DNA
<213> ORGANISM: Gemella sp.

<400> SEQUENCE: 37
tagggaatct tccgcaatgg gcgaaagcct gacggagcaa cgccgcgtga gtgaagaagg    60
atttcggttc gtaaagctct gttgttaggg aagaatgatt gtgtagtaac tatacacagt   120
agagacggta cctaaccaga aagccacggc taactacgtg ccagcagccg cggtaatacg   180
taggtggcaa gcgttgtccg gaattattgg gcgtaaagcg cgcgcaggtg gtttaataag   240
tctgatgtga agcccacgg ctcaaccgtg gagggtcatt ggaaactgtt aaacttgagt    300
gcaggagaga aaagtggaat tcctagtgta gcggtgaaat gcgtagagat taggaggaac   360
accagtggcg aaggcggctt tttggcctgt aactgacact gaggcgcgaa agcgtgggga   420
gcaaaca                                                             427

<210> SEQ ID NO 38
<211> LENGTH: 428
<212> TYPE: DNA
<213> ORGANISM: Bilophila sp.

<400> SEQUENCE: 38
tggggaatat tgcgcaatgg gcgaaagcct gacgcagcga cgccgcgtga gggatgaagg    60
ttctcggatc gtaaacctct gtcagggggg aagaaacccc ctcgtgtgaa taatgcgagg   120
gcttgacggt acccccaaag gaagcaccgg ctaactccgt gccagcagcc gcggtaatac   180
ggagggtgca agcgttaatc ggaatcactg ggcgtaaagc gcacgtaggc ggcttggtaa   240 gtcagggtg aaatcccaca gcccaactgt ggaactgcct tgatactgc caggcttgag    300 taccggagag ggtggcggaa ttccaggtgt aggagtgaaa tccgtagata tctggaggaa   360
caccggtggc gaaggcggcc acctggacgg taactgacgc tgaggtgcga agcgtgggt   420 agcaaaca                                                            428

<210> SEQ ID NO 39
<211> LENGTH: 423
<212> TYPE: DNA
<213> ORGANISM: Unknown
```

-continued

```
<220> FEATURE:
<221> NAME/KEY: source
<223> OTHER INFORMATION: /note="Description of Unknown:
      Bacterial sequence"

<400> SEQUENCE: 39
tgaggaatat tggtcaatgg acgcgagtct gaaccagcca agtagcgtgc aggatgacgg    60
ccctatgggt tgtaaactgc ttttgcgcgg ggataacacc ctccacgtgc tggaggtctg   120
caggtaccgc gcgaataagg accggctaat tccgtgccag cagccgcggt aatacgaag   180 gtccgggcgt tatccggatt tattgggttt aaagggagcg taggccgtga ggtaagcgtg   240
ttgtgaaatg taggcgccca acgtctgcac tgcagcgcga actgccccac ttgagtgcgc   300
gcaacgccgg cggaactcgt cgtgtagcgg tgaaatgctt agatatgacg aagaaccccg   360
attgcgaagg cagctggcgg gagcgtaact gacgctgaag ctcgaaagcg cgggtatcga   420
aca                                                                 423

<210> SEQ ID NO 40
<211> LENGTH: 401
<212> TYPE: DNA
<213> ORGANISM: Parvimonas sp.

<400> SEQUENCE: 40
tggggaatat tgcacaatgg ggggaaccct gatgcagcga cgccgcgtga gcgaagaagg    60
ttttcgaatc gtaaagctct gtcctatgag aagataatga cggtatcata ggaggaagcc   120
ccggctaaat acgtgccagc agccgcggta atacgtatgg ggcgagcgtt gtccggaatt   180
attgggcgta aagggtacgt aggcggtttt ttaagtcagg tgtgaaagcg tgaggcttaa   240
cctcattaag cacttgaaac tggaagactt gagtgaagga gagaaagtg gaattcctag    300 tgtagcggtg aaatgcgtag atattaggag gaataccggt ggcgaaggcg actttctgga   360
cttttactga cgctcaggta cgaaagcgtg gggagcaaac a                       401

<210> SEQ ID NO 41
<211> LENGTH: 422
<212> TYPE: DNA
<213> ORGANISM: Barnesiella sp.

<400> SEQUENCE: 41
tgaggaatat tggtcaatgg tcggcagact gaaccagcca agtcgcgtga gggaagacgg    60
ccctacgggt tgtaaacctc ttttgtcgga gagtaaagta cgctacgtgt agcgtattgc   120
aagtatccga agaaaaagca tcggctaact ccgtgccagc agccgcggta atacggagga   180
tgcaagcgtt atccggattt attgggttta aagggtgcgt aggcggcacg ccaagtcagc   240
ggtgaaattt ccgggctcaa cccggactgt gccgttgaaa ctggcgagct agagtgcaca   300
agaggcaggc ggaatgcgtg gtgtagcggt gaaatgcata gatatcacgc agaaccccga   360
ttgcgaaggc agcctgctag ggtgcgacag acgctgaggc acgaaagcgt gggtatcgaa   420
ca                                                                  422

<210> SEQ ID NO 42
<211> LENGTH: 427
<212> TYPE: DNA
<213> ORGANISM: Haemophilus sp.

<400> SEQUENCE: 42
tggggaatat tgcgcaatgg ggggaaccct gacgcagcca tgccgcgtga atgaagaagg    60
```

```
ccttcgggtt gtaaagttct ttcggtattg aggaaggagt gtatgttaat agcatacatt    120
attgacgtta aatacagaag aagcaccggc taactccgtg ccagcagccg cggtaatacg    180
gagggtgcga gcgttaatcg gaataactgg gcgtaaaggg cacgcaggcg gttatttaag    240
tgaggtgtga aagccccggg cttaacctgg gaattgcatt tcagactggg taactagagt    300
actttaggga ggggtagaat tccacgtgta gcggtgaaat gcgtagagat gtggaggaat    360
accgaaggcg aaggcagccc cttgggaatg tactgacgct catgtgcgaa agcgtgggga    420
gcaaaca                                                             427

<210> SEQ ID NO 43
<211> LENGTH: 402
<212> TYPE: DNA
<213> ORGANISM: Clostridium sp.

<400> SEQUENCE: 43
tgagggatat tgggcaatgg gggaaaccct gacccagcaa cgccgcgtga gggatgacgg     60
ttttcggatt gtaaacctct gtcctctgtg aagatagtga cggtagcaga ggaggaagct    120
ccggctaact acgtgccagc agccgcggta atacgtaggg agcaagcgtt gtccggattt    180
actgggtgta aagggtgcgt aggcggattg gcaagtcaga agtgaaatcc atgggcttaa    240
cccatgaact gcttttgaaa ctgttagtct tgagtgaagt agaggtaggc ggaattcccg    300
gtgtagcggt gaaatgcgta gagatcggga ggaacaccag tggcgaaggc ggcctactgg    360
gctttaactg acgctgaggc acgaaagtgt gggtagcaaa ca                       402

<210> SEQ ID NO 44
<211> LENGTH: 422
<212> TYPE: DNA
<213> ORGANISM: Prevotella sp.

<400> SEQUENCE: 44
tgaggaatat tggtcaatgg acgcaagtct gaaccagcca gtagcgtgc aggatgacgg      60 ccctatgggt tgtaaactgc ttttatgtgg gaataaattg gcgcacgtgt gcgccattgc    120
atgtacctca tgaataagga ccggctaatt ccgtgccagc agccgcggta atacggaagg    180
tccgggcgtt atccggattt attgggttta aagggagtgt aggcggtctg ttaagcgtgt    240
tgtgaaattt aggtgctcaa catttaactt gcagcgcgaa ctgtcagact tgagtacacg    300
cagcgcaggc ggaattcatg gtgtagcggt gaaatgctta gatatcatga ggaactccga    360
tcgcgaaggc agcctgcggg agtgttactg acgcttaagc tcgaaggtgc gggtatcgaa    420
ca                                                                  422

<210> SEQ ID NO 45
<211> LENGTH: 401
<212> TYPE: DNA
<213> ORGANISM: Peptostreptococcus sp.

<400> SEQUENCE: 45
tggggaatat tgcacaatgg gcgaaagcct gatgcagcaa cgccgcgtga acgatgaagg     60
tcttcggatc gtaaagttct gttgcagggg aagataatga cggtaccctg tgaggaagcc    120
ccggctaact acgtgccagc agccgcggta atacgtaggg ggctagcgtt atccggattt    180
actgggcgta aagggtgcgt aggtggtcct tcaagtcggt ggttaaaggc tacggctcaa    240
ccgtagtaag ccgccgaaac tggaggactt gagtgcagga gaggaaagtg gaattcccag    300
tgtagcggtg aaatgcgtag atattgggag gaacaccagt agcgaaggcg ctttctgga    360
```

```
ctgcaactga cactgaggca cgaaagcgtg ggtagcaaac a                  401
```

<210> SEQ ID NO 46
<211> LENGTH: 405
<212> TYPE: DNA
<213> ORGANISM: Clostridium sp.

<400> SEQUENCE: 46

```
tgggggatat tgcgcaatgg gggaaaccct gacgcagcaa cgccgcgtga aggaagaagg    60
tcttcggatt gtaaacttct tttgtcaggg acgaagaaag tgacggtacc tgacgaataa   120
gctccggcta actacgtgcc agcagccgcg gtaatacgta gggagcgagc gttgtccgga   180
tttactgggt gtaaagggtg cgtaggcggc cgagcaagtc agttgtgaaa actatgggct   240
taacccataa cgtgcaattg aaactgtccg gcttgagtga agtagaggta ggcggaattc   300
ccggtgtagc ggtgaaatgc gtagagatcg gaggaacac cagtggcgaa ggcggcctac    360
tgggctttaa ctgacgctga ggcacgaaag catgggtagc aaaca                   405
```

<210> SEQ ID NO 47
<211> LENGTH: 423
<212> TYPE: DNA
<213> ORGANISM: Porphyromonas sp.

<400> SEQUENCE: 47

```
tgaggaatat tggtcaatgg gcgagagcct gaaccagcca agtcgcgtga aggaagactg    60
cccgcaaggg ttgtaaactt cttttgtatg ggattaaagt cgtctacgtg tagacgtttg   120
cagttaccat acgaataagc atcggctaac tccgtgccag cagccgcggt aatacggagg   180
atgcgagcgt tatccggaat tattgggttt aaagggtgcg taggttgcaa gggaagtcag   240
ggtgaaaag ctgtagctca actatggtct tgcctttgaa actctctagc tagagtgtac    300
tgaggtacg tggaacgtgt ggtgtagcgg tgaaatgcat agatatcaca cagaactccg    360
attgcgcagg cagcgtacta cattacaact gacactgaag cacgaaagcg tgggtatcaa   420
aca                                                                 423
```

<210> SEQ ID NO 48
<211> LENGTH: 402
<212> TYPE: DNA
<213> ORGANISM: Clostridium sp.

<400> SEQUENCE: 48

```
tggggaatat tgcacaatgg gcgaaagcct gatgcagcga cgccgcgtga gtgaagaagt    60
atttcggtat gtaaagctct atcagcaggg aagaaaatga cggtacctga ctaagaagcc   120
ccggctaact acgtgccagc agccgcggta atacgtaggg gcaagcgtt atccggattt    180
actgggtgta aagggagcgt agacggcgaa gcaagtctga agtgaaaacc cagggctcaa   240
ccctgggact gctttggaaa ctgttttgct agagtgtcgg agaggtaagt ggaattccta   300
gtgtagcggt gaaatgcgta gatattagga ggaacaccag tggcgaaggc ggcttactgg   360
acgataactg acgttgaggc tcgaaagcgt ggggagcaaa ca                      402
```

<210> SEQ ID NO 49
<211> LENGTH: 427
<212> TYPE: DNA
<213> ORGANISM: Parasutterella sp.

<400> SEQUENCE: 49

```
tggggaattt tggacaatgg gcgcaagcct gatccagcta ttccgcgtgt gggatgaagg    60
ccctcgggtt gtaaaccact tttgtagaga cgaaaagac accttcgaat aaagggtgtt   120
gctgacggta ctctaagaat aagcaccggc taactacgtg ccagcagccg cggtaatacg   180
tagggtgcga gcgttaatcg gaattactgg gcgtaaaggg tgcgcaggcg gttgagtaag   240
acagatgtga atccccgag cttaactcgg gaatggcata tgtgactgct cgactagagt   300
gtgtcagagg gaggtggaat tccacgtgta gcagtgaaat gcgtagatat gtggaagaac   360
accgatggcg aaggcagcct cctgggacat aactgacgct caggcacgaa agcgtgggga   420
gcaaaca                                                             427
```

<210> SEQ ID NO 50
<211> LENGTH: 402
<212> TYPE: DNA
<213> ORGANISM: Clostridium sp.

<400> SEQUENCE: 50

```
tggggaatat tgcacaatgg gggaaaccct gatgcagcga cgccgcgtga gtgaagaagt    60
atttcggtat gtaaagctct atcagcaggg aagaaaatga cggtacctga ctaagaagcc   120
ccggctaact acgtgccagc agccgcggta atacgtaggg gcaagcgtt atccggattt    180 actgggtgta aagggagcgt agacggtcaa gcaagtcaga agtgaaaggc tggggctcaa   240
ccccgggact gcttttgaaa ctgtttgact ggagtgctgg agaggtaagc ggaattccta   300
gtgtagcggt gaaatgcgta gatattagga ggaacaccag tggcgaaggc ggcttactgg   360
acagtaactg acgttgaggc tcgaaagcgt ggggagcaaa ca                      402
```

<210> SEQ ID NO 51
<211> LENGTH: 409
<212> TYPE: DNA
<213> ORGANISM: Bifidobacterium sp.

<400> SEQUENCE: 51

```
tggggaatat tgcacaatgg gcgcaagcct gatgcagcga cgccgcgtga gggatggagg    60
ccttcgggtt gtaaacctct tttgtttggg agcaagcctt cgggtgagtg tacctttcga   120
ataagcgccg gctaactacg tgccagcagc cgcggtaata cgtagggcgc aagcgttatc   180
cggatttatt gggcgtaaag ggctcgtagg cggctcgtcg cgtccggtgt gaaagtccat   240
cgcttaacgg tggatctgcg ccgggtacgg gcgggctgga gtgcggtagg ggagactgga   300
attcccggtg taacggtgga atgtgtagat atcgggaaga acaccgatgg cgaaggcagg   360
tctctgggcc gtcactgacg ctgaggagcg aaagcgtggg gagcgaaca              409
```

<210> SEQ ID NO 52
<211> LENGTH: 421
<212> TYPE: DNA
<213> ORGANISM: Solobacterium sp.

<400> SEQUENCE: 52

```
tagggaattt tcggcaatgg gggcaaccct gaccgagcaa cgccgcgtga gtgaagacgg    60
ccttcgggtt gtaaagctct gttgtaaggg aagaacggta gatagagaat atctaagtga   120
cggtacctta ccagaaagcc acggctaact acgtgccagc agccgcggta atacgtaggt   180
ggcgagcgtt atccggaatt attgggcgta aagggtgcgt aggcggcctg ttaagtaagt   240
ggttaaattg ttgggctcaa cccaatccag ccacttaaac tggcaggcta gagtattgga   300
gaggcaagtg gaattccatg tgtagcggta aaatgcgtag atatatggag gaacaccagt   360
```

```
ggcgaaggcg gcttgctagc caaagactga cgctcatgca cgaaagcgtg gggagcaaat    420
a                                                                    421

<210> SEQ ID NO 53
<211> LENGTH: 427
<212> TYPE: DNA
<213> ORGANISM: Phascolarctobacterium sp.

<400> SEQUENCE: 53
tggggaatct tccgcaatgg gcgaaagcct gacggagcaa tgccgcgtga gtgatgaagg    60
aattcgttcc gtaaagctct tttgtttatg acgaatgtgc aggttgtgaa taatgacttg    120
taatgacggt agtaaacgaa taagccacgg ctaactacgt gccagcagcc gcggtaatac    180
gtaggtggcg agcgttgtcc ggaattattg ggcgtaaaga gcatgtaggc ggttttttaa    240
gtctggagtg aaaatgcggg gctcaaccccc gtatggctct ggatactgga agacttgagt    300
gcaggagagg aaaggggaat tcccagtgta gcggtgaaat gcgtagatat tgggaggaac    360
accagtggcg aaggcgcctt tctggactgt gtctgacgct gagatgcgaa agccagggta    420
gcgaacg                                                              427

<210> SEQ ID NO 54
<211> LENGTH: 402
<212> TYPE: DNA
<213> ORGANISM: Hespellia sp.

<400> SEQUENCE: 54
tggggaatat tgcacaatgg gggaaaccct gatgcagcga cgccgcgtga aggatgaagt    60
atttcggtat gtaaacttct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggtatg gcaagtctga tgtgaaaggc cagggctcaa    240
ccctgggact gcattggaaa ctgtcgaact agagtgtcgg agaggcaagt ggaattccta    300
gtgtagcggt gaaatgcgta gatattagga ggaacaccag tggcgaaggc ggcttgctgg    360
acgatgactg acgttgaggc tcgaaagcgt ggggagcaaa ca                       402

<210> SEQ ID NO 55
<211> LENGTH: 427
<212> TYPE: DNA
<213> ORGANISM: Aggregatibacter sp.

<400> SEQUENCE: 55
tggggaatat tgcgcaatgg gggcaaccct gacgcagcca tgccgcgtga atgaagaagg    60
ccttcgggtt gtaaagttct ttcggtgacg aggaaggcgt gatgtttaat aggcatcacg    120
attgacgtta atcacagaag aagcaccggc taactccgtg ccagcagccg cggtaatacg    180
gagggtgcga gcgttaatcg gaataactgg gcgtaaaggg cacgcaggcg gctatttaag    240
tgaggtgtga atccccgggg cttaacctgg gaattgcatt tcagactggg tagctagagt    300 acttaggga ggggtagaat tccacgtgta gcggtgaaat gcgtagagat gtggaggaat    360
accgaaggcg aaggcagccc cttgggaatg tactgacgct catgtgcgaa agcgtgggga    420
gcaaaca                                                              427

<210> SEQ ID NO 56
<211> LENGTH: 427
<212> TYPE: DNA
```

<213> ORGANISM: Dialister sp.

<400> SEQUENCE: 56

```
tggggaatct tccgcaatgg acgaaagtct gacggagcaa cgccgcgtga acgaagaagg    60
tcttcggatt gtaaagttct gtgattcggg acgaaagggt tgtggtgaa taatcataga   120
cattgacggt accgaaaaag caagccacgg ctaactacgt gccagcagcc gcggtaatac   180
gtaggtggca agcgttgtcc ggaattattg ggcgtaaagc gcgcgcaggc ggtttcttaa   240
gtccatctta aaagcgtggg gctcaacccc atgagtggat ggaaactggg aagctggagt   300
atcggagagg aaagtggaat tcctagtgta gcggtgaaat gcgtagagat taggaagaac   360
accggtggcg aaggcgactt tctagacgaa aactgacgct gaggcgcgaa agcgtgggga   420
gcaaaca                                                             427
```

<210> SEQ ID NO 57
<211> LENGTH: 405
<212> TYPE: DNA
<213> ORGANISM: Flavonifractor sp.

<400> SEQUENCE: 57

```
tggggaatat tgggcaatgg gcgcaagcct gacccagcaa cgccgcgtga aggaagaagg    60
ctttcgggtt gtaaacttct tttgtcgggg acgaaacaaa tgacggtacc cgacgaataa   120
gccacggcta actacgtgcc agcagccgcg gtaatacgta ggtggcaagc gttatccgga   180
tttactgggt gtaaagggcg tgtaggcggg attgcaagtc agatgtgaaa actgggggct   240
caacctccag cctgcatttg aaactgtagt tcttgagtgc tggagaggca atcggaattc   300
cgtgtgtagc ggtgaaatgc gtagatatac ggaggaacac cagtggcgaa ggcggattgc   360
tggacagtaa ctgacgctga ggcgcgaaag cgtgggagc aaaca                    405
```

<210> SEQ ID NO 58
<211> LENGTH: 402
<212> TYPE: DNA
<213> ORGANISM: Blautia sp.

<400> SEQUENCE: 58

```
tggggaatat tgcacaatgg gggaaaccct gatgcagcga cgccgcgtga aggaagaagt    60
atctcggtat gtaaacttct atcagcaggg aagaaaatga cggtacctga ctaagaagcc   120
ccggctaact acgtgccagc agccgcggta atacgtaggg ggcaagcgtt atccggattt   180
actgggtgta aagggagcgt agacggcata acaagtctga tgtgaaaggc tggggcttaa   240
ccccgggact gcattggaaa ctgttaagct tgagtgccgg aggggtaagc ggaattccta   300
gtgtagcggt gaaatgcgta gatattagga ggaacaccag tggcgaaggc ggcttactgg   360
acggtaactg acgttgaggc tcgaaagcgt ggggagcaaa ca                      402
```

<210> SEQ ID NO 59
<211> LENGTH: 427
<212> TYPE: DNA
<213> ORGANISM: Lactobacillus sp.

<400> SEQUENCE: 59

```
tagggaatct tccacaatgg acgcaagtct gatggagcaa cgccgcgtga gtgaagaagg    60
ttttcggatc gtaaagctct gttgttggtg aagaaggata gaggcagtaa ctggtctttt   120
tttgacggta atcaaccaga aagtcacggc taactacgtg ccagcagccg cggtaatacg   180
taggtggcaa gcgttgtccg gatttattgg gcgtaaagcg agcgcaggcg gaatgataag   240
```

```
tctgatgtga aagcccacgg ctcaaccgtg gaactgcatc ggaaactgtc attcttgagt    300
gcagaagagg agagtggaat tccatgtgta gcggtggaat gcgtagatat atggaagaac    360
accagtggcg aaggcggctc tctggtctgc aactgacgct gaggctcgaa agcatgggta    420
gcgaaca                                                              427

<210> SEQ ID NO 60
<211> LENGTH: 405
<212> TYPE: DNA
<213> ORGANISM: Leptotrichia sp.

<400> SEQUENCE: 60
tggggaatat tggacaatgg gggcaaccct gatccagcaa ttctgtgtgc acgaagaagg     60
ttttcggatt gtaaagtgct ttcagcaggg aagaagaaag tgacggtacc tgcagaagaa    120
gcgacggcta atacgtgcc agcagccgcg gtaatacgta tgtcgcaagc gttatccgga     180
attattgggc ataaagggca tctaggcggc cctgtaagtc tagggtgaaa acctgcggct    240
caaccgcagg cctgccccgg aaactacagg ctagagtat cggagaggtg acggaactg     300 cacgagtaga ggtgaaattc gtagatatgt gcaggaatgc cgatgatgaa gatagttcac    360
tggacggtaa ctgacgctga agtgcgaaag ctaggggagc aaaca                    405

<210> SEQ ID NO 61
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 61
tggggaatat tgcacaatgg aggcaactct gatgcagcga cgccgcgtga gtgaagaagt     60
atttcggtat gtaaagctct atcagtaggg aagataatga cggtacctac agaagaagcc   120
ccggctaaat acgtgccagc agccgcggta atacgtatgg ggcaagcgtt atccggattt    180
actgggtgta aagggagtgt aggcggcagt acaagtcagg agtgaaaact tggggctcaa    240
ccccaagact gcttttgaaa ctgtacagct agagtgtagg aagggcaagc ggaattcctg    300
gtgtagcggt gaaatgcgta gatatcagga agaacaccgg tggcgaaggc ggcttgctgg    360
actataactg acgctgagac tcgaaagcgt ggggagcgaa ca                      402

<210> SEQ ID NO 62
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 62
tggggaatat tgcacaatgg gggaaaccct gatgcagcga cgccgcgtga gcgaagaagt     60
atttcggtat gtaaagctct atcagcaggg aagataatga cggtacctga ctaagaagcc   120
ccggctaact acgtgccagc agccgcggta atacgtaggg ggcaagcgtt atccggattt    180
actgggtgta aagggagcgt agacggcaag gcaagtctga tgtgaaaacc cagggcttaa   240
ccctgggact gcattggaaa ctgtctggct cgagtgccgg agaggtaagc ggaattccta   300
```

```
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 63
<211> LENGTH: 427
<212> TYPE: DNA
<213> ORGANISM: Streptococcus sp.

<400> SEQUENCE: 63

```
tagggaatct tcggcaatgg ggggaaccct gaccgagcaa cgccgcgtga gtgaagaagg    60
ttttcggatc gtaaagctct gttgttaagg aagaacgtgt gtgagagtgg aaagttcaca   120
cagtgacggt acttaaccag aaagggacgg ctaactacg ccagcagcc gcggtaatac     180 gtaggtcccg agcgttgtcc ggatttattg ggcgtaaagc gagcgcaggc ggttagataa   240
gtctgaagtg aaaggcagtg gctcaaccat tgtaggcttt ggaaactgtt taacttgagt   300
gcagaagggg agagtggaat tccatgtgta gcggtgaaat gcgtagatat atggaggaac   360
accggtggcg aaagcggctc tctggtctgt aactgacgct gaggctcgaa agcgtgggga   420
gcgaaca                                                             427
```

<210> SEQ ID NO 64
<211> LENGTH: 427
<212> TYPE: DNA
<213> ORGANISM: Unknown
<220> FEATURE:
<221> NAME/KEY: source
<223> OTHER INFORMATION: /note="Description of Unknown:
     Bacterial sequence"

<400> SEQUENCE: 64

```
tggggaatct tccgcaatgg acgaaagtct gacggagcaa cgccgcgtga gtgatgaagg    60
tcttcggatt gtaaaactct gttgttaggg acgaaagcac cgtgttcgaa caggtcatgg   120
tgttgacggt acctaacgag gaagccacgg ctaactacgt gccagcagcc gcggtaatac   180
gtaggtggca agcgttgtcc ggaattattg ggcgtaaaga gcatgtaggc gggcttttaa   240
gtctgacgtg aaaatgcggg gcttaacccc gtatggcgtt ggatactgga agtcttgagt   300
gcaggagagg aaaggggaat tcccagtgta gcggtgaaat gcgtagatat tgggaggaac   360
accagtggcg aaggcgcctt tctggactgt gtctgacgct gagatgcgaa agccagggta   420
gcaaacg                                                             427
```

<210> SEQ ID NO 65
<211> LENGTH: 404
<212> TYPE: DNA
<213> ORGANISM: Unknown
<220> FEATURE:
<221> NAME/KEY: source
<223> OTHER INFORMATION: /note="Description of Unknown:
     Bacterial sequence"

<400> SEQUENCE: 65

```
tggggaatat tgggcaatgg gcgaaagcct gacccagcaa cgccgcgtga aggaagaagg    60
ccttcgggtt gtaaacttct tttaagaggg acgaagaagt gacggtacct cttgaataag   120
ccacggctaa ctacgtgcca gcagccgcgg taatacgtag gtggcgagcg ttatccggat   180
ttactgggtg taaagggcgc gtaggcggga atgcaagtca gatgtgaaat ccaagggctc   240
aacccttgaa ctgcatttga aactgtatt  cttgagtgtc ggagaggttg acggaattcc   300
tagtgtagcg gtgaaatgcg tagatattag gaggaacacc agtggcgaag gcggtcaact   360
```

```
ggacgataac tgacgctgag gcgcgaaagc gtggggagca aaca          404
```

<210> SEQ ID NO 66
<211> LENGTH: 427
<212> TYPE: DNA
<213> ORGANISM: Kingella sp.

<400> SEQUENCE: 66

```
tggggaattt tggacaatgg gcgcaagcct gatccagcca tgccgcgtgt ctgaagaagg     60
ccttcgggtt gtaaaggact tttgttaggg aagaaaagga tagtgttaat accattatct   120
gctgacggta cctaaagaat aagcaccggc taactacgtg ccagcagccg cggtaatacg   180
tagggtgcga gcgttaatcg gaattactgg gcgtaaagcg agcgcagacg gtttattaag   240
caagatgtga aatccccgag cttaacttgg gaactgcgtt ttgaactggt aagctagagt   300
atgtcagagg ggggtagaat tccacgtgta gcagtgaaat gcgtagagat gtggaggaat   360
accgatggcg aaggcagccc cctgggataa tactgacgtt catgctcgaa agcgtgggta   420
gcaaaca                                                             427
```

<210> SEQ ID NO 67
<211> LENGTH: 427
<212> TYPE: DNA
<213> ORGANISM: Aggregatibacter sp.

<400> SEQUENCE: 67

```
tggggaatat tgcgcaatgg gggcaaccct gacgcagcca tgccgcgtga atgaagaagg     60
ccttcgggtt gtaaagttct ttcggtgacg aggaaggttg ttgtgttaat agcgcaacaa   120
attgacgtta atcacagaag aagcaccggc taactccgtg ccagcagccg cggtaatacg   180
gagggtgcga gcgttaatcg gaataactgg gcgtaaaggg cacgcaggcg gctatttaag   240
tgaggtgtga atccccggg cttaacctgg gaattgcatt tcagactggg tagctagagt    300
actttaggga ggggtagaat tccacgtgta gcggtgaaat gcgtagagat gtggaggaat   360
accgaaggcg aaggcagccc cttgggaatg tactgacgct catgtgcgaa agcgtgggga   420
gcaaaca                                                             427
```

<210> SEQ ID NO 68
<211> LENGTH: 403
<212> TYPE: DNA
<213> ORGANISM: Campylobacter sp.

<400> SEQUENCE: 68

```
tagggaatat tgcgcaatgg gggaaaccct gacgcagcaa cgccgcgtgg aggatgacac     60
ttttcggagc gtaaactcct tttgttaggg aagaataatg acgtaccta acgaataagc    120
accggctaac tccgtgccag cagccgcggt aatacggagg gtgcaagcgt tactcggaat   180
cactgggcgt aaaggacgcg taggcggatt atcaagtctc ttgtgaaatc taacggctta   240
accgttaaac tgcttgggaa actgataatc tagagtaagg gagaggcaga tggaattctt   300
ggtgtagggg taaaatccgt agatatcaag aagaatacct attgcgaagg cgatctgctg   360
gaacttaact gacgctaatg cgtgaaagcg tggggagcaa aca                     403
```

<210> SEQ ID NO 69
<211> LENGTH: 421
<212> TYPE: DNA
<213> ORGANISM: Paraprevotella sp.

-continued

<400> SEQUENCE: 69

```
tgaggaatat tggtcaatgg gcgggagcct gaaccagcca agtagcgtga aggacgacgg      60
ccctacgggt tgtaaacttc ttttataagg gaataaagtt cgccacgtgt ggtgttttgt     120
atgtacctta tgaataagca tcggctaatt ccgtgccagc agccgcggta atacggaaga    180
tgcgagcgtt atccggattt attgggttta aagggagcgt aggcgggctt ttaagtcagc    240
ggtcaaatgt cgtggctcaa ccatgtcaag ccgttgaaac tgtaagcctt gagtctgcac    300
agggcacatg gaattcgtgg tgtagcggtg aaatgcttag atatcacgaa gaactccgat    360
cgcgaaggca ttgtgccggg gcataactga cgctgaggct cgaaagtgcg ggtatcaaac    420
a                                                                    421
```

<210> SEQ ID NO 70
<211> LENGTH: 422
<212> TYPE: DNA
<213> ORGANISM: Bacteroides sp.

<400> SEQUENCE: 70

```
tgaggaatat tggtcaatgg acgagagtct gaaccagcca agtagcgtga aggatgactg      60
ccctatgggt tgtaaacttc ttttatacgg gaataaagtg gagtatgcat actcctttgt    120
atgtaccgta tgaataagga tcggctaact ccgtgccagc agccgcggta atacggagga    180
tccgagcgtt atccggattt attgggttta aagggagcgt aggcgggtgc ttaagtcagt    240
tgtgaaagtt tgcggctcaa ccgtaaaatt gcagttgata ctgggcgcct tgagtgcagc    300
ataggtaggc ggaattcgtg tgtagcggtg aaatgcttag atatcacgaa gaactccta    360
ttgcgaaggc agcttactgg actgtaactg acgctgatgc tcgaaagtgt gggtatcaaa    420
ca                                                                   422
```

<210> SEQ ID NO 71
<211> LENGTH: 402
<212> TYPE: DNA
<213> ORGANISM: Clostridium sp.

<400> SEQUENCE: 71

```
tgggggatat tgcacaatgg gggaaaccct gatgcagcaa cgccgcgtga aggaagaagg      60
tcttcggatt gtaaacttct gtcctcaggg aagataatga cggtacctga ggaggaagct    120
ccggctaact acgtgccagc agccgcggta atacgtaggg agcgagcgtt gtccggattt    180
actgggtgta aagggtgcgt aggcggatcc gcaagtcagt agtgaaatcc cagggcttaa    240
ccctggaact gctattgaaa ctgtgggtct tgagtgaggt agaggcaggc ggaattcccg    300
gtgtagcggt gaaatgcgta gagatcggga ggaacaccag tggcgaaggc ggcctgctgg    360
gccttaactg acgctgaggc acgaaagcat gggtagcaaa ca                       402
```

<210> SEQ ID NO 72
<211> LENGTH: 401
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 72

```
tggggaatat tgcacaatgg gggaaaccct gatgcagcaa cgccgcgtga aggatgaagg      60
cctttgggtc gtaaacttct gttctaaggg aagatagtga cggtaccttA ggagcaagtc    120
```

```
ccggctaact acgtgccagc agccgcggta atacgtaggg ggcaagcgtt atccggaatt    180
attgggcgta aagagtacgt aggtggtttt ctaagcacgg ggtttaaggc aatggcttaa    240
ccattgttcg ccttgtgaac tggaagactt gagtgcagga gaggaaagcg gaattcctag    300
tgtagcggtg aaatgcgtag atattaggag gaacaccagt ggcgaaggcg gctttctgga    360
ctgtaactga cactgaggta cgaaagcgtg gggagcaaac a                        401
```

<210> SEQ ID NO 73
<211> LENGTH: 421
<212> TYPE: DNA
<213> ORGANISM: Alloprevotella sp.

<400> SEQUENCE: 73

```
tgaggaatat tggtcaatgg acgaaagtct gaaccagcca agtagcgtgc aggatgacgg     60
ccctctgggt tgtaaactgc ttttagttgg gaataaaaaa gaggacgtgt cctctattgt    120
atgtaccttc agaaaaagga ccggctaatt ccgtgccagc agccgcggta atacggaagg    180
tccaggcgtt atccggattt attgggttta aagggagcgt aggcggatta ttaagtcagt    240
ggtgaaagac ggtggctcaa ccatcgttag ccattgaaac tggtagtctt gagtgcagac    300
agggatgctg gaactcgtgg tgtagcggtg aaatgcttag atatcacgat gaactccgat    360
cgcgaaggca ggtgtccggg ctgcaactga cgctgaggct cgaaagtgtg ggtatcaaac    420
a                                                                    421
```

<210> SEQ ID NO 74
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 74

```
tgaggaatat tggtcaatgg acggaagtct gaaccagcca tgccgcgtgc aggatgaatg     60
tgctatgcat tgtaaactgc ttttgtacga gggtaaacac agatacgcgt atctgcttga    120
aagtatcgta cgaataagga tcggctaact ccgtgccagc agccgcggta atacggagga    180
tccgagcgtt atccggattt attgggttta aagggtgcgt aggctgtttt ttaagttaga    240
ggtgaaagct cgacgctcaa cgtcgaaatt gcctctgata ctgagagact agagtgtagt    300
tgcggaaggc ggaatgtgtg gtgtagcggt gaaatgctta gatatcacac agaacaccga    360
ttgcgaaggc agctttccaa gctattactg acgctgaggc acgaaagcgt ggggagcgaa    420
ca                                                                   422
```

<210> SEQ ID NO 75
<211> LENGTH: 422
<212> TYPE: DNA
<213> ORGANISM: Capnocytophaga sp.

<400> SEQUENCE: 75

```
tgaggaatat tggtcaatgg tcggaagact gaaccagcca tgccgcgtgc aggaagaatg     60
ccttatgggt tgtaaactgc ttttatatgg gaagaataag gagtacgtgt actttgatga    120
cggtaccata tgaataagca tcggctaact ccgtgccagc agccgcggta atacggagga    180
tgcgagcgtt attcggaatc attgggttta aagggtctgt aggcgggcta ttaagtcagg    240
```

-continued

```
ggtgaaaggt tcagcttaa ctgagaaatt gcctttgata ctggtagtct tgaatatctg    300
tgaagttctt ggaatgtgta gtgtagcggt gaaatgctta gatattacac agaacaccga    360
ttgcggaggc aggggactaa cagacgattg acgctgagag acgaaagcgt ggggagcgaa    420
ca                                                                    422
```

<210> SEQ ID NO 76
<211> LENGTH: 422
<212> TYPE: DNA
<213> ORGANISM: Capnocytophaga sp.

<400> SEQUENCE: 76

```
tgaggaatat tggacaatgg tcggaagact gatccagcca tgccgcgtgc aggaagacgg    60
ccttatgggt tgtaaactgc ttttgcaggg gaagaataag gagtacgtgt actttgatga    120
cggtactctg cgaataagca tcggctaact ccgtgccagc agccgcggta atacggagga    180
tgcgagcgtt atccggaatc attgggttta agggtccgt aggcgggcta ataagtcaga    240
ggtgaaagcg ctcagctcaa ctgagcaact gcctttgaaa ctgttagtct tgaatggttg    300
tgaagtagtt ggaatgtgta gtgtagcggt gaaatgctta gatattacac agaacaccga    360
tagcgaaggc atattactaa caattaattg acgctgatgg acgaaagcgt ggggagcgaa    420
ca                                                                    422
```

<210> SEQ ID NO 77
<211> LENGTH: 405
<212> TYPE: DNA
<213> ORGANISM: Pseudoflavonifractor sp.

<400> SEQUENCE: 77

```
tggggaatat tgggcaatgg gcgcaagcct gacccagcaa cgccgcgtga aggaagaagg    60
ctttcgggtt gtaaacttct tttcttaggg acgaagcaag tgacggtacc taaggaataa    120
gccacggcta actacgtgcc agcagccgcg gtaatacgta ggtggcaagc gttatccgga    180
tttactgggt gtaaagggcg tgtaggcggg attgcaagtc agatgtgaaa accacgggct    240
caacctgtgg cctgcatttg aaactgtagt tcttgagtac tggagaggca gacgaattc    300 ctagtgtagc ggtgaaatgc gtagatatta ggaggaacac cagtggcgaa ggcggtctgc    360
tggacagcaa ctgacgctga ggcgcgaaag cgtggggagc aaaca                    405
```

<210> SEQ ID NO 78
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 78

```
tggggaatat tgggcaatgg gcgaaagcct gacccagcaa cgccgcgtga aggaagaagg    60
ttttcggatc gtaaacttct atccttggtg aagataatga cggtagccaa gaaggaagcc    120
ccggctaact acgtgccagc agccgcggta atacgtaggg gcaagcgtt gtccggaatg    180 attgggcgta aagggcgcgt aggcggccaa ctaagtctgg agtgaaagtc ctgcttttaa    240
ggtgggaatt gctttggaaa ctggatggct tgagtgcagg agaggtaagc ggaattcccg    300
gtgtagcggt gaaatgcgta gagatcggga ggaacaccag tggcgaaggc ggcttactgg    360
actgtaactg acgctgaggc gcgaaagtgt ggggagcaaa ca                        402
```

<210> SEQ ID NO 79
<211> LENGTH: 427
<212> TYPE: DNA
<213> ORGANISM: Eikenella sp.

<400> SEQUENCE: 79

```
tggggaattt tggacaatgg gggcaaccct gatccagcca tgccgcgtgt atgaagaagg      60
ccttcgggtt gtaaagtact tttgttaggg aagaaaaggg aagtgctaat accactttt     120 gctgacggta cctaaagaat aagcaccggc taactacgtg ccagcagccg cggtaatacg    180
tagggtgcga gcgttaatcg gaattactgg gcgtaaagcg agcgcagacg gttatttaag    240
caggatgtga aatccccggg cttaacctgg gaactgcgtt ctgaactgga tagctagagt    300
gtgtcagagg ggggtagaat tccacgtgta gcagtgaaat gcgtagagat gtggaggaat    360
accgatggcg aaggcagccc cctgggataa cactgacgtt catgctcgaa agcgtgggta    420
gcaaaca                                                              427
```

<210> SEQ ID NO 80
<211> LENGTH: 422
<212> TYPE: DNA
<213> ORGANISM: Tannerella sp.

<400> SEQUENCE: 80

```
tgaggaatat tggtcaatgg gcgagagcct gaaccagcca agtcgcgtga aggatgacgg     60
ccctatgggt tgtaaacttc ttttgcaggg gaataaagat attcacgtgt gggtagttgt    120
atgtaccctg cgaataagca tcggctaact ccgtgccagc agccgcggta atacggagga    180
tgcgagcgtt atccggattt attgggttta aaggggtgcgt aggtgggcta ttaagtcagt    240
ggtgaaagtt tgtcgctcaa cgataaaatt gccgttgaaa ctggtggtct tgagtatgga    300
tgaagtaggc ggaatgcgtg gtgtagcggt gaaatgcata gagatcacgc agaactccga    360
ttgcgaaggc agcttactaa ggcataactg acactgaagc acgaaagcgt gggtatcaaa    420
ca                                                                   422
```

<210> SEQ ID NO 81
<211> LENGTH: 427
<212> TYPE: DNA
<213> ORGANISM: Neisseria sp.

<400> SEQUENCE: 81

```
tggggaattt tggacaatgg gggcaaccct gatccagcca tgccgcgtgt ctgaagaagg     60
ccttcgggtt gtaaaggact tttgtccggg aagaaaagcg cgatgttaat accattgcgt    120
gctgacggta ccggaagaat aagcaccggc taactacgtg ccagcagccg cggtaatacg    180
tagggtgcga gcgttaatcg gaattactgg gcgtaaagcg ggcgcagacg gttacttaag    240
caggatgtga aatccccggg ctcaacctgg gaattgcgtt ctgaactggg tggctagagt    300
gtgtcagagg ggggtagaat tccacgtgta gcagtgaaat gcgtagagat gtggaggaat    360
accgatggcg aaggcagccc cctgggatag cactgacgtt catgcccgaa agcgtgggta    420
gcaaaca                                                              427
```

<210> SEQ ID NO 82
<211> LENGTH: 422
<212> TYPE: DNA
<213> ORGANISM: Prevotella sp.

<400> SEQUENCE: 82

```
tgaggaatat tggtcaatgg gcgagagcct gaaccagcca agtagcgtgc aggacgacgg      60
ccctatgggt tgtaaactgc ttttgtatgg ggataaagtc aatcacgtgt gattgtttgc     120
aggtaccata cgaataagga ccggctaatt ccgtgccagc agccgcggta atacggaagg     180
ttcgggcgtt atccggattt attgggttta aagggagcgt aggccggaga ttaagtgtgt     240
tgtgaaatgt agacgctcaa cgtctgactt gcagcgcata ctggtttcct tgagtacgca     300
caacgttggc ggaattcgtc gtgtagcggt gaaatgctta gatatgacga agaactccga     360
ttgcgaaggc agctgacggg agcgccactg acgcttaagc tcgaaggtgc gggtatcgaa     420
ca                                                                    422
```

<210> SEQ ID NO 83
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      unclassified.Flavobacteriaceae"

<400> SEQUENCE: 83

```
tgaggaatat tggacaatgg gtggaagcct gatccagcca tcccgcgtgc aggacgactg      60
ccctatgggt tgtaaactgc ttttatatag ggataaacct actctcgtga gagtagctga     120
aggtactata tgaataagca ccggctaact ccgtgccagc agccgcggta atacggaggg     180
tgcaagcgtt atccggattt attgggttta aagggtccgt aggtgggctg ataagtcagc     240
ggtgaaatcc tgcagcttaa ctgtagaact gccgttgata ctgttagtct tgagtgtatt     300
tgaagtggct ggaataagta gtgtagcggt gaaatgcata gatattactt agaacaccaa     360
ttgcgaaggc aggtcactaa gatacaactg acgctgaggg acgaaagcgt ggggagcgaa     420
ca                                                                    422
```

<210> SEQ ID NO 84
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 84

```
tgggggatat tgcacaatgg gggaaaccct gatgcagcaa cgccgcgtga gggaagaagg      60
ttttcggatt gtaaacctct gttcttagtg acgataatga cggtagctaa ggagaaagct     120
ccggctaact acgtgccagc agccgcggta atacgtaggg agcgagcgtt gtccggattt     180
actgggtgta aagggtgcgt aggcggcgag gcaagtcagg cgtgaaatct atgggcttaa     240
cccataaact gcgcttgaaa ctgtcttgct tgagtgaagt agaggtaggc ggaattcccg     300
gtgtagcggt gaaatgcgta gagatcggga ggaacaccag tggcgaaggc ggcctactgg     360
gctttaactg acgctgaagc acgaaagcat gggtagcaaa ca                        402
```

<210> SEQ ID NO 85
<211> LENGTH: 402
<212> TYPE: DNA
<213> ORGANISM: Lachnoanaerobaculum sp.

<400> SEQUENCE: 85

```
tggggaatat tggacaatgg gggaaaccct gatccagcga cgccgcgtga gtgaagaagt    60
atttcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgc agacggccaa gcaagtctga agtgaaatgc atgggctcaa   240
cccatgaatt gctttggaaa ctgttaggct tgagtgtcgg aggggtaagc ggaattccta   300
gtgtagcggt gaaatgcgta gatattagga ggaacaccgg aggcgaaggc ggcttactgg   360
acgacaactg acgttgaggc tcgaaggcgt ggggagcaaa ca                      402
```

<210> SEQ ID NO 86
<211> LENGTH: 427
<212> TYPE: DNA
<213> ORGANISM: Selenomonas sp.

<400> SEQUENCE: 86

```
tggggaatct tccgcaatgg gcgcaagcct gacggagcaa cgccgcgtga gtgaagaagg    60
tcttcggatc gtaaagctct gttgatgggg acgaacgtgc ctaatgcgaa tagttttagg   120
caatgacggt acccatcgag gaagccacgg ctaactacgt gccagcagcc gcggtaatac   180
gtaggtggcg agcgttgtcc ggaatcattg ggcgtaaagg gagcgcaggc gggcatgtaa   240
gtctttctta aaagtgcggg gctcaacccc gtgatgggaa agaaactatg tgtcttgagt   300
acaggagagg aaagcggaat cccagtgta gcggtgaaat gcgtagatat gggaggaac    360 accagtggcg aaggcggctt tctggactgc aactgacgct gaggctcgaa agccagggga   420
gcgaacg                                                            427
```

<210> SEQ ID NO 87
<211> LENGTH: 426
<212> TYPE: DNA
<213> ORGANISM: Cardiobacterium sp.

<400> SEQUENCE: 87

```
tggggaatat tggacaatgg ggggaaccct gatccagcaa tgccgcgtgt gtgaagaagg    60
ccttcgggtt gtaaagcact ttcagcaggg aggaaaggtg cgtagttaat agctgcgcaa   120
ttgacgttac ctgcagaaga agcaccggct aactccgtgc cagcagccgc ggtaatacgg   180
agggtgcaag cgttattcgg aattactggg cgtaaagcgc acgcaggcgg ttgcccaagt   240
cagatgtgaa agccccgggc ttaacctggg aactgcattt gaaactgggc gactagagta   300
tgaaagagga aagcggaatt ccagtgtag cagtgaaatg cgtagatatt ggaaggaaca   360
ccgatggcga aggcagcttt ctgggtcgat actgacgctc atgtgcgaaa gcgtggggag   420
caaaca                                                             426
```

<210> SEQ ID NO 88
<211> LENGTH: 422
<212> TYPE: DNA
<213> ORGANISM: Prevotella sp.

<400> SEQUENCE: 88

```
tgaggaatat tggtcaatgg atggaaatct gaaccagcca gtagcgtgca aggatgacgg    60
ccctatgggt tgtaaactgc ttttatgtga gaataaagtt aggtatgtat acttatttgc   120
atgtatcaca tgaataagga ccggctaatt ccgtgccagc agccgcggta atacggaagg   180
tccaggcgtt atccggattt attgggttta aagggtgcgt aggccgtttg ataagcgtgc   240
```

```
tgtgaaatat agtggctcaa cctctatcgt gcagcgcgaa ctgtcgaact tgagtgcgta    300
gtaggtaggc ggaattcgtg gtgtagcggt gaaatgctta gatatcacga agaactccga    360
ttgcgaaggc agcttaccgt aacgttactg acgcttaagc acgaaggtgc gggtatcgaa    420
ca                                                                   422
```

<210> SEQ ID NO 89
<211> LENGTH: 424
<212> TYPE: DNA
<213> ORGANISM: Actinomyces sp.

<400> SEQUENCE: 89

```
tgggggatttt tgcacaatgg gcgcaagcct gatgcagcga cgccgcgtga gggatggagg    60
ccttcgggtt gtgaacctct gtcgccggtg atgtaggctc tgctttgtgg gtggggttga   120
cggtagccgg ggtatgaagt gccggctaac tacgtgccag cagccgcggt aatacgtagg   180
gcgcgagcgt tgtccggaat tattgggcgt aaagagctcg taggcggctg gtcgcgtctg   240
tcgtgaaatc ctctggctta actggggcg tgcggtgggt acgggccggc ttgagtgcgg    300 tagggaggc tggaattcct ggtgtagcgg tggaatgcgc agatatcagg aggaacaccg    360
gtggcgaagg cgggtctctg ggccgtgtac tgacgctgag gagcgaaagc gtggggagcg    420
aaca                                                                 424
```

<210> SEQ ID NO 90
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 90

```
tggggaatat tgcacaatgg ggggaaccct gatgcagcga cgccgcgtga gggaagaagg    60
ttttcggatt gtaaacctct gtccttggtg acgataatga cggtagccaa ggaggaagcc   120
acggctaact acgtgccagc agccgcggta atacgtaggg ggcaagcgtt gtccggaatt   180
actgggtgta aagggagcgt aggcgggaag acaagttggg agtgaaatgt atgggcttaa   240
cccataaact gctttcaaaa ctgttttttct tgagtgaagt agaggcaggc ggaattccta   300
gtgtagcggt gaaatgcgta aatattagga ggaacaccag tggcgaaggc ggcctgctgg   360
gctttaactg acgctgaggc tcgaaagcgt gggtagcaaa ca                       402
```

<210> SEQ ID NO 91
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 91

```
tgagggatat tggcaatggg ggaaaccct gacccagcga cgccgcgtga gggaagacgg    60
tcttcggatt gtaaacctct gtctttgggg acgaaaaagg acggtaccca aggaggaagc   120
tccggctaac tacgtgccag cagccgcggt aatacgtagg gagcgagcgt tgtccggaat   180
tactgggtgt aaagggagcg taggcgggaa ggcaagttgg atgtgaaaac tgtgggctta   240
accgacagac tgcattcaaa actgttttttc ttgagtgaag tagaggcaag cggaattcct   300
```

```
agtgtagcgg tgaaatgcgt agatattagg aggaacacca gtggcgaagg cggcttgctg    360
ggcttttact gacgctgagg ctcgaaagtg tggggagcaa aca                      403

<210> SEQ ID NO 92
<211> LENGTH: 426
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 92
tagggaattt tcggcaatgg gcgaaagcct gaccgagcaa cgccgcgtga gtgaagaagg     60
ccttcgggtt gtaaagctct gttgtgaagg aagaacggct catacaggga atggtatggg   120
agtgacggta ctttaccaga aagccacggc taactacgtg ccagcagccg cggtaatacg   180
taggtggcga gcgttatccg gaattattgg gcgtaaaggg tgcgcaggcg gtttgttaag   240
tttaaggtga aagcgtgggg cttaacccca tatagcctta gaaactgaca gactagagta   300
caggagaggg caatggaatt ccatgtgtag cggtaaaatg cgtagatata tggaggaaca   360
ccagtggcga aggcggttgc ctggcctgta actgacgctc atgcacgaaa gcgtggggag   420
caaata                                                              426

<210> SEQ ID NO 93
<211> LENGTH: 421
<212> TYPE: DNA
<213> ORGANISM: Butyricimonas sp.

<400> SEQUENCE: 93
tgaggaatat tggtcaatgg gcgagagcct gaaccagcca agtcgcgtga gggaagaatg     60
gtctatggcc tgtaaacctc ttttgccagg gaagaataaa aggtacgtgt accttcttgc   120
cagtacctga cgaataagca tcggctaact ccgtgccagc agccgcggta atacggggga   180
tgcgagcgtt atccggattt attgggttta aagggcgcgt aggcgggacg ccaagtcagc   240
ggtaaaagac tgcagctaaa ctgtagcacg ccgttgaaac tggcgacctg agacgagac   300 gagggaggcg gaacaagtga agtagcggtg aaatgcttag atatcacttg gaaccccgat   360
agcgaaggca gcttcccagg ctcgatctga cgctgatgcg cgagagcgtg ggtagcgaac   420
a                                                                   421

<210> SEQ ID NO 94
<211> LENGTH: 408
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 94
tagggaattt tcggcaatgg acggaagtct gaccgagcaa cgccgcgtga atgatgaagt     60
atttcggtat gtaaagttct tttatttggg aagaaaaaac aaattgacgg taccaaatga   120
ataagccccg gctaactacg tgccagcagc cgcggtaata cgtaggggc aagcgttatc    180 cggaattatt gggcgtaaag ggtgcgtagg cgggttatca agtctttggt taaaatgcgg   240
tgctcaacgc cgtagtgcca aagaaactga tagtctagag tatggtagaa gtgagtggaa   300
```

```
ctccatgtgt agcggtaaaa tgcgtaaata tatggaagaa caccagtggc gaaggcggct    360
cactaggcca atactgacgc tgagacacga aagcgtgggg agcaaaca                 408

<210> SEQ ID NO 95
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      unclassified.Clostridiales"

<400> SEQUENCE: 95
tggggaatat tgggcaatgg gggaaaccct gacccagcaa cgccgcgtgg aggaagaagg     60
tcttcggatt gtaaactcct gtccttaggg aagaaacaaa tgacggtacc tgaggaggaa    120
gctccggcta actacgtgcc agcagccgcg gtaatacgta gggagcgagc gttgtccgga    180
attactgggc gtaagggtg cgtaggcggt ctgaaaagtc ggatgtgaaa tccccgtgct    240
taacatggga gctgcattcg aaactttcgg acttgagtgt cggagaggta agcggaattc    300
ccggtgtagc ggtgaaatgc gtagatatcg gaggaacac cagtggcgaa ggcggcttac    360
tggacgacaa ctgacgctga ggcacgaaag cgtgggagc aaaca                    405

<210> SEQ ID NO 96
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 96
tggggaatat tgggcaatgg agggaactct gacccagcaa cgccgcgtga gtgaagaagg     60
ttttcggatt gtaaaactct ttaagcgggg acgaagaaag tgactgtacc cgcagaataa    120
gcatcggcta actacgtgcc agcagccgcg gtaatacgta ggatgcaagc gttatccgga    180
atgactgggc gtaagggtg cgtaggtggt ttgccaagtt ggcagcgtaa ttccgtggct    240
taaccgcgga actactgcca aaactggtag gcttgagtgc ggcaggggta tgtggaattc    300
ctagtgtagc ggtggaatgc gtagatatta ggaggaacac cggtggcgaa agcgacatac    360
tgggccgtaa ctgacactga ggcacgaaag cgtggggagc aaaca                   405

<210> SEQ ID NO 97
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 97
tggggaatat tgggcaatgg acgcaagtct gacccagcaa cgccgcgtga aggaagaagg     60
ctttcgggtt gtaaacttct tttgtcaggg aacagtagaa gagggtacct gacgaataag    120
ccacggctaa ctacgtgcca gcagccgcgg taatacgtag gtggcaagcg ttgtccggat    180
ttactgggtg taaagggcgt gcagccgggc tggcaagtca ggcgtgaaat cccagggctc    240
aaccctggaa ctgcgtttga aactgctggt cttgagtacc ggagaggtca tcggaattcc    300
ttgtgtagcg gtgaaatgcg tagatataag gaagaacacc agtggcgaag gcggatgact    360
```

```
ggacggcaac tgacggtgag gcgcgaaagc gtggggagca aaca              404
```

<210> SEQ ID NO 98
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 98

```
tgggggatat tgcacaatgg aggaaactct gatgcagcaa cgccgcgtga gggaagaagg    60
ttttcggatt gtaaacctct gtttttagtg aagaaacaaa tgacggtagc taaagaggaa   120
gccacggcta actacgtgcc agcagccgcg gtaatacgta ggtggcaagc gttgtccgga   180
attactgggt gtaaagggtg cgcaggcggg attgcaagtt ggatgtgaaa taccggggct   240
taaccccgga gctgcatcca aaactgtagt tcttgagtgg agtagaggta agcggaattc   300
cgagtgtagc ggtgaaatgc gtagatattc ggaggaacac cagtggcgaa ggcggcttac   360
tgggctctaa ctgacgctga ggcacgaaag catgggtagc aaaca                  405
```

<210> SEQ ID NO 99
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 99

```
tggggaattt tgcgcaatgg gggcaaccct gacgcagcga cgccgcgtgc gggacgaagt    60
cattcgtgac gtaaaccgct ttcagcgagg aagaaccatg acggtactcg cagaagaagc   120
cccggctaac tacgtgccag cagccgcggt aatacgtagg gggcgagcgt tatccggaat   180
cattgggcgt aaagcgcgcg caggcgggct ttcaagcggc ggcgtcgaag ccggggggctc   240 aaccccgga agcgccccga actggaagcc tcggatgcgg caggggagg cggaattccc   300 ggtgtagcgg tgaaatgcgc agatatcggg aagaacaccg acggcgaagg cagcctcctg   360
ggccggcatc gacgctgagg cgcgaaagct ggggagcga aca                    403
```

<210> SEQ ID NO 100
<211> LENGTH: 422
<212> TYPE: DNA
<213> ORGANISM: Prevotella sp.

<400> SEQUENCE: 100

```
tgaggaatat tggtcaatgg gcgtgagcct gaaccagcca agtagcgtgc aggatgacgg    60
ccctatgggt tgtaaactgc ttttatacgg gataaaagg gtgaacgtgt tctcctttgc   120
aggtaccgta tgaataagga ccggctaatt ccgtgccagc agccgcggta atacggaagg   180
tcctggcgtt atccggattt attgggttta aagggagcgc aggctgcact ttaagcgtgt   240
tgtgaaatgt accggctcaa ccggtaacgt gcagcgcgaa ctgggtgct tgagtacgaa   300 gagggaaggc ggaactcgtg gtgtagcggt gaaatgctta gatatcacga ggaactccga   360
tcgcgaaggc agctttccgt ttcggaactg acgctgaggc tcgaaagtgc gggtatcgaa   420
ca                                                                422
```

<210> SEQ ID NO 101
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 101
tgggggatat tgcacaatgg gcgaaagcct gatgcagcga cgccgcgtga gggaagacgg     60
ccttcgggtt gtaaacctct gtcattcggg acgaattaga tgacggtacc gaagaaggaa    120
gctccggcta actacgtgcc agcagccgcg gtaatacgta gggagcgagc gttgtccgga    180
attactgggt gtaaagggag cgtaggcggg aaagcaagtt ggaagtgaaa tgcatgggct    240
taacccatga gctgctttca aaactgtttt tcttgagtga agtagaggca ggcggaattc    300
ctagtgtagc ggtgaaatgc gtagatatta ggaggaacac cagtggcgaa ggcggcctgc    360
tgggctttaa ctgacgctga ggctcgaaag cgtgggtagc aaaca                    405

<210> SEQ ID NO 102
<211> LENGTH: 402
<212> TYPE: DNA
<213> ORGANISM: Gemmiger sp.

<400> SEQUENCE: 102
tgggggatat tgcacaatgg gggaaaccct gatgcagcga cgccgcgtgg aggaagaagg     60
ttttcggatt gtaaactcct gtcgttaggg acgataatga cggtacctaa caagaaagca    120
ccggctaact acgtgccagc agccgcggta aacgtaggg tgcaagcgtt gtccggaatt    180
actgggtgta aagggagcgc aggcgggaag acaagttgga agtgaaaacc atgggctcaa    240
cccatgaatt gctttcaaaa ctgttttgct tgagtagtgc agaggtagat ggaattcccg    300
gtgtagcggt ggaatgcgta gatatcggga ggaacaccag tggcgaaggc ggtctactgg    360
gcaccaactg acgctgaggc tcgaaagcat gggtagcaaa ca                      402

<210> SEQ ID NO 103
<211> LENGTH: 422
<212> TYPE: DNA
<213> ORGANISM: Prevotella sp.

<400> SEQUENCE: 103
tgaggaatat tggtcaatgg gcgagagcct gaaccagcca agtagcgtgc aggatgacgg     60
ccctatgggt tgtaaactgc ttttatgcgg ggataaagtg agggacgtgt ccttcattgc    120
aggtaccgca tgaataagga ccggctaatt ccgtgccagc agccgcgta atacggaagg    180 tccgggcgtt atccggattt attgggttta aagggagcgt aggccgtgga ttaagcgtgt    240
tgtgaaatgc aggtgctcaa cgtctgcact gcagcgcgaa ctggtccact tgagtgtgcg    300
caacgcaggc ggaattcgtc gtgtagcggt gaaatgctta gatatgacga agaactccga    360
ttgcgaaggc agcttgcggg agcacaactg acgctgaagc tcgaaagtgc gggtatcgaa    420
ca                                                                  422

<210> SEQ ID NO 104
<211> LENGTH: 427
<212> TYPE: DNA
<213> ORGANISM: Selenomonas sp.

<400> SEQUENCE: 104

```
tggggaatct tccgcaatgg gcgcaagcct gacggagcaa cgccgcgtga gtgaagaagg      60
tcttcggatc gtaaagctct gttgatgggg acgaacgtgc gaagggtgaa taatcctttg     120
caatgacggt acctatcgag gaagccacgg ctaactacgt gccagcagcc gcggtaatac     180
gtaggtggcg agcgttgtcc ggaatcattg ggcgtaaagg gagcgcaggc gggcatgtaa     240
gtctttctta aaagttcggg gctcaacccc gtgatgggaa agaaactaca tgtcttgagt     300
acaggagagg aaagcggaat tcccagtgta gcggtgaaat gcgtagatat gggaggaac      360 accagtggcg aaggcggctt tctggactgc aactgacgct gaggctcgaa agccagggga     420
gcgaacg                                                                427
```

<210> SEQ ID NO 105
<211> LENGTH: 427
<212> TYPE: DNA
<213> ORGANISM: Veillonella sp.

<400> SEQUENCE: 105

```
tggggaatct tccgcaatgg acgaaagtct gacggagcaa cgccgcgtga gtgatgacgg      60
ccttcgggtt gtaaagctct gttaatcggg acgaatggtt cttgtgcgaa tagtgcgagg    120
atttgacggt accggaatag aaagccacgg ctaactacgt gccagcagcc gcggtaatac     180
gtaggtggca agcgttgtcc ggaattattg ggcgtaaagc gcgcgcaggc ggatcagtta     240
gtctgtctta aaagttcggg gcttaacccc gtgatgggat ggaaactgct gatctagagt     300
atcggagagg aaagtggaat tcctagtgta gcggtgaaat gcgtagatat taggaagaac     360
accagtggcg aaggcgactt tctggacgaa aactgacgct gaggcgcgaa agccagggga    420
gcgaacg                                                                427
```

<210> SEQ ID NO 106
<211> LENGTH: 402
<212> TYPE: DNA
<213> ORGANISM: Dorea sp.

<400> SEQUENCE: 106

```
tggggaatat tgcacaatgg gcgaaagcct gatgcagcga cgccgcgtga aggatgaagt      60
atttcggtat gtaaacttct atcagcaggg aagaaaatga cggtacctga ctaagaagcc    120
ccggctaact acgtgccagc agccgcggta atacgtaggg gcaagcgtt  atccggattt    180 actgggtgta aagggagcgt agacggctgt gcaagtctga agtgaaaggc atgggcgcaa     240
cctgtggact gctttggaaa ctgtgcagct agagtgtcgg agaggtaagt ggaattccta     300
gtgtagcggt gaaatgcgta gatattagga ggaacaccag tggcgaaggc ggcttactgg     360
acgatgactg acgttgaggc tcgaaagcgt ggggagcaaa ca                         402
```

<210> SEQ ID NO 107
<211> LENGTH: 422
<212> TYPE: DNA
<213> ORGANISM: Prevotella sp.

<400> SEQUENCE: 107

```
tgaggaatat tggtcaatgg gcggaagcct gaaccagcca gtagcgtgc  aggatgacgg      60 ccctacgggt tgtaaactgc ttttatgcgg ggataaagtg agggacgcgt cccttttgc     120 aggtaccgca tgaataagga ccggctaatt ccgtgccagc agccgcggta atacggaagg     180
tccgggcgtt atccggattt attgggttta aagggagcgt aggccgggga ttaagtgtgt     240
```

-continued

```
tgtgaaatgt aggcgcccaa cgtctgactt gcagcgcata ctggttccct tgagtacgcg    300
caacgccggc ggaattcgtc gtgtagcggt gaaatgctta gatatgacga agaaccccga    360
ttgcgaaggc agccggcggg agcgcaactg acgctgaagc tcgaaggtgc gggtatcgaa    420
ca                                                                   422
```

<210> SEQ ID NO 108
<211> LENGTH: 427
<212> TYPE: DNA
<213> ORGANISM: Selenomonas sp.

<400> SEQUENCE: 108

```
tggggaatct tccgcaatgg gcgcaagcct gacggagcaa cgccgcgtga gtgaagaagg     60
tcttcggatc gtaaagctct gttgaagggg acgaacgatc gagggggcgaa caggctctcg   120 gtatgacggt acctttgag gaagccacgg ctaactacgt gccagcagcc gcggtaatac    180
gtaggtggcg agcgttgtcc ggaatcattg ggcgtaaagg gagcgcaggc ggccatgtaa    240
gtcttgctta aaagttcggg gctcaacccc gtgatgggca agaaactata tggcttgagt    300
gcaggagagg aaagcggaat tcccagtgta gcggtgaaat gcgtagatat tgggaggaac    360
accagtggcg aaggcggctt tctggactgc aactgacgct gaggctcgaa agccagggga    420
gcgaacg                                                              427
```

<210> SEQ ID NO 109
<211> LENGTH: 404
<212> TYPE: DNA
<213> ORGANISM: Unknown
<220> FEATURE:
<221> NAME/KEY: source
<223> OTHER INFORMATION: /note="Description of Unknown:
       Bacterial sequence"

<400> SEQUENCE: 109

```
tggggaatat tgggcaatgg gcgaaagcct gacccagcga cgccgcgtga aggatgaagg     60
tcttcggatt gtaaacttct gtctacaggg acgaacaaat gacggtacct gtaaagaaag   120
ccacggctaa ctacgtgcca gcagccgcgg taatacgtag gtggcaagcg ttatccggat   180
ttactgggtg taagggtgt gtaggcggga agccaagtca gatgtgaaaa tcatgggctc    240
aactcatgac ttgcatttga aactggtttt cttgagtatg ggagaggtaa atggaattcc    300
cggtgtagcg gtgaaatgcg tagatatcgg gaggaacacc agtggcgaag gcggtttact   360
ggaccacaac tgacgctgat acacgaaagc gtgggagca aaca                      404
```

<210> SEQ ID NO 110
<211> LENGTH: 404
<212> TYPE: DNA
<213> ORGANISM: Lachnoanaerobaculum sp.

<400> SEQUENCE: 110

```
tggggaatat tggacaatgg gggcaaccct gatccagcga cgccgcgtga gtgaagaagt     60
atttcggtat gtaaagctct atcgataacg gaagaagatg acaagccgtt aaggaagaag   120
ccccggctaa ctacgtgcca gcagccgcgg taatacgtag gggcaagcg ttatccggat    180 ttactgggtg taagggagc gtagacggcg aataaagtct gaagtgaaat cccgcagctc    240
aactgcggag ttgctttgga aacttataag ctggagtgtc ggaggggtaa gcggaattcc    300
cagtgtagcg gtgaaatgcg tagatattgg gaggaacacc ggaggcgaag gcggcttact   360
ggaagataac tgacgttgag gctcgaaggc gtgggtagca aaca                     404
```

<210> SEQ ID NO 111
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 111
tgggggatat tgcacaatgg gggaaaccct gatgcagcaa cgccgcgtga aggaagaagg      60
tcttcggatt gtaaactttt gtcctcagtg aagataatga cggtagctga ggaggaagct    120
ccggctaact acgtgccagc agccgcggta atacgtaggg agcgagcgtt gtccggattt    180
actgggtgta aagggtgcgt aggcggactg gcaagtcagt ggtgaaaact atgggcttaa    240
cccatagact gccattgaaa ctgttggtct tgagtgaagt agaggtaggc ggaattcccg    300
gtgtagcggt gaaatgcgta gagatcggga ggaacaccag tggcgaaggc ggcctactgg    360
gctttaactg acgctgaggc acgaaagtgt gggtagcaaa ca                       402

<210> SEQ ID NO 112
<211> LENGTH: 422
<212> TYPE: DNA
<213> ORGANISM: Tannerella sp.

<400> SEQUENCE: 112
tgaggaatat tggtcaatgg gcgagagcct gaaccagcca gtcgcgtga aggatgactg       60 ccctatgggt tgtaaacttc ttttacaggg gaataaaatg agatacgtgt attttattgc    120
atgtaccttg tgaataagca tcggctaact ccgtgccagc agccgcgta atacggagga     180 tgcgagcgtt atccggattt attgggttta aagggtgcgt aggtgggctg ttaagtccgc    240
ggtgaaagtt tgtcgcttaa cgataaaatt gccgttgaaa ctggtagtct tgagtataga    300
tgaagtaggc ggaatgcgtg gtgtagcggt gaaatgcata gagatcacgc agaactccga    360
ttgcgaaggc agcttactaa ggtataactg acactgaagc acgaaagcgt gggtatcaaa    420
ca                                                                   422

<210> SEQ ID NO 113
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 113
tggggaatct tgcacaatgg gcgaaagcct gatgcagcaa cgccgcgtga gcgaagaagg      60
cctttgggtc gtaaagctct gtcggtaggg aagaaggaag tgacggtacc taccgaggaa    120
gccccggcta actacgtgcc agcagccgcg gtaatacgta gggggcgagc gttatccgga    180
attattgggc gtaaagagta cgtaggcggt tttttaagcg aggggtataa ggcagcggct    240
taactgctgt tggccccctcg aactggagga cttgagtgtc ggagaggaaa gcggaattcc    300
tagtgtagcg gtgaaatgcg tagagattag gaggaacacc agtggcgaag cggctttct    360 ggacgacaac tgacgctgag gtacgaaagc gtggggagca aaca                    404

<210> SEQ ID NO 114

```
<211> LENGTH: 420
<212> TYPE: DNA
<213> ORGANISM: Unknown
<220> FEATURE:
<221> NAME/KEY: source
<223> OTHER INFORMATION: /note="Description of Unknown:
      unclassified.Porphyromonadaceae"

<400> SEQUENCE: 114
tgaggaatat tggtcaatgg acgagagtct gaaccagcca agtcgcgtga aggaagacgg      60
atctatggtt tgtaaacttc tttagtgcgg gaacaaagcg gcgtcgtgac gccggatgag     120
tgtaccgcaa gaataagcat cggctaactc cgtgccagca gccgcggtaa tacgaggat     180 gcgagcgtta tccggattta tgggtttaa agggagcgca ggctgcgagg caagtcagcg     240
gtcaaatgtc ggggctcaac cccggcctgc cgttgaaact gtcctgctag agttcgagtg    300
aggtatgcgg aatgcgttgt gtagcggtga aatgcataga tatgacgcag aactccgatt    360
gcgaaggcag cataccaact cgcgactgac gctgaggctc gaaagcgtgg gtatcgaaca    420

<210> SEQ ID NO 115
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 115
tagggaatat tgggcaatgg gcgaaagcct gacccagcaa cgccgcgtga aggaagaagg     60
tcttcggatt gtaaactttt gttgtcaggg aagaagaagg acagtacctg acgaggaagc    120
cccggctaac tacgtgccag cagccgcggt aatacgtagg gggcgagcgt tgtccggaat    180
tactgggcgt aaagggcgcg taggcggcat attaagttag atgtgaaatt cccgggctta    240
acctgggcgt tgcatttaaa actgataagc ttgagtgccg gagaggaaag cggaattcct    300
agtgtagcgg tgaaatgcgt agatattagg aggaacatca gtggcgaagg cggctttctg    360
gacggtaact gacgctgagg cgcgaaagcg tgggtagcaa aca                      403

<210> SEQ ID NO 116
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 116
tggggaatat tgcacaatgg gggaaaccct gatgcagcga cgccgcgtga aggaagaagt     60
atttcggtat gtaaacttct atcagcaggg aagaaagtga cagtacctga ctaagaagcc    120
ccggctaact acgtgccagc agccgcggta atacgtaggg ggcaagcgtt atccggattt    180
actgggtgta aagggagcgt aggtggcgat gcaagccaga agtgaaaacc ggggctcaa    240 ccccgaggac tgcttttgga actgtgttgc tggagtgcag gagaggtaag tggaattcct   300
agtgtagcgg tgaaatgcgt agatattagg aggaacaccg gtggcgaagg cggcttactg   360
gactgtaact gacactgagg ctcgaaagcg tggggagcaa aca                     403

<210> SEQ ID NO 117
<211> LENGTH: 427
```

```
<212> TYPE: DNA
<213> ORGANISM: Abiotrophia sp.

<400> SEQUENCE: 117
tagggaatct tccgcaatgg acgcaagtct gacggagcaa cgccgcgtga gtgaagaagg      60
tcttcggatc gtaaagctct gttgttagag aagaacagcg catagagtaa ctgctatgcg     120
tgtgacggta tctaaccaga aagccacggc taactacgtg ccagcagccg cggtaatacg     180
taggtggcga gcgttgtccg gatttattgg gcgtaaaggg agtgtaggcg gtcttttaag     240
tctgatgtga aagcccacgg ctcaaccgtg gagggtcatt ggaaactggg agacttgagt     300
gcagaagagg agagcggaat tccatgtgta gcggtgaaat gcgtagatat atggaggaac     360
accagtggcg aaggcggctc tctggtctgt aactgacgct gaggctcgaa agcgtgggga     420
gcaaaca                                                               427

<210> SEQ ID NO 118
<211> LENGTH: 427
<212> TYPE: DNA
<213> ORGANISM: Treponema sp.

<400> SEQUENCE: 118
ctaagaatat tccgcaatgg acggaagtct gacggagcga cgccgcgtgg atgaagaagg      60
ctgaaaagtt gtaaaatcct tttgttgatg aagaataagg gtgagaggga atgctcatct     120
gatgacggta atcgacgaat aagccccggc taattacgtg ccagcagccg cggtaacacg     180 taagggcga gcgttgttcg gaattattgg gcgtaaaggg catgtaggcg gctatgtaag     240
cctgatgtga aatcctgggg cttaacccta gaatagcatt gggtactgta tagcttgaat     300
tacgaaaggg aaactggaat tccaagtgta ggggtggaat ctgtagatat ttggaagaac     360
accggtggcg aaggcgggtt tctggccgat aattgacgct gagatgcgaa agtgtgggga     420
tcgaaca                                                               427

<210> SEQ ID NO 119
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 119
tggggaatat taggcaatgg gcgaaagcct gacctagcga cgccgcgtga gggaagacgg      60
tcttcggatt gtaaacctct gtcttcaggg acgaagaaga tgacggtacc tgaagaggaa     120
gccacggcta actacgtgcc agcagccgcg gtaatacgta ggtggcgagc gttgtccgga     180
attactgggt gtaagggag cgtaggcggg tacgcaagtt gaatgtgaaa actaacggct     240
caaccgatag ttgcgttcaa aactgcggat cttgagtgaa gtagaggcag gcggaattcc     300
tagtgtagcg gtaaaatgcg tagatattag gaggaacacc agtggcgaag gcggcctgct     360
gggctttaac tgacgctgag gctcgaaagt gtggggagca aaca                      404

<210> SEQ ID NO 120
<211> LENGTH: 419
<212> TYPE: DNA
<213> ORGANISM: Actinomyces sp.

<400> SEQUENCE: 120
```

```
tggggaatat tgcacaatgg gcgcaagcct gatgcagcga cgccgcgtga gggatggagg      60
ccttcgggtt gtgaacctct ttcgcccgtg gtcaagccgc gacgtgggtc gtggtgaggg    120
tagtgggtaa agaagcgccg gctaactacg tgccagcagc cgcggtaata cgtagggcgc    180
gagcgttgtc cggaattatt gggcgtaaag gcttgtagg cggctggtcg cgtctgccgt     240
gaaatcctct ggctcaactg ggggcgtgcg gtgggtacgg gctggcttga gtgcggtagg    300
ggaggctgga actcctggtg tagcggtgga atgcgcagat atcaggaaga acaccggtgg    360
cgaaggcggg tctctgggcc gttactgacg ctgaggagcg aaagcgtggg gagcgaaca    419
```

<210> SEQ ID NO 121
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 121

```
tggggaatat tgcacaatgg ggggaaccct gatgcagcaa cgccgcgtga gtgaagaagt     60
atttcggtat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgc aggcggtctg gcaagtctga tgtgaaatcc cggggctcaa    240
ctccggaatt gcattggaaa ctgtcagact agagtgccgg agaggtaagt ggaattccta    300
gtgtagcggt gaaatgcgta gatattagga ggaacaccag tggcgaaggc ggcttactgg    360
acggtaactg acgctgaggc tcgaaagcgt ggggagcaaa ca                       402
```

<210> SEQ ID NO 122
<211> LENGTH: 426
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 122

```
tagggaattt tcggcaatgg gcgaaagcct gaccgagcaa cgccgcgtga aggaagaagt     60
cattcgtgat gtaaacttct gttatgaagg aagaacggca gatggaggga atgccatgtg    120
cgtgacggta cttcatgagg aagccacggc taactacgtg ccagcagccg cggtaatacg    180
taggtggcga gcgttatccg gaatcattgg gcgtaaagag ggagcaggcg gcagtgcagg    240
tctgcggtga agaccggag ctaaacttcg gtaagccgtg gaaaccgcac agctagagag    300
catcagagga tcgcggaatt ccatgtgtag cggtgaaatg cgtagatata tggaggaaca    360
ccagtggcga aggcggcggt ctggggtgca gctgacgctc agtcccgaaa gcgtggggag    420
caaata                                                                426
```

<210> SEQ ID NO 123
<211> LENGTH: 402
<212> TYPE: DNA
<213> ORGANISM: Lachnoanaerobaculum sp.

<400> SEQUENCE: 123

```
tggggaatat tggacaatgg gggaaccct gatccagcga cgccgcgtga gtgaagaagt      60
atttcggtat gtaaagctct atcagcaggg aagaaaatga cggtacctga ctaagaagcc    120
```

```
ccggctaact acgtgccagc agccgcggta atacgtaggg ggcaagcgtt atccggattt      180
actgggtgta aagggagcgt agacggcgat gtaagtctga agtgaaagcc cacggctcaa      240
ctgtgggact gctttggaaa ctatatagct agagtatcgg aggggcaagc ggaattccta      300
gtgtagcggt gaaatgcgta gatattagga ggaacaccgg aggcgaaggc ggcttgctgg      360
acgaagactg acgttgaggc tcgaaggcgt ggggagcaaa ca                         402
```

```
<210> SEQ ID NO 124
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      unclassified.Candidatus_Saccharibacteria"

<400> SEQUENCE: 124
```

```
tgaggaatct tccacaatgg gcgaaagcct gatggagcaa cgccgcgtgc aggacgaagg      60
ccttcgggtt gtaaactgct tttataagtg aggaatatga cggtaactta tgaataagga     120
tcggctaact acgtgccagc agccgcggtc atacgtagga tccgagcgtt atccggagtg     180
actgggcgta aagagttgcg taggcggttg tataagtgaa tagtgaaatc tggtggctca     240
accatacagg ctattgttca aactgtacaa cttgagagtg gtagaggtca ctggaatttc     300
ttgtgtagga gtgaaatccg tagatataag aaggaacacc aatggcgtag gcaggtgact     360
ggaccatttc tgacgctaag gcacgaaagc gtggggagcg aacc                      404
```

```
<210> SEQ ID NO 125
<211> LENGTH: 426
<212> TYPE: DNA
<213> ORGANISM: Schwartzia sp.

<400> SEQUENCE: 125
```

```
tggggaatct tccgcaatgg gcgaaagcct gacggagcaa cgccgcgtga gtgaagaagg      60
tcttcggatc gtaaagctct gttgtcgggg acgaaagagt agacgaggaa atgcgtctac     120
taagacggta cctgacgagg aagccacggc taactacgtg ccagcagccg cggtaatacg     180
taggcggcaa cgttgtccg gaattattgg gcgtaagggagcgcaggtg ggacggtaag        240 tccgtcttaa aaggcagggg ctcagcccct gtaagggatg gaaactatcg atcttgagtg     300
ccggagagga aagcggaatt cccagtgtag cggtgaaatg cgtagatatt gggaagaaca     360
ccagtggcga aggcggcttt ctggacggca actgacactg aggctcgaaa gccaggggag     420
cgaacg                                                                426
```

```
<210> SEQ ID NO 126
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 126
```

```
tggggaatat tgggcaatgg gggaaaccct gacccagcaa cgccgcgtga aggaagaagg      60
ccctcgggtt gtaaacttct tttaccaggg acgaaggaag tgacggtacc tggagaaaaa     120
gccacggcta actacgtgcc agcagccgcg gtaatacgta ggtggcaagc gttgtccgga     180
```

```
tttactgggt gtaaagggcg tgtaggcggg actgcaagtc tgatgtgtaa tctggtggct    240
caaccaccaa actgcattgg aaactgtagt tcttgagtat cggagaggca ggcggaattc    300
ctagtgtagc ggtgaaatgc gtagatatta ggaagaacac cagtggcgaa ggcggcctgc    360
tggacgacaa ctgacgctga ggcgcgaaag cgtggggagc aaaca                   405
```

<210> SEQ ID NO 127
<211> LENGTH: 405
<212> TYPE: DNA
<213> ORGANISM: Leptotrichia sp.

<400> SEQUENCE: 127

```
tggggaatat tggacaatgg agggaactct gatccagcaa ttctgtgtgc atgaagaagg     60
ttttcggatt gtaaagtgct ttcagcaggg aagaagaaag tgacggtacc tgcagaagaa    120
gcgacggcta aatacgtgcc agcagccgcg gtaatacgta tgtcgcgagc gttatccgga    180
attattgggc ataaagggca tctaggcggc acgacaagtc aggggtgaaa acttgcggct    240
caactgcaag cttgcctttg aaactgtagt gctagatgat tggaaaggtg gcggaacta     300 cacgagtaga ggtgaaattc gtagatatgt gtaggaatgc cgatgatgaa gatagctcac    360
tggacgataa ctgacgctga agtgcgaaag ctaggggagc gaaca                   405
```

<210> SEQ ID NO 128
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 128

```
tggggaatat tgcacaatgg gggaaaccct gatgcagcga cgccgcgtga gggaagaagg     60
ttttcggatt gtaaacctct gtcttcaggg acgatagtga cggtacctga ggaggaagct    120
ccggctaact acgtgccagc agccgcggta atacgtaggg agcgagcgtt gtccggaatt    180
actgggtgta aagggagcgt aggcgggaca gcaagttgaa tgtgaaatct atgggctcaa    240
cccataaact gcgttcaaaa ctgttgttct tgagtgaagt agaggtaggc ggaattccta    300
gtgtagcggt gaaatgcgta gatattagga ggaacaccag tggcgaaggc ggcctactgg    360
gctttaactg acgctgaggc tcgaaagcgt gggtagcaaa ca                       402
```

<210> SEQ ID NO 129
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 129

```
tggggaatat tgggcaatgg gcgcaagcct gacccagcaa cgccgcgtga aggaagaagg     60
ctttcgggtt gtaaacttct tttctcaggg acgaaacaaa tgacggtacc tgaggaataa    120
gccacggcta actacgtgcc agcagccgcg gtaatacgta ggtggcaagc gttatccgga    180
tttactgggt gtaaagggcg tgtaggcggg cgagcaagtc agatgtgaaa ttccagggct    240
caaccctgga actgcatttg aaactgttgg tcttgagtgc tggagaggca atcggaattc    300
cgtgtgtagc ggtgaaatgc gtagatatac ggaggaacac cagtggcgaa ggcggattgc    360
```

```
tggacagtaa ctgacgctga ggcgcgaaag cgtggggagc aaaca            405
```

<210> SEQ ID NO 130
<211> LENGTH: 422
<212> TYPE: DNA
<213> ORGANISM: Unknown
<220> FEATURE:
<221> NAME/KEY: source
<223> OTHER INFORMATION: /note="Description of Unknown:
    Bacterial sequence"

<400> SEQUENCE: 130

```
tgaggaatat tggtcaatgg acgagagtct gaaccagcca agtagcgtgc aggaagacgg     60
ccctatgggt tgtaaactgc ttttataagg gaataaagtg agtctcgtga gacttttttgc   120
atgtacctta tgaataagga ccggctaatt ccgtgccagc agccgcggta atacggaagg   180
tccgggcgtt atccggattt attgggttta aagggagcgt agatggatgt ttaagtcagt   240
tgtgaaagtt tgcggctcaa ccgtaaaatt gcagttgata ctggatatct tgagtgcagt   300
tgaggcaggc ggaattcgtg tgtagcggt gaaatgctta gatatcacga agaactccga   360
ttgcgaaggc agctcactgg agcgcaactg acgctgaagc tcgaaagtgc gggtatcgaa   420
ca                                                                  422
```

<210> SEQ ID NO 131
<211> LENGTH: 402
<212> TYPE: DNA
<213> ORGANISM: Clostridium sp.

<400> SEQUENCE: 131

```
tggggaatat tgcacaatgg gggaaaccct gatgcagcaa cgccgcgtga gtgaagaagt     60
atttcggtat gtaaagctct atcagcagga agaaaatga cggtacctga ctaagaagcc   120
ccggctaact acgtgccagc agccgcggta atacgtaggg ggcaagcgtt atccggattt   180
actgggtgta aagggagcgt agacggcatg gcaagtctga agtgaaatgc ggggctcaa   240
cccctgaact gctttggaaa ctgtcaggct ggagtgcagg agaggtaagt ggaattccta   300
gtgtagcggt gaaatgcgta gatattagga ggaacaccag tggcgaaggc ggcttactgg   360
actgtaactg acgttgaggc tcgaaagcgt ggggagcaaa ca                     402
```

<210> SEQ ID NO 132
<211> LENGTH: 402
<212> TYPE: DNA
<213> ORGANISM: Unknown
<220> FEATURE:
<221> NAME/KEY: source
<223> OTHER INFORMATION: /note="Description of Unknown:
    Bacterial sequence"

<400> SEQUENCE: 132

```
tggggaatat tgcacaatgg gggaaaccct gatgcagcga cgccgcgtga gtgaagaagt     60
atttcggtat gtaaagctct atcagcaggg agaaaatga cggtacctga ctaagaagcc   120
ccggctaact acgtgccagc agccgcggta atacgtaggg ggcaagcgtt atccggattt   180
actgggtgta aagggagcgt aggtggtagt gcaagtcaga agtgaaaacc caaggcttaa   240
ccatgggatt gcttttgaaa ctgcataact agagtgctgg agaggtaagt ggaattccta   300
gtgtagcggt gaaatgcgta gatattagga ggaacaccgg tggcgaaggc ggcttactgg   360
acagtaactg acactgaggc tcgaaagcgt ggggagcaaa ca                     402
```

<210> SEQ ID NO 133
<211> LENGTH: 405
<212> TYPE: DNA
<213> ORGANISM: Leptotrichia sp.

<400> SEQUENCE: 133

| | | |
|---|---|---|
| tggggaatat tggacaatgg gggcaaccct gatccagcaa ttctgtgtgc acgatgaagg | 60 |
| tcttcggatt gtaaagtgct ttcagcaggg aagaaagaaa tgacggtacc tgcagaagaa | 120 |
| gcgacggcta aatacgtgcc agcagccgcg gtaatacgta tgtcgcgagc gttatccgga | 180 |
| attattgggc ataaagggca tctaggcggc cggataagtc tggggtgaaa acttgcggct | 240 |
| caaccgcaag cctgccctgg aaactatgcg gctagagtac tggagaggtg gacggaactg | 300 |
| cacgagtaga ggtgaaattc gtagatatgt gcaggaatgc cgatgatgaa gatagttcac | 360 |
| tggacggtaa ctgacgctga agtgcgaaag ctaggggagc aaaca | 405 |

<210> SEQ ID NO 134
<211> LENGTH: 402
<212> TYPE: DNA
<213> ORGANISM: Unknown
<220> FEATURE:
<221> NAME/KEY: source
<223> OTHER INFORMATION: /note="Description of Unknown: unclassified.Lachnospiraceae"

<400> SEQUENCE: 134

| | | |
|---|---|---|
| tggggaatat tgcacaatgg gggaaaccct gatgcagcaa cgccgcgtga gtgaagaagt | 60 |
| atttcggtat gtaaagctct atcagcaggg aagaaagtga cggtacctga ctaagaagcc | 120 |
| ccggctaact acgtgccagc agccgcggta atacgtaggg ggcaagcgtt atccggattt | 180 |
| actgggtgtg aagggagcgt agacggcaca gcaagtctga agtgaaatcc ccgggctcaa | 240 |
| cccgggaact gctttggaaa ctgttgggct ggagtgctgg agaggcaagc ggaattccta | 300 |
| gtgtagcggt gaaatgcgta gatattagga ggaacaccag tggcgaaggc ggcttgctgg | 360 |
| acagtaactg acgttgaggc tcgaaagcgt ggggagcaaa ca | 402 |

<210> SEQ ID NO 135
<211> LENGTH: 422
<212> TYPE: DNA
<213> ORGANISM: Prevotella sp.

<400> SEQUENCE: 135

| | | |
|---|---|---|
| tgaggaatat tggtcaatgg gcggaagcct gaaccagcca gtagcgtgc aggatgacgg | 60 |
| ccctatgggt tgtaaactgc ttttacaggg gaataaaaag gagcacgtgt gctctgttgc | 120 |
| atgtaccctg cgaataagga ccggctaatt ccgtgccagc agccgcggta atacggaagg | 180 |
| tcctggtgtt atccggattt attgggttta aagggagcgt aggccgtaga ttaagtgtgt | 240 |
| tgtgaaatgt aggcgcccaa cgtctgcctt gcagcgcaaa ctggtttact tgagtacgcg | 300 |
| caacgcaggc ggaattcgtc gtgtagcggt gaaatgctta gatatgacga agaactccta | 360 |
| ttgcgaaggc agcttgcggg agcgttactg acgctgaagc tcgaaagtgc gggtatcgaa | 420 |
| ca | 422 |

<210> SEQ ID NO 136
<211> LENGTH: 402
<212> TYPE: DNA
<213> ORGANISM: Blautia sp.

<400> SEQUENCE: 136

-continued

```
tggggaatat tgcacaatgg gggaaaccct gatgcagcga cgccgcgtga aggaagaagt      60
atctcggtat gtaaacttct atcagcaggg aagataatga cggtacctga ctaagaagcc     120
ccggctaact acgtgccagc agccgcggta atacgtaggg ggcaagcgtt atccggattt     180
actgggtgta aagggagcgt agacggcgca gcaagtctga tgtgaaaggc agggcttaa     240 ccctggact gcattggaaa ctgctgtgct tgagtgccgg aggggtaagc ggaattccta      300
gtgtagcggt gaaatgcgta gatattagga ggaacaccag tggcgaaggc ggcttactgg     360
acgaccactg acgctgaggc tcgaaagcgt ggggagcaaa ca                        402
```

<210> SEQ ID NO 137
<211> LENGTH: 402
<212> TYPE: DNA
<213> ORGANISM: Ruminococcus sp.

<400> SEQUENCE: 137

```
tggggaatat tgcacaatgg gcgaaagcct gatgcagcga cgccgcgtga gcgaagaagt      60
atttcggtat gtaaagctct atcagcaggg aagataatga cggtacctga ctaagaagca     120
ccggctaaat acgtgccagc agccgcggta atacgtatgg tgcaagcgtt atccggattt     180
actgggtgta aagggagcgt agacggcaag gcaagtctga tgtgaaaacc cagggcttaa     240
ccctgggact gcattggaaa ctgtctggct cgagtgccgg agaggtaagc ggaattccta     300
gtgtagcggt gaaatgcgta gatattagga ggaacaccag tggcgaaggc ggcttactgg     360
acgataactg acgctgaggc tcgaaagcgt ggggagcaaa ca                        402
```

<210> SEQ ID NO 138
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 138

```
tggggaatat tgcacaatgg gcggaagcct gatgcagcga cgccgcgtga gtgaagaagt      60
atctcggtat gtaaagctct atcagcaggg aagaaaatga cggtacctga ctaagaagcc     120
ccggctaact acgtgccagc agccgcggta atacgtaggg ggcaagcgtt atccggattt     180
actgggtgta aagggagcgt agacggcgac gcaagtctgg agtgaaagcc ggggcccaa     240 ccccgggact gctttggaaa ctgtgctgct ggagtgcagg agaggtaagt ggaattccta     300
gtgtagcggt gaaatgcgta gatattagga ggaacaccag tggcgaaggc ggcttactgg     360
acggtaactg acgttgaggc tcgaaagcgt ggggagcaaa ca                        402
```

<210> SEQ ID NO 139
<211> LENGTH: 422
<212> TYPE: DNA
<213> ORGANISM: Prevotella sp.

<400> SEQUENCE: 139

```
tgaggaatat tggtcaatgg gcgagagcct gaaccagcca gtagcgtgc aggatgacgg      60 ccttatgggt tgtaaactgc ttttatgcga ggataaagtt acccacgtgt gggtgtttgc     120
aggtatcgca tgaataagga ccggctaatt ccgtgccagc agccgcggta atacggaagg     180
ttctggcgtt atccggattt attgggttta aagggagcgt aggctgtttt ttaagcgtgt     240
```

```
tgtgaaatgt accggctcaa ccggtgatgt gcagcgcgaa ctggaagact tgagtgtgtt    300
gtaagtaggc ggaattcgtg gtgtagcggt gaaatgctta gatatcacga ggaactccga    360
ttgcgtaggc agcttactgt ctcactactg acgctgatgc tcgaaagcgc gggtatcgaa    420
ca                                                                   422
```

<210> SEQ ID NO 140
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 140

```
tgaggaatat tggtcaatgg gcgcaggcct gaaccagcca gtagcgtga aggatgactg      60 ccctatgggt tgtaaacttc ttttataaag gaataaagtc gggtatgtat acccgtttgc    120
atgtacttta tgaataagga tcggctaact ccgtgccagc agccgcggta atacggagga    180
tccgagcgtt atccggattt attgggttta agggagcgt aggcgggttg ttaagtcagt     240
tgtgaaagtt tgcggctcaa ccgtaaaatt gcagttgata ctggcgacct tgagtgcaac    300
agaggtaggc ggaattcgtg gtgtagcggt gaaatgctta gatatcacga agaactccga    360
ttgcgaaggc agcctgctaa gctgcaactg acattgaggc tcgaaagtgt gggtatcaaa    420
ca                                                                   422
```

<210> SEQ ID NO 141
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 141

```
tggggaatat tgcacaatgg gggaaaccct gatgcagcga cgccgcgtga ttgaagaagt     60
atttcggtat gtaaagatct atcagcaagg aagaaaatga cggtacttga ctaagaagcc    120
ccggctaact acgtgccagc agccgcggta atacgtaggg ggcaagcgtt atccggattt    180
actgggtgta aagggagcgt aggcggtctg gcaagccaga agtgaaagcc cggggcttaa    240
ccccgggact gcttttggaa ctgttagact agagtgtcgg agaggtaagt ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 142
<211> LENGTH: 401
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 142

```
tggggaatat tgcacaatgg gggaaaccct gatgcagcaa cgccgcgtga aggaagaagg     60
tctttgggtc gtaaacttct gttctgaggg aagaaagtga cggtacctca ggagcaagtc    120
ccggctaact acgtgccagc agccgcggta atacgtaggg ggcaagcgtt atccggaatt    180
```

-continued

```
attgggcgta aagagtacgt aggtggttac ctaagcacgg ggtataaggc aatggctcaa      240
ccattgtttg ccttgtgaac tgggctactt gagtgcagga gaggaaagcg gaattcctag      300
tgtagcggtg aaatgcgtag atattaggag gaacaccagt ggcgaaggcg gctttctgga      360
ctgtaactga cactgaggta cgaaagcgtg gggagcaaac a                          401
```

<210> SEQ ID NO 143
<211> LENGTH: 402
<212> TYPE: DNA
<213> ORGANISM: Clostridium sp.

<400> SEQUENCE: 143

```
tggggaatat tgcacaatgg gggaaaccct gatgcagcga cgccgcgtga gtgaagaagt      60
atttcggtat gtaaagctct atcagcaggg aagaaaatga cggtacctga ctaagaagcc      120
ccggctaact acgtgccagc agccgcggta atacgtaggg ggcaagcgtt atccggattt      180
actgggtgta aagggagcgt agacggcatg gcaagccaga tgtgaaaacc cagggctcaa      240
ccttgggatt gcatttggaa ctgccaggct ggagtgcagg agaggtaagc ggaattccta      300
gtgtagcggt gaaatgcgta gatattagga ggaacaccag tggcgaaggc ggcttactgg      360
acgatgactg acgttgaggc tcgaaagcgt ggggagcaaa ca                          402
```

<210> SEQ ID NO 144
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 144

```
tggggaatat tgcacaatgg gggaaaccct gatgcagcga cgccgcgtgg aggaagaagg      60
tcttcggatt gtaaactcct gttgttgagg aagataatga cggtactcaa caaggaagtg      120
acggctaact acgtgccagc agccgcggta aaacgtaggt cacaagcgtt gtccggaatt      180
actgggtgta aagggagcgt agacggcaag gcaagtctga tgtgaaaacc cagggcttaa      240
ccctgggact gcattggaaa ctgtctggct cgagtgccgg agaggtaagc ggaattccta      300
gtgtagcggt gaaatgcgta gatatcggga ggaacaccag tggcgaaggc ggcctactgg      360
gcaccaactg acgctgaggc tcgaaagtgt gggtagcaaa ca                          402
```

<210> SEQ ID NO 145
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 145

```
tggggaatat tgcacaatgg gggaaaccct gatgcagcaa cgccgcgtga gtgaagaaat      60
atttcggtat gtaaagctct atcagcaggg aagaaaatga cggtacctga gtaagaagcc      120
ccggctaact acgtgccagc agccgcggta atacgtaggg ggcaagcgtt atccggattt      180
actgggtgta aagggagcgt agacggcgag gcaagtctga tgtgaaagcc tggggcttaa      240
ccccggaact gcattggaaa ctgctttgct ggagtgccgg agaggtaagc ggaattccta      300
```

```
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 146
<211> LENGTH: 423
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 146

```
tgaggaatat tggtcaatgg acgagagtct gaaccagcca agtagcgtgc aggatgacgg     60
ccctatgggt tgtaaactgc ttttgcgcgg ggataacacc ctccacgtgc tggaggtctg    120
caggtaccgc gcgaataagg accggctaat tccgtgccag cagccgcggt aatacggaag    180
gtccgggcgt tatccggatt tattgggttt aaagggagcg taggccggag attaagcgtg    240
ttgtgaaatg tagacgctca acgtctgcac tgcagcgcga actggtttcc ttgagtacgc    300
acaaagtggg cggaattcgt ggtgtagcgg tgaaatgctt agatatgacg aagaaccccg    360
attgcgaagg cagctggcgg gagcgtaact gacgctgaag ctcgaaagcg cgggtatcga    420
aca                                                                 423
```

<210> SEQ ID NO 147
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 147

```
tggggaatat tgcacaatgg gggaaaccct gatgcagcga cgccgcgtga aggaagaagt     60
atctcggtat gtaaacttct atcagcaggg aagatagtga cggtacctga ctaagaagcc    120
ccggctaact acgtgccagc agccgcggta atacgtaggg ggcaagcgtt atccggattt    180
actgggtgta aagggcgtgc agccgggtct gcaagtcaga tgtgaaatcc atgggctcaa    240
cccatgaact gcatttgaaa ctgtagatct tgagtgtcgg aggggcaatc ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 148
<211> LENGTH: 427
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 148

```
ttaggaatat tcgtcaatgg gggaaaccct gaacgagcaa tgccgcgtga acgatgaagg     60
ccctatgggt tgtaaagttc tgttgcatgg gacgaacgat taggatagga aatgatctta    120 atgtgacgg accatgccag aaagctccgg ctaactacgt gccagcagcc gcggtaatac    180
gtagggagca agcgttatcc ggattattg gcgtaaagg gtgcgtaggc ggcttgttaa    240
gtatgagatt aaagcccgag gcttaacctc ggttcgtttc ataaactggc aggcttgagt    300
```

```
gtggcagagg taaacggaat ttctagtgta gcggttaaat gcgtagatat tagaaggaac    360
accagtggcg aaggcggttt actgggccat aactgacgct gaggcacgaa agcgtgggga    420
gcaaata                                                              427
```

<210> SEQ ID NO 149
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 149

```
tggggaatat tgcacaatgg gggaaaccct gatgcagcga cgccgcgtga gtgaagaagt     60
aattcgttat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggccgt gcaagtctga tgtgaaaggc tggggctcaa    240
ccccgggact gcattggaaa ctgtatggct ggagtgccgg agaggtaagc ggaattccta    300
gtgtagcggt gaaatgcgta gatattagga ggaacaccag tggcgaaggc ggcttactgg    360
actgtaactg acgttgaggc tcgaaagcgt ggggagcaaa ca                       402
```

<210> SEQ ID NO 150
<211> LENGTH: 427
<212> TYPE: DNA
<213> ORGANISM: Escherichia sp.

<400> SEQUENCE: 150

```
tggggaatat tgcacaatgg gcgcaagcct gatgcagcca tgccgcgtgt atgaagaagg     60
ccttcgggtt gtaaagtact ttcagcgggg aggaagggag taaagttaat acctttgctc    120
attgacgtta cccgcagaag aagcaccggc taactccgtg ccagcagccg cggtaatacg    180
gagggtgcaa gcgttaatcg gaattactgg gcgtaaagcg cacgcaggcg gtttgttaag    240
tcagatgtga atccccgggg ctcaacctgg gaactgcatc tgatactggc aagcttgagt    300
ctcgtagagg ggggtagaat tccaggtgta gcggtgaaat gcgtagagat ctggaggaat    360
accggtggcg aaggcggccc cctggacatt aactgacgct gaggcacgaa ggccagggga    420
gcgaaag                                                              427
```

<210> SEQ ID NO 151
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 151

```
tgaggaatat tggtcaatgg acgagagtct gaaccagcca agtagcgtga aggatgactg     60
ccctatgggt tgtaaacttc ttttatacgg gaataaagtg aggcacgtgt gccttttgt     120 atgtaccgta tgaataagga tcggctaact ccgtgccagc agccgcggta atacggagga    180
tccgagcgtt atccggattt attgggttta aagggtgcgt aggcggcacg ccaagtcagc    240
ggtgaaattt ccgggctcaa cccggagtgt gccgttgaaa ctggcgagct agagtacaca    300
```

```
agaggcaggc ggaatgcgtg gtgtagcggt gaaatgcata gatatcacga agaactccga    360
ttgcgaaggc agcctgctaa gctgcaactg acattgaggc tcgaaagtgt gggtatcaaa    420
ca                                                                   422

<210> SEQ ID NO 152
<211> LENGTH: 405
<212> TYPE: DNA
<213> ORGANISM: Leptotrichia sp.

<400> SEQUENCE: 152
tggggaatat tggacaatgg gggcaaccct gatccagcaa ttctgtgtgc acgaagaagg     60
ctttcgggct gtaaagtgct ttcagcagag aagaagcaag tgacggtacc tgcagaagaa   120
gcgacggcta atacgtgcc agcagccgcg gtaatacgta tgtcgcaagc gttatccgga    180
attattgggc ataaagggca tctaggcggc caggcaagtc tggggtgaaa acctgcggct   240
caaccgcagg cctgccctgg aaactgcgtg gctagagtac tggagaggtg gacggaactg   300
cacgagtaga ggtgaaattc gtagatatgt gcaggaatgc cgatgatgaa gatagttcac   360
tggacggcaa ctgacgctga agtgcgaaag ccgggggagc gaaca                   405

<210> SEQ ID NO 153
<211> LENGTH: 402
<212> TYPE: DNA
<213> ORGANISM: Blautia sp.

<400> SEQUENCE: 153
tggggaatat tgcacaatgg gggaaaccct gatgcagcga cgccgcgtga aggaagaagt    60
atctcggtat gtaaacttct atcagcaggg aagaaaatga cggtacctga ctaagaagcc   120
ccggctaact acgtgccagc agccgcggta atacgtaggg ggcaagcgtt atccggattt   180
actgggtgta aagggagcgt agacggtgtt gcaagtctga tgtgaaaggc gggggctcaa   240 ccccctggact gcattggaaa ctgtgatact cgagtgccgg agaggtaagc ggaattccta   300
gtgtagcggt gaaatgcgta gatattagga ggaacaccag tggcgaaggc ggcttgctgg   360
acgatgactg acgttgaggc tcgaaagcgt ggggagcaaa ca                      402

<210> SEQ ID NO 154
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 154
tggggaatat tgcacaatgg gggaaaccct gatgcagcaa cgccgcgtga gtgaagaagt    60
atttcggtat gtaaagctct atcagcaggg aagataatga cggtacctga ctaagaagct   120
ccggctaaat acgtgccagc agccgcggta atacgtatgg agcaagcgtt atccggattt   180
actgggtgta aagggagcgt agacggcaag gcaagtctga tgtgaaaacc cagggcttaa   240
ccctgggact gcattggaaa ctgtctggct cgagtgccgg agaggtaagc ggaattccta   300
gtgtagcggt gaaatgcgta gatattagga ggaacatcag tggcgaaggc ggcttactgg   360
actgaaactg acactgaggc acgaaagcgt ggggagcaaa ca                      402

<210> SEQ ID NO 155
<211> LENGTH: 402
```

```
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 155
tggggaatat tgcacaatgg gggaaaccct gatgcagcga cgccgcgtga gcgatgaagt    60
atttcggtat gtaaagctct atcagcaggg aagaaaatga cggtacctga ctaagaagca   120
ccggctaaat acgtgccagc agccgcggta atacgtatgg tgcaagcgtt atccggattt   180
actgggtgta aagggagcgt aggcggcgga gcaagtcaga agtgaaagcc cggggctcaa   240
ccccgggacg gcttttgaaa ctgccctgct tgatttcagg agaggtaagc ggaattccta   300
gtgtagcggt gaaatgcgta gatattagga ggaacaccag tggcgaaggc ggcttactgg   360
acggtaactg acgttgaggc tcgaaagcgt ggggagcaaa ca                      402

<210> SEQ ID NO 156
<211> LENGTH: 404
<212> TYPE: DNA
<213> ORGANISM: Roseburia sp.

<400> SEQUENCE: 156
tggggaatat tgggcaatgg gcgcaagcct gacccagcaa cgccgcgtga gcgaagaagt    60
atttcggtat gtaaagctct atcagcaggg aagaagaaat gacggtacct gactaagaag   120
caccggctaa atacgtgcca gcagccgcgg taatacgtat ggtgcaagcg ttatccggat   180
ttactgggtg taagggagc gcaggcggta cggcaagtct gatgtgaaag cccggggctc   240
aaccccggta ctgcattgga aactgtcgga ctagagtgtc ggaggggtaa gtggaattcc   300
tagtgtagcg gtgaaatgcg tagatattag gaggaacacc agtggcgaag gcggcttact   360
ggacgattac tgacgctgag gctcgaaagc gtggggagca aaca                    404

<210> SEQ ID NO 157
<211> LENGTH: 402
<212> TYPE: DNA
<213> ORGANISM: Faecalibacterium sp.

<400> SEQUENCE: 157
tggggaatat tgcacaatgg gggaaaccct gatgcagcga cgccgcgtgg aggaagaagg    60
tcttcggatt gtaaactcct gttgttgagg aagataatga cggtactcaa caaggaagtg   120
acggctaact acgtgccagc agccgcggta aacgtaggt cacaagcgtt gtccggaatt    180
actgggtgta aagggagcgc aggcgggcga tcaagttgga agtgaaatcc atgggctcaa   240
cccatgaact gctttcaaaa ctggtcgtct tgagtagtgc agaggtaggc ggaattcccg   300
gtgtagcggt ggaatgcgta gatatcggga ggaacaccag tggcgaaggc ggcctgctaa   360
gctgcaactg acattgaggc tcgaaagtgt gggtatcaaa ca                      402

<210> SEQ ID NO 158
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 158
```

```
tggggaatat tgcacaatgg gggaaaccct gatgcagcga cgccgcgtga gcgaagaagt    60
atttcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgt agacggatag gcaagtctgg agtgaaaacc cagggctcaa   240
ccctgggact gctttggaaa ctgcagatct ggagtgccgg agaggtaagc ggaattccta   300
gtgtagcggt gaaatgcgta gatattagga ggaacaccag tggcgaaggc ggcttactgg   360
acggtaactg acgttgaggc tcgaaagcgt ggggagcaaa ca                      402
```

<210> SEQ ID NO 159
<211> LENGTH: 427
<212> TYPE: DNA
<213> ORGANISM: Neisseria sp.

<400> SEQUENCE: 159

```
tggggaattt tggacaatgg gcgcaagcct gatccagcca tgccgcgtgt ctgaagaagg    60
ccttcgggtt gtaaaggact tttgtcaggg aagaaaagga gttggttaat acccgactct   120
gatgacggta cctgaagaat aagcaccggc taactacgtg ccagcagccg cggtaatacg   180
tagggtgcga cgttaatcg gaattactgg gcgtaaagcg agcgcagacg gtttgttaag   240
caggatgtga aatccccggg ctcaacctgg gaactgcgtt ctgaactggc aggctagagt   300
gtgtcagagg ggggtagaat tccacgtgta gcagtgaaat gcgtagagat gtggaggaat   360
accgatggcg aaggcagcct cctgggataa cactgacgtt catgctcgaa agcgtgggta   420
gcaaaca                                                            427
```

<210> SEQ ID NO 160
<211> LENGTH: 402
<212> TYPE: DNA
<213> ORGANISM: Clostridium sp.

<400> SEQUENCE: 160

```
tggggaatat tggacaatgg gcgaaagcct gatccagcga cgccgcgtga gtgaagaagt    60
atttcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgt agacggttaa gcaagtctga agtgaaagcc cggggctcaa   240
ccccggtact gctttggaaa ctgtttgact tgagtgcagg agaggtaagt ggaattccta   300
gtgtagcggt gaaatgcgta gatattagga ggaacaccag tggcgaaggc ggcttactgg   360
acgataactg acgttgaggc tcgaaagcgt ggggagcaaa ca                      402
```

<210> SEQ ID NO 161
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 161

```
tggggaatat tgcacaatgg gggaaaccct gatgcagcga cgccgcgtgg aggaagaagg    60
tcttcggatt gtaaactcct gttgttgagg aagataatga cggtactcaa caaggaagtg   120
acggctaact acgtgccagc agccgcggta aaacgtaggc acaagcgtt gtccggaatt   180 actgggtgta aagggcgtgt aggcggagaa gcaagtcaga agtgaaatcc atgggcttaa   240
```

-continued

```
cccatgaact gcttttgaaa ctgtttccct tgagtatcgg agaggcaggc ggaattccta    300
gtgtagcggt gaaatgcgta gatattagga ggaacaccag tggcgaaggc ggtctactgg    360
gcaccaactg acgctgaggc tcgaaagcat gggtagcaaa ca                       402
```

<210> SEQ ID NO 162
<211> LENGTH: 402
<212> TYPE: DNA
<213> ORGANISM: Coprococcus sp.

<400> SEQUENCE: 162

```
tggggaatat tgcacaatgg gggaaaccct gatgcagcga cgccgcgtga aggaagaagt    60
atctcggtat gtaaacttct atcagcaggg aagatagtga cggtacctga ctaagaagcc    120
ccggctaact acgtgccagc agccgcggta atacgtaggg ggcaagcgtt atccggattt    180
actgggtgta aagggagcgt aggtggcaag gcaagccaga agtgaaaacc cggggctcaa    240
ccgcgggatt gcttttggaa ctgtcatgct agagtgcagg aggggtgagc ggaattccta    300
gtgtagcggt gaaatgcgta gatattagga ggaacaccag tggcgaaggc gacttactgg    360
actgctactg acactgaggc acgaaagcgt ggggagcaaa ca                       402
```

<210> SEQ ID NO 163
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 163

```
tggagaatat tgcgcaatgg gggcaaccct gacgcagcaa cgccgcgtgc aggaagaagg    60
tcttcggatt gtaaactgtt gtcgcaaggg aagaagacag tgacggtacc ttgtgagaaa    120
gtcacggcta actacgtgcc agcagccgcg gtaatacgta ggtgacaagc gttgtccgga    180
tttactgggt gtaaagggcg cgtaggcgga ctgtcaagtc agtcgtgaaa taccggggct    240
taaccccggt actgcattgg aaactgtcgt actagagtgt cggagggta agcggaattc    300 ctagtgtagc ggtgaaatgc gtagatatta ggaggaacac cagtggcgaa ggcgacttac    360
tggactgaaa ctgacgttga ggcacgaaag tgtggggagc aaaca                    405
```

<210> SEQ ID NO 164
<211> LENGTH: 402
<212> TYPE: DNA
<213> ORGANISM: Blautia sp.

<400> SEQUENCE: 164

```
tgggggatat tgcacaatgg aggaaactct gatgcagcga cgccgcgtga gtgaagaagt    60
atttcggtat gtaaagctct atcagcaggg aagacagtga cggtacctga ctaagaagcc    120
ccggctaact acgtgccagc agccgcggta atacgtaggg ggcaagcgtt atccggattt    180
actgggtgta aagggagcgt agacggatgg acaagtctga tgtgaaaggc tggggctcaa    240
ccccgggact gcattggaaa ctgcccgtct tgagtgccgg agaggtaagc ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402
```

<210> SEQ ID NO 165

```
<211> LENGTH: 422
<212> TYPE: DNA
<213> ORGANISM: Parabacteroides sp.

<400> SEQUENCE: 165
tgaggaatat tggtcaatgg gcgtaagcct gaaccagcca agtcgcgtga gggatgaagg      60
ttctatggat cgtaaacctc ttttataagg gaataaagtg cgggacgtgt cctgttttgt     120
atgtacctta tgaataagga tcggctaact ccgtgccagc agccgcggta atacggagga     180
tccgagcgtt atccggattt attgggttta aagggtgcgt aggcggcctt ttaagtcagc     240
ggtgaaagtc tgtggctcac ccatagaatt gccgttgaaa ctgggggct tgagtatgtt      300 tgaggcaggc ggaatgcgtg gtgtagcggt gaaatgctta gatatcacgc agaaccccga     360
ttgcgaaggc agcctgccaa gccatgactg acgctgatgc acgaaagcgt ggggatcaaa     420
ca                                                                   422

<210> SEQ ID NO 166
<211> LENGTH: 402
<212> TYPE: DNA
<213> ORGANISM: Blautia sp.

<400> SEQUENCE: 166
tggggaatat tgcacaatgg gggaaaccct gatgcagcga cgccgcgtga aggaagaagt      60
atctcggtat gtaaacttct atcagcaggg aagataatga cggtacctga ctaagaagcc     120
ccggctaact acgtgccagc agccgcggta atacgtaggg ggcaagcgtt atccggattt     180
actgggtgta aagggagcgt agacggcaag gcaagtctga agtgaaagcc cggtgcttaa     240
cgccgggact gctttggaaa ctgctgtgct tgagtgccgg aggggtaagc ggaattccta     300
gtgtagcggt gaaatgcgta gatattagga ggaacaccag tggcgaaggc ggcttactgg     360
acggtaactg acgttgaggc tcgaaagcgt ggggagcaaa ca                       402

<210> SEQ ID NO 167
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 167
tgggggatat tgcacaatgg gggaaaccct gatgcagcga cgccgcgtgg aggaagaagg      60
ttttcggatt gtaaactcct gtcgttaggg acgataatga cggtacctaa caagaaagca     120
ccggctaact acgtgccagc agccgcggta aaacgtaggt cacaagcgtt gtccggaatt     180
actgggtgta aagggagcgc aggcgggcga tcaagttgga agtgaaatcc atgggctcaa     240
cccatgaact gctttcaaaa ctggtcgtct tgagtagtgc agaggtaggt ggaattcccg     300
gtgtagcggt ggaatgcgta gatatcggga ggaacaccag tggcgaaggc gacctactgg     360
gcaccaactg acgctgaggc tcgaaagcat gggtagcaaa ca                       402

<210> SEQ ID NO 168
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"
```

<400> SEQUENCE: 168

```
tggggaatat tgcacaatgg ggaaaccct gatgcagcga cgccgcgtga gcgaagaagt    60
atttcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgt aggcggcacg ccaagccaga tgtgaaagcc cgaggcttaa   240
cctcgcggat tgcatttgga actggcgagc tagagtacag gagaggaaag cggaattcct   300
agtgtagcgg tgaaatgcgt agatattagg aggaacacca gtggcgaagg cggcttactg   360
gacggtaact gacgttgagg ctcgaaagcg tggggagcaa aca                     403
```

<210> SEQ ID NO 169
<211> LENGTH: 406
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 169

```
tggggaatat tgcacaatgg ggggaaccct gatgcagcaa cgccgcgtga aggaagacgg    60
ttttcggatt gtaaacttct atcaatagggg acgaagaaag tgacggtacc taaataagaa   120
gccccggcta actacgtgcc agcagccgcg gtaatacgta gggggcaagc gttatccgga   180
attactgggt gtaaagggtg agtaggcggc acggcaagta agatgtgaaa gcccacggct   240
taactgtggg attgcattt aaactgttga gctagagtac aggagaggaa agcggaattc   300
ctagtgtagc ggtgaaatgc gtagatatta ggaagaacac cagtggcgaa ggcggctttc   360
tggacgggaa actgacgctg aggcacgaaa gcgtgggag cgaaca                   406
```

<210> SEQ ID NO 170
<211> LENGTH: 402
<212> TYPE: DNA
<213> ORGANISM: Lachnoanaerobaculum sp.

<400> SEQUENCE: 170

```
tggggaatat tggacaatgg ggaaaccct gatccagcga cgccgcgtga gtgaagaagt    60
atttcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgc agacggttgc gcaagtctga agtgaaatcc cgaggcttaa   240 ccacggggact gctttggaaa ctgtgcgact tgagtatcgg aggggcaggc ggaattccta   300
gtgtagcggt gaaatgcgta gatattagga agaacaccgg tggcgaaggc ggcctgctgg   360
acgaaaactg acgttgaggc tcgaaggcgt ggggagcaaa ca                      402
```

<210> SEQ ID NO 171
<211> LENGTH: 426
<212> TYPE: DNA
<213> ORGANISM: Streptococcus sp.

<400> SEQUENCE: 171

```
tagggaatct tcggcaatgg acggaagtct gaccgagcaa cgccgcgtga gtgaagaagg    60
ttttcggatc gtaaagctct gttgttagag aagaacagcg catagagtaa ctgttatgcg   120
tgtgacggta tcttaccaga aagggacggc taactacgtg ccagcagccg cggtaatacg   180
```

```
taggtcccga gcgttgtccg gatttattgg gcgtaaagcg agcgcaggcg gttagataag      240
tctgaagtta aaggctgtgg cttaaccata gtacgctttg gaaactgttt aacttgagtg      300
caagagggga gagtggaatt ccatgtgtag cggtgaaatg cgtagatata tggaggaaca      360
ccggtggcga aagcggctct ctggcttgta actgacgctg aggctcgaaa gcgtggggag      420
caaaca                                                                 426

<210> SEQ ID NO 172
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 172
tggggaatat tgcacaatgg gggaaaccct gatgcagcga cgccgcgtga aggaagaagt       60
atctcggtat gtaaacttct atcagcaggg aagaaaatga cggtacctga ctaagaagcc      120
ccggctaact acgtgccagc agccgcggta atacgtaggg ggcaagcgtt atccggattt      180
actgggtgta aagggcgcgt aggcggctcg gtaagtctgg agtgaaagtc ctgcttttaa      240
ggtgggaatt gctttggata ctgtcgggct tgagtgcagg agaggtaagc ggaattccta      300
gtgtagcggt gaaatgcgta gatattagga ggaacaccag tggcgaaggc ggcttactgg      360
actgtaactg acgttgaggc tcgaaagcgt ggggagcaaa ca                         402

<210> SEQ ID NO 173
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 173
tagggaatct tcggcaatgg gggcaaccct gaccgagcaa cgccgcgtga gtgaagaagt       60
atttcggtat gtaaagctct atcagcaggg aagataatga cggtacctga ctaagaagct      120
ccggctaaat acgtgccagc agccgcggta atacgtatgg agcaagcgtt atccggattt      180
actgggtgta aagggtgcgt aggtggcagt gcaagtcaga tgtgaaaggc cggggctcaa      240
ccccggagct gcatttgaaa ctgcatagct ggagtacagg agaggcaggc ggaattccta      300
gtgtagcggt gaaatgcgta gatattagga ggaacaccag tggcgaaggc ggcctgctgg      360
actgttactg acactgaggc acgaaagcgt ggggagcaaa ca                         402

<210> SEQ ID NO 174
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 174
tgaggaatat tggtcaatgg gcgagagcct gaaccagcca gtagcgtgaa aggatgactg       60
ccctatgggt tgtaaacttc ttttataaag gaataaagtc gggtatggat acccgtttgc      120
atgtacttta tgaataagga tcggctaact ccgtgccagc agccgcggta atacggagga      180
```

```
tccgagcgtt atccggattt attgggttta aagggtgcgt aggtggtgat ttaagtcagc    240
ggtgaaagtt tgtggctcaa ccataaaatt gccgttgaaa ctgggttact tgagtgcagt    300
tgaggcaggc ggaattcgtg gtgtagcggt gaaatgctta gatatcacga agaactccga    360
ttgcgaaggc agcctgctaa gctgcaactg acattgaggc tcgaaagtgt gggtatcaaa    420
ca                                                                  422
```

<210> SEQ ID NO 175
<211> LENGTH: 422
<212> TYPE: DNA
<213> ORGANISM: Bacteroides sp.

<400> SEQUENCE: 175

```
tgaggaatat tggtcaatgg gcgcaggcct gaaccagcca agtagcgtga aggatgactg     60
ccctatgggt tgtaaacttc ttttataaag gaataaagtc gggtatggat accgtttgc    120 atgtacttta tgaataagga tcggctaact ccgtgccagc agccgcggta atacggagga    180
tccgagcgtt atccggattt attgggttta aagggagcgt agatggatgt ttaagtcagt    240
tgtgaaagtt tgcggctcaa ccgtaaaatt gcagttgata ctgggcgcct tgagtgcagc    300
ataggtaggc ggaattcgtg gtgtagcggt gaaatgctta gatatcacga agaactccga    360
ttgcgaaggc agcctgctgg actgtaactg acattgaggc tcgaaagtgt gggtatcaaa    420
ca                                                                  422
```

<210> SEQ ID NO 176
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 176

```
tggggaatat tgcacaatgg gcgaaagcct gatgcagcga cgccgcgtga gcgaagaagt     60
atttcggtat gtaaagctct atcagcaggg aagataatga cggtacctga ctaagaagca    120
ccggctaaat acgtgccagc agccgcggta atacgtatgg tgcaagcgtt atccggattt    180
actgggtgta aagggtgcgt aggtggcagt gcaagtcaga tgtgaaaggc cggggctcaa    240
ccccggagct gcatttgaaa ctgcatagct agagtacagg agaggcaggc ggaattccta    300
gtgtagcggt gaaatgcgta gatattagga ggaacaccag tggcgaaggc ggcctactgg    360
gcaccaactg acgctgaggc tcgaaagtgt gggtagcaaa ca                      402
```

<210> SEQ ID NO 177
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      unclassified.Clostridiales"

<400> SEQUENCE: 177

```
tcgggaatat tgcgcaatgg aggaaactct gacgcagtga cgccgcgtgc aggaagaagg     60
ttttcggatt gtaaactgct ttagacaggg aagaacaaag acagtacctg tagaataagc    120
tccggctaac tacgtgccag cagccgcggt aatacgtagg gagcgagcgt tatccggatt    180
```

```
tattgggtgt aaagggtgcg tagacgggaa gtcaagttag ttgtgaaatc cctcggctta    240
actgaggaac tgcaactaaa actgattttc ttgagtactg gagaggaaag tggaattcct    300
agtgtagcgg tgaaatgcgt agatattagg aggaacacca gtggcgaagg cggcttactg    360
gactgtaact gacgttgagg cgcgaaagtg tggggagcaa aca                      403
```

<210> SEQ ID NO 178
<211> LENGTH: 405
<212> TYPE: DNA
<213> ORGANISM: Unknown
<220> FEATURE:
<221> NAME/KEY: source
<223> OTHER INFORMATION: /note="Description of Unknown:
       Bacterial sequence"

<400> SEQUENCE: 178

```
tggggaatat tgggcaatgg gggaaaccct gacccagcaa cgccgcgtga aggaagaagg     60
ctttcgggtt gtaaacttct tttaccaggg acgaaggacg tgacggtacc tggagaaaaa    120
gccacggcta actacgtgcc agcagccgcg gtaatacgta ggtggcaagc gttgtccgga    180
tttactgggt gtaaagggag cgtagacggc tttgcaagtc tgacgtgaaa ctccggggct    240
caactccgga actgcgttgg aaactgtaag gcttgagtgc ggagaggta agcggaattc     300 ctagtgtagc ggtgaaatgc gtagatatta ggaggaacac cagtggcgaa ggcggcttac    360
tggacggtaa ctgacgttga ggctcgaaag cgtggggagc aaaca                    405
```

<210> SEQ ID NO 179
<211> LENGTH: 404
<212> TYPE: DNA
<213> ORGANISM: Unknown
<220> FEATURE:
<221> NAME/KEY: source
<223> OTHER INFORMATION: /note="Description of Unknown:
       Bacterial sequence"

<400> SEQUENCE: 179

```
tggggtatat tgggcaatgg aggaaactct gacccagcaa cgccgcgtgg aggaagaagg     60
ttttcggatc gtaaacttcct gtccttggag acgagtagaa gacggtatcc aaggaggaag   120
ccccggctaa ctacgtgcca gcagccgcgg taatacgtag ggggcaagcg ttatccggat    180
ttactgggtg taaagggagc gtagacggca aggcaagtct gatgtgaaaa cccagggctt    240
aaccctggga ctgcattgga aactgtctgg ctcgagtgcc ggagaggtaa gcggaattcc    300
tagtgtagcg gtgaaatgcg tagagattgg gaggaacacc agtggcgaag gcggattgct    360
ggacgataac tgacggtgag gcgcgaaagt gtggggagca aaca                     404
```

<210> SEQ ID NO 180
<211> LENGTH: 422
<212> TYPE: DNA
<213> ORGANISM: Tannerella sp.

<400> SEQUENCE: 180

```
tgaggaatat tggtcaatgg gcgagagcct gaaccagcca gtcgcgtgaa ggatgactg      60 tcttatggat tgtaaacttc ttttatacgg gaataacaag agtcacgtgt gactccctgc    120
atgtaccgta tgaataagca tcggctaact ccgtgccagc agccgcggta atacggagga    180
tgcgagcgtt atccggattt attgggttta aagggtgcgt aggtgggcta ttaagtcagt    240
ggtgaaagtt tgtcgctcaa cgataaaatt gccgttgaaa ctggtggtct tgagtgtaga    300
tgaggtaggc ggaatgcgtg gtgtagcggt ggaatgcata gatatcacgc agaactccga    360
```

```
ttgcgaaggc agcttactaa ggtacaactg acgctgaagc acgaaagcgt gggtatcaaa    420
ca                                                                    422
```

<210> SEQ ID NO 181
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 181

```
tggggaatat tgcacaatgg gggaaaccct gatgcagcga cgccgcgtga gcgaagaagt     60
atttcggtat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggaatg gcaagtctga tgtgaaagac cggggctcaa    240
ccccgggact gcattggaaa ctgtcaatct agagtaccgg aggggtaagt ggaattccta    300
gtgtagcggt gaaatgcgta gatattagga ggaacaccag tggcgaaggc ggcttaccaa    360
actatatctg acgttgaggc acgaaagcgt ggggagcaaa ca                       402
```

<210> SEQ ID NO 182
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 182

```
tggggaatat tgcacaatgg gggaaaccct gatgcagcga cgccgcgtga aggaagaagt     60
atctcggtat gtaaacttct atcagcaggg aagaagaatg acggtacctg actaagaagc    120
accggctaaa tacgtgccag cagccgcggt aatacgtagg gggcaagcgt tatccggatt    180
tactgggtgt aaagggagcg tagacggcaa ggcaagtctg atgtgaaagg ctggggctca    240
accccgggac tgcattggaa actgtcctgc tggagtgccg gagaggtaag cggaattcct    300
agtgtagcgg tgaaatgcgt agatattagg aggaacacca gtggcgaagg cggcttgctg    360
gacgatgact gacgttgagg ctcgaaagcg tggggagcaa aca                      403
```

<210> SEQ ID NO 183
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 183

```
tggggaatat tgcacaatgg gggaaaccct gatgcagcga cgccgcgtga gtgaagaagt     60
atctcggtat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggcgga gcaagtctga agtgaaagcc ggggctcaa     240 ccccgggact gctttggaaa ctgttctgct agagtgctgg agaggcaagc ggaattccta    300
```

```
gtgtagcggt gaaatgcgta gatattagga agaacaccag tggcgaaggc ggctttctgg    360
acgatgactg acgttgaggc tcgaaagcgt ggggagcaaa ca                       402
```

<210> SEQ ID NO 184
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 184

```
tggggaatat tgcacaatgg gggaaaccct gatgcagcga cgccgcgtga gcgatgaagt    60
atttcggtat gtaaagctct atcagcaggg aagaaaatga cggtacctga ctaagaagca   120
ccggctaaat acgtgccagc agccgcggta atacgtatgt gcaagcgtt atccggattt    180 actgggtgta aagggagcgc aggcggtctg gcaagtctga tgtgaaaatc cggggctcaa   240
ctccggaact gcattggaaa ctgtcagact agagtgtcgg aggggtaagc ggaattccta   300
gtgtagcggt gaaatgcgta gatattagga ggaacaccag tggcgaaggc ggcttactgg   360
acagtaactg acgttgaggc tcgaaagcgt ggggagcaaa ca                       402
```

<210> SEQ ID NO 185
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 185

```
tggggaatat tgcacaatgg aggaaactct gatgcagcga tgccgcgtga aggatgaagt    60
atttcggtat gtaaacttct atcagcaggg aagaaaatga cggtacctga ctaagaagcc   120
ccggctaact acgtgccagc agccgcggta atacgtatgg tgcaagcgtt atccggattt    180
actgggtgta aagggagcgt agacggagtg gcaagtctga tgtgaaaacc cggggctcaa   240
ccccgggact gcattggaaa ctgtcaatct agagtaccgg agaggtaagc ggaattccta   300
gtgtagcggt gaaatgcgta gatattagga ggaacaccag tggcgaaggc ggctttctgg   360
acgatgactg acgttgaggc tcgaaagcgt gggaagcaaa ca                       402
```

<210> SEQ ID NO 186
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 186

```
tggggaatat tgcacaatgg gggaaaccct gatgcagcga cgccgcgtga aggatgaagt    60
atttcggtat gtaaacttct atcagcaggg aagaaagtga cggtacctga gtaagaagcc   120
ccggctaact acgtgccagc agccgcggta atacgtaggg ggcaagcgtt atccggattt    180
actgggtgta aagggagcgt agacggcgga gcaagtctga tgtgaaaggc aggggcttaa   240
cccctggact gcattggaaa ctgtttagct ggagtgccgg agaggtaagc ggaattccta   300
gtgtagcggt gaaatgcgta gatattagga agaacaccag tggcgaaggc ggcttactgg   360
```

-continued acggtaactg acgttgaggc tcgaaagcgt ggggagcaaa ca    402

<210> SEQ ID NO 187
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 187
tggggaatat tgcacaatgg ggggaaccct gatgcagcaa cgtcgcgtga gtgaagaagt    60
atttcggtat gtaaacttct atcagcaggg aagaaaatga cggtacctga ctaagaagcc    120
ccggctaact acgtgccagc agccgcggta atacgtaggg gcaagcgtt atccggattt    180 actgggtgta aagggagcgt agacggagca gcaagtctga tgtgaaaggc gggggctcaa    240
cccccggact gcattggaaa ctgttgatct tgagtaccgg agaggtaagc ggaattccta    300
gtgtagcggt gaaatgcgta gatattagga ggaacaccag tggcgaaggc ggcttactgg    360
acggtaactg acgttgaggc tcgaaagcgt ggggagcaaa ca    402

<210> SEQ ID NO 188
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 188
tggggaatat tgcacaatgg gggaaaccct gatgcagcga cgccgcgtgg aggaagaagg    60
tcttcggatt gtaaactcct gttgttgggg aagataatga cggtacccaa caaggaagtg    120
acggctaact acgtgccagc agccgcggta aaacgtaggt cacaagcgtt gtccggaatt    180
actgggtgta aagggagcgc aggcgggata gcaagtcagc tgtgaaaact atgggctcaa    240
cccataaact gcagttgaaa ctgttattct tgagtggagt agaggcaagc ggaattccga    300
gtgtagcggt gaaatgcgta gatattagga ggaacaccag tggcgaaggc ggccaactgg    360
gcttttactg acgctgaggc tcgaaagtgt ggggagcaaa ca    402

<210> SEQ ID NO 189
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (42)..(42)
<223> OTHER INFORMATION: a, c, t, g, unknown or other

<400> SEQUENCE: 189
tcgtcggcag cgtcagatgt gtataagaga cagcctacgg gnggcwgcag    50

<210> SEQ ID NO 190
<211> LENGTH: 55
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 190
gtctcgtggg ctcggagatg tgtataagag acaggactac hvgggtatct aatcc         55

<210> SEQ ID NO 191
<211> LENGTH: 427
<212> TYPE: DNA
<213> ORGANISM: Streptococcus sp.

<400> SEQUENCE: 191
tagggaatct tcggcaatgg acggaagtct gaccgagcaa cgccgcgtga gtgaagaagg     60
ttttcggatc gtaaagctct gttgtaagag aagaacgagt gtgagagtgg aaagttcaca    120
ctgtgacggt atcttaccag aaagggacgg ctaactacgc cagcagcc gcggtaatac      180 gtaggtcccg agcgttgtcc ggatttattg ggcgtaaagc gagcgcaggc ggttagataa    240
gtctgaagtt aaaggctgtg gcttaaccat agtacgcttt ggaaactgtt aacttgagt    300 gcaagagggg agagtggaat tccatgtgta gcggtgaaat gcgtagatat atggaggaac    360
accggtggcg aaagcggctc tctggcttgt aactgacgct gaggctcgaa agcgtgggga    420
gcaaaca                                                              427

<210> SEQ ID NO 192
<211> LENGTH: 427
<212> TYPE: DNA
<213> ORGANISM: Streptococcus sp.

<400> SEQUENCE: 192
tagggaatct tcggcaatgg gggcaaccct gaccgagcaa cgccgcgtga gtgaagaagg    60
ttttcggatc gtaaagctct gttgtaagtc aagaacgagt gtgagagtgg aaagttcaca    120
ctgtgacggt agcttaccag aaagggacgg ctaactacgt gccagcagcc gcggtaatac    180
gtaggtcccg agcgttgtcc ggatttattg ggcgtaaagc gagcgcaggc ggtttgataa    240
gtctgaagtt aaaggctgtg gctcaaccat agttcgcttt ggaaactgtc aaacttgagt    300
gcagaagggg agagtggaat tccatgtgta gcggtgaaat gcgtagatat atggaggaac    360
accggtggcg aaagcggctc tctggtctgt aactgacgct gaggctcgaa agcgtgggga    420
gcgaaca                                                              427

<210> SEQ ID NO 193
<211> LENGTH: 402
<212> TYPE: DNA
<213> ORGANISM: Ruminococcus sp.

<400> SEQUENCE: 193
tggggaatat tgcacaatgg gggaaaccct gatgcagcga cgccgcgtga gcgatgaagt    60
atttcggtat gtaaagctct atcagcaggg aagaaaatga cggtacctga ctaagaagca   120
ccggctaaat acgtgccagc agccgcggta atacgtatgg tgcaagcgtt atccggattt    180
actgggtgta aagggagcgt agacggagtg gcaagtctga tgtgaaaacc cggggctcaa    240
ccccgggact gcattggaaa ctgtcaatct agagtaccgg agaggtaagc ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402

```
<210> SEQ ID NO 194
<211> LENGTH: 402
<212> TYPE: DNA
<213> ORGANISM: Roseburia sp.

<400> SEQUENCE: 194
tggggaatat tgcacaatgg gcgaaagcct gatgcagcga cgccgcgtga gcgaagaagt      60
atttcggtat gtaaagctct atcagcaggg aagataatga cggtacctga ctaagaagca     120
ccggctaaat acgtgccagc agccgcggta atacgtatgg tgcaagcgtt atccggattt     180
actgggtgta aagggagcgc aggcggtgcg gcaagtctga tgtgaaagcc cggggctcaa     240
ccccggtact gcattggaaa ctgtcgtact agagtgtcgg aggggtaagc ggaattccta     300
gtgtagcggt gaaatgcgta gatattagga ggaacaccag tggcgaaggc ggcttactgg     360
acgataactg acgctgaggc tcgaaagcgt ggggagcaaa ca                        402

<210> SEQ ID NO 195
<211> LENGTH: 427
<212> TYPE: DNA
<213> ORGANISM: Gemella sp.

<400> SEQUENCE: 195
tagggaatct tccgcaatgg gcgaaagcct gacggagcaa cgccgcgtga gtgaagaagg      60
atttcggttc gtaaagctct gttgttaggg aagaatgatt gtgtagtaac tatacacagt     120
agagacggta cctaaccaga aagccacggc taactacgtg ccagcagccg cggtaatacg     180
taggtggcaa gcgttgtccg gaattattgg gcgtaaagcg cgcgcaggtg gtttaataag     240
tctgatgtga agcccacgg ctcaaccgtg gagggtcatt ggaaactgtt aaacttgagt      300
gcaggagaga aaagtggaat tcctagtgta gcggtgaaat gcgtagagat taggaggaac     360
accagtggcg aaggcggctt tttggcctgt aactgacact gaggcgcgaa agcgtgggga     420
gcaaaca                                                               427

<210> SEQ ID NO 196
<211> LENGTH: 422
<212> TYPE: DNA
<213> ORGANISM: Bacteroides sp.

<400> SEQUENCE: 196
tgaggaatat tggtcaatgg gcgctagcct gaaccagcca gtagcgtgaa ggatgaaggc     60 tctatgggt cgtaaacttc ttttatataa gaataaagtg cagtatgtat actgttttgt     120
atgtattata tgaataagga tcggctaact ccgtgccagc agccgcggta atacggagga     180
tccgagcgtt atccggattt attgggttta aagggagcgt aggtggactg gtaagtcagt     240
tgtgaaagtt tgcggctcaa ccgtaaaatt gcagttgata ctgtcagtct tgagtacagt     300
agaggtgggc ggaattcgtg tgtagcggtg aaatgcttag atatcacga agaactccga     360 ttgcgaaggc agctcactgg actgcaactg acactgatgc tcgaaagtgt gggtatcaaa     420
ca                                                                    422

<210> SEQ ID NO 197
<211> LENGTH: 402
<212> TYPE: DNA
<213> ORGANISM: Anaerostipes sp.

<400> SEQUENCE: 197
tggggaatat tgcacaatgg gggaaaccct gatgcagcga cgccgcgtga gtgaagaagt      60
```

```
atctcggtat gtaaagctct atcagcaggg aagaaaatga cggtacctga ctaagaagcc    120
ccggctaact acgtgccagc agccgcggta atacgtaggg ggcaagcgtt atccggaatt    180
actgggtgta aagggtgcgt aggtggtatg gcaagtcaga agtgaaaacc cagggcttaa    240
ctctgggact gcttttgaaa ctgtcagact ggagtgcagg agaggtaagc ggaattccta    300
gtgtagcggt gaaatgcgta gatattagga ggaacatcag tggcgaaggc ggcttactgg    360
actgaaactg acactgaggc acgaaagcgt ggggagcaaa ca                      402
```

<210> SEQ ID NO 198
<211> LENGTH: 404
<212> TYPE: DNA
<213> ORGANISM: Prevotella sp.

<400> SEQUENCE: 198

```
tggggaatat tgcacaatgg gggaaaccct gatgcagcga cgccgcgtga gcgaagaagt    60
atttcggtat gtaaagctct atcagcaggg aagaagaaat gacggtacct gactaagaag    120
caccggctaa atacgtgcca gcagccgcgg taatacgtat ggtgcaagcg ttatccggat    180
ttactgggtg taaagggagc gcaggcggaa ggctaagtct gatgtgaaag cccggggctc    240
aaccccggta ctgcattgga aactggtcat ctagagtgtc ggaggggtaa gtggaattcc    300
tagtgtagcg gtgaaatgcg tagatattag gaggaacacc agtggcgaag gcggcttact    360
ggacgataac tgacgctgag gctcgaaagc gtggggagca aaca                    404
```

<210> SEQ ID NO 199
<211> LENGTH: 422
<212> TYPE: DNA
<213> ORGANISM: Bacteroides sp.

<400> SEQUENCE: 199

```
tgaggaatat tggtcaatgg gcgcaggcct gaaccagcca gtagcgtgaa ggatgactg     60 ccctatgggt tgtaaacttc ttttatatgg gaataaagtt ttccacgtgt ggaattttgt    120
atgtaccata tgaataagga tcggctaact ccgtgccagc agccgcggta atacggagga    180
tccgagcgtt atccggattt attgggttta aaggagcgt aggtggacag ttaagtcagt     240
tgtgaaagtt tgcggctcaa ccgtaaaatt gcagttgata ctggctgtct tgagtacagt    300
agaggtgggc ggaattcgtg gtgtagcggt gaaatgctta gatatcacga gaactccga    360 ttgcgaaggc agctcactgg actgcaactg acactgatgc tcgaaagtgt gggtatcaaa    420
ca                                                                   422
```

<210> SEQ ID NO 200
<211> LENGTH: 427
<212> TYPE: DNA
<213> ORGANISM: Haemophilus sp.

<400> SEQUENCE: 200

```
tggggaatat tgcgcaatgg gggaaaccct gacgcagcca tgccgcgtga atgaagaagg    60
ccttcgggtt gtaaagttct ttcggtattg aggaaggagt gtatgttaat agcatacatt    120
attgacgtta aatacagaag aagcaccggc taactccgtg ccagcagccg cggtaatacg    180
gagggtgcga gcgttaatcg gaataactgg gcgtaaaggg cacgcaggcg gttatttaag    240
tgaggtgtga agcccccggg cttaacctgg gaattgcatt tcagactggg taactagagt    300
actttaggga ggggtagaat tccacgtgta gcggtgaaat gcgtagagat gtggaggaat    360
accgaaggcg aaggcagccc cttgggaatg tactgacgct catgtgcgaa agcgtgggga    420
``` gcaaaca 427

<210> SEQ ID NO 201
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 201
tggggaatat tgcacaatgg gggaaaccct gatgcagcaa cgccgcgtga gtgaagaagt    60
atttcggtat gtaaagctct atcagcaggg aagataatga cggtacctga ctaagaagct   120
ccggctaaat acgtgccagc agccgcggta atacgtatgg agcaagcgtt atccggattt   180
actgggtgta aagggtgcgt aggtggcagt gcaagtcaga tgtgaaaggc cggggctcaa   240
ccccggagct gcatttgaaa ctgctcggct agagtacagg agaggcaggc ggaattccta   300
gtgtagcggt gaaatgcgta gatattagga ggaacaccag tggcgaaggc ggcctgctgg   360
actgttactg acactgaggc acgaaagcgt ggggagcaaa ca                      402

<210> SEQ ID NO 202
<211> LENGTH: 405
<212> TYPE: DNA
<213> ORGANISM: Fusobacterium sp.

<400> SEQUENCE: 202
tggggaatat tggacaatgg accaaaagtc tgatccagca attctgtgtg cacgatgacg    60
tttttcggaa tgtaaagtgc tttcagttgg gaagaaaaaa atgacggtac caacagaaga   120
agtgacggct aaatacgtgc cagcagccgc ggtaatacgt atgtcacaag cgttatccgg   180
atttattggg cgtaaagcgc gtctaggtgg ttatgtaagt ctgatgtgaa aatgcagggc   240
tcaactctgt attgcgttgg aaactgcatg actagagtac tggagaggta agcggaacta   300
caagtgtaga ggtgaaattc gtagatattt gtaggaatgc cgatgggaa gccagcttac   360 tggacagata ctgacgctaa agcgcgaaag cgtgggtagc aaaca                   405

<210> SEQ ID NO 203
<211> LENGTH: 427
<212> TYPE: DNA
<213> ORGANISM: Neisseria sp.

<400> SEQUENCE: 203
tggggaattt tggacaatgg gcgcaagcct gatccagcca tgccgcgtgt ctgaagaagg    60
ccttcgggtt gtaaaggact tttgtcaggg aagaaaaggg cggggttaat acccctgtct   120
gatgacggta cctgaagaat aagcaccggc taactacgtg ccagcagccg cggtaatacg   180
tagggtgcga gcgttaatcg gaattactgg gcgtaaagcg ggcgcagacg gttacttaag   240
caggatgtga atccccggg ctcaacctgg gaactgcgtt ctgaactggg tgactagagt   300
gtgtcagagg gaggtagaat tccacgtgta gcagtgaaat gcgtagagat gtggaggaat   360
accgatggcg aaggcagcct cctgggataa cactgacgtt catgcccgaa agcgtgggta   420
gcaaaca                                                             427

<210> SEQ ID NO 204
<211> LENGTH: 402
<212> TYPE: DNA

<213> ORGANISM: Clostridium sp.

<400> SEQUENCE: 204

```
tggggaatat tgcacaatgg gggaaaccct gatgcagcaa cgccgcgtga gtgatgacgg      60
ccttcgggtt gtaaagctct gtcttcaggg acgataatga cggtacctga ggaggaagcc    120
acggctaact acgtgccagc agccgcggta atacgtaggt ggcgagcgtt gtccggattt    180
actgggcgta aagggagcgt aggcggactt ttaagtgaga tgtgaaatac ccggctcaa     240
cttgggtgct gcatttcaaa ctggaagtct agagtgcagg agaggagaat ggaattccta    300
gtgtagcggt gaaatgcgta gagattagga agaacaccag tggcgaaggc gattctctgg    360
actgtaactg acgctgaggc tcgaaagcgt ggggagcaaa ca                       402
```

<210> SEQ ID NO 205
<211> LENGTH: 402
<212> TYPE: DNA
<213> ORGANISM: Coprococcus sp.

<400> SEQUENCE: 205

```
tggggaatat tgcacaatgg gggaaaccct gatgcagcga cgccgcgtga aggaagaagt     60
atctcggtat gtaaacttct atcagcaggg aagataatga cggtacctga ctaagaagcc   120
ccggctaact acgtgccagc agccgcggta atacgtaggg ggcaagcgtt atccggattt   180
actgggtgta aagggagcgt aggcggcgga gcaagtcaga agtgaaagcc ggggctcaa    240
ccccgggacg gcttttgaaa ctgccctgct tgatttcagg agaggtaagc ggaattccta   300
gtgtagcggt gaaatgcgta gatattagga ggaacaccag tggcgaaggc ggcttactgg   360
actgacaatg acgctgaggc tcgaaagcgt ggggagcaaa ca                      402
```

<210> SEQ ID NO 206
<211> LENGTH: 402
<212> TYPE: DNA
<213> ORGANISM: Clostridium sp.

<400> SEQUENCE: 206

```
tggggaatat tgcacaatgg gcgaaagcct gatgcagcaa cgccgcgtga gtgaagaagt     60
atctcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgc agacggcact gcaagtctga agtgaaagcc ggggctcaa    240
ccccgggact gctttggaaa ctgtagagct agagtgctgg agaggcaagc ggaattccta   300
gtgtagcggt gaaatgcgta gatattagga agaacaccag tggcgaaggc ggcttgctgg   360
acagtaactg acgttcaggc tcgaaagcgt ggggagcaaa ca                      402
```

<210> SEQ ID NO 207
<211> LENGTH: 422
<212> TYPE: DNA
<213> ORGANISM: Prevotella sp.

<400> SEQUENCE: 207

```
tgaggaatat tggtcaatgg gcgcgagcct gaaccagcca gtagcgtgc aggatgacgg      60
ccctatgggt tgtaaactgc ttttgtatgg ggataaagtc aatcacgtgt gattgtttgc    120
aggtaccata cgaataagga ccggctaatt ccgtgccagc agccgcggta atacggaagg   180
tccgggcgtt atccggattt attgggttta aagggagcgt aggccggaga ttaagtgtgt   240
tgtgaaatgt agacgctcaa cgtctgactt gcagcgcata ctggtttcct tgagtacgca   300
```

```
caacgttggc ggaattcgtc gtgtagcggt gaaatgctta gatatgacga agaactccga    360
ttgcgaaggc agctgacggg agcgcaactg acgcttaagc tcgaaggtgc gggtatcgaa    420
ca                                                                   422

<210> SEQ ID NO 208
<211> LENGTH: 422
<212> TYPE: DNA
<213> ORGANISM: Bacteroides sp.

<400> SEQUENCE: 208
tgaggaatat tggtcaatgg acgagagtct gaaccagcca agtagcgtga aggatgaagg     60
ttctatggat tgtaaacttc ttttatacgg gaataaacga atccacgtgt ggattttgc    120 atgtaccgta tgaataagga tcggctaact ccgtgccagc agccgcgta atacggagga    180 tccgagcgtt atccggattt attgggttta agggagcgt agatgggttg ttaagtcagt    240
tgtgaaagtt tgcggctcaa ccgtaaaatt gcaattgata ctggcagtct tgagtacagt    300
tgaggtaggc ggaattcgtg gtgtagcggt gaaatgctta gatatcacga agaactccga    360
ttgcgaaggc agcttactaa cctgtaactg acattgatgc tcgaaagtgt gggtatcaaa    420
ca                                                                   422

<210> SEQ ID NO 209
<211> LENGTH: 426
<212> TYPE: DNA
<213> ORGANISM: Clostridium sp.

<400> SEQUENCE: 209
tagggaattt tcggcaatgg gggaaaccct gaccgagcaa cgccgcgtga aggaagaagt     60
aattcgttat gtaaacttct gtcatagagg aagaacggtg gatataggga atgatatcca    120
agtgacggta ctctataaga aagccacggc taactacgtg ccagcagccg cggtaatacg    180
taggtggcga gcgttatccg gaattattgg gcgtaaagag ggagcaggcg gcactaaggg    240
tctgtggtga agatcgaag cttaacttcg gtaagccatg gaaaccgtag agctagagtg    300
tgtgagagga tcgtggaatt ccatgtgtag cggtgaaatg cgtagatata tggaggaaca    360
ccagtggcga aggcgacgat ctggcgcata actgacgctc agtcccgaaa gcgtggggag    420
caaata                                                               426

<210> SEQ ID NO 210
<211> LENGTH: 427
<212> TYPE: DNA
<213> ORGANISM: Streptococcus sp.

<400> SEQUENCE: 210
tagggaatct tcggcaatgg acgaaagtct gaccgagcaa cgccgcgtga gtgaagaagg     60
ttttcggatc gtaaagctct gttgtaagtc aagaacgtgt gtgagagtgg aaagttcaca    120
cagtgacggt agcttaccag aaagggacgg ctaactacgt gccagcagcc gcggtaatac    180
gtaggtcccg agcgttgtcc ggatttattg ggcgtaaagg gagcgcaggc ggtcaggaaa    240
gtctggagta aaaggctatg gctcaaccat agtgtgctct ggaaactgtc tgacttgagt    300
gcagaagggg agagtggaat tccatgtgta gcggtgaaat gcgtagatat atggaggaac    360
accagtggcg aaagcggctc tctggtctgt cactgacgct gaggctcgaa agcgtgggta    420
gcgaaca                                                              427
```

<210> SEQ ID NO 211
<211> LENGTH: 402
<212> TYPE: DNA
<213> ORGANISM: Unknown
<220> FEATURE:
<221> NAME/KEY: source
<223> OTHER INFORMATION: /note="Description of Unknown: unclassified.Lachnospiraceae"

<400> SEQUENCE: 211

| | | | | | |
|---|---|---|---|---|---|
| tggggaatat | tgcacaatgg | aggaaactct | gatgcagcga | cgccgcgtga | gtgaagaagt | 60 |
| atttcggtat | gtaaagctct | atcagcaggg | aagaaaatga | cggtacctga | ctaagaagca | 120 |
| ccggctaaat | acgtgccagc | agccgcggta | atacgtatgg | tgcaagcgtt | atccggattt | 180 |
| actgggtgta | aagggagcgt | aggtggcaag | gcaagccaga | agtgaaaacc | cggggctcaa | 240 |
| ccgcgggatt | gcttttggaa | ctgtcatgct | agagtgcagg | aggggtgagc | ggaattccta | 300 |
| gtgtagcggt | gaaatgcgta | gatattagga | ggaacaccgg | aggcgaaggc | ggctcactgg | 360 |
| actgtaactg | acactgaggc | tcgaaagcgt | ggggagcaaa | ca | | 402 |

<210> SEQ ID NO 212
<211> LENGTH: 422
<212> TYPE: DNA
<213> ORGANISM: Porphyromonas sp.

<400> SEQUENCE: 212

| | | | | | |
|---|---|---|---|---|---|
| tgaggaatat | tggtcaatgg | gcgagagcct | gaaccagcca | agtcgcgtga | aggatgactg | 60 |
| tcttatggat | tgtaaacttc | ttttatacgg | gaataacaag | agtcacgtgt | ggctccctgc | 120 |
| atgtaccgta | tgaataagca | tcggctaact | ccgtgccagc | agccgcggta | atacggagga | 180 |
| tgcgagcgtt | atccggattt | attgggttta | aagggtgcgt | aggcggcctg | ttaagtcagc | 240 |
| ggtgaaatct | aggagcttaa | ctcctaaatt | gccattgata | ctggcgggct | tgagtgtaga | 300 |
| tgaggtaggc | ggaatgcgtg | gtgtagcggt | ggaatgcata | gatatcacgc | agaactccga | 360 |
| ttgcgaaggc | agcttactaa | ggtacaactg | acgctgaagc | acgaaagcgt | gggtatcaaa | 420 |
| ca | | | | | | 422 |

<210> SEQ ID NO 213
<211> LENGTH: 421
<212> TYPE: DNA
<213> ORGANISM: Alloprevotella sp.

<400> SEQUENCE: 213

| | | | | | |
|---|---|---|---|---|---|
| tgaggaatat | tggtcaatgg | gcgagagcct | gaaccagcca | agtagcgtgc | aggatgacgg | 60 |
| ccctccgggt | tgtaaactgc | ttttagttgg | gaataaaaaa | agggacttgt | cccttcttgt | 120 |
| atgtaccttc | agaaaaagga | ccggctaatt | ccgtgccagc | agccgcggta | atacggaagg | 180 |
| tccaggcgtt | atccggattt | attgggttta | aagggagcgt | aggcggattg | ttaagtcagc | 240 |
| ggttaaaggg | tgtggctcaa | ccatgcattg | ccgttgaaac | tggcgatctt | gagtgcagac | 300 |
| agggatgccg | gaattcgtgg | tgtagcggtg | aaatgcttag | atatcacgaa | gaactccgat | 360 |
| cgcgaaggca | ggtgtccggg | ctgcaactga | cgctgaggct | cgaaagtgtg | ggtatcaaac | 420 |
| a | | | | | | 421 |

<210> SEQ ID NO 214
<211> LENGTH: 406
<212> TYPE: DNA
<213> ORGANISM: Clostridium sp.

<400> SEQUENCE: 214

```
tggggaatat tgcacaatgg gggaaaccct gatgcagcaa cgccgcgtga aggaagaagg      60
ttttcggatc gtaaacttct atcaacaggg acgaagaaag tgacggtacc tgaataagaa    120
gccccggcta actacgtgcc agcagccgcg gtaatacgta gggggcaagc gttatccgga    180
attactgggt gtaaagggag cgtaggcggc acgccaagcc agatgtgaaa gcccgaggct    240
taacctcgcg gattgcattt ggaactggcg agctagagta caggagagga aagcggaatt    300
cctagtgtag cggtgaaatg cgtagatatt aggaagaaca ccagtggcga aggcggcttt    360
ctggactgaa actgacgctg aggctcgaaa gcgtggggag caaaca              406
```

<210> SEQ ID NO 215
<211> LENGTH: 427
<212> TYPE: DNA
<213> ORGANISM: Sutterella sp.

<400> SEQUENCE: 215

```
tggggaattt tggacaatgg gggcaaccct gatccagcca tgccgcgtgc aggatgaagg      60
tcttcggatt gtaaactgct tttgtcaggg acgaaaaggg atgcgataac accgcattcc    120
gctgacggta cctgaagaat aagcaccggc taactacgtg ccagcagccg cggtaatacg    180
tagggtgcaa gcgttaatcg gaattactgg gcgtaaagcg tgcgcaggcg gttctgtaag    240
atagatgtga atccccgggg ctcaacctgg gaattgcata tatgactgca ggacttgagt    300
tgtcagagg agggtggaat tccacgtgta gcagtgaaat gcgtagatat gtggaagaac    360
accgatggcg aaggcagccc tctgggacat gactgacgct catgcacgaa agcgtgggga    420
gcaaaca                                                               427
```

<210> SEQ ID NO 216
<211> LENGTH: 402
<212> TYPE: DNA
<213> ORGANISM: Clostridium sp.

<400> SEQUENCE: 216

```
tggggaatat tgcacaatgg gcgaaagcct gatgcagcga cgccgcgtga gtgaagaagt      60
atttcggtat gtaaagctct atcagcaggg aagaaaatga cggtacctga ctaagaagcc    120
ccggctaact acgtgccagc agccgcggta atacgtaggg gcaagcgtt atccggattt    180
actgggtgta agggagcgt agacggcgaa gcaagtctga agtgaaaacc cagggctcaa    240
ccctgggact gctttggaaa ctgttttgct agagtgtcgg agaggtaagt ggaattccta    300
gtgtagcggt gaaatgcgta gatattagga ggaacaccag tggcgaaggc ggcttactgg    360
acgataactg acgttgaggc tcgaaagcgt ggggagcaaa ca                       402
```

<210> SEQ ID NO 217
<211> LENGTH: 403
<212> TYPE: DNA
<213> ORGANISM: Collinsella sp.

<400> SEQUENCE: 217

```
tggggaatct tgcgcaatgg ggggaaccct gacgcagcga cgccgcgtgc gggacggagg      60
ccttcgggtc gtaaaccgct ttcagcaggg aagagtcaag actgtacctg cagaagaagc    120
cccggctaac tacgtgccag cagccgcggt aatacgtagg gggcgagcgt tatccggatt    180
cattgggcgt aaagcgcgcg taggcggccc ggcaggccgg gggtcgaagc gggggggctca    240
```

```
acccccccgaa gccccccggaa cctccgcggc ttgggtccgg taggggaggg tggaacaccc    300
ggtgtagcgg tggaatgcgc agatatcggg tggaacaccg gtggcgaagg cggccctctg    360
ggccgagacc gacgctgagg cgcgaaagct gggggagcga aca                       403
```

<210> SEQ ID NO 218
<211> LENGTH: 402
<212> TYPE: DNA
<213> ORGANISM: Clostridium sp.

<400> SEQUENCE: 218

```
tggggaatat tgcacaatgg gggaaaccct gatgcagcga cgccgcgtga gtgaagaagt    60
atttcggtat gtaaagctct atcagcaggg aagaaagtga cggtacctga ataagaagcc    120
ccggctaact acgtgccagc agccgcggta atacgtaggg ggcaagcgtt atccggattt    180
actgggtgta aagggagcgt agacggcaag gcaagtctga agtgaaagcc cggtgcttaa    240
cgccgggact gctttggaaa ctgtttggct ggagtgccgg agaggtaagc ggaattccta    300
gtgtagcggt gaaatgcgta gatattagga agaacaccag tggcgaaggc ggcttactgg    360
acggtaactg acgttgaggc tcgaaagcgt ggggagcaaa ca                       402
```

<210> SEQ ID NO 219
<211> LENGTH: 404
<212> TYPE: DNA
<213> ORGANISM: Oscillibacter sp.

<400> SEQUENCE: 219

```
tggggaatat tggcaatgg gcgcaagcct gacccagcaa cgccgcgtga aggaagaagg    60
ctttcgggtt gtaaacttct tttaagtggg aagagtagaa gacggtacca cttgaataag    120
ccacggctaa ctacgtgcca gcagccgcgg taatacgtag gtggcaagcg ttgtccggat    180
ttactgggtg taaagggcgt gcagccgggc atgcaagtca gatgtgaaat ctcagggctt    240
aaccctgaaa ctgcatttga aactgtatgt cttgagtgcc ggagaggtaa tcggaattcc    300
ttgtgtagcg gtgaaatgcg tagatataag gaagaacacc agtggcgaag gcggattact    360
ggacggtaac tgacggtgag gcgcgaaagc gtggggagcg aaca                      404
```

<210> SEQ ID NO 220
<211> LENGTH: 401
<212> TYPE: DNA
<213> ORGANISM: Peptostreptococcus sp.

<400> SEQUENCE: 220

```
tggggaatat tgcacaatgg gcgaaagcct gatgcagcaa cgccgcgtga acgatgaagg    60
tcttcggatc gtaaagttct gttgcagggg aagataatga cggtaccctg tgaggaagcc    120
ccggctaact acgtgccagc agccgcggta atacgtaggg ggctagcgtt atccggattt    180
actgggcgta aagggtgcgt aggtggtcct tcaagtcggt ggttaaaggc tacggctcaa    240
ccgtagtaag ccgccgaaac tggaggactt gagtgcagga gaggaaagtg gaattcccag    300
tgtagcggtg aaatgcgtag atattggag gaacaccagt agcgaaggcg gctttctgga    360
ctgcaactga cactgaggca cgaaagcgtg ggtagcaaac a                         401
```

<210> SEQ ID NO 221
<211> LENGTH: 404
<212> TYPE: DNA
<213> ORGANISM: Unknown
<220> FEATURE:
<221> NAME/KEY: source
<223> OTHER INFORMATION: /note="Description of Unknown:
       unclassified.Firmicutes"

<400> SEQUENCE: 221

| tggggaatat tgggcaatgg aggaaactct gacccagcaa cgccgcgtgg aggaagaagg | 60 |
| ttttcggatc gtaaactcct gtccttggag acgagtagaa gacggtatcc aaggaggaag | 120 |
| ccccggctaa ctacgtgcca gcagccgcgg taatacgtag ggggcaagcg ttgtccggaa | 180 |
| taattgggcg taaagggcgc gtaggcggct cggtaagtct ggagtgaaag tcctgctttt | 240 |
| aaggtgggaa ttgctttgga tactgtcggg cttgagtgca ggagaggtta gtggaattcc | 300 |
| cagtgtagcg gtgaaatgcg tagagattgg gaggaacacc agtggcgaag gcgactaact | 360 |
| ggactgtaac tgacgctgag gcgcgaaagt gtggggagca aaca | 404 |

<210> SEQ ID NO 222
<211> LENGTH: 402
<212> TYPE: DNA
<213> ORGANISM: Clostridium sp.

<400> SEQUENCE: 222

| tggggaatat tgcacaatgg gggaaaccct gatgcagcaa cgccgcgtga gtgaagaagt | 60 |
| atttcggtat gtaaagctct atcagcaggg aagaaaatga cggtacctga ctaagaagcc | 120 |
| ccggctaact acgtgccagc agccgcggta atacgtaggg ggcaagcgtt atccggattt | 180 |
| actgggtgta aagggagcgt agacggcgag acaagtctga agtgaaagcc ggggctcaa | 240 |
| ccccgggact gctttggaaa ctgccttgct agagtgctgg agaggtaagt ggaattccta | 300 |
| gtgtagcggt gaaatgcgta gatattagga ggaacaccag tggcgaaggc ggcttactgg | 360 |
| acagtaactg acgttgaggc tcgaaagcgt ggggagcaaa ca | 402 |

<210> SEQ ID NO 223
<211> LENGTH: 428
<212> TYPE: DNA
<213> ORGANISM: Bilophila sp.

<400> SEQUENCE: 223

| tggggaatat tgcgcaatgg gcgaaagcct gacgcagcga cgccgcgtga gggatgaagg | 60 |
| ttctcggatc gtaaacctct gtcaggggg aagaaacccc ctcgtgtgaa taatgcgagg | 120 |
| gcttgacggt accccaaag gaagcaccgg ctaactccgt gccagcagcc gcggtaatac | 180 |
| ggagggtgca agcgttaatc ggaatcactg ggcgtaaagc gcacgtaggc ggcttggtaa | 240 |
| gtcagggtg aaatcccaca gcccaactgt ggaactgcct tgatactgc caggcttgag | 300 |
| taccggagag ggtggcggaa ttccaggtgt aggagtgaaa tccgtagata tctggaggaa | 360 |
| caccggtggc gaaggcggcc acctggacgg taactgacgc tgaggtgcga agcgtgggt | 420 |
| agcaaaca | 428 |

<210> SEQ ID NO 224
<211> LENGTH: 402
<212> TYPE: DNA
<213> ORGANISM: Clostridium sp.

<400> SEQUENCE: 224

| tgagggatat tgggcaatgg gggaaaccct gacccagcaa cgccgcgtga gggatgacgg | 60 |
| ttttcggatt gtaaacctct gtcctctgtg aagatagtga cggtagcaga ggaggaagct | 120 |
| ccggctaact acgtgccagc agccgcggta atacgtaggg agcaagcgtt gtccggattt | 180 |

```
actgggtgta aagggtgcgt aggcggattg gcaagtcaga agtgaaatcc atgggcttaa    240
cccatgaact gcttttgaaa ctgttagtct tgagtgaagt agaggtaggc ggaattcccg    300
gtgtagcggt gaaatgcgta gagatcggga ggaacaccag tggcgaaggc ggcctactgg    360
gctttaactg acgctgaggc acgaaagtgt gggtagcaaa ca                       402
```

<210> SEQ ID NO 225
<211> LENGTH: 427
<212> TYPE: DNA
<213> ORGANISM: Unknown
<220> FEATURE:
<221> NAME/KEY: source
<223> OTHER INFORMATION: /note="Description of Unknown:
      unclassified.Erysipelotrichaceae"

<400> SEQUENCE: 225

```
tagggaattt tcgtcaatgg ggggaaccct gaacgagcaa tgccgcgtga gtgaggaagg     60
tcttcggatc gtaaagctct gttgtaagag aaaaacggca ctcataggga atgatgagtg    120
agtgatggta tcttaccaga aagtcacggc taactacgtg ccagcagccg cggtaatacg    180
taggtggcga gcgttatccg gaatgattgg gcgtaaaggg tgcgtaggtg cagatcaag    240 tctggagtaa aaggtatggg ctcaacccgt actggctctg gaaactgatc agctagagaa    300
cagaagagga cggcggaact ccatgtgtag cggtaaaatg cgtagatata tggaagaaca    360
ccggtggcga aggcggccgt ctggtctgga ttctgacact gaagcacgaa agcgtgggga    420
gcaaata                                                               427
```

<210> SEQ ID NO 226
<211> LENGTH: 403
<212> TYPE: DNA
<213> ORGANISM: Campylobacter sp.

<400> SEQUENCE: 226

```
tagggaatat tgcgcaatgg gggaaaccct gacgcagcaa cgccgcgtgg aggatgacac     60
ttttcggagc gtaaactcct tttgttaggg aagaataatg acggtaccta acgaataagc    120
accggctaac tccgtgccag cagccgcggt aatacggagg gtgcaagcgt tactcggaat    180
cactgggcgt aaaggacgcg taggcggatt atcaagtctc ttgtgaaatc taacggctta    240
accgttaaac tgcttgggaa actgataatc tagagtaagg gagaggcaga tggaattctt    300
ggtgtagggg taaaatccgt agatatcaag aagaatacct attgcgaagg cgatctgctg    360
gaacttaact gacgctaatg cgtgaaagcg tggggagcaa aca                      403
```

<210> SEQ ID NO 227
<211> LENGTH: 422
<212> TYPE: DNA
<213> ORGANISM: Prevotella sp.

<400> SEQUENCE: 227

```
tgaggaatat tggtcaatgg gcgcaagcct gaaccagcca gtagcgtgca aggaagacgg     60
ccctatgggt tgtaaactgc ttttatacga gaataatttg atgcacgtgt gcgttattgc    120
atgtatcgta tgaataagga ccggctaatt ccgtgccagc agccgcggta atacggaagg    180
tccaggcgtt atccggattt attgggttta aagggagtgt aggcggtttg ttaagcgtgt    240
tgtgaaattt agatgctcaa catttaactt gcagcgcgaa ctgtcagact tgagtacacg    300
caacgtatgc ggaattcatg gtgtagcggt gaaatgctta gatatcatga gaactccga    360 ttgcgaaggc agcatacggg agtgtaactg acgcttaagc tcgaaggtgc gggtatcgaa    420
```

```
ca                                                                          422
```

<210> SEQ ID NO 228
<211> LENGTH: 406
<212> TYPE: DNA
<213> ORGANISM: Atopobium sp.

<400> SEQUENCE: 228

```
tggggaatct tgcacaatgg gcgaaagcct gatgcagcga cgccgcgtgc gggatgaagg    60
ccttcgggtt gtaaaccgct ttcagcaggg acgaggcgaa agtgacggta cctgcagaag   120
aagccccggc taactacgtg ccagcagccg cggtaatacg taggggggcaa gcgttatccg   180 gattcattgg gcgtaaagcg ctcgtaggcg gtctgttagg tcgggagtta aatccggggg   240
ctcaaccccc gttcgctccc gataccggca gacttgagtt tggtagggga aggtggaatt   300
cctagtgtag cggtggaatg cgcagatatt aggaagaaca ccagtggcga aggcggcctt   360
ctgggccata actgacgctg aggagcgaaa gctaggggag caaaca              406
```

<210> SEQ ID NO 229
<211> LENGTH: 403
<212> TYPE: DNA
<213> ORGANISM: Acetanaerobacterium sp.

<400> SEQUENCE: 229

```
tgggggatat tgcacaatgg gggaaaccct gatgcagcga cgccgcgtga gggaagacgg    60
tcctctggat tgtaaacctc tgtcttcggg gacgaaacga gacggtaccc gaggaggaag   120
ccacggctaa ctacgtgcca gcagccgcgg taatacgtag gtggcaagcg ttgtccggaa   180
ttactgggtg taaagggagc gtaggcgggc aggcaagtca ggcgtgaaat atatcggctc   240
aaccggtaac ggcgcttgaa actgcaggtc ttgagtgaag tagaggttgg cggaattcct   300
agtgtagcgg tgaaatgcgt agatattagg aggaacacca gtggcgaagg cggccaactg   360
ggcttttact gacgctgagg ctcgaaagtg tggggagcaa aca                 403
```

<210> SEQ ID NO 230
<211> LENGTH: 422
<212> TYPE: DNA
<213> ORGANISM: Parabacteroides sp.

<400> SEQUENCE: 230

```
tgaggaatat tggtcaatgg gcgtaagcct gaaccagcca gtcgcgtga gggatgaagg    60 ttctatggat cgtaaacctc ttttataagg aataaagtg cggacgtgt cccgttttgt   120 atgtacctta tgaataagga tcggctaact ccgtgccagc agccgcggta atacggagga   180
tccgagcgtt atccggattt attgggttta aagggtgcgt aggcggcctt ttaagtcagc   240
ggtgaaagtc tgtggctcaa ccatagaatt gccgttgaaa ctgggaggct tgagtatgtt   300
tgaggcaggc ggaatgcgtg gtgtagcggt gaaatgctta gatatcacgc agaaccccga   360
ttgcgaaggc agcctgccaa gccatgactg acgctgatgc acgaaagcgt ggggatcaaa   420
ca                                                                          422
```

<210> SEQ ID NO 231
<211> LENGTH: 427
<212> TYPE: DNA
<213> ORGANISM: Veillonella sp.

<400> SEQUENCE: 231

```
tggggaatct tccgcaatgg acgaaagtct gacggagcaa cgccgcgtga gtgatgacgg      60
ccttcgggtt gtaaagctct gttaatcggg acgaatggtt cttgtgcgaa tagtgcgagg     120
atttgacggt accggaatag aaagccacgg ctaactacgt gccagcagcc gcggtaatac     180
gtaggtggca agcgttgtcc ggaattattg ggcgtaaagc gcgcgcaggc ggatcagtta     240
gtctgtctta aaagttcggg gcttaacccc gtgatgggat ggaaactgct gatctagagt     300
atcggagagg aaagtggaat tcctagtgta gcggtgaaat gcgtagatat taggaagaac     360
accagtggcg aaggcgactt tctggacgaa aactgacgct gaggcgcgaa agccagggga     420
gcgaacg                                                               427
```

<210> SEQ ID NO 232
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      unclassified.Flavobacteriaceae"

<400> SEQUENCE: 232

```
tgaggaatat tggacaatgg gtggaagcct gatccagcca tcccgcgtgc aggacgactg      60
ccctatgggt tgtaaactgc ttttatatag ggataaacct actctcgtga gagtagctga     120
aggtactata tgaataagca ccggctaact ccgtgccagc agccgcggta atacggaggg     180
tgcaagcgtt atccggattt attgggttta aagggtccgt aggtgggctg ataagtcagc     240
ggtgaaatcc tgcagcttaa ctgtagaact gccgttgata ctgttagtct tgagtgtatt     300
tgaagtggct ggaataagta gtgtagcggt gaaatgcata gatattactt agaacaccaa     360
ttgcgaaggc aggtcactaa gatacaactg acgctgaggg acgaaagcgt ggggagcgaa     420
ca                                                                    422
```

<210> SEQ ID NO 233
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 233

```
tggggaatat tgcacaatgg gggaaaccct gatgcagcga cgccgcgtga aggatgaagt      60
atttcggtat gtaaacttct atcagcaggg aagaaaatga cggtacctga ctaagaagcc     120
ccggctaact acgtgccagc agccgcggta atacgtaggg ggcaagcgtt atccggattt     180
actgggtgta aagggagcgt agacggtatg gcaagtctga tgtgaaaggc cagggctcaa     240
ccctgggact gcattggaaa ctgtcgaact agagtgtcgg agaggcaagt ggaattccta     300
gtgtagcggt gaaatgcgta gatattagga ggaacaccag tggcgaaggc ggcttgctgg     360
acgatgactg acgttgaggc tcgaaagcgt ggggagcaaa ca                        402
```

<210> SEQ ID NO 234
<211> LENGTH: 427
<212> TYPE: DNA
<213> ORGANISM: Dialister sp.

<400> SEQUENCE: 234

```
tggggaatct tccgcaatgg acgaaagtct gacggagcaa cgccgcgtga acgaagaagg      60
```

```
tcttcggatt gtaaagttct gtgattcggg acgaaagggt ttgtggtgaa taatcataga    120
cattgacggt accgaaaaag caagccacgg ctaactacgt gccagcagcc gcggtaatac    180
gtaggtggca agcgttgtcc ggaattattg ggcgtaaagc gcgcgcaggc ggtttcttaa    240
gtccatctta aaagcgtggg gctcaacccc atgagggggg ggaaactggg aagctggagt    300
atcggagagg aaagtggaat tcctagtgta gcggtgaaat gcgtagagat taggaagaac    360
accggtggcg aaggcgactt tctagacgaa aactgacgct gaggcgcgaa agcgtgggga    420
gcaaaca                                                              427

<210> SEQ ID NO 235
<211> LENGTH: 422
<212> TYPE: DNA
<213> ORGANISM: Capnocytophaga sp.

<400> SEQUENCE: 235
tgaggaatat tggtcaatgg tcggaagact gaaccagcca tgccgcgtgc aggaagaatg     60
ccttatgggt tgtaaactgc ttttatatgg aagaataag gagtacgtgt actttgatga    120
cggtaccata tgaataagca tcggctaact ccgtgccagc agccgcggta atacggagga    180
tgcgagcgtt attcggaatc attgggttta aagggtctgt aggcgggcta ttaagtcagg    240
ggtgaaaggt tcagcttaa ctgagaaatt gcctttgata ctggtagtct tgaatatctg    300
tgaagttctt ggaatgtgta gtgtagcggt gaaatgctta gatattacac agaaccga     360 ttgcggaggc agggggactaa cagacgattg acgctgagag cgaaagcgt ggggagcgaa    420 ca                                                                    422

<210> SEQ ID NO 236
<211> LENGTH: 422
<212> TYPE: DNA
<213> ORGANISM: Prevotella sp.

<400> SEQUENCE: 236
tgaggaatat tggtcaatgg atggaaatct gaaccagcca agtagcgtgc aggatgacgg     60
ccctatgggt tgtaaactgc ttttatgtga gaataaagtt aggtatgtat acttatttgc    120
atgtatcaca tgaataagga ccggctaatt ccgtgccagc agccgcggta atacggaagg    180
tccaggcgtt atccggattt attgggttta aagggtgcgt aggccgtttg ataagcgtgc    240
tgtgaaatat agtggctcaa cctctatcgt gcagcgcgaa ctgtcgaact tgagtgcgta    300
gtaggtaggc ggaattcgtg gtgtagcggt gaaatgctta gatattcacga agaactccga    360 ttgcgaaggc agcttaccgt aacgttactg acgcttaagc acgaaggtgc gggtatcgaa    420
ca                                                                    422

<210> SEQ ID NO 237
<211> LENGTH: 422
<212> TYPE: DNA
<213> ORGANISM: Tannerella sp.

<400> SEQUENCE: 237
tgaggaatat tggtcaatgg gcgagagcct gaaccagcca agtcgcgtga aggatgacgg     60
ccctatgggt tgtaaacttc ttttgcaggg gaataaagat attcacgtgt gggtagttgt    120
atgtaccctg cgaataagca tcggctaact ccgtgccagc agccgcggta atacggagga    180
tgcgagcgtt atccggattt attgggttta aagggtgcgt aggtgggcta ttaagtcagt    240
```

```
ggtgaaagtt tgtcgctcaa cgataaaatt gccgttgaaa ctggtggtct tgagtatgga      300
tgaagtaggc ggaatgcgtg gtgtagcggt gaaatgcata gagatcacgc agaactccga      360
ttgcgaaggc agcttactaa ggcataactg acactgaagc acgaaagcgt gggtatcaaa      420
ca                                                                    422
```

<210> SEQ ID NO 238
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 238

```
tggggaatat tgcacaatgg aggcaactct gatgcagcga cgccgcgtga gtgaagaagt       60
atttcggtat gtaaagctct atcagtaggg aagataatga cggtacctac agaagaagcc      120
ccggctaaat acgtgccagc agccgcgta atacgtatgg gcaagcgtt atccggattt       180 actgggtgta aagggagtgt aggcggcagt acaagtcagg agtgaaaact ggggctcaa       240 ccccaagact gcttttgaaa ctgtacagct agagtgtagg aagggcaagc ggaattcctg      300
gtgtagcggt gaaatgcgta gatatcagga agaacaccgg tggcgaaggc ggcttgctgg      360
actataactg acgctgagac tcgaaagcgt ggggagcgaa ca                        402
```

<210> SEQ ID NO 239
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 239

```
tggggaatat tgggcaatgg gcgaaagcct gacccagcaa cgccgcgtga aggaagaagg       60
ccttcgggtt gtaaacttct tttaagaggg acgaagaagt gacggtacct cttgaataag      120
ccacggctaa ctacgtgcca gcagccgcgg taatacgtag gtggcgagcg ttatccggat      180
ttactgggtg taaagggcgc gtaggcggga atgcaagtca gatgtgaaat ccaagggctc      240
aacccttgaa ctgcatttga aactgtattt cttgagtgtc ggagaggttg acggaattcc      300
tagtgtagcg gtgaaatgcg tagatattag gaggaacacc agtggcgaag gcggtcaact      360
ggacgataac tgacgctgag gcgcgaaagc gtggggagca aaca                      404
```

<210> SEQ ID NO 240
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 240

```
tgaggaatat tggtcaatgg acggaagtct gaaccagcca tgccgcgtgc aggaagacgg       60
ctctatgagt tgtaaactgc ttttgtacga gggtaaacgc agatacgtgt atctgcctga      120
aagtatcgta cgaataagga tcggctaact ccgtgccagc agccgcggta atacggagga      180
tccaagcgtt atccggattt attgggttta aagggtgcgt aggcggttta gtaagtcagc      240
```

```
ggtgaaattt tggtgcttaa caccaaacgt gccgttgata ctgctgggct agagagtagt    300
tgcggtaggc ggaatgtatg gtgtagcggt gaaatgctta gagatcatac agaacaccga    360
ttgcgaaggc agcttaccaa actatatctg acgttgaggc acgaaagcgt ggggagcaaa    420
ca                                                                   422
```

<210> SEQ ID NO 241
<211> LENGTH: 402
<212> TYPE: DNA
<213> ORGANISM: Unknown
<220> FEATURE:
<221> NAME/KEY: source
<223> OTHER INFORMATION: /note="Description of Unknown: unclassified.Lachnospiraceae"

<400> SEQUENCE: 241

```
tagggaatat tgcacaatgg gggaaaccct gatgcagcga cgccgcgtga aggaagaagt    60
atttcggtat gtaaacttct atcagcaagg aagaaaatga cggtacttga ctaagaagcc    120
ccggctaaat acgtgccagc agccgcggta atacgtatgg gcaagcgtt atccggattt     180 actgggtgta aagggagcgt aggcggcatg gcaagtcaga agtgaaagcc tggggctcaa    240
ccccggaatt gcttttgaaa ctgtcaggct agagtgtcgg aggggtaagc ggaattccta    300
gtgtagcggt gaaatgcgta gatattagga ggaacaccgg tggcgaaggc ggcttactgg    360
acgattactg acgctgaggc tcgaaagcgt ggggagcaaa ca                       402
```

<210> SEQ ID NO 242
<211> LENGTH: 428
<212> TYPE: DNA
<213> ORGANISM: Megasphaera sp.

<400> SEQUENCE: 242

```
tggggaatct tccgcaatgg gcgaaagcct gacggagcaa cgccgcgtga gtgaagacgg    60
ccttcgggtt gtaaagctct gttatacggg acgaataatc ttgtggttaa tacccatgag    120
aagtgacggt accgtaagag aaagccacgg ctaactacgt gccagcagcc gcggtaatac    180
gtaggtggca agcgttgtcc ggaattattg ggcgtaaagg gcgcgcaggc ggcttcttaa    240
gtctgtctta aaagtgcggg gcttaaccccc gtgatgggat ggaaactggg aagctcagag    300
tatcggagag gaaagcggaa ttcctagtgt agcggtgaaa tgcgtagata ttaggaggaa    360
caccagtggc gaaagcggct ttctggacga aaactgacgc tgaggcgcga agccagggg    420 agcgaacg                                                             428
```

<210> SEQ ID NO 243
<211> LENGTH: 422
<212> TYPE: DNA
<213> ORGANISM: Alistipes sp.

<400> SEQUENCE: 243

```
tgaggaatat tggtcaatgg acgcaagtct gaaccagcca tgccgcgtgc aggaagacgg    60
ctctatgagt tgtaaactgc ttttgtacga gagtaaacgc tcttacgtgt aagagcctga    120
aagtatcgta cgaataagga tcggctaact ccgtgccagc agccgcggta atacggagga    180
tccaagcgtt atccggattt attgggttta aagggtgcgt aggcggtttg ataagttaga    240
ggtgaaatac cggtgcttaa caccggaact gcctctaata ctgttgaact agagagtagt    300
tgcggtaggc ggaatgtatg gtgtagcggt gaaatgctta gagatcatac agaacaccga    360
```

```
ttgcgaaggc agcttaccaa actatatctg acgttgaggc acgaaagcgt ggggagcaaa    420
ca                                                                  422
```

<210> SEQ ID NO 244
<211> LENGTH: 427
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 244

```
tggggaatct tccgcaatgg acgaaagtct gacggagcaa cgccgcgtga gtgatgaagg     60
tcttcggatt gtaaaactct gttgttaggg acgaaagcac cgtgttcgaa caggtcatgg    120
tgttgacggt acctaacgag gaagccacgg ctaactacgt gccagcagcc gcggtaatac    180
gtaggtggca agcgttgtcc ggaattattg ggcgtaaaga gcatgtaggc gggcttttaa    240
gtctgacgtg aaaatgcggg gcttaacccc gtatggcgtt ggatactgga agtcttgagt    300
gcaggagagg aaaggggaat tcccagtgta gcggtgaaat gcgtagatat tgggaggaac    360
accagtggcg aaggcgcctt tctggactgt gtctgacgct gagatgcgaa agccagggta    420
gcaaacg                                                              427
```

<210> SEQ ID NO 245
<211> LENGTH: 421
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 245

```
tgaggaatat tggtcaatgg gcgggagcct gaaccagcca agtagcgtga aggacgacgg     60
ccctacgggt tgtaaacttc ttttataagg gaataaagtt cgccacgtgt ggtgttttgt    120
atgtaccttg tgaataagca tcggctaatt ccgtgccagc agccgcgta atacggaaga    180 tgcgagcgtt atccggattt attgggttta aagggagcgt aggcgggctt ttaagtcagc    240
ggtcaaatgt cgtggctcaa ccatgtcaag ccgttgaaac tgtaagcctt gagtctgcac    300
agggcacatg gaattcgtgg tgtagcggtg aaatgcttag atatcacgaa gaactccgat    360
cgcgaaggca ttgtgccggg gcataactga cgctgaggct cgaaagtgcg ggtatcaaac    420
a                                                                    421
```

<210> SEQ ID NO 246
<211> LENGTH: 422
<212> TYPE: DNA
<213> ORGANISM: Porphyromonas sp.

<400> SEQUENCE: 246

```
tgaggaatat tggtcaatgg gcgagagcct gaaccagcca agtcgcgtga aggatgactg     60
tcttatggat tgtaaacttc ttttgtaggg gaataaagaa cggtacgtgt accgtagtga    120
atgtacccta cgaataagca tcggctaact ccgtgccagc agccgcggta atacggagga    180
tgcgagcgtt atccggattt attgggttta aagggtgcgt aggcggcctg ttaagtcagc    240
ggtgaaatct aggagcttaa ctcctaaatt gccattgata ctggcgggct tgagtgtaga    300
tgaggtaggc ggaatgcgtg gtgtagcggt ggaatgcata gatatcacgc agaactccga    360
```

```
ttgcgaaggc agcttactaa ggtacaactg acgctgaagc acgaaagcgt gggtatcaaa    420
ca                                                                   422
```

<210> SEQ ID NO 247
<211> LENGTH: 426
<212> TYPE: DNA
<213> ORGANISM: Cardiobacterium sp.

<400> SEQUENCE: 247

```
tggggaatat tggacaatgg ggggaaccct gatccagcaa tgccgcgtgt gtgaagaagg    60
ccttcgggtt gtaaagcact ttcagtaggg aggaaaggtg cgtagttaat acctgcgcaa   120
ttgacgttac ctacagaaga agcaccggct aactccgtgc cagcagccgc ggtaatacgg   180
agggtgcgag cgttattcgg aattactggg cgtaaagcgc acgcaggcgg ttgcccaagt   240
cagatgtgaa agccccgggc ttaacctggg aactgcattt gaaactgggc gactagagta   300
tgaaagagga aagcggaatt ccagtgtag cagtgaaatg cgtagatatt ggaaggaaca    360
ccgatggcga aggcagcttt ctgggtcgat actgacgctc atgtgcgaaa gcgtggggag   420
caaaca                                                             426
```

<210> SEQ ID NO 248
<211> LENGTH: 422
<212> TYPE: DNA
<213> ORGANISM: Capnocytophaga sp.

<400> SEQUENCE: 248

```
tgaggaatat tggacaatgg tcggaagact gatccagcca tgccgcgtgc aggatgaagg    60
tcttatggat tgtaaactgc ttttgcaggg aagaataag gactacgcgt agtttgatga   120
cggtactctg tgaataagca tcggctaact ccgtgccagc agccgcggta atacggagga   180
tgcgagcgtt atccggaatc attgggttta aagggtctgt aggcgggctg gtaagtcaga   240
ggtgaaagcg cttagctcaa ctaagcaact gccttgaaa ctgctggtct tgaatggttg    300
tgaagtagtt ggaatgtgta gtgtagcggt gaaatgctta gatattacac agaacaccga   360
tagcgaaggc atattactaa caattaattg acgctgatgg acgaaagcgt ggggagcgaa   420
ca                                                                 422
```

<210> SEQ ID NO 249
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      unclassified.Ruminococcaceae"

<400> SEQUENCE: 249

```
tggggaatat tgggcaatgg gcgaaagcct gacccagcaa cgccgcgtga aggaagaagg    60
tcttcggatt gtaaacttct tttatcaggg acgaagtaag tgacggtacc tgatgaataa   120
gccacggcta actacgtgcc agcagccgcg gtaatacgta ggtggcaagc gttatccgga   180
tttactgggt gtaaagggcg cgtaggcggg atacaagtc agatgtgaaa tctatgggct    240
taacccataa actgcatttg aaactgtatc tcttgagtgt cggagaggta acggaattc    300 ctagtgtagc ggtgaaatgc gtagatatta ggaggaacac cagtgcgaa ggcggtctac    360 tggacgataa ctgacgctga ggcgcgaaag cgtggggagc aaaca                  405
```

<210> SEQ ID NO 250
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 250

```
tgggggatat tgcacaatgg gggaaaccct gatgcagcaa cgccgcgtga gggaagaagg      60
ttttcggatt gtaaacctct gttcttagtg acgataatga cggtagctaa ggagaaagct     120
ccggctaact acgtgccagc agccgcggta atacgtaggg agcgagcgtt gtccggattt     180
actgggtgta aagggtgcgt aggcggcgag gcaagtcagg cgtgaaatct atgggcttaa     240
cccataaact gcgcttgaaa ctgtcttgct tgagtgaagt agaggtaggc ggaattcccg     300
gtgtagcggt gaaatgcgta gagatcggga ggaacaccag tggcgaaggc ggcctactgg     360
gctttaactg acgctgaagc acgaaagcat gggtagcaaa ca                        402
```

<210> SEQ ID NO 251
<211> LENGTH: 422
<212> TYPE: DNA
<213> ORGANISM: Tannerella sp.

<400> SEQUENCE: 251

```
tgaggaatat tggtcaatgg gcgagagcct gaaccagcca agtcgcgtga aggatgactg      60
ccctatgggt tgtaaacttc ttttacaggg gaataaaatg agatacgtgt attttattgc     120
atgtaccttg tgaataagca tcggctaact ccgtgccagc agccgcggta atacggagga     180
tgcgagcgtt atccggattt attgggttta aagggtgcgt aggtgggctg ttaagtccgc     240
ggtgaaagtt tgtcgcttaa cgataaaatt gccgttgaaa ctggtagtct tgagtataga     300
tgaagtaggc ggaatgcgtg gtgtagcggt gaaatgcata gagatcacgc agaactccga     360
ttgcgaaggc agcttactaa ggtataactg acactgaagc acgaaagcgt gggtatcaaa     420
ca                                                                    422
```

<210> SEQ ID NO 252
<211> LENGTH: 422
<212> TYPE: DNA
<213> ORGANISM: Prevotella sp.

<400> SEQUENCE: 252

```
tgaggaatat tggtcaatgg gcgagagcct gaaccagcca agtagcgtgc aggatgacgg      60
ccctatgggt tgtaaactgc ttttataggg gaataaagtg atctacgtgt agtttattgt     120
atgtacccta tgaataagga ccggctaatt ccgtgccagc agccgcggta atacggaagg     180
ttcgggcgtt atccggattt attgggttta aagggagcgt aggccgtaga ttaagcgtgt     240
tgtgaaatgt agatgctcaa catctgactt gcagcgcgaa ctggtttact agagtgtgcg     300
caacgtaggc ggaattcgtc gtgtagcggt gaaatgctta gatatgacga agaactccga     360
ttgcgaaggc agcttacggg agcacaactg acgctgaagc tcgaaggtgc gggtatcaaa     420
ca                                                                    422
```

<210> SEQ ID NO 253
<211> LENGTH: 422
<212> TYPE: DNA
<213> ORGANISM: Bacteroides sp.

<400> SEQUENCE: 253

```
tgaggaatat tggtcaatgg acgtaagtct gaaccagcca agtagcgtga aggatgactg    60
ccctatgggt tgtaaacttc ttttatatgg gaataaagta ttccacgtgt gggattttgt   120
atgtaccata tgaataagga tcggctaact ccgtgccagc agccgcggta atacggagga   180
tccgagcgtt atccggattt attgggttta aagggagcgt aggtggattg ttaagtcagt   240
tgtgaaagtt tgcggctcaa ccgtaaaatt gcagttgaaa ctggcagtct tgagtacagt   300
agaggtgggc ggaattcgtg gtgtagcggt gaaatgctta gatatcacga agaactccga   360
ttgcgaaggc agctcactag actgtcactg acactgatgc tcgaaagtgt gggtatcaaa   420
ca                                                                 422
```

<210> SEQ ID NO 254
<211> LENGTH: 427
<212> TYPE: DNA
<213> ORGANISM: Abiotrophia sp.

<400> SEQUENCE: 254

```
tagggaatct tccgcaatgg acgcaagtct gacggagcaa cgccgcgtga gtgaagaagg    60
tcttcggatc gtaaagctct gttgttagag aagaacagcg catagagtaa ctgctatgcg   120
tgtgacggta tctaaccaga aagccacggc taactacgtg ccagcagccg cggtaatacg   180
taggtggcga gcgttgtccg gatttattgg gcgtaaaggg agtgtaggcg gtcttttaag   240
tctgatgtga aagcccacgg ctcaaccgtg gagggtcatt ggaaactggg agacttgagt   300
gcagaagagg agagcggaat tccatgtgta gcggtgaaat gcgtagatat atggaggaac   360
accagtggcg aaggcggctc tctggtctgt aactgacgct gaggctcgaa agcgtgggga   420
gcaaaca                                                            427
```

<210> SEQ ID NO 255
<211> LENGTH: 404
<212> TYPE: DNA
<213> ORGANISM: Mogibacterium sp.

<400> SEQUENCE: 255

```
tagggaatct tgcacaatgg gcgaaagcct gatgcagcaa cgccgcgtga aggatgaagg    60
ccttcgggtt gtaaacttct gttctaaggg aagaaacaaa tgacggtacc ttaggagcaa   120
gccccggcta actacgtgcc agcagccgcg gtaatacgta gggggcaagc gttatccgga   180
attattgggc gtaagagtg cgtaggtggt tacctaagcg caaggtttaa tttagaggct   240
caacctctac ttgccttgcg aactgggcta cttgagtgca ggagggggaaa gcggaattcc   300
tagtgtagcg gtgaaatgcg tagatattag gaggaacacc agcggcgaag gcggctttct   360
ggactgtaac tgacactgag gcacgaaagc gtgggtagca aaca                   404
```

<210> SEQ ID NO 256
<211> LENGTH: 427
<212> TYPE: DNA
<213> ORGANISM: Selenomonas sp.

<400> SEQUENCE: 256

```
tggggaatct tccgcaatgg gcgcaagcct gacggagcaa cgccgcgtga gtgaagaagg    60
tcttcggatc gtaaagctct gttgatgggg acgaacgtgc gaagggtgaa taatcctttg   120
caatgacggt acctatcgag gaagccacgg ctaactacgt gccagcagcc gcggtaatac   180
```

```
gtaggtggcg agcgttgtcc ggaatcattg ggcgtaaagg gagcgcaggc gggcatgtaa    240
gtctttctta aaagttcggg gctcaacccc gtgatgggaa agaaactaca tgtcttgagt    300
acaggagagg aaagcggaat tcccagtgta gcggtgaaat gcgtagatat tgggaggaac    360
accagtggcg aaggcggctt tctggactgc aactgacgct gaggctcgaa agccagggga    420
gcgaacg                                                              427
```

<210> SEQ ID NO 257
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      unclassified.Ruminococcaceae"

<400> SEQUENCE: 257

```
tggggaatat tgggcaatgg gcgaaagcct gacccagcaa cgccgcgtga aggaagaagg    60
tcttcggatt gtaaacttct tttatgaggg acgaaggacg tgacggtacc tcatgaataa   120
gccacggcta actacgtgcc agcagccgcg gtaatacgta ggtggcaagc gttatccgga   180
tttactgggt gtaaagggcg cgtaggcggg gatgcaagtc agatgtgaaa tctatgggct   240
taacccataa actgcatttg aaactgtatc tcttgagtgc tggagaggta gacggaattc   300
cttgtgtagc ggtgaaatgc gtagatataa ggaagaacac cagtggcgaa ggcggtctac   360
tggacagtaa ctgacgctga ggcgcgagag cgtggggagc aaaca                   405
```

<210> SEQ ID NO 258
<211> LENGTH: 402
<212> TYPE: DNA
<213> ORGANISM: Blautia sp.

<400> SEQUENCE: 258

```
tggggaatat tgcacaatgg gggaaaccct gatgcagcga cgccgcgtga gcgaagaagt    60
atttcggtat gtaaacttct atcagcaggg aagatagtga cggtacctga ctaagaagcc   120
ccggctaact acgtgccagc agccgcggta atacgtaggg ggcaagcgtt atccggattt   180
actgggtgta aagggagcgt agacggactg gcaagtctga tgtgaaaggc ggggggctcaa   240 cccctggact gcattggaaa ctgttagtct tgagtgccgg agaggtaagc ggaattccta   300
gtgtagcggt gaaatgcgta gatattagga ggaacaccag tggcgaaggc ggcttactgg   360
acggtaactg acgttgaggc tcgaaagcgt ggggagcaaa ca                      402
```

<210> SEQ ID NO 259
<211> LENGTH: 427
<212> TYPE: DNA
<213> ORGANISM: Treponema sp.

<400> SEQUENCE: 259

```
gtaagaatat tccgcaatgg ggggaacccct gacggagcga cgccgcgtga acgaagaagg    60
ccggaaggtt gtaaagttct tttctgtccg aggaataagt gtaggaggaa atgcctgcat   120
ggtgacggta gggcaggaat aagcaccggc taattacgtg ccagcagccg cggtaacacg   180
taaggtgcga gcgttgttcg gaattattgg gcgtaaaggg catgcaggcg ggtcgccaag   240
cttggtaaga ataccggggg ctcaactccg gagctatatt gagaactggc gagctagagt   300
tgccgaaggg tatccggaat tccgcgtgaa ggggtgaaat ctgtagatat gcggaagaac   360
accgatggcg aaggcaggat accggcggac gactgacgct gaggtgcgaa ggtgcgggga   420
```

```
gcaaaca                                                            427
```

<210> SEQ ID NO 260
<211> LENGTH: 402
<212> TYPE: DNA
<213> ORGANISM: Gemmiger sp.

<400> SEQUENCE: 260

```
tgggggatat tgcacaatgg gggaaaccct gatgcagcga cgccgcgtgg aggaagaagg    60
ttttcggatt gtaaactcct gtcgttaggg acgataatga cggtacctaa caagaaagca   120
ccggctaact acgtgccagc agccgcggta aaacgtaggg tgcaagcgtt gtccggaatt   180
actgggtgta aagggagcgc aggcgggaag acaagttgga agtgaaaacc atgggctcaa   240
cccatgaatt gctttcaaaa ctgttttgct gagtagtgc agaggtagat ggaattcccg    300
gtgtagcggt ggaatgcgta gatatcggga ggaacaccag tggcgaaggc ggtctactgg   360
gcaccaactg acgctgaggc tcgaaagcat gggtagcaaa ca                      402
```

<210> SEQ ID NO 261
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 261

```
tgggggatat tgcacaatgg gcgaaagcct gatgcagcga cgccgcgtga gggaagacgg    60
ccttcgggtt gtaaacctct gtcattcggg acgaattaga tgacggtacc gaagaaggaa   120
gctccggcta actacgtgcc agcagccgcg gtaatacgta gggagcgagc gttgtccgga   180
attactgggt gtaagggag cgtaggcggg aaagcaagtt ggaagtgaaa tgcatgggct    240
taacccatga gctgctttca aaactgtttt tcttgagtga agtagaggca ggcggaattc   300
ctagtgtagc ggtgaaatgc gtagatatta ggaggaacac cagtggcgaa ggcggcctgc   360
tgggctttaa ctgacgctga ggctcgaaag cgtgggtagc aaaca                   405
```

<210> SEQ ID NO 262
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 262

```
tggggaatat tgcacaatgg gcgaaagcct gatgcagcaa cgccgcgtga aggaagaagg    60
ccttcgggtc gtaaacttct gtcctatggg aagaaaaaaa tgacggtacc ataggaggaa   120
gccccggcta actacgtgcc agcagccgcg gtaatacgta gggggcgagc gttatccgga   180
attattgggc gtaagagtg cgtaggtggt aacttaagcg cggggtttaa ggcaatggct    240
taaccattgt tcgccctgcg aactgggata cttgagtgca ggagaggaaa gcggaattcc   300
tagtgtagcg gtgaaatgcg tagatattag gaggaacacc agtggcgaag gcggcttttct  360 ggactgaaac tgcactgag gcacgaaagt gtggggagca aaca                     404
```

<210> SEQ ID NO 263

```
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 263
tggggaatat tgggcaatgg gggaaaccct gacccagcaa cgccgcgtga aggaagaagg      60
tcttcggatc gtaaacttct atcctcggtg aagaggagaa gacggtagcc gagaaggaag    120
ccccggctaa ctacgtgcca gcagccgcgg taatacgtag ggggcaagcg ttgtccggaa    180
tgattgggcg taaagggcgt gtaggcggct aagtaagtct ggagtgaaag tcctgctttt    240
aaggtgggaa ttgctttgga tactgcatag ctagagtgca ggagaggtaa gtggaattcc    300
cagtgtagcg gtgaaatgcg tagagattgg gaggaacacc agtggcgaag gcgacttact    360
ggactgtaac tgacgctgag gcgcgaaagt gtggggagca aaca                     404

<210> SEQ ID NO 264
<211> LENGTH: 408
<212> TYPE: DNA
<213> ORGANISM: Olsenella sp.

<400> SEQUENCE: 264
tggggaatct tgcacaatgg gcgaaagcct gatgcagcga cgccgcgtgc gggacgaagg     60
ccttcgggtc gtaaaccgct ttcagcaggg acgaggccgc gaggtgacgg tacctgcaga   120
agaagccccg gctaactacg tgccagcagc cgcggtaata cgtaggggc gagcgttatc    180 cggattcatt gggcgtaaag cgcgcgcagg cggcctgctc ggtcgggagt caaatccggg   240
ggctcaaccc cgcccgctc ccgataccgg cgggcttgag tctggtaggg gaaggcggaa    300
ttcccagtgt agcggtggaa tgcgcagata ttgggaagaa caccggtggc gaaggcggcc   360
ttctggccca cgactgacgc tgaggcgcga aagctagggg agcgaaca                 408

<210> SEQ ID NO 265
<211> LENGTH: 402
<212> TYPE: DNA
<213> ORGANISM: Lachnoanaerobaculum sp.

<400> SEQUENCE: 265
tggggaatat tggacaatgg gggaaaccct gatccagcga cgccgcgtga gtgaagaagt     60
atttcggtat gtaaagctct atcagcaggg aagaaaatga cggtacctga ctaagaagcc   120
ccggctaact acgtgccagc agccgcggta atacgtaggg ggcaagcgtt atccggattt   180
actgggtgta aagggagcgt agacggcgat gtaagtctga agtgaaagcc cacggctcaa   240
ctgtgggact gctttggaaa ctatatagct agagtatcgg aggggcaagc ggaattccta   300
gtgtagcggt gaaatgcgta gatattagga ggaacaccgg aggcgaaggc ggcttgctgg   360
acgaagactg acgttgaggc tcgaaggcgt ggggagcaaa ca                       402

<210> SEQ ID NO 266
<211> LENGTH: 422
<212> TYPE: DNA
<213> ORGANISM: Alloprevotella sp.

<400> SEQUENCE: 266
tgaggaatat tggtcaatgg acgagagtct gaaccagcca agtagcgtgc aggatgacgg     60
ccctctgggt tgtaaactgc ttttagttgg gaacaaaaaa ggcgacgtgt cgcctctgga   120
```

```
gtgtaccatc agaaaaagga ccggctaatt ccgtgccagc agccgcggta atacggaagg    180
tccaggcgtt atccggattt attgggttta aagggagcgt aggcggacga ttaagtcagc    240
tgtgaaagtt tgcggctcaa ccgtaaaatt gcagttgaaa ctggttgtct tgagtgcacg    300
cagggatgtt ggaattcatg gtgtagcggt gaaatgctta gatatcatga agaactccga    360
tcgcgaaggc atatgtctgg agtgcaactg acgctgaggc tcgaaagtgc gggtatcgaa    420
ca                                                                   422
```

<210> SEQ ID NO 267
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 267

```
tgaggaatat tggtcaatgg acgcaagtct gaaccagcca tgccgcgtgc aggaagacgg    60
ctctatgagt tgtaaactgc ttttgtatta gggtaaactc aggtacgtgt acctgactga   120
aagtataata cgaataagga tcggctaact ccgtgccagc agccgcggta atacggagga   180
tccaagcgtt atccggattt attgggttta aagggtgcgt aggcggtttg ataagttaga   240
ggtgaaagac cggggcttaa ctccggaact gcctctaata ctgttgaact agagagtagt   300
tgcggtaggc ggaatgtatg gtgtagcggt gaaatgctta gagatcatac agaacaccga   360
ttgcgaaggc agcttaccaa actatatctg acgttgaggc acgaaagcgt ggggagcaaa   420
ca                                                                  422
```

<210> SEQ ID NO 268
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 268

```
tgggaatat tgggcaatgg gcgcaagcct gacccagcaa cgccgcgtga aggaagaagg    60
ctttcgggtt gtaaacttct tttctggggg acgaacaaat gacggtaccc caggaataag   120
ccacggctaa ctacgtgcca gcagccgcgg taatacgtag gtggcaagcg ttatccggat   180
ttattgggtg taaagggcgt gtaggcggga atgcaagtca gatgtgaaaa ctcagggctc   240
aaccctgagc ctgcatttga aactgtgttt cttgagtgct ggagaggcaa tcggaattcc   300
gtgtgtagcg gtgaaatgcg tagatatacg gaggaacacc agtggcgaag cggattgct   360 ggacagtaac tgacgctgag gcgcgaaagc gtgggagca aaca                     404
```

<210> SEQ ID NO 269
<211> LENGTH: 405
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 269

```
tggggaatat tgggcaatgg gcgaaagcct gacccagcaa cgccgcgtga gggaagaagg    60 tttcggatt gtaaacctct gtcctcaggg acgaaggaag tgacggtacc tgaggaggaa   120
gccccggcta actacgtgcc agcagccgcg gtaatacgta gggggcaagc gttgtccgga   180
atgactgggc gtaaagggcg tgtaggcggc ctgataagta tgaagtgaaa gtcctgcttt   240
caaggtggga attgctttgt agactgtcgg gcttgagtgc ggaagaggta agtggaattc   300
ccagtgtagc ggtgaaatgc gtagagattg ggaggaacac cagtggcgaa ggcgacttac   360
tgggccgtaa ctgacgctga ggcgcgaaag cgtggggagc gaaca              405

<210> SEQ ID NO 270
<211> LENGTH: 422
<212> TYPE: DNA
<213> ORGANISM: Bacteroides sp.

<400> SEQUENCE: 270
tgaggaatat tggtcaatgg gcgatggcct gaaccagcca agtagcgtga aggatgactg    60
ccctatgggt tgtaaacttc ttttataaag gaataaagtc gggtatgcat acccgtttgc   120
atgtacttta tgaataagga tcggctaact ccgtgccagc agccgcgta atacggagga   180 tccgagcgtt atccggattt attgggttta aaggagcgcg aggtggattg ttaagtcagt   240
tgtgaaagtt tgcggctcaa ccgtaaaatt gcagttgaaa ctggcagtct gagtacagt    300 agaggtgggc ggaattcgtg gtgtagcggt gaaatgctta gatatcacga agaactccga   360
ttgcgaaggc agcctgctaa gctgcaactg acattgaggc tcgaaagtgt gggtatcaaa   420
ca                                                                 422

<210> SEQ ID NO 271
<211> LENGTH: 422
<212> TYPE: DNA
<213> ORGANISM: Prevotella sp.

<400> SEQUENCE: 271
tgaggaatat tggtcaatgg gcgagagcct gaaccagcca agtagcgtgc aggatgacgg    60
ccttatgggt tgtaaactgc ttttatgcga ggataaagtt acccacgtgt gggtgtttgc   120
aggtatcgca tgaataagga ccggctaatt ccgtgccagc agccgcggta atacggaagg   180
ttctggcgtt atccggattt attgggttta aaggagcgt aggctgtttt ttaagcgtgt    240
tgtgaaatgt accggctcaa ccggtgatgt gcagcgcgaa ctggaagact tgagtgtgtt   300
gtaagtaggc ggaattcgtg gtgtagcggt gaaatgctta gatatcacga ggaactccga   360
ttgcgtaggc agcttactgt ctcactactg acgctgatgc tcgaaagcgc gggtatcgaa   420
ca                                                                 422

<210> SEQ ID NO 272
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 272
tggggaatat tgcacaatgg gggaaaccct gatgcagcaa cgccgcgtga gtgaagaagt    60
atttcggtat gtaaagctct atcagcaggg aagaaaatga cggtacctga ctaagaagcc   120
ccggctaact acgtgccagc agccgcggta atacgtaggg ggcaagcgtt atccggattt   180
```

```
actgggtgta aagggagcgc aggcggtacg gcaagtcaga tgtgaaaacc cggggctcaa    240
ccccgggact gcatttgaaa ctgtcggact agagtgccgg agaggtaagt ggaattccta    300
gtgtagcggt gaaatgcgta gatattagga ggaacaccag tggcgaaggc ggcttactgg    360
acggtaactg acgctgaggc tcgaaagcgt ggggagcaaa ca                      402
```

<210> SEQ ID NO 273
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 273

```
tggggaatat tgggcaatgg gggcaaccct gacccagcaa cgccgcgtga gggaagaagg    60
ttttcggatt gtaaacctct gtccttgggg acgaagaagt gacggtaccc aaggaggaag   120
ctccggctaa ctacgtgcca gcagccgcgg taatacgtag ggagcgagcg ttgtccggaa   180
ttactgggcg taaaggggtgc gtaggcggtt tggtaagtca gatgtgaaat acccgggctt   240
aacccggggg ctgcatctga tactgtcaga cttgagtgca ggagaggaaa gcggaattcc   300
tagtgtagcg gtgaaatgcg tagatattag gaggaacacc agtggcgaag gcggctttct   360
ggactgtaac tgacgctgag gcacgaaagc gtggggagca aaca                    404
```

<210> SEQ ID NO 274
<211> LENGTH: 408
<212> TYPE: DNA
<213> ORGANISM: Rothia sp.

<400> SEQUENCE: 274

```
tagggaatct tcggcaatgg acggaagtct gaccgagcaa cgccgcgtga gggatgacgg    60
ccttcgggtt gtaaacctct gttagcaggg aagaagagaa attgacggta cctgcagaga   120
aagcgccggc taactacgtg ccagcagccg cggtaatacg tagggcgcga gcgttgtccg   180
gaattattgg gcgtaaagag cttgtaggcg gtttgtcgcg tctgctgtga aaggccgggg   240
cttaaccccg tgtattgcag tgggtacggg cagactagag tgcagtaggg gagactggaa   300
ctcctggtgt agcggtggaa tgcgcagata tcaggaagaa caccgatggc gaaggcaggt   360
ctctgggctg taactgacgc tgagaagcga aagcatgggg agcgaaca                408
```

<210> SEQ ID NO 275
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 275

```
tggggaatat tgcacaatgg gggaaaccct gatgcagcga cgccgcgtga aggaagaagt    60
atctcggtat gtaaacttct atcagcaggg aagatagtga cggtacctga ctaagaagcc   120
ccggctaact acgtgccagc agccgcggta atacgtaggg ggcaagcgtt atccggattt   180
actgggtgta aagggtgcgt aggtggcagt gcaagtcaga tgtgaaaggc cggggctcaa   240
ccccggagct gcatttgaaa ctgctcggct agagtacagg agaggcaggc ggaattccta   300
```

```
gtgtagcggt gaaatgcgta gatattagga ggaacaccag tggcgaaggc ggcttactgg    360
acggtaactg acgttgaggc tcgaaagcgt ggggagcaaa ca                       402
```

```
<210> SEQ ID NO 276
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 276
tggggaatat tgcacaatgg gggaaaccct gatgcagcaa cgccgcgtga gtgaagaagt     60
atttcggtat gtaaagctct atcagcaggg aagaaaatga cggtacctga ctaagaagca    120
ccggctaaat acgtgccagc agccgcggta atacgtatgg tgcaagcgtt atccggattt    180
actgggtgta aagggagcgc aggcggtctg gcaagtctga tgtgaaaatc cggggctcaa    240
ctccggaact gcattggaaa ctgtcagact agagtgtcgg agaggtaagt ggaattccta    300
gtgtagcggt gaaatgcgta gatattagga ggaacaccag tggcgaaggc ggcttactgg    360
acggtaactg acgttgaggc tcgaaagcgt ggggagcaaa ca                       402
```

```
<210> SEQ ID NO 277
<211> LENGTH: 402
<212> TYPE: DNA
<213> ORGANISM: Clostridium sp.

<400> SEQUENCE: 277
tggggaatat tgcacaatgg gggaaaccct gatgcagcga cgccgcgtga gtgaagaagt     60
atttcggtat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggcatg gcaagtctga agtgaaatgc gggggctcaa    240 ccccctgaact gctttggaaa ctgtcaggct ggagtgcagg agaggtaagt ggaattccta    300
gtgtagcggt gaaatgcgta gatattagga agaacaccag tggcgaaggc ggcttactgg    360
acggtaactg acgttgaggc tcgaaagcgt ggggagcaaa ca                       402
```

```
<210> SEQ ID NO 278
<211> LENGTH: 422
<212> TYPE: DNA
<213> ORGANISM: Prevotella sp.

<400> SEQUENCE: 278
tgaggaatat tggtcaatgg gcgcaagcct gaaccagcca gtagcgtgc aggatgacgg      60 ccctatgggt tgtaaactgc ttttatgcgg ggataaagtg acccacgtgt gggttttgc     120 aggtaccgca tgaataagga ccggctaatt ccgtgccagc agccgcggta atacggaagg    180
tccgggcgtt atccggattt attgggttta aagggagcgt aggccgcgcc ttaagcgtgt    240
tgtgaaatcc ggttgctcaa catccggctt gcagcgcgaa ctgggcgct tgagtgcgct    300 gaaagtaggc ggaattcgtg gtgtagcggt gaaatgctta gatatcacga ggaactccga    360
ttgcgaaggc agcctactgt agcgctactg acgctgatgc tcgaaagcgt gggtatcgaa    420
ca                                                                   422
```

```
<210> SEQ ID NO 279
<211> LENGTH: 402
```

```
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 279
tggggaatat tgcacaatgg aggaaactct gatgcagcga cgccgcgtga gtgaagaagt    60
atttcggtat gtaaagctct atcagcaggg aagacagtga cggtacctga ctaagaagct   120
ccggctaaat acgtgccagc agccgcggta atacgtatgg agcaagcgtt atccggattt   180
actgggtgta aagggagtgt aggtggtatc acaagtcaga agtgaaagcc cggggcgcaa   240
ccccgggact gcttttgaaa ctgtggaact ggagtgcagg agaggtaagt ggaattccta   300
gtgtagcggt gaaatgcgta gatattagga ggaacaccag tggcgaaggc ggcttactgg   360
actgtaactg acactgaggc tcgaaagcgt ggggagcaaa ca                      402

<210> SEQ ID NO 280
<211> LENGTH: 401
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 280
tggggaatat tgcacaatgg gggaaaccct gatgcagcaa cgccgcgtga aggaagaagg    60
tctttgggtc gtaaacttct gttctgaggg aagaaagtga cggtacctca ggagcaagtc   120
ccggctaact acgtgccagc agccgcggta atacgtaggg ggcaagcgtt atccggaatt   180
attgggcgta aagagtacgt aggtggttac ctaagcacgg ggtataaggc aatggctcaa   240
ccattgtttg ccttgtgaac tgggctactt gagtgcagga gaggaaagcg gaattcctag   300
tgtagcggtg aaatgcgtag atattaggag gaacaccagt ggcgaaggcg gctttctgga   360
ctgtaactga cactgaggta cgaaagcgtg gggagcaaac a                       401

<210> SEQ ID NO 281
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 281
tggggaatat tgcacaatgg gggaaaccct gatgcagcga cgccgcgtgg aggaagaagg    60
tcttcggatt gtaaactcct gttgttgagg aagataatga cggtactcaa caaggaagtg   120
acggctaact acgtgccagc agccgcggta aaacgtaggt cacaagcgtt gtccggaatt   180
actgggtgta aagggagcgc aggcgggaga acaagttgga agtgaaatcc atgggctcaa   240
cccatgaact gctttcaaaa ctgttttttct tgagtagtgc agaggtaggc ggaattcccg   300
gtgtagcggt ggaatgcgta gatatcggga ggaacaccag tggcgaaggc ggcctactgg   360
gcaccaactg acgctgaggc acgaaggcca ggggagcgaa ag                      402

<210> SEQ ID NO 282
<211> LENGTH: 405
<212> TYPE: DNA
```

```
<213> ORGANISM: Unknown
<220> FEATURE:
<221> NAME/KEY: source
<223> OTHER INFORMATION: /note="Description of Unknown:
      Bacterial sequence"

<400> SEQUENCE: 282
tgggggatat tggtcaatgg gggaaaccct gaaccagcaa tgccgcgtga gggaagaagg      60
tcttcggatt gtaaacctaa gtagtcaggg acgaaggaag tgacggtacc tgaagagtaa     120
gctccggcta actacgtgcc agcagccgcg gtaatacgta gggagcgagc gttgtccgga     180
attactgggt gtaaagggtg cgtaggcggg cttgcaagtc agatgtgaaa taccggggct     240
taaccccggg gctgcatttg aaactgtagg tcttgagtga agtagaggca ggcggaattc     300
ctagtgtagc ggtgaaatgc gtagatatta ggaggaacac cagtggcgaa ggcggcctgc     360
tgggctttaa ctgacgctga ggcacgaaag catggggagc aaaca                     405

<210> SEQ ID NO 283
<211> LENGTH: 401
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 283
tggggaatat tgcacaatgg gggaaaccct gatgcagcaa cgccgcgtga aggaagaagg      60
cctttgggtc gtaaacttct gtcctaaggg aagataatga cggtaccttt ggaggaagcc    120
ccggctaact acgtgccagc agccgcggta atacgtaggg ggcgagcgtt atccggaatt    180
attgggcgta aagagtgcgt aggcggtttt ttaagcgcgg ggtgaaaggc aatggcttaa    240
ccattgttag ccctgcgaac tgggagactt gagtgcagga gaggaaagcg gaattcctag    300
tgtagcggtg aaatgcgtag atattaggag gaacaccagt ggcgaaggcg gctttctgga    360
ctgtaactga cgctgaggca cgaaagtgtg gggagcaaac a                        401

<210> SEQ ID NO 284
<211> LENGTH: 408
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 284
tcgagaatca ttcacaatgg gggaaaccct gatggtgcga cgccgcgtgg gggaatgaag      60
gtcttcggat tgtaaacccc tgtcatgtgg gagcaaatta aaaagatagt accacaagag    120
gaagagacgg ctaactctgt gccagcagcc gcggtaatac agaggtctca agcgttgttc    180
ggaatcactg ggcgtaaagc gtgcgtaggc ggtttcgtaa gtcgtgtgtg aaaggcgggg    240
gctcaacccc cggactgcac atgatactgc gagactagag taatggaggg ggaaccggaa    300
ttctcggtgt agcagtgaaa tgcgtagata tcgagaggaa cactcgtggc gaaggcgggt    360
tcctggacat taactgacgc tgatgctcga aagtgtgggt atcaaaca                 408

<210> SEQ ID NO 285
<211> LENGTH: 421
<212> TYPE: DNA
<213> ORGANISM: Prevotella sp.
```

<400> SEQUENCE: 285

```
tgaggaatat tggtcaatgg acggaagtct gaaccagcca agtagcgtgc aggatgacgg      60
ccctatgggt tgtaaactgc ttttgtatgg ggataaagtt agggacgtgt ccctatttgc     120
aggtaccata cgaataagga ccggctaatt ccgtgccagc agccgcggta atacggaagg     180
tccaggcgtt atccggattt attgggttta aagggagcgt aggcggattg ttaagtcagc     240
ggttaaaggg tgtggctcaa ccatgcattg ccgttgaaac tggcgatctt gagtgcagac     300
agggatgccg gaattcgtgg tgtagcggtg aaatgcttag atatgacgaa gaactccgat     360
tgcgaaggca gctgacggga gcgcaactga cgcttaagct cgaaggtgcg ggtatcaaac     420
a                                                                    421
```

<210> SEQ ID NO 286
<211> LENGTH: 427
<212> TYPE: DNA
<213> ORGANISM: Neisseria sp.

<400> SEQUENCE: 286

```
tggggaattt tggacaatgg gcgcaagcct gatccagcca tgccgcgtgt ctgaagaagg      60
ccttcgggtt gtaaaggact tttgtcaggg aagaaaagga gttggttaat acccgactct     120
gatgacggta cctgaagaat aagcaccggc taactacgtg ccagcagccg cggtaatacg     180
tagggtgcga gcgttaatcg gaattactgg gcgtaaagcg agcgcagacg gtttgttaag     240
caggatgtga aatccccggg ctcaacctgg gaactgcgtt ctgaactggc aggctagagt     300
gtgtcagagg ggggtagaat tccacgtgta gcagtgaaat gcgtagagat gtggaggaat     360
accgaaggcg aaggcagccc cttgggaatg tactgacgct catgtgcgaa agcgtgggga     420
gcaaaca                                                              427
```

<210> SEQ ID NO 287
<211> LENGTH: 403
<212> TYPE: DNA
<213> ORGANISM: Ruminococcus sp.

<400> SEQUENCE: 287

```
tgggggatat tgcgcaatgg gggcaaccct gacgcagcaa cgccgcgtga aggatgaagg      60
ttttcggatt gtaaacttct tttattaagg acgaaaaatg acggtactta atgaataagc     120
tccggctaac tacgtgccag cagccgcggt aatacgtagg gagcaagcgt tgtccggatt     180
tactgggtgt aaagggtgcg taggcggctt gcaagtcag atgtgaaatc tatgggctca     240
acccataaac tgcatttgaa actgtagagc ttgagtgaag tagaggcagg cggaattccc     300
cgtgtagcgg tgaaatgcgt agagatgggg aggaacacca gtggcgaagg cggcctgctg     360
ggctttaact gacgctgagg cacgaaggcc aggggagcga aag                      403
```

<210> SEQ ID NO 288
<211> LENGTH: 423
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 288

```
tgaggaatat tggtcaatgg acgagagtct gaaccagcca agtagcgtgc aggatgacgg      60
```

```
ccctatgggt tgtaaactgc ttttgcgcgg ggataacacc ctccacgtgc tggaggtctg      120
caggtaccgc gcgaataagg accggctaat tccgtgccag cagccgcggt aatacggaag      180
gtccgggcgt tatccggatt tattgggttt aagggagcg tagatggatg tttaagtcag       240
ttgtgaaagt tgcggctca accgtaaaat tgcagttgat actggatatc ttgagtgcag       300
ttgaggcagg cggaattcgt ggtgtagcgg tgaaatgctt agatatgacg aagaaccccg      360
attgcgaagg cagctggcgg gagcgtaact gacgctgaag ctcgaaagcg cgggtatcga      420
aca                                                                   423

<210> SEQ ID NO 289
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 289
tgaggaatat tggtcaatgg gcgagagcct gaaccagcca agtagcgtga aggatgaagg       60
tcctacggat tgtaaacttc ttttatacg gaataaagta tcctacgtgt aggattttgt      120
atgtaccgta tgaataagca tcggctaact ccgtgccagc agccgcggta atacggagga      180
tgcgagcgtt atccggattt attgggttta aaggagcgt aggtggattg ttaagtcagt       240
tgtgaaagtt gcggctcaa ccgtaaaatt gcagttgaaa ctggcagtct tgagtacagt      300
agaggtgggc ggaattcgtg gtgtagcggt gaaatgctta gatatcacga agaacccga      360
ttgcgaaggc agcttgctaa actgtaactg acgttcatgc tcgaaagtgt gggtatcaaa     420
ca                                                                    422

<210> SEQ ID NO 290
<211> LENGTH: 427
<212> TYPE: DNA
<213> ORGANISM: Haemophilus sp.

<400> SEQUENCE: 290
tgaggaatat tggtcaatgg tcggaagact gaaccagcca tgccgcgtga atgaagaagg       60
ccttcgggtt gtaaagttct ttcggtagcg aggaaggcat ttagtttaat aaactgga tg     120
attgacgtta actacagaag aagcaccggc taactccgtg ccagcagccg cggtaatacg      180
gagggtgcga cgttaatcg gaataactgg gcgtaaaggg cacgcaggcg gtgacttaag       240
tgaggtgtga aagccccggg cttaacctgg gaattgcatt tcatactggg tcgctagagt      300
actttaggga ggggtagaat tccacgtgta gcggtgaaat gcgtagagat gtggaggaat     360
accgaaggcg aaggcagccc cttgggaatg tactgacgct catgtgcgaa agcgtgggga    420
gcaaaca                                                               427

<210> SEQ ID NO 291
<211> LENGTH: 402
<212> TYPE: DNA
<213> ORGANISM: Clostridium sp.

<400> SEQUENCE: 291
tggggaatat tgcacaatgg gggaaaccct gatgcagcga cgccgcgtga gcgaagaagt       60
atttcggtat gtaaagctct atcagcaggg aagaaaatga cggtacctga ctaagaagcc      120
ccggctaact acgtgccagc agccgcggta atacgtaggg ggcaagcgtt atccggattt     180
```

```
actgggtgta aagggagcgt agacggatag gcaagtctgg agtgaaaacc cagggctcaa    240
ccctgggact gctttggaaa ctgcagatct ggagtgccgg agaggtaagc ggaattccta    300
gtgtagcggt gaaatgcgta gatattagga ggaacaccag tggcgaaggc ggcttactgg    360
acggtaactg acgttgaggc tcgaaagcgt ggggagcaaa ca                      402
```

<210> SEQ ID NO 292
<211> LENGTH: 427
<212> TYPE: DNA
<213> ORGANISM: Selenomonas sp.

<400> SEQUENCE: 292

```
tggggaatct tccgcaatgg gcgcaagcct gacggagcaa cgccgcgtga gtgaagaagg    60
tcttcggatc gtaaagctct gttgaagggg cgaacgtac gcagtgcgaa tagtgctgcg    120
cagtgacggt acctttcgag gaagccacgg ctaactacgt gccagcagcc gcggtaatac    180
gtaggtggcg agcgttgtcc ggaatcattg ggcgtaaagg gagcgcaggc ggtgatgtaa    240
gtcttgctta aaagttcggg gctcaacccc gtgatgggca agaaactata tgacttgagt    300
gcaggagagg aaagcggaat tcccagtgta gcggtgaaat gcgtagatat tgggaggaac    360
accagtggcg aaggcggctt tctggactgc aactgacgct gaggctcgaa agccagggga    420
gcgaacg                                                              427
```

<210> SEQ ID NO 293
<211> LENGTH: 427
<212> TYPE: DNA
<213> ORGANISM: Neisseria sp.

<400> SEQUENCE: 293

```
tggggaattt tggacaatgg gcgcaagcct gatccagcca tgccgcgtgt ctgaagaagg    60
ccttcgggtt gtaaaggact tttgtcaggg aagaaaaggg cggggttaat acccctgtct    120
gatgacggta cctgaagaat aagcaccggc taactacgtg ccagcagccg cggtaatacg    180
tagggtgcga cgttaatcg gaattactgg gcgtaaagag tgcgcaggcg gttttgcaag    240
accgatgtga atccccggg cttaacctgg gaactgcatt ggtgactgca aggctagagt    300
gtgtcagagg gaggtggaat tccgcatgta gcagtgaaat gcgtagagat gtggaggaat    360
accgatggcg aaggcagcct cctgggataa cactgacgtt catgcccgaa agcgtgggta    420
gcaaaca                                                              427
```

<210> SEQ ID NO 294
<211> LENGTH: 421
<212> TYPE: DNA
<213> ORGANISM: Unknown
<220> FEATURE:
<221> NAME/KEY: source
<223> OTHER INFORMATION: /note="Description of Unknown: unclassified.Actinomycetales"

<400> SEQUENCE: 294

```
tggggaatat tgcacaatgg gcgcaagcct gatgcagcga cgccgcgtgg gggatgacgg    60
ccttcgggtt gtaaactcct ttcgttaggg acgaagccac acttttggg tgtggtgacg    120 gtacctttgt taagaagcac cggctaacta cgtgccagca gccgcggtaa tacgtagggc    180
gcgagcgttg tccggaatta ttgggcgtaa agggctcgta ggcggcttgt cgcgtctgct    240
gtgaaaatgc ggggcttaac tccgtacgtg cagtgggtac gggcaggcta gagtgcggta    300
```

```
ggggtgactg gaattcctgg tgtagcggtg aatgcgcag atatcaggag gaacaccgat    360
ggcgaaggca ggtctctggg cagtaactga cgctgaggag cgaaagcatg gggagcgaac    420
a                                                                   421
```

<210> SEQ ID NO 295
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 295

```
tgggggatat tgcacaatgg gggaaaccct gatgcagcga cgccgcgtgg aggaagaagg     60
ttttcggatt gtaaactcct gtcgttaggg acgataatga cggtacctaa caagaaagca    120
ccggctaact acgtgccagc agccgcggta aaacgtaggt cacaagcgtt gtccggaatt    180
actgggtgta aagggagcgc aggcgggcga tcaagttgga agtgaaatcc atgggctcaa    240
cccatgaact gctttcaaaa ctggtcgtct tgagtagtgc agaggtaggt ggaattcccg    300
gtgtagcggt ggaatgcgta gatatcggga ggaacaccag tggcgaaggc gacctactgg    360
gcaccaactg acgctgaggc tcgaaagcat gggtagcaaa ca                      402
```

<210> SEQ ID NO 296
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 296

```
tggggaatat tgcacaatgg gggaaaccct gatgcagcga cgccgcgtga aggaagaagt     60
atctcggtat gtaaagctct atcagcaggg aagaaaatga cggtacctga ctaagaagcc    120
ccggctaact acgtgccagc agccgcggta atacgtaggg ggcaagcgtt atccggattt    180
actgggtgta aagggagcgt agacggaatg gcaagtctga tgtgaaagac cggggctcaa    240
ccccgggact gcattggaaa ctgtcaatct agagtaccgg agaggtaagc ggaattccta    300
gtgtagcggt gaaatgcgta gatattagga agaacaccag tggcgaaggc ggcttactgg    360
acggtaactg acgttgaggc tcgaaagcgt ggggagcaaa ca                      402
```

<210> SEQ ID NO 297
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 297

```
tgaggaatat tggtcaatgg ccgagaggct gaaccagcca agtcgcgtga aggaagaagg     60
atctatggtt tgtaaacttc ttttataggg gaataaagtg gaggacgtgt cctttttgt    120
atgtacccta tgaataagca tcggctaact ccgtgccagc agccgcggta atacggagga    180
tgcgagcgtt atccggattt attgggttta aagggtgcgt aggcggcacg ccaagtcagc    240
ggtgaaattt ccgggctcaa cccggactgt gccgttgaaa ctggcgagct agagtgcaca    300
```

```
agaggcaggc ggaatgcgtg gtgtagcggt gaaatgcata gatatcacgc agaactccga    360
ttgcgaaggc agcttactaa accataactg acactgaagc acgaaagcgt ggggatcaaa    420
ca                                                                  422
```

<210> SEQ ID NO 298
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 298

```
tgaggaatat tggtcaatgg gcgcaggcct gaaccagcca agtagcgtga aggatgactg     60
ccctatgggt tgtaaacttc ttttataaag gaataaagtc gggtatggat accgtttgc    120 atgtacttta tgaataagga tcggctaact ccgtgccagc agccgcggta atacggagga   180
tccgagcgtt atccggattt attgggttta aagggagcgt agatggatgt ttaagtcagt   240
tgtgaaagtt tgcggctcaa ccgtaaaatt gcagttgata ctgggcgcct tgagtgcagc   300
ataggtaggc ggaattcgtg gtgtagcggt gaaatgctta gatatcacga agaactccga   360
ttgcgaaggc agcctgctgg actgtaactg acattgaggc tcgaaagtgt gggtatcaaa   420
ca                                                                 422
```

<210> SEQ ID NO 299
<211> LENGTH: 402
<212> TYPE: DNA
<213> ORGANISM: Clostridium sp.

<400> SEQUENCE: 299

```
tggggaatat tgcacaatgg gggaaaccct gatgcagcaa cgccgcgtga gtgaagaagt     60
atttcggtat gtaaagctct atcagcagga agaaaatga cggtacctga ctaagaagcc    120
ccggctaact acgtgccagc agccgcggta atacgtaggg ggcaagcgtt atccggattt    180
actgggtgta aagggagcgt aggtggtatg gcaagtcaga agtgaaaacc cagggcttaa   240
ctctgggact gcttttgaaa ctgtcagact ggagtgcagg agaggtaagc ggaattccta   300
gtgtagcggt gaaatgcgta gatattagga ggaacaccag tggcgaaggc ggcttactgg   360
acggtaactg acgttgaggc tcgaaagcgt ggggagcaaa ca                      402
```

<210> SEQ ID NO 300
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 300

```
tggggaatat tgcacaatgg gggaaaccct gatgcagcga cgccgcgtga aggaagaagt     60
atctcggtat gtaaacttct atcagcaggg agaaaatga cggtacctga ctaagaagcc    120
ccggctaact acgtgccagc agccgcggta atacgtaggg ggcaagcgtt atccggattt    180
actgggtgta aagggcgcgt aggcggctcg gtaagtctgg agtgaaagtc ctgcttttaa   240
ggtgggaatt gctttggata ctgtcggggct tgagtgcagg agaggtaagc ggaattccta   300
```

```
gtgtagcggt gaaatgcgta gatattagga ggaacaccag tggcgaaggc ggcttactgg      360
actgtaactg acgttgaggc tcgaaagcgt ggggagcaaa ca                         402
```

<210> SEQ ID NO 301
<211> LENGTH: 403
<212> TYPE: DNA
<213> ORGANISM: Unknown
<220> FEATURE:
<221> NAME/KEY: source
<223> OTHER INFORMATION: /note="Description of Unknown:
    Bacterial sequence"

<400> SEQUENCE: 301

```
tggggaatat tgcacaatgg gggaaaccct gatgcagcga cgccgcgtga gcgaagaagt       60
atttcggtat gtaaagctct atcagcaggg aagaagaatg acggtacctg actaagaagc      120
accggctaaa tacgtgccag cagccgcggt aatacgtatg gtgcaagcgt tatccggatt      180
tactgggtgt aaagggagcg caggcggtgc ggcaagtctg aagtgaaaat ccggggctta      240
accccggaac tgctttggaa actgcctgac tagagtacag gagaggtaag tggaattcct      300
agtgtagcgg tgaaatgcgt agatattagg aggaacacca gtggcgaagg cggcttactg      360
gacggtaact gacgttgagg ctcgaaagcg tggggagcaa aca                        403
```

<210> SEQ ID NO 302
<211> LENGTH: 405
<212> TYPE: DNA
<213> ORGANISM: Unknown
<220> FEATURE:
<221> NAME/KEY: source
<223> OTHER INFORMATION: /note="Description of Unknown:
    Bacterial sequence"

<400> SEQUENCE: 302

```
tggggaatat tgggcaatgg gcgaaagcct gacccagcaa cgccgcgtga aggaagaagg       60
ccctcgggtt gtaaacttct tttgtcaggg acgaagcaag tgacggtacc tgacgaataa      120
gccacggcta actacgtgcc agcagccacg gtaatacgta ggtggcaagc gttatccgga      180
tttactgggt gtaagggcg tgtaggcggg agtgcaagtc agatgtgaaa actatgggct      240
caacccatag cctgcatttg aaactgtact tcttgagtga tggagaggca ggcggaattc      300
cctgtgtagc ggtgaaatgc gtagatatag ggaggaacac cagtggcgaa ggcgatctgc      360
tggacagcaa ctgacgctga ggcgcgaaag cgtggggagc aaaca                      405
```

<210> SEQ ID NO 303
<211> LENGTH: 440
<212> TYPE: DNA
<213> ORGANISM: Unknown
<220> FEATURE:
<221> NAME/KEY: source
<223> OTHER INFORMATION: /note="Description of Unknown:
    unclassified.Lachnospiraceae"

<400> SEQUENCE: 303

```
gactacacgg gtatctaatc ctgtttgctc cccacgcttt cgtgcctcag tgtcagtaac       60
agtccagcag gccgccttcg ccactggtgt tcctcctaat atctacgcat tcaccgcta       120 cactaggaat tccgcctgcc tctcctgtac tctagccgcg cagtttcaaa tgcagctccg      180
gggttgagcc ccggccttc acatctgact gcactgcca cctacgcacc ctttacaccc       240
agtaaatccg gataacgctt gctccatacg tattaccgcg gctgctggca cgtatttagc      300
cggagcttct tagtcaggta ccgtcattat cttccctgct gatagagctt tacataccga      360
```

-continued

```
aatacttctt cactcacgcg gcgttgctgc atcagggttt cccccattgt gcaatattcc      420
ccactgcagc cccccgtagg                                                  440
```

<210> SEQ ID NO 304
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 304

```
tggggaatat tgcacaatgg gggaaaccct gatgcagcga cgccgcgtga gcgatgaagt      60
atttcggtat gtaaagctct atcagcaggg aagaaaatga cggtacctga ctaagaagca     120
ccggctaaat acgtgccagc agccgcggta atacgtatgg tgcaagcgtt atccggattt     180
actgggtgta aagggagcgt agacggcaag gcaagtctga agtgaaagcc ggtgcttaa      240 cgccgggact gctttggaaa ctgtttagct ggagtgccgg agaggtaagc ggaattccta     300
gtgtagcggt gaaatgcgta gatattagga ggaacaccag tggcgaaggc ggcttactgg     360
actgcaactg acactgaggc acgaaagcgt gggtagcaaa ca                        402
```

<210> SEQ ID NO 305
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 305

```
tggggaatat tgcacaatgg gggaaaccct gatgcagcaa cgccgcgtga gtgaagaagt      60
atttcggtat gtaaagctct atcagcagga aagaaaatga cggtacctga ctaagaagcc     120
ccggctaact acgtgccagc agccgcggta atacggagga tgcgagcgtt atccggattt     180
actgggtgta aagggagcgt agacggaatg gcaagtctga tgtgaaaggc cggggctcaa     240
ccccgggact gcattggaaa ctgtcaatct agagtaccgg aggggtaagt ggaattccta     300
gtgtagcggt gaaatgcgta gatattagga ggaacaccag tggcgaaggc ggcttactgg     360
actgtaactg acactgaggc tcgaaagcgt ggggagcaaa ca                        402
```

<210> SEQ ID NO 306
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 306

```
tggggaatat tgcacaatgg gggaaaccct gatgcagcga cgccgcgtga aggaagaagt      60
atctcggtat gtaaacttct atcagcaggg aagaaaatga cggtacctga ctaagaagcc     120
ccggctaact acgtgccagc agccgcggta atacgtaggg ggcaagcgtt atccggattt     180
actgggtgta aagggagcgt agacggtaat gcaagtctgg agtgaaaacc ggggctcaa      240 ccccgggact gctttggaaa ctgtgtaact agagtgtcgg agaggcaagt ggaattccta     300
```

```
gtgtagcggt gaaatgcgta gatattagga agaacaccag tggcgaaggc ggcttactgg    360
acggtaactg acgttgaggc tcgaaagcgt ggggagcaaa ca                       402
```

<210> SEQ ID NO 307
<211> LENGTH: 404
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 307

```
tggggaatat tgcacaatgg gggaaaccct gatgcagcga cgccgcgtga aggaagaagt    60
atctcggtat gtaaagctct atcagcaggg aagaagaaat gacggtacct gactaagaag   120
caccggctaa atacgtgcca gcagccgcgg taatacgtat ggtgcaagcg ttattcggat   180
ttactgggtg taaagggagc gtagacggtt ttgcaagtct gaagtgaaag cccagggctt   240
aaccccggga ctgctttgga aactgtagga ctagagtgca ggagaggtaa gtggaattcc   300
tagtgtagcg gtgaaatgcg tagatattag gaggaacacc agtggcgaag gcggcttact   360
ggacgataac tgacgctgag gctcgaaagc gtggggagca aaca                    404
```

<210> SEQ ID NO 308
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 308

```
tggggaatat tgcacaatgg aggaaactct gatgcagcga cgccgcgtga gtgaagaagt    60
aattcgttat gtaaagctct atcagcaggg aagatagtga cggtacctga ctaagaagct   120
ccggctaaat acgtgccagc agccgcggta atacgtaggg ggcaagcgtt atccggattt   180
actgggtgta aagggagcgc aggcggcagg gcaagtcaga tgtgaaatac tggggctcaa   240
ccccgggact gcatttgaaa ctgtccggct agagtgcagg agaggcaggc ggaattccta   300
gtgtagcggt gaaatgcgta gatattagga ggaacaccag tggcgaaggc ggctcactgg   360
actgtaactg acactgaggc tcgaaagcgt ggggagcaaa ca                      402
```

<210> SEQ ID NO 309
<211> LENGTH: 405
<212> TYPE: DNA
<213> ORGANISM: Leptotrichia sp.

<400> SEQUENCE: 309

```
tggggaatat tggacaatgg gggcaaccct gatccagcaa ttctgtgtgc acgaagaagg    60
ttttcggatt gtaaagtgct ttcagcaggg aagaagagag tgacggtacc tgcagaagaa   120
gcgacggcta atacgtgcca gcagccgcg gtaatacgta tgtcgcgagc gttatccgga    180
attattgggc ataaagggca tctaggcggc taacaagtc aggggtgaaa acctgcggct    240
caaccgcagg cctgcctttg aaactgtgag gctggagtac cggagaggtg acggaactg    300 cacgagtaga ggtgaaattc gtagatatgt gcaggaatgc cgatgatgaa gatagtccac   360
tggacggaaa ctgacgctga ggagcgaaag catgggagc gaaca                    405
```

<210> SEQ ID NO 310
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 310

```
tgaggaatat tggtcaatgg acgagagtct gaaccagcca agtagcgtga aggatgactg      60
ccctatgggt tgtaaacttc ttttatatgg gaataaagta ttccacgtgt gggattttgt     120
atgtaccata tgaataagga tcggctaact ccgtgccagc agccgcggta atacggagga     180
tccgagcgtt atccggattt attgggttta aagggagcgt aggcggacgc ttaagtcagt     240
tgtgaaagtt tgcggctcaa ccgtaaaatt gcagttgata ctgggtgtct tgagtacagt     300
agaggcaggc ggaattccta gtgtagcggt gaaatgctta gatatcacga agaactccga     360
ttgcgaaggc agctcactag actgcaactg acgctgaggc tcgaaagtgt gggtagcaaa     420
ca                                                                    422
```

<210> SEQ ID NO 311
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 311

```
tgaggaatat tggtcaatgg tcggcagact gaaccagcca agtcgcgtga gggaagacgg      60
ccctacgggt tgtaaacctc ttttgtcgga gagtaaagta cgctacgtgt agcgtattgc     120
aagtatccga agaaaaagca tcggctaact ccgtgccagc agccgcggta atacggagga     180
tgcaagcgtt atccggattt attgggttta aagggagcgt agatggatgt ttaagtcagt     240
tgtgaaagtt tgcggctcaa ccgtaaaatt gcagttgata ctggatatct tgagtgcagt     300
tgaggcaggc ggaatgcgtg gtgtagcggt gaaatgcata gatatcacgc agaaccccga     360
ttgcgaaggc agcctgctag ggtgcgacag acgctgaggc acgaaagcgt gggtatcgaa     420
ca                                                                    422
```

<210> SEQ ID NO 312
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 312

```
tgaggaatat tggtcaatgg gcgtaagcct gaaccagcca agtcgcgtga gggatgaagg      60
ttctatggat cgtaaacctc ttttataagg gaataaagtg cgggacgtgt cctgttttgt     120
atgtacctta tgaataagga tcggctaact ccgtgccagc agccgcggta atacggagga     180
tccgagcgtt atccggattt attgggttta aagggtgcgt aggcggcacg ccaagtcagc     240
ggtgaaattt ccgggctcaa cccggagtgt gccgttgaaa ctggcgagct agagtacaca     300
agaggcaggc ggaatgcgtg gtgtagcggt gaaatgcata gatatcacgc agaaccccga     360
```

```
ttgcgaaggc agcatactgg gctataactg acgctgaagc acgaaagcgt gggtatcgaa    420
ca                                                                  422

<210> SEQ ID NO 313
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 313
tggggaatat tgcacaatgg gggaaaccct gatgcagcga cgccgcgtga gtgaagaagt     60
atctcggtat gtaaagctct atcagcaggg aagaaaatga cggtacctga ctaagaagcc    120
ccggctaact acgtgccagc agccgcggta atacgtaggg ggcaagcgtt atccggaatt    180
actgggtgta aagggtgcgt agacggatgg acaagtctga tgtgaaaggc tggggctcaa    240
ccccgggact gcattggaaa ctgcccgtct tgagtgccgg agaggtaagc ggaattccta    300
gtgtagcggt gaaatgcgta gagatcggga ggaacaccag tggcgaaggc ggcctactgg    360
gctttaactg acgctgaggc acgaaagtgt gggtagcaaa ca                      402

<210> SEQ ID NO 314
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 314
tggggaatat tgcacaatgg aggaaactct gatgcagcga cgccgcgtga aggatgaagt     60
atttcggtat gtaaacttct atcagcaggg aagaaaatga cggtacctga ctaagaagcc    120
ccggctaact acgtgccagc agccgcggta atacgtaggg ggcaagcgtt atccggattt    180
actgggtgta aagggcgtgt aggcggggaa gcaagtcaga tgtgaaaacc agtggctcaa    240
ccactggcct gcatttgaaa ctgttttttct tgagtgatgg agaggcaggc ggaattccgt    300
gtgtagcggt gaaatgcgta gatattagga ggaacaccag tggcgaaggc ggcttactgg    360
acggtaactg acgttgaggc tcgaaagcgt ggggagcaaa ca                      402

<210> SEQ ID NO 315
<211> LENGTH: 422
<212> TYPE: DNA
<213> ORGANISM: Corynebacterium sp.

<400> SEQUENCE: 315
tggggaatat tgcacaatgg gcgcaagcct gatgcagcga cgccgcgtgg gggatgacgg     60
ccttcgggtt gtaaactcct ttcgttaggg acgaagccac acttttttggg tgtggtgacg    120 gtacctttgt taagaagcac cggctaacta cgtgccagca gccgcggtaa tacgtagggt    180
gcgagcgttg tccggaatta ctgggcgtaa agagctcgta ggtggtgtgt cgcgtcgtct    240
gtgaaattcc ggggcttaac tccgggcgtg caggcgatac gggcacgact agagtgctgt    300
aggggtaact ggaattcctg gtgtagcggt ggaatgcgca gatatcagga ggaacaccga    360
tggcgaaggc aggtctctgg gcagtaactg acgctgagga cgaaagcat ggggagcgaa    420 cc                                                                  422
```

<210> SEQ ID NO 316
<211> LENGTH: 440
<212> TYPE: DNA
<213> ORGANISM: Faecalibacterium sp.

<400> SEQUENCE: 316

| | | | | | |
|---|---|---|---|---|---|
| gactacaggg | gtatctaatc | ctgtttgcta | cccacactt | cgagcctcag | cgtcagttgg | 60 |
| tgcccagtag | gccgccttcg | ccactggtgt | tcctcccgat | atctacgcat | tccaccgcta | 120 |
| caccgggaat | tccgcctacc | tctgcactac | tcaagaaaaa | cagttttgaa | agcagttcat | 180 |
| gggttgagcc | catggatttc | acttccaact | tgttctcccg | cctgcgctcc | ctttacaccc | 240 |
| agtaattccg | gacaacgctt | gtgacctacg | ttttaccgcg | gctgctggca | cgtagttagc | 300 |
| cgtcacttcc | ttgttgagta | ccgtcattat | cttcctcaac | aacaggagtt | tacaatccga | 360 |
| agaccttctt | cctccacgcg | gcgtcgctgc | atcagggttt | cccccattgt | gcaatattcc | 420 |
| ccactgcagc | ccccgtagg | | | | | 440 |

<210> SEQ ID NO 317
<211> LENGTH: 404
<212> TYPE: DNA
<213> ORGANISM: Unknown
<220> FEATURE:
<221> NAME/KEY: source
<223> OTHER INFORMATION: /note="Description of Unknown: Bacterial sequence"

<400> SEQUENCE: 317

| | | | | | |
|---|---|---|---|---|---|
| tggggaatat | tgggcaatgg | ggggaaccct | gacccagcaa | cgccgcgtgg | aggaagaagg | 60 |
| ttttcggatc | gtaaactcct | gtccttggag | acgagtagaa | gacggtatcc | aaggaggaag | 120 |
| ccccggctaa | ctacgtgcca | gcagccgcgg | taatacgtag | ggggcaagcg | ttgtccggat | 180 |
| ttactgggtg | taaagggcgt | gcagccgggt | ttgcaagtca | gatgtgaaat | ccatgggctc | 240 |
| aacccatgaa | ctgcatttga | aactgtagat | cttgagtgtc | ggaggggcaa | tcggaattcc | 300 |
| tagtgtagcg | gtgaaatgcg | tagatataag | gaagaacacc | agtggcgaag | gcggattact | 360 |
| ggacggtaac | tgacggtgag | gcgcgaaagc | gtggggagcg | aaca | | 404 |

<210> SEQ ID NO 318
<211> LENGTH: 465
<212> TYPE: DNA
<213> ORGANISM: Veillonella sp.

<400> SEQUENCE: 318

| | | | | | |
|---|---|---|---|---|---|
| gactactagg | gtatctaatc | ccgttcgctc | ccctggcttt | cgcgcctcag | cgtcagttt | 60 |
| cgtccagaaa | gtcgccttcg | ccactggtgt | tcttcctaat | atctacgcat | ttcaccgcta | 120 |
| cactaggaat | tccacttcc | tctccgatac | tctagattgg | cagtttccat | cccatcacgg | 180 |
| ggttaagccc | cgaactttta | agacagactg | accaatccgc | ctgcgcgcgc | tttacgccca | 240 |
| ataattccgg | acaacgcttg | ccacctacgt | attaccgcgg | ctgctggcac | gtagttagcc | 300 |
| gtggctttct | attccggtac | cgtcaatcct | tctaactgtt | cgcaagaagg | cctttcgtcc | 360 |
| cgattaacag | agctttacaa | cccgaaggcc | gtcatcactc | acgcggcgtt | gctccgtcag | 420 |
| actttcgtcc | attgcggaag | attccccact | gcagccccc | gtagg | | 465 |

<210> SEQ ID NO 319
<211> LENGTH: 402
<212> TYPE: DNA

```
<213> ORGANISM: Unknown
<220> FEATURE:
<221> NAME/KEY: source
<223> OTHER INFORMATION: /note="Description of Unknown:
      unclassified.Lachnospiraceae"

<400> SEQUENCE: 319
tggggaatat tgcacaatgg gcgaaagcct gatgcagcga cgccgcgtga gcgaagaagt     60
atttcggtat gtaaagctct atcagcaggg aagataatga cggtacctga ctaagaagca    120
ccggctaaat acgtgccagc agccgcggta atacgtatgg tacaagcgtt atccggattt    180
actgggtgta aagggagcgt agacggcgac gcaagtctga agtgaaatac ccgggctcaa    240
cctgggaact gctttggaaa ctgtgttgct ggagtgctgg agaggtaagc ggaattccta    300
gtgtagcggt gaaatgcgta gatattagga ggaacaccag tggcgaaggc ggcttactgg    360
acgataactg acgctgaggc tcgaaagcgt ggggagcaaa ca                       402

<210> SEQ ID NO 320
<211> LENGTH: 422
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 320
tgaggaatat tggtcaatgg acgagagtct gaaccagcca agtagcgtga aggatgactg     60
ccctatgggt tgtaaacttc ttttatacgg gaataaagtg gtccacgtgt ggattttgt    120 atgtaccgta tgaataagga tcggctaact ccgtgccagc agccgcggta atacggagga    180
tccgagcgtt atccggattt attgggttta aaggagcgt aggtggacat gtaagtcagt    240
tgtgaaagtt tgcggctcaa ccgtaaaatt gcagttgata ctgcgtgtct tgagtacagt    300
agaggtgggc ggaattcgtg gtgtagcggt gaaatgctta gatatcacga agaactccga    360
ttgcgaaggc agctcactgg agtgtaactg acgctgatgc tcgaaagtgt gggtatcaaa    420
ca                                                                   422

<210> SEQ ID NO 321
<211> LENGTH: 403
<212> TYPE: DNA
<213> ORGANISM: Blautia sp.

<400> SEQUENCE: 321
tggggaatat tgcacaatgg gggaaaccct gatgcagcga cgccgcgtga gtgaagaagt     60
atttcggtat gtaaagctct atcagcaggg aagaactagg acggtacctg actaagaagc    120
cccggctaac tacgtgccag cagccgcggt aatacgtagg gggcaagcgt tatccggatt    180
tactgggtgt aaagggagcg tagacggcgt atcaagtctg atgtgaaagg caggggctta    240 accccctggac tgcattggaa actggtatgc ttgagtgccg gaggggtaag cggaattcct    300
agtgtagcgg tgaaatgcgt agatattagg aggaacacca gtggcgaagg cggcttactg    360
gacggtaact gacgttgagg ctcgaaagcg tggggagcaa aca                      403

<210> SEQ ID NO 322
<211> LENGTH: 443
<212> TYPE: DNA
<213> ORGANISM: Fusobacterium sp.

<400> SEQUENCE: 322
```

```
gactactggg gtatctaatc ctgtttgcta cccacgcttt cgcgcttcag cgtcagtatc      60
tgtccagtaa gctggcttcc ccatcggcat tcctacaaat atctacgaat ttcacctcta     120
cacttgtagt tccgcttacc tctccagtac tctagttaca cagtttccaa cgcaatacag     180
agttgagccc tgcattttca catcagactt acataaccac ctagacgcgc tttacgccca     240
ataaatccgg ataacgcttg tgacatacgt attaccgcgg ctgctggcac gtatttagcc     300
gtcacttctt ctgttggtac cgtcattttt ttcttcccaa ctgaaagcac tttacattcc     360
gaaaaacttc atcgtgcaca cagaattgct ggatcagact cttggtccat tgtccaatat     420
tccccactgc agcctcccgt agg                                             443
```

<210> SEQ ID NO 323
<211> LENGTH: 402
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 323

```
tggggaatat tgcacaatgg gggaaaccct gatgcagcga cgccgcgtga aggaagaagt      60
atttcggtat gtaaacttct atcagcaggg aagaaaatga cggtacctga ctaagaagcc     120
ccggctaact acgtgccagc agccgcggta atacgtaggt ggcaagcgtt gtccggaatt     180
actgggtgta aagggagcgt agacggccgt gcaagtctga tgtgaaaggc tggggctcaa     240
ccccgggact gcattggaaa ctgtatggct ggagtgccgg agaggtaagc ggaattccta     300
gtgtagcggt gaaatgcgta gatattagga ggaacaccag tggcgaaggc ggcttactgg     360
acggtaactg acgttgaggc tcgaaagcgt ggggagcaaa ca                        402
```

<210> SEQ ID NO 324
<211> LENGTH: 403
<212> TYPE: DNA
<213> ORGANISM: Unknown
<220> FEATURE:
<221> NAME/KEY: source
<223> OTHER INFORMATION: /note="Description of Unknown:
      Bacterial sequence"

<400> SEQUENCE: 324

```
tggggaatat tgcacaatgg gggaaaccct gatgcagcga cgccgcgtga gcgaagaagt      60
atttcggtat gtaaagctct atcagcaggg aagaagaaat gacggtacct gactaagaag     120
caccggctaa atacgtgcca gcagccgcgg taatacgtat ggtgcaagcg ttgtccggaa     180
ttactgggtg taaagggagc gtaggcgggc aggcaagtca ggcgtgaaat atatcggctc     240
aaccggtaac ggcgcttgaa actgcaggtc ttgagtgaag tagaggttgg cggaattcct     300
agtgtagcgg tgaaatgcgt agatattagg aggaacacca gtggcgaagg cggcttactg     360
gacgataact gacgctgagg ctcgaaagcg tggggagcaa aca                       403
```

<210> SEQ ID NO 325
<211> LENGTH: 465
<212> TYPE: DNA
<213> ORGANISM: Streptococcus sp.

<400> SEQUENCE: 325

```
gactactcgg gtatctaatc ctgtttgctc cccacgcttt cgagcctcag cgtcagttac      60
```

```
aagccagaga gccgctttcg ccaccggtgt tcctccatat atctacgcat ttcaccgcta      120
cacatggaat tccactctcc cctcttgcac tcaagttaaa cagtttccaa agcgtactat      180
ggttaagcca cagcctttaa cttcagactt atctaaccgc ctgcgctcgc tttacgccca      240
ataaatccgg acaacgctcg ggacctacgt attaccgcgg ctgctggcac gtagttagcc      300
gtccctttct ggtaagatac cgtcacagtg tgaactttcc actctcacac tcgttcttct      360
cttacaacag agctttacga tccgaaaacc ttcttcactc acgcggcgtt gctcggtcag      420
acttccgtcc attgccgaag attccctact gcagccccc gtagg                      465

<210> SEQ ID NO 326
<211> LENGTH: 460
<212> TYPE: DNA
<213> ORGANISM: Parabacteroides sp.

<400> SEQUENCE: 326
gactactagg gtatctaatc ctgtttgatc cccacgcttt cgtgcttcag tgtcagttat       60
ggtttagtaa gctgccttcg caatcggagt tctgcgtgat atctatgcat ttcaccgcta      120
caccacgcat tccgcctacc tcaaacacac tcaagtaacc cagtttcaac ggcaatttta      180
tggttgagcc acaaactttc accgctgact taaatcacca cctacgcacc ctttaaaccc      240
aataaatccg gataacgctc gcatcctccg tattaccgcg gctgctggca cggagttagc      300
cgatgcttat tcatagggta catacaaaaa aggacacgtc ctccacttta ttcccctata      360
aaagaagttt acaaaccata gatccttctt ccttcacgcg acttggctgg ttcagcctct      420
cggccattga ccaatattcc tcactgctgc cgcccgtagg                            460
```